(12) United States Patent
Yamaguchi et al.

(10) Patent No.: US 8,153,634 B2
(45) Date of Patent: Apr. 10, 2012

(54) CARBINOL DERIVATIVES HAVING CYCLIC LINKER

(75) Inventors: Yuki Yamaguchi, Tokyo (JP); Minoru Koura, Tokyo (JP); Sayaka Kurobuchi, Tokyo (JP); Takayuki Matsuda, Tokyo (JP); Ayumu Okuda, Tokyo (JP); Hisashi Sumida, Tokyo (JP); Yuichiro Watanabe, Tokyo (JP); Takashi Enomoto, Tokyo (JP); Kimiyuki Shibuya, Tokyo (JP)

(73) Assignee: Kowa Company, Ltd., Nagoya-shi (JP)

( * ) Notice: Subject to any disclaimer, the term of this patent is extended or adjusted under 35 U.S.C. 154(b) by 208 days.

(21) Appl. No.: 12/474,799

(22) Filed: May 29, 2009

(65) Prior Publication Data
US 2010/0048610 A1 Feb. 25, 2010

Related U.S. Application Data

(60) Provisional application No. 61/057,070, filed on May 29, 2008.

(51) Int. Cl.
| | |
|---|---|
| *A61K 31/4166* | (2006.01) |
| *A61K 31/4178* | (2006.01) |
| *A61K 31/4355* | (2006.01) |
| *A61K 31/4439* | (2006.01) |
| *A61K 31/497* | (2006.01) |
| *A61K 31/501* | (2006.01) |
| *A61K 31/506* | (2006.01) |
| *C07D 401/02* | (2006.01) |
| *C07D 401/06* | (2006.01) |
| *C07D 405/14* | (2006.01) |
| *C07D 405/02* | (2006.01) |
| *C07D 491/048* | (2006.01) |
| *C07D 233/72* | (2006.01) |
| *C07D 403/02* | (2006.01) |
| *C07D 403/06* | (2006.01) |

(52) U.S. Cl. ............... 514/252.05; 514/389; 514/341; 514/255.05; 514/256; 544/238; 544/333; 544/405; 546/274.4; 546/115; 548/311.4; 548/311.7; 548/319.1

(58) Field of Classification Search .................. None
See application file for complete search history.

(56) References Cited

U.S. PATENT DOCUMENTS
6,316,503 B1 11/2001 Li et al.
2005/0215577 A1 9/2005 Dehmlow et al.

FOREIGN PATENT DOCUMENTS
| EP | 527433 A1 * | 2/1993 |
|---|---|---|
| JP | 2002-539155 A | 11/2002 |
| JP | 2004-509161 A | 3/2004 |
| JP | 2007-284367 A | 11/2007 |
| WO | 00/54759 A2 | 9/2000 |
| WO | 02/24632 A2 | 3/2002 |
| WO | 03/082192 A2 | 10/2003 |
| WO | 2004/024161 A1 | 3/2004 |
| WO | 2004/058717 A1 | 7/2004 |
| WO | 2004/072046 A2 | 8/2004 |
| WO | 2005/023188 A2 | 3/2005 |
| WO | 2005/023782 A1 | 3/2005 |
| WO | 2005/058834 A2 | 6/2005 |
| WO | 2008/065754 A1 | 6/2008 |

OTHER PUBLICATIONS

Byrn et al., Solid-State Chemistry of Drugs, 2d, Chapter 11 Hydrates and Solvates, 233-247 (1999).*
Morissette et al., Adv. Drug Delivery Rev., 56:275 (2004).*
A.M. Rouhi, Chem. & Eng. News, 81:32 (Feb. 24, 2003).*
Horig et al. Journal of Translational Medicine, 2:44 (2004).*
Schafer et al. Drug Discovery Today, 13:913 (2008).*
G. Cao et al., "Antidiabetic Action of a Liver X Receptor Agonist Mediated By Inhibition of Hepatic Gluconeogenesis", The Journal of Biological Chemistry, Oct. 31, 2002, pp. 1131-1136.
X. Fu et al., "27-Hydroxycholesterol Is an Endogenous Ligand for Liver X Receptor in Cholesterol-loaded Cells", The Journal of Biological Chemistry, Jun. 22, 2001, pp. 38378-38387.
R. Geyeregger et al., "Liver X receptors in cardiovascular and metabolic disease", Cellular and Molecular Life Sciences, 2006, pp. 524-539, vol. 63.
B. A. Janowski et al., "An oxysterol signalling pathway mediated by the nuclear receptor LXRα", Nature, Oct. 24, 1996, pp. 728-731, vol. 383.
B. Hu et al., "Discovery of Phenyl Acetic Acid Substituted Quinolines as Novel Liver X Receptor Agonists for the Treatment of Atherosclerosis", Journal of Medical Science, 2006, pp. 6151-6154, vol. 49.
B. A. Laffitte et al., "Activation of liver X receptor improves glucose tolerance through coordinate regulation of glucose metabolism in liver and adipose tissue", PNAS, Apr. 29, 2003, pp. 5419-5424, vol. 100, No. 9.

(Continued)

*Primary Examiner* — Yong Chu
*Assistant Examiner* — Michael Barker
(74) *Attorney, Agent, or Firm* — Westerman, Hattori, Daniels & Adrian, LLP

(57) ABSTRACT

[Object] To provide a novel LXRβ agonist that is useful as a preventative and/or therapeutic agent for atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.
[Solving Means] A carbinol compound represented by the following general formula (I) or salt thereof, or their solvate.

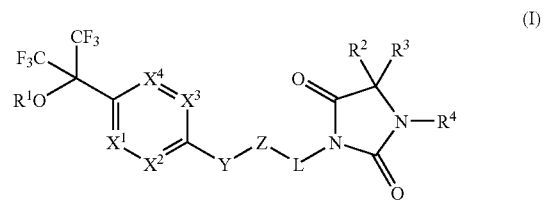

(I)

6 Claims, 16 Drawing Sheets

OTHER PUBLICATIONS

D. S. Lala, "The liver X receptors", Current Opinion in Investigational Drugs, 2005, pp. 934-943, vol. 6, No. 9.

J. M. Lehmann et al., "Activation of the Nuclear Receptor LXR by Oxysterols Defines a New Hormone Response Pathway", The Journal of Biological Chemistry, 1997, pp. 3137-3140, vol. 272, No. 6.

T. T. Lu et al., "Orphan Nuclear Receptors as eLiXiRs and FiXeRs of Sterol Metabolism", The Journal of Biological Chemistry, Jul. 17, 2001, pp. 37735-37738, vol. 276, No. 41.

E. G. Lund et al., "Liver X Recptor Agonists as Potential Therapeutic Agents for Dyslipidemia and Atherosclerosis", Arterioscler Thromb Vasc Biol., Jul. 2003, pp. 1169-1177.

S. B. Joseph et al., "Reciprocal regulation of inflammation and lipid metabolism by liver X receptors", Nature Medicine, Feb. 2003, pp. 213-219, vol. 9, No. 2.

D. J. Peet et al., "Cholesterol and Bile Acid Metabolism Are Impaired in Mice Lacking the Nuclear Oxysterol Receptor LXR$\alpha$", 1998.

P. H. E. Groot et al., "Synthetic LXR agonists increase LDL in CETP species", Journal of Lipid Research, 2005, pp. 2182-2191, vol. 46.

R. K. Tangirala et al., "Identification of macrophage liver X receptors as inhibitors of atherosclerosis", PNAS, Sep. 3, 2002, pp. 11896-11901, vol. 99, No. 18.

N. Terasaka et al., T-0901317, a synthetic liver X receptor ligand, inhibits development of atherosclerosis in LDL receptor-deficient mice, FEBS Letters 536, 2003, vol. 6, No. 11.

N. Zelcer et al., "Liver X receptors as integrators of metabolic and inflammatory signaling",The Journal of Clinical Investigation, Mar. 2006, pp. 607-614, vol. 116, No. 3.

S. Alberti et al., "Hepatic cholesterol metabolism and resistance to dietary cholesterol in LXR$\beta$-deficient mice", The Journal of Clinical Investigation, Mar. 2001, pp. 565-573, vol. 107, No. 5.

D. Auboeuf et al., "Tissue Distribution and Quantification of the Expression of mRNAs of Peroxisome Proliferator-Activated Receptors and Liver X Receptor-$\alpha$ in Humans, No Alteration in Adipose Tissue of Obese adn NIDDM Patients", Diabetes, Aug. 1997, pp. 1319-1327, vol. 46.

B. Hu et al., "Further modification on phenyl acetic acid based quinolines as liver X receptor modulators", Bioorganic & Medicinal Chemistry, 2007, pp. 3321-3332, vol. 15.

B. Hu et al., "Carboxylic acid based quinolines as liver X receptor modulators that have LxR$\beta$ receptor binding selectivity", Bioorganic & Medicinal Chemistry, 2008, pp. 54-59, vol. 18.

M. N. Bradley et al., "LXR: A nuclear receptor target for cardiovascular disease?", Drug Discovery Today: Therapeutic Strategies, 2005, pp. 97-103, vol. 2, No. 2.

J. R. Schultz et al., "Role of LXRs in control of lipogenesis", Genes & Development, 2000, pp. 2831-3838.

Notification of Transmittal of Translation of the International Preliminary Report on Patent on Patentability (Forms PCT/IB/338) of International Application No. PCT/JP2009/002406 mailed Jan. 20, 2011 with Forms PCT/IB/373 and PCT/ISA/237.

International Search Report of PCT/JP2009/002406, date of mailing Jun. 23, 2009.

* cited by examiner

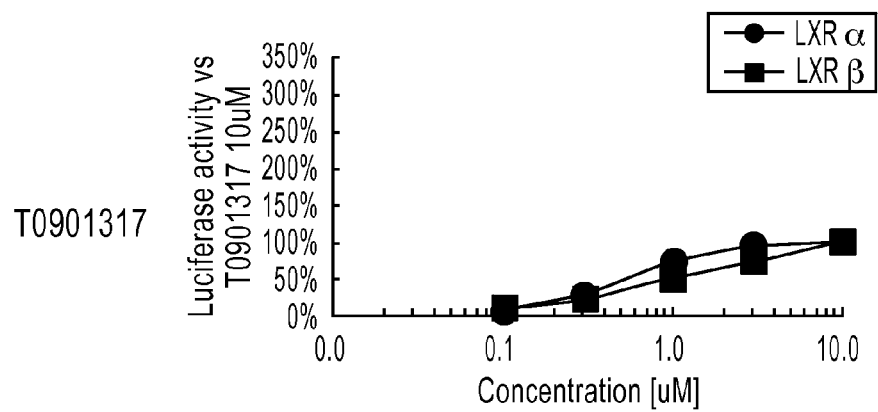
Fig.1a  T0901317
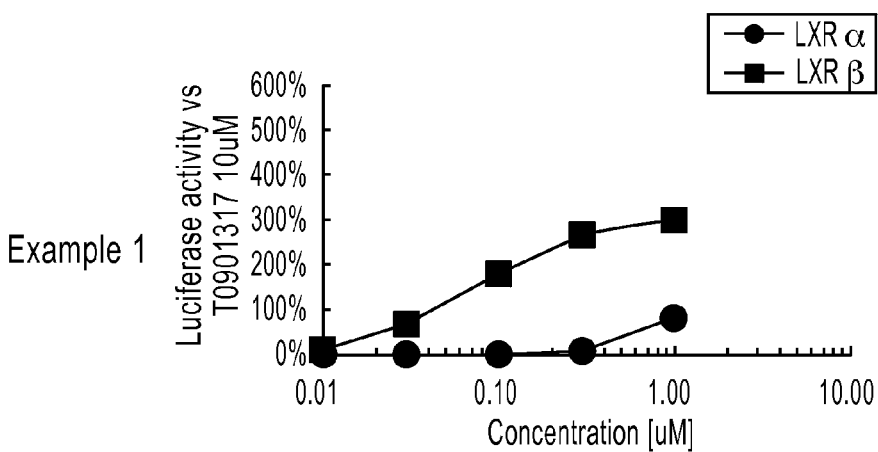
Fig.1b  Example 1
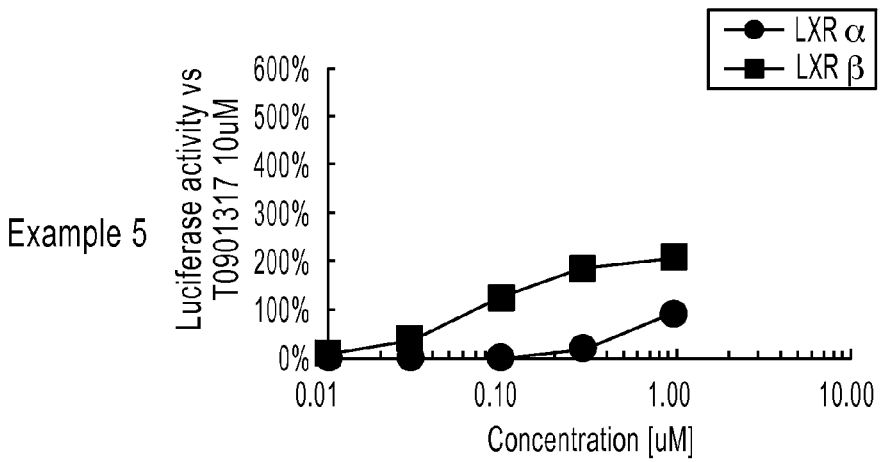
Fig.1c  Example 5

Example 28

Example 40

Example 45

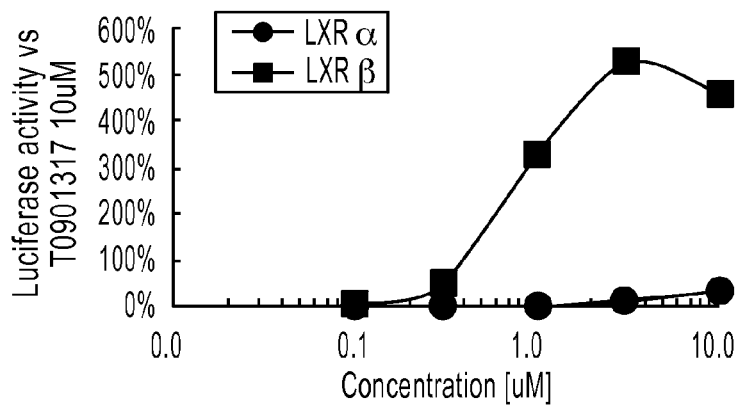
Fig.1g Example 62
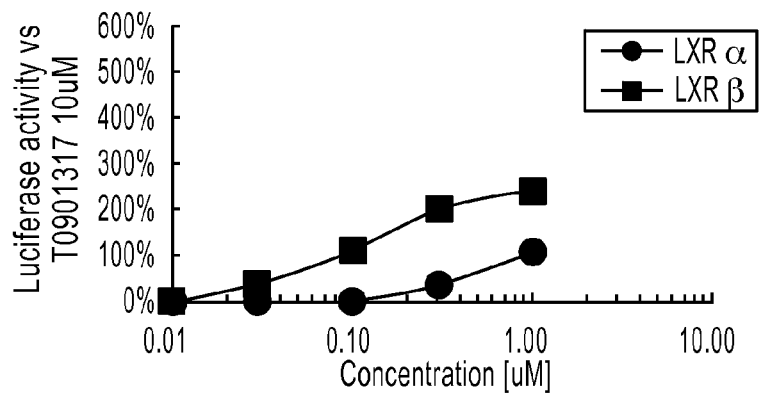
Fig.1h Example 67
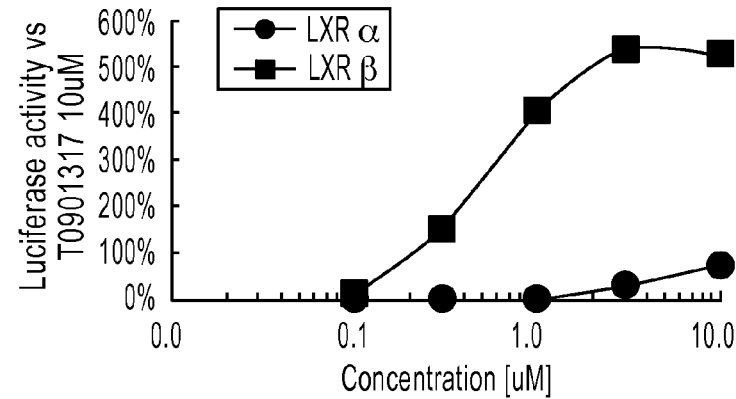
Fig.1i Example 69

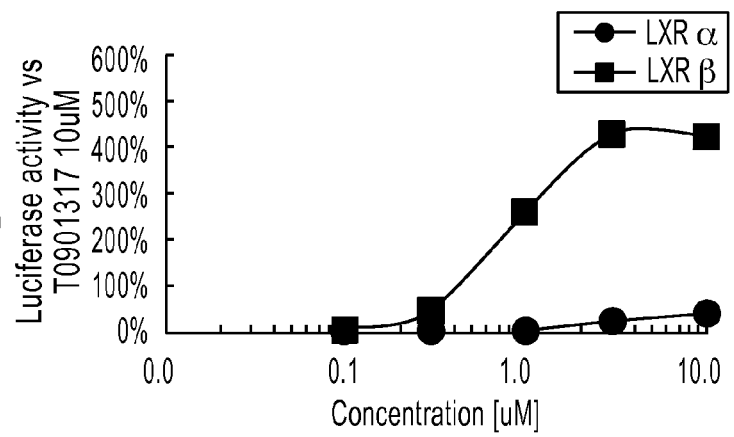
Fig.1j Example 80
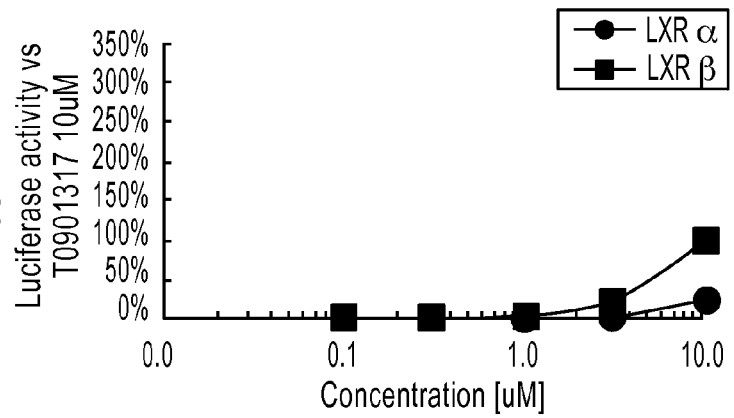
Fig.1k Example 92

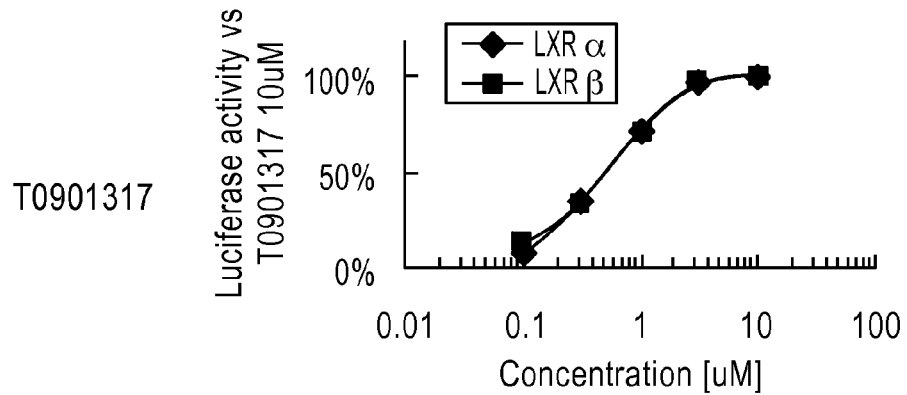
Fig.2a  T0901317
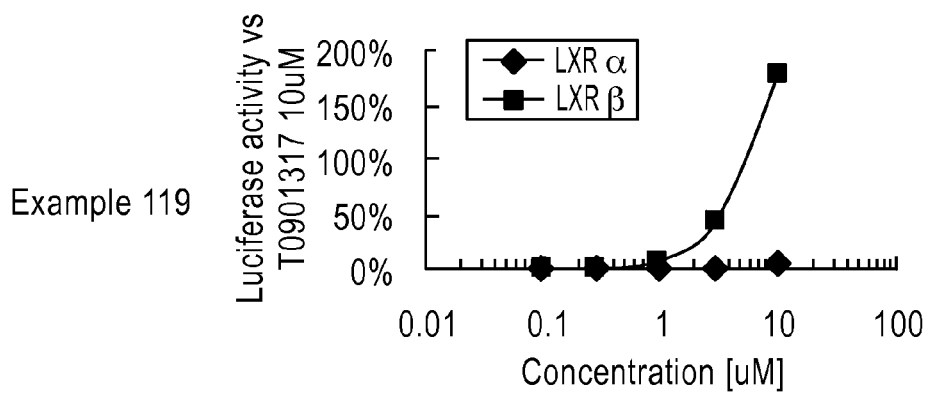
Fig.2b  Example 119
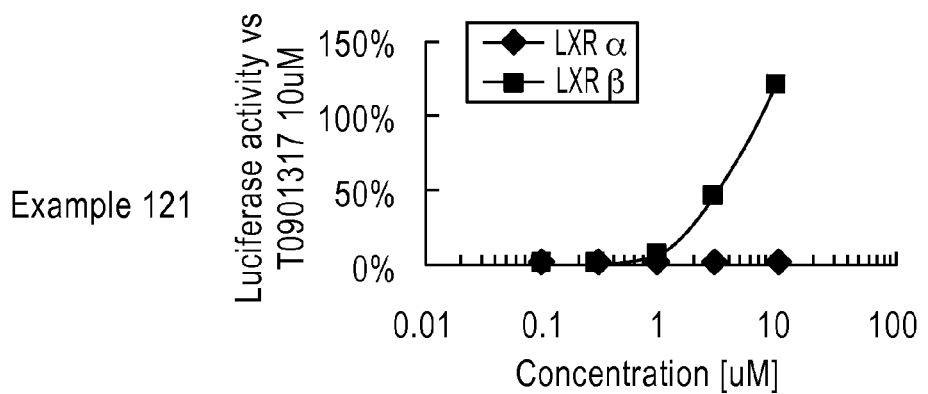
Fig.2c  Example 121

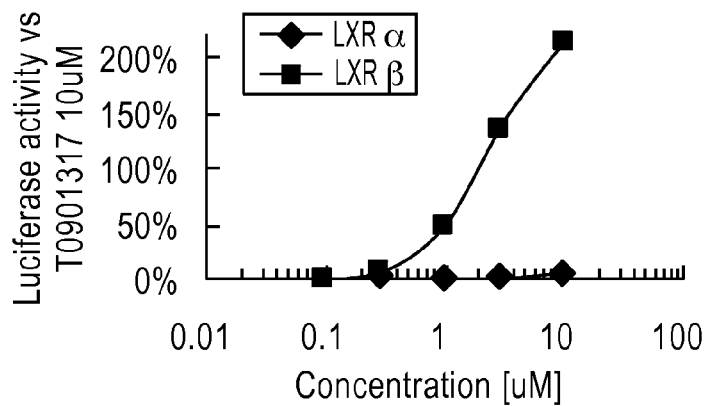
Fig.2d  Example 123
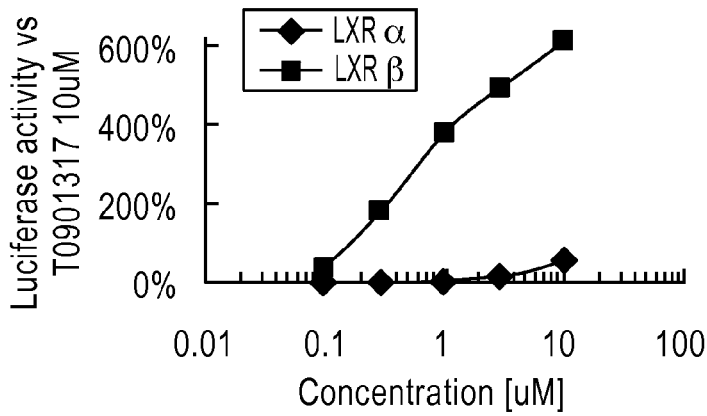
Fig.2e  Example 126
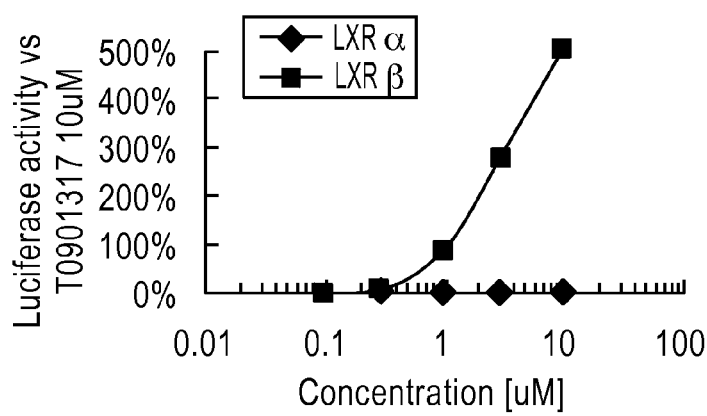
Fig.2f  Example 127

Example129

Example130

Example131

Example 133

Example 162

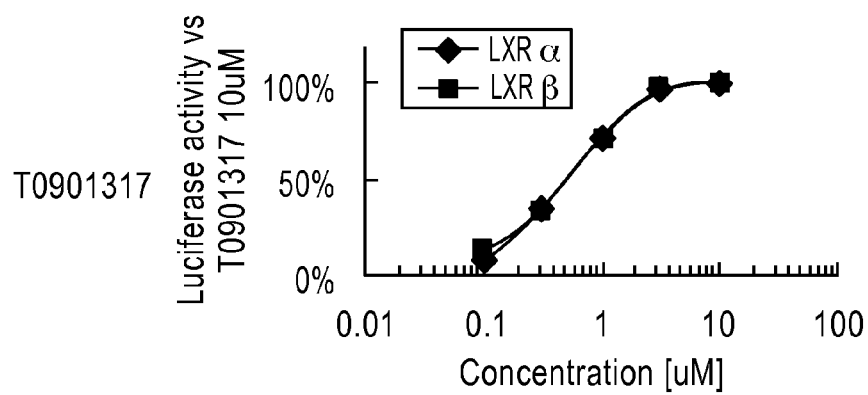
Fig.3a  T0901317
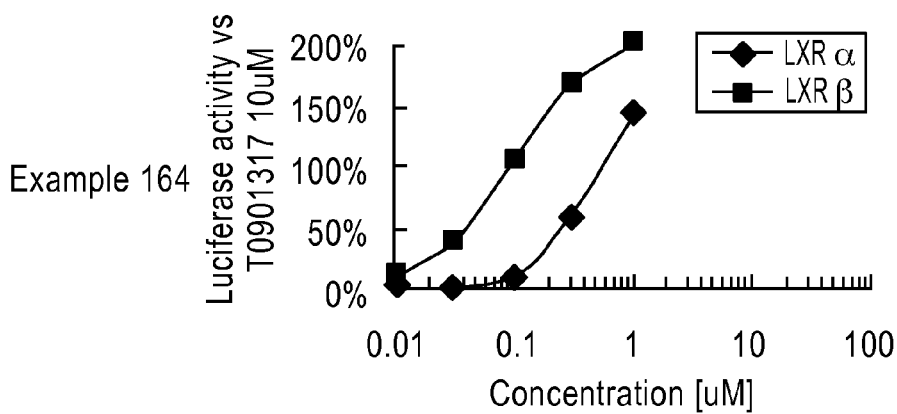
Fig.3b  Example 164
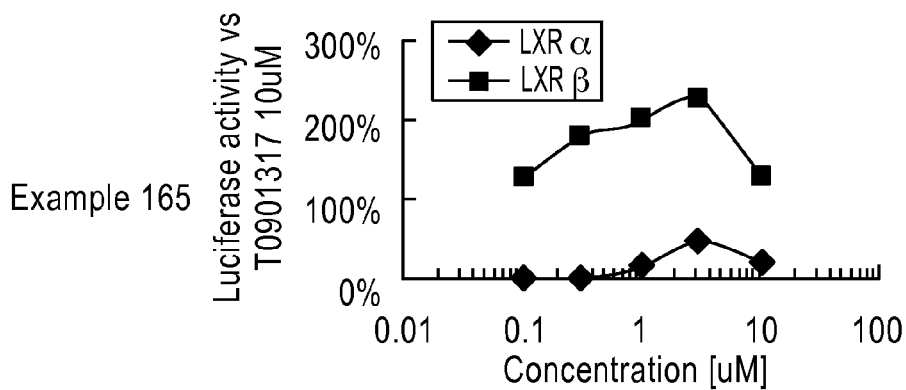
Fig.3c  Example 165

Example 171

Example 172

Example 180

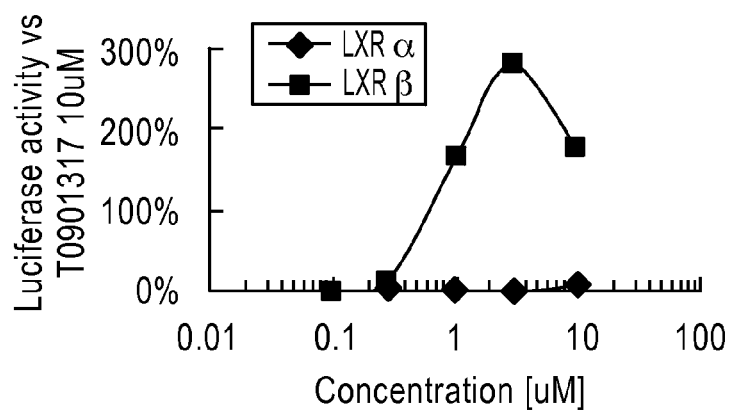
Fig.3g Example 185
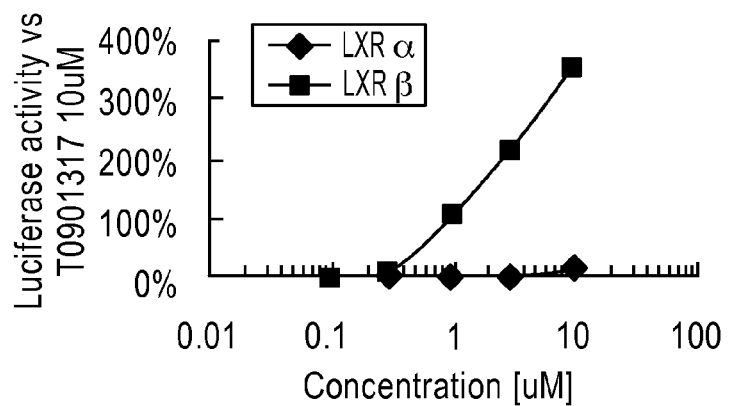
Fig.3h Example 195
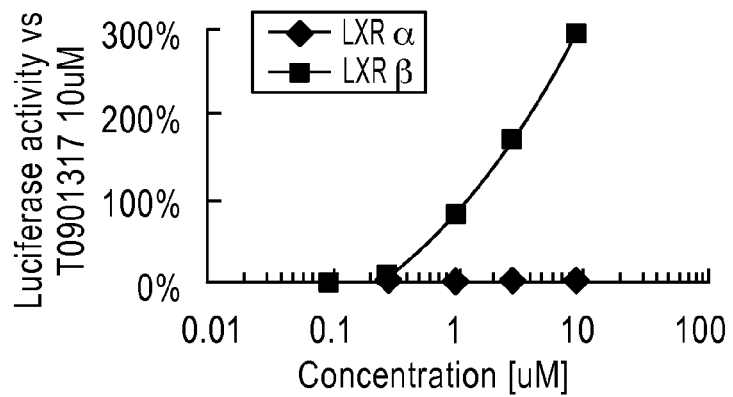
Fig.3i Example 196

Example 199

Example 203

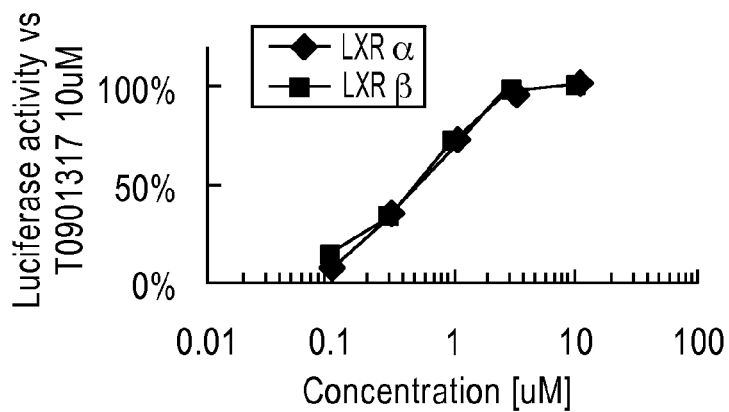
Fig.4a TO901317
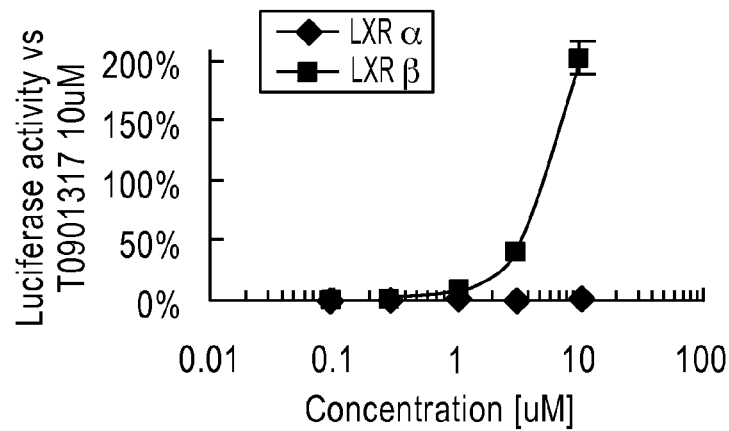
Fig.4b Example 204
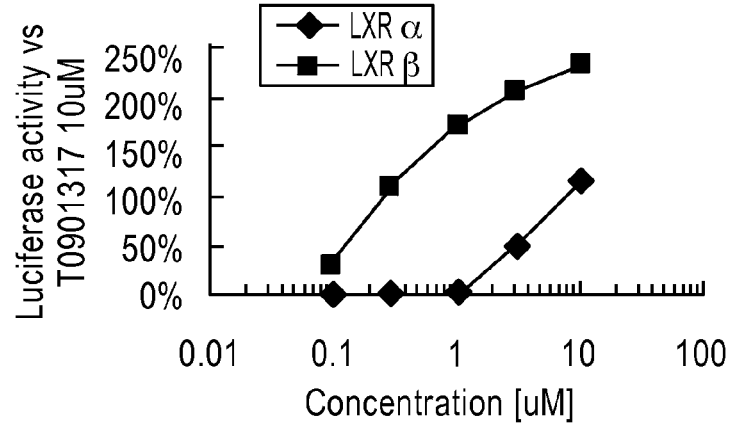
Fig.4c Example 205

Example 206

Example 210

Example 212

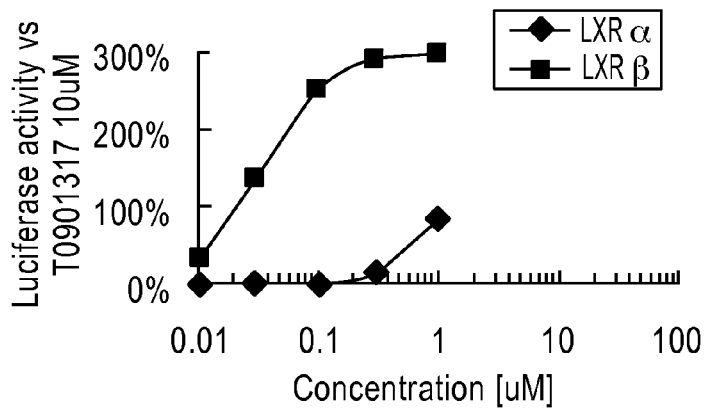
Fig.4g  Example 214
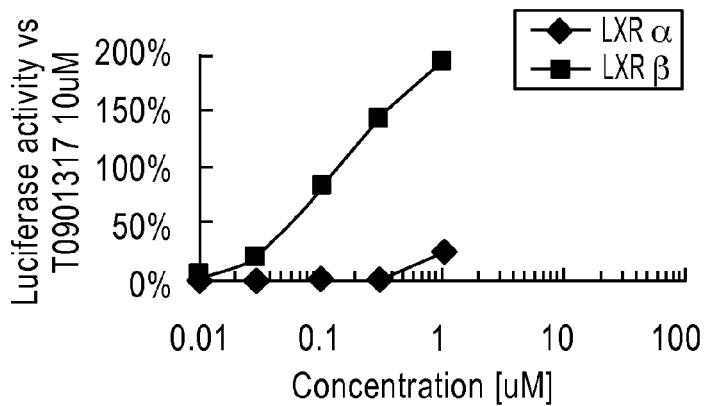
Fig.4h  Example 216
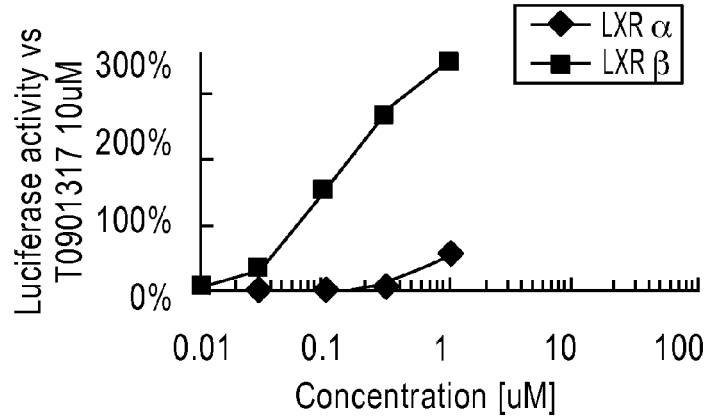
Fig.4i  Example 222

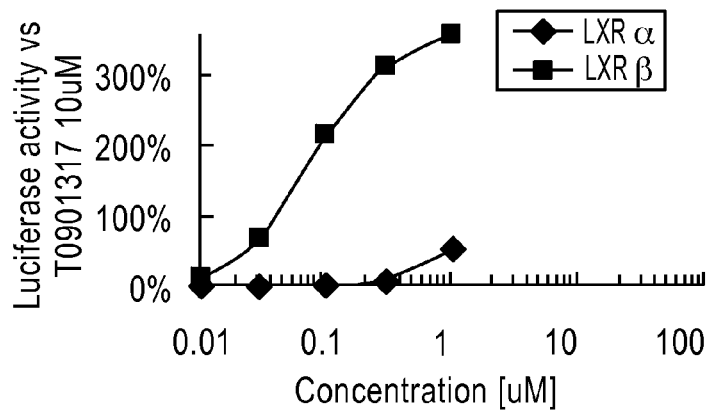
Fig.4j Example 224
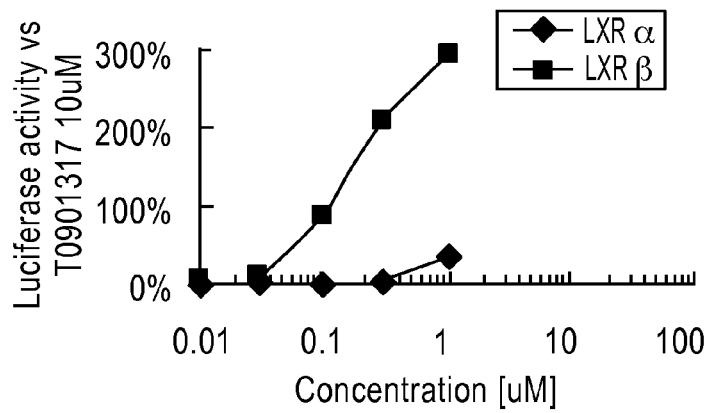
Fig.4k Example 227
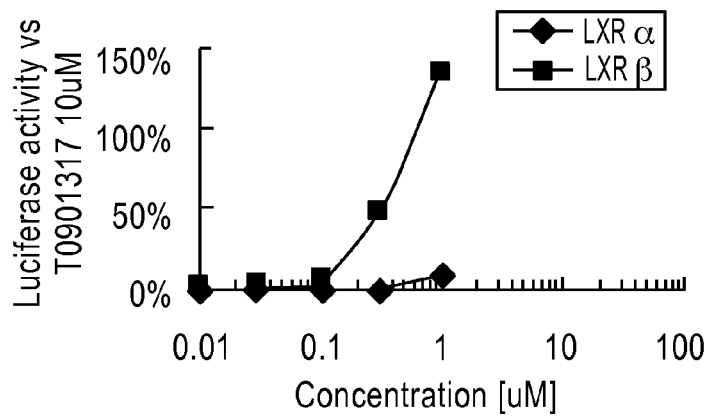
Fig.4l Example 229

CARBINOL DERIVATIVES HAVING CYCLIC LINKER

TECHNICAL FIELD

The present invention relates to a substituted carbinol compound having a cyclic linker, which is a novel LXRβ agonist useful as a preventative and/or therapeutic agent for atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.

BACKGROUND ART

Liver X receptor (LXR) is a nuclear receptor that was cloned as an orphan receptor whose ligand and function were both unknown. Subsequent study reported that some oxysterols including 22-R-hydroxycholesterol act as a ligand for LXR (non-patent documents 1 to 3). LXR, together with retinoid X receptor (RXR) which is another nuclear receptor, forms a heterodimer to ligand-dependently control the transcription of a target gene.

As mammal LXR sub-types, two types of LXR genes (α and β) are known to exist. LXRα and LXRβ recognize the same sequence on a DNA and activate the transcription of a neighboring target gene. However, the expression-distributions of the two genes differ greatly. LXRα is specifically expressed on cholesterol metabolism-related tissues such as the liver, small intestines, or adipose tissues, whereas LXRβ is expressed ubiquitously on almost all tissues that have been examined (non-patent documents 4 and 5).

Many of the group of genes identified as target genes of LXRs are genes (ApoE, CETP, and LPL) related to a reverse cholesterol transport (RCT), including ABC transporters (ABCA1, ABCG1, ABCG5, and ABCG8). Therefore, it is expected that the activation of LXRs elevates the expression of these genes and activates reverse cholesterol transport pathways, thereby increases cholesterol efflux from the periphery and then increases HDL cholesterols and also lowers cholesterol content at an arteriosclerosis-affected region (non-patent document 6).

Further, LXRs are reported to play an important role via NF-κB suppression, in the expression control of inflammatory mediators such as NO-synthase, cyclooxygenase-2 (COX-2), and interleukin-6 (IL-6) (non-patent document 7). It is well known that the inflammation is very important at an arteriosclerosis-affected region, and it is expected that LXR ligands or LXR agonists will prevent arteriosclerosis exacerbation due to the expression of macrophage-inflammatory mediators at the affected region (non-patent documents 6 and 8).

Further, LXR α- and LXR β-deficient mice fed on high-cholesterol diet have been reported to show symptoms such as fatty liver and elevated LDL-cholesterol level as well as reduced HDL-cholesterol level in the blood as compared to the case of normal mice fed on high-cholesterol diet (non-patent documents 9 and 10). More specifically, it is strongly suggested that LXRs play an important role in cholesterol metabolism. Moreover, by analyzing the symptoms of arteriosclerosis mouse models having normal LXRα and LXRβ functions in the liver, small intestines and the like but lacking LXRα and LXR in macrophages, it has been revealed that LXRα and LXRβ activities in macrophages strongly affect the incidence of arteriosclerosis (non-patent document 11). Therefore, the activation of reverse cholesterol transport through the LXR activation especially in macrophages is considered to be important for the treatment of arteriosclerosis.

As for the applications, LXR regulators or LXR agonists disclosed in the prior art documents are reported to have been applied to diseases such as hypercholesterolemia and atherosclerosis (patent documents 1 and 2). Further, LDL-receptor-deficient mice loaded with high-fat food, and administered with LXR ligand, have been reported to show an elevated HDL cholesterol level, lowered VLDL and LDL cholesterol levels, and reduced area of arteriosclerosis-affected region (non-patent document 12).

Further, LXR ligands or LXR agonists are expected to control sugar metabolism in the liver and adipose tissues, and thus to improve diabetes (non-patent documents 6 and 8). Recently, it has been reported that an administration of LXR agonist improved insulin sensitivity and blood glucose level in diabetes animal models (non-patent documents 13 and 14). Moreover, it is indicated as a potential therapeutic drug for Alzheimer's disease, inflammatory diseases, or skin diseases (non-patent document 15).

LXR agonists, however, are reported to increase LDL cholesterol in animal species having cholesteryl ester transfer proteins (CETP) (non-patent document 16). Further, in animal experiments, it has been observed that LXR activation in the liver by the LXR agonist administration enhances fatty-acid and triglyceride syntheses through the transcriptional activation of enzymes that are important for fatty-acid synthesis, for example, fatty-acid synthase (FAS) or stearyl-CoA fatty-acid desaturase (SCD-1) (non-patent document 17). Meanwhile, nothing is disclosed in the prior art documents on LXR α/β selectivity in relation to the disclosed LXR regulators, LXR ligands, LXR agonists and the like.

Therefore, there have been demands for an ideal synthetic LXR-binding compound without a dyslipidemia-exacerbating effect which acts through an elevated fatty-acid and triglyceride syntheses, while maintaining the agonist activity for reverse cholesterol transport activation by ABC transporters and for increased cholesterol-efflux from macrophages. As one approach to solve the problem, a compound that selectively activates LXR is considered to have an ideal profile that is expected to suppress the activation of LXRβ highly expressed on the liver, as compared to the LXR regulators disclosed in the prior art documents, and to suppress the concerned side-effects of fatty-acid and triglyceride synthesis elevations (non-patent documents 6, 8, 15, 18, and 19). However, because ligand-binding sites of LXRα and LXRβ are highly homologous, it is considered that the creation of a compound that acts differently on LXRα and LXRβ is not easy.

In fact, compounds having an LXR-agonist effect have been reported, such as a benzofuran-5-acetic acid derivative (patent document 3), 2-aminoquinazolin-4-one derivative (patent document 4), tetrahydroquinoline derivative (non-patent document 5), tetrahydrocarbazol derivative (patent document 6), isoquinoline derivative (patent document 7), and naphthalene derivative (patent document 8), GW3965 which is an aromatic aminoalcohol derivative (Example 16 described in patent document 9), and T0901317 which is a benzenesulfonamide derivative (Example 12 described in patent document 10), but no agonist with high LXRβ selectivity has been reported to date and a compound with high LXRβ selectivity has been awaited.

Meanwhile, an LXR agonist having a quinoline skeleton has been reported (patent document 11, non-patent documents 20 to 22). For example, WAY-254011 (compound 4 of non-patent document 22) which is a quinoline derivative has been reported to have LXRβ-selective binding affinity (α/β ratio is 1 to 5). Non-patent document 22 further reports on a compound showing an α/β ratio of up to 1 to 50 in terms of binding-affinity. However, as for an agonist effect which was measured by Gal 4 transactivation activity, the highest selectivity confirmed was an α/β ratio of merely up to about 1 to 2.7. This shows that the effect of the compound on LXR for expressing the target gene is weak despite the selective binding of the compound to LXRβ. Therefore, there are still strong demands for a compound having an effect of expressing a target gene in an LXRβ selective manner.

[Patent Document 1] Published Japanese translation of PCT international publication No. 2002-539155
[Patent Document 2] Published Japanese translation of PCT international publication No. 2004-509161
[Patent Document 3] WO2003/82192
[Patent Document 4] WO2004/24161
[Patent Document 5] WO2004/72046
[Patent Document 6] U.S. Patent publication No. 2005/215577
[Patent Document 7] WO2004/58717
[Patent Document 8] WO2005/23188
[Patent Document 9] WO2002/24632
[Patent Document 10] WO2000/54759
[Patent Document 11] WO2005/58834
[Non-patent Document 1] Janowski et al., Nature, 383, pp. 728-731, 1996
[Non-patent Document 2] Lehmann et al., J. Biol. Chem., 272, pp. 3137-3140, 1997
[Non-patent Document 3] Fu et al., J. Biol. Chem., 276, pp. 38378-38387, 2001
[Non-patent Document 4] Auboeuf et al., Diabetes, 46, pp. 1319-1327, 1997
[Non-patent Document 5] Lu et al., J. Biol. Chem., 276, pp. 37735-37738, 2001
[Non-patent Document 6] Zelcer et al., J. Clin. Invest, 116, pp. 607-614, 2006
[Non-patent Document 7]: Joseph et al., Nat. Med., 9, pp. 213-219, 2003
[Non-patent Document 8] Geyeregger et al., Cell. Mol. Life. Sci. 63, pp. 524-539, 2006
[Non-patent Document 9] Peet et al., Cell, 93, pp. 693-704, 1998
[Non-patent Document 10] Alberti et al., J. Clin. Invest., 107, pp. 565-573, 2001
[Non-patent Document 11] Tangirala et al., Proc. Natl. Acad. Sci. USA, 99, pp. 11896-11901, 2002
[Non-patent Document 12] Terasaka et al., FEBS Lett., 536, pp. 6-11, 2003
[Non-patent Document 13] Cao et al., J. Biol. Chem., 278, pp. 1131-1136, 2003
[Non-patent Document 14] Laffitte et al., Proc. Natl. Acad. Sci. USA, 100, pp. 5419-5424, 2003
[Non-patent Document 15] Lala et al., Curr. Opin. Investig. Drugs, 6, pp. 934-943, 2005
[Non-patent Document 16]: Groot et al., J. Lipid Res., 46, pp. 2182-2191, 2005
[Non-patent Document 17] Schultz et al., Genes Dev., 14, pp. 2831-2838, 2000
[Non-patent Document 18]: Lund et al., Arterioscler. Thromb. Vasc. Biol., 23, pp. 1169-1177, 2003
[Non-patent Document 19] Bradley et al., Drug Discov. Today Ther. Strateg. 2, pp. 97-103, 2005
[Non-patent Document 20] Hu et al., J. Med. Chem., 49, pp. 6151-6154, 2006
[Non-patent Document 21] Hu et al., Bioorg. Med. Chem., 15, pp. 3321-3333, 2007
[Non-patent Document 22] Hu et al., Bioorg. Med. Chem. Lett., 18, pp. 54-59, 2008

DISCLOSURE OF THE INVENTION

Thus, the object of the present invention is to prepare a novel compound that exhibits an agonist activity with high LXRβ selectivity.

The present inventors made a keen study to achieve the above object and consequently, found that a compound having a structure wherein a carbinol skeleton and an imidazolidine-2,4-dione skeleton are bound via a cyclic linker, that is, a compound represented by general formula (I) described hereinbelow has an agonist activity with high LXRβ selectivity, and thus completed the present invention.

More specifically, the present invention relates to
[1] a carbinol compound represented by the following general formula (I) or salt thereof, or their solvate:

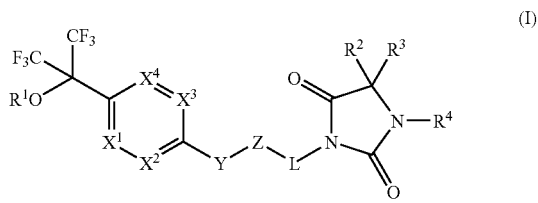

[wherein $R^1$ represents a hydrogen atom, $C_{1-8}$ alkyl group, $C_{1-8}$ alkoxy $C_{1-8}$ alkyl group or $C_{1-8}$ acyl group; $R^2$ and $R^3$ each independently represents a hydrogen atom, $C_{1-8}$ alkyl group, $C_{3-8}$ cycloalkyl group, $C_{6-10}$ aryl group, or 5- to 11-membered heterocyclic group, wherein the $C_{6-10}$ aryl and 5- to 11-membered heterocycle may be substituted with 1 to 3 same or different substituents selected from the following group A, or $R^2$ and $R^3$ may together form a 5- to 7-membered carbocycle; $R^4$ represents a hydrogen atom, $C_{1-8}$ alkyl group, halo $C_{1-8}$ alkyl group, or $C_{3-8}$ cycloalkyl group; $X^1$, $X^2$, $X^3$, and $X^4$ each independently represents an N or $CR^5$; $R^5$ represents a hydrogen atom, halogen atom, $C_{1-8}$ alkyl group, $C_{3-8}$ cycloalkyl group, $C_{2-8}$ alkenyl group, $C_{3-8}$ cycloalkenyl group, $C_{3-8}$ cycloalkenyl $C_{1-8}$ alkyl group, $C_{1-8}$ alkoxy group, $C_{6-10}$ aryl group, $C_{6-10}$ aryl $C_{1-8}$ alkyl group, $C_{6-10}$ aryl $C_{2-6}$ alkenyl group, $C_{1-8}$ acyl group, $C_{6-10}$ arylcarbonyl group, $C_{1-8}$ alkylthio group, $C_{1-8}$ alkylsulfinyl group, $C_{1-8}$ alkylsulfonyl group, $C_{6-10}$ arylsulfonyl group, nitro group, amino group, mono $C_{1-8}$ alkylamino group, di $C_{1-3}$ alkylamino group, $C_{3-8}$ cycloalkyl $C_{1-8}$ alkyl group, $C_{3-8}$ cycloalkyl $C_{2-8}$ alkenyl group, $C_{3-8}$ cycloalkyl $C_{2-8}$ alkynyl group, halo $C_{1-8}$ alkyl group, or cyano group, wherein the $C_{6-10}$ aryl may be substituted with 1 to 3 same or different substituents selected from the following group A; Y represents a single bond or a —O—, —S—, —SO—, or —SO$_2$—; Z represents a $C_{6-10}$ aryl chain or 5- to 11-membered heteroaryl chain, wherein the $C_{6-10}$ aryl and 5- to 11-membered heteroaryl may be substituted with 1 to 3 same or different substituents selected from the following group A; L represents a $C_{1-8}$ alkyl chain that may be substituted with an oxo group, —O— ($C_{1-8}$ alkyl chain) or $C_{2-8}$ alkenyl chain]

<Group A> halogen atom, $C_{1-8}$ alkyl group, halo $C_{1-8}$ alkyl group, $C_{2-8}$ alkenyl group, $C_{2-8}$ alkynyl group, $C_{3-8}$ cycloalkyl group, cyano group, nitro group, hydroxy group, amino group, mono $C_{1-8}$ alkylamino group, di $C_{1-8}$ alkylamino group, $C_{1-8}$ alkoxy group, $C_{3-8}$ cycloalkyloxy group, halo $C_{1-8}$ alkoxy group, $C_{1-8}$ acyl group, carboxyl group, $C_{1-8}$ acyloxy group, $C_{1-8}$ alkoxycarbonyl group, carbamoyl group, $C_{6-10}$ aryl group, 5- to 11-membered heteroaryl group, $C_{6-10}$ aryl $C_{1-8}$ alkoxy group that may be substituted with 1 to 3 $C_{1-8}$ alkyl groups, $C_{1-8}$ alkylthio group, $C_{3-8}$ cycloalkylthio group, $C_{1-8}$ alkylsulfinyl group, $C_{1-8}$ alkylsulfonyl group, $C_{6-10}$ arylthio group, $C_{6-10}$ arylsulfinyl group, and $C_{6-10}$ arylsulfonyl group];

[2] a medicine containing the carbinol derivative or salt thereof, or their solvate according to [1] as an active ingredient;

[3] the medicine according to [2], which is a preventative and/or therapeutic agent for atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease;

[4] an LXR regulator containing the carbinol derivative or salt thereof, or their solvate according to [1] as an active ingredient;

[5] a pharmaceutical composition consisting of the carbinol derivative or salt thereof, or their solvate according to [1] and a pharmaceutically acceptable carrier;

[6] a method for preventing and/or treating atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease, which method comprises administering an effective amount of the carbinol derivative or salt thereof, or their solvate according to [1] to a patient in need of a treatment; and

[7] use of the carbinol derivative or salt thereof, or their solvate according to [1] for a production of a formulation for preventing and/or treating atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease.

Effect of the Invention

The carbinol derivative represented by general formula (I) of the present invention has an LXRβ agonist effect and is useful as a preventative and/or therapeutic agent or the like for atherosclerosis, arteriosclerosis such as those resulting from diabetes; dyslipidemia; hypercholesterolemia; lipid-related diseases; inflammatory diseases caused by inflammatory cytokines, such as rheumatoid arthritis, osteoarthritis, allergic diseases, asthma, sepsis, psoriasis, and osteoporosis; autoimmune diseases such as systemic erythematosus, ulcerative colitis, and Crohn's disease; cardiovascular diseases such as ischemic cardiac disease and heart failure; cerebrovascular diseases; kidney diseases; diabetes; diabetes complications such as retinopathy, nephropathy, nerve disease, and coronary arterial disease; skin diseases such as allergic skin disease; obesity; nephritis; hepatitis; cancer; or Alzheimer's disease, and more preferably, as a preventative and/or therapeutic agent or the like for atherosclerosis, arteriosclerosis such as those resulting from diabetes, dyslipidemia, hypercholesterolemia, lipid-related diseases, inflammatory diseases that are caused by inflammatory cytokines, skin diseases such as allergic skin diseases, diabetes, or Alzheimer's disease.

BRIEF DESCRIPTION OF THE DRAWINGS

FIGS. 1a to 1k shows the luciferase activity results as activity values (% eff) at the respective concentration of the test compound Examples 1, 5, 28, 40, 45, 62, 67, 69, 80 and 92, relative to the T0901317 luminescence intensity of 100 at 10 μM.

FIGS. 2a to 2k shows the luciferase activity results as activity values (% eff) at the respective concentration of the test compound Examples 119, 121, 123, 126, 127, 129, 130, 131, 133 and 162, relative to the T0901317 luminescence intensity of 100 at 10 μM.

FIGS. 3a to 3k shows the luciferase activity results as activity values (% eff) at the respective concentration of the test compound Examples 164, 165, 171, 172, 180, 185, 195, 196, 199 and 203, relative to the T0901317 luminescence intensity of 100 at 10 μM.

FIGS. 4a to 4l shows the luciferase activity results as activity values (% eff) at the respective concentration of the test compound Examples 204, 205, 206, 210, 212, 214, 216, 222, 224, 227 and 229, relative to the T0901317 luminescence intensity of 100 at 10 μM.

DETAILED DESCRIPTION OF THE INVENTION

Figure 1D:
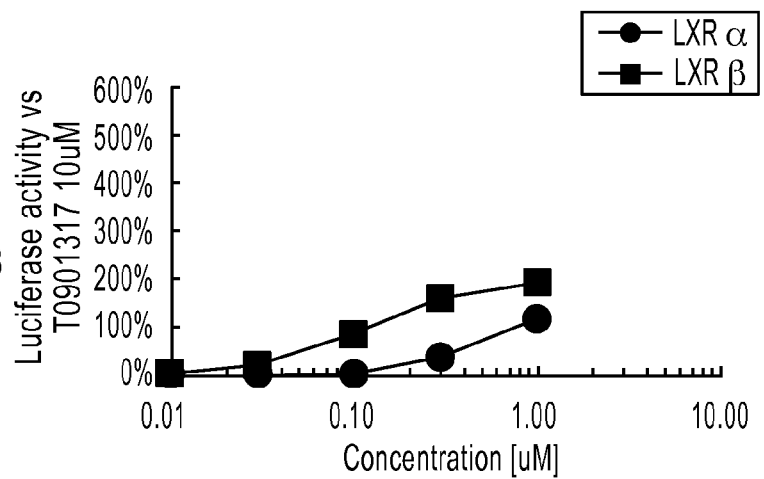
Figure 1E:
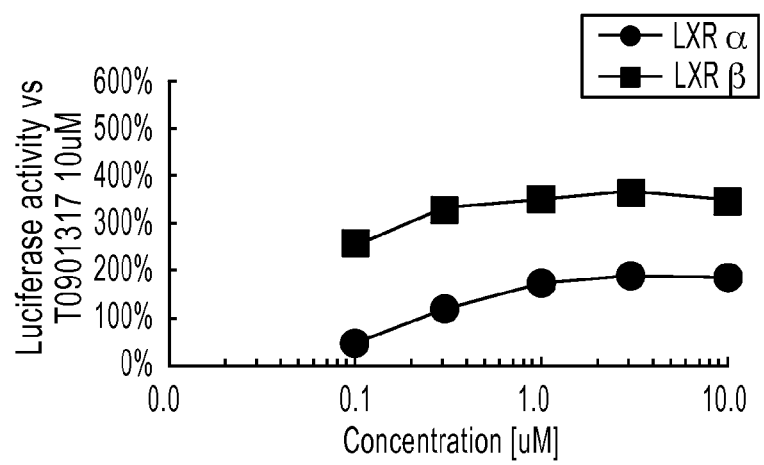
Figure 1F:
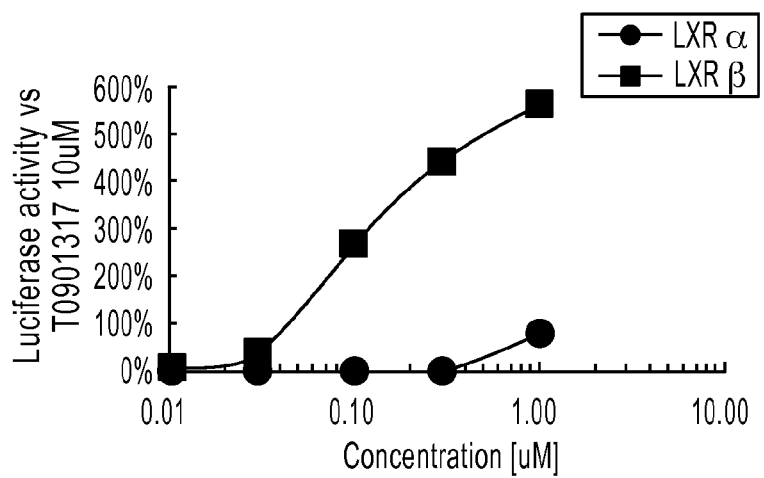
Figure 2G:
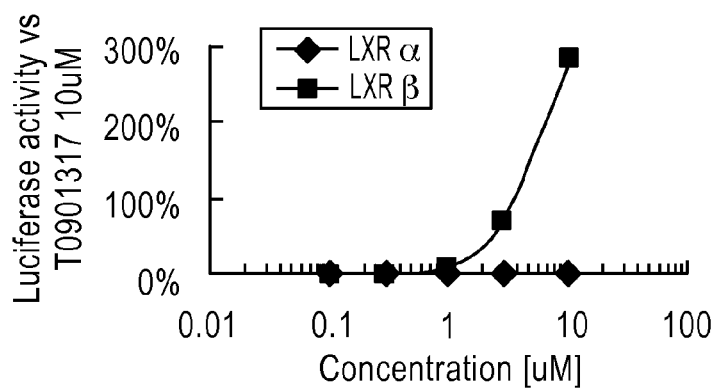
Figure 2H:
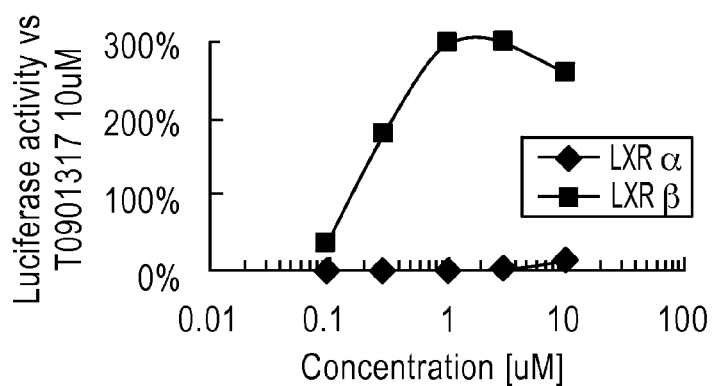
Figure 2I:
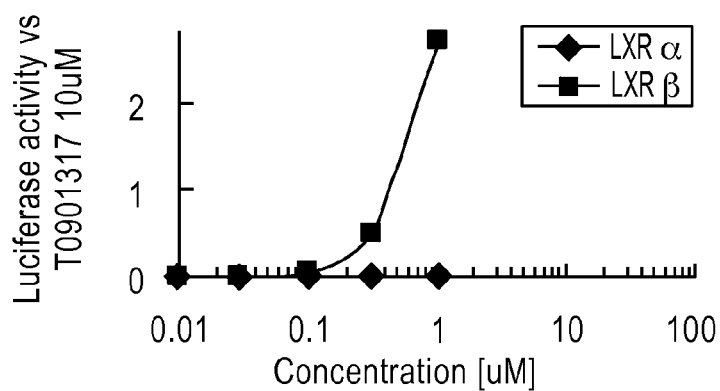
Figure 2J:
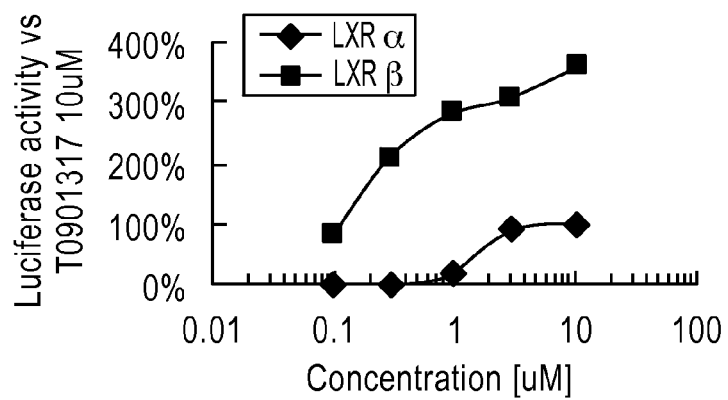
Figure 2K:
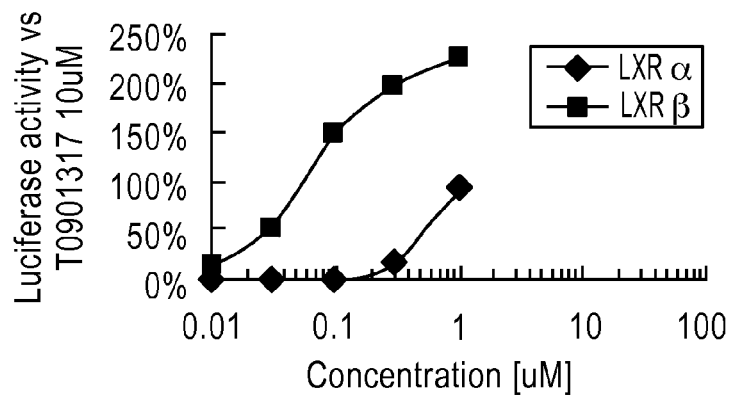
Figure 3D:
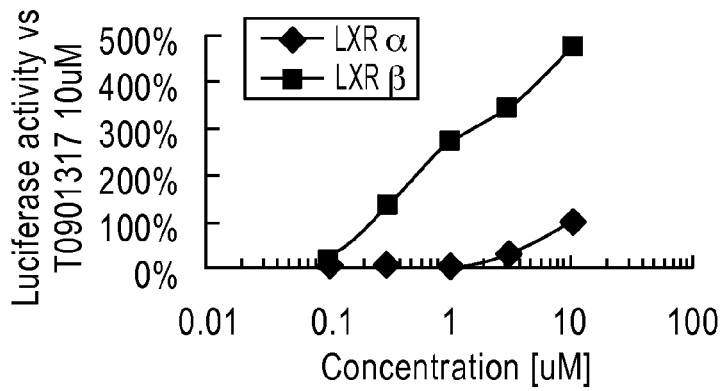
Figure 3E:
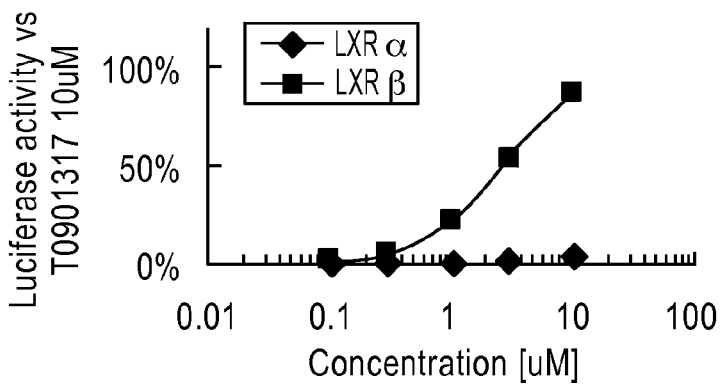
Figure 3F:
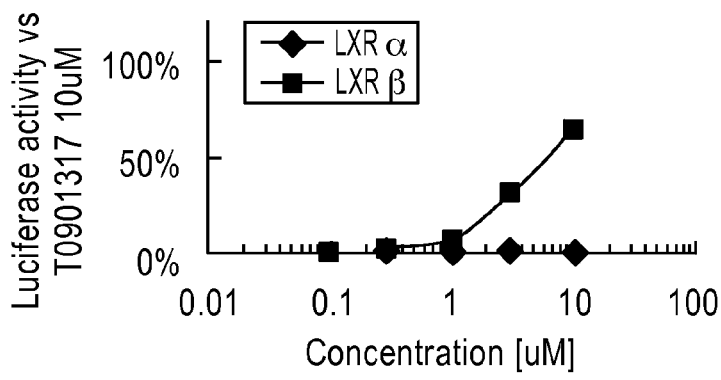
Figure 3J:
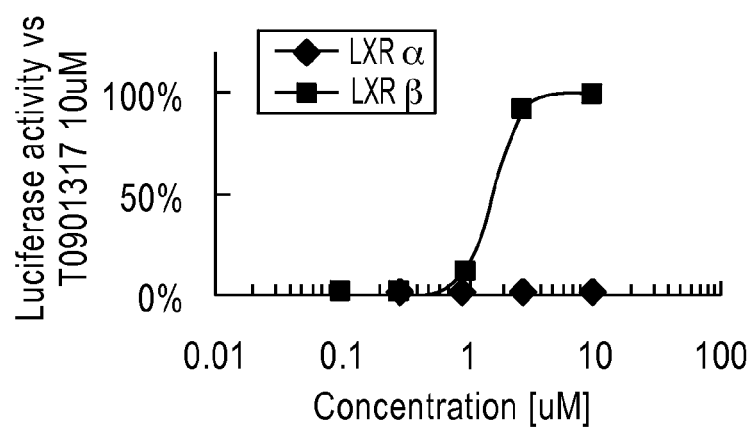
Figure 3K:
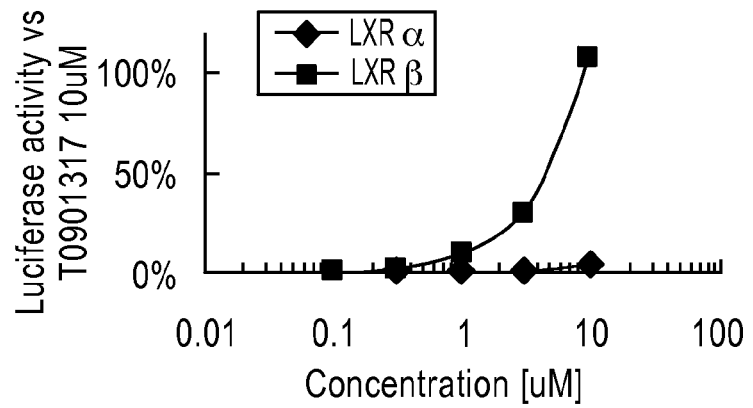
Figure 4D:
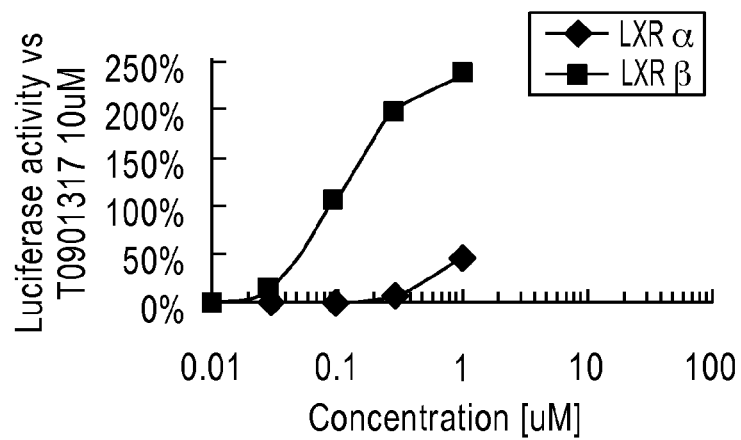
Figure 4E:
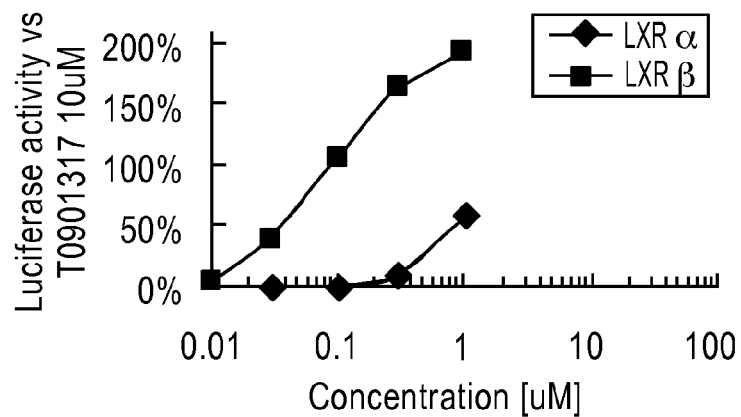
Figure 4F:
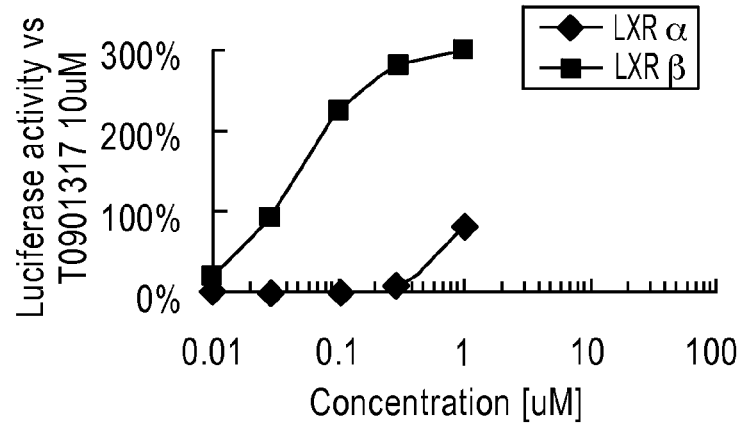

The terms in the present invention are defined as follows.

In the present invention, examples of a "halogen" atom in the halogen atom, halo $C_{1-8}$ alkyl group, or halo $C_{1-8}$ alkoxy group include a fluorine atom, chlorine atom, bromine atom, and iodine atom.

In the present invention, a "$C_{1-8}$ alkyl group" means a straight-chained or branched-chained alkyl group with 1 to 8 carbons, and the examples include a methyl group, ethyl group, n-propyl group, isopropyl group, n-butyl group, isobutyl group, t-butyl group, n-pentyl group, isopentyl group, neopentyl group, 2-methylbutyl group, 2,2-dimethylpropyl group, n-hexyl group, isohexyl group, n-heptyl group, and n-octyl group.

In the present invention, a "halo $C_{1-8}$ alkyl group" means a group wherein one or more, preferably, 1 to 9 halogen atoms are bound to the $C_{1-8}$ alkyl group and the examples include trifluoromethyl group, 2-fluoroethyl group, 2-chloroethyl group, 2-bromoethyl group, 3-fluoropropyl group, 3-chloropropyl group, 4-fluorobutyl group, 4-chlorobutyl group, 2,2,2-trifluoroethyl group, 3,3,3-trifluoropropyl group, pentafluoroethyl group, and 2,2,2-trifluoro-1-trifluoromethylethyl group.

In the present invention, a "$C_{2-8}$ alkenyl group" means a straight-chained or branched-chained alkenyl group with 2 to 8 carbons, having a carbon-carbon double bond at any one or more sites on the alkyl chain. The examples include an ethenyl group, prop-1-en-1-yl group, prop-2-en-1-yl group, prop-1-en-2-yl group, but-1-en-1-yl group, but-2-en-1-yl group, but-3-en-1-yl group, but-1-en-2-yl group, but-3-en-2-yl group, pent-1-en-1-yl group, pent-4-en-1-yl group, pent-1-en-2-yl group, pent-4-en-2-yl group, 3-methyl-but-1-en-1-yl group, hex-1-en-1-yl group, hex-5-en-1-yl group, hept-1-en-1-yl group, hept-6-en-1-yl group, oct-1-en-1-yl group, and oct-7-en-1-yl group.

In the present invention, a "$C_{2-8}$ alkynyl group" means a straight-chained or branched-chained alkynyl group with 2 to 8 carbons, having a carbon-carbon triple bond at any one or more sites on the alkyl chain. The examples include an ethynyl group, prop-1-yn-1-yl group, prop-2-yn-1-yl group, but-1-yn-1-yl group, but-3-yn-1-yl group, 1-methylprop-2-yn-1-yl group, pent-1-yn-1-yl group, pent-4-yn-1-yl group, hex-1-yn-1-yl group, and hex-5-yn-1-yl group.

Specific examples of a "$C_{1-8}$ alkoxy group" in the present invention include a methoxy group, ethoxy group, n-propoxy group, 1-methylethoxy group, n-butoxy group, isobutoxy group, sec-butoxy group, tert-butoxy group, n-pentoxy group, isopentoxy group, neopentoxy group, 1-methylbutoxy group, 1-ethylpropoxy group, n-hexyloxy group, isohexyloxy group, 3-methylpentoxy group, 2-methylpentoxy group, 1-methylpentoxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 1-ethylbutoxy group, and 2-ethylbutoxy group. Further, a "$C_{1-8}$ alkoxy $C_{1-8}$ alkyl group" refers to a group wherein a "$C_{1-8}$ alkoxy group" is bound to the above "$C_{1-8}$ alkyl group", and the examples include a methoxymethyl group, methoxyethyl group, ethoxymethyl group, and ethoxyethyl group.

Further, specific examples of a "$C_{3-8}$ cycloalkyloxy group" of the present invention include a cyclopropyloxy group, cyclobutyloxy group, cyclopentyloxy group, and cyclohexyloxy group.

In the present invention, a "halo $C_{1-8}$ alkoxy group" means a group wherein the above halo $C_{1-8}$ alkyl group is bound to an oxygen atom, and the examples include a trifluoromethoxy group, 2-fluoroethoxy group, 2-chloroethoxy group, 2-bromoethoxy group, 3-fluoropropoxy group, 3-chloropropoxy group, 4-fluorobutoxy group, 4-chlorobutoxy group, 2,2,2-trifluoroethoxy group, 3,3,3-trifluoropropoxy group, pentafluoroethoxy group, and 2,2,2-trifluoro-1-trifluoromethylethoxy group.

In the present invention, examples of a "$C_{1-8}$ acyl group" include an alkylcarbonyl group such as a formyl group, acetyl group, propionyl group, butyryl group, isobutyryl group, valeryl group, isovaleryl group, and pivaloyl group; an alkenylcarbonyl group such as an acryloyl group; and an arylcarbonyl group such as a benzoyl group. Further, examples of a "$C_{1-8}$ acyloxy group" include an alkylcarbonyloxy group such as a formyloxy group, acetyloxy group, propionyloxy group, butyryloxy group, isobutyryloxy group, valeryloxy group, isovaleryloxy group, and pivaloyloxy group; an alkenylcarbonyloxy group such as an acryloyloxy group; and an arylcarbonyloxy group such as a benzoyloxy group.

In the present invention, a "$C_{6-10}$ aryl group" means a monocyclic or polycyclic aryl group with 6 to 10 carbons. Here, a polycyclic aryl group encompasses partially saturated groups in addition to fully unsaturated groups. The examples include a phenyl group, naphthyl group, azulenyl group, indenyl group, indanyl group, and tetralinyl group.

In the present invention, examples of a "$C_{6-10}$ arylcarbonyl group" include a benzoyl group and naphthoyl group.

In the present invention, a "$C_{6-10}$ aryl $C_{1-8}$ alkyl group" means a group wherein the $C_{6-10}$ aryl group mentioned hereinbelow and the abovementioned $C_{1-8}$ alkyl group are bound. The examples include a benzyl group, phenethyl group, 3-phenyl-n-propyl group, 4-phenyl-n-butyl group, 5-phenyl-n-pentyl group, 8-phenyl-n-octyl group, and naphthylmethyl group.

In the present invention, a "$C_{3-8}$ cycloalkyl group" means a cyclic alkyl group with 3 to 8 carbons. The examples include a cyclopropyl group, cyclobutyl group, cyclopentyl group, cyclohexyl group, cycloheptyl group, and cyclooctyl group. Preferably, the "$C_{3-8}$ cycloalkyl group" is a "$C_{3-6}$ cycloalkyl group" with 3 to 6 carbons.

In the present invention, a "5- to 11-membered heterocyclic group" means a 5- to 7-membered aromatic heterocycle, saturated heterocycle, unsaturated heterocycle or a condensed heterocycle made by a condensation of the above heterocycles and a benzene ring or a pyridine ring, wherein the above heterocycles contain 1 to 4 heteroatoms selected from a nitrogen atom, oxygen atom and sulfur atom in addition to a carbon atom, as atoms constituting the ring. The examples include a 2-furyl group, 3-furyl group, 2-thienyl group, 3-thienyl group, pyrrol-1-yl group, pyrrol-2-yl group, pyrrol-3-yl group, pyridin-2-yl group, pyridin-3-yl group, pyridin-4-yl group, pyrazin-2-yl group, pyrazin-3-yl group, pyrimidin-2-yl group, pyrimidin-4-yl group, pyrimidin-5-yl group, pyrimidin-6-yl group, pyridazin-3-yl group, pyridazin-4-yl group, 1,3-benzodioxol-4-yl group, 1,3-benzodioxol-5-yl group, 1,4-benzodioxin-5-yl group, 1,4-benzodioxin-6-yl group, 3,4-dihydro-2H-1,5-benzodioxepin-6-yl group, 3,4-dihydro-2H-1,5-benzodioxepin-7-yl group, 2,3-dihydrobenzofuran-4-yl group, 2,3-dihydrobenzofuran-5-yl group, 2,3-dihydrobenzofuran-6-yl group, 2,3-dihydrobenzofuran-7-yl group, benzofuran-2-yl group, benzofuran-3-yl group, benzofuran-4-yl group, benzofuran-5-yl group, benzofuran-6-yl group, benzofuran-7-yl group, benzothiophen-2-yl group, benzothiophen-3-yl group, benzothiophen-4-yl group, benzothiophen-5-yl group, benzothiophen-6-yl group, benzothiophen-7-yl group, quinoxalin-2-yl group, quinoxalin-5-yl group, quinoxalin-6-yl group, indol-1-yl group, indol-2-yl group, indol-3-yl group, indol-4-yl group, indol-5-yl group, indol-6-yl group, indol-7-yl group, isoindol-1-yl group, isoindol-2-yl group, isoindol-4-yl group, isoindol-5-yl group, isoindol-6-yl group, isoindol-7-yl group, isobenzofuran-1-yl group, isobenzofuran-4-yl group, isobenzofuran-5-yl group, isobenzofuran-6-yl group, isobenzofuran-7-yl group, chromen-2-yl group, chromen-3-yl group, chromen-4-yl group, chromen-5-yl group, chromen-6-yl group, chromen-7-yl group, chromen-8-yl group, imidazol-1-yl group, imidazol-2-yl group, imidazol-4-yl group, imidazol-5-yl group, pyrazol-1-yl group, pyrazol-3-yl group, pyrazol-4-yl group, pyrazol-5-yl group, thiazol-2-yl group, thiazol-4-yl group, thiazol-5-yl group, oxazol-2-yl group, oxazol-4-yl group, oxazol-5-yl group, isoxazol-3-yl group, isoxazol-4-yl group, isoxazol-5-yl group, pyrrolidin-2-yl group, pyrrolidin-3-yl group, benzoimidazol-1-yl group, benzoimidazol-2-yl group, benzoimidazol-4-yl group, benzoimidazol-5-yl group, benzothiazol-2-yl group, benzothiazol-4-yl group, benzothiazol-5-yl group, benzoxazol-2-yl group, benzoxazol-4-yl group, benzoxazol-5-yl group, quinolin-2-yl group, quinolin-3-yl group, quinolin-4-yl group, quinolin-5-yl group, quinolin-6-yl group, quinolin-7-yl group, quinolin-8-yl group, isoquinolin-1-yl group, isoquinolin-3-yl group, isoquinolin-4-yl group, isoquinolin-5-yl group, isoquinolin-6-yl group, isoquinolin-7-yl group, isoquinolin-8-yl group, 1,3,4-thiadiazol-2-yl group, morpholino group, 1,2,3-triazol-1-yl group, 1,2,3-triazol-4-yl group, 1,2,3-triazol-5-yl group, 1,2,4-triazol-1-yl group, 1,2,4-triazol-3-yl group, 1,2,4-triazol-5-yl group, tetrazol-1-yl group, tetrazol-2-yl group, indolin-4-yl group, indolin-5-yl group, indolin-6-yl group, indolin-7-yl group, 1,2,3,4-tetrahydroquinolin-5-yl group, 1,2,3,4-tetrahydroquinolin-6-yl group, 1,2,3,4-tetrahydroquinolin-7-yl group, 1,2,3,4-tetrahydroquinolin-8-yl group, 1,2,3,4-tetrahydroisoquinolin-5-yl group, 1,2,3,4-tetrahydroisoquinolin-6-yl group, 1,2,3,4-tetrahydroisoquinolin-7-yl group, and 1,2,3,4-tetrahydroisoquinolin-8-yl group.

Specific examples of a "mono $C_{1-8}$ alkylamino group" of the present invention include a methylamino group, ethylamino group, n-propylamino group, isopropylamino group, n-butylamino group, sec-butylamino group, tert-butylamino group, n-pentylamino group, isopentylamino group, neopentylamino group, 1-methylbutylamino group, 1-ethylpropylamino group, n-hexylamino group, isohexylamino group, 4-methylpentylamino group, 3-methylpentylamino group, 2-methylpentylamino group, 1-methylpentylamino group, 3,3-dimethylbutylamino group, 2,2-dimethylbutylamino group, 1,1-dimethylbutylamino group, 1,2-dimethylbutylamino group, 1,3-dimethylbutylamino group, 2,3-dimethylbutylamino group, 1-ethylbutylamino group, and 2-ethylbutylamino group.

Specific examples of a "di $C_{1-8}$ alkylamino group" of the present invention include a dimethylamino group, methylethylamino group, diethylamino group, methyl-n-propylamino group, ethyl-n-propylamino group, di-n-propylamino group, methyl isopropylamino group, ethyl isopropylamino group, diisopropylamino group, methyl-n-butylamino group, ethyl-n-butylamino group, n-propyl-n-butylamino group, di-n-butylamino group, di-sec-butylamino group, di-tert-butylamino group, dipentylamino group, and dihexylamino group.

Specific examples of a "$C_{1-8}$ alkylthio group" of the present invention include a methylthio group, ethylthio group, n-propylthio group, isopropylthio group, n-butylthio group, isobutylthio group, sec-butylthio group, tert-butylthio group, n-pentylthio group, isopentylthio group, neopentylthio group, 1-methylbutylthio group, 1-ethylpropylthio group, n-hexylthio group, isohexylthio group, 4-methylpentylthio group, 3-methylpentylthio group, 2-methylpentylthio group, 1-methylpentylthio group, 3,3-dimethylbutylthio group, 2,2-dimethylbutylthio group, 1,1-dimethylbutylthio group, 1,2-dimethylbutylthio group, 1,3-dimethylbutylthio group, 2,3-dimethylbutylthio group, 1-ethylbutylthio group, 2-ethylbutylthio group, trifluoromethylthio group, and trichloromethylthio group.

Specific examples of a "$C_{3-8}$ cycloalkylthio group" of the present invention include a cyclopropylthio group, cyclobutylthio group, cyclopentylthio group, cycloheptylthio group, cycloheptylthio group, and cyclooctylthio group.

Specific examples of a "$C_{1-8}$ alkylsulfinyl group" of the present invention include a methylsulfinyl group, ethylsulfinyl group, n-propylsulfinyl group, isopropylsulfinyl group, n-butylsulfinyl group, isobutylsulfinyl group, sec-butylsulfinyl group, tert-butylsulfinyl group, n-pentylsulfinyl group, isopentylsulfinyl group, neopentylsulfinyl group, 1-methylbutylsulfinyl group, 1-ethylpropylsulfinyl group, n-hexylsulfinyl group, isohexylsulfinyl group, 4-methylpentylsulfinyl group, 3-methylpentylsulfinyl group, 2-methylpentylsulfinyl group, 1-methylpentylsulfinyl group, 3,3-dimethylbutylsulfinyl group, 2,2-dimethylbutylsulfinyl group, 1,1-dimethylbutylsulfinyl group, 1,2-dimethylbutylsulfinyl group, 1,3-dimethylbutylsulfinyl group, 2,3-dimethylbutylsulfinyl group, 1-ethylbutylsulfinyl group, 2-ethylbutylsulfinyl group, trifluoromethylsulfinyl group, and trichloromethylsulfinyl group.

Specific examples of a "$C_{1-8}$ alkylsulfonyl group" of the present invention include a methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, isopentylsulfonyl group, neopentylsulfonyl group, 1-methylbutylsulfonyl group, 1-ethylpropylsulfonyl group, n-hexylsulfonyl group, isohexylsulfonyl group, 4-methylpentylsulfonyl group, 3-methylpentylsulfonyl group, 2-methylpentylsulfonyl group, 1-methylpentylsulfonyl group, 3,3-dimethylbutylsulfonyl group, 2,2-dimethylbutylsulfonyl group, 1,1-dimethylbutylsulfonyl group, 1,2-dimethylbutylsulfonyl group, 1,3-dimethylbutylsulfonyl group, 2,3-dimethylbutylsulfonyl group, 1-ethylbutylsulfonyl group, 2-ethylbutylsulfonyl group, trifluoromethylsulfonyl group, and trichloromethylsulfonyl group.

Specific examples of a "$C_{6-10}$ arylthio group" of the present invention include a phenylthio group, p-tolylthio group, p-chlorophenylthio group, naphthylthio group, and azulenylthio group.

Specific examples of a "$C_{6-10}$ arylsulfinyl group" of the present invention include a benzenesulfinyl group, p-toluenesulfinyl group, p-chlorobenzenesulfinyl group, naphthalen-1-ylsulfinyl group, and naphthalen-2-ylsulfinyl group.

Specific examples of a "$C_{6-10}$ arylsulfonyl group" of the present invention include a benzenesulfonyl group, p-toluenesulfonyl group, p-chlorobenzenesulfonyl group, naphthalen-1-ylsulfonyl group, and naphthalen-2-ylsulfonyl group.

Specific examples of a "$C_{1-8}$ alkoxycarbonyl group" of the present invention include a methoxycarbonyl group, ethoxycarbonyl group, n-propoxycarbonyl group, 1-methylethoxycarbonyl group, n-butoxycarbonyl group, isobutoxycarbonyl group, sec-butoxycarbonyl group, tert-butoxycarbonyl group, n-pentoxycarbonyl group, isopentoxycarbonyl group, neopentoxycarbonyl group, 1-methylbutoxycarbonyl group, 1-ethylpropoxycarbonyl group, n-hexyloxycarbonyl group, isohexyloxycarbonyl group, 3-methylpentoxycarbonyl group, 2-methylpentoxycarbonyl group, 1-methylpentoxycarbonyl group, 3,3-dimethylbutoxycarbonyl group, 2,2-dimethylbutoxycarbonyl group, 1,1-dimethylbutoxycarbonyl group, 1,2-dimethylbutoxycarbonyl group, 1,3-dimethylbutoxycarbonyl group, 2,3-dimethylbutoxycarbonyl group, 1-ethylbutoxycarbonyl group, and 2-ethylbutoxycarbonyl group.

In the present invention, a "$C_{3-8}$ cycloalkenyl group" means a group having a carbon-carbon double bond at any one or more sites on the carbocycle of the above "$C_{3-8}$ cycloalkyl group", and the examples include a cyclopropene group, cyclobutene group, cyclopentene group, cyclohexene group, cycloheptene group, cyclooctene group, and cyclohexadiene group. Further, a "$C_{3-8}$ cycloalkenyl $C_{1-8}$ alkyl group" means a group wherein a "$C_{3-8}$ cycloalkenyl group" is bound to a $C_{1-8}$ alkyl group.

In the present invention, a "5- to 7-membered carbocycle" means a hydrocarbon ring with 5 to 7 carbons, and the examples include a cyclopentane ring, cyclohexane ring, cycloheptane ring, cyclopentene ring, cyclohexene ring, and cycloheptene ring.

In the present invention, a "$C_{3-8}$ cycloalkyl $C_{1-8}$ alkyl group" means a group wherein the above "$C_{3-8}$ cycloalkyl group" is bound to a $C_{1-8}$ alkyl group, and the examples include a cyclopropylmethyl group, cyclobutylmethyl group, cyclopentylmethyl group, and cyclohexylmethyl group.

In the present invention, a "$C_{3-8}$ cycloalkyl $C_{2-8}$ alkenyl group" means a group wherein the above "$C_{3-8}$ cycloalkyl group" is bound to a $C_{2-8}$ alkenyl group, and the examples include a 2-cyclopropylethen-1-yl group, 2-cyclobutylethen-1-yl group, 2-cyclopentylethen-1-yl group, and 2-cyclohexylethen-1-yl group.

In the present invention, a "$C_{3-8}$ cycloalkyl $C_{2-8}$ alkynyl group" means a group wherein the above "$C_{3-8}$ cycloalkyl group" is bound to a $C_{2-8}$ alkynyl group, and the examples include a 2-cyclopropylethynyl group, 2-cyclobutylethynyl group, 2-cyclopentylethynyl group, and 2-cyclohexylethynyl group.

In the present invention, a "$C_{6-10}$ aryl $C_{2-8}$ alkenyl group" means a group wherein the above "$C_{6-10}$ aryl group" is bound to a $C_{2-8}$ alkenyl group, and the examples include a styryl group, cinnamyl group, 4-phenyl-3-buten-1-yl group, 5-phenyl-4-penten-1-yl group, and 6-phenyl-6-hexen-1-yl group.

In the present invention, a "$C_{6-10}$ aryl $C_{1-8}$ alkoxy group that may be substituted with 1 to 3 $C_{1-8}$ alkyl groups" means a group wherein the above "$C_{6-10}$ aryl $C_{1-8}$ alkyl group" that may be substituted with 1 to 3 $C_{1-8}$ alkyl groups on the ring is bound to an oxygen atom, and the examples include a benzyloxy group, phenethyloxy group, naphthylmethyloxy group, 2-methylbenzyloxy group, 3-methylbenzyloxy group, 4-methylbenzyloxy group, and 3,4-dimethylbenzyloxy group.

In the present invention, a "$C_{1-8}$ alkoxy $C_{1-8}$ alkyl group" means a group wherein the above mentioned $C_{1-8}$ alkoxy group is bound to the $C_{1-8}$ alkyl group, and the examples include an ethoxymethyl group, ethoxyethyl group, ethoxyhexyl group, ethoxyoctyl group, n-propoxymethyl group, 1-methylethoxymethyl group, n-butoxyethyl group, n-butoxymethyl group, t-butoxypropyl group, n-pentoxyethyl group, neopentoxymethyl group, isohexyloxyethyl group, 3-methylpentoxymethyl group, 2-methylpentoxypropyl group, 1-methylpentoxypropyl group, and 2-ethylbutoxyhexyl group.

In the present invention, a "$C_{1-8}$ alkyl chain" means a divalent hydrocarbon chain with 1 to 8 carbons having a straight-chain or a branch, and the examples include a methylene chain, ethylene chain, trimethylene chain, methylethylene chain, tetramethylene chain, 1-methylmethylene chain, 1,2-dimethylethylene chain, pentamethylene chain, 1-methyltetramethylene chain, 2-methyltetramethylene chain, hexamethylene chain, heptamethylene chain, and octamethylene chain.

In the present invention, a "—O—($C_{1-8}$ alkyl) chain" means a group wherein the above "$C_{1-8}$ alkyl chain" is bound to an oxygen atom, and the examples include a —O-(methylene) chain, —O-(ethylene) chain, —O-(trimethylene) chain, —O-(1-methylethylene) chain, —O-(tetramethylene) chain, —O-(1-methylmethylene) chain, —O-(1,2-dimethylethylene) chain, —O-(pentamethylene) chain, —O-(1-methyltetramethylene) chain, —O-(2-methyltetramethylene) chain, —O-(hexamethylene) chain, —O-(heptamethylene) chain, and —O-(octamethylene) chain.

In the present invention, a "$C_{2-8}$ alkenyl chain" means a straight-chained or branched-chained divalent hydrocarbon chain with 2 to 8 carbons having a carbon-carbon double bond at any one or more sites on the $C_{2-8}$ alkyl chain. The examples include a vinylene chain, propenylene chain, 1-methylvinylene chain, butenylene chain (for example, 1-butenylene chain, 2-butenylene chain or the like), 1,2-dimethylvinylene chain, pentenylene chain, 1-methylbutenylene chain, 2-methylbutenylene chain, hexenylene chain, heptenylene chain, octenylene chain, and isoprene chain.

In the present invention a "$C_{6-10}$ aryl chain" means a divalent aromatic hydrocarbon-ring group, and the examples include an o-phenylene chain, m-phenylene chain, and p-phenylene chain.

In the present invention, a "5- to 11-membered heteroaryl chain" means a divalent group which is a 5- to 7-membered aromatic heterocycle containing 1 to 4 heteroatoms selected from a nitrogen atom, oxygen atom and sulfur atom in addition to a carbon atom as atoms constituting the ring or a condensed heterocycle made by a condensation of a benzene ring and a 5- to 7-membered heterocycle having 1 to 4 nitrogen atom, oxygen atom or sulfur atom as hetero atoms. The examples include a 2,3-furandiyl group, 2,3-thiophenediyl group, 2,3-pyrrolediyl group, 2,3-pyridinediyl group, 2,4-pyridinediyl group, 2,6-pyridinediyl group, 2,5-pyridinediyl group, 3,5-pyridinediyl group 2,3-pyrazinediyl group, 2,4-pyrimidinediyl group, 3,4-pyridazinediyl group, 2,3-benzofurandiyl group, 2,3-benzothiophenediyl group, 2,3-quinoxalinediyl group, 2,3-indolediyl group, 1,3-isoindolediyl group, 1,3-isobenzofurandiyl group, 2,4-chromenediyl group, 2,4-imidazolediyl group, 3,4-pyrazolediyl group, 2,4-thiazolediyl group, 2,4-oxazole diyl group, 3,4-isoxazolediyl group, 2,4-benzoimidazolediyl group, 2,4-benzothiazolediyl group, 2,4-benzoxazolediyl group, 2,4-quinolinediyl group, and 1,4-isoquinolinediyl group.

Other groups that are not defined herein follow common definitions.

Followings are examples of the preferred modes of the present invention.

In general formula (I), $R^1$ is preferably a hydrogen atom or $C_{1-8}$ alkoxy $C_{1-8}$ alkyl group, more preferably a hydrogen atom or methoxymethyl group, and particularly preferably a hydrogen atom.

In general formula (I), $R^2$ and $R^3$ are preferably a $C_{1-8}$ alkyl group, $C_{6-10}$ aryl group, or a 5- to 11-membered heterocyclic group.

In general formula (I), the $C_{1-8}$ alkyl group of $R^2$ and $R^3$ are preferably a straight-chained $C_{1-8}$ alkyl group, more preferably a straight-chained alkyl group with 1 to 6 carbons such as a methyl group, ethyl group, n-propyl group, or n-butyl group, and particularly preferably a methyl group or ethyl group.

In general formula (I), the $C_{6-10}$ aryl group of $R^2$ and $R^3$ is preferably a phenyl group or naphthyl group, and more preferably a phenyl group. A preferred phenyl group has a substituent, and the substituent is preferably a halogen atom such as a fluorine atom and chlorine atom; a $C_{1-8}$ alkyl group such as a methyl group, 1-methylethyl group, and 1,1-dimethylethyl group; a $C_{1-8}$ alkoxy group such as a methoxy group, ethoxy group, n-propoxy group, n-butoxy group, 1-methylethoxy group, and cyclopropyloxy group; a $C_{1-8}$ alkylthio group such as a methylthio group and cyclopropylthio group; a $C_{1-8}$ alkylsulfinyl group such as a methylsulfinyl group; a $C_{1-8}$ alkylsulfonyl group such as a methylsulfonyl group; a nitro group; a $C_{6-10}$ aryl $C_{1-8}$ alkoxy group such as a phenylmethoxy group; and particularly preferably a $C_{1-8}$ alkoxy group such as a 1-methylethoxy group.

In general formula (I), a 5- to 11-membered heterocyclic group of $R^2$ and $R^3$ is preferably a 5- to 7-membered aromatic heterocycle, unsaturated heterocycle or a condensed heterocycle made by a condensation of the above heterocycles and a benzene ring or a pyridine ring, wherein the above heterocycles contain 1 or 2 heteroatoms selected from a nitrogen atom and oxygen atom in addition to a carbon atom, as atoms constituting the ring. The examples include a pyridyl group, furanyl group, pyrazinyl group, 1,3-benzodioxonyl group, 1,4-benzodioxinyl group, 2,3-dihydrobenzofuranyl group, quinoxalinyl group, furo[2,3-b]pyridinyl group, 2,3-dihydrofuro[2,3-b]pyridinyl group, and 2,3-dihydro-[1,4]dioxyno[2,3-c]pyridinyl group, and more preferably a 1,3-benzodioxonyl group, 1,4-benzodioxinyl group, and 2,3-dihydrobenzofuranyl group. These 5- to 11-membered heterocyclic groups may have a substituent, and the substituent is preferably a $C_{1-8}$ alkoxy group such as a methoxy group, ethoxy group, n-propoxy group, 1-methylethoxy group, and n-butoxy group.

In a preferred combination of $R^2$ and $R^3$ of general formula (I), either one of the $R^2$ and $R^3$ is a $C_{1-8}$ alkyl group and the other is a $C_{6-10}$ aryl group or 5- to 11-membered heterocyclic group.

When $R^2$ and $R^3$ together form a 5- to 7-membered carbocycle, $R^2$ and $R^3$ are preferably a cyclopentane ring.

In general formula (I), $R^4$ is preferably a hydrogen atom or a $C_{1-8}$ alkyl group such as a methyl group.

In general formula (I), preferred $X^1$, $X^2$, $X^3$, and $X^4$ are N or $CR^5$.

In general formula (I), $R^5$ is preferably a hydrogen atom or $C_{1-8}$ alkyl group. Examples of the $C_{1-8}$ alkyl group of $R^5$ include a methyl group, ethyl group, n-propyl group, isopropyl group, n-butyl group, isobutyl group, t-butyl group, n-pentyl group, isopentyl group, neopentyl group, 2-methylbutyl group, 2,2-dimethylpropyl group, n-hexyl group, isohexyl group, n-heptyl group, and n-octyl group. Among these, a $C_{1-8}$ alkyl group such as a methyl group, n-propyl group, isopropyl group, isobutyl group, n-pentyl group, and n-octyl group are preferred.

In general formula (I), Y is preferably a single bond or —O—.

In general formula (I), a $C_{6-10}$ aryl chain of Z is preferably an m-phenylene group or p-phenylene group, and a 5- to 11-membered heteroaryl chain is preferably a 2,3-pyridinediyl group, 2,4-pyridinediyl group, 2,6-pyridinediyl group, or 3,5-pyridinediyl group.

Further, a preferred substituent that is bound to these $C_{6-10}$ aryl chain or 5- to 11-membered heteroaryl chain is a halogen atom such as a chlorine atom and iodine atom; a CIA alkyl group such as a methyl group; a cyano group; a hydroxy group; a $C_{1-8}$ alkoxy group such as a methoxy group and ethoxy group; a $C_{6-10}$ aryl $C_{1-8}$ alkoxy group such as a benzyloxy group; or a $C_{1-8}$ alkoxy $C_{1-8}$ alkyl group such as a methoxymethyl group.

In general formula (I), L is preferably a $C_{1-8}$ alkyl chain, $C_{1-8}$ alkyl chain substituted with an oxo group or —O—($C_{1-8}$ alkyl) chain, more preferably a $C_{1-8}$ alkyl chain. A particularly preferred alkyl-chain moiety is a methylene chain, ethylene chain, trimethylene chain, 1-methylmethylene chain, tetramethylene chain, or pentamethylene chain, and particularly preferably an ethylene chain.

Examples of an addition salt of a carbinol derivative represented by general formula (I) include alkaline metal salts such as sodium salt and potassium salt; alkaline earth metal salts such as calcium salt and magnesium salt; organic base salts such as ammonium salt and trialkylamine salt; mineral acid salts such as hydrochloride salt and sulfate; and organic acid salts such as acetate. There is no particular limitation as long as it is a pharmaceutically acceptable salt.

Examples of a solvate of a carbinol derivative represented by general formula (I) include a hydrate. When there is a geometric isomer or optical isomer of a compound of the present invention, such isomers are included in the scope of the present invention. When there is a geometric isomer, an (E)-isomer is preferred.

Compound (I) can be produced by various known methods without particular limitation, and for example, can be produced according to the following reaction process. More specifically, by reacting a derivative shown by general formula (II) with an imidazolidine-2,4-dione compound shown by general formula a compound (I) can be produced. This reaction path shown by a chemical reaction formula is as follows:

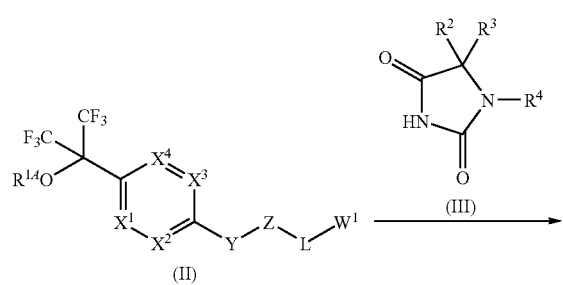

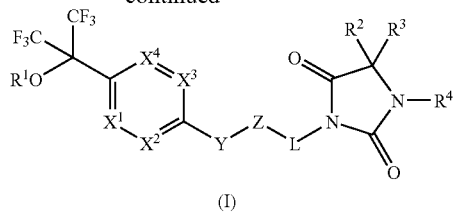

(wherein $R^{1A}$ shows the above $R^1$ or a protective group for a hydroxyl group; $R^2$, $R^3$, $R^4$, $X^1$, $X^2$, $X^3$, $X^4$, Y, Z, and L have the same meaning as above; and $W^1$ shows a halogen atom or hydroxyl group).

The protective group $R^{1A}$ can be converted to $R^1$ using a commonly used method (Protective Groups in Organic Synthesis Third Edition: John Wiley & Sons, Inc.).

Further, if there are other functional groups that react with an imidazolidine-2,4-dione compound shown by general formula (III), a compound of interest can be obtained by a protection by a commonly used method (Protective Groups in Organic Synthesis Third Edition: John Wiley & Sons, Inc.), followed by a deprotection at an appropriate time.

When $W^1$ is a halogen atom, a substance of interest (I) can be produced by reacting a derivative shown by general formula (II) with an imidazolidine-2,4-dione compound (III) in a solvent in the presence or absence of a base. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, or water. The base is not particularly limited, and for example, the followings can be used: alkaline metal hydrides such as lithium hydride, sodium hydride, and potassium hydride; alkaline metal hydroxides such as lithium hydroxide, sodium hydroxide, and potassium hydroxide; alkaline metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, or t-butyllithium. The substance of interest can be obtained by conducting a reaction under the reaction conditions of −80 to 150° C., preferably of 0 to 100° C., for 1 minute to 5 days, preferably for 1 hour to 3 days.

When $W^1$ is a hydroxyl group, a compound (I) can be produced by subjecting to the Mitsunobu reaction a derivative shown by general formula (II) and an imidazolidine-2,4-dione compound shown by general formula (III). The reaction can be conducted by dissolving a derivative shown by general formula (II), an imide compound shown by general formula (III), and a phosphine reagent in a reaction solvent, then adding thereto an azo reagent or an ethylenedicarboxylic acid reagent, and allowing the reaction to take place under an argon or nitrogen atmosphere at 0° C. to 100° C., preferably at room temperature to 80° C. for 2 hours to 1 day. The followings can be used as a solvent in this reaction: N,N-dimethylformamide, tetrahydrofuran, dioxane, acetonitrile, nitromethane, acetone, ethyl acetate, benzene, chlorobenzene, toluene, chloroform, or methylene chloride. Among these, N,N-dimethylformamide, tetrahydrofuran, dioxane, and acetonitrile are preferred, and N,N-dimethylformamide and tetrahydrofuran are particularly preferred. Examples of a phosphine reagent include trialkylphosphines such as trimethylphosphine, triethylphosphine, tripropylphosphine, triisopropylphosphine, tributylphosphine, triisobutylphosphine, and tricyclohexylphosphine; and triarylphosphines such as triphenylphosphine and diphenylphosphino polystyrene. Among these, trimethylphosphine, tributylphosphine, and triphenylphosphine are preferred. Examples of an azo reagent include diethyl azodicarboxylate (DEAD), diisopropyl azodicarboxylate, 1,1'-azobis(N,N-dimethylformamide) (TMAD), 1,1'-(azodicarbonyl)dipiperidine (ADDP), 1,1'-azobis(N,N-diisopropylformamide) (TIPA), 1,6-dimethyl-1,5,7-hexahydro-1,4,6,7-tetrazocine-2,5-dione (DHTD) and the like, and diethyl azodicarboxylate is particularly preferred.

A derivative shown by general formula (II) can be produced by the following reaction process:

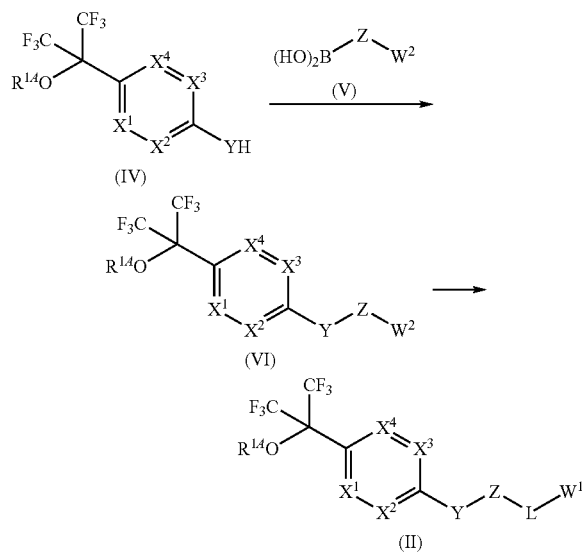

(wherein $R^{1A}$ shows the above $R^1$ or a protective group for a hydroxyl group; $X^1$, $X^2$, $X^3$, $X^4$, Y, Z, and L have the same meaning as above; $W^1$ shows a halogen atom or hydroxyl group; and $W^2$ shows a group from which can be led to a L-$W^1$).

A derivative of general formula (VI) which is a substance of interest can be obtained by reacting a derivative shown by general formula (IV) with a boronic acid derivative (V) in a solvent in the presence of a base and in the presence of a metal catalyst. The solvent is not particularly limited, and for example, the followings can be used independently or in combination: dichloromethane, chloroform, carbon tetrachloride, tetrahydrofuran, toluene, dioxane, N,N-dimethylformamide, N-methylpyrrolidone, dimethylsulfoxide, acetonitrile, or propionitrile. The base is not particularly limited, and for example, pyridine or triethylene amine can be used. The metal catalyst is not particularly limited, and a palladium catalyst, nickel catalyst, cupric oxide, or copper salt can be used. Preferably, copper acetate (II) is used. A reagent for removing water formed in the reaction, such as a molecular sieve, may be present in the reaction mixture. A derivative of general formula (IV) which is the substance of interest can be obtained by conducting a reaction under the reaction conditions of −80 to 150° C., preferably of 0 to 100° C. for 1 minute to 5 days, preferably for 1 hour to 3 days. —$W^2$ shows a group that can be converted to a L-$W^1$ (for example, a $CH_3$, —CH=$CH_2$, —CHO, —CN, or —$CO_2Me$), and a $W^2$ can be converted to a L-W' by a known method.

A derivative (IX) which is a compound of general formula (VI) with its Y being an oxygen atom can be produced by the following reaction process:

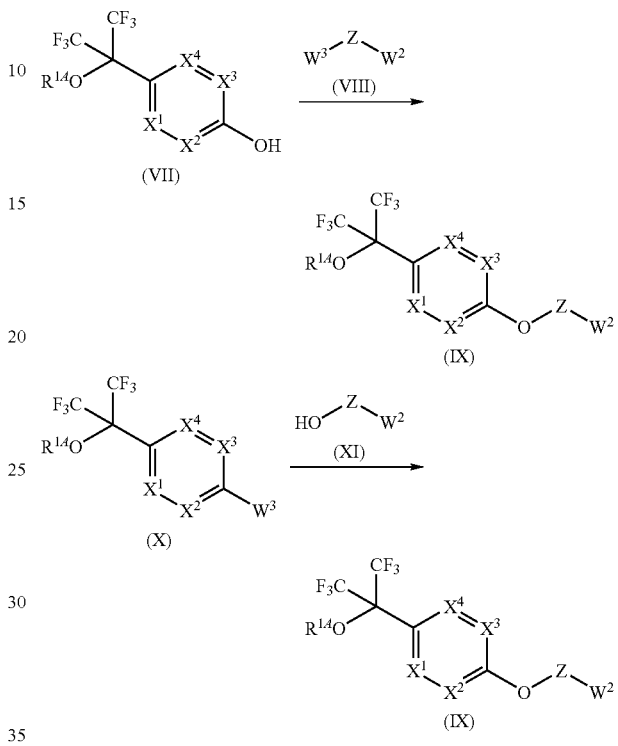

(wherein $R^{1A}$ shows the above $R^1$ or a protective group for a hydroxyl group; $X^1$, $X^2$, $X^3$, $X^4$, Z, and $W^2$ have the same meaning as above; and $W^3$ shows a leaving group such as a halogen atom, methanesulfonyl group and trifluoromethanesulfonyl group).

Diaryl ether can be produced from a phenol derivative shown by general formula (VII) or general formula (XI) and an aryl derivative shown by general formula (VIII) or general formula (X) having a leaving group. A method for preparing diaryl ethers are described in a literature (Tetrahedron 56 (2000) pp 5045-5065) or the like. A derivative of general formula (IX) which is the substance of interest can be obtained by reacting (VII) with (VIII) or reacting (X) with (XI) in a solvent in the presence of a base and in the presence of a metal catalyst. The solvent is not particularly limited, and for example, the followings can be used independently or in combination: dichloromethane, chloroform, carbon tetrachloride, tetrahydrofuran, toluene, dioxane, N,N-dimethylformamide, N-methylpyrrolidone, dimethylsulfoxide, acetonitrile, or propionitrile. The base is not particularly limited, and for example, the followings can be used: alkaline metal hydrides such as lithium hydride, sodium hydride, and potassium hydride; alkaline metal hydroxides such as lithium hydroxide, sodium hydroxide, and potassium hydroxide; alkaline metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, or t-butyllithium. The metal catalyst is not particularly limited, and a palladium catalyst, nickel catalyst, cupric oxide, copper salt or the like can be used. A derivative of general formula (IX) which is the substance of interest can be obtained by conducting a reaction under the reaction conditions of −80 to 150° C., preferably of 0 to 100° C., for 1 minute to 5 days, preferably for 1 hour to 3 days.

A derivative (IX') which is a compound of general formula (VI) with its Y being a single bond can be produced by the following reaction process through a condensation reaction generally known as the Suzuki reaction.

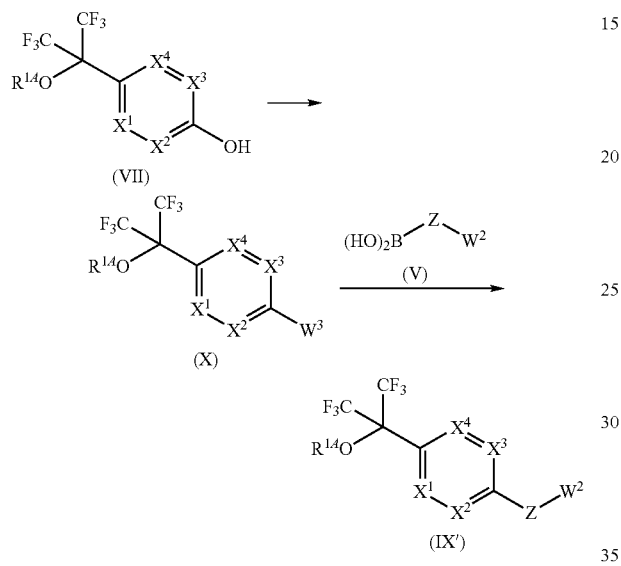

(wherein $R^{1A}$ shows the above $R^1$ or a protective group for a hydroxyl group; and $X^1$, $X^2$, $X^3$, $X^4$, $W^1$, $W^2$, $W^3$ and Z have the same meaning as above).

A derivative of general formula (IX') which is the substance of interest can be obtained by introducing a leaving group into a derivative shown by general formula (VII) by a commonly known method (Comprehensive Organic Transformations Second Edition, John Wiley & Sons, Inc.) to derive a derivative (X) and then reacting the derivative (X) with a boronic acid derivative (V) in a solvent in the presence of a base and in the presence of a palladium catalyst. The solvent is not particularly limited, and for example, the followings can be used independently or in combination: dichloromethane, chloroform, carbon tetrachloride, tetrahydrofuran, toluene, dioxane, N,N-dimethylformamide, N-methylpyrrolidone, dimethylsulfoxide, acetonitrile, or propionitrile. The palladium catalyst is not particularly limited, and the followings can be used: [1,1'-bis(diphenylphosphino)ferrocene]dichloropallaciium(II), bis(triphenylphosphine)palladium(II) diacetate, bis(triphenylphosphine)dichloropalladium(II), palladium(II)diacetate, tetrakis(triphenylphosphine)palladium(0) or the like. In this reaction, a base is used to achieve a preferable reaction rate and various organic or inorganic bases, for example, such as the followings can be used: lithium carbonate, sodium carbonate, potassium carbonate, lithium hydroxide, sodium hydroxide, potassium hydroxide, lithium acetate, sodium acetate, potassium acetate, magnesium oxide, calcium oxide, barium hydroxide, trilithium phosphate, trisodium phosphate, tripotassium phosphate, cesium fluoride, cesium carbonate, aluminum oxide, trimethylamine, triethylamine, tributylamine, N,N,N',N'-tetramethylethylenediamine, diisopropylethylamine, N-methylpiperidine, 2,2,6,6-tetramethyl-N-methylpiperidine, pyridine, 4-dimethylaminopyridine, N-methylmorpholine, sodium ethoxide, or potassium tert-butoxide. A derivative of general formula (IX) which is the substance of interest can be obtained by conducting a reaction under the reaction conditions of −80 to 150° C., preferably of 0 to 100° C., for 1 minute to 5 days, preferably for 1 hour to 3 days.

A derivative shown by general formula (VII) can be produced by various methods without particular limitation, and for example, can be produced according to the following reaction process:

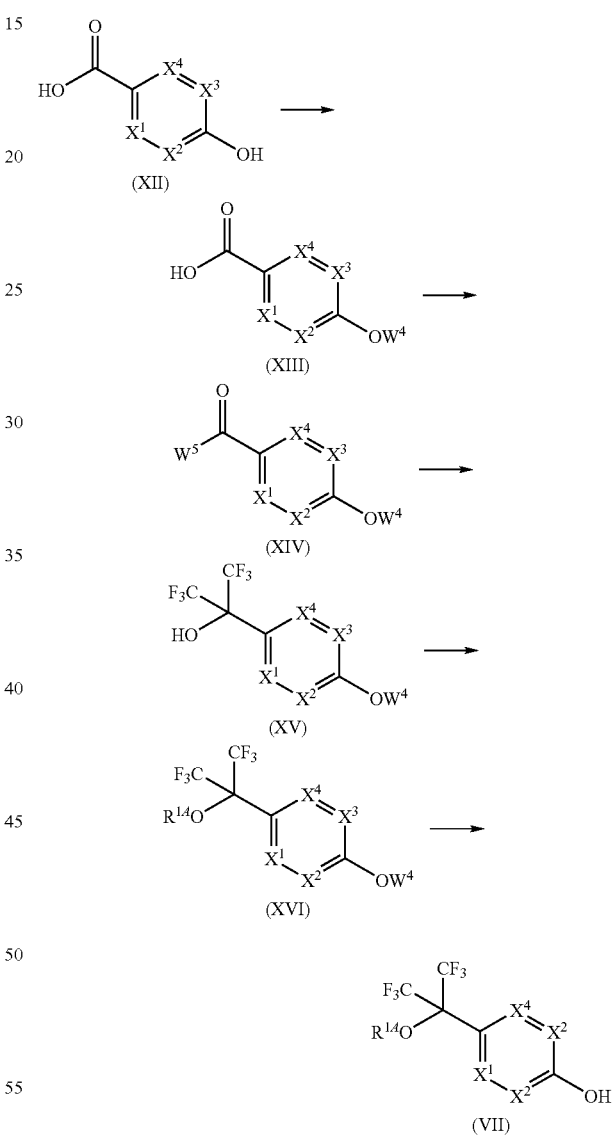

(wherein $R^{1A}$ shows the above $R^1$ or a protective group; $X^1$, $X^2$, $X^3$, and $X^4$ have the same meaning as above; $W^4$ shows a protective group for a hydroxyl group; and $W^5$ shows a halogen atom or a leaving residue).

The protective group $W^5$ can be introduced into a 4-hydroxy benzoic acid derivative (XII) with reference to a commonly used method (Protective Groups in Organic Synthesis Third Edition, John Wiley & Sons, Inc.) for a protection condition of the protective group.

A hexafluorocarbinol compound (XV) can be derived from the carboxylic acid compound (XIII) obtained by the above method by a conversion with reference to a known literature (Tetrahedron 61 (2005) 1813-1819). The carboxylic acid compound (XIII) is converted to an acid halide, acid anhydride, ester, or amide (XIV) with reference to a commonly used method (Comprehensive Organic Transformations Second Edition, John Wiley & Sons, Inc.), and then a hexafluorocarbinol compound (XV) can be derived using (trifluoromethyl)trimethylsilane and tetramethylammoniumfluoride.

The literature uses (trifluoromethyl)trimethylsilane as a source of trifluoromethyl, but such sources are not limited to the same and the followings can also be used: triethyl(trifluoromethyl)silane, triisopropyl(trifluoromethyl)silane, methyldiphenyl(trifluoromethyl)silane, dimethyl(diphenyl)trifluoromethyl silane or the like. Further, a perfluoroalkylation is also possible when perfluoroalkylsilanes such as (pentafluoroethyl)trimethylsilane and (heptafluoropropyl)trimethylsilane are used. The literature uses tetramethylammonium fluoride as a fluorine compound, but such compounds are not limited to the same and the followings can also be used: tetraalkylammonium salts such as tetraethylammoniumfluoride and tetrabutylammonium fluoride; and metallic salts such as lithium fluoride, sodium fluoride, potassium fluoride, and cesium fluoride. In addition to dimethoxyethane, the followings can be used independently or in combination as a solvent: tetrahydrofuran, toluene, dioxane, N,N-dimethylformamide, N-methylpyrrolidone, tetramethylurea, dimethylsulfoxide, acetonitrile, propionitrile, acetone, methylethylketone or the like.

By reacting the obtained hexafluorocarbinol compound (XV) with a halide of $R^{14}$ in a solvent in the presence or absence of a base, a substance of interest (XVI) can be produced. The solvent is not particularly limited, and for example, the followings can be used independently or in combination: tetrahydrofuran, toluene, dioxane, N,N-dimethylformamide, N-methylpyrrolidone, tetramethylurea, dimethylsulfoxide, acetonitrile, propionitrile, acetone, methylethyl ketone, or water. The halide of $R^{14}$ can also be used as a solvent. The base is not particularly limited, and for example, the followings can be used: alkaline metal hydrides such as lithium hydride, sodium hydride, and potassium hydride; alkaline metal hydroxides such as lithium hydroxide, sodium hydroxide, and potassium hydroxide; alkaline metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; and organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium.

Further, it is also possible to introduce $R^{14}$ as a protective group into a hexafluorocarbinol compound (XV). A commonly used method (Protective Groups in Organic Synthesis Third Edition, John Wiley & Sons, Inc.) can be referred to for a protection condition of the protective group.

A deprotection method of protective group $W^5$ of the compound (XVI) obtained in the above method is not particularly limited, and can be conducted with reference to a commonly used method (Protective Groups in Organic Synthesis Third Edition, John Wiley & Sons, Inc.) for a deprotection condition of the protective group.

Further, a derivative shown by general formula (VII) can be produced using the following method:

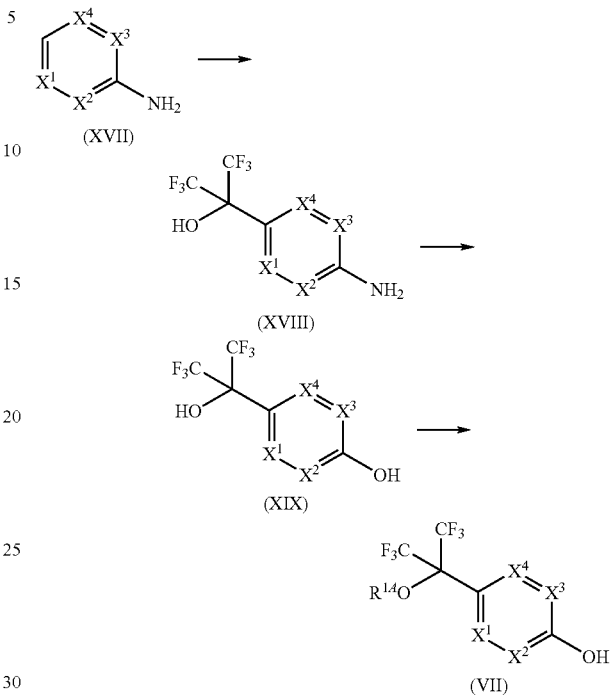

(wherein $R^{14}$ shows the above $R^1$ or a protective group; and $X^1$, $X^2$, $X^3$, and $X^4$ have the same meaning as above).

By reacting an aniline derivative (XVII) with hexafluoroacetone in a solvent or without a solvent in the presence or absence of an acid, a compound (XVIII) can be synthesized. The solvent is not particularly limited, and for example, the followings can be used independently or in combination: tetrahydrofuran, toluene, dioxane, N,N-dimethylformamide, N-methylpyrrolidone, tetramethylurea, dimethylsulfoxide, or water. The acid is not particularly limited, and p-toluenesulfonic acid, benzenesulfonic acid, methanesulfonic acid, trifluoromethanesulfonic acid, acetic acid, formic acid, sulfuric acid, trifluoroacetic acid or the like can also be used without limitation to those. The substance of interest can be obtained by conducting a reaction under the reaction conditions of 0 to 250° C., preferably of 100 to 200° C., for 1 minute to 5 days, preferably for 1 hour to 3 days.

The amino group of a compound (XVIII) can be converted to a hydroxyl group with reference to a commonly used method (Comprehensive Organic Transformations Second Edition, John Wiley & Sons, Inc.). More specifically, a diazonium salt obtained by a diazotation of the compound (XVIII) can be thermally decomposed in an acidic aqueous solution to derive a phenol derivative (XIX).

$R^{14}$ can be introduced as a protective group into a phenol derivative (XIX). A commonly used method (Protective Groups in Organic Synthesis Third Edition, John Wiley & Sons, Inc.) can be referred to for a protection condition of a protective group.

Further, a 4-hydroxyphenylhexafluoropropyl derivative shown by general formula (XXII) can be produced using a known method (WO2006/037480, U.S. Patent Publication No. 3396159).

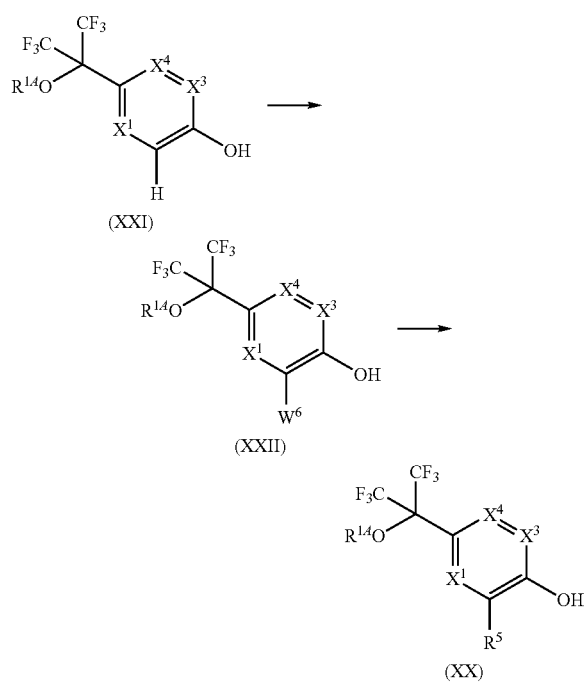

(wherein $R^{1A}$ shows the above $R^1$ or a protective group; $R^5$, $X^1$, $X^3$, and $X^4$ have the same meaning as above; and $W^6$ shows a halogen atom).

By reacting a derivative shown by general formula (XXI) with a halogenating agent in a solvent in the presence or absence of a base, a derivative of general formula (XXII) which is the substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, methanol, ethanol, isopropanol or water. Further, a halogenating agent or a base can also be used as a solvent. The base is not particularly limited, and for example, the followings can be used: alkaline metal hydrides such as lithium hydride, sodium hydride, and potassium hydride; alkaline metal hydroxides such as lithium hydroxide, sodium hydroxide, and potassium hydroxide; alkaline metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium; or organic base compounds such as pyridine and triethylamine. The halogenating agent is not particularly limited, and for example, chlorine, bromine, iodine, tetrabutylammonium chloride, tetrabutylammonium bromide, tetrabutylammonium iodide, N-chlorosuccinimide, N-bromosuccinimide, N-iodo succinimide, or carbon tetrabromide can be used. Further, a halide salt such as potassium bromide, potassium iodide, sodium bromide, and sodium iodide can be oxidized with an oxidant such as a hydrogen peroxide solution or an aqueous solution of sodium hypochlorite to produce a halogenating agent in the system, which is to be used in the reaction. A derivative of general formula (XXII) which is the substance of interest can be obtained by conducting a reaction under the reaction conditions of −80 to 150° C., preferably of 0 to 100° C., for 1 minute to 5 days, preferably for 1 hour to 3 days.

By reacting a derivative shown by general formula (XXII) with an organic metal compound in a solvent in the presence of a catalyst and in the presence or absence of a base, a derivative of general formula (XX) which is the substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, methanol, ethanol, isopropanol or water. The base is not particularly limited, and for example, the followings can be used: alkaline metal hydrides such as lithium hydride, sodium hydride, and potassium hydride; alkaline metal hydroxides such as lithium hydroxide, sodium hydroxide, and potassium hydroxide; alkaline metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium; or fluoride salts such as tetraethylammonium fluoride, tetrabutylammonium fluoride, lithium fluoride, sodium fluoride, potassium fluoride, and cesium fluoride. The catalyst is not particularly limited, and for example, palladium reagents or the like such as the followings can be used: [1,1'-bis(diphenylphosphino)ferrocene]dichloropalladium (II), bis(triphenylphosphine)palladium(II) diacetate, bis (triphenylphosphine)dichloropalladium(II), palladium(II) diacetate, or tetrakis(triphenylphosphine)palladium(0). The organic metal compound is not particularly limited, and an organic boron compound, organic zinc compound, organic tin compound or the like having $R^5$ can be used. Further, a halogenated metal such as copper bromide(I), copper iodide(I) or the like can be added to conduct a transmetalation and then used for the reaction. A derivative of general formula (XX) which is the substance of interest can be obtained by conducting a reaction under the reaction conditions of −80 to 150° C., preferably of 0 to 100° C., for 1 minute to 5 days, preferably for 1 hour to 3 days.

A method for producing imidazolidine-2,4-dione derivative (III) is described in German Patent No. 335993, and various imidazolidine-2,4-dione derivatives can be produced with reference to this patent.

A carbinol compound represented by general formula (I) of the present invention can be obtained by the above-mentioned methods, and further and optionally, can be purified using an ordinary purifying method such as recrystallization method and a column chromatography. Moreover, the above compound can optionally be processed into an above-mentioned desired salt or solvate by a usual method.

So obtained carbinol compound represented by general formula (I) or salt thereof, or their solvate (hereinafter, sometimes collectively described as "compounds represented by general formula (I)") shows a superior LXRβ agonist effect as shown in test examples described hereinbelow, and is useful as an active ingredient of a preventative and/or therapeutic agent for diseases of animal including humans, resulting from abnormal cholesterol metabolism, for example, atherosclerosis; arteriosclerosis such as those resulting from diabetes; dyslipidemia; hypercholesterolemia; lipid-related diseases;

inflammatory diseases that are caused by inflammatory cytokines; skin diseases such as allergic skin diseases; diabetes; or Alzheimer's disease.

The pharmaceutical composition of the present invention contains a carbinol compound represented by general formula (I) or salt thereof, or their solvate. The pharmaceutical composition may be used independently, but generally, is used by formulating with a pharmaceutically acceptable carrier, additive and the like. The administration form of the pharmaceutical composition is not particularly limited, and can be selected as desired according to the therapeutic purpose. For example, the administration form can be any of oral preparation, injection, suppository, ointment, inhalation, eye-drops, nasal preparation, adhesive patch and the like. The pharmaceutical composition suitable for these administration forms can be produced according to a known method of drug formulation.

When prepared into a solid oral formulation, a carbinol compound represented by general formula (I) can be added with an excipient and optionally, further with a binder, disintegrant, lubricant, coloring agent, flavoring agent, odor improving agent or the like, and then processed into a tablet, coated tablet, granules, powder, capsule or the like by a usual method. The additive may be those commonly used in this field. Examples of the excipient include lactose, sucrose, sodium chloride, glucose, starch, calcium carbonate, Kaolin, microcrystalline cellulose, and silicate. Examples of the binder include water, ethanol, propanol, simple syrup, dextrose solution, starch solution, gelatin solution; carboxymethylcellulose, hydroxypropylcellulose, hydroxypropyl starch, methylcellulose, ethylcellulose, shellack, calcium phosphate, and polyvinylpyrrolidone. Examples of the disintegrant include dry starch, sodium alginate, powdered agar, sodium hydrogen carbonate, calcium carbonate, sodium lauryl sulfate, monoglyceride stearate, and lactose. Examples of the lubricant include purified talc, stearate, borax, polyethyleneglycol and the like. Examples of the flavoring agent include sucrose, orange peel, citric acid, and tartaric acid.

When prepared into a liquid oral formulation, a carbinol compound represented by general formula (I) can be added with a flavoring agent, buffer, stabilizer, odor improving agent or the like, and then processed into an internal liquid formulation, syrup, elixir or the like by a usual method. The flavoring agent may be those mentioned above, and examples of the buffer include sodium citrate, and examples of the stabilizer include tragacanth, gum Arabic, and gelatin.

When prepared into an injection, a carbinol compound represented by general formula (I) can be added with a pH adjuster, buffer, stabilizer, isotonic agent, local anesthetic or the like, and then processed into a subcutaneous, intramuscular, and intravenous injection by a usual method. Examples of the pH adjuster and buffer include sodium citrate, sodium acetate, and sodium phosphate. Examples of the stabilizer include sodium pyrosulfite, EDTA, thioglycolic acid, and thiolactic acid. Examples of the local anesthetic include procaine hydrochloride and lidocaine hydrochloride. Examples of the isotonic agent include sodium chloride and glucose.

When prepared into a suppository, a carbinol compound represented by general formula (I) can be added with a known carrier for suppository, for example, with polyethyleneglycol, lanolin, cacao butter, or fatty acid triglyceride and optionally, further with a surfactant such as Tween®, and then processed into a suppository by a usual method.

When prepared into an ointment, a carbinol compound represented by general formula (I) can be optionally formulated with a commonly used base, stabilizer, moisturizer, preservative or the like, and then mixed and formulated by a usual method. Examples of the base include liquid paraffin, white petrolatum, white beeswax, octyldodecyl alcohol, and paraffin. Examples of the preservative include methyl p-hydroxybenzoate, ethyl p-hydroxybenzoate, and propyl p-hydroxybenzoate.

In addition to the above, a carbinol compound represented by general formula (I) can be processed into an inhalation, eye-drops, or nasal preparation by a usual method.

The dose of a carbinol compound represented by general formula (I) varies depending on the age, weight, symptom, administration form, the number of doses and the like, but generally, it is preferable to administer a carbinol compound represented by general formula (I) to an adult in an amount of 1 to 1000 mg per day as a single or several separate doses either orally or parenterally.

Example

The present invention will be described further with reference to the following examples, while the scope of the present invention will not be limited to these examples.

Preparation Example 1

Preparation of 4-(1,1,1,3,3,3-hexafluoro-2-(methoxymethoxy)propan-2-yl)-2-propylphenol a) Preparation of methyl 4-(2-propen-1-yl)oxybenzoate

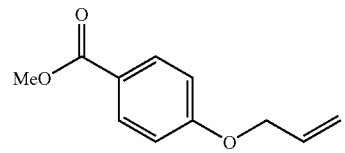

A solution of methyl 4-hydroxybenzoate (15.21 g, 0.10 mol), allyl chloride (11.48 g, 0.15 mol), and potassium carbonate (20.73 g, 0.15 mol) in N,N-dimethylformamide (40 mL) was stirred at 50° C. overnight. The reaction solution was added with water and extracted with ethyl acetate. Subsequently, the organic layer was washed with brine, dried using anhydrous sodium sulfate, and concentrated in vacuo. The obtained residue was purified using silica-gel column chromatography (hexane/ethyl acetate) and the title compound (19.27 g, yield 100%) was obtained as a pale yellow oil.

$^1$H-NMR (CDCl$_3$) δ: 3.86 (3H, s), 4.55 (2H, ddd, J=1.6, 1.6, 5.3 Hz), 5.29 (1H, ddd, J=1.6, 3.0, 10.6 Hz), 5.41 (1H, ddd, J=1.6, 3.0, 17.5 Hz), 6.02 (1H, ddd, J=5.3, 10.6, 17.5 Hz), 6.90 (2H, d, J=8.9 Hz), 7.97 (2H, d, J=8.9 Hz).

b) Preparation of methyl 4-hydroxy-3-(2-propen-1-yl)benzoate

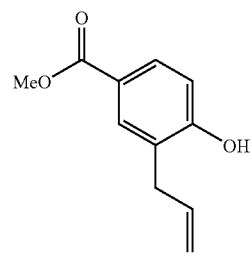

A mixed solution of methyl 4-(2-propen-1-yl)oxybenzoate (19.17 g, 0.10 mol) and N,N-dimethylaniline (40 mL) was heated to reflux at 210° C. for 18 hours. The reaction solution was added with dilute hydrochloric acid (1 mol/L) and extracted with ethyl acetate. Subsequently, the organic layer was washed with brine, dried using anhydrous sodium sulfate, and concentrated in vacuo. The obtained residue was purified using silica-gel column chromatography (hexane/ethyl acetate) and the title compound (12.26 g, yield 64%) was obtained as a colorless powder.

$^1$H-NMR (CDCl$_3$) δ: 3.44 (2H, d, J=6.2 Hz), 3.89 (3H, s), 5.10-5.16 (1H, m), 5.18 (1H, s), 5.93-6.17 (2H, m), 6.85 (1H, d, J=8.9 Hz), 7.78-7.88 (2H, m).

c) Preparation of methyl 4-hydroxy-3-propylbenzoate

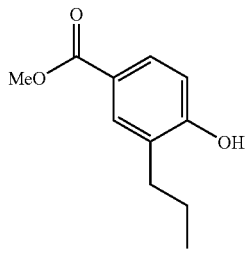

To a mixed solution of methyl 4-hydroxy-3-(2-propen-1-yl)benzoate (12.16 g, 0.63 mol) and methanol (50 mL), 10% palladium carbon catalyst (608 mg) was added, and the mixture was stirred overnight under a hydrogen atmosphere. The catalyst was separated by filtration from the reaction solution which was then concentrated in vacuo. The obtained residue was purified using silica-gel column chromatography (hexane/ethyl acetate) and the title compound (10.83 g, yield 88%) was obtained as a colorless powder.

$^1$H-NMR (CDCl$_3$) δ: 0.96 (3H, t, J=7.6 Hz), 1.65 (2H, qt, J=7.6, 7.6 Hz), 2.61 (2H, t, J=7.6 Hz), 3.89 (3H, s), 4.16 (1H, brs), 6.82 (1H, d, J=8.6 Hz), 7.78 (1H, dd, J=2.0, 8.6 Hz) 7.83 (1H, d, J=2.0 Hz).

d) Preparation of methyl 4-benzyloxy-3-propylbenzoate

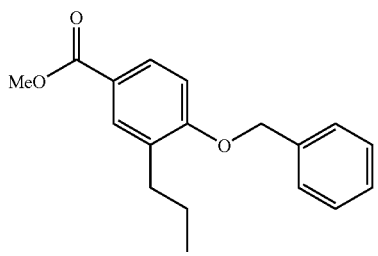

A solution of methyl 4-hydroxy-3-propylbenzoate (7.00 g, 36.0 mmol), benzyl bromide (11.48 g, 0.15 mol), and potassium carbonate (20.73 g, 0.15 mol) in N,N-dimethylformamide (20 mL) was heated and stirred at 80° C. for 2 hours. The reaction solution was added with water and extracted with ethyl acetate. Subsequently, the organic layer was washed with brine, dried using anhydrous sodium sulfate, and concentrated in vacuo. The obtained residue was purified using silica-gel column chromatography (hexane/ethyl acetate) and the title compound (10.25 g, yield 100%) was obtained as a pale yellow oil.

$^1$H-NMR (CDCl$_3$) δ: 0.95 (3H, t, J=7.6 Hz), 1.66 (2H, qt, J=7.6, 7.6 Hz), 2.67 (2H, t, J=7.6 Hz), 3.86 (3H, s), 5.11 (2H, s), 6.88 (1H, d, J=9.2 Hz), 7.27-7.43 (5H, m) 7.83-7.88 (2H, m).

e) Preparation of 4-benzyloxy-3-propylbenzoate

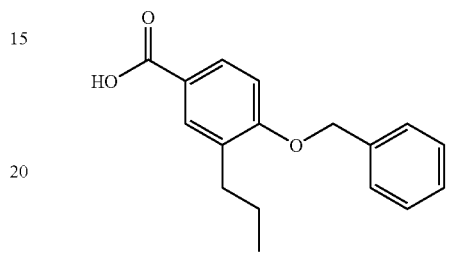

A solution of methyl 4-benzyloxy-3-propylbenzoate (6.84 g, 24.1 mmol) and an aqueous solution of sodium hydroxide (2 mol/L, 30 ml) in ethanol (100 mL) was heated to reflux for 2 hours. The reaction solution was concentrated, then acidized with dilute hydrochloric acid, and extracted with ethyl acetate. The organic layer was washed with brine, dried using anhydrous sodium sulfate, and concentrated in vacuo. The obtained residue was recrystallized (hexane/ethyl acetate) and the title compound (6.35 g, yield 98%) was obtained as a white powder.

$^1$H-NMR (CD3OD) δ: 0.94 (3H, t, J=7.6 Hz), 1.65 (2H, qt, J=7.6, 7.6 Hz), 2.68 (2H, t, J=7.6 Hz), 5.09 (2H, s), 6.93 (1H, d, J=9.2 Hz), 7.31-7.49 (7H, m).

f) Preparation of 2-(4-benzyloxy-3-propylphenyl)-1,1,1,3,3,3-hexafluoropropan-2-ol

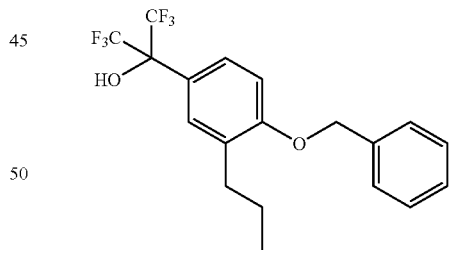

A mixed solution of 4-benzyloxy-3-propylbenzoate (6.34 g, 23.5 mmol) and thionyl chloride (6.3 mL) was heated at 70° C. for 2 hours. The solvent was distilled away in vacuo. The resultant residue was added with dimethoxyethane (20 mL) and tetramethylammonium fluoride (4.82 g, 51.7 mmol), then added dropwisely with (trifluoromethyl)trimethylsilane (7.35 g, 51.7 mmol) at −78° C. under an argon atmosphere, and stirred overnight. The reaction solution was added with dilute hydrochloric acid (1 mol/L) and extracted with ethyl acetate. Subsequently, the organic layer was washed with a saturated solution of sodium hydrogen carbonate and brine, dried using anhydrous sodium sulfate, and concentrated in vacuo. The obtained residue was purified using silica-gel column chromatography (hexane/ethyl acetate) and the title compound (6.58 g, yield 72%) was obtained as a pale yellow oil.

$^1$H-NMR (CDCl$_3$) δ: 0.94 (3H, t, J=7.6 Hz), 1.65 (2H, qt, J=7.6, 7.6 Hz), 2.68 (2H, t, J=7.6 Hz), 3.39 (1H, s), 5.10 (2H, s), 6.93 (1H, dd, J=2.3, 7.3 Hz), 7.30-7.51 (7H, m).

g) Preparation of 4-(1,1,1,3,3,3-hexafluoro-2-(methoxymethoxy)propan-2-yl)-2-propylphenyl(benzyl) ether

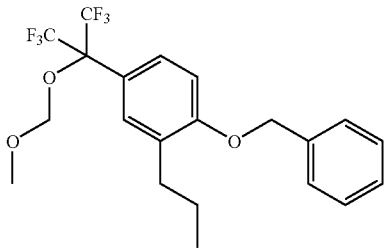

A mixed solution of 2-(4-benzyloxy-3-propylphenyl)-1,1,1,3,3,3-hexafluoropropan-2-ol (264.0 mg, 0.67 mmol) in tetrahydrofuran (5 mL) was added with sodium hydride (purity 50%) (38.9 mg, 0.81 mmol) under ice-cold conditions and then added with chloromethyl methyl ether (65.0 mg, 0.81 mmol). The resultant mixture was stirred overnight. The reaction solution was added with water and extracted with ethyl acetate. Subsequently, the organic layer was washed with brine, dried using anhydrous sodium sulfate, and concentrated in vacuo. The obtained residue was purified using silica-gel thin-layer preparative chromatography (hexane/ethyl acetate) and the title compound (264.9 mg, yield 90%) was obtained as a pale yellow oil.

$^1$H-NMR (CDCl$_3$) δ: 0.94 (3H, t, J=7.6 Hz), 1.65 (2H, qt, J=7.6, 7.6 Hz), 2.68 (2H, t, J=7.6 Hz), 3.54 (3H, s), 4.83 (2H, s), 5.10 (2H, s), 6.93 (1H, d, J=8.9 Hz), 7.29-7.44 (7H, m).

h) Preparation of 4-(1,1,1,3,3,3-hexafluoro-2-(methoxymethoxy)propan-2-yl)-2-propylphenol

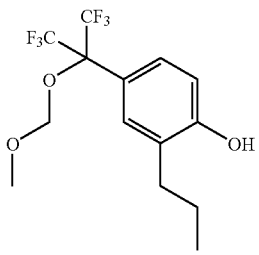

To a mixed solution of 4-(1,1,1,3,3,3-hexafluoro-2-(methoxymethoxy)propan-2-yl)-2-propylphenyl(benzyl)ether (264.9 mg, 0.61 mmol) in methanol (10 mL), 10% palladium carbon catalyst (30 mg) was added, and the resultant mixture was stirred under a hydrogen atmosphere overnight. The catalyst was separated by filtration from the reaction solution which was then concentrated in vacuo. The title compound (221.1 mg, yield 100%) was obtained as a pale yellow oil.

$^1$H-NMR (CDCl$_3$) δ: 0.94 (3H, t, J=7.6 Hz), 1.62 (2H, qt, J=7.6, 7.6 Hz), 2.60 (2H, t, J=7.6 Hz), 3.56 (3H, s), 4.84 (2H, s), 5.77 (1H, brs), 6.81 (1H, d, J=8.6 Hz), 7.30 (1H, d, J=8.6 Hz) 7.33 (1H, s).

Preparation Example 2

Preparation of 4-(1,1,1,3,3,3-hexafluoro-2-(methoxymethoxy)propan-2-yl)-2-propylphenol a) Preparation of 2-(4-amino-3-propylphenyl)-1,1,1,3,3,3-hexafluoro-2-propanol

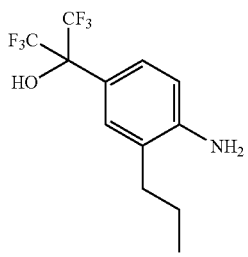

A mixture of 2-propylaniline (3.00 g, 21.2 mmol), trifluoroacetone hydrate (4.5 mL), and p-toluenesulfonic acid monohydrate (422 mg, 2.12 mmol) was allowed to react in a microwave reactor (Biotage: Initiator) at 170° C. for 1.5 hours. The reaction was conducted for 7 lots and in total, 20.86 g (0.15 mol) of 2-propylaniline was subjected to the reaction. The obtained reaction solutions were united, added with water, and extracted with ethyl acetate. The organic layer was washed with brine, dried using anhydrous sodium sulfate, and concentrated in vacuo. The obtained residue was purified using silica-gel column chromatography (hexane/ethyl acetate) and the title compound (34.70 g, yield 75%) was obtained as a yellow-brown crystalline powder.

$^1$H-NMR (CDCl$_3$) δ: 0.94 (3H, t, J=7.4 Hz), 1.65 (2H, qt, J=7.6, 7.6 Hz), 2.68 (2H, t J=7.6 Hz), 3.39 (1H, s), 5.10 (2H, s), 6.93 (1H, dd, J=2.3, 7.3 Hz), 7.30-7.51 (2H, m).

b) Preparation of 2-(4-hydroxy-3-propylphenyl)-1,1,1,3,3,3-hexafluoro-2-propanol

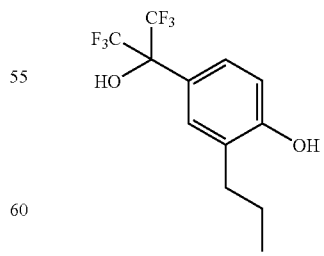

With reference to the method of U.S. Patent Publication No. 3396159, the title compound was obtained as a colorless oil from 2-(4-amino-3-propylphenyl)-1,1,1,3,3,3-hexafluoro-2-propanol.

¹H-NMR (CDCl₃) δ: 0.97 (3H, t, J=7.3 Hz), 1.57-1.72 (2H, m), 2.61 (2H, t, J=7.5 Hz), 3.39 (1H, s), 4.97 (1H, s), 6.82 (1H, d, J=8.4 Hz), 7.39-7.44 (2H, m).

c) Preparation of 2-propyl-4-(1,1,1,3,3,3-hexafluoro-2-hydroxypropan-2-yl)phenylacetate

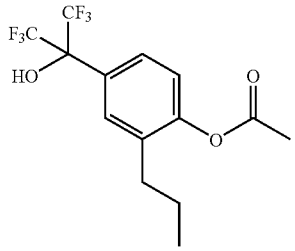

2-(4-Hydroxy-3-propylphenyl)-1,1,1,3,3,3-hexafluoro-2-propanol (13.76 g, 45.5 mmol) in dichloromethane (200 mL) was added with pyridine (14.7 mL) at room temperature and then with acetic anhydride (17.3 mL). After stirred overnight, the mixture was added with methanol (300 mL) and further stirred at room temperature for 1 hour. The reaction solution was then concentrated in vacuo. The obtained residue was added with water and extracted with ethyl acetate. The organic layer was washed with brine, dried using anhydrous sodium sulfate, and concentrated in vacuo. The obtained residue was purified using silica-gel column chromatography (hexane/ethyl acetate) and the title compound (13.67 g, yield 87%) was obtained as a red-brown oil.

¹H-NMR (CDCl3) δ: 0.96 (3H, t, J=7.6 Hz), 1.59 (2H, qt, J=7.6, 7.6 Hz), 2.33 (3H, s), 2.53 (2H, t, J=7.6 Hz), 4.75 (1H, brs), 7.10 (1H, d, J=8.6 Hz), 7.55 (1H, d, J=8.6 Hz), 7.59 (1H, s).

d) Preparation of 4-(1,1,1,3,3,3-hexafluoro-2-(methoxymethoxy)propan-2-yl)-2-propylphenol

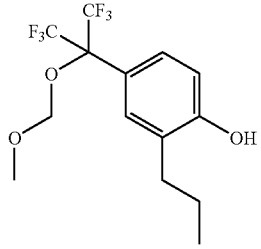

2-Propyl-4-(1,1,1,3,3,3-hexafluoro-2-hydroxypropan-2-yl)phenylacetate (13.67 g, 39.7 mmol) in dichloromethane (160 mL) was added with N,N-diisopropylethylamine (27.6 mL) and then with chloromethyl methyl ether (6.0 mL). The resultant mixture was stirred at 40° C. for 18 hours, added with methanol at room temperature (20 mL), stirred for 1.5 hours, then added with potassium carbonate (11 g, 39.7 mmol), and stirred overnight. The reaction solution was added with water and extracted with ethyl acetate. The organic layer was washed with brine, dried using anhydrous sodium sulfate, and concentrated in vacuo. The obtained residue was purified using silica-gel column chromatography (hexane/ethyl acetate) and the title compound (10.87 g, yield 79%) was obtained as a pale yellow oil.

¹H-NMR (CDCl3) δ: 0.94 (3H, t, J=7.6 Hz), 1.62 (2H, qt, J=7.6, 7.6 Hz), 2.60 (2H, t, J=7.6 Hz), 3.56 (3H, s), 4.84 (2H, s), 5.77 (1H, brs), 6.81 (1H, d, J=8.6 Hz), 7.30 (1H, d, J=8.6 Hz) 7.33 (1H, s).

Preparation Example 3

Preparation of 1-(3-(bromomethyl)phenoxy)-4-(1,1,1,3,3,3-hexafluoro-2-(methoxymethoxy(propan-2-yl)-2-propylbenzene a) Preparation of (3-(4-(1,1,1,3,3,3-hexafluoro-2-(methoxymethoxy)propan-2-yl)-2-propylphenoxy)phenyl) methanol

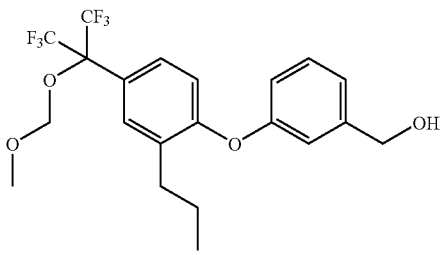

A solution of 4-(1,1,1,3,3,3-hexafluoro-2-(methoxymethoxy)propan-2-yl)-2-propylphenol (1.58 g, 4.56 mmol) in dichloromethane (45 mL) was added with molecular sieves 4 A (3.00 g), 3-(hydroxymethyl)phenylbronic acid (2.08 g), copper acetate(II) (1.66 g) at room temperature, and then with pyridine (1.85 mL). The resultant mixture was stirred for 12 hours. The reaction solution was filtered using celite and the filtrate was concentrated in vacuum. The residue was purified using silica-gel column chromatography (hexane/ethyl acetate) and the title compound (1.65 g, yield 80%) was obtained as a colorless crystalline powder.

¹H-NMR (CDCl₃) δ: 0.95 (3H, t, J=7.6 Hz), 1.62-1.71 (2H, m), 2.68 (2H, t, J=7.6 Hz), 3.56 (3H, s), 4.70-4.71 (2H, m), 4.86 (2H, s), 6.83 (1H, d, J=8.9 Hz), 6.90-6.92 (1H, m), 7.03-7.15 (2H, m), 7.31-7.47 (3H, m).

b) Preparation of 1-(3-(bromomethyl)phenoxy)-4-(1,1,1,3,3,3-hexafluoro-2-(methoxymethoxy)propan-2-yl)-2-propylbenzene:

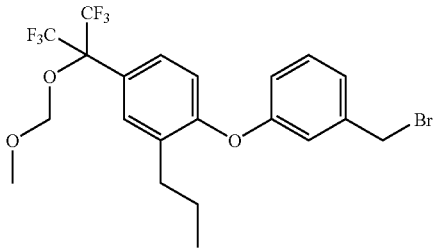

A solution of (3-(4-(1,1,1,3,3,3-hexafluoro-2-(methoxymethoxy)propan-2-yl)-2-propylphenoxy)phenyl) methanol (1.09 g, 2.40 mmol) in methylene chloride (24 mL) was added with triphenylphosphine (0.95 g) and carbon tetrabromide (1.27 g) at 0° C. After completion of the reaction, the reaction solution was concentrated in vacuo. The obtained residue was purified using silica-gel column chromatography (hexane/ethyl acetate) and the title compound (1.04 g, yield 85%) was obtained as a colorless oil.

¹H-NMR (CDCl₃) δ: 0.95 (3H, t, J=7.3 Hz), 1.59-1.70 (2H, m), 2.67 (2H, t, J=7.3 Hz), 3.56 (3H, s), 4.47 (2H, s), 4.86 (2H, s), 6.84 (1H, d, J=8.9 Hz), 6.90 (1H, ddd, J=1.0, 2.0, 8.0 Hz), 7.05 (1H, dd, J=1.0, 1.5 Hz), 7.16 (1H, ddd, J=1.5, 2.0, 8.0 Hz), 7.30-7.48 (3H, m).

Preparation Example 4

Preparation of (3-(4-(1,1,1,3,3,3-hexafluoro-2-(methoxymethoxy)propan-2-yl)-2-propylphenoxy)phenyl) methanol a) Preparation of 3-(4-(1,1,1,3,3,3-hexafluoro-2-(methoxymethoxy)propan-2-yl)-2-propylphenoxy) benzaldehyde

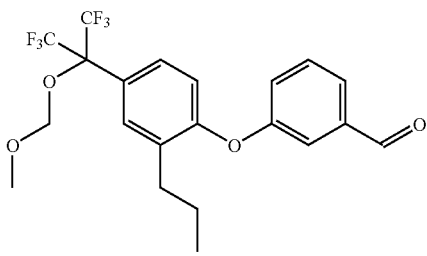

3-Formylboronic acid was used in place of 3-(hydroxymethyl)phenylboronic acid for a similar reaction and treatment as Preparation example 3 a), and the compound of interest was obtained as a colorless oil.

¹H-NMR (CDCl₃) δ: 0.94 (3H, t, J=7.6 Hz), 1.63-1.69 (2H, m), 2.64 (2H, t, J=7.3 Hz), 3.56 (3H, s), 4.87 (2H, s), 6.87 (1H, d, J=8.9 Hz), 7.24-7.66 (5H, m), 7.89 (1H, d, J=8.4 Hz), 9.99 (1H, s).

b) Preparation of (3-(4-(1,1,1,3,3,3-hexafluoro-2-(methoxymethoxy)propan-2-yl)-2-propylphenoxy) phenyl) methanol

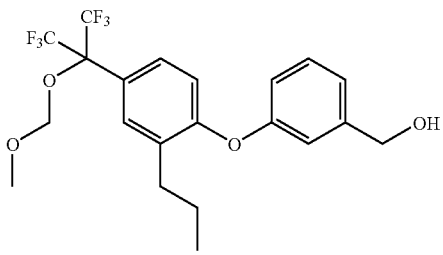

To a solution of 3-(4-(1,1,1,3,3,3-hexafluoro-2-(methoxymethoxy)propan-2-yl)-2-propylphenoxy)benz aldehyde (1.79 g, 3.97 mmol) in methanol, sodium borohydride (0.16 g) was added at 0° C. After completion of the reaction, the reaction solution was added with water, extracted with ethyl acetate, and then concentrated in vacuo. The obtained residue was purified using thin-layer silica-gel column chromatography (hexane/ethyl acetate) and the title compound (1.79 g, yield 100%) was obtained as a colorless oil.

¹H-NMR (CDCl₃) δ: 0.95 (3H, t, J=7.6 Hz), 1.62-1.71 (2H, m), 2.68 (2H, t, J=7.6 Hz), 3.56 (3H, s), 4.70-4.71 (2H, m), 4.86 (2H, s), 6.83 (1H, d, J=8.9 Hz), 6.90-6.92 (1H, m), 7.03-7.15 (2H, m), 7.31-7.47 (3H, m).

Example 1

Preparation of 5-(benzo[d][1,3]dioxol-5-yl)-3-(3-(4-(1,1,1,3,3,3-hexafluoro-2-hydroxypropan-2-yl)-2-propylphenoxy)benzyl)-5-methylimidazolidine-2,4-dione

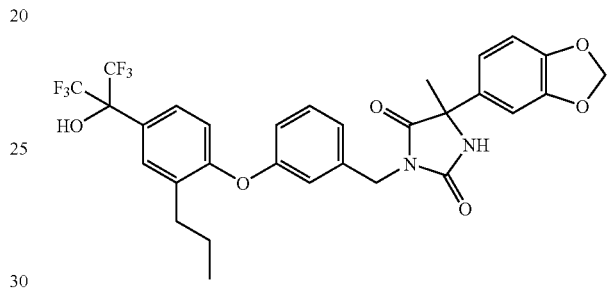

1-a) Preparation of 5-(benzo[d][1,3]dioxol-5-yl)-5-methylimidazolidine-2,4-dione 1-(Benzo[d][1,3]dioxol-5-yl)ethanone (446 mg, 2.72 mmol) was dissolved in ethanol (200 mL) and water (200 mL). The resultant mixture was added with sodium cyanide (200 mg, 4.08 mmol) and ammonium carbonate (918 mg, 9.55 mmol) and stirred at 70° C. overnight. The reaction solution was filtered, washed with water and hexane/ethyl acetate, and dried using anhydrous sodium sulfate. 5-(Benzo[d][1,3]dioxol-5-yl)-5-methylimidazolidine-2,4-dione (326 mg, yield 51.2%) was obtained as a white crystal.

¹H-NMR (CDCl₃) δ: 1.83 (3H, s), 5.99 (2H, s), 6.81 (1H, d, J=8.3 Hz), 6.95 (1H, dd, J=2.2, 8.3 Hz), 6.99 (1H, d, J=2.2 Hz).

To a solution of 1-(3-(bromomethyl)phenoxy)-4-(1,1,1,3,3,3-hexafluoro-2-(methoxymethoxy)propan-2-yl)-2-propylbenzene (15.5 mg, 30.0 μmol) in N,N-dimethylformamide (0.25 mL), potassium carbonate (8.3 mg) and 5-(benzo[d][1,3]dioxol-5-yl)-5-methylimidazolidine-2,4-dione (156 mg) were added, and the resultant mixture was stirred overnight. The reaction solution was neutralized by adding 2 mol/L of hydrochloric acid, added with water, and extracted with ethyl acetate. Subsequently, the organic layer was washed with brine, dried using anhydrous sodium sulfate, and concentrated in vacuo. The obtained residue was added with 2 mol/L of hydrogen chloride-ethyl acetate solution (1 mL) at room temperature. After completion of the reaction, the solution was concentrated in vacuo and the residue was purified using thin-layer silica-gel column chromatography (hexane/ethyl acetate) and the title compound (9.1 mg, yield 57%) was obtained as a colorless oil.

$^1$H-NMR (CDCl$_3$) δ: 0.93 (3H, t, J=7.3 Hz), 1.58-1.68 (2H, m), 1.76 (3H, s), 2.64 (2H, t, J=7.6 Hz), 3.60 (1H, s), 4.64 (2H, s), 5.73 (2H, s), 6.73-7.56 (10H, m).

Example 2

Preparation of 5-(benzo[d][1,3]dioxol-5-yl)-5-ethyl-3-(3-(4-(1,1,1,3,3,3-hexafluoro-2-hydroxypropan-2-yl)-2-propylphenoxy)benzyl)imidazolidine-2,4-dione

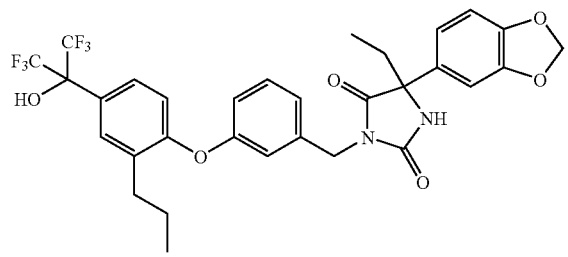

2-a) Preparation of 5-(benzo[d][1,3]dioxol-5-yl)-5-ethylimidazolidine-2,4-dione 2-a-1) Preparation of 1-(benzo[d][1,3]dioxol-5-yl)propan-1-one To a solution of 1-(benzo[d][1,3]dioxol-5-yl)nitrile (20 g, 136 mmol) in tetrahydrofuran (680 mL), ethylmagnesium bromide (204 mL) was added under ice-cold conditions, and the resultant mixture was stirred under ice-cold conditions for 2 hours and then at room temperature overnight. Under ice-cold conditions, the reaction solution was added with water and 1M sulfuric acid and extracted with ethyl acetate. Subsequently, the organic layer was washed with saturated sodium hydrogen carbonate and brine, dried using anhydrous sodium sulfate, and concentrated in vacuo. The obtained residue was purified using thin-layer silica-gel column chromatography (hexane/ethyl acetate) and 1-(benzo[d][1,3]dioxol-5-yl)propan-1-one (17.7 g, yield 73%) was obtained as a yellow oil.

$^1$H-NMR (CDCl$_3$) δ: 1.21 (3H, t, J=7.3 Hz), 2.93 (2H, q, J=7.3 Hz), 6.04 (2H, s), 6.85 (1H, d, J=8.1 Hz), 7.45 (1H, d, J=1.7 Hz), 7.57 (1H, dd, J=1.7, 8.1 Hz).

2-a-2) Preparation of 5-(benzo[d][1,3]dioxol-5-yl)-5-ethylimidazolidine-2,4-dione 1-(Benzo[d][1,3]dioxol-5-yl)propan-1-one was used for a similar reaction and treatment as Example 1-a), and 5-(benzo[d][1,3]dioxol-5-yl)-5-ethylimidazolidine-2,4-dione was obtained as a white crystal.

$^1$H-NMR (CDCl$_3$) δ: 0.80 (3H, t, J=7.3 Hz), 1.97-2.21 (2H, m), 4.21 (2H, s), 6.81 (1H, d, J=8.1 Hz), 6.93 (1H, dd, J=2.2, 8.1 Hz), 6.95 (1H, d, J=2.2 Hz).

5-(benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.80 (3H, t, J=7.3 Hz), 0.92 (3H, t, J=7.3 Hz), 1.57-1.66 (2H, m), 1.97-2.21 (2H, m), 2.63 (2H, t, J=7.6 Hz), 3.84 (1H, s), 4.63 (2H, s), 5.95 (1H, s), 6.16 (1H, s), 6.73-7.55 (10H, m).

Example 3

Preparation of 5-(2,3-dihydrobenzo[b][1,4]dioxin-6-yl)-3-(3-(4-(1,1,1,3,3,3-hexafluoro-2-hydroxypropan-2-yl)-2-propylphenoxy)benzyl)-5-methylimidazolidine-2,4-dione

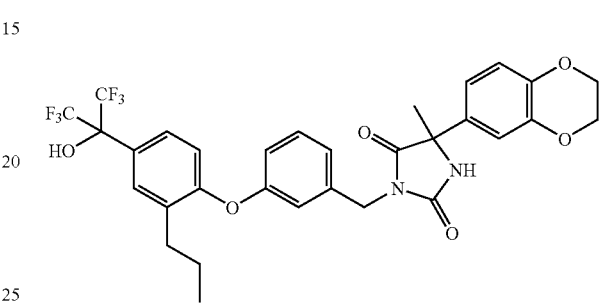

3-a) Preparation of 5-(2,3-dihydrobenzo[b][1,4]dioxin-6-yl)-5-methylimidazolidine-2,4-dione 1,4-Benzodioxan-6-yl methyl ketone was used for a similar reaction and treatment as Example 1-a), and 5-(2,3-dihydrobenzo[b][1,4]dioxin-6-yl)-5-methylimidazolidine-2,4-dione was obtained as a white crystal.

$^1$H-NMR (CDCl$_3$) δ: 1.73 (3H, s), 4.21 (4H, s), 7.39 (1H, d, J=8.0 Hz), 7.43 (1H, dd, J=2.7, 8.0 Hz), 7.84 (1H, d, J=2.7 Hz).

5-(2,3-dihydrobenzo[b][1,4]dioxin-6-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.93 (3H, t, J=7.3 Hz), 1.56-1.70 (2H, m), 1.74 (3H, s), 2.64 (2H, 1, J=7.6 Hz), 4.21-4.30 (4H, m), 4.63 (2H, s), 5.86 (1H, s), 6.75-6.96 (5H, m), 7.05-7.08 (1H, m), 7.14-7.29 (2H, m), 7.39-7.44 (1H, m), 7.54-7.56 (1H, m).

Example 4

Preparation of 5-(2,3-dihydrobenzo[b][1,4]dioxin-6-yl)-5-ethyl-3-(3-(4-(1,1,1,3,3,3-hexafluoro-2-hydroxypropan-2-yl)-2-propylphenoxy)benzyl)imidazolidine-2,4-dione

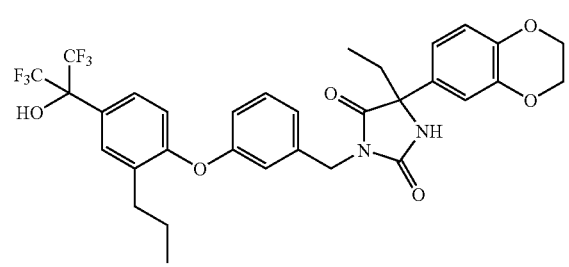

4-a) Preparation of 5-(2,3-dihydrobenzo[b][1,4]dioxin-6-yl)-5-ethylimidazolidine-2,4-dione

4-a-1) Preparation of 1-(2,3-dihydrobenzo[b][1,4]dioxin-6-yl)propan-1-one 1-(2,3-Dihydrobenzo[b][1,4]dioxin-6-yl)nitrile was used for a similar reaction and treatment as Example 2-a), and 1-(2,3-dihydrobenzo[b][1,4]dioxin-6-yl)propan-1-one was obtained as a white crystal.

$^1$H-NMR (CDCl$_3$) δ: 1.21 (3H, t, J=7.3 Hz), 2.93 (2H, q, J=7.3 Hz), 5.64 (4H, s), 6.45 (1H, d, J=8.1 Hz), 7.05 (1H, d, J=1.7 Hz), 7.17 (1H, dd, J=1.7, 8.1 Hz).

4-a-2) 1-(2,3-Dihydrobenzo[b][1,4]dioxin-6-yl)propan-1-one was used for a similar reaction and treatment as Example 1-a), and 5-(2,3-dihydrobenzo[b][1,4]dioxin-6-yl)-5-ethylimidazolidine-2,4-dione was obtained as a white crystal.

$^1$H-NMR (CDCl$_3$) δ: 1.69 (3H, t, J=7.3 Hz), 1.97-2.21 (m), 4.21 (4H, s), 6.81 (1H, d, J=8.1 Hz), 6.93 (1H, dd, J=2.2, 8.1 Hz), 6.95 (1H, d, J=2.2 Hz).

5-(2,3-dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.80 (3H, t, J=7.3 Hz), 0.93 (3H, t, J=7.3 Hz), 1.59-1.68 (2H, m), 1.98-2.22 (2H, m), 2.64 (2H, t, J=7.6 Hz), 3.83 (1H, s), 4.23-4.24 (4H, m), 4.62 (2H, s), 5.71 (1H, s), 6.73-7.55 (10H, m).

Example 5

Preparation of 5-(2,3-dihydrobenzofuran-5-yl)-3-(3-(4-(1,1,1,3,3,3-hexafluoro-2-hydroxypropan-2-yl)-2-propylphenoxy)benzyl)-5-methylimidazolidine-2,4-dione

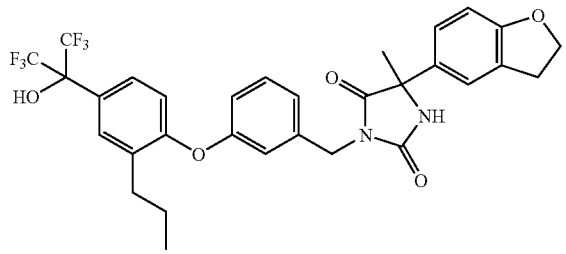

5-a) Preparation of 5-(2,3-dihydrobenzofuran-5-yl)-5-methylimidazolidine-2,4-dione 2,3-Dihydrobenzofuran (10 g, 83.2 mmol) was dissolved in dichloromethane (400 mL). The resultant mixture was added sequentially with acetyl chloride (11.8 mL, 167 mmol) and aluminum chloride (33.3 g, 250 mmol) at −10° C., and stirred at −10° C. for 0.5 hour. The reaction solution was added with 5% aqueous solution of hydrochloric acid and extracted with ethyl acetate. The organic layer was washed with a saturated aqueous solution of sodium hydrogen carbonate and brine, dried using anhydrous sodium sulfate, and concentrated in vacuo. 1-(2,3-Dihydrobenzofuran-5-yl)ethanone (13.4 g, yield 99%) was obtained as a colorless oil.

$^1$H-NMR (CDCl$_3$) δ: 2.55 (3H, s), 3.25 (2H, t, J=8.6 Hz), 4.67 (2H, t, J=8.6 Hz), 6.80 (1H, d, J=8.1 Hz), 7.80 (1H, dd, J=1.9, 8.1 Hz), 7.85 (1H, d, J=1.9 Hz).

1-(2,3-Dihydrobenzofuran-5-yl)ethanone was used for a similar reaction and treatment as Example 1-a), and 5-(2,3-dihydrobenzofuran-5-yl)-5-methylimidazolidine-2,4-dione was obtained as a white crystal.

$^1$H-NMR (CDCl$_3$) δ: 1.69 (3H, s), 3.32 (2H, t, J=8.6 Hz), 4.74 (2H, t, J=8.6 Hz), 6.87 (1H, d, J=8.8 Hz), 7.22 (1H, dd, J=2.2, 8.8 Hz), 7.34 (1H, d, J=2.2 Hz).

5-(2,3-Dihydrobenzofuran-5-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.93 (3H, t, J=7.3 Hz), 1.58-1.69 (2H, m), 1.77 (3H, s), 2.65 (2H, t, J=7.6 Hz), 3.12 (2H, t, J=8.3 Hz), 3.81 (1H, s), 4.56 (2H, t, J=8.3 Hz), 4.65 (2H, s), 5.83 (1H, s), 6.69-7.27 (8H, m), 7.39 (1H, d, J=8.6 Hz), 7.55 (1H, s).

Example 6

Preparation of 3-(3-(4-(1,1,1,3,3,3-hexafluoro-2-hydroxypropan-2-yl)-2-propylphenoxy)benzyl)-5-methyl-5-(quinoxaline-6-yl)imidazolidine-2,4-dione

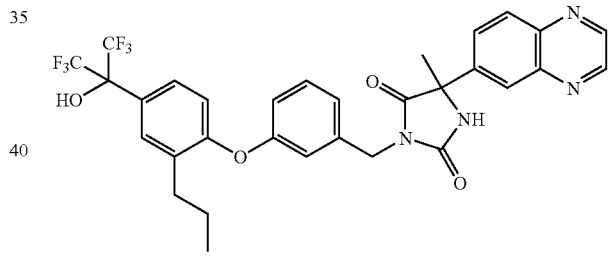

6-a) Preparation of 5-methyl-5-(quinoxalin-6-yl)imidazolidine-2,4-dione

5-Methyl-5-(quinoxalin-6-yl)imidazolidine-2,4-dione was obtained according to the method described in Japanese Laid-Open Patent Application No. 63-280080.

$^1$H-NMR (CDCl$_3$) δ: 1.91 (3H, s), 8.07 (1H, dd, J=2.2, 8.8 Hz), 8.15 (1H, d, J=8.8 Hz), 8.25 (1H, d, J=2.2 Hz), 8.90 (1H, d, J=2.0 Hz), 8.92 (1H, d, J=2.0 Hz).

5-Methyl-5-(quinoxalin-6-yl)imidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.81 (3H, t, J=7.3 Hz), 1.43-1.53 (2H, m), 1.93 (3H, s), 2.55 (2H, t, J=7.6 Hz), 4.67 (2H, s), 5.03 (1H, s), 6.67-7.30 (6H, m), 7.40-7.55 (2H, m), 7.90-8.30 (3H, m), 8.88-8.90 (2H, m).

Example 7

Preparation of 3-(3-(4-(1,1,1,3,3,3-hexafluoro-2-hydroxypropan-2-yl)-2-propylphenoxy)benzyl)-5-(4-methoxyphenyl)-5-methylimidazolidine-2,4-dione

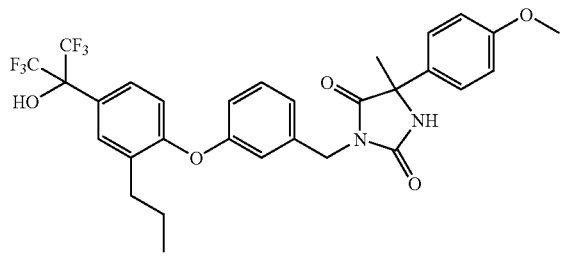

7-a) Preparation of 5-(4-methoxyphenyl)-5-methylimidazolidine-2,4-dione 1-(1-Methoxyphenyl-4-yl)ethanone was used for a similar reaction and treatment as Example 1-a), and 5-(4-methoxyphenyl)-5-methylimidazolidine-2,4-dione was obtained as a white crystal.

$^1$H-NMR (DMSO) δ: 1.78 (3H, s), 3.69 (3H, s), 6.95 (2H, d, J=8.4 Hz), 7.40 (2H, d, J=8.4 Hz), 8.58 (1H, s), 10.71 (1H, s).

5-(4-Methoxyphenyl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.92 (3H, t, J=7.3 Hz), 1.56-1.67 (2H, m), 1.78 (3H, s), 2.63 (2H, t, J=7.6 Hz), 3.77 (3H, s), 3.78 (1H, s), 4.64 (2H, s), 6.74-7.56 (11H, m).

Example 8

Preparation of 3-(3-(4-(1,1,1,3,3,3-hexafluoro-2-hydroxypropan-2-yl)-2-propylphenoxy)benzyl)-5-(2-methoxyphenyl)-5-methylimidazolidine-2,4-dione

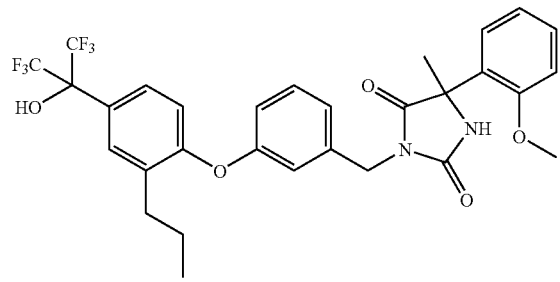

8-a) Preparation of 5-(2-methoxyphenyl)-5-methylimidazolidine-2,4-dione 1-(1-Methoxyphenyl-2-yl)ethanone was used for a similar reaction and treatment as Example 1-a), and 5-(2-methoxyphenyl)-5-methylimidazolidine-2,4-dione was obtained as a white crystal.

$^1$H-NMR (DMSO) δ: 1.63 (3H, s), 3.71 (3H, s), 6.94-7.04 (2H, m), 7.32-7.40 (2H, m), 7.93 (1H, s), 10.59 (1H, s).

5-(2-Methoxyphenyl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.93 (3H, t, J=7.3 Hz), 1.57-1.71 (2H, m), 1.75 (3H, s), 2.65 (2H, t, J=7.6 Hz), 3.70 (3H, s), 3.79 (1H, s), 4.71 (2H, s), 6.20 (1H, s), 6.79 (1H, d, J=8.6 Hz), 6.81-7.57 (10H, m).

Example 9

Preparation of 3-(3-(4-(1,1,1,3,3,3-hexafluoro-2-hydroxypropan-2-yl)-2-propylphenoxy)benzyl)-5-(4-(1-methylethoxy)phenyl)-5-methylimidazolidine-2,4-dione

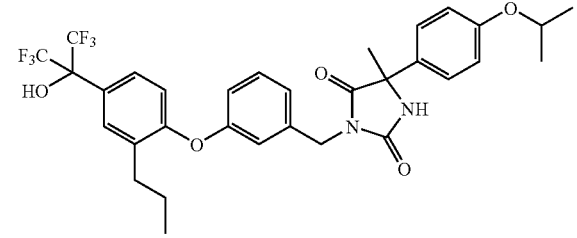

9-a-1) Preparation of 1-[4-(1-methylethoxy)phenyl]ethanone 1-(4-Hydroxyphenyl)ethanone (15.0 g, 110 mmol) was dissolved in acetone (125 mL). The resultant mixture was sequentially added with potassium carbonate (30.4 g, 220 mmol) and 1-methylethyl iodide (16.5 mL, 165 mmol) and then stirred at 70° C. for 8 hours. The reaction solution was filtered, washed with acetone, and concentrated in vacuo. The obtained residue was added with water and ethyl acetate, and then extracted with ethyl acetate. The organic layer was washed with 1N aqueous solution of sodium hydroxide and brine, dried using anhydrous sodium sulfate, and concentrated in vacuo. 1-[4-(1-Methylethoxy)phenyl]ethanone (18.2 g, yield 93%) was obtained as a white crystal.

$^1$H-NMR (CDCl$_3$) δ: 1.37 (6H, d, J=5.9 Hz), 2.56 (3H, s), 4.65 (1H, sept, J=5.9 Hz), 6.90 (2H, d, J=8.9 Hz). 7.92 (2H, d, J=8.9 Hz).

9-a-2) Preparation of 5-(4-(1-methylethoxy) phenyl)-5-methylimidazolidine-2,4-dione 1-[4-(1-methylethoxy)phenyl]ethanone was used for a similar reaction and treatment as Example 1-a), and 5-(4-(1-methylethoxy)phenyl)-5-methylimidazolidine-2,4-dione was obtained as a white crystal.

$^1$H-NMR (CDCl$_3$) δ: 1.28 (6H, d, J=5.9 Hz), 1.72 (3H, s), 4.59 (1H, sept, J=5.9 Hz), 6.89 (2H, d, J=8.6 Hz), 7.38 (2H, d, J=8.6 Hz).

5-(4-(1-Methylethoxy)phenyl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

¹H-NMR (CDCl₃) δ: 0.93 (3H, t, J=7.3 Hz), 1.31 (61-1, d, J=5.4 Hz), 1.56-1.68 (2H, m), 1.78 (3H, s), 2.64 (2H, t, J=7.6 Hz), 3.67 (1H, s), 4.52 (1H, sept, J=5.4 Hz), 4.64 (2H, s), 5.71 (1H, s), 6.74-7.40 (11H, m).

Example 10

Preparation of 5-(4-butoxyphenyl)-3-(3-(4-(1,1,1,3,3,3-hexafluoro-2-hydroxypropan-2-yl)-2-propylphenoxy) benzyl)-5-methylimidazolidine-2,4-dione

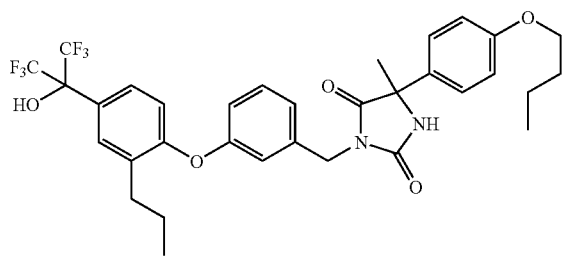

10-a-1) Preparation of 1-(4-butoxyphenyl)ethanone

1-Butyl iodide was used for a similar reaction and treatment as Example 9-a-1), and 1-(4-butoxyphenyl)ethanone was obtained as a white crystal.

¹H-NMR (CDCl₃) δ: 0.97 (3H, t, J=7.3 Hz), 1.41-1.49 (2H, m), 1.70-1.81 (2H, m), 2.50 (3H, s), 3.97 (2H, t, J=7.3 Hz), 6.88 (2H, d, J=8.9 Hz), 7.88 (2H, d, J=8.9 Hz).

10-a-2) Preparation of 5-(4-butoxyphenyl)-5-methylimidazolidine-2,4-dione

1-[4-(1-Butoxy)phenyl]ethanone was used for a similar reaction and treatment as Example 1-a), and 5-(4-butoxyphenyl)-5-methylimidazolidine-2,4-dione was obtained as a white crystal.

¹H-NMR (DMSO) δ: 0.92 (3H, t, J=7.3 Hz), 1.35-1.73 (4H, m), 3.95 (2H, t, J=7.3 Hz), 6.93 (2H, d, J=8.9 Hz), 7.34 (2H, d, J=8.9 Hz), 8.52 (1H, s), 10.69 (1H, s).

5-(4-Butoxyphenyl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

¹H-NMR (CDCl₃) δ: 0.89-0.99 (6H, m), 1.40-1.80 (6H, m), 1.77 (3H, s), 2.64 (2H, t, J=7.6 Hz), 3.74 (1H, s), 3.93 (2H, t, J=6.5 Hz), 4.64 (2H, s), 5.80 (1H, s), 6.76 (1H, d, J=8.6 Hz), 6.82-6.88 (3H, m), 6.93 (1H, dd, J=1.0, 1.0 Hz), 7.04-7.08 (1H, m), 7.15-7.55 (5H, m).

Example 11

Preparation of 3-(3-(4-(1,1,1,3,3,3-hexafluoro-2-hydroxypropan-2-yl)-2-propylphenoxy)benzyl)-5-methyl-5-(4-(4-methylbenzyloxy)phenyl)idmidazolidine-2,4-dione

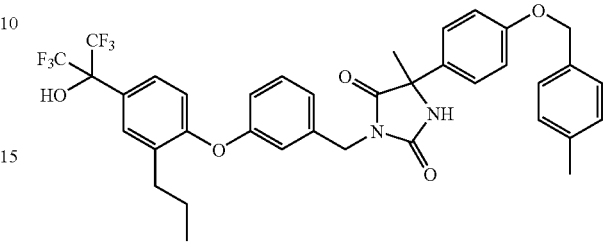

11-a-1) Preparation of 1-[4-(1-(4-methylphenylmethoxy))phenyl]ethanone

4-Methylbenzyl bromide was used for a similar reaction and treatment as Example 9-a-1), and the title compound was obtained as a white crystal.

¹H-NMR (CDCl₃) δ: 2.35 (3H, s), 2.50 (3H, s), 4.99 (2H, s), 6.90-6.96 (4H, m), 7.29 (2H, d, J=7.8 Hz), 7.33 (2H, d, J=8.9 Hz).

11-a-2) Preparation of 5-methyl-5-(4-(1-methylbenzyloxy)phenyl)imidazolidine-2,4-dione 1-[4-(1-(4-Methyl phenylmethoxy))phenyl]ethanone was used for a similar reaction and treatment as Example 1-a), and 5-methyl-5-(4-(4-methyl benzyloxy)phenyl)imidazolidine-2,4-dione was obtained as a white crystal.

¹H-NMR (CDCl₃) δ: 1.74 (3H, s), 2.35 (3H, s), 4.99 (2H, s), 5.80 (1H, s), 6.90-6.96 (4H, m), 7.29 (2H, d, J=7.8 Hz), 7.33 (2H, d, J=8.9 Hz), 8.60 (1H, s).

5-Methyl-5-(4-(4-methylbenzyloxy)phenyl)imidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

¹H-NMR (CDCl₃) δ: 0.93 (3H, t, J=7.3 Hz), 1.56-1.70 (2H, m), 1.76 (3H, s), 2.34 (3H, s), 2.64 (2H, t, J=7.6 Hz), 3.70 (1H, s), 4.63 (2H, s), 4.99 (2H, s), 5.80 (1H, s), 6.77 (1H, d, J=8.6 Hz), 6.83-7.55 (14H, m).

Example 12

Preparation of 3-(3-(4-(1,1,1,3,3,3-hexafluoro-2-hydroxypropan-2-yl)-2-propylphenoxy)benzyl)-5-(6-methoxypyridin-3-yl)-5-methylimidazolidine-2,4-dione

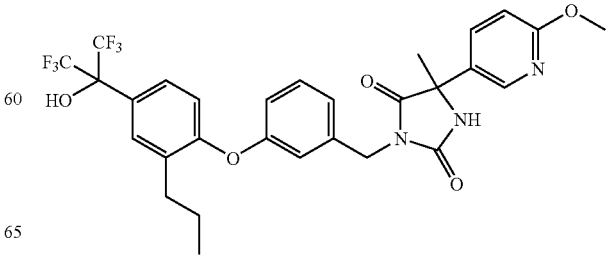

12-a) Preparation of 5-(6-methoxypyridin-3-yl)-5-methylimidazolidine-2,4-dione 1-(6-Methoxypyridin-3-yl)ethanone was used for a similar reaction and treatment as Example 1-a), and 5-(6-methoxypyridin-3-yl)-5-methylimidazolidine-2,4-dione was obtained as a white crystal.

$^1$H-NMR (CDCl$_3$) δ: 1.74 (3H, s), 3.90 (3H, s), 6.81 (1H, d, J=8.6 Hz), 7.81 (1H, dd, J=2.7, 8.6 Hz), 8.23 (1H, d, J=2.7 Hz).

5-(6-Methoxypyridin-3-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.86 (3H, t, J=7.3 Hz), 1.51-1.59 (2H, m), 1.76 (3H, s), 2.57 (2H, t, J=7.6 Hz), 4.10 (3H, s), 4.64 (2H, s), 6.70-7.30 (6H, m), 7.40-7.56 (2H, m), 7.83-7.84 (1H, m), 8.10-8.20 (1H, m).

Example 13

Preparation of 5-(6-ethoxypyridin-3-yl)-3-(3-(4-(1,1,1,3,3,3-hexafluoro-2-hydroxypropan-2-yl)-2-propylphenoxy) benzyl)-5-methylimidazolidine-2,4-dione

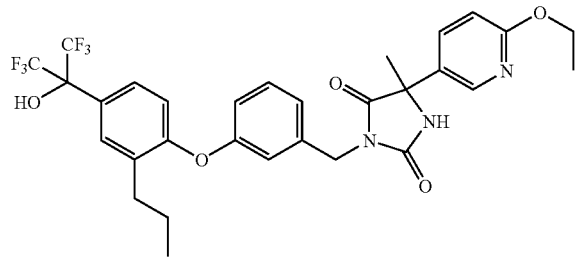

13-a-1) Preparation of 6-chloro-N-methylnicotinamide

To a solution of 6-chloro-N-methylnicotinoyl chloride (7.39 g, 42.0 mmol) in tetrahydrofuran (50 mL), methylamine (42 mL, 84.0 mmol) and triethylamine (6.4 mL, 46.2 mmol) were added under ice-cold conditions, and the resultant mixture was stirred at room temperature for 3 hours. After completion of the reaction, the reaction solution was concentrated in vacuo, then filtered, and washed with tetrahydrofuran. The obtained residue was recrystallized (ethyl acetate/hexane) and 6-chloro-N-methylnicotinamide (6.52 g, yield 91%) was obtained as a white crystal.

$^1$H-NMR (CDCl$_3$) δ: 3.04 (3H, d, J=4.9 Hz), 6.39 (1H, brs), 7.41 (1H, d, J=8.6 Hz), 8.10 (1H, dd, J=2.4, 8.6 Hz), 8.74 (1H, d, J=2.4 Hz).

13-a-2) Preparation of 6-ethoxy-N-methylnicotinamide

To a solution of 6-chloro-N-methylnicotinamide (500 mg, 2.93 mmol) in ethanol (10 mL), sodium hydride (purity 50%) (176 mg, 7.33 mmol) was added under ice-cold conditions. The resultant mixture was heated to reflux for 8 hours. After completion of the reaction, the reaction solution was concentrated in vacuo, then filtered, washed with water and ethyl acetate, and then dried. 6-Ethoxy-N-methylnicotinamide (556 mg, yield >100%) was obtained as a white crystal.

$^1$H-NMR (CDCl$_3$) δ: 1.41 (3H, t, J=7.3 Hz), 3.02 (3H, d, J=4.9 Hz), 4.40 (2H, q, J=7.3 Hz), 6.01 (1H, brs), 6.75 (1H, d, J=8.6 Hz), 7.99 (1H, dd, J=2.4, 8.6 Hz), 8.53 (1H, d, J=2.4 Hz).

13-a-3) Preparation of 6-ethoxy-N-methoxy-N-methylnicotinamide

To a solution of 6-ethoxy-N-methylnicotinamide (556 mg, 3.09 mmol) in ethanol (10 mL), 4N aqueous solution of sodium hydroxide (4.0 mL) was added under ice-cold conditions, and the resultant mixture was stirred at 50° C. overnight. After completion of the reaction, the reaction solution was concentrated in vacuo, then added with 4N aqueous solution of hydrochloric acid, and extracted with chloroform. The organic layer was washed with a saturated aqueous solution of sodium hydrogen carbonate and concentrated in vacuo. To a solution of the obtained crude product in ethanol (10 mL), 4N aqueous solution of hydrochloric acid (4.0 mL) was added under ice-cold conditions and the resultant mixture was stirred at 50° C. overnight. After completion of the reaction, the reaction solution was concentrated in vacuo, then added with 4N aqueous solution of sodium hydroxide, and extracted with chloroform. The organic layer was washed with a saturated aqueous solution of sodium hydrogen carbonate and brine and concentrated in vacuo. Subsequently, the obtained crude product was dissolved in thionyl chloride (3.0 mL) and the resultant mixture was stirred at room temperature for 1 hour. After completion of the reaction, the reaction solution was concentrated in vacuo. The obtained residue was dissolved in dichloromethane (3.0 mL). The resultant mixture was added with N,O-dimethylhydroxyamine hydrochloride (643 mg, 6.60 mmol) and diisopropylethylamine (223 µL, 1.28 mmol) and stirred at room temperature overnight. After completion of the reaction, the reaction solution was added with water and extracted with ethyl acetate. The organic layer was washed with brine, dried over sodium sulfate, and concentrated in vacuo. The obtained residue was purified using column chromatography (hexane/ethyl acetate) and 6-ethoxy-N-methoxy-N-methylnicotinamide (493 mg, 2.35 mmol) was obtained as a yellow oil.

$^1$H-NMR (CDCl$_3$) δ: 1.41 (3H, t, J=7.3 Hz), 3.38 (3H, s), 3.58 (3H, s), 4.41 (2H, q, J=7.3 Hz), 6.73 (1H, d, J=8.6 Hz), 7.99 (1H, dd, J=2.2, 8.6 Hz), 8.63 (1H, d, J=2.2 Hz).

13-a-4) Preparation of 1-(6-ethoxypyridin-3-yl)ethanone

6-Ethoxy-N-methoxy-N-methylnicotinamide was used for a similar reaction and treatment as Example 2-a), and the title compound of 1-(6-ethoxypyridin-3-yl)ethanone was obtained as a white crystal.

$^1$H-NMR (CDCl$_3$) δ: 1.42 (3H, t, J=7.3 Hz), 2.57 (3H, s), 4.44 (2H, q, J=7.3 Hz), 6.76 (1H, d, J=8.6 Hz), 8.14 (1H, dd, J=2.4, 8.6 Hz), 8.76 (1H, d, J=2.4 Hz).

13-a-5) Preparation of 5-(6-ethoxypyridin-3-yl)-5-methylimidazolidine-2,4-dione 1-(6-Ethoxypyridin-3-yl)ethanone was used for a similar reaction and treatment as Example 1-a), and 5-(6-ethoxypyridin-3-yl)-5-methylimidazolidine-2,4-dione was obtained as a white crystal.

¹H-NMR (CDCl₃) δ: 1.74 (3H, s), 3.90 (3H, s), 6.81 (1H, d, J=8.6 Hz), 7.81 (1H, dd, J=2.7, 8.6 Hz), 8.23 (1H, d, J=2.7 Hz).

5-(6-Ethoxypyridin-3-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

¹H-NMR (CDCl₃) δ: 0.88 (3H, t, J=7.3 Hz), 1.19-1.61 (5H, m), 1.76 (3H, s), 2.59 (2H, t, J=7.6 Hz), 4.35-4.50 (2H, m), 4.63 (2H, s), 6.70-7.57 (8H, m), 8.00-8.29 (2H, m).

Example 14

Preparation of 3-(3-(4-(1,1,1,3,3,3-hexafluoro-2-hydroxypropan-2-yl)-2-propylphenoxy)benzyl)-5-methyl-5-(6-propoxypyridin-3-yl)imidazolidine-2,4-dione

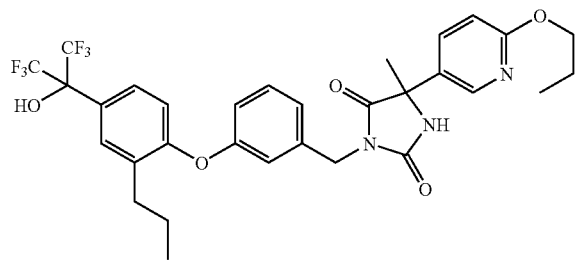

14-a-1) Preparation of N-methyl-6-propoxy nicotinamide

The similar reaction and treatment were conducted to 6-chloro-N-methylnicotinamide by using 1-propanol in place of ethanol in Example 13-a), and N-methyl-6-propoxynicotinamide was obtained as a colorless oil.

¹H-NMR (CDCl₃) δ: 1.03 (3H, t, J=7.3 Hz), 1.81 (2H, tq, J=7.0, 7.3 Hz), 3.02 (3H, d, J=4.9 Hz), 4.29 (2H, t, J=7.0 Hz), 6.05 (1H, brs), 6.76 (1H, d, J=8.6 Hz), 7.99 (1H, dd, J=2.4, 8.6 Hz), 8.53 (1H, d, J=2.4 Hz).

14-a-2) Preparation of N-methoxy-N-methyl-6-propoxynicotinamide

N-methyl-6-propoxynicotinamide was used for a similar reaction and treatment as Example 13-a), and N-methoxy-N-methyl-6-propoxynicotinamide was obtained as a white crystal.

¹H-NMR (CDCl₃) δ: 1.03 (3H, t, J=7.3 Hz), 1.82 (2H, tq, J=6.8, 7.3 Hz), 3.37 (3H, s), 3.58 (3H, s), 4.30 (2H, t, J=6.8 Hz), 6.74 (1H, d, J=8.6 Hz), 7.99 (1H, dd, J=1.9, 8.6 Hz), 8.63 (1H, d, J=1.9 Hz).

14-a-3) Preparation of 1-(6-propoxypyridin-3-yl)ethanone

N-methoxy-N-methyl-6-propoxynicotinamide was used for a similar reaction and treatment as Example 2-a), and 1-(6-propoxypyridin-3-yl)ethanone was obtained as a yellow oil.

¹H-NMR (CDCl₃) δ: 1.03 (3H, t, J=7.3 Hz), 1.82 (2H, tq, J=7.0, 7.3 Hz), 2.57 (3H, s), 4.33 (2H, t, J=7.0 Hz), 6.78 (1H, d, J=8.9 Hz), 8.14 (1H, dd, J=2.2, 8.9 Hz), 8.76 (1H, d, J=2.2 Hz).

14-a-4) Preparation of 5-methyl-5-(6-propoxypyridin-3-yl)imidazolidine-2,4-dione 1-(6-Propoxypyridin-3-yl)ethanone was used for a similar reaction and treatment as Example 1-a), and 5-methyl-5-(6-propoxypyridin-3-yl)imidazolidine-2,4-dione was obtained as a white crystal.

¹H-NMR (CDCl₃) δ: 1H-NMR (CD3OD): 1.31 (6H, d, J=6.1 Hz), 1.75 (3H, s), 5.18-5.27 (1H, m), 6.74 (1H, d, J=8.8 Hz), 7.78 (1H, dd, J=1.9, 8.8 Hz), 8.22 (1H, d, J=1.9 Hz).

5-Methyl-5-(6-propoxypyridin-3-yl)imidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

¹H-NMR (CDCl₃) δ: 0.87 (3H, t, J=7.3 Hz), 1.04 (3H, t, J=7.6 Hz), 1.51-1.91 (4H, m), 1.75 (3H, s), 2.57 (2H, t, J=7.6 Hz), 4.11-4.60 (4H, m), 6.70-7.49 (8H, m), 7.80-8.20 (2H, m).

Example 15

Preparation of 5-(3,4-dimethoxyphenyl)-3-(3-(4-(1,1,1,3,3,3-hexafluoro-2-hydroxypropan-2-yl)-2-propylphenoxy)benzyl)-5-methylimidazolidine-2,4-dione

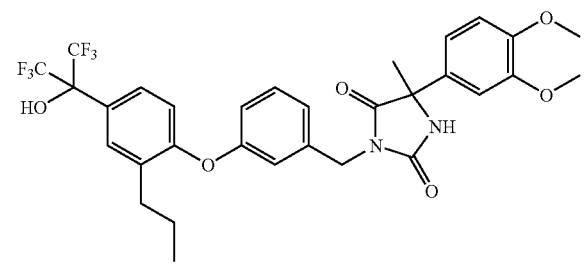

15-a-1) Preparation of 5-(3,4-dimethoxyphenyl)-5-methylimidazolidine-2,4-dione

1-[4-(1,2-Dimethoxy)phenyl]ethanone was used for a similar reaction and treatment as Example 1-a), and 5-(3,4-dimethoxyphenyl)-5-methylimidazolidine-2,4-dione was obtained as a white crystal.

¹H-NMR (DMSO) δ: 1.62 (3H, s), 3.74 (3H, s), 3.76 (3H, s), 6.93-7.01 (3H, m), 8.58 (1H, s), 10.73 (1H, s).

5-(3,4-Dimethoxyphenyl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.92 (3H, t, J=7.3 Hz), 1.56-1.70 (2H, m), 1.79 (3H, s), 2.64 (2H, t, J=7.6 Hz), 3.79 (3H, s), 3.84 (1H, s), 3.85 (3H, s), 4.65 (2H, s), 5.92 (1H, s), 6.72 (1H, d, J=8.6 Hz), 6.81-7.56 (9H, m).

Example 16

Preparation of 3-(3-(4-(1,1,1,3,3,3-hexafluoro-2-hydroxypropan-2-yl)-2-propylphenoxy)benzyl)-5-methyl-5-p-tolylimidazolidine-2,4-dione

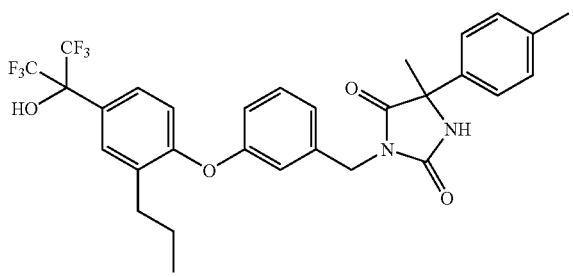

16-a-1) Preparation of 5-methyl-5-p-tolylimidazolidine-2,4-dione

1-[4-(1-Methyl)phenyl]ethanone was used for a similar reaction and treatment as Example 1-a), and 5-methyl-5-p-tolylimidazolidine-2,4-dione was obtained as a white crystal.

$^1$H-NMR (CDCl$_3$) δ: 1.74 (3H, s), 2.32 (3H, s), 7.20 (2H, d, J=8.6 Hz), 7.38 (2H, d, J=8.6 Hz).

5-Methyl-5-p-tolylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.93 (3H, t, J=7.3 Hz), 1.59-1.70 (2H, m), 1.78 (3H, s), 2.33 (3H, s), 2.64 (2H, t, J=7.6 Hz), 3.62 (1H, s), 4.64 (2H, s), 5.73 (1H, s), 6.77 (1H, d, J=8.6 Hz), 6.83-6.88 (1H, m), 6.93-6.95 (1H, m), 7.04-7.35 (6H, m), 7.38-7.56 (2H, m).

Example 17

Preparation of 3-(3-(4-(1,1,1,3,3,3-hexafluoro-2-hydroxypropan-2-yl)-2-propylphenoxy)benzyl)-5-methyl-5-(4-nitrophenyl)imidazolidine-2,4-dione

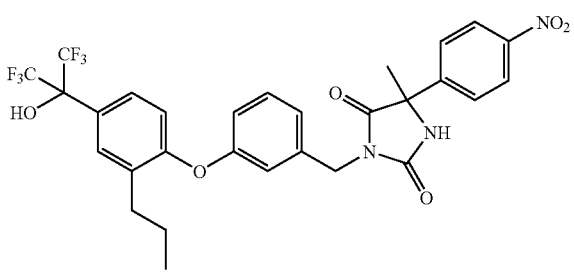

17-a) Preparation of 5-methyl-5-(4-nitrophenyl)imidazolidine-2,4-dione

1-[4-(1-Nitro)phenyl]ethanone was used for a similar reaction and treatment as Example 1-a), and 5-methyl-5-(4-nitrophenyl)imidazolidine-2,4-dione was obtained as a white crystal.

$^1$H-NMR (CDCl$_3$) δ: 1.71 (3H, s), 7.78 (2H, d, J=8.6 Hz), 8.27 (2H, d, J=8.6 Hz), 8.82 (1H, s), 10.98 (1H, s).

5-Methyl-5-(4-nitrophenyl)imidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.92 (3H, t, J=7.3 Hz), 1.55-1.69 (2H, m), 1.84 (3H, s), 2.62 (2H, t, J=7.6 Hz), 3.85 (1H, s), 4.65 (2H, s), 6.48 (1H, s), 6.79 (1H, d, J=8.3 Hz), 6.84-6.91 (1H, m), 7.02-7.06 (1H, m), 7.30-7.32 (2H, m), 7.40-7.44 (1H, m), 7.55-7.57 (1H, m), 7.68-7.72 (2H, m), 8.18-8.23 (2H, m).

Example 18

Preparation of 5-(3,4-dichlorophenyl)-3-(3-(4-(1,1,1,3,3,3-hexafluoro-2-hydroxypropan-2-yl)-2-propylphenoxy)benzyl)-5-methylimidazolidine-2,4-dione

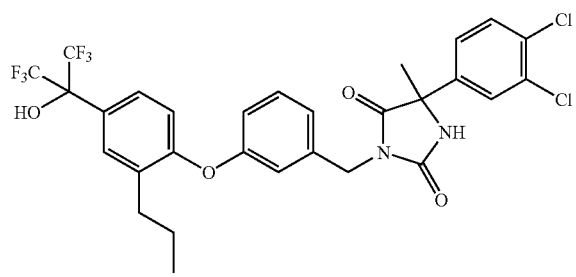

18-a-1) Preparation of 5-(3,4-dichlorophenyl)-5-methylimidazolidine-2,4-dione 1-[4-(3,4-Dichloro)phenyl]ethanone was used for a similar reaction and treatment as Example 1-a), and 5-(3,4-dichlorophenyl)-5-methylimidazolidine-2,4-dione was obtained as a white crystal.

$^1$H-NMR (DMSO) δ: 1.65 (3H, s), 7.46-7.54 (1H, m), 7.67-7.73 (2H, m), 8.70 (1H, s), 10.91 (1H, s).

5-(3,4-Dichlorophenyl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.93 (3H, t, J=7.3 Hz), 1.59-1.70 (2H, m), 1.78 (3H, s), 2.64 (2H, t, J=7.6 Hz), 3.61 (1H, s), 4.64 (2H, s), 5.84 (1H, s), 6.79 (1H, d, J=8.6 Hz), 6.84-7.58 (9H, m).

Example 19

Preparation of 3-(3-(4-(1,1,1,3,3,3-hexafluoro-2-hydroxypropan-2-yl)-2-propylphenoxy)benzyl)-5-methyl-5-(6-(methylthio)pyridin-3-yl)imidazolidine-2,4-dione

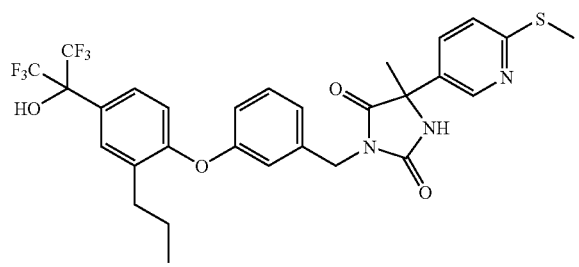

19-a-1) Preparation of methyl 6-(methylthio)nicotinate

Methyl 6-chloronicotinate (100 mg, 0.583 mmol) in N,N'-dimethylformamide (1.5 mL) was added with sodium thiomethoxide (41 mg) under ice-cold conditions, and then stirred at room temperature for 3 hours. The reaction solution was added with water and extracted with ethyl acetate. The organic layer was washed with brine, dried using anhydrous sodium sulfate, and concentrated in vacuo. The obtained residue was purified using silica-gel column chromatography (hexane/ethyl acetate), and methyl 6-(methylthio)nicotinate (120 mg, yield >100%) was obtained as a yellow oil.

$^1$H-NMR (CDCl$_3$) δ: 2.61 (3H, s), 3.93 (3H, s), 7.23 (1H, d, J=8.1 Hz), 8.05 (1H, dd, J=1.6, 8.1 Hz), 9.02 (1H, d, J=1.6 Hz).

19-a-2) Preparation of 6-(methylthio)nicotinic acid

Ethyl 6-thiomethoxynicotinate (120 mg, 0.583 mmol) in methanol (3.0 mL) was added with an aqueous solution of sodium hydroxide (5 mL) under ice-cold conditions, and the resultant mixture was stirred at room temperature for 1 hour. The reaction solution was concentrated in vacuo, added with 4N aqueous solution of hydrochloric acid, and extracted with chloroform. The organic layer was washed with brine and dried using anhydrous sodium sulfate. 6-(Methylthio)nicotinic acid (78 mg, yield 79%) was obtained as a white crystal.

$^1$H-NMR (CDCl$_3$) δ: 2.62 (3H, s), 7.27 (1H, d, J=8.4 Hz), 8.09 (1H, dd, J=1.6, 8.4 Hz), 9.09 (1H, d, J=1.6 Hz).

19-a-3) Preparation of N-methoxy-N-methyl-6-(methylthio)nicotinamide 6-(Methylthio)nicotinic acid was used for a similar reaction and treatment as Example 13-a), and N-methoxy-N-methyl-6-(methylthio)nicotinamide was obtained as a white crystal.

$^1$H-NMR (CDCl$_3$) δ: 2.60 (3H, s), 3.38 (3H, s), 3.57 (3H, s), 7.23 (1H, d, J=8.6 Hz), 7.88 (1H, dd, J=1.6, 8.6 Hz), 8.84 (1H, d, J=1.6 Hz).

19-a-4) Preparation of 1-(6-(methylthio)pyridin-3-yl)ethanone

N-methoxy-N-methyl-6-(methylthio)nicotinamide was used for a similar reaction and treatment as Example 13-a), and 1-(6-(methylthio)pyridin-3-yl)ethanone was obtained as a white crystal.

$^1$H-NMR (CDCl$_3$) δ: 2.59 (3H, s), 2.61 (3H, s), 7.25 (1H, d, J=8.4 Hz), 8.02 (1H, dd, J=2.4, 8.4 Hz), 8.98 (1H, d, J=2.4 Hz).

19-a-5) Preparation of 5-methyl-5-(6-(methylthio)pyridin-3-yl)imidazolidine-2,4-dione 1-(6-(Methylthio)pyridin-3-yl)ethanone was used for a similar reaction and treatment as Example 1-a), and 5-methyl-5-(6-(methylthio)pyridin-3-yl)imidazolidine-2,4-dione was obtained as a white crystal.

$^1$H-NMR (CDCl$_3$) δ: 1.75 (3H, s), 2.53 (3H, s), 7.28 (1H, d, J=8.6 Hz), 7.76 (1H, dd, J=1.9, 8.6 Hz), 8.50 (1H, d, J=1.9 Hz).

5-methyl-5-(6-methylthio)pyridin-3-yl)imidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.76 (3H, t, J=7.3 Hz), 1.36-1.47 (2H, m), 1.70 (3H, s), 2.43-2.48 (2H, m), 2.49 (3H, s), 4.52-4.60 (2H, m), 5.52 (1H, brs), 6.43 (1H, s), 6.53 (1H, s), 6.73 (1H, d, J=8.5 Hz), 6.85-6.94 (2H, m), 7.09 (1H, d, J=8.5 Hz), 7.18-7.22 (1H, m), 7.37-7.40 (1H, m), 7.52 (1H, d, J=1.5 Hz), 7.57 (1H, dd, J=2.4, 8.5 Hz), 8.21 (1H, d, J=1.7 Hz).

Example 20

Preparation of 3-(3-(4-(1,1,1,3,3,3-hexafluoro-2-hydroxypropan-2-yl)-2-propylphenoxy)benzyl)-5-methyl-5-(6-(methylsulfinyl)pyridin-3-yl)imidazolidine-2,4-dione

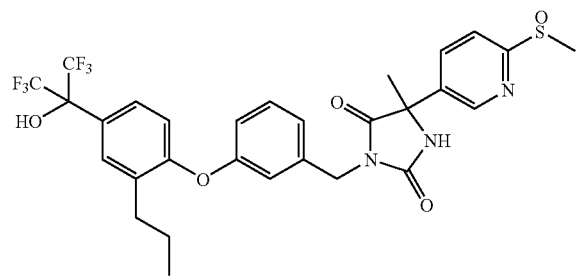

To a solution of 3-(3-(4-(1,1,1,3,3,3-hexafluoro-2-hydroxypropan-2-yl)-2-propylphenoxy)benzyl)-5-methyl-5-(6-(methylthio)pyridin-3-yl) imidazolidine-2,4-dione (10 mg, 0.0159 mmol) in acetonitrile (640 tantalum chloride (0.6 mg, 0.00159 mmol) and 30% hydrogen peroxide solution (71 μL) were added under ice-cold conditions, and the resultant mixture was stirred under ice-cold conditions for 1 hour and then stirred at room temperature for 9 hours. The reaction solution was added with water and extracted with ethyl acetate. The organic layer was washed with brine, dried using anhydrous sodium sulfate, and concentrated in vacuo. The obtained residue was purified using silica-gel column chromatography (ethyl acetate) and the title compound (7.2 mg, yield 70%) was obtained as a yellow oil.

$^1$H-NMR (CDCl$_3$) δ: 0.91 (31-1, t, J=7.3 Hz), 1.56-1.65 (2H, m), 1.88 (3H, s), 2.62-2.65 (2H, m), 2.81-2.83 (3H, m), 4.64-4.74 (2H, m), 5.74 (1H, brs), 6.36 (1H, d, J=8.1 Hz), 6.51 (1H, dd, J=7.4, 8.1 Hz), 6.73-6.78 (1H, m), 6.95 (1H, d, J=8.3 Hz), 7.14 (1H, d, J=7.3 Hz), 7.30-7.38 (2H, m), 7.57 (1H, s), 7.70 (1H, d, J=8.3 Hz), 7.87-7.92 (1H, m), 8.71 (1H, d, J=2.2, 10.1 Hz).

Example 21

Preparation of 3-(3-(4-(1,1,1,3,3,3-hexafluoro-2-hydroxypropan-2-yl)-2-propylphenoxy)benzyl)-5-methyl-5-(6-(methylsulfonyl)pyridin-3-yl)imidazolidine-2,4-dione

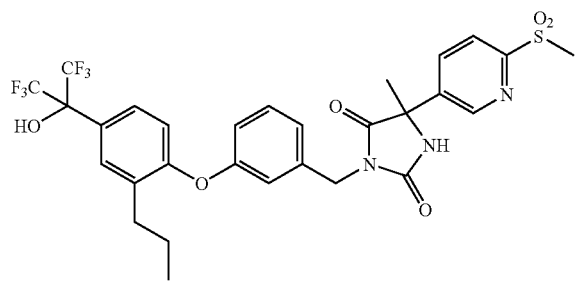

To a solution of 3-(3-(4-(1,1,1,3,3,3-hexafluoro-2-hydroxypropan-2-yl)-2-propylphenoxy)benzyl)-5-methyl-5-(6-(methylthio)pyridin-3-yl)imidazolidine-2,4-dione (10 mg, 0.0159 mmol) in methanol (640 μL), tantalum chloride (0.6 mg, 0.00159 mmol) and 30% hydrogen peroxide solution (71 μL, 0.07967 mmol) were added under ice-cold conditions and the resultant mixture was stirred under ice-cold conditions for 1 hour and then stirred at room temperature for 2 hours. The reaction solution was added with water and extracted with ethyl acetate. The organic layer was washed with brine, dried using anhydrous sodium sulfate, and concentrated in vacuo. The obtained residue was purified using silica-gel column chromatography (ethyl acetate) and the title compound (11.3 mg, yield >99%) was obtained as a yellow oil.

$^1$H-NMR (CDCl$_3$) δ: 0.91 (3H, t, J=7.3 Hz), 1.56-1.65 (2H, m), 1.85 (3H, s), 2.62 (2H, t, J=7.8 Hz), 3.21 (3H, s), 4.31 (1H, brs), 4.66 (2H, s), 6.61 (1H, s), 6.75 (1H, d, J=8.5 Hz), 6.87-6.92 (2H, m), 7.07 (1H, d, J=7.8 Hz), 7.30 (1H, t, J=7.8 Hz), 7.44 (1H, dd, J=2.0, 8.5 Hz), 7.58 (1H, s), 8.02 (1H, d, J=8.3 Hz), 8.10 (1H, dd, J=2.2, 8.3 Hz), 8.84 (1H, d, J=2.0 Hz).

Example 22

Preparation of 5-(furan-2-yl)-3-(3-(4-(1,1,1,3,3,3-hexafluoro-2-hydroxypropan-2-yl)-2-propylphenoxy)benzyl)-5-methylimidazolidine-2,4-dione

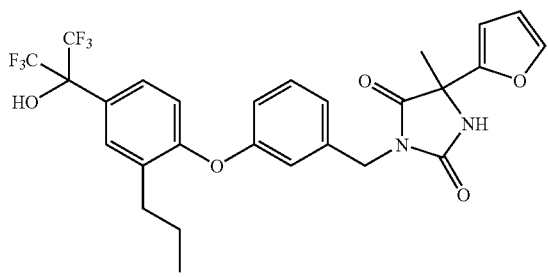

22-a-1) Preparation of 5-(furan-2-yl)-5-methylimidazolidine-2,4-dione

1-[Furan-2-yl]ethanone was used for a similar reaction and treatment as Example 1-a), and 5-(furan-2-yl)-5-methylimidazolidine-2,4-dione was obtained as a white crystal.

$^1$H-NMR (DMSO) δ: 1.62 (3H, s), 6.43 (1H, s), 6.97-7.06 (2H, m), 7.42-7.46 (1H, m), 8.58 (1H, s).

5-(Furan-2-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.94 (3H, t, J=7.3 Hz), 1.58-1.72 (2H, m), 1.77 (3H, s), 2.66 (2H, t, J=7.3 Hz), 3.66 (1H, s), 4.70 (2H, s), 5.65 (1H, s), 6.30-6.35 (2H, m), 6.79 (1H, d, J=1.5 Hz), 6.84-6.90 (1H, m), 6.98 (1H, dd, J=2.0, 2.0 Hz), 7.07-7.56 (5H, m).

Example 23

Preparation of 3-(3-(4-(1,1,1,3,3,3-hexafluoro-2-hydroxypropan-2-yl)-2-propylphenoxy)benzyl)-1,5,5-trimethylimidazolidine-2,4-dione

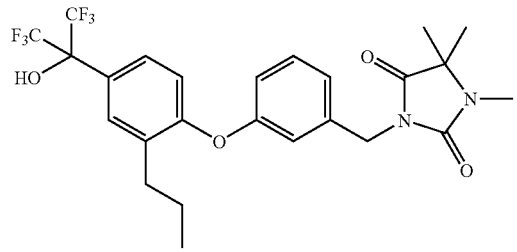

1,5,5-Trimethylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.93 (3H, t, J=7.3 Hz), 1.34 (6H, s), 1.57-1.69 (2H, m), 2.65 (2H, t, J=7.6 Hz), 2.87 (3H, s), 4.00 (1H, s), 4.63 (2H, s), 6.80-7.57 (7H, m).

Example 24

Preparation of 3-(3-(4-(1,1,1,3,3,3-hexafluoro-2-hydroxypropan-2-yl)-2-propylphenoxy)benzyl)-1,3-diazaspiro[4.4]nonane-2,4-dione:

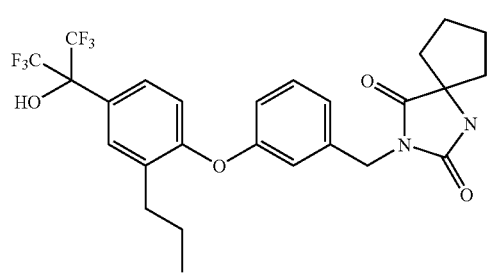

24-a-1) Preparation of 1,3-diazaspiro[4.4]nonane-2,4-dione

Cyclopentanon was used for a similar reaction and treatment as Example 1-a), and 1,3-diazaspiro[4.4]nonane-2,4-dione was obtained as a white crystal.

$^1$H-NMR (CDCl$_3$) δ: 1.78-2.09 (8H, m).

1,3-Diazaspiro[4.4]nonane-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.93 (3H, t, J=7.3 Hz), 1.57-2.20 (10H, m), 2.65 (2H, t, J=7.6 Hz), 3.92 (1H, s), 4.64 (2H, s), 5.90 (1H, s), 6.81 (1H, d, J=8.6 Hz), 6.84-6.95 (2H, m), 7.07-7.31 (2H, m), 7.43 (1H, dd, J=1.5, 8.6 Hz), 7.56 (1H, d, J=1.5 Hz).

Example 25

Preparation of (E)-3-(3-(5-(1,1,1,3,3,3-hexafluoro-2-hydroxypropan-2-yl)-3-(prop-1-enyl)pyridin-2-yloxy)benzyl)-5-(4-(1-methylethoxy)phenyl)-5-methylimidazolidine-2,4-dione a) Preparation of 2-chloro-5-(1,1,1,3,3,3-hexafluoro-2-(methoxymethoxy)propan-2-yl)pyridine

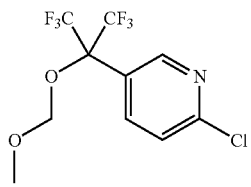

To a solution of 6-chloronicotinate chloride (500 mg, 2.84 mmol) in ethyleneglycoldimethyl ether (20 mL), tetramethylammoniumfluoride (794 mg, 8.52 mmol) and trifluoromethyltrimethylsilane (1.4 mL, 8.52 mmol) were added under −78° C. The resultant mixture was gradually warmed to room temperature and stirred for 12 hours. The reaction solution was added with water and 1N-hydrochloric acid solution under ice-cold conditions and extracted with ethyl acetate. The organic layer was washed with brine, dried using anhydrous sodium sulfate, and concentrated in vacuo to obtain a crude product (1.0 g). To a solution of the crude product (1.0 g) in dichloromethane (30 mL), diisopropylethylamine (1.5 mL, 8.52 mmol) and chloromethylmethyl ether (324 μL, 4.26 mmol) were added and the resultant mixture was stirred at 40° C. overnight. Subsequently, diisopropylethylamine (1.5 mL, 8.52 mmol) and chloromethylmethyl ether (324 μL, 4.26 mmol) were added and the resultant mixture was stirred at 40° C. overnight. The reaction solution was added with water and extracted with chloroform. Subsequently, the organic layer was washed with brine, dried using anhydrous sodium sulfate, and concentrated in vacuo. The obtained residue was purified using silica-gel column chromatography (hexane/ethyl acetate), and the title compound (790 mg, yield 86%) was obtained as a yellow crystal.

$^1$H-NMR (CDCl$_3$) δ: 3.57 (3H, s), 4.90 (2H, s), 7.46 (1H, d, J=8.6 Hz), 7.93 (1H, dd, J=2.9, 8.6 Hz), 8.67 (1H, d, J=2.9 Hz).

b) Preparation of 3-allyl-2-chloro-5-(1,1,1,3,3,3-hexafluoro-2-(methoxymethoxy)propan-2-yl)pyridine

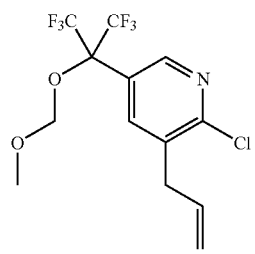

To a solution of 2-chloro-5-(1,1,1,3,3,3-hexafluoro-2-(methoxymethoxy)propan-2-yl)pyridine (50 mg, 0.155 mmol) in tetrahydrofuran (2 mL), butyllithium (71 μL, 1.70 mmol) was added under −78° C. and the resultant mixture was stirred for 0.5 hour. Allyl iodide (71 μL, 0.773 mmol) was added under −78° C. and the resultant mixture was stirred at room temperature for 1 hour. The reaction solution was added with a saturated aqueous solution of ammonium chloride and water under room temperature and extracted with ethyl acetate. The organic layer was washed with brine, dried using anhydrous sodium sulfate, and concentrated in vacuo. The obtained residue was purified using silica-gel column chromatography (hexane/ethyl acetate), and the title compound (36 mg, yield 64%) was obtained as a yellow oil.

$^1$H-NMR (CDCl$_3$) δ: 3.54-3.57 (5H, m), 4.88 (2H, s), 5.12-5.25 (2H, m), 5.88-5.98 (1H, s), 7.81 (1H, d, J=2.2 Hz), 8.52 (1H, d, J=2.2 Hz).

c) Preparation of methyl (E)-3-(5-(1,1,1,3,3,3-hexafluoro-2-(methoxymethoxy)propan-2-yl)-3-(prop-1-enyl)pyridin-2-yloxy)benzoate

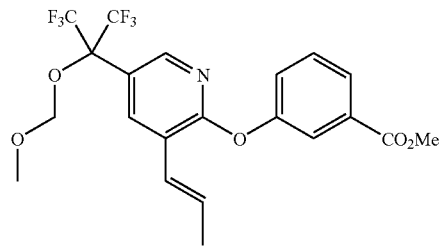

To a solution of 3-allyl-2-chloro-5-(1,1,1,3,3,3-hexafluoro-2-(methoxymethoxy)propan-2-yl)pyridine (80 mg, 0.220 mmol) in N,N-dimethylformamide (2 mL), sodium hydride (14.4 mg, 0.330 mmol) and 3-hydroxybenzoic acid methyl ester (50 mg, 0.330 mmol) were added under ice-cold conditions, and the resultant mixture was stirred at 80° C. for 18 hours and further stirred at 100° C. for 3 hours. The reaction solution was added with water under room temperature and extracted with ethyl acetate. The organic layer was washed with brine, dried using anhydrous sodium sulfate, and concentrated in vacuo. The obtained residue was purified using silica-gel column chromatography (hexane/ethyl acetate), and the title compound (81 mg, yield 76.5%) was obtained as a colorless oil.

$^1$H-NMR (CDCl$_3$) δ: 1.98 (3H, dd, J=1.7, 6.6 Hz), 3.55 (3H, s), 3.92 (3H, s), 4.87 (2H, s), 6.46 (1H, qd, J=6.6, 15.6 Hz), 6.71 (1H, dd, J=1.7, 15.6 Hz), 7.36-7.39 (1H, m), 7.49-7.53 (1H, m), 7.83 (1H, t, J=2.0 Hz), 7.92-7.95 (1H, m), 7.97 (1H, d, J=2.2 Hz), 8.18 (1H, d, J=2.2 Hz).

d) Preparation of (E)-(3-(5-(1,1,1,3,3,3-hexafluoro-2-(methoxymethoxy)propan-2-yl)-3-(prop-1-enyl)pyridin-2-yloxy)phenyl)methanol

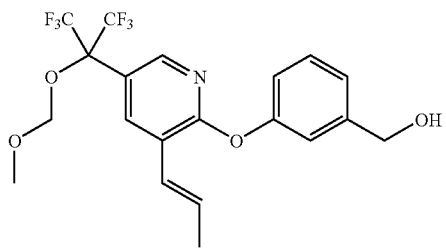

To a solution of methyl (E)-3-(5-(1,1,1,3,3,3-hexafluoro-2-(methoxymethoxy)propan-2-yl)-3-(prop-1-enyl)pyridin-2-yloxy)benzoate (81 mg, 0.168 mmol) in tetrahydrofuran (2 mL), lithium aluminum hydride (9.6 mg, 0.252 mmol) was added under ice-cold conditions, and the resultant mixture was stirred at room temperature for 3 hours. The reaction solution was added with methanol and water, filtered using celite, and extracted with ethyl acetate. The organic layer was washed with brine, dried using anhydrous sodium sulfate, and concentrated in vacuo. The obtained residue was purified using silica-gel column chromatography (ethyl acetate), and the title compound (72 mg, yield 94.9%) was obtained as a yellow oil.

$^1$H-NMR (CDCl$_3$) δ: 1.97 (3H, dd, J=1.7, 6.6 Hz), 3.55 (3H, s), 4.68 (1H, s), 4.74 (2H, s), 4.87 (2H, s), 6.45 (1H, qd, J=6.6, 15.3 Hz), 6.70 (1H, dd, J=1.7, 15.3 Hz), 6.95-7.10 (2H, m), 7.19-7.30 (1H, m), 7.41-7.44 (1H, m), 7.95 (1H, s), 8.19 (1H, s).

e) Preparation of (E)-3-(3-(5-(1,1,1,3,3,3-hexafluoro-2-hydroxypropan-2-yl)-3-(prop-1-enyl)pyridin-2-yloxy)benzyl)-5-(4-(1-methylethoxy)phenyl)-5-methylimidazolidine-2,4-dione

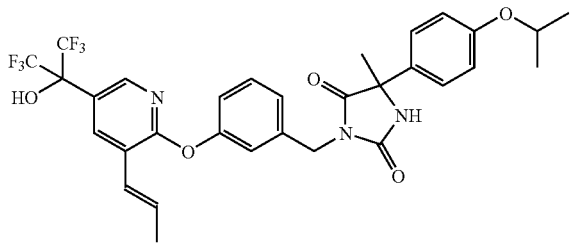

After reacting and treating (E)-(3-(5-(1,1,1,3,3,3-hexafluoro-2-(methoxymethoxy)propan-2-yl)-3-(prop-1-enyl)pyridin-2-yloxy)phenyl)methanol in a similar manner to Preparation example 3 b), 5-(4-(1-methylethoxy)phenyl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 1.31 (6H, d, J=5.9 Hz), 1.77 (3H, s), 1.96 (3H, dd, J=1.4, 6.8 Hz), 4.25 (1H, s), 4.51 (1H, sept, J=5.9 Hz), 4.66 (2H, s), 5.91 (1H, s), 6.44 (1H, dd, J=6.8, 15.9 Hz), 6.68 (1H, dd, J=1.4, 15.9 Hz), 6.83 (2H, d, J=8.9 Hz), 7.05-7.38 (6H, m), 8.02 (1H, d, J=2.2 Hz), 8.23 (1H, d, J=2.2 Hz).

Example 26

Preparation of 3-(3-(5-(1,1,1,3,3,3-hexafluoro-2-hydroxypropan-2-yl)-3-propylpyridin-2-yloxy)benzyl)-5-(4-(1-methylethoxy)phenyl)-5-methylimidazolidine-2,4-dione

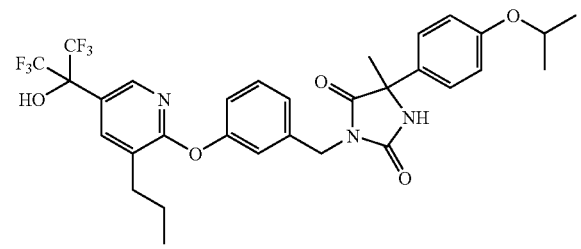

(E)-3-(3-(5-(1,1,1,3,3,3-hexafluoro-2-hydroxypropan-2-yl)-3-(prop-1-enyl)pyridin-2-yloxy)benzyl)-5-(4-(1-methylethoxy)phenyl)-5-methylimidazolidine-2,4-dione was used for a similar reaction and treatment as Preparation example 1 c), and the title compound was obtained as a colorless oil.

$^1$H-NMR (CDCl$_3$) δ: 0.99 (3H, t, J=7.3 Hz), 1.31 (6H, d, J=6.5 Hz), 1.64-1.78 (5H, m), 2.71 (2H, t, J=7.6 Hz), 4.51 (1H, sept, J=6.5 Hz), 4.65-4.66 (2H, m), 6.11 (1H, s), 6.81-6.87 (3H, m), 7.02-7.20 (3H, m), 7.26-7.37 (3H, m), 7.79 (1H, d, J=2.2 Hz), 8.25 (1H, d, J=2.2 Hz).

Example 27

Preparation of 3-(1-(3-(4-(1,1,1,3,3,3-hexafluoro-2-hydroxypropan-2-yl)-2-propylphenoxy)phenyl)ethyl)-5-(4-(1-methylethoxy)phenyl)-5-methylimidazolidine-2,4-dione a) Preparation of 1-(3-(4-(1,1,1,3,3,3-hexafluoro-2-(methoxymethoxy)propan-2-yl)-2-propylphenoxy)phenyl)ethanol:

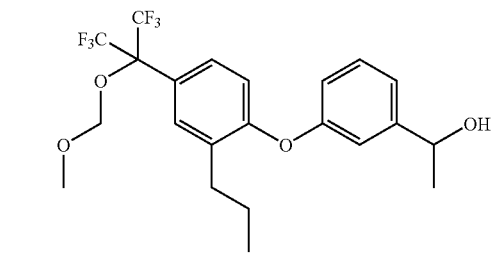

To a tetrahydrofuran solution (6 mL) of 3-(4-(1,1,1,3,3,3-hexafluoro-2-(methoxymethoxy)propan-2-yl)-2-propyl phenoxy)benzaldehyde (300 mg, 6661=01), a tetrahydrofuran solution of methylmagnesium bromide (0.97 mol/L, 830 μL) was added at 0° C. under an argon atmosphere. After completion of the reaction, the reaction solution was neutralized by adding 2 mol/L of hydrochloric acid, added with water, extracted with ethyl acetate, and then concentrated in vacuo. The obtained residue was purified using silica-gel column chromatography (hexane/ethyl acetate) and the title compound (308 mg, yield 99%) was obtained as a colorless oil.

$^1$H-NMR (CDCl$_3$) δ: 0.95 (3H, t, J=7.3 Hz), 1.50 (3H, d, J=6.8 Hz), 1.59-1.71 (2H, m), 2.69 (2H, t, J=7.6 Hz), 3.55 (3H, s), 4.85-4.90 (3H, m), 6.80-6.88 (2H, m), 7.06-7.16 (2H, m), 7.30-7.46 (3H, m).

b) Preparation of 3-(1-(3-(4-(1,1,1,3,3,3-hexafluoro-2-hydroxypropan-2-yl)-2-propylphenoxy)phenyl)ethyl)-5-(4-(1-methylethoxy)phenyl)-5-methylimidazolidine-2,4-dione

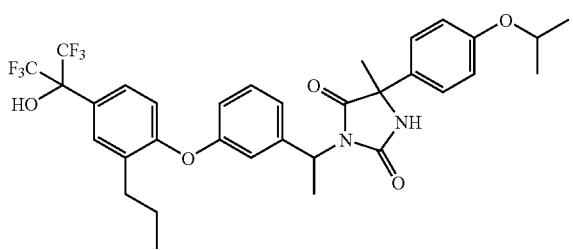

To a solution of 1-(3-(4-(1,1,1,3,3,3-hexafluoro-2-(methoxymethoxy)propan-2-yl)-2-propylphenoxy)phenyl) ethanol (40.0 mg, 85.8 mmol), 5-(4-(1-methylethoxy)phenyl)-5-methylimidazolidine-2,4-dione (32.0 mg) and triphenylphosphine (56.3 mg) in tetrahydrofuran (5 mL), diethylazodicarboxylate (about 2.2 mol/L toluene solution, 97.5 μL) was added under ice-cold conditions. After completion of the reaction, the reaction solution was concentrated in vacuo. The obtained residue was purified using silica-gel thin-layer chromatography (hexane/ethyl acetate). The obtained compound was added with 2 mol/L hydrogen chloride-ethyl acetate solution (1 mL) at room temperature. After completion of the reaction, the solution was concentrated in vacuo and purified using thin-layer silica-gel column chromatography (hexane/ethyl acetate) and the title compound (37.2 mg, yield 66%) was obtained as a colorless oil.

$^1$H-NMR (CDCl$_3$) δ: 0.93 (3H, t, J=7.3 Hz), 1.31 (6H, d, J=5.9 Hz), 1.56-1.84 (8H, m), 2.66 (2H, t, J=7.6 Hz), 3.68 (1H, s), 4.51 (1H, sept, J=5.9 Hz), 5.31 (1H, q, J=7.0 Hz), 5.66 (1H, s), 6.68-7.55 (11H, m).

Example 28

Preparation of 5-(2,3-dihydrobenzofuran-5-yl)-3-(1-(3-(4-(1,1,1,3,3,3-hexafluoro-2-hydroxypropan-2-yl)-2-propylphenoxy)phenyl)ethyl)-5-methylimidazolidine-2,4-dione

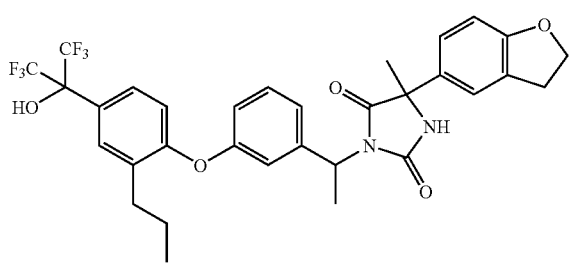

5-(2,3-Dihydrobenzofuran-5-yl)-5-methylimidazolidine-2,4-dione was used in place of 5-(4-(1-methylethoxy)phenyl)-5-methylimidazolidine-2,4-dione of Example 27 b) for a similar reaction and treatment, and the title compound was obtained as a colorless oil.

$^1$H-NMR (CDCl$_3$) δ: 0.94 (3H, t, J=7.3 Hz), 1.60-1.84 (8H, m), 2.66 (2H, t, J=7.6 Hz), 3.13-3.20 (2H, m), 3.82 (1H, s), 4.51-4.60 (2H, m), 5.30 (1H, q, J=6.5 Hz), 5.80 (1H, s), 6.65-7.55 (10H, m).

Example 29

Preparation of 3-(1-(3-(4-(1,1,1,3,3,3-hexafluoro-2-hydroxypropan-2-yl)-2-propylphenoxy)phenyl)ethyl)-5-(6-methoxypyridin-3-yl)-5-methylimidazolidine-2,4-dione

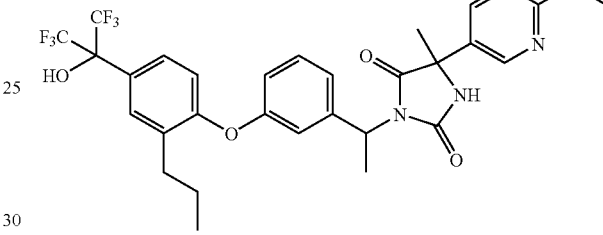

5-(6-Methoxypyridin-3-yl)-5-methylimidazolidine-2,4-dione was used in place of 5-(4-(1-methylethoxy)phenyl)-5-methylimidazolidine-2,4-dione of Example 27 b) for a similar reaction and treatment, and the title compound was obtained as a colorless oil.

$^1$H-NMR (CDCl$_3$) δ: 0.88 (3H, t, J=7.3 Hz), 1.54-1.80 (8H, m), 2.58 (2H, t, J=7.6 Hz), 4.09 (3H, s), 4.16-4.24 (2H, m), 5.23 (1H, s), 6.72-7.57 (8H, m), 8.02-8.34 (2H, m).

Example 30

Preparation of 5-(benzo[d][1,3]dioxol-5-yl)-3-(3-(4-(1,1,1,3,3,3-hexafluoro-2-hydroxypropan-2-yl)-2-propylphenoxy) phenethyl)-5-methylimidazolidine-2,4-dione a) Preparation of 4-(1,1,1,3,3,3-hexafluoro-2-(methoxymethoxy)propan-2-yl)-2-propyl-1-(3-vinylphenoxy) benzene

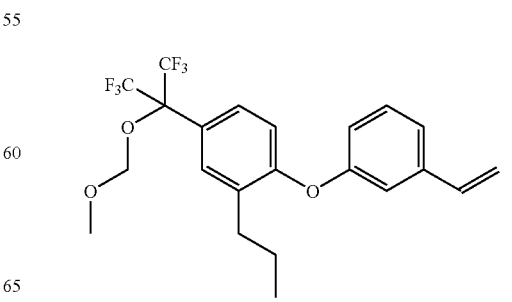

3-Vinylphenylboronic acid was used in place of 3-(hydroxymethyl)phenylboronic acid for a similar reaction and treatment as Preparation example 3 a), and the title compound was obtained as a colorless oil.

¹H-NMR (CDCl₃) δ: 0.96 (3H, t, J=7.3 Hz), 1.61-1.74 (2H, m), 2.70 (2H, t, J=7.3 Hz), 3.56 (3H, s), 4.86 (2H, s), 5.28 (1H, dd, J=0.5, 10.8 Hz), 5.74 (1H, dd, J=0.5, 17.6 Hz), 6.69 (1H, dd, J=10.8, 17.6 Hz), 6.83 (1H, d, J=8.6 Hz), 6.87 (1H, ddd, J=1.4, 2.4, 8.1 Hz), 7.07 (1H, dd, J=1.9, 2.4 Hz), 7.19 (1H, ddd, J=1.4, 1.9, 8.1 Hz), 7.31 (1H, dd, J=8.1, 8.1 Hz), 7.30-7.50 (2H, m).

b) Preparation of 2-(3-(4-(1,1,1,3,3,3-hexafluoro-2-(methoxymethoxy)propan-2-yl)-2-propylphenoxy) phenyl) oxirane

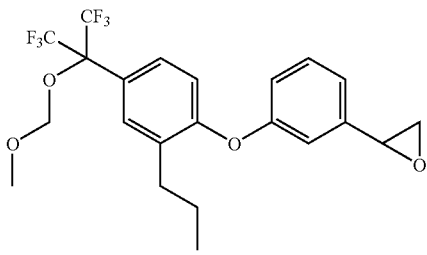

To a solution of 4-(1,1,1,3,3,3-hexafluoro-2-(methoxymethoxy)propan-2-yl)-2-propyl-1-(3-vinylphenoxy) benzene (686 mg, 1.52 mmol) in chloroform (10 mL), sodium hydrogen carbonate (510 mg), m-chloroperbenzoic acid (60%) (880 mg) were added at room temperature and the resultant mixture was stirred. After completion of the reaction, the reaction solution was added with an aqueous solution of sodium thiosulfate and a saturated aqueous solution of sodium hydrogen carbonate, extracted with ethyl acetate, and then concentrated in vacuo. The obtained residue was purified using silica-gel column chromatography (hexane/ethyl acetate) and the title compound (552 mg, yield 78%) was obtained as a colorless oil.

¹H-NMR (CDCl₃) δ: 0.95 (3H, t, J=7.3 Hz), 1.59-1.70 (2H, m), 2.68 (2H, t, J=7.6 Hz), 2.78 (1H, dd, J=2.7, 5.7 Hz), 3.15 (1H, dd, J=4.1, 5.7 Hz), 3.56 (3H, s), 3.85 (1H, dd, J=2.7, 4.1 Hz), 4.85 (2H, s), 6.81 (1H, d, J=8.9 Hz), 6.89-6.96 (2H, m), 7.07 (1H, ddd, J=1.4 Hz, 1.4, 8.1 Hz), 7.30-7.40 (2H, m), 7.48 (1H, d, J=1.4 Hz).

c) Preparation of 2-(3-(4-(1,1,1,3,3,3-hexafluoro-2-(methoxymethoxy)propan-2-yl)-2-propylphenoxy) phenyl) ethanol

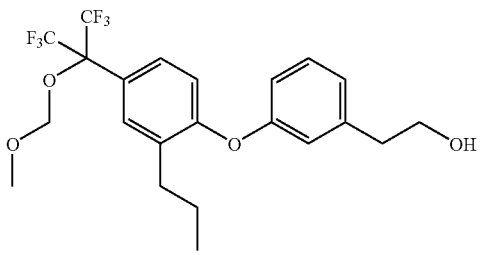

To a solution of 2-(3-(4-(1,1,1,3,3,3-hexafluoro-2-(methoxymethoxy)propan-2-yl)-2-propylphenoxy)phenyl) oxirane (550 mg, 1.18 mmol) in tetrahydrofuran (10 mL), boron trifluoride diethyl ether complex (400 μl) and sodium cyanoborohydride (222 mg) were added at 0° C. under an argon atmosphere, and the resultant mixture was stirred. After completion of the reaction, the reaction solution was added with a saturated aqueous solution of sodium hydrogen carbonate, extracted with ethyl acetate, and then concentrated in vacuo. The obtained residue was purified using silica-gel column chromatography (hexane/ethyl acetate) and the title compound (252 mg, yield 46%) was obtained as a colorless oil.

¹H-NMR (CDCl₃) δ: 0.95 (3H, t, J=7.3 Hz), 1.62-1.71 (2H, m), 2.68 (2H, t, J=7.3 Hz), 2.87 (2H, t, J=6.5 Hz), 3.41-4.57 (4H, m), 3.88 (2H, dt, J=6.5, 6.5 Hz), 4.86 (2H, s), 6.81-7.08 (4H, m), 7.27-7.46 (3H, m).

d) Preparation of 5-(benzo[d][1,3]dioxol-5-yl)-3-(3-(4-(1,1,1,3,3,3-hexafluoro-2-hydroxypropan-2-yl)-2-propylphenoxy)phenethyl)-5-methylimidazolidine-2,4-dione

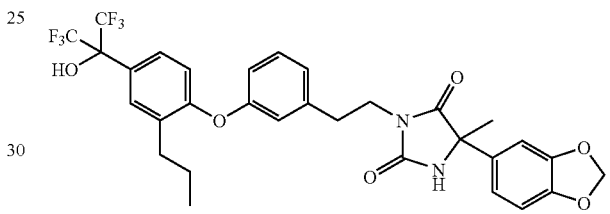

2-(3-(4-(1,1,1,3,3,3-Hexafluoro-2-(methoxymethoxy) propan-2-yl)-2-propylphenoxy) phenyl)ethanol was used in place of 1-(3-(4-(1,1,1,3,3,3-hexafluoro-2-(methoxymethoxy)propan-2-yl)-2-propyl phenoxy)phenyl) ethanol; and 5-(benzo[d][1,3]dioxol-5-yl)-5-methylimidazolidine-2,4-dione was used in place of 5-(4-(1-methylethoxy) phenyl)-5-methylimidazolidine-2,4-dione for a similar operation as Example 27 b), and the title compound was obtained as a colorless oil.

¹H-NMR (CDCl₃) δ: 0.95 (3H, t, J=7.3 Hz), 1.57-1.70 (2H, m), 1.69 (3H, s), 2.67 (2H, 1, J=7.6 Hz), 2.93 (2H, t, J=7.3 Hz), 3.70-3.79 (3H, m), 5.77 (1H, s), 5.94 (2H, s), 6.73-6.95 (7H, m), 7.17 (1H, d, J=8.6 Hz), 7.43 (1H, d, J=8.6 Hz), 7.55 (1H, s).

Example 31

Preparation of 5-(benzo[d][1,3]dioxol-5-yl)-5-ethyl-3-(3-(4-(1,1,1,3,3,3-hexafluoro-2-hydroxypropan-2-yl)-2-propylphenoxy)phenethyl)imidazolidine-2,4-dione

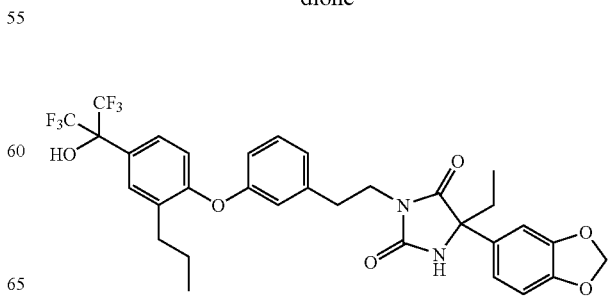

5-(Benzo[d][1,3]dioxol-5-yl)-5-ethylimidazolidine-2,4-dione was used in place of 5-(benzo[d][1,3]dioxol-5-yl)-5-methylimidazolidine-2,4-dione of Example 30 d) for a similar reaction and treatment, and the title compound was obtained as a colorless oil.

¹H-NMR (CDCl₃) δ: 0.82 (3H, t, J=7.3 Hz), 0.95 (3H, t, J=7.3 Hz), 1.58-1.71 (2H, m), 1.98-2.13 (2H, m), 2.67 (2H, t, J=7.6 Hz), 2.91 (2H, t, J=7.3 Hz), 3.62 (1H, s), 3.74 (2H, t, J=7.3 Hz), 5.85 (1H, s), 5.94 (2H, s), 6.74-6.96 (7H, m), 7.18 (1H, d, J=8.6 Hz), 7.43 (1H, d, J=8.6 Hz), 7.55 (1H, s).

Example 32

Preparation of 5-(2,3-dihydrobenzo[b][1,4]dioxin-6-yl)-5-ethyl-3-(3-(4-(1,1,1,3,3,3-hexafluoro-2-hydroxypropan-2-yl)-2-propylphenoxy)phenethyl)imidazolidine-2,4-dione

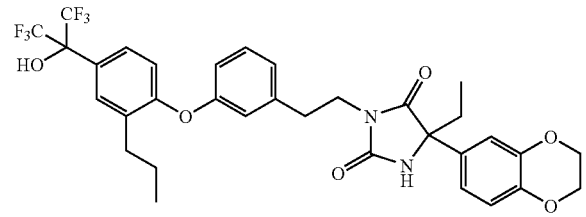

5-(2,3-Dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione of Example 30 d) for a similar reaction and treatment, and the title compound was obtained as a colorless oil.

¹H-NMR (CDCl₃) δ: 0.82 (3H, t, J=7.3 Hz), 0.95 (3H, t, J=7.3 Hz), 1.58-1.70 (2H, m), 1.98-2.13 (2H, m), 2.67 (2H, t, J=7.6 Hz), 2.91 (2H, t, J=7.8 Hz), 3.70 (1H, s), 3.73 (2H, t, J=7.6 Hz), 4.22-4.25 (4H, m), 5.77 (1H, s), 6.73-7.29 (8H, m), 7.43 (1H, d, J=8.6 Hz), 7.55 (1H, s).

Example 33

Preparation of 3-(3-(4-(1,1,1,3,3,3-hexafluoro-2-hydroxypropan-2-yl)-2-propylphenoxy)phenethyl)-5-(4-(1-methylethoxy)phenyl)-5-methylimidazolidine-2,4-dione

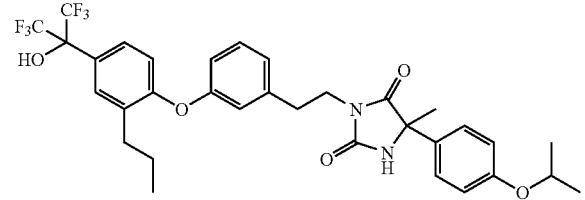

5-(4-(1-Methylethoxy)phenyl)-5-methylimidazolidine-2,4-dione was used in place of 5-(benzo[d][1,3]dioxol-5-yl)-5-methylimidazolidine-2,4-dione of Example 30 d) for a similar reaction and treatment, and the title compound was obtained as a colorless oil.

¹H-NMR (CDCl₃) δ: 0.95 (3H, t, J=7.3 Hz), 1.31 (6H, d, J=6.5 Hz), 1.59-1.69 (2H, m), 1.71 (3H, s), 2.67 (2H, t, J=7.6 Hz), 2.93 (2H, t, J=7.0 Hz), 3.69 (1H, s), 3.76 (2H, t, J=7.0 Hz), 4.51 (1H, sept, J=6.5 Hz), 6.74-6.86 (6H, m), 6.93 (1H, d, J=7.8 Hz), 7.16-7.27 (3H, m), 7.42 (1H, d, J=8.6 Hz), 7.55 (1H, s).

Example 34

Preparation of 5-(benzo[d][1,3]dioxol-5-yl)-3-(4-(4-(1,1,1,3,3,3-hexafluoro-2-hydroxypropan-2-yl)-2-propylphenoxy) benzyl)-5-methylimidazolidine-2,4-dione a) Preparation of 4-(4-(1,1,1,3,3,3-hexafluoro-2-(methoxymethoxy)propan-2-yl)-2-propylphenoxy) benzaldehyde

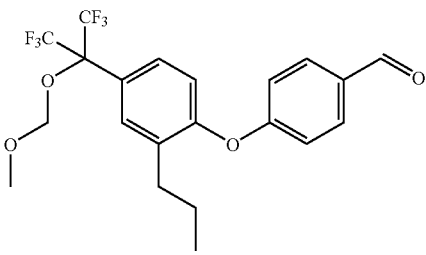

4-Formylboronic acid was used in place of 3-(hydroxymethyl)phenylboronic acid for a similar reaction and treatment as Preparation example 3 a), and the title compound was obtained as a colorless oil.

¹H-NMR (CDCl₃) δ: 0.92 (3H, t, J=7.3 Hz), 1.54-1.66 (2H, m), 2.61 (2H, t, J=7.6 Hz), 3.57 (3H, s), 4.88 (2H, s), 7.01 (1H, d, J=8.6 Hz), 7.02-7.07 (2H, m), 7.44-7.55 (2H, m), 7.85-7.91 (2H, m), 9.95 (1H, s).

b) Preparation of (4-(4-(1,1,1,3,3,3-hexafluoro-2-(methoxymethoxy)propan-2-yl)-2-propylphenoxy) phenyl) methanol

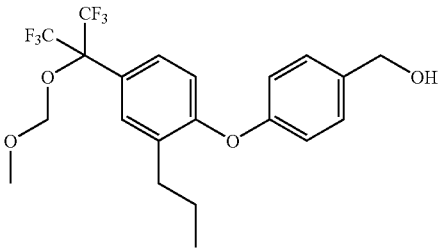

4-(4-(1,1,1,3,3,3-Hexafluoro-2-(methoxymethoxy)propan-2-yl)-2-propylphenoxy) benzaldehyde was used for a similar operation as Preparation example 4 b), and the title compound was obtained as a colorless oil.

¹H-NMR (CDCl₃) δ: 0.95 (3H, t, J=7.3 Hz), 1.53-1.70 (3H, m), 2.68 (2H, t, J=7.6 Hz), 3.55 (3H, s), 4.69 (2H, d, J=5.9 Hz), 4.85 (2H, s), 6.83 (1H, d, J=8.6 Hz), 6.96-7.01 (2H, m), 7.30-7.47 (4H, m).

c) Preparation of 5-(benzo[d][1,3]dioxol-5-yl)-3-(4-(4-(1,1,1,3,3,3-hexafluoro-2-hydroxypropan-2-yl)-2-propylphenoxy) benzyl)-5-methylimidazolidine-2,4-dione

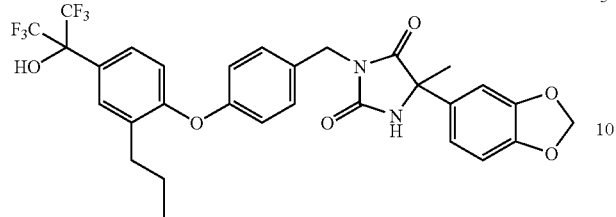

4-(4-(1,1,1,3,3,3-Hexafluoro-2-(methoxymethoxy)propan-2-yl)-2-propylphenoxy)phenyl) methanol was used for a similar operation as Example 30 d), and the title compound was obtained as a colorless oil.

$^1$H-NMR (CDCl$_3$) δ: 0.93 (3H, t, J=7.3 Hz), 1.57-1.71 (2H, m), 1.78 (3H, s), 2.65 (2H, t, J=7.6 Hz), 3.62 (1H, s), 4.63 (2H, s), 5.85 (1H, s), 5.95 (2H, s), 6.75-7.00 (6H, m), 7.32 (2H, d, J=8.6 Hz), 7.43 (1H, d, J=8.6 Hz), 7.55 (1H, s).

Example 35

Preparation of 5-(benzo[d][1,3]dioxol-5-yl)-5-ethyl-3-(4-(4-(1,1,1,3,3,3-hexafluoro-2-hydroxypropan-2-yl)-2-propylphenoxy)benzyl)imidazolidine-2,4-dione

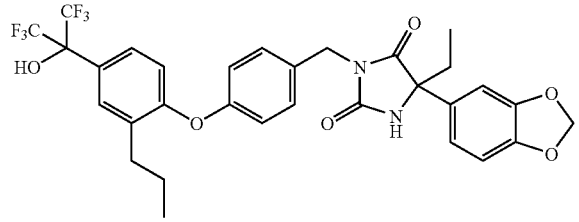

5-(Benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 34 c) for a similar reaction and treatment, and the title compound was obtained as a colorless oil.

$^1$H-NMR (CDCl$_3$) δ: 0.80 (3H, t, J=7.3 Hz), 0.95 (3H, t, J=7.3 Hz), 1.57-1.70 (4H, m), 2.67 (2H, t, J=7.6 Hz), 2.93 (2H, t, J=7.3 Hz), 3.70-3.79 (3H, m), 5.77 (1H, s), 5.94 (2H, s), 6.73-6.95 (7H, m), 7.17 (1H, d, J=8.6 Hz), 7.43 (1H, d, J=8.6 Hz), 7.55 (1H, s).

Example 36

Preparation of 5-(2,3-dihydrobenzo[b][1,4]dioxin-6-yl-5-ethyl-3-(4-(4-(1,1,1,3,3,3-hexafluoro-2-hydroxypropan-2-yl)-2-propylphenoxy)benzyl)imidazolidine-2,4-dione

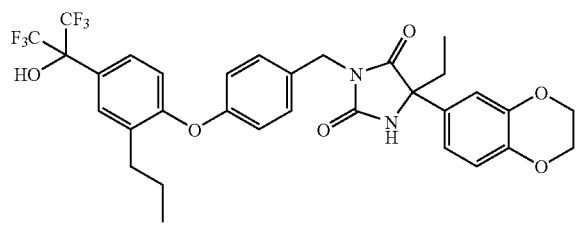

5-(2,3-Dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 34 c) for a similar reaction and treatment, and the title compound was obtained as a colorless oil.

$^1$H-NMR (CDCl$_3$) δ: 0.81 (3H, t, J=7.3 Hz), 0.93 (3H, t, J=7.3 Hz), 1.58-1.68 (2H, m), 2.01-2.25 (2H, m), 2.65 (2H, t, J=7.6 Hz), 3.57 (1H, s), 4.20-4.24 (4H, m), 4.61 (2H, s), 5.83 (1H, s), 6.78-7.00 (6H, m), 7.33 (2H, d, J=8.6 Hz), 7.43 (1H, d, J=8.6 Hz), 7.55 (1H, s).

Example 37

Preparation of 3-(4-(4-(1,1,1,3,3,3-hexafluoro-2-hydroxypropan-2-yl)-2-propoxyphenoxy)benzyl)-5-(4-(1-methylethoxy)phenyl)-5-methylimidazolidine-2,4-dione

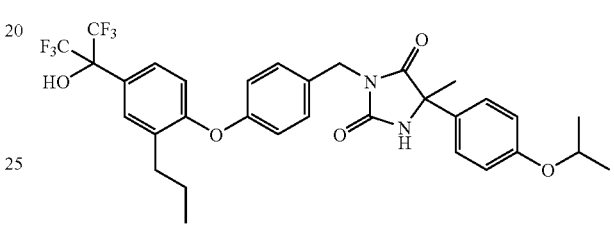

5-(4-(1-Methylethoxy)phenyl)-5-methylimidazolidine-2,4-dione was used in place of 5-(benzo[d][1,3]dioxol-5-yl)-5-methylimidazolidine-2,4-dione in Example 34 c) for a similar reaction and treatment, and the title compound was obtained as a colorless oil.

$^1$H-NMR (CDCl$_3$) δ: $^1$H-NMR (CDCl$_3$) δ: 0.93 (3H, t, J=7.3 Hz), 1.32 (6H, d, J=5.9 Hz), 1.59-1.68 (2H, m), 1.79 (3H, s), 2.65 (2H, t, J=7.6 Hz), 3.56 (1H, s), 4.53 (1H, sept, J=5.9 Hz), 4.63 (2H, s), 5.71 (1H, s), 6.80-6.91 (5H, m), 7.30-7.35 (2H, m), 7.43 (1H, d, J=8.6 Hz), 7.56 (2H, s).

Example 38

Preparation of 3-(4-(4-(1,1,1,3,3,3-hexafluoro-2-hydroxypropan-2-yl)-2-propylphenoxy)phenethyl)-5-(4-(1-methylethoxy)phenyl)-5-methylimidazolidine-2,4-dione a) Preparation of 4-(1,1,1,3,3,3-hexafluoro-2-(methoxymethoxy)propan-2-yl)-2-propyl-1-(4-vinylphenoxy) benzene

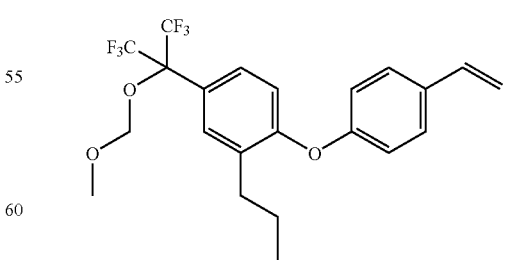

4-Vinylphenylboronic acid was used in place of phenylboronic acid for a similar reaction and treatment as Preparation example 3 a), and the title compound was obtained as a colorless oil.

¹H-NMR (CDCl₃) δ: 0.94 (3H, t, J=7.3 Hz), 1.61-1.70 (2H, m), 2.68 (2H, t, J=7.6 Hz), 3.56 (3H, s), 4.86 (2H, s), 5.21 (1H, dd, J=1.5, 10.8 Hz), 5.68 (1H, dd, J=1.5, 17.6 Hz), 6.70 (1H, dd, J=10.8, 17.6 Hz), 6.85 (1H, d, J=8.6 Hz), 6.92-6.99 (2H, m), 7.34-7.48 (4H, m).

b) Preparation of 2-(4-(4-(1,1,1,3,3,3-hexafluoro-2-(methoxymethoxy)propan-2-yl)-2-propylphenoxy) phenyl) ethanol

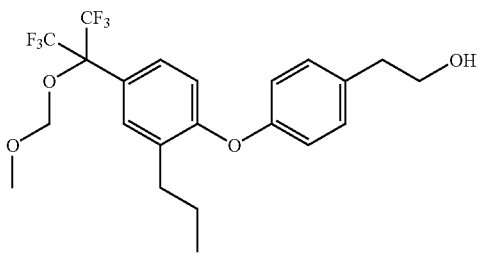

To a solution of 4-(1,1,1,3,3,3-hexafluoro-2-(methoxymethoxy)propan-2-yl)-2-propyl-1-(4-vinylphenoxy) benzene (242 mg, 539 mmol) in chloroform (5 mL), sodium hydrogen carbonate (181 mg) and m-chloroperbenzoic acid (60%) (310 mg) were added at room temperature and the resultant mixture was stirred. After completion of the reaction, the reaction solution was added with an aqueous solution of sodium thiosulfate and a saturated aqueous solution of sodium hydrogen carbonate, extracted with ethyl acetate, and then concentrated in vacuo. The obtained residue was purified using silica-gel column chromatography (hexane/ethyl acetate) and a colorless oil was obtained. To a tetrahydrofuran solution (2 mL) of this substance, boron trifluoride diethyl ether complex (40 μL) and sodium cyanoborohydride (40 mg) were added at 0° C. under an argon atmosphere, and the resultant mixture was stirred. After completion of the reaction, the reaction solution was added with a saturated aqueous solution of sodium hydrogen carbonate, extracted with ethyl acetate, and then concentrated in vacuo. The obtained residue was purified using silica-gel column chromatography (hexane/ethyl acetate) and the title compound (76 mg, yield 30%) was obtained as a colorless oil.

¹H-NMR (CDCl₃) δ: 0.95 (3H, t, J=7.3 Hz), 1.59-1.71 (2H, m), 2.69 (2H, t, J=7.6 Hz), 2.87 (2H, t, J=6.5 Hz), 3.55 (3H, s), 3.88 (2H, t, J=6.5 Hz), 4.85 (2H, s), 6.82 (1H, d, J=8.6 Hz), 6.93-6.98 (2H, m), 7.20-7.23 (2H, m), 7.30-7.47 (2H, m).

c) Preparation of 1-(4-(2-bromoethyl)phenoxy)-4-(1,1,1,3,3,3-hexafluoro-2-(methoxymethoxy)propan-2-yl)-2-propylbenzene

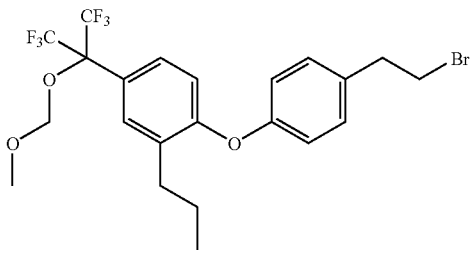

2-(4-(4-(1,1,1,3,3,3-Hexafluoro-2-(methoxymethoxy)propan-2-yl)-2-propylphenoxy) phenyl)ethanol was used for a similar operation as Preparation Example 3 b), and the title compound was obtained as a colorless oil.

¹H-NMR (CDCl₃) δ: 0.94 (3H, t, J=7.3 Hz), 1.59-1.71 (2H, m), 2.68 (2H, t, J=7.6 Hz), 3.15 (2H, t, J=7.6 Hz), 3.55 (3H, s), 3.56 (2H, t, J=7.6 Hz), 4.85 (2H, s), 6.83 (1H, d, J=8.6 Hz), 6.91-6.97 (2H, m), 7.18-7.21 (2H, m), 7.43 (1H, d, J=8.6 Hz), 7.56 (1H, s).

d) Preparation of 3-(4-(4-(1,1,1,3,3,3-hexafluoro-2-hydroxypropan-2-yl)-2-propylphenoxy)phenethyl)-5-(4-(1-methylethoxy)phenyl)-5-methylimidazoline-2,4-dione

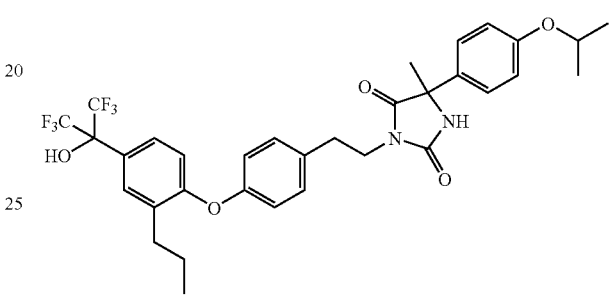

1-(4-(2-Bromoethyl)phenoxy)-4-(1,1,1,3,3,3-hexafluoro-2-(methoxymethoxy)propan-2-yl)-2-propylbenzene was used for a similar operation as Example 9, and the title compound was obtained as a colorless oil.

¹H-NMR (CDCl₃) δ: 0.94 (3H, t, J=7.3 Hz), 1.29 (6H, d, J=6.2 Hz), 1.62-1.71 (2H, m), 1.72 (3H, s), 2.67 (2H, t, J=7.6 Hz), 2.92 (2H, t, J=6.2 Hz), 3.75 (2H, t, J=6.2 Hz), 3.77 (1H, s), 4.49 (1H, sept, J=6.2 Hz), 5.73 (1H, s), 6.73 (2H, d, J=8.6 Hz), 6.81-6.91 (4H, m), 7.10-7.14 (2H, m), 7.42 (1H, d, J=8.6 Hz), 7.55 (2H, s).

Example 39

Preparation of 5-(2,3-dihydrobenzo[b][1,4]dioxin-6-yl)-5-ethyl-3-(4-(4-(1,1,1,3,3,3-hexafluoro-2-hydroxypropan-2-yl)-2-propylphenoxy)phenethyl)imidazolidine-2,4-dione

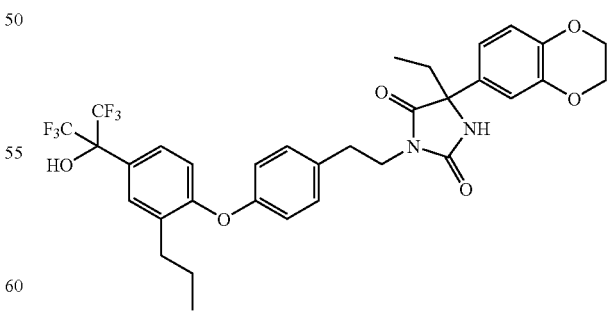

5-(2,3-Dihydrobenzo[b][1,4]dioxin-6-yl)-5-ethylimidazolidine-2,4-dione was used in place of 5-(4-(1-methylethoxy)phenyl)-5-methylimidazolidine-2,4-dione in Example 38 d) for a similar reaction and treatment, and the title compound was obtained as a colorless oil.

¹H-NMR (CDCl₃) δ: 0.82 (3H, t, J=7.3 Hz), 0.94 (3H, t, J=7.3 Hz), 1.59-1.70 (2H, m), 1.96-2.16 (2H, m), 2.67 (2H, t, J=7.6 Hz), 2.91 (2H, t, J=7.3 Hz), 3.73 (2H, t, J=7.3 Hz), 3.78 (1H, s), 4.11-4.18 (4H, m), 5.88 (1H, s), 6.70-7.12 (8H, m), 7.42 (1H, d, J=8.6 Hz), 7.54 (1H, s).

Example 40

Preparation of 5-(benzo[d][1,3]dioxol-5-yl)-3-((4-(4-(1,1,1,3,3,3-hexafluoro-2-hydroxypropan-2-yl)-2-propylphenoxy)pyridin-2-yl)methyl)-5-methylimidazolidine-2,4-dione a) Preparation of 2-chloro-4-(4-(1,1,1,3,3,3-hexafluoro-2-(methoxymethoxy)propan-2-yl)-2-propylphenoxy) pyridine

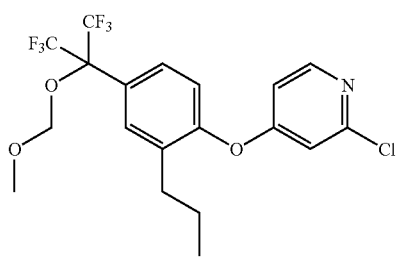

2-Chloropyridine-4-boronic acid was used in place of 3-(hydroxymethyl)phenylboronic acid for a similar reaction and treatment as Preparation example 3 a), and the compound of interest was obtained as a colorless oil.

¹H-NMR (CDCl₃) δ: 0.91 (3H, t, J=7.3 Hz), 1.52-1.66 (2H, m), 2.55 (2H, t, J=7.3 Hz), 3.58 (3H, s), 4.89 (2H, s), 6.76 (1H, dd, J=2.2, 5.4 Hz), 7.07 (1H, d, J=8.6 Hz), 7.50-7.57 (3H, m), 8.26 (1H, d, J=5.4 Hz).

b) Preparation of 4-(4-(1,1,1,3,3,3-hexafluoro-2-(methoxymethoxy)propan-2-yl)-2-propylphenoxy)-2-methylpyridine

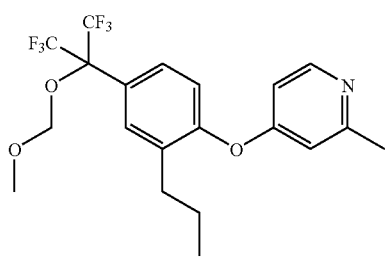

To a solution of 2-chloro-4-(4-(1,1,1,3,3,3-hexafluoro-2-(methoxymethoxy)propan-2-yl)-2-propylphenoxy) pyridine (867 mg, 559 μmol) in 1,4-dioxane, trimethylaluminum heptane solution (2 mol/L, 1.13 mL) and tetrakis triphenylphosphine palladium complex (218 mg) were added at room temperature under an argon atmosphere, and then the resultant mixture was heated at 80° C. After completion of the reaction, the reaction solution was neutralized by adding water and 2 mol/L of hydrochloric acid, extracted with ethyl acetate, and then concentrated in vacuo. The obtained residue was purified using silica-gel column chromatography (hexane/ethyl acetate) and the title compound (780 mg, yield 94%) was obtained as a colorless oil.

¹H-NMR (CDCl₃) δ: 0.91 (3H, t, J=7.3 Hz), 1.53-1.64 (2H, m), 2.52 (3H, s), 2.57 (2H, t, J=7.6 Hz), 3.58 (3H, s), 4.89 (2H, s), 6.30 (1H, dd, J=2.2, 5.7 Hz), 7.03 (1H, d, J=8.6 Hz), 7.46-7.55 (3H, m), 8.36 (1H, d, J=5.7 Hz).

c) Preparation of (4-(4-(1,1,1,3,3,3-hexafluoro-2-(methoxymethoxy)propan-2-yl)-2-propylphenoxy) pyridin-2-yl)methyl acetate

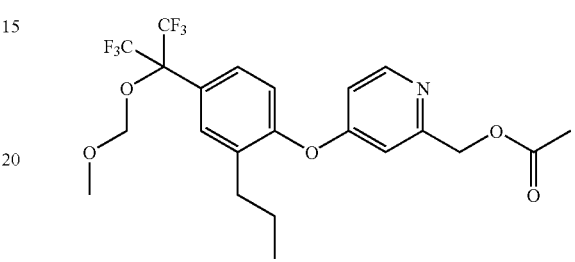

To a solution of 4-(4-(1,1,1,3,3,3-hexafluoro-2-(methoxymethoxy)propan-2-yl)-2-propylphenoxy)-2-methylpyridine (780 mg, 1.78 mmol) in chloroform (2 mL), m-chloroperbenzoic acid (2.05 g) was added at room temperature and the resultant mixture was stirred. After completion of the reaction, the reaction solution was added with an aqueous solution of sodium thiosulfate and a saturated aqueous solution of sodium hydrogen carbonate, extracted with ethyl acetate, and then dried using sodium sulfate. After filtration, the filtrate was concentrated in vacuo. The obtained residue was added with acetic anhydride and heated at a surrounding temperature of 140° C. After completion of the reaction, the reaction solution was added with methanol (4 mL) at room temperature, then neutralized by adding a saturated aqueous solution of sodium hydrogen carbonate, extracted with ethyl acetate, and then concentrated in vacuo. The obtained residue was purified using silica-gel column chromatography (hexane/ethyl acetate) and the title compound (490 mg, yield 56%) was obtained as a colorless oil.

¹H-NMR (CDCl₃) δ: 0.91 (3H, t, J=7.6 Hz), 1.56-1.66 (2H, m), 2.14 (3H, s), 2.57 (2H, t, J=7.6 Hz), 3.58 (3H, s), 4.89 (2H, s), 5.20 (2H, s), 6.71 (1H, dd, J=2.4, 5.7 Hz), 6.89 (1H, d, J=2.4 Hz), 7.05 (1H, d, J=8.6 Hz), 7.50-7.57 (2H, m), 8.47 (1H, d, J=5.7 Hz).

d) Preparation of (4-(4-(1,1,1,3,3,3-hexafluoro-2-(methoxymethoxy)propan-2-yl)-2-propylphenoxy) pyridin-2-yl)methanol

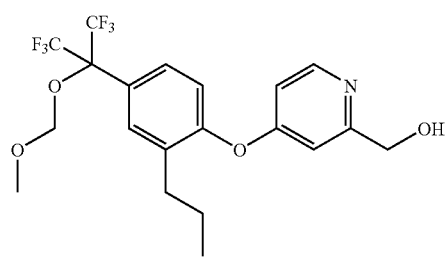

To a solution of (4-(4-(1,1,1,3,3,3-hexafluoro-2-(methoxymethoxy)propan-2-yl)-2-propylphenoxy)pyridin-2-yl) methyl acetate (221 mg, 446 μmol) in methanol (3 mL), potassium carbonate (123 mg) was added at room temperature and the resultant mixture was stirred. After completion of the reaction, the reaction solution was concentrated in vacuo. The residue was neutralized by adding water and 2 mol/L of hydrochloric acid at room temperature, extracted with ethyl acetate, and then concentrated in vacuo. The obtained residue was purified using silica-gel column chromatography (hexane/ethyl acetate) and the title compound (167 mg, yield 83%) was obtained as a colorless oil.

$^1$H-NMR (CDCl$_3$) δ: 0.90 (3H, t, J=7.3 Hz), 1.55-1.63 (2H, m), 2.56 (2H, t, J=7.6 Hz), 3.58 (3H, s), 4.71 (2H, s), 4.89 (2H, s), 6.74 (1H, dd, J=2.4, 5.7 Hz), 6.78 (1H, d, J=2.4 Hz), 7.04 (1H, d, J=8.6 Hz), 7.48-7.56 (2H, m), 8.43 (1H, d, J=5.7 Hz).

e) Preparation of 2-(bromomethyl)-4-(4-(1,1,1,3,3,3-hexafluoro-2-(methoxymethoxy)propan-2-yl)-2-propylphenoxy) pyridine

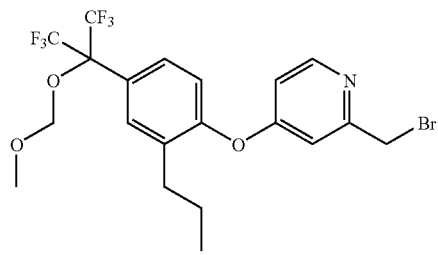

(4-(4-(1,1,1,3,3,3-Hexafluoro-2-(methoxymethoxy)propan-2-yl)-2-propylphenoxy) pyridin-2-yl)methanol was subjected to a similar operation as Preparation example 3 b), and the title compound was obtained as a colorless oil.

$^1$H-NMR (CDCl$_3$) δ: 0.91 (3H, t, J=7.3 Hz), 1.50-1.64 (2H, m), 2.57 (2H, t, J=7.6 Hz), 3.58 (3H, s), 4.50 (2H, s), 4.89 (2H, s), 6.70 (1H, dd, J=2.4, 5.7 Hz), 6.99 (1H, d, J=2.4 Hz), 7.06 (1H, d, J=8.6 Hz), 7.49-7.57 (2H, m), 8.45 (1H, d, J=5.7 Hz).

f) Preparation of 5-(benzo[d][1,3]dioxol-5-yl)-3-((4-(4-(1,1,1,3,3,3-hexafluoro-2-hydroxypropan-2-yl)-2-propylphenoxy)pyridin-2-yl)methyl)-5-methylimidazolidine-2,4-dione

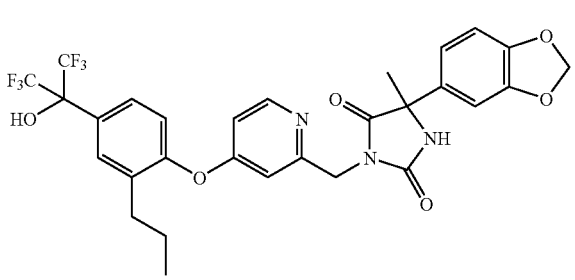

2-(Bromomethyl)-4-(4-(1,1,1,3,3,3-hexafluoro-2-(methoxymethoxy)propan-2-yl)-2-propylphenoxy)pyridine was used for a similar operation as Example 1, and the title compound was obtained as a colorless oil.

$^1$H-NMR (CD$_3$OD) δ: 0.89 (3H, t, J=7.3 Hz), 1.52-1.61 (2H, m), 1.75 (3H, s), 2.48 (2H, t, J=7.6 Hz), 5.02 (2H, s), 5.98 (2H, s), 6.77-7.28 (6H, m), 7.72 (1H, d, J=8.6 Hz), 7.79 (1H, s), 8.68 (1H, d, J=6.5 Hz).

Example 41

Preparation of 5-(benzo[d][1,3]dioxol-5-yl)-5-ethyl-3-((4-(4-(1,1,1,3,3,3-hexafluoro-2-hydroxypropan-2-yl)-2-propylphenoxy)pyridin-2-yl)methyl)imidazolidine-2,4-dione

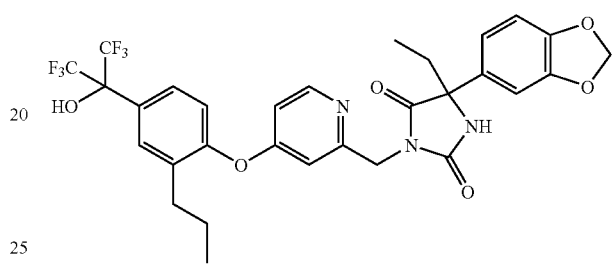

5-(Benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 40 0 for a similar reaction and treatment, and the title compound was obtained as a colorless oil.

$^1$H-NMR (CD$_3$OD) δ: 0.80-0.92 (6H, m), 1.51-1.1.60 (2H, m), 2.00-2.19 (2H, m), 2.46 (2H, t, J=7.6 Hz), 5.00 (2H, s), 5.98 (2H, s), 6.81 (1H, d, J=8.4 Hz), 6.98 (1H, d, J=8.4 Hz), 7.03 (1H, s), 7.04 (1H, s), 7.09 (1H, d, J=8.6 Hz), 7.17 (1H, d, J=6.5 Hz), 7.72 (1H, d, J=8.6 Hz), 7.79 (1H, s), 8.67 (1H, d, J=6.5 Hz).

Example 42

Preparation of 5-(2,3-dihydrobenzo[b][1,4]dioxin-6-yl)-5-ethyl-3-((4-(4-(1,1,1,3,3,3-hexafluoro-2-hydroxypropan-2-yl)-2-propylphenoxy)pyridin-2-yl)methyl)imidazolidine-2,4-dione

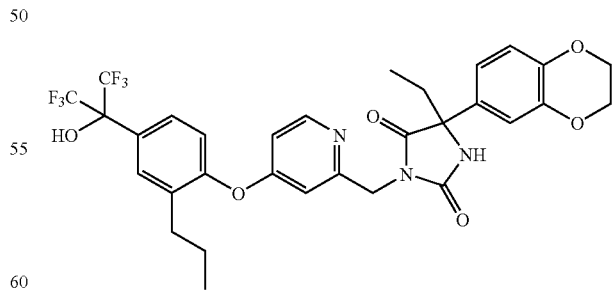

5-(2,3-Dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in *Example* 40 f) for a similar reaction and treatment, and the title compound was obtained as a colorless oil.

¹H-NMR (CDCl₃) δ: 0.80-0.92 (6H, m), 1.50-1.70 (2H, m), 1.90-2.20 (2H, m), 2.46 (2H, t, J=7.6 Hz), 4.00-4.30 (4H, m), 4.63 (2H, s), 5.86 (1H, s), 6.78-7.26 (6H, m), 7.70-7.80 (2H, m), 7.72-7.78 (1H, m).

Example 43

Preparation of 5-(2,3-dihydrobenzofuran-5-yl)-3-((4-(4-(1,1,1,3,3,3-hexafluoro-2-hydroxypropan-2-yl)-2-propylphenoxy)pyridin-2-yl)methyl)-5-methylimidazolidine-2,4-dione

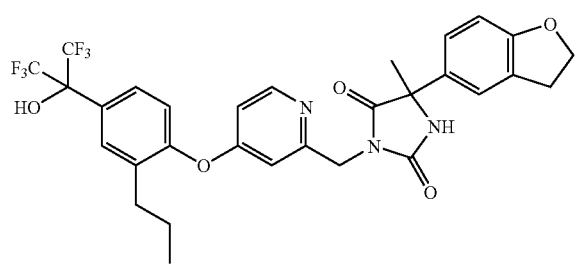

5-(2,3-Dihydrobenzofuran-5-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a colorless oil.

¹H-NMR (CD₃OD) δ: 0.89 (3H, t, J=7.3 Hz), 1.50-1.61 (2H, m), 1.76 (3H, s), 2.46 (2H, t, J=7.6 Hz), 3.23 (2H, t, J=8.1 Hz), 3.39 (1H, s), 4.59 (2H, t, J=8.1 Hz), 5.11 (2H, s), 6.77 (1H, d, 8.6 Hz), 6.91 (1H, s), 7.06-7.28 (4H, m), 7.71 (1H, d, J=8.6 Hz), 7.77 (1H, s), 8.71 (1H, d, J=5.9 Hz).

Example 44

Preparation of 3-((4-(4-(1,1,1,3,3,3-hexafluoro-2-hydroxypropan-2-yl)-2-propylphenoxy)pyridin-2-yl)methyl)-5-(2-methoxyphenyl)-5-methylimidazolidine-2,4-dione

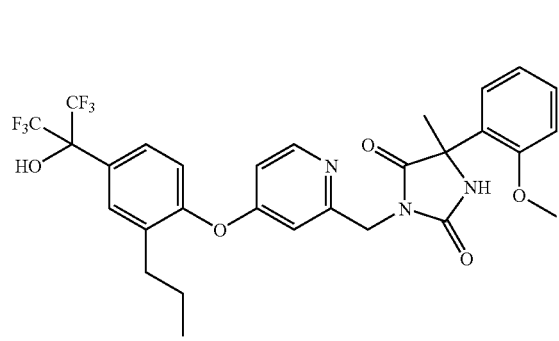

5-(2-Methoxyphenyl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a colorless oil.

¹H-NMR (CD₃OD) δ: 0.91 (3H, t, J=7.3 Hz), 1.55-1.65 (2H, m), 1.80 (3H, s), 2.51 (2H, t, J=7.6 Hz), 3.81 (3H, s), 5.14 (2H, s), 6.95-7.44 (7H, m), 7.72 (1H, d, J=8.6 Hz), 7.80 (1H, s), 8.68 (1H, d, J=6.5 Hz).

Example 45

Preparation of 3-((4-(4-(1,1,1,3,3,3-hexafluoro-2-hydroxypropan-2-yl)-2-propylphenoxy)pyridin-2-yl)methyl)-5-(4-(1-methylethoxy)phenyl)-5-methylimidazolidine-2,4-dione

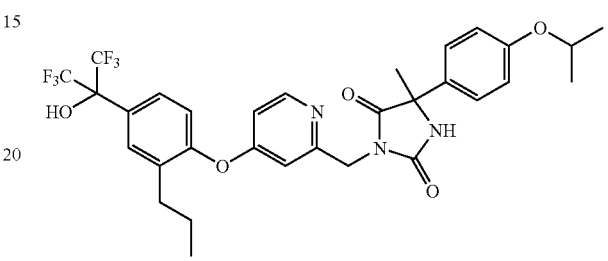

5-(4-(1-Methylethoxy)phenyl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a colorless oil.

¹H-NMR (CDCl₃) δ: 0.88 (3H, t, J=7.3 Hz), 1.31 (6H, d, J=5.9 Hz), 1.34-1.58 (2H, m), 1.73 (3H, s), 2.53 (2H, t, J=7.6 Hz), 3.57 (1H, s), 4.49-4.60 (1H, m), 4.77 (2H, s), 4.88 (1H, s), 6.48 (1H, s), 6.65-6.99 (3H, m), 7.00 (1H, d, J=8.6 Hz), 7.36 (2H, d, J=8.6 Hz), 7.43-7.54 (2H, m), 8.37 (1H, d, J=5.9 Hz).

Example 46

Preparation of 5-(4-butoxyphenyl)-3-((4-(4-(1,1,1,3,3,3-hexafluoro-2-hydroxypropan-2-yl)-2-propylphenoxy) pyridin-2-yl)methyl)-5-methylimidazolidine-2,4-dione

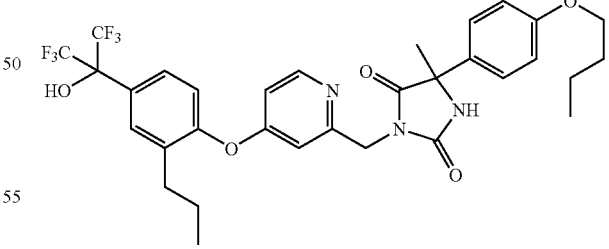

5-(4-Butoxyphenyl)-5-methylimidazolidine-2,4-dione was used in place of 5-(benzo[d][1,3]dioxol-5-yl)-5-methylimidazolidine-2,4-dione in Example 40 l) for a similar reaction and treatment, and the title compound was obtained as a colorless oil.

¹H-NMR (CD₃OD) δ: 0.88 (3H, t, J=7.0 Hz), 0.96 (3H, t, J=7.3 Hz), 1.37-1.59 (4H, m), 1.70-1.81 (5H, m), 2.46 (2H, t, J=7.6 Hz), 3.96 (2H, 1, J=6.5 Hz), 5.03 (2H, s), 6.91 (2H, d, J=8.6 Hz), 6.95 (1H, d, J=1.5 Hz), 7.08 (1H, d, J=8.6 Hz), 7.17 (1H, d, J=6.5 Hz), 7.40 (2H, d, J=8.6 Hz), 7.71 (1H, d, J=8.6 Hz), 7.78 (1H, s), 8.68 (1H, d, J=6.5 Hz).

Example 47

Preparation of 3-((4-(4-(1,1,1,3,3,3-hexafluoro-2-hydroxypropan-2-yl)-2-propylphenoxy)pyridin-2-yl)methyl)-5-methyl-5-(4-(4-methylbenzyloxy)phenyl)imidazolidine-2,4-dione

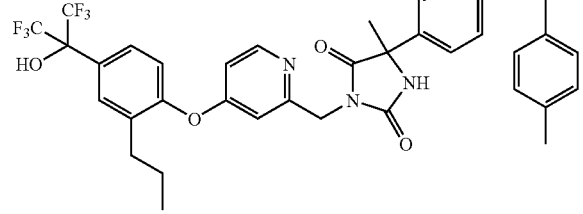

5-Methyl-5-(4-(4-methylbenzyloxy)phenyl)imidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a colorless oil.

$^1$H-NMR (CD$_3$OD) δ: 0.88 (3H, t, J=7.3 Hz), 1.50-1.59 (5H, m), 2.35 (3H, s), 2.46 (2H, t, J=7.6 Hz), 5.01 (2H, s), 5.02 (2H, s), 6.97-7.39 (11H, s), 7.71 (1H, d, J=8.6 Hz), 7.78 (1H, s), 8.67 (1H, d, J=6.5 Hz).

Example 48

Preparation of 3-((4-(4-(1,1,1,3,3,3-hexafluoro-2-hydroxypropan-2-yl)-2-propylphenoxy)pyridin-2-yl)methyl)-5-(6-methoxypyridin-3-yl)-5-methylimidazolidine-2,4-dione

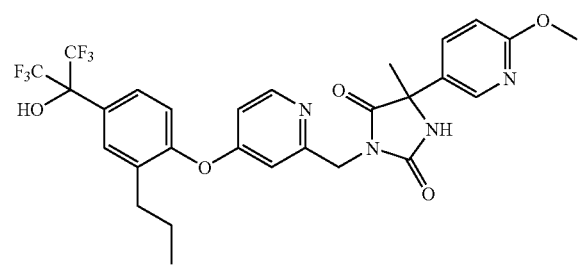

5-(6-Methoxypyridin-3-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a colorless oil.

$^1$H-NMR (CDCl$_3$) δ: 0.90 (3H, t, J=7.3 Hz), 1.53-1.62 (2H, m), 1.81 (3H, s), 2.49 (2H, t, J=7.6 Hz), 3.38 (1H, s), 4.18 (3H, s), 5.08 (2H, s), 7.08-7.33 (5H, m), 7.00 (1H, d, J=8.6 Hz), 7.73 (2H, d, J=8.6 Hz), 7.79 (1H, s), 8.69 (1H, d, J=6.8 Hz).

Example 49

Preparation of 3-((4-(4-(1,1,1,3,3,3-hexafluoro-2-hydroxypropan-2-yl)-2-propylphenoxy)pyridin-2-yl)methyl)-5-methyl-5-p-tolylimidazolidine-2,4-dione

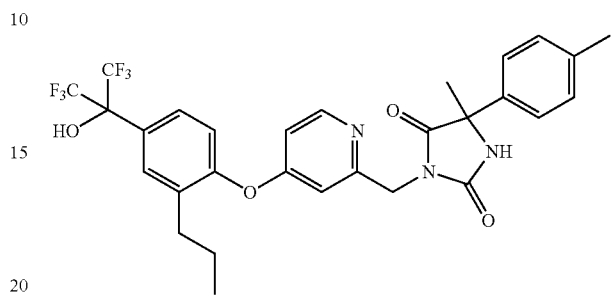

5-Methyl-5-p-tolylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a colorless oil.

$^1$H-NMR (CD$_3$OD) δ: 0.89 (3H, t, J=7.3 Hz), 1.52-1.60 (2H, m), 1.77 (3H, s), 2.36 (3H, s), 2.46 (2H, t, J=7.6 Hz), 5.00 (2H, s), 7.01-7.45 (7H, m), 7.72 (1H, d, J=8.6 Hz), 7.80 (1H, s), 8.68 (1H, d, J=6.5 Hz).

Example 50

Preparation of 3-((4-(4-(1,1,1,3,3,3-hexafluoro-2-hydroxypropan-2-yl)-2-propylphenoxy)pyridin-2-yl)methyl)-5-methyl-5-(4-nitrophenyl)imidazolidine-2,4-dione

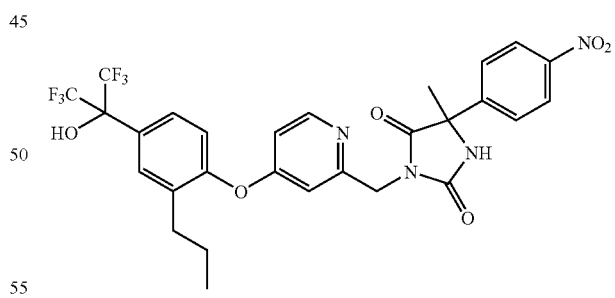

5-Methyl-5-(4-nitrophenyl)imidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a colorless oil.

$^1$H-NMR (CD$_3$OD) δ: 0.88 (3H, t, J=7.3 Hz), 1.51-1.60 (2H, m), 1.83 (3H, s), 2.47 (2H, t, J=7.6 Hz), 5.03 (2H, s), 7.03-7.25 (3H, m), 7.70-7.81 (4H, m), 8.27 (2H, d, J=8.6 Hz), 8.68 (1H, d, J=6.5 Hz).

Example 51

Preparation of 3-((4-(4-(1,1,1,3,3,3-hexafluoro-2-hydroxypropan-2-yl)-2-propylphenoxy)pyridin-2-yl)methyl)-5-methyl-5-(6-(methylthio)pyridin-3-yl)imidazolidine-2,4-dione

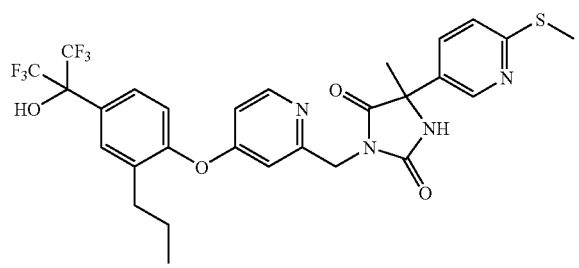

5-Methyl-5-(6-methylthio)pyridin-3-yl)imidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a colorless oil.

$^1$H-NMR (CDCl$_3$) δ: 0.76 (3H, t, J=7.3 Hz), 1.37 (2H, qt, J=7.3, 7.6 Hz), 1.82 (3H, s), 2.40 (2H, t, 7.6 Hz), 2.59 (3H, s), 4.76-4.79 (2H, m), 5.65 (1H, s), 6.19 (1H, s), 6.43 (1H, s), 6.82-6.86 (1H, m), 6.96 (1H, d, J=8.1 Hz), 7.21 (1H, d, J=8.1 Hz), 7.59 (1H, d, J=8.6 Hz), 7.68 (1H, d, J=2.2 Hz), 7.77 (1H, dd, J=2.7, 8.6 Hz), 8.12 (1H, d, J=2.2 Hz), 8.39 (1H, d, J=5.4 Hz).

Example 52

Preparation of 3-((4-(4-(1,1,1,3,3,3-hexafluoro-2-hydroxypropan-2-yl)-2-propylphenoxy)pyridin-2-yl)methyl)-5-methyl-5-(6-(methylsulfonyl)pyridin-3-yl)imidazolidine-2,4-dione

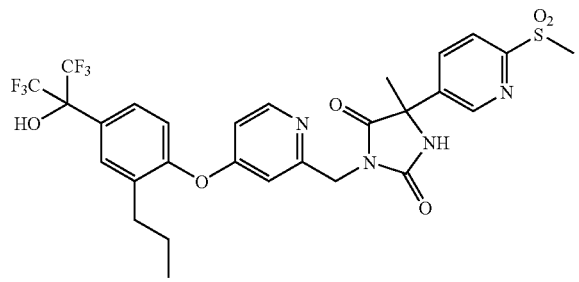

3-((4-(4-(1,1,1,3,3,3-Hexafluoro-2-hydroxypropan-2-yl)-2-propyl phenoxy)pyridin-2-yl)methyl)-5-methyl-5-(6-(methylthio)pyridin-3-yl)imidazolidine-2,4-dione was used for a similar reaction and treatment as Example 21, and the title compound was obtained as a colorless oil.

$^1$H-NMR (CDCl$_3$) δ: 0.86 (3H, t, J=7.3 Hz), 1.53 (2H, qt, J=7.3, 7.6 Hz), 1.89 (3H, s), 2.50 (2H, t, J=7.6 Hz), 3.22 (3H, s), 4.73-4.82 (2H, m), 5.30 (1H, s), 6.65 (1H, d, J=2.2 Hz), 6.75 (1H, dd, J=2.2, 5.7 Hz), 7.01 (1H, d, J=8.6 Hz), 7.19 (1H, s), 7.59 (1H, d, J=5.7, 8.6 Hz), 7.67 (1H, s), 8.06 (1H, d, J=8.3 Hz), 8.21 (1H, dd, J=2.2, 8.3 Hz), 8.33 (1H, d, J=5.7 Hz), 8.91 (1H, d, J=2.2 Hz).

Example 53

Preparation of 5-(furan-2-yl)-3-((4-(4-(1,1,1,3,3,3-hexafluoro-2-hydroxypropan-2-yl)-2-propylphenoxy) pyridin-2-yl)methyl)-5-methylimidazolidine-2,4-dione

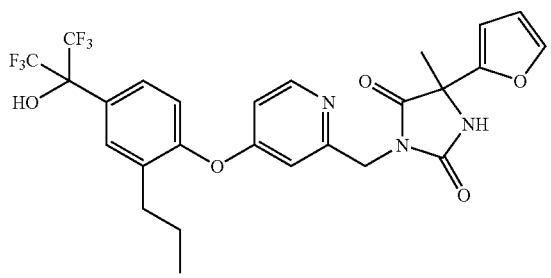

5-(Furan-2-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a colorless oil.

$^1$H-NMR (CD$_3$OD) δ: 0.91 (3H, t, J=7.3 Hz), 1.55-1.64 (2H, m), 1.80 (3H, s), 2.52 (2H, 1, J=7.3 Hz), 5.10 (2H, s), 6.36-6.45 (2H, m), 7.10-7.25 (3H, m), 7.40 (1H, s), 7.72 (1H, d, J=8.6 Hz), 7.79 (1H, s), 8.69 (1H, d, J=5.4 Hz).

Example 54

Preparation of 3-((4-(4-(1,1,1,3,3,3-hexafluoro-2-hydroxypropan-2-yl)-2-propylphenoxy)pyridin-2-yl)methyl)-1,5,5-trimethylimidazolidine-2,4-dione

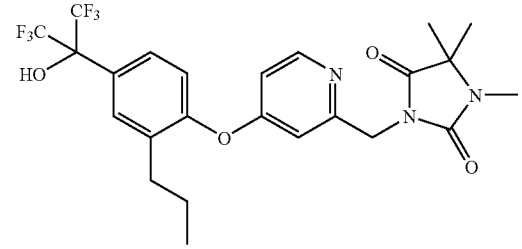

1,5,5-Trimethylimidazolidine-2,4-dione was used in place of 5-(benzo[d][1,3]dioxol-5-yl)-5-methylimidazolidine-2,4-dione in Example 40.0 for a similar reaction and treatment, and the title compound was obtained as a colorless oil.

$^1$H-NMR (CDCl$_3$) δ: 0.91 (3H, t, J=7.4 Hz), 1.39 (6H, s), 1.52-1.64 (2H, m), 2.52 (2H, t, J=7.6 Hz), 2.90 (3H, s), 5.02 (2H, s), 6.95 (1H, s), 7.13 (1H, d, J=8.6 Hz), 7.30 (1H, d, J=7.3 Hz), 7.72 (1H, d, J=8.6 Hz), 7.79 (1H, s), 8.69 (1H, d, J=7.3 Hz).

Example 55

Preparation of 3-((4-(4-(1,1,1,3,3,3-hexafluoro-2-hydroxypropan-2-yl)-2-propylphenoxy)pyridin-2-yl)methyl)-1,3-diazaspiro[4.4]nonane-2,4-dione

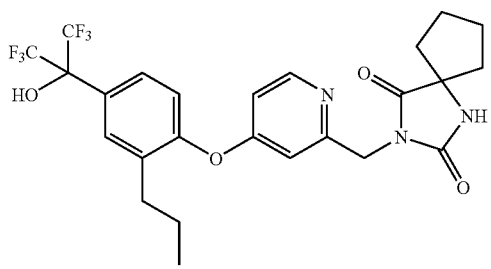

1,3-Diazaspiro[4.4]nonane-2,4-dione was used in place of 5-(benzo[d][1,3]dioxol-5-yl)-5-methylimidazolidine-2,4-dione in Example 40 f) for a similar reaction and treatment, and the title compound was obtained as a colorless oil.

$^1$H-NMR (CD$_3$OD) δ: 0.91 (3H, t, J=7.3 Hz), 1.27-2.36 (10H, m), 2.52 (2H, t, J=7.6 Hz), 5.01 (2H, s), 7.02 (1H, s), 7.13 (1H, d, J=8.6 Hz), 7.27 (1H, d, J=7.3 Hz), 7.73 (1H, d, J=8.6 Hz), 7.80 (1H, s), 8.70 (1H, d, J=7.3 Hz).

Example 56

Preparation of 3-(1-(4-(4-(1,1,1,3,3,3-hexafluoro-2-hydroxypropan-2-yl)-2-propylphenoxy)pyridin-2-yl)ethyl)-5-(4-(1-methylethoxy)phenyl)-5-methylimidazolidine-2,4-dione a) Preparation of 4-(4-(1,1,1,3,3,3-hexafluoro-2-(methoxymethoxy)propan-2-yl)-2-propylphenoxy) picolinaldehyde

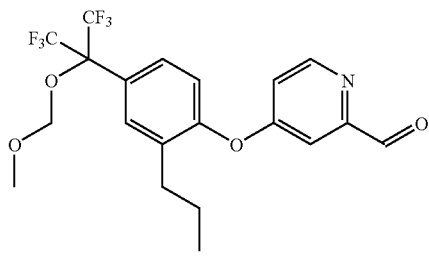

To a solution of (4-(4-(1,1,1,3,3,3-hexafluoro-2-(methoxymethoxy)propan-2-yl)-2-propylphenoxy)pyridin-2-yl)methanol (110 mg, 446 μmol) in dimethylsulfoxide (3 mL), 2-iodoxyperbenzoic acid (136 mg) was added at room temperature, and the resultant mixture was stirred. After completion of the reaction, the reaction solution was added with a saturated aqueous solution of sodium thiosulfate and a saturated aqueous solution of sodium hydrogen carbonate at room temperature, extracted with ethyl acetate, and then concentrated in vacuo. The obtained residue was purified using silica-gel column chromatography (hexane/ethyl acetate) and the title compound (100 mg, yield 92%) was obtained as a colorless oil.

$^1$H-NMR (CDCl$_3$) δ: 0.90 (3H, t, J=7.6 Hz), 1.52-1.66 (2H, m), 2.55 (2H, t, J=7.6 Hz), 3.58 (3H, s), 4.90 (2H, s), 7.02-7.08 (2H, m), 7.46 (1H, d=2.7 Hz), 7.50-7.58 (2H, m), 8.66 (1H, d, J=5.4 Hz), 10.05 (1H, s).

b) Preparation of 1-(4-(4-(1,1,1,3,3,3-hexafluoro-2-(methoxymethoxy)propan-2-yl)-2-propylphenoxy)pyridin-2-yl)ethanol

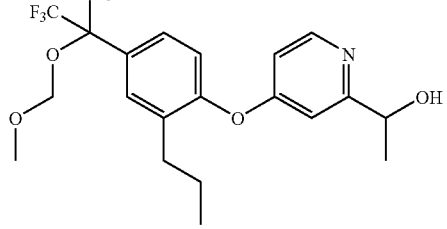

4-(4-(1,1,1,3,3,3-Hexafluoro-2-(methoxymethoxy)propan-2-yl)-2-propylphenoxy) picolinaldehyde was used for a similar operation as Example 27 a), and the title compound was obtained as a colorless oil.

$^1$H-NMR (CDCl$_3$) δ: 0.90 (3H, t, J=7.3 Hz), 1.40 (3H, d, J=6.5 Hz), 1.53-1.67 (2H, m), 2.57 (2H, t, J=7.6 Hz), 3.58 (3H, s), 4.00-4.15 (1H, m), 4.80-4.89 (3H, m), 6.68 (1H, dd, J=2.3, 5.7 Hz), 6.83 (1H, d, J=2.3 Hz), 7.03 (1H, d, J=8.6 Hz), 7.47-7.56 (2H, m), 8.40 (1H, d, J=5.7 Hz).

c) Preparation of 3-(1-(4-(4-(1,1,1,3,3,3-hexafluoro-2-hydroxypropan-2-yl)-2-propylphenoxy)pyridin-2-yl)ethyl)-5-(4-(1-methylethoxy)phenyl)-5-methylimidazolidine-2,4-dione

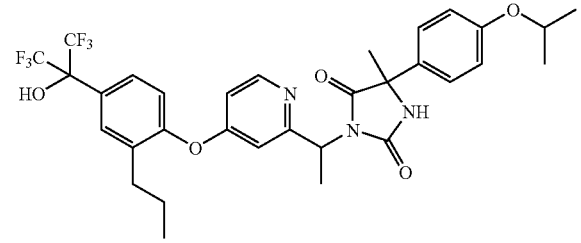

1-(4-(4-(1,1,1,3,3,3-Hexafluoro-2-(methoxymethoxy)propan-2-yl)-2-propylphenoxy) pyridin-2-yl)ethanol was used for a similar operation as Example 27 b), and the title compound was obtained as a colorless oil.

$^1$H-NMR (CDCl$_3$) δ: 0.93 (3H, t, J=7.3 Hz), 1.31 (6H, d, J=5.9 Hz), 1.52-1.85 (8H, m), 2.55 (2H, t, J=7.6 Hz), 4.48-4.54 (1H, m), 4.69 (1H, s), 5.32-5.36 (1H, m), 6.32 (1H, s), 6.86-6.92 (1H, m), 6.78-6.88 (3H, m), 6.98-7.04 (1H, m), 7.34-7.40 (2H, m), 7.57 (1H, d, J=8.6 Hz), 7.63 (1H, s), 8.36 (1H, d, J=6.5 Hz).

Example 57

Preparation of 5-(2,3-dihydrobenzofuran-5-yl)-3-(1-(4-(4-(1,1,1,3,3,3-hexafluoro-2-hydroxypropan-2-yl)-2-propylphenoxy)pyridin-2-yl)ethyl)-5-methylimidazolidine-2,4-dione

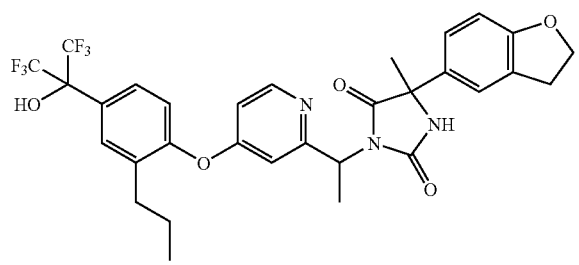

5-(2,3-Dihydrobenzofuran-5-yl)-5-methylimidazolidine-2,4-dione was used in place of 5-(4-(1-methylethoxy)phenyl)-5-methylimidazolidine-2,4-dione in Example 56 c) for a similar reaction and treatment, and the title compound was obtained as a colorless oil.

$^1$H-NMR (CDCl$_3$) δ: 0.90 (3H, t, J=7.3 Hz), 1.53-1.85 (8H, m), 2.55 (2H, t, J=7.6 Hz), 3.20 (2H, t, J=8.1 Hz), 3.82 (1H, s), 4.52-4.60 (2H, m), 5.32-5.36 (1H, m), 6.12 (1H, s), 6.44-7.36 (6H, m), 7.57 (1H, d, 8.6 Hz), 7.64 (1H, s), 8.35 (1H, t, J=5.9 Hz).

Example 58

Preparation of 3-(1-(4-(4-(1,1,1,3,3,3-hexafluoro-2-hydroxypropan-2-yl)-2-propylphenoxy)pyridin-2-yl)ethyl)-5-(6-methoxypyridin-3-yl)-5-methylimidazolidine-2,4-dione

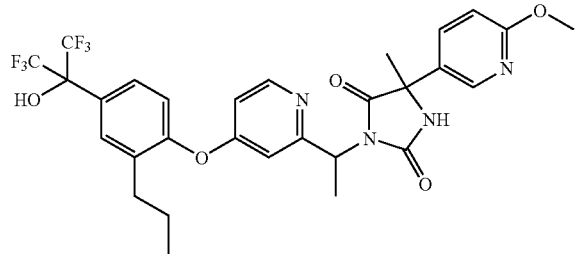

5-(6-Methoxypyridin-3-yl)-5-methylimidazolidine-2,4-dione was used in place of 5-(4-(1-methylethoxy)phenyl)-5-methylimidazolidine-2,4-dione in Example 56 c) for a similar reaction and treatment, and the title compound was obtained as a colorless oil.

$^1$H-NMR (CDCl$_3$) δ: 0.83 (3H, t, J=7.3 Hz), 1.42-1.84 (8H, m), 2.48 (2H, t, J=7.6 Hz), 3.97 (3H, s), 4.64 (2H, m), 6.70-7.30 (6H, m), 7.40-7.56 (2H, m), 7.83-7.84 (1H, m), 8.10-8.20 (1H, m).

Example 59

Preparation of 5-(benzo[d][1,3]dioxol-5-yl)-3-((5-(4-(1,1,1,3,3,3-hexafluoro-2-hydroxypropan-2-yl)-2-propylphenoxy)pyridin-3-yl)methyl)-5-methylimidazolidine-2,4-dione a) Preparation of 3-bromo-5-(4-(1,1,1,3,3,3-hexafluoro-2-(methoxymethoxy)propan-2-yl)-2-propylphenoxy) pyridine

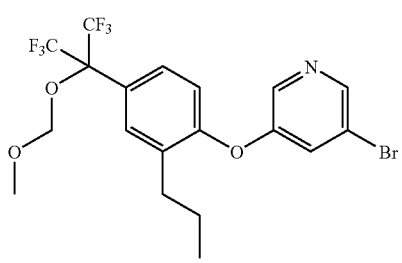

2-Chloropyridine-4-boronic acid was used in place of 3-(hydroxymethyl)phenylboronic acid for a similar reaction and treatment as Preparation example 3 a), and the compound of interest was obtained as a colorless oil.

$^1$H-NMR (CDCl$_3$) δ: 0.94 (3H, t, J=7.3 Hz), 1.60-1.68 (2H, m), 2.65 (2H, t, J=7.3 Hz), 3.51 (3H, s), 4.88 (2H, s), 6.20 (1H, d, J=8.4 Hz), 7.45-7.48 (2H, m), 7.55 (1H, d, J=2.2 Hz), 8.32 (1H, dd, J=1.4, 2.2 Hz), 8.46 (1H, d, J=1.4 Hz).

b) Preparation of 5-(4-(1,1,1,3,3,3-hexafluoro-2-(methoxymethoxy)propan-2-yl)-2-propylphenoxy) nicotinonitrile

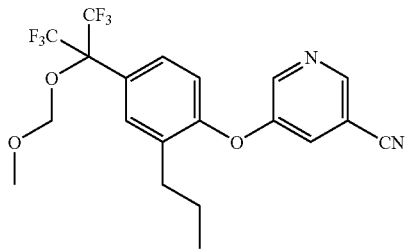

To a solution of 3-bromo-5-(4-(1,1,1,3,3,3-hexafluoro-2-(methoxymethoxy)propan-2-yl)-2-propylphenoxy) pyridine (320 mg, 637 μmol) in N,N-dimethylformamide (5 mL), zinc cyanide (112 mg) and tetrakis triphenylphosphine palladium complex (74 mg) were added at room temperature under an argon atmosphere, and the resultant mixture was allowed to react in a microwave (80 watts, 10 minutes). After completion of the reaction, the reaction solution was added with water at room temperature, extracted with ethyl acetate, and then concentrated in vacuo. The obtained residue was purified using silica-gel column chromatography (hexane/ethyl acetate) and the title compound (239 mg, yield 84%) was obtained as a colorless oil.

$^1$H-NMR (CDCl$_3$) δ: 0.94 (3H, t, J=7.3 Hz), 1.58-1.68 (2H, m), 2.62 (2H, t, J=7.6 Hz), 3.58 (3H, s), 4.89 (2H, s), 6.95 (1H, d, J=8.6 Hz), 7.45 (1H, dd, J=1.6, 2.4 Hz), 7.49-7.59 (2H, m), 8.59 (1H, d, J=2.4 Hz), 8.63 (1H, d, J=1.4 Hz).

c) Preparation of methyl 5-(4-(1,1,1,3,3,3-hexafluoro-2-hydroxypropan-2-yl)-2-propylphenoxy)nicotinate

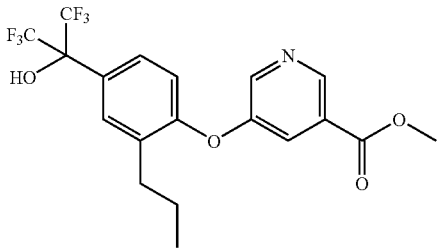

To a solution of 5-(4-(1,1,1,3,3,3-hexafluoro-2-(methoxymethoxy)propan-2-yl)-2-propylphenoxy)nicotinonitrile (508 mg, 1.13 mmol) in methanol solution (5 mL), sulfuric acid (280 µL) was added and then heated to reflux. After completion of the reaction, the reaction solution was concentrated in vacuo, neutralized by adding a saturated aqueous solution of sodium hydrogen carbonate at 0° C., extracted with ethyl acetate, and then concentrated in vacuo. The obtained residue was purified using silica-gel column chromatography (hexane/ethyl acetate) and the title compound (340 mg, yield 69%) was obtained as a colorless oil.

$^1$H-NMR (CDCl$_3$) δ: 0.94 (3H, t, J=7.6 Hz), 1.58-1.72 (2H, m), 2.65 (2H, t, J=7.3 Hz), 3.95 (3H, s), 4.74 (1H, s), 6.88 (1H, d, J=8.9 Hz), 7.55 (1H, dd, J=2.0, 8.9 Hz), 7.65 (1H, d, J=2.0 Hz), 7.66 (1H, dd, J=1.6, 2.7 Hz), 8.48 (1H, d, J=2.7 Hz), 8.96 (1H, d, J=1.6 Hz).

d) Preparation of 3-(bromomethyl)-5-(4-(1,1,1,3,3,3-hexafluoro-2-(methoxymethoxy)propan-2-yl)-2-propylphenoxy) pyridine

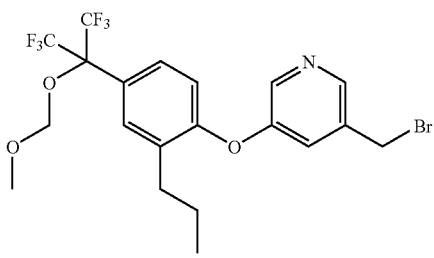

To a solution of methyl 5-(4-(1,1,1,3,3,3-hexafluoro-2-hydroxypropan-2-yl)-2-propylphenoxy)nicotinate (340 mg, 777 µmol) in methylene chloride (7 mL), N,N-diisopropylethylamine (540 µL) and chloromethylmethyl ether (117 µL) were added at room temperature. After completion of the reaction, the reaction solution was added with water, extracted with chloroform, and then dried using sodium sulfate. After filtration, the filtrate was concentrated in vacuo. To a solution of the obtained residue in tetrahydrofuran (7 mL), lithium aluminum hydride (33 mg) was added at 0° C. under an argon atmosphere. After completion of the reaction, the reaction solution was neutralized by adding water and 2 mol/L of hydrochloric acid, extracted with ethyl acetate, and then dried using sodium sulfate. After filtration, the filtrate was concentrated in vacuo. To a solution of the obtained residue in methylene chloride (7 mL), triphenylphosphine (178 mg) and carbon tetrabromide (245 mg) were added at 0° C. After completion of the reaction, the reaction solution was concentrated in vacuo. The obtained residue was purified using silica-gel column chromatography (hexane/ethyl acetate) and the title compound (341 mg, yield 85%) was obtained as a colorless oil.

$^1$H-NMR (CDCl$_3$) δ: 0.95 (3H, t, J=7.6 Hz), 1.57-1.72 (2H, m), 2.67 (2H, t, J=7.3 Hz), 3.66 (3H, s), 4.46 (2H, s), 4.87 (2H, s), 6.87 (1H, d, J=8.4 Hz), 7.33 (1H, dd, J=2.0, 2.7 Hz), 7.43 (1H, dd, J=2.0, 8.4 Hz), 7.52 (1H, d, J=2.0 Hz), 8.30 (1H, d, J=2.7 Hz), 8.41 (1H, d, J=2.0 Hz).

e) Preparation of 5-(benzo[d][1,3]dioxol-5-yl)-3-((5-(4-(1,1,1,3,3,3-hexafluoro-2-hydroxypropan-2-yl)-2-propylphenoxy)pyridin-3-yl)methyl)-5-methylimidazolidine-2,4-dione

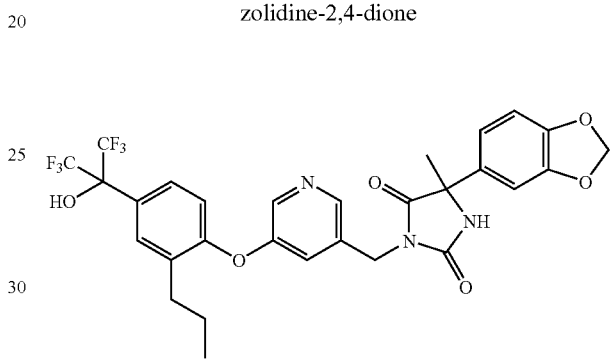

3-(Bromomethyl)-5-(4-(1,1,1,3,3,3-hexafluoro-2-(methoxymethoxy)propan-2-yl)-2-propylphenoxy)pyridin was used for a similar operation as Example 1, and the title compound was obtained as a colorless oil.

$^1$H-NMR (CD$_3$OD) δ: 0.90 (3H, t, J=7.3 Hz), 1.48-1.71 (2H, m), 1.77 (3H, s), 2.53 (2H, t, J=7.6 Hz), 4.78 (2H, s), 5.95 (2H, s), 6.76-7.85 (7H, m), 8.31 (1H, s), 8.70 (1H, s).

Example 60

Preparation of 5-(2,3-dihydrobenzo[b][1,4]dioxin-6-yl)-5-ethyl-3-((5-(4-(1,1,1,3,3,3-hexafluoro-2-hydroxypropan-2-yl)-2-propylphenoxy)pyridin-3-yl)methyl)imidazolidine-2,4-dione

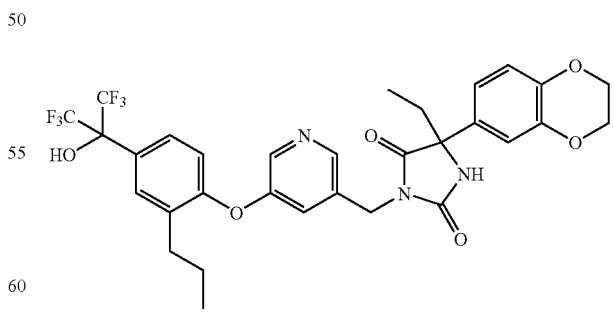

5-(2,3-Dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 59 e) for a similar reaction and treatment, and the title compound was obtained as a colorless oil.

$^1$H-NMR (CDCl$_3$) δ: 0.82-0.93 (6H, m), 1.45-1.65 (2H, m), 1.90-2.20 (2H, m), 2.52 (2H, t. J=7.6 Hz), 4.02-4.30 (4H, m), 4.76 (2H, s), 6.83-7.26 (4H, m), 7.50-7.90 (3H, m), 8.33 (1H, s), 8.78 (1H, s).

Example 61

Preparation of 5-(2,3-dihydrobenzofuran-5-yl)-3-((5-(4-(1,1,1,3,3,3-hexafluoro-2-hydroxypropan-2-yl)-2-propylphenoxy)pyridin-3-yl)methyl)-5-methylimidazolidine-2,4-dione

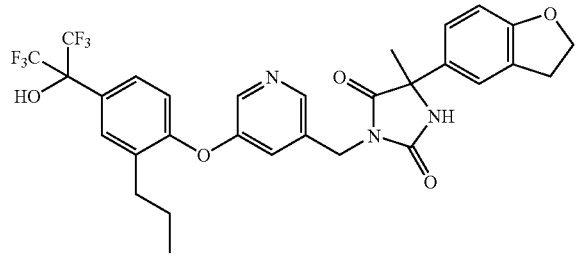

5-(2,3-Dihydrobenzofuran-5-yl)-5-methylimidazolidine-2,4-dione was used in place of 5-(benzo[d][1,3]dioxol-5-yl)-5-methylimidazolidine-2,4-dione in Example 59 e) for a similar reaction and treatment, and the title compound was obtained as a colorless oil.

$^1$H-NMR (CD$_3$OD) δ: 0.91 (3H, t, J=7.3 Hz), 1.47-1.70 (2H, m), 1.79 (3H, s), 2.55 (2H, t, J=7.6 Hz), 3.20 (2H, t, J=7.3 Hz), 4.57 (2H, t, J=7.3 Hz), 4.77 (2H, s), 6.77-7.83 (7H, m), 8.30 (1H, s), 8.71 (1H, s).

Example 62

Preparation of 3-((5-(4-(1,1,1,3,3,3-hexafluoro-2-hydroxypropan-2-yl)-2-propylphenoxy)pyridin-3-yl)methyl)-5-(4-(1-methylethoxy)phenyl)-5-methylimidazolidine-2,4-dione

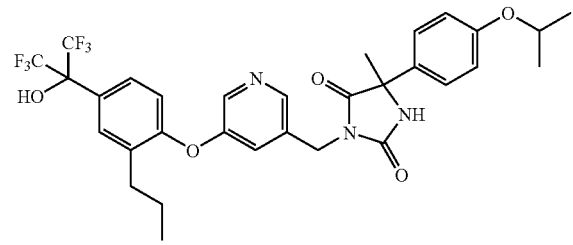

5-(4-(1-Methylethoxy)phenyl)-5-methylimidazolidine-2,4-dione was used in place of 5-(benzo[d][1,3]dioxol-5-yl)-5-methylimidazolidine-2,4-dione in Example 59 e) for a similar reaction and treatment, and the title compound was obtained as a colorless oil.

$^1$H-NMR (CD$_3$OD) δ: 0.89 (3H, t, J=7.6 Hz), 1.30 (6H, d, J=6.5 Hz), 1.40-1.90 (5H, m), 2.52 (2H, t, J=7.6 Hz), 4.40-4.60 (1H, m), 4.78 (2H, s), 6.83-7.82 (8H, m), 8.30 (1H, s), 8.74 (1H, s).

Example 63

Preparation of 3-((5-(4-(1,1,1,3,3,3-hexafluoro-2-hydroxypropan-2-yl)-2-propylphenoxy)pyridin-3-yl)methyl)-5-(6-methoxypyridin-3-yl)-5-methylimidazolidine-2,4-dione

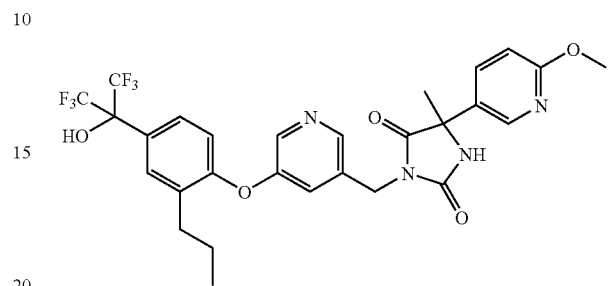

5-(6-Methoxypyridin-3-yl)-5-methylimidazolidine-2,4-dione was used in place of 5-(benzo[d][1,3]dioxol-5-yl)-5-methylimidazolidine-2,4-dione in Example 59 e) for a similar reaction and treatment, and the title compound was obtained as a colorless oil.

$^1$H-NMR (CD$_3$OD) δ: 0.91 (3H, t, J=7.3 Hz), 1.50-1.70 (2H, m), 1.80 (3H, s), 2.55 (2H, t, J=7.6 Hz), 3.37 (3H, s), 4.11 (2H, s), 7.00-7.20 (3H, m), 7.60-7.75 (2H, m), 7.96 (1H, s), 8.22-8.53 (3H, m).

Example 64

Preparation of 5-(benzo[d][1,3]dioxol-5-yl)-3-((2-(4-(1,1,1,3,3,3-hexafluoro-2-hydroxypropan-2-yl)-2-propylphenoxy)pyridin-4-yl)methyl)-5-methylimidazolidine-2,4-dione a) Preparation of methyl 2-chloro-5-nitroisonicotinate

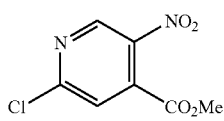

2-Chloro-4-methyl-5-nitropyridine (2.19 g, 12.7 mmol) was added with sulfuric acid (12.7 mL) and then with chromium trioxide (3.80 g). After completion of the reaction, the reaction solution was added with ice chips and stirred. Resultant solid deposits were separated by filtration, washed using cold water, and then dried in vacuo. To a solution of the obtained solids in tetrahydrofuran (20 mL), 2 mol/L trimethylsilyldiazomethanediethyl ether solution (4.4 mL) was added at room temperature. After completion of the reaction, the reaction solution was concentrated in vacuo. The obtained residue was purified using silica-gel column chromatography (hexane/ethyl acetate) and the title compound (1.90 g, yield 70%) was obtained as a colorless oil.

¹H-NMR (CDCl₃) δ: 3.99 (3H, s), 7.61 (1H, s), 9.06 (1H, s).

b) Preparation of methyl 2-(4-(1,1,1,3,3,3-hexafluoro-2-(methoxymethoxy)propan-2-yl)-2-propylphenoxy)-5-nitroisonicotinate

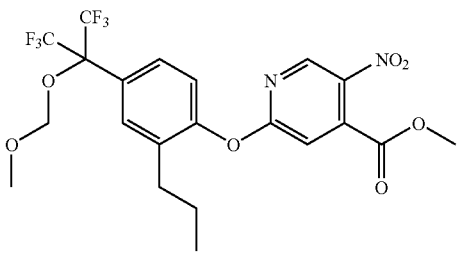

To a solution of 4-(1,1,1,3,3,3-hexafluoro-2-(methoxymethoxy)propan-2-yl)-2-propylphenol (1.68 g, 4.86 mmol) in N,N-dimethylformamide (30 mL), potassium carbonate (1.34 g) and methyl 2-chloro-5-nitroisonicotinate (1.58 g) were added, and the resultant mixture was stirred in an oil bath with the oil temperature at 80° C. After completion of the reaction, the reaction solution was neutralized by adding 2 mol/L of hydrochloric acid, added with water, and extracted with ethyl acetate. Subsequently, the organic layer was washed with brine, dried using anhydrous sodium sulfate, and concentrated in vacuo. The residue was purified using thin-layer silica-gel column chromatography (hexane/ethyl acetate) and the title compound (1.86 g, yield 73%) was obtained as a colorless oil.

¹H-NMR (CDCl₃) δ: 0.90 (3H, t, J=7.3 Hz), 1.52-1.64 (2H, m), 2.53 (2H, t, J=7.3 Hz), 3.58 (3H, s), 4.01 (3H, s), 4.89 (2H, s), 7.13 (1H, d, J=8.6 Hz), 7.14 (1H, s), 7.50-7.56 (2H, m), 8.88 (1H, s).

c) Preparation of methyl 2-(4-(1,1,1,3,3,3-hexafluoro-2-(methoxymethoxy)propan-2-yl)-2-propylphenoxy)-5-iodoisonicotinate

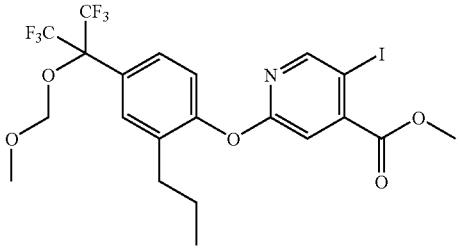

To a solution of methyl 2-(4-(1,1,1,3,3,3-hexafluoro-2-(methoxymethoxy)propan-2-yl)-2-propylphenoxy)-5-nitroisonicotinate (1.80 g, 3.41 mmol) in methanol (20 mL), 20 wt % palladium carbon (300 mg) was added and the resultant mixture was stirred at room temperature under an hydrogen atmosphere. After completion of the reaction, the reaction solution was filtered using celite, and the filtrate was concentrated in vacuo. To a solution of the residue and p-toluenesulfonic acid monohydrate (1.32 g) in acetonitrile (10 mL), potassium iodide (1.07 g) and an aqueous solution (2 mL) of sodium nitrite (0.32 g) were added at room temperature. After completion of the reaction, the reaction solution was added with a saturated aqueous solution of sodium thiosulfate and a saturated aqueous solution of sodium hydrogen carbonate at room temperature, extracted with ethyl acetate, and concentrated in vacuo. The obtained residue was purified using silica-gel column chromatography (hexane/ethyl acetate) and the title compound (750 mg, yield 54%) was obtained as a colorless oil.

¹H-NMR (CDCl₃) δ: 0.90 (3H, t, J=7.3 Hz), 1.56-1.70 (2H, m), 2.56 (2H, t, J=7.3 Hz), 3.57 (3H, s), 3.99 (3H, s), 4.88 (2H, s), 7.08 (1H, d, J=8.6 Hz), 7.45 (1H, s), 7.47-7.51 (2H, m), 8.59 (1H, s).

d) Preparation of methyl 2-(4-(1,1,1,3,3,3-hexafluoro-2-(methoxymethoxy)propan-2-yl)-2-propylphenoxy)isonicotinate

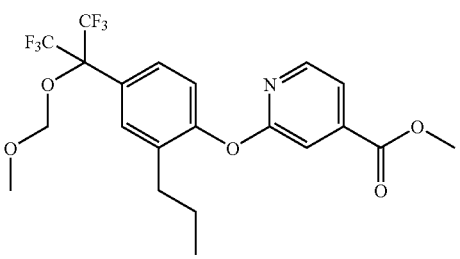

To a solution of methyl 2-(4-(1,1,1,3,3,3-hexafluoro-2-(methoxymethoxy)propan-2-yl)-2-propylphenoxy)-5-iodoisonicotinate (88 mg, 146 µmol) in methanol (2 mL), 20 wt % palladium carbon (10 mg) was added and the resultant mixture was stirred at room temperature under an hydrogen atmosphere. After completion of the reaction, the reaction solution was filtered using celite, and the filtrate was concentrated in vacuo. The obtained residue was purified using silica-gel column chromatography (hexane/ethyl acetate) and the title compound (52 mg, yield 75%) was obtained as a colorless oil.

¹H-NMR (CDCl₃) δ: 0.90 (3H, t, J=7.3 Hz), 1.54-1.68 (2H, m), 2.59 (2H, t, J=7.6 Hz), 3.56 (3H, s), 3.97 (3H, s), 4.88 (2H, s), 7.11 (1H, d, J=8.9 Hz), 7.45-7.52 (3H, m), 7.57 (1H, d, J=5.4 Hz) 8.30 (1H, d, J=5.4 Hz).

e) Preparation of 4-(bromomethyl)-2-(4-(1,1,1,3,3,3-hexafluoro-2-(methoxymethoxy)propan-2-yl)-2-propylphenoxy) pyridine

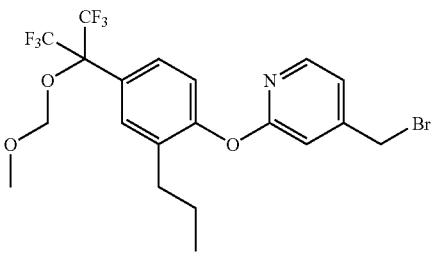

To a solution of methyl 2-(4-(1,1,1,3,3,3-hexafluoro-2-(methoxymethoxy)propan-2-yl)-2-propylphenoxy)isonicotinate (52 mg, 103 µmol) in tetrahydrofuran (1 mL), lithium aluminum hydride (6 mg) was added at 0° C. under an argon atmosphere. After completion of the reaction, the reaction solution was neutralized by adding water and 2 mol/L of hydrochloric acid, extracted with ethyl acetate, and then dried using sodium sulfate. After filtration, the filtrate was concentrated in vacuo. To a solution of the obtained residue in methylene chloride (1 mL), triphenylphosphine (50 mg) and carbon tetrabromide (67 mg) were added at 0° C. After completion of the reaction, the reaction solution was concentrated in vacuo. The obtained residue was purified using silica-gel column chromatography (hexane/ethyl acetate) and the title compound (54 mg, yield 99%) was obtained as a colorless oil.

$^1$H-NMR (CDCl$_3$) δ: 0.91 (3H, t, J=7.3 Hz), 1.54-1.68 (2H, m), 2.59 (2H, t, J=7.6 Hz), 3.56 (3H, s), 4.40 (2H, s), 4.88 (2H, s), 6.96 (1H, d, J=0.8 Hz), 7.05 (1H, dd, J=0.8, 5.4 Hz), 7.09 (1H, d, J=8.6 Hz), 7.43-7.51 (2H, m), 8.15 (1H, d, J=5.4 Hz).

f) Preparation of 5-(benzo[d][1,3]dioxol-5-yl)-3-((2-(4-(1,1,1,3,3,3-hexafluoro-2-hydroxypropan-2-yl)-2-propylphenoxy)pyridin-4-yl)methyl)-5-methylimidazolidine-2,4-dione

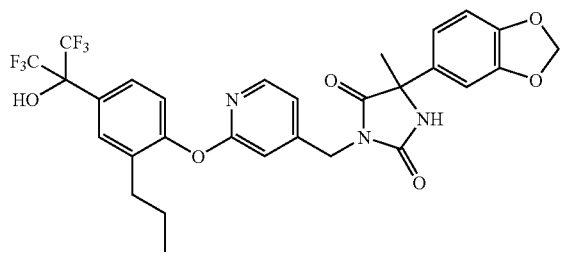

4-(Bromomethyl)-2-(4-(1,1,1,3,3,3-hexafluoro-2-(methoxymethoxy)propan-2-yl)-2-propylphenoxy)pyridine was used for a similar operation as Example 1, and the title compound was obtained as a colorless oil.

$^1$H-NMR (CD$_3$OD) δ: 0.89 (3H, t, J=7.3 Hz), 1.53-1.66 (2H, m), 1.74 (3H, s), 2.53 (2H, t, J=7.6 Hz), 4.73 (2H, s), 5.97 (2H, s), 6.55-7.28 (6H, m), 7.61 (1H, d, J=8.6 Hz), 7.68 (1H, s), 8.22 (1H, d, J=5.1 Hz).

Example 65

Preparation of 5-(benzo[d][1,3]dioxol-5-yl)-5-ethyl-3-((2-(4-(1,1,1,3,3,3-hexafluoro-2-hydroxypropan-2-yl)-2-propylphenoxy)pyridin-4-yl)methyl)imidazolidine-2,4-dione

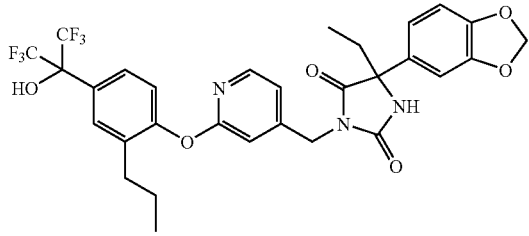

5-(Benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 64 f) for a similar reaction and treatment, and the title compound was obtained as a colorless oil.

$^1$H-NMR (CD$_3$OD) δ: 0.81-0.92 (6H, m), 1.51-1.62 (2H, m), 2.00-2.20 (2H, m), 2.52 (2H, t, J=7.6 Hz), 4.65 (2H, s), 5.98 (2H, s), 6.79-6.84 (2H, m), 6.96 (1H, dd, J=1.9, 8.1 Hz), 7.02-7.06 (3H, m), 7.59 (1H, d, J=8.6 Hz), 7.67 (1H, s), 8.16 (1H, d, J=5.7 Hz).

Example 66

Preparation of 5-(2,3-dihydrobenzo[b][1,4]dioxin-6-yl)-3-((2-(4-(1,1,1,3,3,3-hexafluoro-2-hydroxypropan-2-yl)-2-propylphenoxy)pyridin-4-yl)methyl)-5-methylimidazolidine-2,4-dione

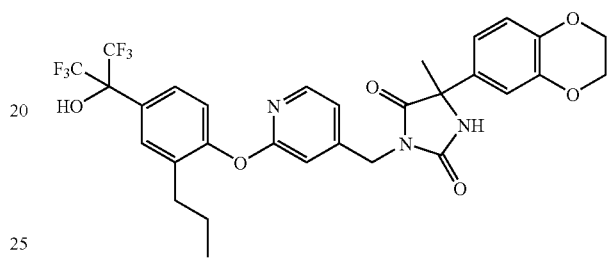

5-(2,3-Dihydrobenzo[b][1,4]dioxin-6-yl)-5-methylimidazolidine-2,4-dione was used in place of 5-(benzo[d][1,3]dioxol-5-yl)-5-methylimidazolidine-2,4-dione in Example 64 f) for a similar reaction and treatment, and the title compound was obtained as a colorless oil.

$^1$H-NMR (CDCl$_3$) δ: 0.90 (3H, t, J=7.3 Hz), 1.52-1.66 (2H, m), 1.74 (3H, s), 2.54 (2H, t, J=7.6 Hz), 4.00-4.30 (4H, m), 4.67 (2H, s), 6.81-7.26 (6H, m), 7.57-7.68 (2H, m), 8.19 (1H, d, J=5.4 Hz).

Example 67

Preparation of 5-(2,3-dihydrobenzofuran-5-yl)-3-((2-(4-(1,1,1,3,3,3-hexafluoro-2-hydroxypropan-2-yl)-2-propylphenoxy)pyridin-4-yl)methyl)-5-methylimidazolidine-2,4-dione

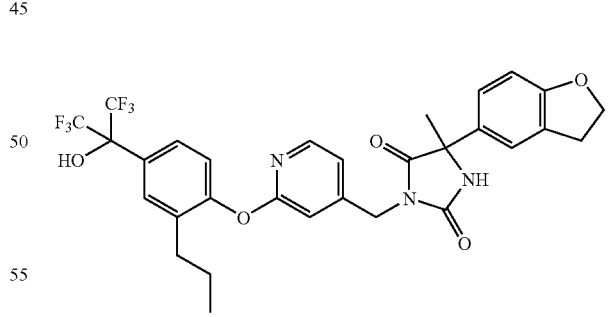

5-(2,3-Dihydrobenzofuran-5-yl)-5-methylimidazolidine-2,4-dione was used in place of 5-(benzo[d][1,3]dioxol-5-yl)-5-methylimidazolidine-2,4-dione in Example 64 f) for a similar reaction and treatment, and the title compound was obtained as a colorless oil.

$^1$H-NMR (CDCl$_3$) δ: 0.88 (3H, t, J=7.3 Hz), 1.54-1.63 (2H, m), 1.68 (3H, s), 2.55 (2H, t, J=7.6 Hz), 3.20 (2H, t, J=8.8 Hz), 4.00 (1H, s), 4.13 (2H, t, J=8.8 Hz), 4.70 (2H, s), 5.98 (1H, s), 6.75-6.80 (2H, m), 6.90 (1H, dd, J=1.2, 5.1 Hz), 7.01 (1H,

J=8.6 Hz), 7.18 (1H, dd, J=2.2, 8.3 Hz), 7.29 (1H, s), 7.51 (1H, dd, J=1.9, 8.6 Hz), 7.60 (1H, d, J=1.9 Hz), 8.08 (1H, d, J=5.1 Hz).

Example 68

Preparation of 3-((2-(4-(1,1,1,3,3,3-hexafluoro-2-hydroxypropan-2-yl)-2-propylphenoxy)pyridin-4-yl)methyl)-5-(2-methoxyphenyl)-5-methylimidazolidine-2,4-dione

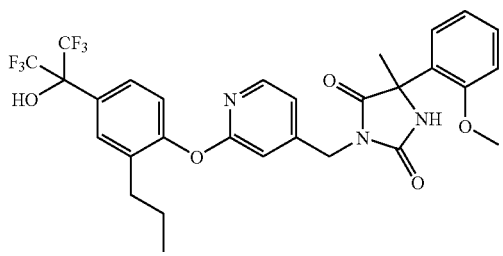

5-(2-Methoxyphenyl)-5-methylimidazolidine-2,4-dione was used in place of 5-(benzo[d][1,3]dioxol-5-yl)-5-methylimidazolidine-2,4-dione in Example 64 f) for a similar reaction and treatment, and the title compound was obtained as a colorless oil.

$^1$H-NMR (CD$_3$OD) δ: 0.90 (3H, t, J=7.3 Hz), 1.53-1.67 (2H, m), 1.80 (3H, s), 2.55 (2H, t, J=7.6 Hz), 3.72 (3H, s), 4.76 (2H, s), 6.91-7.45 (7H, m), 7.58 (1H, d, J=8.6 Hz), 7.67 (1H, s), 8.19 (1H, d, J=5.4 Hz).

Example 69

Preparation of 3-((2-(4-(1,1,1,3,3,3-hexafluoro-2-hydroxypropan-2-yl)-2-propylphenoxy)pyridin-4-yl)methyl)-5-(4-(1-methylethoxy)phenyl)-5-methylimidazolidine-2,4-dione

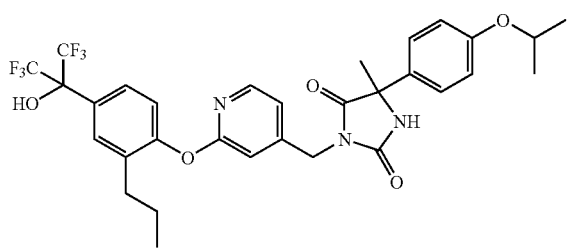

5-(4-(1-Methylethoxy)phenyl)-5-methylimidazolidine-2,4-dione was used in place of 5-(benzo[d][1,3]dioxol-5-yl)-5-methylimidazolidine-2,4-dione in Example 64 f) for a similar reaction and treatment, and the title compound was obtained as a colorless oil.

$^1$H-NMR (CDCl$_3$) δ: 0.88 (3H, t, J=7.3 Hz), 1.31 (6H, d, J=5.9 Hz), 1.51-1.65 (2H, m), 1.73 (3H, s), 2.55 (2H, t, J=7.6 Hz), 4.01 (1H, s), 4.48-4.60 (1H, m), 4.75 (2H, s), 5.93 (1H, s), 6.77 (1H, s), 6.86-6.91 (2H, m), 7.02 (2H, d, J=8.6 Hz), 7.34 (2H, d, J=8.6 Hz), 7.51 (1H, d, J=8.6 Hz), 7.59 (1H, s), 8.09 (1H, d, J=5.1 Hz).

Example 70

Preparation of 3-((2-(4-(1,1,1,3,3,3-hexafluoro-2-hydroxypropan-2-yl)-2-propylphenoxy)pyridin-4-yl)methyl)-5-(6-methoxypyridin-3-yl)-5-methylimidazolidine-2,4-dione

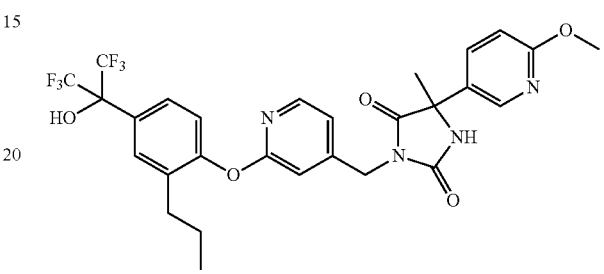

5-(6-Methoxypyridin-3-yl)-5-methylimidazolidine-2,4-dione was used in place of 5-(benzo[d][1,3]dioxol-5-yl)-5-methylimidazolidine-2,4-dione in Example 64f) for a similar reaction and treatment, and the title compound was obtained as a colorless oil.

$^1$H-NMR (CDCl$_3$) δ: 0.81 (3H, t, J=7.3 Hz), 1.44-1.54 (2H, m), 1.80 (3H, s), 2.50 (2H, t, J=7.6 Hz), 3.96 (3H, s), 4.48 (1H, d, J=10.8 Hz), 4.69 (1H, d, J=10.8 Hz), 5.28 (1H, s), 6.27 (1H, s), 6.53 (1H, d, J=1.2 Hz), 6.78 (1H, d, J=8.8 Hz), 6.91 (1H, dd, J=1.2, 5.1 Hz), 7.02 (1H, J=8.6 Hz), 7.55 (1H, d, J=8.6 Hz), 7.62 (1H, s), 7.72 (1H, dd, J=2.7, 8.8 Hz), 8.05 (1H, d, J=2.7 Hz), 8.14 (1H, d, J=5.1 Hz).

Example 71

Preparation of 3-((2-(4-(1,1,1,3,3,3-hexafluoro-2-hydroxypropan-2-yl)-2-propylphenoxy)pyridin-4-yl)methyl)-5-methyl-5-p-tolylimidazolidine-2,4-dione

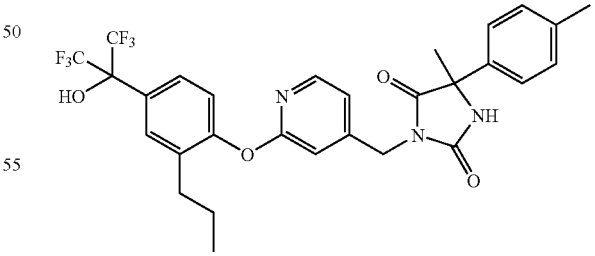

5-Methyl-5-p-tolylimidazolidine-2,4-dione was used in place of 5-(benzo[d][1,3]dioxol-5-yl)-5-methylimidazolidine-2,4-dione in Example 64 f) for a similar reaction and treatment, and the title compound was obtained as a colorless oil.

$^1$H-NMR (CD$_3$OD) δ: 0.89 (3H, t, J=7.3 Hz), 1.51-1.65 (2H, m), 1.78 (3H, s), 2.34 (3H, s), 2.52 (2H, t, J=7.6 Hz), 4.67

(2H, s), 6.80 (1H, s), 7.01-7.06 (2H, m), 7.16-7.38 (4H, m), 7.58 (1H, d, J=8.6 Hz), 7.66 (1H, s), 8.16 (1H, d, J=5.4 Hz).

Example 72

Preparation of 5-(3,4-dichlorophenyl)-3-((2-(4-(1,1,1,3,3,3-hexafluoro-2-hydroxypropan-2-yl)-2-propylphenoxy) pyridin-4-yl)methyl)-5-methylimidazolidine-2,4-dione

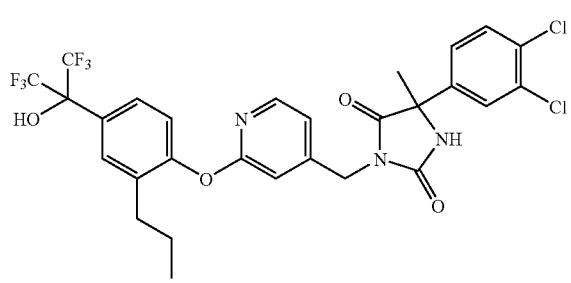

5-(3,4-Dichlorophenyl)-5-methylimidazolidine-2,4-dione was used in place of 5-(benzo[d][1,3]dioxol-5-yl)-5-methylimidazolidine-2,4-dione in Example 64 l) for a similar reaction and treatment, and the title compound was obtained as a colorless oil.

$^1$H-NMR (CDCl$_3$) δ: 0.89 (3H, t, J=7.3 Hz), 1.53-1.62 (2H, m), 1.76 (3H, s), 2.53 (2H, t, J=7.6 Hz), 4.67 (2H, s), 6.81 (1H, s), 7.01-7.67 (7H, m), 8.17 (1H, d, J=5.4 Hz).

Example 73

Preparation of 5-(furan-2-yl)-3-((2-(4-(1,1,1,3,3,3-hexafluoro-2-hydroxypropan-2-yl)-2-propylphenoxy)pyridin-4-yl)methyl)-5-methylimidazolidine-2,4-dione

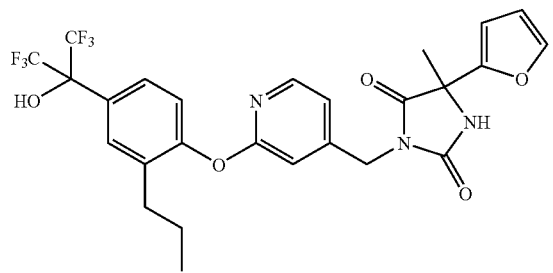

5-(Furan-2-yl)-5-methylimidazolidine-2,4-dione was used in place of 5-(benzo[d][1,3]dioxol-5-yl)-5-methylimidazolidine-2,4-dione in Example 64 f) for a similar reaction and treatment, and the title compound was obtained as a colorless oil.

$^1$H-NMR (CD$_3$OD) δ: 0.90 (3H, t, J=7.3 Hz), 1.53-1.67 (2H, m), 1.79 (3H, s), 2.56 (2H, t, J=7.3 Hz), 4.74 (2H, s), 6.36-6.41 (2H, m), 6.88 (1H, s), 7.05-7.28 (2H, m), 7.39 (1H, d, J=1.6 Hz), 7.60 (1H, d, J=8.6 Hz), 7.68 (1H, s), 8.20 (1H, d, J=5.4 Hz).

Example 74

Preparation of 3-((2-(4-(1,1,1,3,3,3-hexafluoro-2-hydroxypropan-2-yl)-2-propylphenoxy)pyridin-4-yl)methyl)-1,5,5-trimethylimidazolidine-2,4-dione

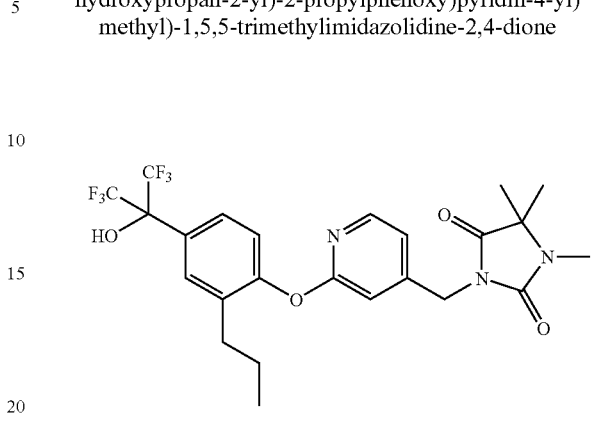

1,5,5-Trimethylimidazolidine-2,4-dione was used in place of 5-(benzo[d][1,3]dioxol-5-yl)-5-methylimidazolidine-2,4-dione in Example 64 f) for a similar reaction and treatment, and the title compound was obtained as a colorless oil.

$^1$H-NMR (CD$_3$OD) δ: 0.90 (3H, t, J=7.3 Hz), 1.40 (6H, s), 1.52-1.64 (2H, m), 2.55 (2H, t, J=7.6 Hz), 2.91 (3H, s), 4.68 (2H, s), 6.77 (1H, s), 6.95 (1H, s), 7.00-7.06 (2H, m), 7.57 (1H, d, J=8.6 Hz), 7.65 (1H, s), 8.19 (1H, d, J=5.1 Hz).

Example 75

Preparation of 3-((2-(4-(1,1,1,3,3,3-hexafluoro-2-hydroxypropan-2-yl)-2-propylphenoxy)pyridin-4-yl)methyl)-1,3-diazaspiro[4.4]nonane-2,4-dione

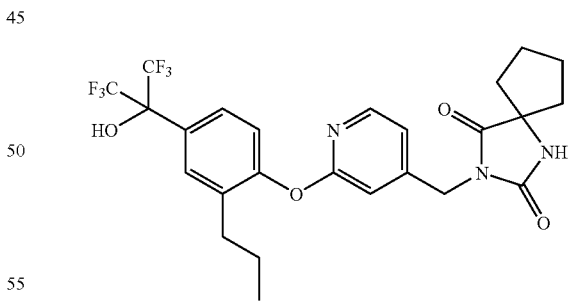

1,3-Diazaspiro[4.4]nonane-2,4-dione was used in place of 5-(benzo[d][1,3]dioxol-5-yl)-5-methylimidazolidine-2,4-dione in Example 640 for a similar reaction and treatment, and the title compound was obtained as a colorless oil.

$^1$H-NMR (CD$_3$OD) δ: 0.90 (3H, t, J=7.3 Hz), 1.53-2.14 (10H, m), 2.55 (2H, t, J=7.6 Hz), 4.68 (2H, s), 6.79 (1H, s), 7.05-7.08 (4H, m), 7.60 (1H, d, J=8.6 Hz), 7.67 (1H, s), 8.20 (1H, d, J=5.9 Hz).

Example 76

Preparation of 5-(benzo[d][1,3]dioxol-5-yl-3-((6-(4-(1,1,1,3,3,3-hexafluoro-2-hydroxypropan-2-yl)-2-propylphenoxy)pyridin-2-yl)methyl)-5-methylimidazolidine-2,4-dione a) Preparation of 6-(4-(1,1,1,3,3,3-hexafluoro-2-(methoxymethoxy)propan-2-yl)-2-propylphenoxy)-2-methyl-3-nitropyridine

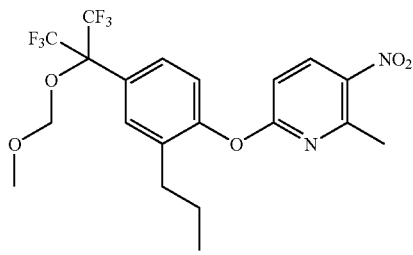

2-Chloro-6-methyl-5-nitropyridine was used in place of methyl 2-chloro-5-nitroisonicotinate for a similar reaction and treatment as Example 64 b), and the title compound (1.90 g, yield 65%) was obtained as a colorless oil.

$^1$H-NMR (CDCl$_3$) δ: 0.89 (3H, t, J=7.3 Hz), 1.52-1.66 (2H, m), 2.55 (2H, t, J=7.6 Hz), 2.74 (3H, s), 3.58 (3H, s), 4.88 (2H, s), 6.82 (1H, d, J=8.6 Hz), 7.15 (1H, d, J=8.6 Hz), 7.47-7.55 (2H, m), 8.38 (1H, d, J=8.6 Hz).

b) Preparation of 6-(4-(1,1,1,3,3,3-hexafluoro-2-(methoxymethoxy)propan-2-yl)-2-propylphenoxy)-3-iodo-2-methylpyridine

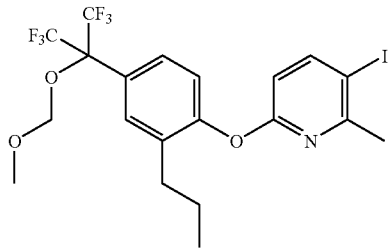

6-(4-(1,1,1,3,3,3-Hexafluoro-2-(methoxymethoxy)propan-2-yl)-2-propylphenoxy)-2-methyl-3-nitropyridine was used for a similar operation as Example 64 c), and the title compound was obtained as a colorless oil.

$^1$H-NMR (CDCl$_3$) δ: 0.90 (3H, t, J=7.3 Hz), 1.56-1.68 (2H, m), 2.56-2.61 (5H, m), 3.56 (3H, s), 4.87 (2H, s), 6.39 (1H, d, J=8.6 Hz), 7.07 (1H, d, J=8.6 Hz), 7.39-7.50 (2H, m), 7.96 (1H, d, J=8.6 Hz).

c) Preparation of 2-(4-(1,1,1,3,3,3-hexafluoro-2-(methoxymethoxy)propan-2-yl)-2-propylphenoxy)-6-methylpyridine

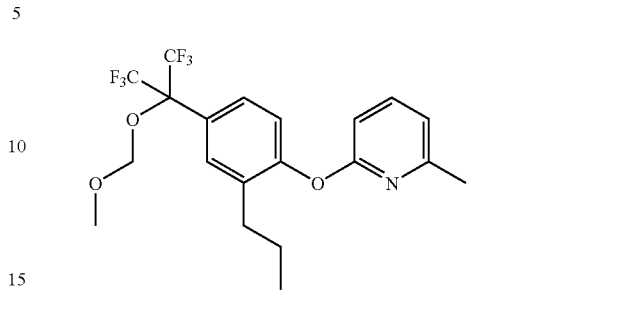

6-(4-(1,1,1,3,3,3-Hexafluoro-2-(methoxymethoxy)propan-2-yl)-2-propylphenoxy)-3-iodo-2-methylpyridine was used for a similar operation as Example 64 d), and the title compound was obtained as a colorless oil.

$^1$H-NMR (CDCl$_3$) δ: 0.91 (3H, t, J=7.3 Hz), 1.56-1.70 (2H, m), 2.47 (3H, s), 2.63 (2H, t, J=7.6 Hz), 3.56 (3H, s), 4.87 (2H, s), 6.55 (1H, d, J=8.1 Hz), 6.90 (1H, d, J=7.3 Hz), 7.05 (1H, d, J=8.6 Hz), 7.38-7.50 (2H, m), 7.57 (1H, dd, J=7.3, 8.1 Hz).

d) Preparation of (6-(4-(1,1,1,3,3,3-hexafluoro-2-(methoxymethoxy)propan-2-yl)-2-propylphenoxy-2-yl) methyl acetate

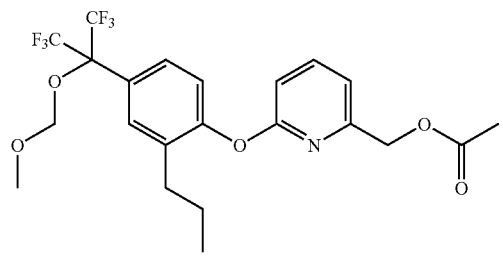

2-(4-(1,1,1,3,3,3-Hexafluoro-2-(methoxymethoxy)propan-2-yl-2-propyl-phenoxy-6-methylpyridine was used for a similar operation as Preparation example 40 c), and the title compound was obtained as a colorless oil.

$^1$H-NMR (CDCl$_3$) δ: 0.90 (3H, t, J=7.3 Hz), 1.56-1.65 (2H, m), 2.08 (3H, s), 2.60 (2H, t, J=7.6 Hz), 3.56 (3H, s), 4.87 (2H, s), 5.10 (2H, s), 6.75 (1H, d, J=8.0 Hz), 7.05 (1H, d, J=8.0 Hz), 7.09 (1H, d, J=8.6 Hz), 7.40-7.50 (2H, m), 7.70 (1H, dd, J=8.0, 8.0 Hz).

e) Preparation of (6-(4-(1,1,1,3,3,3-hexafluoro-2-(methoxymethoxy)propan-2-yl)-2-propylphenoxy)pyridin-2-yl)methanol

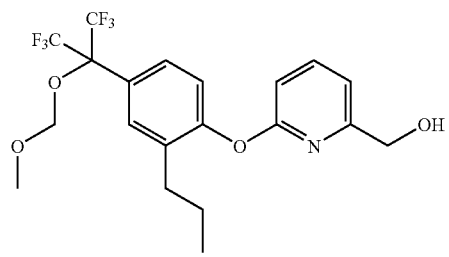

(6-(4-(1,1,1,3,3,3-Hexafluoro-2-(methoxymethoxy)propan-2-yl)-2-propylphenoxy) pyridin-2-yl)methyl acetate was used for a similar operation as Example 40 d), and the title compound was obtained as a colorless oil.

$^1$H-NMR (CDCl$_3$) δ: 0.90 (3H, t, J=7.3 Hz), 1.57-1.77 (2H, m), 2.60 (2H, t, J=7.6 Hz), 3.57 (3H, s), 4.65 (2H, s), 5.10 (2H, s), 6.75 (1H, d, J=7.6 Hz), 6.98 (1H, d, J=7.6 Hz), 7.08 (1H, d, J=8.6 Hz), 7.40-7.52 (2H, m), 7.71 (1H, dd, J=7.6, 7.6 Hz).

f) Preparation of 2-(bromomethyl)-6-(4-(1,1,1,3,3,3-hexafluoro-2-(methoxymethoxy)propan-2-yl)-2-propylphenoxy) pyridine

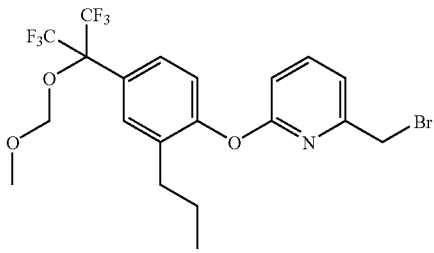

(6-(4-(1,1,1,3,3,3-Hexafluoro-2-(methoxymethoxy)propan-2-yl)-2-propylphenoxy) pyridin-2-yl)methanol was used for a similar operation as Preparation example 3 b), and the title compound was obtained as a colorless oil.

$^1$H-NMR (CDCl$_3$) δ: 0.91 (3H, t, J=7.3 Hz), 1.56-1.65 (2H, m), 2.61 (2H, t, J=7.4 Hz), 3.57 (3H, s), 4.74 (2H, s), 4.89 (2H, s), 6.74 (1H, d, J=8.3 Hz), 7.12 (1H, d, J=7.8 Hz), 7.19 (1H, d, J=7.8 Hz), 7.44 (1H, d, J=8.3 Hz), 7.52 (1H, s), 7.70 (1H, dd, J=7.8, 7.8 Hz).

g) Preparation of 5-(benzo[d][1,3]dioxol-5-yl)-3-((6-(4-(1,1,1,3,3,3-hexafluoro-2-hydroxypropan-2-yl)-2-propylphenoxy)pyridin-2-yl)methyl)-5-methylimidazolidine-2,4-dione

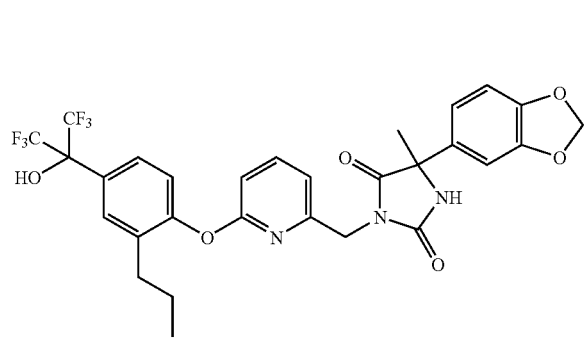

2-(Bromomethyl)-6-(4-(1,1,1,3,3,3-hexafluoro-2-(methoxymethoxy)propan-2-yl)-2-propylphenoxy)pyridine was used for a similar operation as Example 1, and the title compound was obtained as a colorless oil.

$^1$H-NMR (CD$_3$OD) δ: 0.90 (3H, t, J=7.3 Hz), 1.51 (3H, s), 1.52-1.67 (2H, m), 2.59 (2H, t, J=7.6 Hz), 4.76 (2H, s), 5.95 (2H, s), 6.76 (1H, dd, J=7.3, 7.3 Hz), 6.89-7.08 (5H, m), 7.53-7.72 (3H, m).

Example 77

Preparation of 5-(benzo[d][1,3]dioxol-5-yl)-5-ethyl-3-((6-(4-(1,1,1,3,3,3-hexafluoro-2-hydroxypropan-2-yl)-2-propylphenoxy)pyridin-2-yl)methyl)imidazolidine-2,4-dione

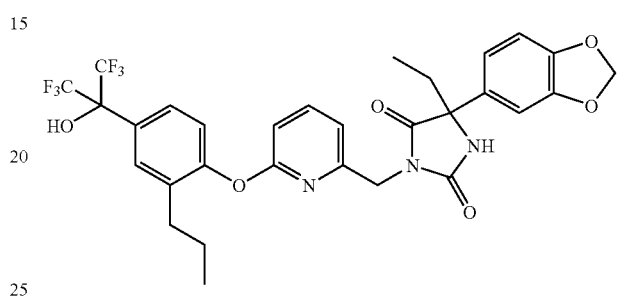

5-(Benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

$^1$H-NMR (CD$_3$OD) δ: 0.82 (3H, t, J=7.3 Hz), 0.91 (3H, t, J=7.3 Hz), 1.55-1.64 (2H, m), 1.94-2.12 (2H, m), 2.58 (2H, t, J=7.6 Hz), 4.67 (2H, s), 5.96 (2H, s), 6.68 (1H, d, J=8.4 Hz), 6.79 (1H, d, J=8.1 Hz), 6.86 (1H, d, J=7.8 Hz), 7.00 (1H, dd, J=1.9, 8.4 Hz), 7.03-7.27 (2H, m), 7.50-7.69 (3H, m).

Example 78

Preparation of 5-(2,3-dihydrobenzofuran-5-yl)-3-((6-(4-(1,1,1,3,3,3-hexafluoro-2-hydroxypropan-2-yl)-2-propylphenoxy)pyridin-2-yl)methyl)-5-methylimidazolidine-2,4-dione

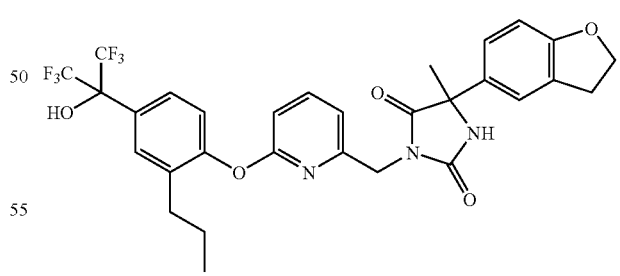

5-(2,3-Dihydrobenzofuran-5-yl)-5-methylimidazolidine-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

$^1$H-NMR (CDCl$_3$) δ: 0.90 (3H, t, J=7.3 Hz), 1.53-1.63 (2H, m), 1.62 (3H, s), 2.55 (2H, t, J=7.6 Hz), 3.18 (2H, t, J=8.9 Hz), 4.56 (2H, t, J=8.9 Hz), 4.67 (2H, s), 6.72 (1H, d, J=8.1 Hz), 6.84 (1H, d, J=8.3 Hz), 6.94 (1H, d, J=7.3 Hz), 7.04-7.12 (2H, m), 7.52 (1H, d, J=8.6 Hz), 7.55 (1H, s), 7.58-7.60 (1H, m), 7.67 (1H, dd, J=8.1, 8.3 Hz).

Example 79

Preparation of 3-((6-(4-(1,1,1,3,3,3-hexafluoro-2-hydroxypropan-2-yl)-2-propylphenoxy)pyridin-2-yl)methyl)-5-(2-methoxyphenyl)-5-methylimidazolidine-2,4-dione

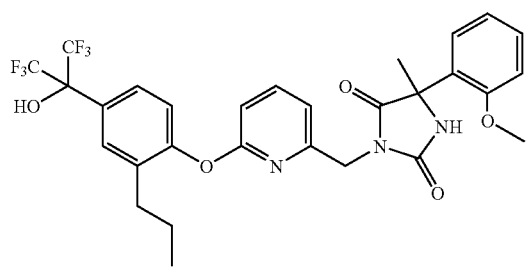

5-(2-Methoxyphenyl)-5-methylimidazolidine-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

$^1$H-NMR (CD$_3$OD) δ: 0.89 (3H, t, J=7.3 Hz), 1.48 (3H, s), 1.49-1.63 (2H, m), 2.55 (2H, t, J=7.6 Hz), 3.82 (3H, s), 4.70 (1H, d, J=16.2 Hz), 4.80 (1H, d, J=16.2 Hz), 6.80 (1H, d, J=8.6 Hz), 6.91-7.73 (9H, m).

Example 80

Preparation of 3-((6-(4-(1,1,1,3,3,3-hexafluoro-2-hydroxypropan-2-yl)-2-propylphenoxy)pyridin-2-yl)methyl)-5-(4-(1-methylethoxy)phenyl)-5-methylimidazolidine-2,4-dione

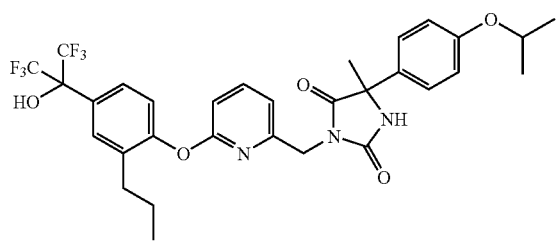

5-(4-(1-Methylethoxy)phenyl)-5-methylimidazolidine-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

$^1$H-NMR (CDCl$_3$) δ: 0.90 (3H, t, J=7.3 Hz), 1.30 (6H, d, J=5.9 Hz), 1.36 (3H, s), 1.51-1.62 (2H, m), 2.55 (2H, t, J=7.6 Hz), 3.41 (1H, s), 4.46-4.56 (1H, m), 4.67 (2H, s), 6.83-6.89 (3H, m), 6.93 (1H, d, J=7.3 Hz), 7.06 (1H, d, J=8.6 Hz), 7.27 (2H, d, J=8.6 Hz), 7.51-7.55 (2H, m), 7.67 (1H, dd, J=7.3, 7.8 Hz).

Example 81

Preparation of 5-(4-butoxyphenyl)-3-((6-(4-(1,1,1,3,3,3-hexafluoro-2-hydroxypropan-2-yl)-2-propylphenoxy)pyridin-2-yl)methyl)-5-methylimidazolidine-2,4-dione

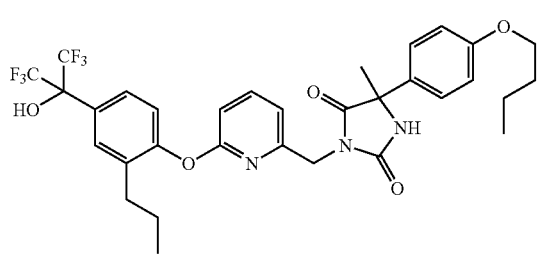

5-(4-Butoxyphenyl)-5-methylimidazolidine-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

$^1$H-NMR (CD$_3$OD) δ: 0.90 (3H, t, J=7.3 Hz), 0.97 (3H, t, J=7.3 Hz), 1.43-1.80 (9H, m), 2.58 (2H, t, J=7.6 Hz), 3.91 (2H, t, J=6.2 Hz), 4.70 (2H, s), 6.76 (2H, d, J=7.8 Hz), 6.84-6.91 (2H, m), 7.07 (1H, d, J=8.6 Hz), 7.35 (2H, d, J=8.6 Hz), 7.54 (1H, d, J=8.6 Hz), 7.59 (1H, s), 7.67 (1H, dd, J=7.8, 7.8 Hz).

Example 82

Preparation of 3-((6-(4-(1,1,1,3,3,3-hexafluoro-2-hydroxypropan-2-yl)-2-propylphenoxy)pyridin-2-yl)methyl)-5-methyl-5-(4-(4-methylbenzyloxy)phenyl)imidazolidine-2,4-dione

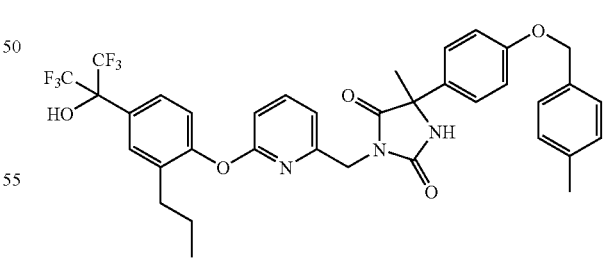

5-Methyl-5-(4-(4-methylbenzyloxy)phenyl)imidazolidine-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

$^1$H-NMR (CD$_3$OD) δ: 0.90 (3H, t, J=7.3 Hz), 1.50 (3H, s), 1.54-1.64 (2H, m), 2.36 (3H, s), 2.58 (2H, t, J=7.6 Hz), 4.70

(2H, s), 5.00 (2H, s), 6.73-7.42 (1H, m), 7.55 (1H, d, J=8.6 Hz), 7.60 (1H, s), 7.67 (1H, dd, J=7.8, 7.8 Hz).

Example 83

Preparation of 3-((6-(4-(1,1,1,3,3,3-hexafluoro-2-hydroxypropan-2-yl)-2-propylphenoxy)pyridin-2-yl)methyl)-5-(6-methoxypyridin-3-yl)-5-methylimidazolidine-2,4-dione

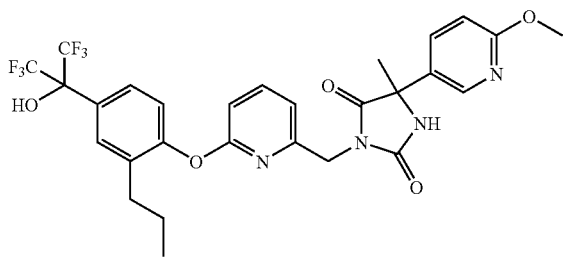

5-(6-Methoxypyridin-3-yl)-5-methylimidazolidine-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

$^1$H-NMR (CDCl$_3$) δ: 0.73 (3H, 1, J=7.3 Hz), 1.33-1.44 (2H, m), 1.48 (3H, s), 2.50 (2H, t, J=7.6 Hz), 3.93 (1H, s), 3.96 (3H, s), 4.68 (1H, d, J=16.7 Hz), 4.76 (1H, d, J=16.7 Hz), 5.85 (1H, s), 6.70 (1H, d, J=8.6 Hz), 6.84 (1H, d, J=8.1 Hz), 6.94 (1H, d, J=7.3 Hz), 7.07 (1H, d, J=8.6 Hz), 7.54 (1H, d, J=8.6 Hz), 7.58 (1H, s), 7.63-7.76 (3H, m).

Example 84

Preparation of 346-(4-(1,1,1,3,3,3-hexafluoro-2-hydroxypropan-2-yl)-2-propylphenoxy)pyridin-2-yl)methyl)-5-methyl-5-p-tolylimidazolidine-2,4-dione

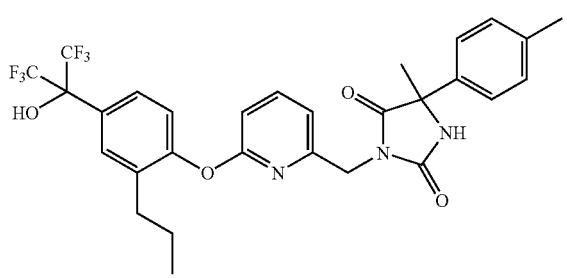

5-Methyl-5-p-tolylimidazolidine-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

$^1$H-NMR (CD$_3$OD) δ: 0.90 (3H, t, J=7.3 Hz), 1.47 (3H, s), 1.53-1.63 (2H, m), 2.32 (3H, s), 2.58 (2H, t, J=7.6 Hz), 4.69 (2H, s), 6.77 (1H, d, J=7.8 Hz), 6.90 (1H, d, J=7.3 Hz), 7.06 (1H, d, J=8.6 Hz), 7.16 (2H, d, J=7.8 Hz), 7.33 (2H, d, J=7.8 Hz), 7.52-7.58 (2H, m), 7.67 (1H, dd, J=7.3, 7.8 Hz).

Example 85

Preparation of 3-((6-(4-(1,1,1,3,3,3-hexafluoro-2-hydroxypropan-2-yl)-2-propylphenoxy)pyridin-2-yl)methyl)-5-methyl-5-(4-nitrophenyl)imidazolidine-2,4-dione

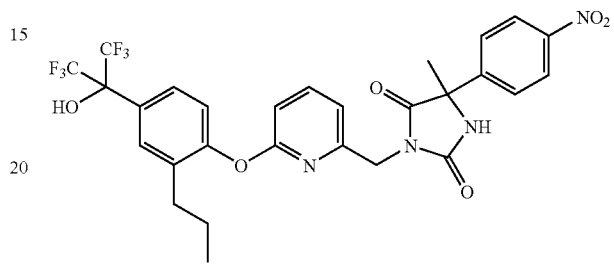

5-Methyl-5-(4-nitrophenyl)imidazolidine-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

$^1$H-NMR (CD$_3$OD) δ: 0.90 (3H, t, J=7.3 Hz), 1.44 (3H, s), 1.51-1.65 (2H, m), 2.54-2.64 (2H, m), 4.71 (2H, s), 6.81 (1H, d, J=8.1 Hz), 6.94 (1H, d, J=7.3 Hz), 7.10 (1H, d, J=8.6 Hz), 7.18-7.72 (5H, m), 8.18 (2H, d, J=8.6 Hz).

Example 86

Preparation of 5-(3,4-dichlorophenyl)-3-((6-(4-(1,1,1,3,3,3-hexafluoro-2-hydroxypropan-2-yl)-2-propylphenoxy) pyridin-2-yl)methyl)-5-methylimidazolidine-2,4-dione

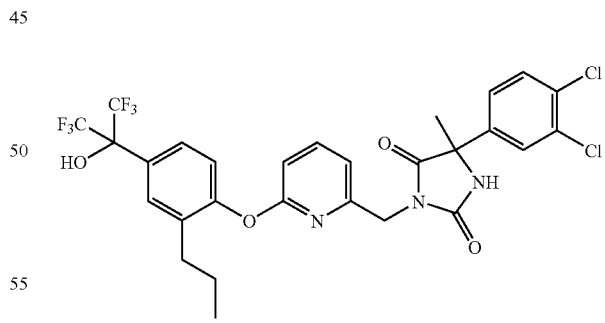

5-(3,4-Dichlorophenyl)-5-methylimidazolidine-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

$^1$H-NMR (CD$_3$OD) δ: 0.90 (3H, t, J=7.3 Hz), 1.44 (3H, s), 1.51-1.64 (2H, m), 2.58 (2H, t, J=7.6 Hz), 4.70 (2H, s), 6.77 (1H, d, J=8.1 HA 6.92 (1H, d, J=7.3 Hz), 7.06 (1H, d, J=8.6 Hz), 7.15-7.60 (5H, m), 7.69 (1H, dd, J=7.3, 8.1 Hz).

Example 87

Preparation of 3-((6-(4-(1,1,1,3,3,3-hexafluoro-2-hydroxypropan-2-yl)-2-propylphenoxy)pyridin-2-yl)methyl)-1,5,5-trimethylimidazolidine-2,4-dione

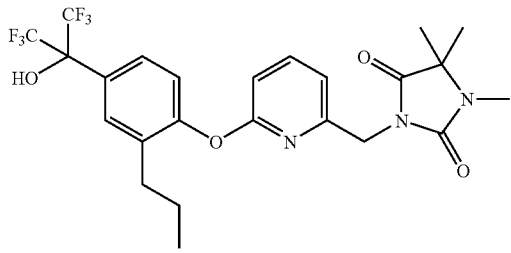

1,5,5-Trimethylimidazolidine-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

¹H-NMR (CDCl₃) δ: 0.89 (3H, t, J=7.3 Hz), 1.15 (6H, s), 1.50-1.63 (2H, m), 2.57 (2H, t, J=7.6 Hz), 2.79 (3H, s), 4.71 (2H, s), 6.79 (1H, d, J=7.8 Hz), 6.95 (1H, d, J=7.8 Hz), 7.00 (1H, d, J=8.6 Hz), 7.51 (1H, d, J=8.6 Hz), 7.56 (1H, s), 7.69 (1H, dd, J=7.8, 7.8 Hz).

Example 88

Preparation of 3-((6-(4-(1,1,1,3,3,3-hexafluoro-2-hydroxypropan-2-yl)-2-propylphenoxy)pyridin-2-yl)methyl)-1,3-diazaspiro[4.4]nonane-2,4-dione

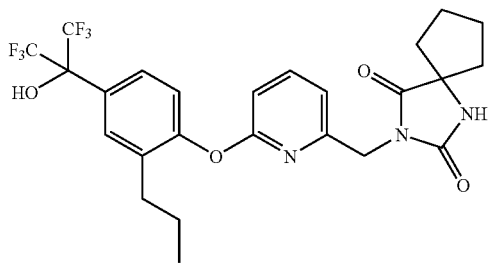

1,3-Diazaspiro[4.4]nonane-2,4-dione was used in place of 5-(benzo[d][1,3]dioxol-5-yl)-5-methylimidazolidine-2,4-dione in Example 76 g) for a similar reaction and treatment, and the title compound was obtained as a colorless oil.

¹H-NMR (CD₃OD) δ: 0.90 (3H, t, J=7.3 Hz), 1.50-2.00 (10H, m), 2.57 (2H, t, J=7.6 Hz), 4.69 (2H, s), 6.78 (1H, d, J=8.1 Hz), 6.93 (1H, d, J=8.6 Hz), 7.04 (1H, d, J=7.8 Hz), 7.52 (1H, d, J=8.6 Hz), 7.58 (1H, s), 7.69 (1H, dd, J=7.8, 8.1 Hz).

Example 89

Preparation of 5-(2,3-dihydrobenzofuran-5-yl)-3-((5-(4-(1,1,1,3,3,3-hexafluoro-2-hydroxypropan-2-yl)-2-propylphenoxy)pyridin-2-yl)methyl)-5-methylimidazolidine-2,4-dione a) Preparation of 2-bromo-5-(4-(1,1,1,3,3,3-hexafluoro-2-(methoxymethoxy)propan-2-yl)-2-propylphenoxy) pyridine

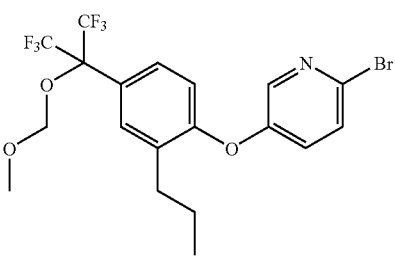

2-Bromopyridine-5-boronic acid was used in place of 3-(hydroxymethyl)phenylboronic acid for a similar reaction and treatment as Preparation example 3 a) and the compound of interest was obtained as a colorless oil.

¹H-NMR (CDCl₃) δ: 0.94 (3H, t, J=7.3 Hz), 1.56-1.71 (2H, m), 2.65 (2H, t, J=7.6 Hz), 3.56 (3H, s), 4.86 (2H, s), 6.87 (1H, d, J=8.6 Hz), 7.16 (1H, dd, J=3.0, 8.6 Hz), 7.40-7.54 (3H, m), 8.16 (1H, d, J=3.0 Hz).

b) Preparation of 5-(4-(1,1,1,3,3,3-hexafluoro-2-(methoxymethoxy)propan-2-yl)-2-propylphenoxy) picolinonitrile

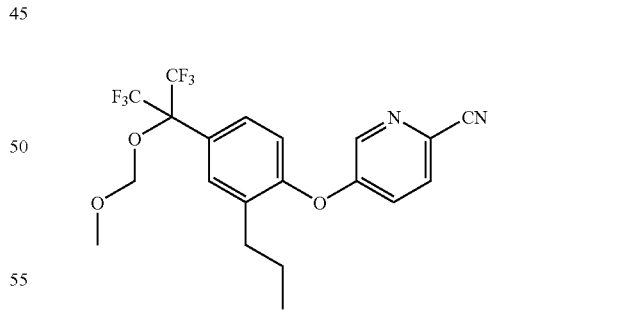

2-Bromo-5-(4-(1,1,1,3,3,3-hexafluoro-2-(methoxymethoxy)propan-2-yl)-2-propyl-phenoxy) pyridine was used for a similar operation as Example 59 b), and the title compound was obtained as a colorless oil.

¹H-NMR (CDCl₃) δ: 0.92 (3H, t, J=7.3 Hz), 1.58-1.68 (2H, m), 2.59 (2H, t, J=7.6 Hz), 3.58 (3H, s), 4.88 (2H, s), 7.01 (1H, d, J=8.6 Hz), 7.20-7.26 (1H, m), 7.49-7.69 (3H, m), 8.45 (1H, d, J=2.4 Hz).

c) Preparation of methyl 5-(4-(1,1,1,3,3,3-hexafluoro-2-hydroxypropan-2-yl)-2-propylphenoxy)picolinate

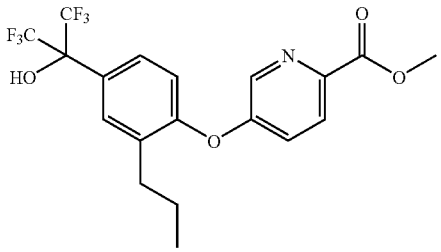

5-(4-(1,1,1,3,3,3-Hexafluoro-2-(methoxymethoxy)propan-2-yl)-2-propylphenoxy) picolinonitrile was used for a similar operation as Example 59 c), and the title compound was obtained as a colorless oil.

$^1$H-NMR (CDCl$_3$) δ: 0.92 (3H, t, J=7.3 Hz), 1.58-1.66 (2H, m), 2.61 (2H, t, J=7.6 Hz), 4.00 (3H, s), 6.99 (1H, d, J=8.6 Hz), 7.21-7.26 (1H, m), 7.50-7.66 (2H, m), 8.11 (1H, d, J=8.9 Hz), 8.47 (1H, d, J=2.7 Hz).

d) Preparation of 2-(bromomethyl)-5-(4-(1,1,1,3,3,3-hexafluoro-2-(methoxymethoxy)propan-2-yl)-2-propylphenoxy) pyridine

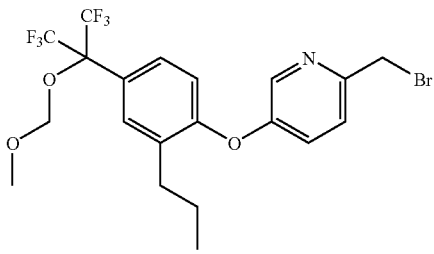

Methyl 5-(4-(1,1,1,3,3,3-hexafluoro-2-hydroxypropan-2-yl)-2-propylphenoxy)picolinate was used for a similar operation as Example 59 d), and the title compound was obtained as a colorless oil.

$^1$H-NMR (CDCl$_3$) δ: 0.94 (3H, t, J=7.3 Hz), 1.60-1.71 (2H, m), 2.66 (2H, t, J=7.6 Hz), 3.56 (3H, s), 4.57 (2H, s), 4.86 (2H, s), 6.89 (1H, d, J=8.6 Hz), 7.22-7.26 (1H, m), 7.40-7.52 (3H, m), 8.33 (1H, d, J=2.7 Hz).

e) Preparation of 5-(2,3-dihydrobenzofuran-5-yl)-3-((5-(4-(1,1,1,3,3,3-hexafluoro-2-hydroxypropan-2-yl)-2-propylphenoxy)pyridin-2-yl)methyl)-5-methylimidazolidine-2,4-dione

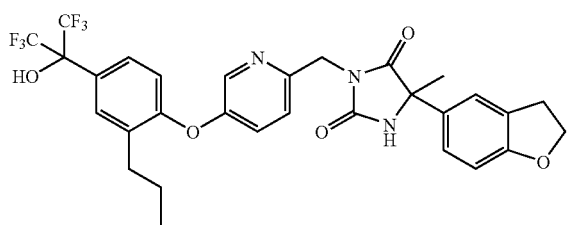

2-(Bromomethyl)-5-(4-(1,1,1,3,3,3-hexafluoro-2-(methoxymethoxy)propan-2-yl)-2-propylphenoxy)pyridine was used for a similar operation as Example 1, and the title compound was obtained as a colorless oil.

$^1$H-NMR (CDCl$_3$) δ: 0.92 (3H, t, J=7.3 Hz), 1.56-1.69 (2H, m), 1.86 (3H, s), 2.63 (2H, t, J=7.6 Hz), 3.18 (2H, t, J=8.5 Hz), 4.16 (1H, s), 4.57 (2H, t, J=8.6 Hz), 4.82 (2H, s), 5.92 (1H, s), 6.75 (1H, d, J=8.3 Hz), 6.83 (1H, d, J=8.6 Hz), 7.15-7.26 (3H, m), 7.39 (1H, s), 7.47 (1H, d, J=8.6 Hz), 7.63 (1H, s), 8.21 (1H, d, J=1.6 Hz).

Example 90

Preparation of 3-((5-(4-(1,1,1,3,3,3-hexafluoro-2-hydroxypropan-2-yl)-2-propylphenoxy)pyridin-2-yl)methyl)-5-(4-(1-methylethoxy)phenyl)-5-methylimidazolidine-2,4-dione

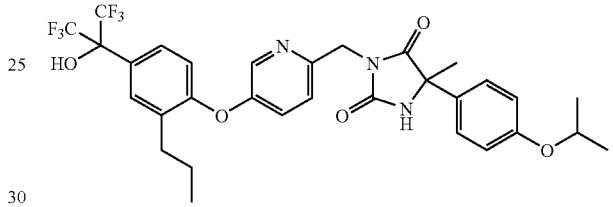

5-(4-(1-Methylethoxy)phenyl)-5-methylimidazolidine-2,4-dione was used in place of 5-(2,3-dihydrobenzofuran-5-yl)-5-methylimidazolidine-2,4-dione in Example 89 e) for a similar reaction and treatment, and the title compound was obtained as a colorless oil.

$^1$H-NMR (CDCl$_3$) δ: 0.93 (3H, t, J=7.3 Hz), 1.32 (6H, d, J=5.9 Hz), 1.56-1.70 (2H, m), 1.80 (3H, s), 2.63 (2H, t, J=7.6 Hz), 3.93 (1H, s), 4.40-4.58 (1H, m), 4.82 (2H, s), 5.82 (1H, s), 6.81-6.89 (3H, m), 7.14-7.49 (6H, m), 8.24 (1H, s).

Example 91

Preparation of 3-((5-(4-(1,1,1,3,3,3-hexafluoro-2-hydroxypropan-2-yl)-2-propylphenoxy)pyridin-2-yl)methyl)-5-(6-methoxypyridin-3-yl)-5-methylimidazolidine-2,4-dione

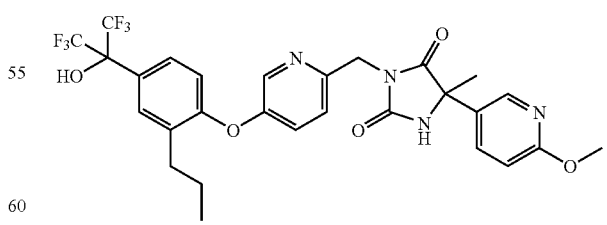

5-(6-Methoxypyridin-3-yl)-5-methylimidazolidine-2,4-dione was used in place of 5-(2,3-dihydrobenzofuran-5-yl)-5-methylimidazolidine-2,4-dione in Example 89 e) for a similar reaction and treatment, and the title compound was obtained as a colorless oil.

¹H-NMR (CDCl₃) δ: 0.92 (3H, t, J=7.3 Hz), 1.55-1.69 (2H, m), 1.88 (3H, s), 2.63 (2H, t, J=7.6 Hz), 3.92 (3H, s), 4.22 (1H, s), 4.82 (2H, s), 6.25 (1H, s), 6.45 (1H, d, J=8.9 Hz), 6.83 (1H, d, J=8.6 Hz), 7.16-7.23 (1H, m), 7.48 (2H, d, J=8.6 Hz), 7.60 (1H, s), 7.77 (1H, dd, J=1.6, 3.5 Hz), 8.22 (1H, s), 8.30 (1H, d, J=1.6 Hz).

Example 92

Preparation of 5-(benzo[d][1,3]dioxol-5-yl)-3-(2-(4'-(1,1,1,3,3,3-hexafluoro-2-hydroxypropan-2-yl)-2'-propylphenyl-3-yl)ethyl)-5-methylimidazolidine-2,4-dione a) Preparation of 4-(1,1,1,3,3,3-hexafluoro-2-(methoxymethoxy)propan-2-yl)-2-propylphenyl trifluoromethanesulfonate

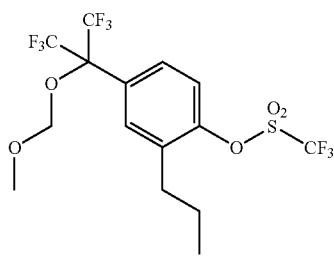

To a solution of 4-(1,1,1,3,3,3-hexafluoro-2-(methoxymethoxy)propan-2-yl)-2-propylphenol (301 mg, 0.869 mmol) in methylene chloride (9 mL), pyridine (0.2 mL) and trifluoromethanesulfonic anhydride (0.21 mL) were added at 0° C. After completion of the reaction, the reaction solution wad added with water, extracted with ethyl acetate, and concentrated in vacuo. The obtained residue was purified using silica-gel column chromatography (hexane/ethyl acetate), and the title compound (360 mg, yield 87%) was obtained as a colorless oil.

MS (EI): 478 b) Preparation of 4-(1,1,1,3,3,3-hexafluoro-2-(methoxymethoxy)propan-2-yl)-2-propyl-3'-vinylbiphenyl

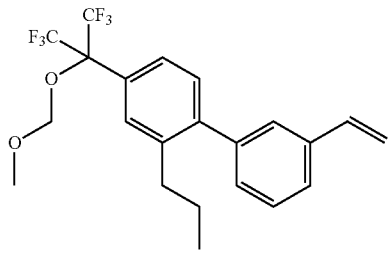

To a solution of 4-(1,1,1,3,3,3-hexafluoro-2-(methoxymethoxy)propan-2-yl)-2-propylphenyl trifluoromethanesulfonate (238 mg, 497 μmol) in 1,4-dioxan, potassium phosphate (401 mg), 3-vinylphenylboronic acid (88 mg), and tetrakis triphenylphosphine palladium complex (57 mg) were added at room temperature under an argon atmosphere, and the resultant mixture was heated at 80° C. After completion of the reaction, the reaction solution was neutralized by adding water and 2 mol/L of hydrochloric acid, extracted with ethyl aceate, and then concentrated in vacuo. The obtained residue was purified using silica-gel column chromatography (hexane/ethyl acetate), and the title compound (175 mg, yield 81%) was obtained as a colorless oil.

¹H-NMR (CDCl₃) δ: 0.82 (3H, t, J=7.3 Hz), 1.53-1.64 (2H, m), 2.57 (2H, t, J=7.6 Hz), 3.58 (3H, s), 4.89 (2H, s), 5.30 (1H, dd, J=0.5, 10.8 Hz), 5.76 (1H, dd, J=0.5, 17.6 Hz), 6.70 (1H, dd, J=10.8, 17.6 Hz), 6.30-7.55 (7H, m).

c) Preparation of 2-(4'-(1,1,1,3,3,3-hexafluoro-2-(methoxymethoxy)propan-2-yl)-2'-propylbiphenyl-3-yl) oxirane

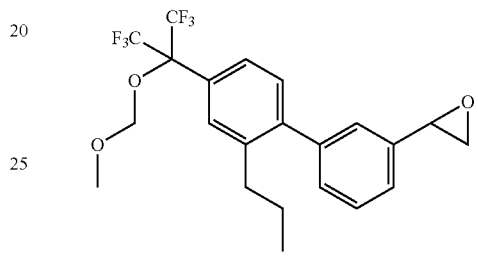

4-(1,1,1,3,3,3-Hexafluoro-2-(methoxymethoxy)propan-2-yl)-2-propyl-3'-vinylbiphenyl was used for a similar operation as Example 30 b), and the title compound was obtained as a colorless oil.

¹H-NMR (CDCl₃) δ: 0.81 (3H, t, J=7.3 Hz), 1.41-1.52 (2H, m), 2.56 (2H, t, J=7.6 Hz), 2.83 (1H, dd, J=2.4, 5.7 Hz), 3.18 (1H, dd, J=4.1, 5.7 Hz), 3.57 (3H, s), 3.85 (1H, dd, J=2.4, 4.1 Hz), 4.89, (2H, s), 7.21-7.51 (7H, m).

d) Preparation of 2-(4'-(1,1,1,3,3,3-hexafluoro-2-(methoxymethoxy)propan-2-yl)-2'-propylbiphenyl-3-yl) ethanol

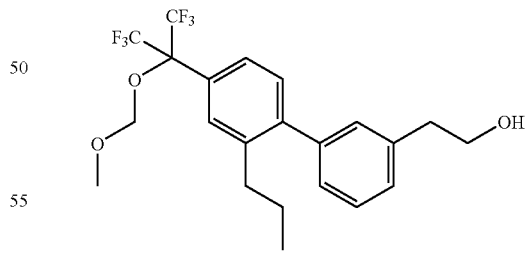

2-(4'-(1,1,1,3,3,3-Hexafluoro-2-(methoxymethoxy)propan-2-yl)-2'-propylbiphenyl-3-yl)oxirane was used for a similar operation as Example 30 c), and the title compound was obtained as a colorless oil.

¹H-NMR (CDCl₃) δ: 0.82 (3H, t, J=7.3 Hz), 1.45-1.54 (2H, m), 2.58 (2H, t, J=7.8 Hz), 2.93 (2H, t, J=6.6 Hz), 3.58 (3H, s), 3.91 (2H, t, J=6.6 Hz), 4.89, (2H, s), 7.17-7.40 (5H, m), 7.46 (1H, d, J=8.6 Hz), 7.51 (1H, s).

e) Preparation of 5-(benzo[d][1,3]dioxol-5-yl)-3-(2-(4'-(1,1,1,3,3,3-hexafluoro-2-hydroxypropan-2-yl)-2'-propylbiphenyl-3-yl)ethyl-5-methylimidazolidine-2,4-dione

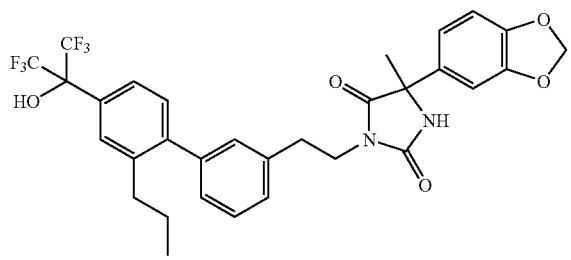

2-(4'-(1,1,1,3,3,3-Hexafluoro-2-(methoxymethoxy)propan-2-yl)-2'-propylbiphenyl-3-yl)ethanol was used for a similar operation as Example 30 d), and the title compound was obtained as a colorless oil.

$^1$H-NMR (CDCl$_3$) δ: 0.80 (3H, t, J=7.3 Hz), 1.43-1.52 (2H, m), 1.67 (3H, s), 2.56 (2H, t, J=7.6 Hz), 2.99 (2H, t, J=7.3 Hz), 3.72 (1H, s), 3.79 (2H, t, J=7.3 Hz), 5.77 (1H, s), 5.93 (2H, s), 6.79 (1H, d, J=8.1 Hz), 6.81 (1H, dd, J=1.9, 8.1 Hz), 6.87 (1H, d, J=1.9 Hz), 7.13-7.29 (5H, m), 7.52 (1H, d, J=8.6 Hz), 7.59 (1H, s).

Example 93

Preparation of 5-(benzo[d][1,3]dioxol-5-yl)-5-ethyl-3-(2-(4'-(1,1,1,3,3,3-hexafluoro-2-hydroxypropan-2-yl)-2'-propylbiphenyl-3-yl)ethyl)imidazolidine-2,4-dione

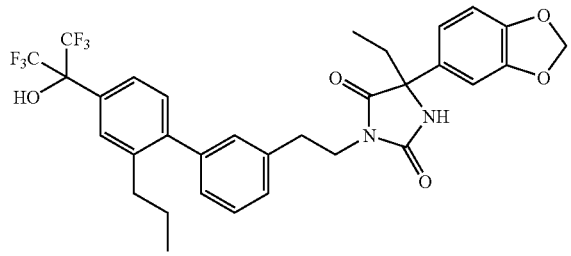

5-(Benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 92 e) for a similar reaction and treatment, and the title compound was obtained as a colorless oil.

$^1$H-NMR (CDCl$_3$) δ: 0.78-0.83 (6H, m), 1.43-1.52 (2H, m), 1.95-2.20 (2H, m), 2.56 (2H, t, J=7.6 Hz), 2.97 (2H, t, J=7.3 Hz), 3.70 (1H, s), 3.77 (2H, t, J=7.3 Hz), 5.86 (1H, s), 5.94 (2H, s), 6.71 (1H, d, J=8.1 Hz), 6.85 (1H, dd, J=1.9, 8.1 Hz), 6.95 (1H, d, J=1.9 Hz), 7.11-7.27 (5H, m), 7.52 (1H, d, J=8.6 Hz), 7.59 (1H, s).

Example 94

Preparation of 5-(2,3-dihydrobenzo[b][1,4]dioxin-6-yl)-5-ethyl-3-(2-(4'-(1,1,1,3,3,3-hexafluoro-2-hydroxypropan-2-yl)-2'-propylbiphenyl-3-yl)ethyl)imidazolidine-2,4-dione

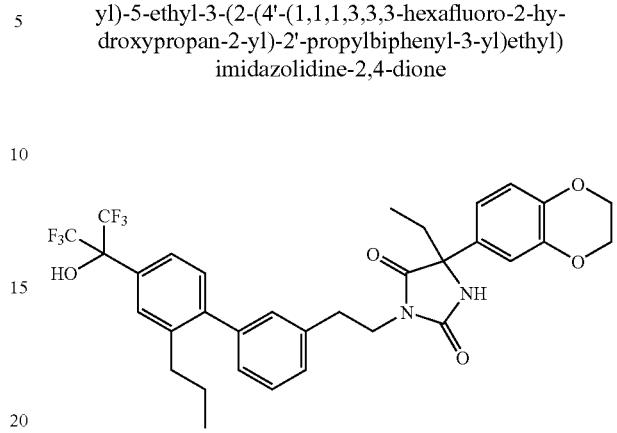

5-(2,3-Dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 92 e) for a similar reaction and treatment, and the title compound was obtained as a colorless oil.

$^1$H-NMR (CDCl$_3$) δ: 0.77-0.83 (6H, m), 1.43-1.52 (2H, m), 1.93-2.12 (2H, m), 2.56 (2H, t, J=7.6 Hz), 2.97 (2H, t, J=7.3 Hz), 3.77 (2H, t, J=7.3 Hz), 3.79 (1H, s), 4.20-4.29 (4H, m), 5.86 (1H, s), 6.77 (1H, d, J=8.1 Hz), 6.85 (1H, dd, J=1.9, 8.1 Hz), 6.97 (1H, d, J=1.9 Hz), 7.12-7.27 (5H, m), 7.52 (1H, d, J=8.6 Hz), 7.59 (1H, s).

Example 95

Preparation of 3-(2-(4'-(1,1,1,3,3,3-hexafluoro-2-hydroxypropan-2-yl)-2'-propylbiphenyl-3-yl)ethyl)-5-(4-(1-methylethoxy)phenyl)-5-methylimidazolidine-2,4-dione

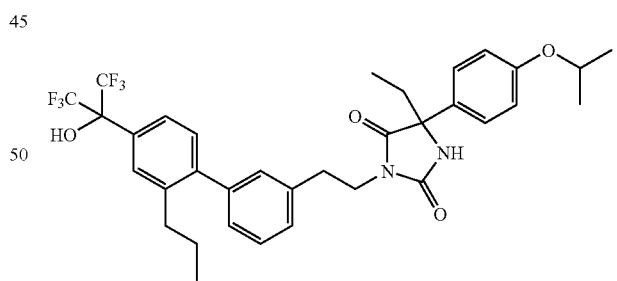

5-(4-(1-Methylethoxy)phenyl-5-methylimidazolidine-2,4-dione was used in place of 5-(benzo[d][1,3]dioxol-5-yl)-5-methylimidazolidine-2,4-dione in Example 92 e) for a similar reaction and treatment, and the title compound was obtained as a colorless oil.

$^1$H-NMR (CDCl$_3$) δ: 0.80 (3H, t, J=7.3 Hz), 1.30 (6H, d, J=5.9 Hz), 1.42-1.51 (2H, m), 1.69 (3H, s), 2.55 (2H, t, J=7.6 Hz), 2.99 (2H, t, J=7.3 Hz), 3.74 (1H, s), 3.80 (2H, t, J=7.3 Hz), 4.50 (1H, sept, J=5.9 Hz), 5.69 (1H, s), 6.79 (2H, d, 8.6 Hz), 7.13-7.31 (7H, m), 7.51 (1H, d, J=8.6 Hz), 7.59 (1H, s).

Example 96

Preparation of 5-(benzo[d][1,3]dioxol-5-yl)-3-(3-(4'-(1,1,1,3,3,3-hexafluoro-2-hydroxypropan-2-yl)-2'-propylbiphenyl-3-yloxy)propyl)-5-methylimidazolidine-2,4-dione a) Preparation of 4'-(1,1,1,3,3,3-hexafluoro-2-(methoxymethoxy)propan-2-yl)-2'-propylbiphenyl-3-ol

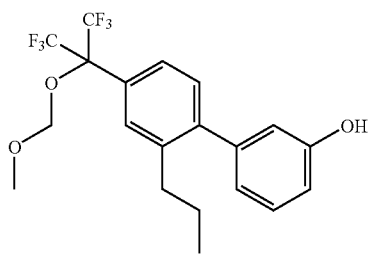

3-Hydroxyphenylboronic acid was used in place of 3-vinylphenylboronic acid in Example 92 b) for a similar reaction and treatment, and the compound of interest was obtained as a colorless oil.

¹H-NMR (CDCl₃) δ: 0.82 (3H, t, J=7.3 Hz), 1.41-1.57 (2H, m), 2.59 (2H, t, J=7.6 Hz), 3.58 (3H, s), 4.90 (2H, s), 6.76-6.78 (1H, m), 6.82-6.85 (2H, m), 7.22-7.32 (2H, m), 7.44 (1H, d, J=8.6 Hz), 7.50 (1H, s).

b) Preparation of 3'-3-(bromopropoxy)-4-(1,1,1,3,3,3-hexafluoro-2-(methoxymethoxy)propan-2-yl)-2'-propylbiphenyl

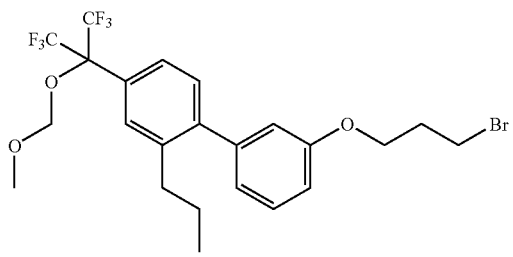

To a solution of 4'-(1,1,1,3,3,3-hexafluoro-2-(methoxymethoxy)propan-2-yl)-2'-propylbiphenyl-3-ol (59.7 mg, 0.141 mmol) in N,N-dimethylformamide (0.25 mL), potassium carbonate (40.0 mg) and 1,3-dibromopropane (0.115 mL) were added, and the resultant mixture was stirred overnight. The reaction solution was neutralized by adding 2 mol/L of hydrochloric acid, added with water, and extracted with ethyl acetate. Subsequently, the organic layer was washed with brine, dried using anhydrous sodium sulfate, and concentrated in vacuo. The obtained residue was purified using thin-layer silica-gel column chromatography (hexane/ethyl acetate) and the title compound (76.2 mg, yield 99%) was obtained as a colorless oil.

¹H-NMR (CDCl₃) δ: 0.83 (3H, t, J=7.3 Hz), 1.42-1.57 (2H, m), 2.29-2.38 (2H, m), 2.59 (2H, t, J=7.6 Hz), 3.58 (3H, s), 3.62 (2H, t, J=6.5 Hz), 4.13 (2H, t, J=5.7 Hz), 4.90 (2H, s), 6.84-6.91 (3H, m), 7.29-7.38 (2H, m), 7.45 (1H, d, J=8.6 Hz), 7.50 (1H, s).

c) Preparation of 5-(benzo[d][1,3]dioxol-5-yl)-3-(3-(4'-(1,1,1,3,3,3-hexafluoro-2-hydroxypropan-2-yl)-2-propylbiphenyl-3-yloxy)propyl)-5-methylimidazolidine-2,4-dione

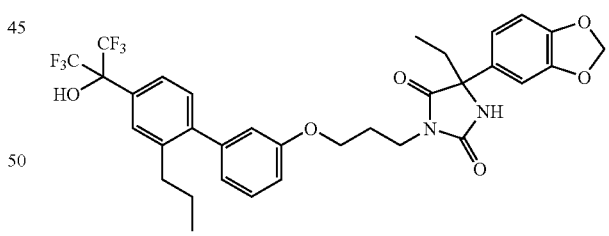

3'-(3-Bromopropoxy)-4-(1,1,1,3,3,3-hexafluoro-2-(methoxymethoxy)propan-2-yl)-2-propylbiphenyl was used for a similar operation as Example 1, and the title compound was obtained as a colorless oil.

¹H-NMR (CDCl₃) δ: 0.81 (3H, t, J=7.3 Hz), 1.42-1.55 (2H, m), 1.76 (3H, s), 2.09-2.18 (2H, m), 2.58 (2H, t, J=7.6 Hz), 3.73 (2H, t, J=6.8 Hz), 3.78 (1H, brs), 3.99 (2H, 1, J=5.9 Hz), 5.93 (2H, s), 5.96 (1H, brs), 6.72-6.98 (6H, m), 7.16-7.31 (2H, m), 7.53 (1H, d, J=8.1 Hz), 7.59 (1H, brs).

Example 97

Preparation of 5-(benzo[d][1,3]dioxol-5-yl)-5-ethyl-3-(3-(4'-(1,1,1,3,3,3-hexafluoro-2-hydroxypropan-2-yl)-2'-propylbiphenyl-3-yloxy)propyl)imidazolidine-2,4-dione 5-(Benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 96 c) for a similar reaction and treatment, and the title compound was obtained as a colorless oil.

¹H-NMR (CDCl₃) δ: 0.81 (31-1, t, J=7.6 Hz), 0.87 (3H, t, J=7.3 Hz), 1.42-1.55 (2H, m), 2.02-2.18 (4H, m), 2.58 (2H, t, J=7.6 Hz), 3.72 (2H, t, J=6.8 Hz), 3.74 (1H, brs), 3.97 (2H, t, J=6.2 Hz), 5.93 (2H, s), 6.12 (1H, brs), 6.73 (1H, d, J=8.1 Hz), 6.76-6.87 (3H, m), 6.93 (1H, dd, J=8.1, 1.9 Hz), 7.03 (1H, d, J=1.9 Hz), 7.16-7.30 (2H, m), 7.53 (1H, d, J=8.1 Hz), 7.59 (1H, brs).

Example 98

Preparation of 5-(2,3-dihydrobenzo[b][1,4]dioxin-6-yl)-5-ethyl-3-(3-(4'-(1,1,1,3,3,3-hexafluoro-2-hydroxypropan-2-yl)-2'-propylbiphenyl-3-yloxy)propyl)imidazolidine-2,4-dione

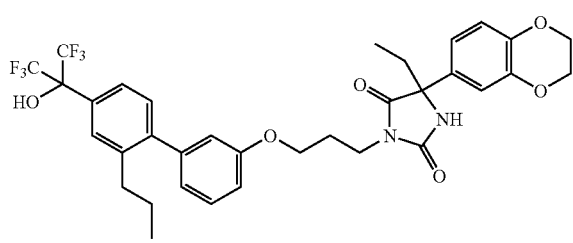

5-(2,3-Dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 96 c) for a similar reaction and treatment, and the title compound was obtained as a colorless oil.

1H-NMR (CDCl3) δ: 0.81 (3H, t, J=7.0 Hz), 0.87 (3H, t, J=7.3 Hz), 1.42-1.55 (2H, m), 2.02-2.18 (4H, m), 2.58 (2H, t, J=7.6 Hz), 3.71 (2H, t, J=6.8 Hz), 3.77 (1H, brs), 3.97 (2H, t, J=6.2 Hz), 4.22 (4H, s), 5.98 (1H, brs), 6.77-6.87 (3H, m), 6.81 (1H, d, J=8.6 Hz), 6.94 (1H, dd, J=8.6, 1.9 Hz), 7.03 (1H, d, J=1.9 Hz), 7.16-7.30 (2H, m), 7.53 (1H, d, J=7.8 Hz), 7.59 (1H, brs).

Example 99

Preparation of 3-(3-(4'-(1,1,1,3,3,3-hexafluoro-2-hydroxypropan-2-yl)-2'-propylbiphenyl-3-yloxy)propyl)-5-(4-(1-methylethoxy)phenyl)-5-methylimidazolidine-2,4-dione

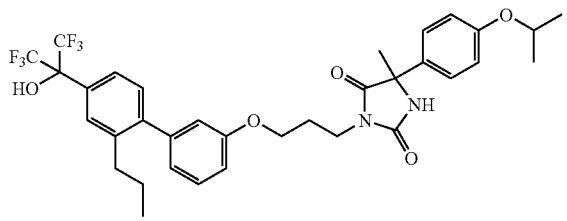

5-(4-(1-Methylethoxy)phenyl)-5-methylimidazolidine-2,4-dione was used in place of 5-(benzo[d][1,3]dioxol-5-yl)-5-methylimidazolidine-2,4-dione in Example 96 c) for a similar reaction and treatment, and the title compound was obtained as a colorless oil.

$^1$H-NMR (CDCl$_3$) δ: 0.81 (3H, t, J=7.3 Hz), 1.31 (6H, d, J=5.9 Hz), 1.42-1.55 (2H, m), 1.78 (3H, s), 2.09-2.18 (2H, m), 2.58 (2H, t, J=7.6 Hz), 3.73 (1H, brs), 3.73 (2H, t, J=6.8 Hz), 3.99 (2H, t, J=6.5 Hz), 4.47-4.56 (1H, m), 5.82 (1H, brs), 6.79-6.87 (5H, m), 7.16-7.36 (4H, m), 7.53 (1H, d, J=7.6 Hz), 7.59 (1H, brs).

Example 100

Preparation of 5-(benzo[d][1,3]dioxol-5-yl)-3-(4-(4'-(1,1,1,3,3,3-hexafluoro-2-hydroxypropan-2-yl)-2'-propylbiphenyl-3-yloxy)butyl)-5-methylimidazolidine-2,4-dione a) Preparation of 3'-(4-bromobutoxy)-4-(1,1,1,3,3,3-hexafluoro-2-(methoxymethoxy)propan-2-yl)-2-propylbiphenyl

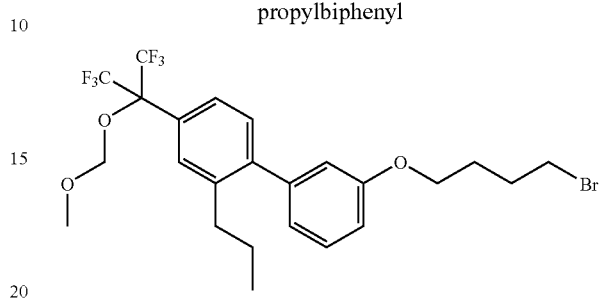

1,4-Dibromobutane was used in place of 1,3-dibromopropane for a similar reaction and treatment as Example 96 b), and the compound of interest was obtained as a colorless oil.

$^1$H-NMR (CDCl$_3$) δ: 0.82 (3H, t, J=7.3 Hz), 1.45-1.57 (2H, m), 1.96-2.11 (4H, m), 2.59 (2H, t, J=7.6 Hz), 3.53 (2H, t, J=6.2 Hz), 3.58 (3H, s), 4.02 (2H, t, J=5.5 Hz), 4.89 (2H, s), 6.81-6.91 (3H, m), 7.25-7.35 (2H, m), 7.45 (1H, d, J=8.6 Hz), 7.50 (1H, s).

b) Preparation of 5-(benzo[d][1,3]dioxol-5-yl)-3-(4-(4'-(1,1,1,3,3,3-hexafluoro-2-hydroxypropan-2-yl)-2'-propylbiphenyl-3-yloxy)butyl)-5-methylimidazolidine-2,4-dione

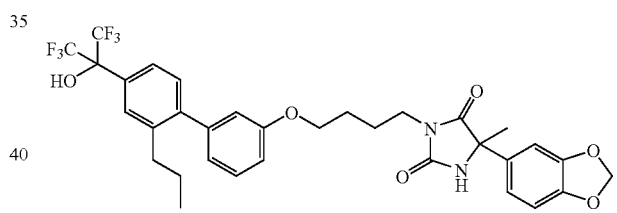

3'-(4-Bromobutoxy)-4-(1,1,1,3,3,3-hexafluoro-2-(methoxymethoxy)propan-2-yl)-2-propylbiphenyl was used for a similar operation as Example 1, and the title compound was obtained as a colorless oil.

$^1$H-NMR (CDCl$_3$) δ: 0.81 (3H, t, J=7.6 Hz), 1.42-1.55 (2H, m), 1.78 (7H, brs), 2.59 (2H, t, J=7.6 Hz), 3.59 (2H, t, J=6.8 Hz), 3.65 (1H, brs), 3.97 (2H, t, J=5.9 Hz), 5.79 (1H, brs), 5.95 (2H, s), 6.77-6.97 (6H, m), 7.16-7.32 (2H, m), 7.53 (1H, d, J=8.4 Hz), 7.59 (1H, brs).

Example 101

Preparation of 5-(benzo[d][1,3]dioxol-5-yl)-5-ethyl-3-(4-(4'-(1,1,1,3,3,3-hexafluoro-2-hydroxypropan-2-yl)-2'-propylbiphenyl-3-yloxy)butyl)imidazolidine-2,4-dione

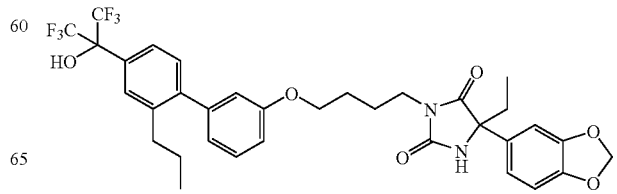

5-(Benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 100 b) for a similar reaction and treatment, and the title compound was obtained as a colorless oil.

¹H-NMR (CDCl₃) δ: 0.81 (3H, t, J=7.3 Hz), 0.89 (3H, t, J=7.3 Hz), 1.42-1.56 (2H, m), 1.78-1.80 (4H, m), 2.00-2.23 (2H, m), 2.58 (2H, t, J=7.6 Hz), 3.57 (2H, t, J=5.9 Hz), 3.74 (1H, brs), 3.96 (2H, t, J=5.1 Hz), 5.95 (2H, s), 6.08 (1H, brs), 6.78 (1H, d, J=8.4 Hz), 6.79-6.87 (3H, m), 6.94 (1H, dd, J=8.4, 1.9 Hz), 7.03 (1H, d, J=1.9 Hz), 7.16-7.32 (2H, m), 7.53 (1H, d, J=7.8 Hz), 7.59 (1H, s).

Example 102

Preparation of 5-(2,3-dihydrobenzo[b][1,4]dioxin-6-yl)-5-ethyl-3-(4-(4'-(1,1,1,3,3,3-hexafluoro-2-hydroxypropan-2-yl)-2'-propylbiphenyl-3-yloxy)butyl)imidazolidine-2,4-dione

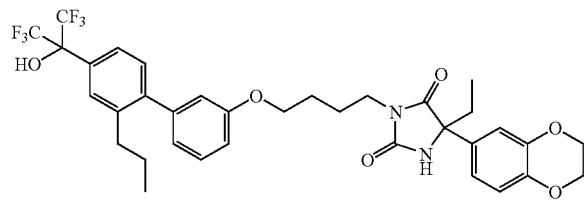

5-(2,3-Dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 100 b) for a similar reaction and treatment, and the title compound was obtained as a colorless oil.

¹H-NMR (CDCl₃) δ: 0.81 (3H, t, J=7.3 Hz), 0.89 (3H, t, J=7.3 Hz), 1.42-1.56 (2H, m), 1.78-1.80 (4H, m), 1.99-2.24 (2H, m), 2.58 (2H, t, J=8.1 Hz), 3.56 (2H, t, J=5.9 Hz), 3.80 (1H, brs), 3.96 (2H, t, J=5.1 Hz), 4.22 (4H, s), 6.02 (1H, brs), 6.79-6.88 (3H, m), 6.85 (1H, d, J=8.6 Hz), 6.95 (1H, dd, J=8.6, 1.9 Hz), 7.02 (1H, d, J=1.9 Hz), 7.16-7.32 (2H, m), 7.53 (1H, d, J=7.6 Hz), 7.59 (1H, s).

Example 103

Preparation of 3-(4-(4'-(1,1,1,3,3,3-hexafluoro-2-hydroxypropan-2-yl)-2'-propylbiphenyl-3-yloxy)buty1)-5-(4-(1-methylethoxy)phenyl)-5-methylimidazolidine-2,4-dione

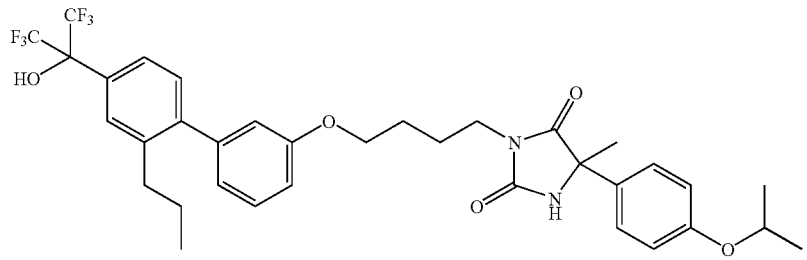

5-(4-(1-Methylethoxy)phenyl)-5-methylimidazolidine-2,4-dione was used in place of 5-(benzo[d][1,3]dioxol-5-yl)-5-methylimidazolidine-2,4-dione in Example 100 b) for a similar reaction and treatment, and the title compound was obtained as a colorless oil.

¹H-NMR (CDCl₃) δ: 0.81 (3H, t, J=7.3 Hz), 1.31 (6H, d, J=5.9 Hz), 1.43-1.56 (2H, m), 1.80 (7H, bs), 2.59 (2H, t, J=7.6 Hz), 3.59 (2H, t, J=6.8 Hz), 3.68 (1H, brs), 3.97 (2H, t, J=5.7 Hz), 4.48-4.57 (1H, m), 5.73 (1H, brs), 6.80-6.89 (5H, m), 7.19-7.37 (4H, m), 7.53 (1H, d, J=7.6 Hz), 7.59 (1H, brs).

Example 104

Preparation of 5-(benzo[d][1,3]dioxol-5-yl)-3-(5-(4'-(1,1,1,3,3,3-hexafluoro-2-hydroxypropan-2-yl)-2'-propylbiphenyl-3-yloxy)pentyl)-5-methylimidazolidine-2,4-dione a) Preparation of 3'-(5-bromopentyloxy)-4-(1,1,1,3,3,3-hexafluoro-2-(methoxymethoxy)propan-2-yl)-2-propylbiphenyl

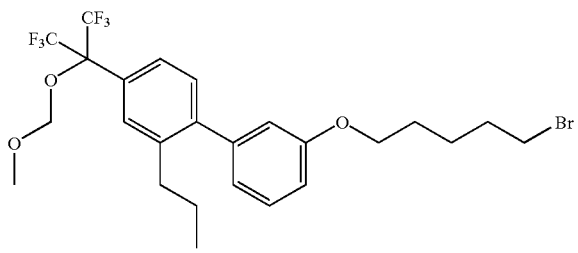

1,5-Dibromopentane was used in place of 1,3-dibromopropane for a similar reaction and treatment as Example 96 b), and the compound of interest was obtained as a colorless oil.

¹H-NMR (CDCl₃) δ: 0.82 (3H, t, J=7.3 Hz), 1.45-1.98 (8H, m), 2.60 (2H, t, J=7.6 Hz), 3.44 (2H, t, J=6.8 Hz), 3.58 (3H, s), 4.00 (2H, t, J=6.3 Hz), 4.90 (2H, s), 6.81-6.91 (3H, m), 7.29-7.35 (2H, m), 7.45 (1H, d, J=8.6 Hz), 7.50 (1H, s).

b) Preparation of 5-(benzo[d][1,3]dioxol-5-yl)-3-(5-(4'-(1,1,1,3,3,3-hexafluoro-2-hydroxypropan-2-yl)-2-propylbiphenyl-3-yloxy)pentyl)-5-methylimidazolidine-2,4-dione

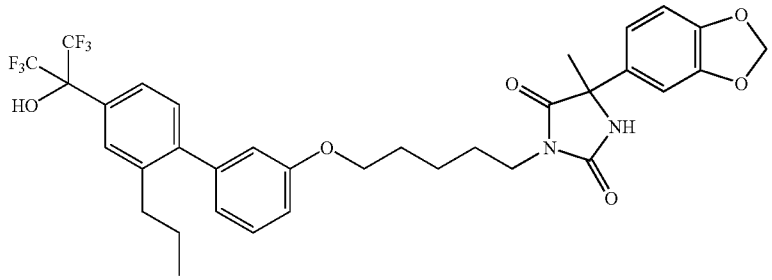

3'-(3-bromopentyloxy)-4-(1,1,1,3,3,3-hexafluoro-2-(methoxymethoxy)propan-2-yl)-2-propylbiphenyl was used for a similar operation as Example 1, and the title compound was obtained as a colorless oil.

$^1$H-NMR (CDCl$_3$) δ: 0.82 (3H, t, J=7.0 Hz), 1.43-1.54 (4H, m), 1.62-1.83 (4H, m), 1.78 (3H, s), 2.59 (2H, t, J=7.6 Hz), 3.53 (2H, t, J=7.3 Hz), 3.69 (1H, bs), 3.93 (2H, t, J=6.2 Hz), 5.80 (1H, brs), 5.93 (2H, s), 6.76-6.96 (6H, m), 7.16-7.32 (2H, m), 7.53 (1H, d, J=8.6 Hz), 7.60 (1H, brs).

Example 105

Preparation of 5-(benzo[d][1,3]dioxol-5-yl)-5-ethyl-3-(5-(4'-(1,1,1,3,3,3-hexafluoro-2-hydroxypropan-2-yl)-2'-propylbiphenyl-3-yloxy)pentyl)imidazolidine-2,4-dione

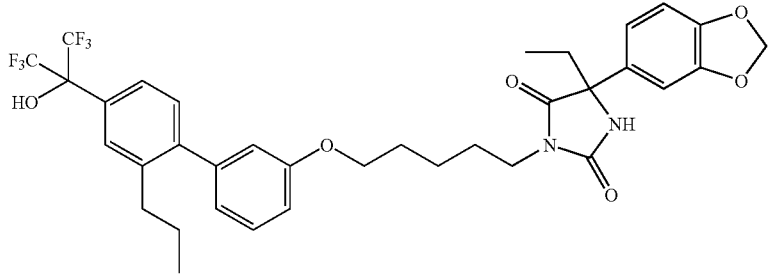

5-(Benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 104 b) for a similar reaction and treatment, and the title compound was obtained as a colorless oil.

$^1$H-NMR (CDCl$_3$) δ: 0.82 (3H, t, J=7.6 Hz), 0.88 (3H, t, J=7.0 Hz), 1.43-1.54 (4H, m), 1.62-1.82 (4H, m), 1.99-2.23 (2H, m), 2.59 (2H, t, J=7.6 Hz), 3.52 (2H, t, J=7.3 Hz), 3.67 (1H, brs), 3.92 (2H, t, J=6.2 Hz), 5.90 (1H, bs), 5.93-5.95 (2H, m), 6.76-7.02 (6H, m), 7.16-7.33 (2H, m), 7.53 (1H, d, J=8.6 Hz), 7.60 (1H, brs).

Example 106

Preparation of 5-(2,3-dihydrobenzo[b][1,4]dioxin-6-yl)-5-ethyl-3-(5-(4'-(1,1,1,3,3,3-hexafluoro-2-hydroxypropan-2-yl)-2'-propylbiphenyl-3-yloxy)pentyl)imidazolidine-2,4-dione

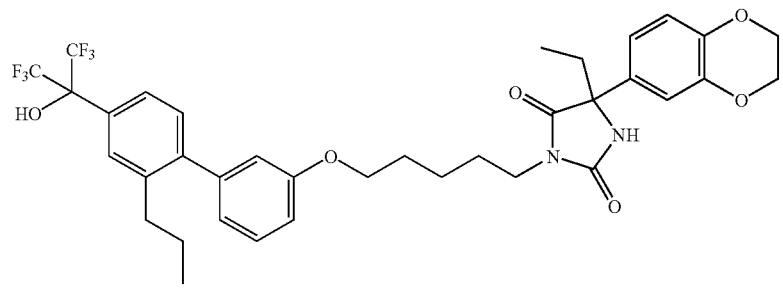

5-(2,3-Dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 104 b) for a similar reaction and treatment, and the title compound was obtained as a colorless oil.

¹H-NMR (CDCl₃) δ: 0.82 (3H, t, J=7.6 Hz), 0.88 (3H, t, J=7.3 Hz), 1.43-1.56 (4H, m), 1.62-1.84 (4H, m), 1.98-2.24 (2H, m), 2.59 (2H, t, J=7.8 Hz), 3.51 (2H, t, J=7.3 Hz), 3.85 (1H, brs), 3.92 (2H, t, J=6.2 Hz), 4.21 (4H, s), 6.01 (1H, brs), 6.79-7.02 (6H, m), 7.16-7.31 (2H, m), 7.53 (1H, d, J=8.4 Hz), 7.60 (1H, brs).

Example 107

Preparation of 3-(5-(4'-(1,1,1,3,3,3-hexafluoro-2-hydroxypropan-2-yl)-2'-propylbiphenyl-3-yloxy)pentyl)-5-(4-(1-methylethoxy)phenyl)-5-methylimidazolidine-2,4-dione

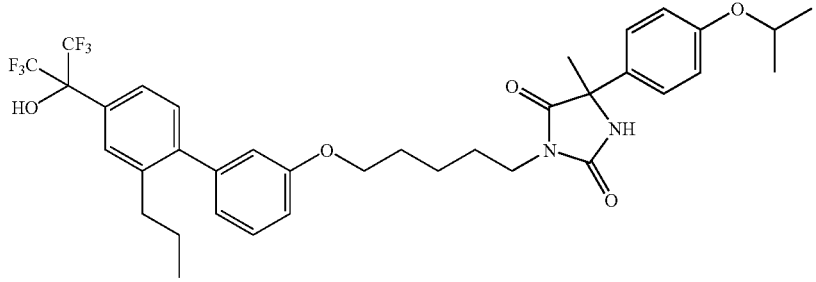

5-(4-(1-Methylethoxy)phenyl)-5-methylimidazolidine-2,4-dione was used in place of 5-(benzo[d][1,3]-dioxol-5-yl)-5-methylimidazolidine-2,4-dione in Example 104 b) for a similar reaction and treatment, and the title compound was obtained as a colorless oil.

¹H-NMR (CDCl₃) δ: 0.82 (3H, t, J=7.0 Hz), 1.31 (6H, d, J=5.9 Hz), 1.43-1.54 (4H, m), 1.59-1.83 (4H, m), 1.79 (3H, s), 2.59 (2H, t, J=7.6 Hz), 3.53 (2H, t, J=7.3 Hz), 3.70 (1H, brs), 3.93 (2H, t, J=6.5 Hz), 4.48-4.57 (1H, m), 5.73 (1H, brs), 6.79-6.88 (5H, m), 7.19-7.36 (4H, m), 7.51-7.60 (2H, m).

Example 108

Preparation of 5-(benzo[d][1,3]dioxol-5-yl)-3-(3-(4'-(1,1,1,3,3,3-hexafluoro-2-hydroxypropan-2-yl)-2'-propylbiphenyl-4-yloxy)propyl)-5-methylimidazolidine-2,4-dione a) Preparation of 4'-(1,1,1,3,3,3-hexafluoro-2-(methoxymethoxy)propan-2-yl)-2'-propylbiphenyl-4-ol

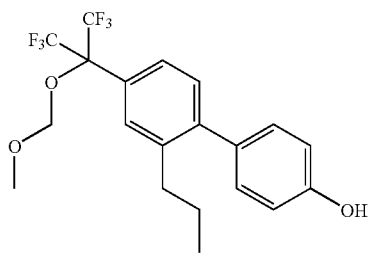

4-Hydroxyphenylboronic acid was used in place of 3-vinylphenylboronic acid for a similar reaction and treatment as Example 92 b), and the compound of interest was obtained as a colorless oil.

¹H-NMR (CDCl₃) δ: 0.82 (3H, t, J=7.3 Hz), 1.44-1.64 (2H, m), 2.60 (2H, t, J=7.6 Hz), 3.60 (3H, s), 4.89 (2H, s), 6.94-6.98 (3H, m), 7.20-7.26 (2H, m), 7.43 (1H, d, J=8.6 Hz), 7.49 (1H, s).

b) Preparation of 4'-(3-bromopropoxy)-4-(1,1,1,3,3,3-hexafluoro-2-(methoxymethoxy)propan-2-yl)-2-propylbiphenyl

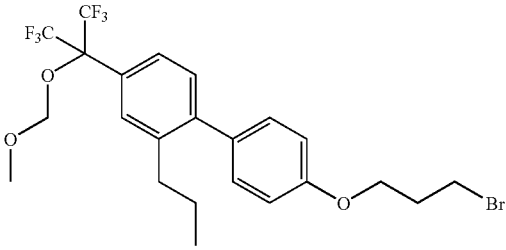

4'-(1,1,1,3,3,3-Hexafluoro-2-(methoxymethoxy)propan-2-yl)-2'-propylbiphenyl-4-ol was used for a similar operation as Example 96 b), and the title compound was obtained as a colorless oil.

¹H-NMR (CDCl₃) δ: 0.82 (3H, t, J=7.3 Hz), 1.44-1.64 (2H, m), 2.31-2.40 (2H, m), 2.60 (2H, t, J=7.6 Hz), 3.60 (3H, s), 3.64 (2H, t, J=6.5 Hz), 4.52 (2H, t, J=6.2 Hz), 4.89 (2H, s), 6.94-6.98 (3H, m), 7.20-7.26 (2H, m), 7.43 (1H, d, J=8.6 Hz), 7.49 (1H, s).

c) Preparation of 5-(benzo[d][1,3]dioxol-5-yl)-3-(3-(4'-(1,1,1,3,3,3-hexafluoro-2-hydroxypropan-2-yl)-2-propylbiphenyl-4-yloxy)propyl)-5-methylimidazolidine-2,4-dione

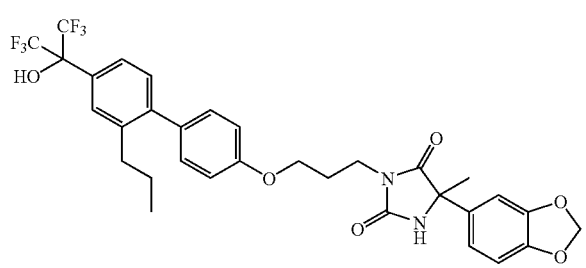

4'(3-Bromopropoxy)-4-(1,1,1,3,3,3-hexafluoro-2-(methoxymethoxy)propan-2-yl)-2-propylbiphenyl was used for a similar operation as Example 1, and the title compound was obtained as a colorless oil.

¹H-NMR (CDCl₃) δ: 0.79-0.96 (3H, m), 1.44-1.64 (2H, m), 1.78-1.79 (3H, m), 2.12-2.17 (2H, m), 2.55-2.64 (2H, m), 3.65 (1H, brs), 3.70-3.78 (2H, m), 3.94-4.04 (2H, m), 5.93 (1H, brs), 5.94-5.96 (2H, m), 6.74-7.00 (5H, m), 7.16-7.26 (3H, m), 7.42-7.59 (2H, m).

Example 109

Preparation of 5-(benzo[d][1,3]dioxol-5-yl)-5-ethyl-3-(3-(4'-(1,1,1,3,3,3-hexafluoro-2-hydroxypropan-2-yl)-2'-propylbiphenyl-4-yloxy)propyl)imidazolidine-2,4-dione

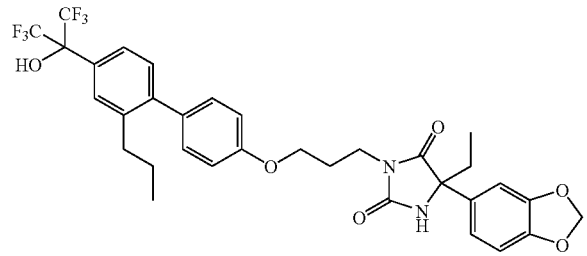

5-(Benzo[d][1,3]dioxol-5-yl)-5-ethylimidazolidine-2,4-dione was used in place of 5-(benzo[d][1,3]dioxol-5-yl)-5-methylimidazolidine-2,4-dione in Example 108 c) for a similar reaction and treatment, and the title compound was obtained as a colorless oil.

$^1$H-NMR (CDCl$_3$) δ: 0.79-0.96 (6H, m), 1.44-1.61 (2H, m), 2.06-2.18 (4H, m), 2.55-2.64 (2H, m), 3.69-3.76 (2H, m), 3.93-4.02 (2H, m), 5.82-5.84 (1H, m), 5.94-5.96 (2H, m), 6.75-7.04 (5H, m), 7.16-7.30 (3H, m), 7.42-7.58 (2H, m).

Example 110

Preparation of 5-(2,3-dihydrobenzo[b][1,4]dioxin-6-yl)-5-ethyl-3-(3-(4'-(1,1,1,3,3,3-hexafluoro-2-hydroxypropan-2-yl)-2'-propylbiphenyl-4-yloxy)propyl)imidazolidine-2,4-dione

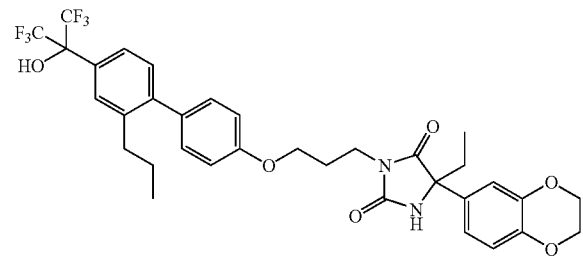

5-(2,3-Dihydrobenzo[b][1,4]dioxin-6-yl)-5-ethylimidazolidine-2,4-dione was used in place of 5-(benzo[d][1,3]dioxol-5-yl)-5-methylimidazolidine-2,4-dione in Example 108 c) for a similar reaction and treatment, and the title compound was obtained as a colorless oil.

$^1$H-NMR (CDCl$_3$) δ: 0.79-0.93 (6H, m), 1.44-1.64 (2H, m), 2.00-2.22 (4H, m), 2.56-2.63 (2H, m), 3.58-3.65 (1H, m), 3.69-3.76 (2H, m), 3.92-4.02 (2H, m), 4.22-4.23 (4H, m), 5.89-5.94 (1H, m), 6.81-7.03 (5H, m), 7.15-7.27 (3H, m), 7.42-7.58 (2H, m).

Example 111

Preparation of 3-(3-(4'-(1,1,1,3,3,3-hexafluoro-2-hydroxypropan-2-yl)-2'-propylbiphenyl-4-yloxy)propyl-5-(4-(1-methylethoxy)phenyl)-5-methylimidazolidine-2,4-dione

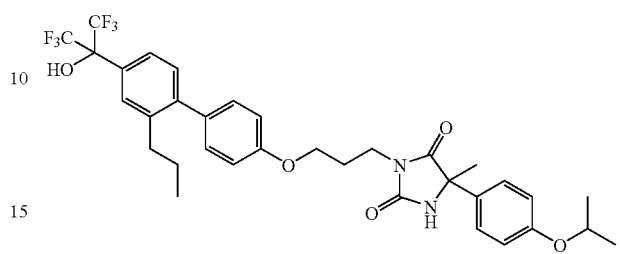

5-(4-(1-Methylethoxy)phenyl)-5-methylimidazolidine-2,4-dione was used in place of 5-(benzo[d][1,3]dioxol-5-yl)-5-methylimidazolidine-2,4-dione in Example 108 c) for a similar reaction and treatment, and the title compound was obtained as a colorless oil.

$^1$H-NMR (CDCl$_3$) δ: 0.79-0.95 (3H, m), 1.29-1.33 (6H, m), 1.44-1.64 (2H, m), 1.78-1.80 (3H, m), 2.12-2.17 (2H, m), 2.56-2.61 (2H, m), 3.64 (1H, brs), 3.73-3.78 (2H, m), 3.94-4.04 (2H, m), 4.49-4.54 (1H, m), 5.77 (1H, brs), 6.82-6.88 (3H, m), 7.16-7.58 (8H, m).

Example 112

Preparation of 5-(4-(1-(1-methylethyl))phenyl)-3-(3-(4-(1,1,1,3,3,3-hexafluoro-2-hydroxypropan-2-yl)-2-propylphenoxy)benzyl)-5-methylimidazolidine-2,4-dione

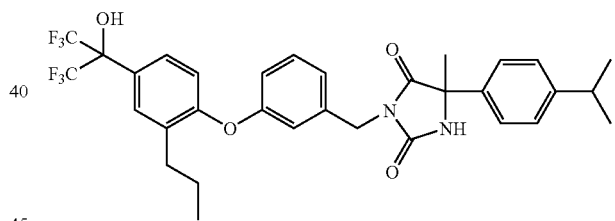

112-a) Preparation of 5-(4-(1-(1-methylethyl))phenyl)-5-methylimidazolidine-2,4-dione 1(4-(1-(1-Methylethyl))phenyl)-ethanone was used for a similar reaction and treatment as Example 1-a), and 5-(4-(1-(1-methylethyl))phenyl)-5-methylimidazolidine-2,4-dione was obtained as a white crystal.

$^1$H-NMR (270 MHz, DMSO) δ: 1.18 (6H, d, J=7.0 Hz), 1.63 (3H, s), 2.87 (1H, sept, J=7.0 Hz), 7.25 (2H, d, J=8.4 Hz), 7.37 (2H, d, J=8.4 Hz), 8.54 (1H, s), 10.73 (1H, s).

5-(4-(1-(1-Methylethyl))phenyl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (270 MHz, CDCl$_3$) δ: 0.92 (3H, t, J=7.4 Hz), 1.22 (6H, d, J=7.0 Hz), 1.62 (2H, qt, J=7.4, 7.6 Hz), 1.78 (3H, s), 2.64 (2H, t, J=7.6 Hz), 2.88 (1H, sept, J=7.0 Hz), 3.82 (1H, brs), 4.63 (2H, s), 5.82 (1H, br-s), 6.78 (1H, d, J=8.9 Hz), 6.86

(1H, dd, J=7.6, 1.9 Hz), 6.94 (1H, s), 7.07 (1H, d, J=7.6 Hz), 7.16-7.30 (3H, m), 7.34 (2H, d, J=8.4 Hz), 7.42 (1H, d, I=8.4 Hz), 7.56 (1H, s).

Example 113

Preparation of 5-(4-(1-(1,1-dimethylethyl))phenyl)-3-(3-(4-(1,1,1,3,3,3-hexafluoro-2-hydroxypropan-2-yl)-2-propylphenoxy)benzyl)-5-methylimidazolidine-2,4-dione

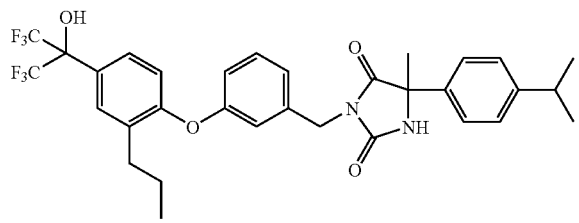

113-a) Preparation of 5-(4-(1-(1,1-dimethylethyl))phenyl)-5-methylimidazolidine-2,4-dione 1(4-(1-(1,1-Dimethylethyl))phenyl)-ethanone was used for a similar reaction and treatment as Example 1-a), and 5-(4-(1-(1,1-dimethylethyl))phenyl)-5-methylimidazolidine-2,4-dione was obtained as a white crystal.

$^1$H-NMR (270 MHz, DMSO) δ: 1.26 (9H, s), 1.63 (3H, s), 7.35-7.43 (4H, m), 8.56 (1H, s), 10.73 (1H, s).

5-(4-(1-(1,1-Dimethylethyl))phenyl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (270 MHz, CDCl$_3$) δ: 0.92 (3H, t, J=7.4 Hz), 1.29 (9H, s), 1.62 (2H, qt, J=7.4, 7.6 Hz), 1.78 (3H, s), 2.64 (2H, t, J=7.6 Hz), 3.89 (1H, br-s), 4.63 (2H, s), 5.91 (1H, br-s), 6.79 (1H, d, J=8.7 Hz), 6.86 (1H, dd, J=7.6, 1.9 Hz), 6.94 (1H, t, J=1.9 Hz), 7.07 (1H, d, J=7.6 Hz), 7.17 (1H, d, J=7.6 Hz), 7.23-7.30 (2H, m), 7.36 (2H, d, J=1.4 Hz), 7.42 (1H, d, J=8.7 Hz), 7.56 (1H, s).

Example 114

Preparation of 5-(2-naphthyl)-3-(3-(4-(1,1,1,3,3,3-hexafluoro-2-hydroxypropan-2-yl)-2-propylphenoxy)benzyl)-5-methylimidazolidine-2,4-dione

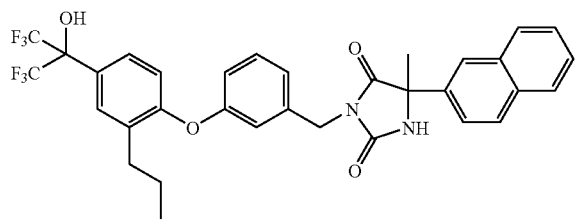

114-a) Preparation of 5-(2-naphthyl)-5-methylimidazolidine-2,4-dione

1(2-Naphthyl)-ethanone was used for a similar reaction and treatment as Example 1-a), and 5-(2-naphthyl)-5-methylimidazolidine-2,4-dione was obtained as a white crystal.

$^1$H-NMR (270 MHz, DMSO) δ: 1.77 (3H, s), 7.51-7.62 (3H, m), 7.62-8.00 (4H, m), 8.73 (1H, s), 10.86 (1H, s).

5-(2-Naphthyl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (270 MHz, CDCl$_3$) δ: 0.90 (3H, t, J=7.4 Hz), 1.59 (2H, qt, J=7.0, 7.6 Hz), 1.89 (3H, s), 2.61 (2H, t, J=7.6 Hz), 3.85 (1H, br-s), 4.66 (2H, s), 6.08 (1H, br s), 6.76 (1H, d, J=8.9 Hz), 6.85 (1H, dd, J=8.1, 1.9 Hz), 6.96 (1H, t, J=1.9 Hz), 7.07 (1H, d, J=8.1 Hz), 7.17 (1H, d, J=7.8 Hz), 7.22-7.28 (2H, m), 7.38 (1H, d, J=8.6 Hz), 7.47-7.52 (2H, m), 7.55 (1H, d, J=1.9 Hz), 7.79-7.84 (2H, m), 7.89 (1H, d, J=1.6 Hz).

Example 115

Preparation of 5-[4-(1-methylethoxy)-3-fluorophenyl]-3-(3-(4-(1,1,1,3,3,3-hexafluoro-2-hydroxypropan-2-yl)-2-propylphenoxy)benzyl)-5-methylimidazolidine-2,4-dione

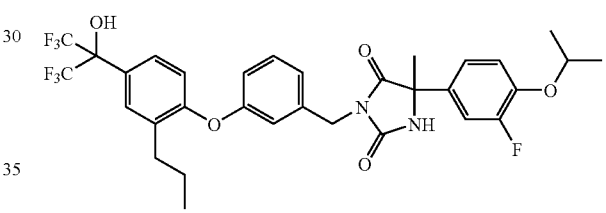

115-a) Preparation of 5-(3-fluoro-4-(1-methylethoxy)phenyl)-5-methylimidazolidine-2,4-dione 115-a-1) Preparation of isopropyl 3-fluoro-4-(1-methylethoxy)benzoate 3-Fluoro-4-hydroxybenzoic acid (500 mg, 3.20 mmol) was dissolved in N,N-dimethylformamide (16 mL). The resultant mixture was sequentially added with sodium hydride (purity 50%) (384 mg, 8.01 mmol) and 1-methylethyl iodide (959 μL, 9.61 mmol) under ice-cold conditions, and stirred at 60° C. for 3 hours and then at room temperature for 3 days. The reaction solution was added with a saturated aqueous solution of ammonium chloride and extracted with ethyl acetate. The organic layer was washed with brine, dried using anhydrous sodium sulfate, and concentrated in vacuo. The obtained residue was purified using column chromatography (hexane/ethyl acetate) and isopropyl 3-fluoro-4-(1-methylethoxy)benzoate (618 mg, yield 80%) was obtained as a colorless oil.

$^1$H-NMR (CDCl$_3$) δ: 1.35 (6H, d, J=6.4 Hz), 1.39 (6H, d, J=6.0 Hz), 4.61-4.70 (1H, m), 5.17-5.26 (1H, m), 6.97 (1H, dd, J=8.3, 8.6 Hz), 7.73 (1H, dd, J=2.2, 11.5 Hz), 7.78 (1H, ddd, J=1.2, 2.2, 8.6 Hz).

115-a-2) Preparation of 3-fluoro-4-(1-methylethoxy)benzoic acid

Isopropyl 3-fluoro-4-(1-methylethoxy)benzoate (618 mg, 2.57 mmol) was dissolved in methanol (13 mL). The resultant mixture was added with 1N aqueous solution of sodium hydroxide (13 mL) under ice-cold conditions and stirred at 60° C. for 1 hour. The reaction solution was added with a saturated solution of ammonium chloride and extracted with ethyl acetate. The organic layer was washed with brine, dried using anhydrous sodium sulfate, and concentrated in vacuo. 3-Fluoro-4-(1-methylethoxy)benzoic acid (505 mg, yield 99%) was obtained as a white crystal.

$^1$H-NMR (CDCl$_3$) δ: 1.42 (6H, d, J=6.1 Hz), 4.65-4.74 (1H, m), 7.00 (1H, dd, J=8.3, 8.6 Hz), 7.80 (1H, dd, J=2.0, 11.5 Hz), 7.85 (1H, ddd, J=1.2, 2.0, 8.6 Hz).

115-a-3) Preparation of 3-fluoro-4-(1-methylethoxy)-N-methoxy-N-methylbenzamide

3-Fluoro-4-(1-methylethoxy)benzoic acid (100 mg, 0.505 mmol) was dissolved in dichloromethane (2.5 mL). The resultant mixture was added with methoxymethylamine hydrochloride (99 mg, 1.01 mmol), WSC-HCl (106 mg, 0.555 mmol), triethylamine (422 μL, 3.03 mmol), and HOBt-H2O (34 mg, 0.252 mmol) sequentially, and stirred at room temperature overnight. The reaction solution was added with water and extracted with ethyl acetate. The organic layer was washed with 5% aqueous solution of hydrochloric acid, a saturated aqueous solution of sodium hydrogen carbonate and brine, dried using anhydrous sodium sulfate, and concentrated in vacuo. 3-Fluoro-4-(1-methylethoxy)-N-methoxy-N-methylbenzamide (117 mg, yield 96%) was obtained as a colorless oil.

$^1$H-NMR (CDCl$_3$) δ: 1.39 (6H, d, J=6.1 Hz), 3.36 (3H, s), 3.57 (3H, s), 4.58-4.67 (1H, m), 6.97 (1H, dd, J=8.3, 8.8 Hz), 7.52 (1H, ddd, J=1.0, 2.0, 8.3 Hz), 7.55 (1H, dd, J=2.0, 12.2 Hz).

115-a-4) Preparation of 1-(3-fluoro-4-(1-methylethoxy)phenyl)ethanone

To a solution of 3-fluoro-4-(1-methylethoxy)-N-methoxy-N-methylbenzamide (117 mg, 0.485 mmol) in tetrahydrofuran (2.4 mL), methylmagnesium bromide (750 μL, 0.728 mmol) was added under ice-cold conditions, and the resultant mixture was stirred for 1 hour under ice-cold conditions. The reaction solution was added with water and 5% aqueous solution of hydrochloric acid under ice-cold conditions, and extracted with ethyl acetate. Subsequently, the organic layer was washed with brine, dried using anhydrous sodium sulfate, and concentrated in vacuo. 1-(3-Fluoro-4-(1-methylethoxy)phenyl)ethanone (94 mg, yield 99%) was obtained as a yellow oil.

$^1$H-NMR (CDCl$_3$) δ: 1.41 (6H, d, J=6.1 Hz), 2.55 (3H, s), 4.64-4.73 (1H, m), 6.99 (1H, dd, J=8.0, 8.8 Hz), 7.69 (1H, dd, J=2.2, 12.0 Hz), 7.71 (1H, ddd, J=1.0, 2.2, 8.0 Hz).

115-a-5) Preparation of 5-[4-(1-methylethoxy)-3-fluorophenyl]-5-methylimidazolidine-2,4-dione 1-(3-Fluoro-4-(1-methylethoxy)phenyl)ethanone was used for a similar reaction and treatment as Example 1-a), and 5-[4-(1-methylethoxy)-3-fluorophenyl]-5-methylimidazolidine-2,4-dione was obtained as a white crystal.

$^1$H-NMR (CDCl$_3$) δ: 1.32 (6H, d, J=6.1 Hz), 1.72 (3H, s), 4.55-4.64 (1H, m), 7.09 (1H, dd, J=8.6, 9.0 Hz), 7.22 (1H, ddd, J=1.0, 2.2, 8.6 Hz), 7.24 (1H, dd, J=2.2, 10.7 Hz).

5-[4-(1-Methylethoxy)-3-fluorophenyl]-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (270 MHz, CDCl$_3$) δ: 0.93 (3H; t, J=7.4 Hz), 1.34 (6H, d, J=6.2 Hz), 1.62 (2H, qt, J=7.4, 7.6 Hz), 1.76 (3H, s), 2.64 (2H, t, J=7.6 Hz), 3.85 (1H, br-s), 4.52 (1H, sept, 6.2 Hz), 4.64 (2H, s), 5.87 (1H, br-s), 6.77 (1H, d, J=8.5 Hz), 6.86 (1H, dd, J=7.8, 1.6 Hz), 6.93 (1H, t, J=8.5 Hz), 7.05-7.12 (2H, m), 7.15 (1H, d, J=2.6 Hz), 7.20 (1H, d, J=2.6 Hz), 7.23-7.30 (1H, m), 7.41 (1H, d, J=8.4 Hz), 7.55 (1H, s).

Example 116

Preparation of 545-(1-methylethoxy)pyridin-2-yl-3-(3-(4-(1,1,1,3,3,3-hexafluoro-2-hydroxypropan-2-yl)-2-propylphenoxy)benzyl)-5-methylimidazolidine-2,4-dione

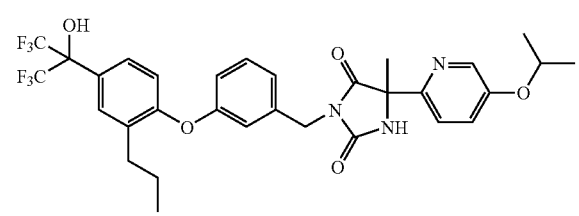

116-a) Preparation of 5-[5-(1-methylethoxy)pyridin-2-yl]-5-methylimidazolidine-2,4-dione 116-a-1) Preparation of 5-(1-methylethoxy)-2-methylpyridine 5-Hydroxy-2-methylpyridine (11.0 g, 100 mmol) was dissolved in N,N'-dimethylformamide (100 mL). The resultant mixture was added with sodium hydride (7.2 g, 150 mmol) and 1-methylethane iodide (12 mL, 121 mmol) under ice-cold conditions, and stirred at room temperature overnight. Subsequently, 1-methylethane iodide (4 mL) was added and the resultant mixture was stirred at 60° C. for 4 hours. The reaction solution was added with water and extracted with diethyl ether. The organic layer was washed with brine, dried using sodium sulfate, and concentrated in vacuo. The obtained residue was purified using silica-gel column chromatography (hexane/ethyl acetate), and 5-(1-methylethoxy)-2-methylpyridine (12.7 g, yield 84%) was obtained as a yellow oil.

$^1$H-NMR (CDCl$_3$) δ: 1.34 (6H, d, J=6.0 Hz), 2.48 (3H, s), 4.52 (1H, sept, J=6.0 Hz), 7.03-7.10 (2H, m), 8.17 (1H, d, J=2.4 Hz).

116-a-2) Preparation of 5-(1-methylethoxy)-2-methylpyridine 1-oxide 5-(1-Methylethoxy)-2-methylpyridine (227 mg, 0.661 mmol) was dissolved in dichloromethane (7.5 mL). The resultant mixture was added with 3-chloroperoxybenzoic acid (408 mg, 0.733 mmol) under ice-cold conditions, and stirred at 0° C. for 45 minutes. The reaction solution was added with ethyl acetate, a saturated aqueous solution of sodium metabisulfite, and an aqueous solution of sodium hydrogen carbonate, and then extracted with ethyl acetate. The organic layer was washed with brine, dried over sodium sulfate and concentrated in vacuo. The obtained residue was purified using silica-gel column chromatography (ethyl acetate) and 5-(1-methylethoxy)-2-methylpyridine 1-oxide (240 mg, yield 6%) was obtained as a colorless oil.

$^1$H-NMR (CDCl$_3$) δ: 1.35 (6H, d, J=6.2 Hz), 2.46 (3H, s), 4.47 (1H, sept, J=6.2 Hz), 6.82 (1H, dd, J=2.2, 8.9 Hz), 7.11 (1H, (1, J=8.9 Hz), 8.05 (1H, d, J=2.2 Hz).

116-a-3) Preparation of [5-(1-methylethoxy)pyridin-2-yl]methyl acetate 5-(1-Methylethoxy)-2-methylpyridine 1-oxide (234 mg, 1.40 mmol) was dissolved in acetic anhydride (3.0 mL) and the resultant mixture was stirred at 140° C. for 1 hour. The reaction solution was added with methanol at room temperature, stirred, then concentrated in vacuo, and extracted with ethyl acetate. The organic layer was washed with an aqueous solution of sodium hydrogen carbonate and brine, dried over sodium sulfate, and concentrated in vacuo. The obtained residue was purified using silica-gel column chromatography (hexane/ethyl acetate), and [5-(1-methylethoxy)pyridin-2-yl] methyl acetate (209 mg, yield 71%) was obtained as a yellow oil.

$^1$H-NMR (CDCl$_3$) δ: 1.36 (61-1, d, J=6.2 Hz), 2.13 (3H, s), 4.58 (1H, sept, J=6.2 Hz), 5.13 (2H, s), 7.17 (1H, dd, J=2.4, 8.1 Hz), 7.26-7.30 (1H, m), 8.27 (1H, d, J=2.4 Hz).

116-a-4) Preparation of [5-(1-methylethoxy)pyridin-2-yl]methanol

[5-(1-Methylethoxy)pyridin-2-yl]methyl acetate (209 mg) was dissolved in methanol (2.0 mL), added with potassium carbonate (276 mg, 2.0 mmol), and the resultant mixture was stirred at room temperature for 1 hour. The reaction solution was concentrated in vacuo, added with water, and extracted with ethyl acetate. The organic layer was washed with brine, dried over sodium sulfate, and concentrated in vacuo. The obtained residue was purified using silica-gel column chromatography (hexane/ethyl acetate) and [5-(1-methylethoxy) pyridin-2-yl]methanol (137 mg, yield 83%) was obtained as a yellow oil.

$^1$H-NMR (CDCl$_3$) δ: 1.36 (6H, d, J=6.0 Hz), 4.57 (1H, sept, J=6.0 Hz), 4.69 (2H, s), 7.15-7.22 (2H, m), 8.23 (1H, s).

116-a-5) Preparation of 5-(1-methylethoxy)picolinaldehyde

[5-(1-Methylethoxy)pyridin-2-yl]methanol (30 mg, 0.198 mmol) was dissolved in acetone (2.0 mL). The resultant mixture was added with 2,2,6,6-tetramethylpiperidine 1-oxyl (3.1 mg, 0.020 mmol) and trichloroisocyanuric acid (50 mg, 0.218 mmol) under ice-cold conditions, and stirred at 0° C. for 5 minutes. The reaction solution was concentrated in vacuo, added with an aqueous solution of sodium hydrogen carbonate, and extracted with ethyl acetate. The organic layer was washed with brine, dried over sodium sulfate, and concentrated in vacuo. The obtained residue was purified using silica-gel column chromatography (hexane/ethyl acetate), and 5-(1-methylethoxy)picolinaldehyde (25 mg, yield 85%) was obtained as a yellow oil.

$^1$H-NMR (CDCl$_3$) δ: 1.41 (6H, d, J=6.4 Hz), 4.71 (1H, sept, J=6.4 Hz), 7.25-7.27 (1H, m), 7.95 (1H, d, J=8.4 Hz), 8.39 (1H, d, J=2.8 Hz), 9.98 (1H, s).

116-a-6) Preparation of 1-[5-(1-methylethoxy)pyridin-2-yl]ethanol 5-(1-Methylethoxy)picolinaldehyde (24 mg, 0.145 mmol) was dissolved in tetrahydrofuran (1.5 mL). The resultant mixture was added with methylmagnesium bromide (230 μL, 0.218 mmol) under ice-cold conditions, stirred at 0° C. for 30 minutes, and further stirred at room temperature for 30 minutes. The reaction solution was added with 1N aqueous solution of hydrochloric acid, an aqueous solution of sodium hydrogen carbonate, and extracted with ethyl acetate. The organic layer was washed with brine, dried over sodium sulfate, and concentrated in vacuo. The obtained residue was purified using silica-gel column chromatography (hexane/ethyl acetate) and 1-[5-(1-methylethoxy)pyridin-2-yl]ethanol (27 mg, yield 98%) was obtained as a brown oil.

$^1$H-NMR (CDCl$_3$) δ: 1.36 (6H, d, J=6.0 Hz), 1.48 (3H, d, J=6.4 Hz), 4.57 (1H, sept, J=6.0 Hz), 4.85 (1H, q, 6.4 Hz), 7.17-7.21 (2H, m), 8.19-8.20 (1H, m).

116-a-7) Preparation of 1-[5-(1-methylethoxy)pyridin-2-yl]ethanone

1-[5-(1-Methylethoxy)pyridin-2-yl]ethanol (22 mg, 0.119 mmol) was dissolved in acetone (1.2 mL). The resultant mixture was added with 2,2,6,6-tetramethylpiperidine 1-oxyl (2.0 mg, 0.012 mmol) and trichloroisocyanuric acid (30 mg, 0.131 mmol) under ice-cold conditions, and stirred at 0° C. for 10 minutes. The reaction solution was concentrated in vacuo, added with an aqueous solution of sodium hydrogen carbonate, and extracted with ethyl acetate. The organic layer was washed with brine, dried over sodium sulfate, and concentrated in vacuo. The obtained residue was purified using silica-gel column chromatography (hexane/ethyl acetate) and 1-[5-(1-methylethoxy)pyridin-2-yl]ethanone (20 mg, yield 94%) was obtained as a yellow oil.

$^1$H-NMR (CDCl$_3$) δ: 1.40 (6H, d, J=6.2 Hz), 2.68 (3H, s), 4.68 (1H, sept, J=6.2 Hz), 7.22 (1H, dd, J=2.7, 8.6 Hz), 8.03 (1H, d, J=8.6 Hz), 8.28 (1H, d, J=2.7 Hz).

116-a-8) Preparation of 5-[5-(1-methylethoxy)pyridin-2-yl]-5-methylimidazolidine-2,4-dione 1-[5-(1-Methylethoxy)pyridin-2-yl]ethanone was used for a similar reaction and treatment as Example 1-a), and 5-[5-(1-methylethoxy)pyridin-2-yl]-5-methylimidazolidine-2,4-dione was obtained as a white crystal.

$^1$H-NMR (CDCl$_3$) δ: 1.33 (6H, d, J=6.2 Hz), 1.79 (3H, s), 4.67 (1H, sept, J=6.2 Hz), 7.36 (1H, dd, J=2.7, 8.9 Hz), 7.46 (1H, d, J=8.9 Hz), 8.18 (1H, d, J=2.7 Hz).

5-[5-(1-Methylethoxy)pyridin-2-yl]-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (270 MHz, CD$_3$OD) δ: 0.91 (3H, t, J=7.3 Hz), 1.36 (6H, d, J=5.8 Hz), 1.63 (2H, qt, J=7.3, 7.6 Hz), 1.83 (3H, s), 2.64 (2H, t, J=7.6 Hz), 4.52 (2H, s), 4.77 (1H, sept, J=5.8 Hz), 6.82-6.89 (2H, m), 6.95 (1H, s), 7.08 (1H, d, J=8.0 Hz), 7.31 (1H, t, J=8.0 Hz), 7.50 (1H, d, J=8.0 Hz), 7.61 (1H, s), 7.74-7.80 (2H, m), 8.26 (1H, s).

Example 117

Preparation of 5-(2-(benzyloxy)pyridin-5-yl)-3-(3-(4-(1,1,1,3,3,3-hexafluoro-2-hydroxypropan-2-yl)-2-propylphenoxy)benzyl)-5-methylimidazolidine-2,4-dione

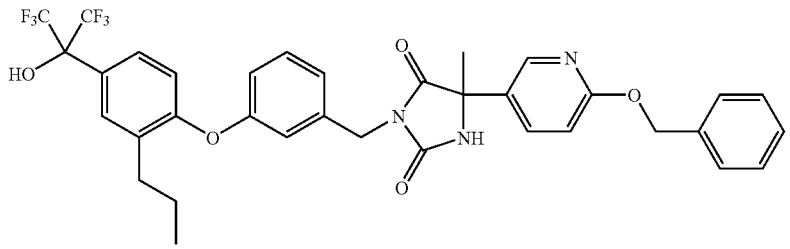

117-a) Preparation of 5-(2-(benzyloxy)pyridin-5-yl)-5-methylimidazolidine-2,4-dione

117-a-1) Preparation of 5-bromo-2-(benzyloxy)pyridine

2-Hydroxy-5-bromopyridine (1.00 g, 5.75 mmol) was dissolved in N,N'-dimethylformamide (23 mL), and the resultant mixture was added with sodium hydride (purity 50%) (253 mg, 6.32 mmol) under an argon atmosphere under ice-cold conditions. Five minutes later, the resultant mixture was added with benzyl bromide (6.82 mL, 6.90 mmol) at the same temperature, and stirred at room temperature for 1 hour. Under ice-cold conditions, the reaction solution was added with water and extracted with ethyl acetate. The organic layer was washed with brine, dried over anhydrous sodium sulfate, then concentrated in vacuo, and purified using silica-gel column chromatography (n-hexane/ethyl acetate=1/1). 5-Bromo-2-(benzyloxy)pyridine (1.51 g, yield 99%) was obtained as a pale yellow solid.

$^1$H-NMR (CDCl$_3$) δ: 5.10 (2H, s), 6.54 (1H, d, J=9.5 Hz), 7.28-7.39 (7H, m).

117-a-2) Preparation of 1-(2-(benzyloxy)pyridin-5-yl)ethanone

Under an argon atmosphere, 5-bromo-2-(benzyloxy)pyridine (100 mg, 0.38 mmol) and tetrakis triphenylphosphine palladium (46 mg, 0.04 mmol) were dissolved in toluene (1.5 mL). The resultant mixture was added with 1-ethoxyethenyl tri-n-butyltin (140 mL, 0.42 mmol) and stirred at 100° C. overnight. The reaction solution was cooled down to room temperature, added with 3N hydrochloric acid, and added with saturated sodium bicarbonate water to adjust to pH8. The reaction solution was filtered using celite, added with ethyl acetate, and extracted. The organic layer was washed with brine, dried over anhydrous sodium sulfate, concentrated in vacuo, and purified using preparative thin-layer chromatography (n-hexane/ethyl acetate=1/1).

1-(2-(Benzyloxy)pyridin-5-yl)ethanone (51 mg, yield 59%) was obtained as a pale yellow oil.

$^1$H-NMR (CDCl$_3$) δ: 2.39 (3H, s), 5.19 (2H, s), 6.61 (1H, d, J=9.7 Hz), 7.30-7.39 (5H, m), 7.86 (1H, dd, J=2.7, 9.7 Hz), 8.09 (1H, d, J=2.7 Hz).

117-a-3) Preparation of 5-(2-(benzyloxy)pyridin-5-yl)-5-methylimidazolidine-2,4-dione 1-(2-(Benzyloxy)pyridin-5-yl)ethanone was used for a similar reaction and treatment as Example 1-a), and 5-(2-(benzyloxy)pyridin-5-yl)-5-methylimidazolidine-2,4-dione was obtained as a white crystal.

$^1$H-NMR (CD$_3$OD) δ: 1.67 (3H, s), 5.19 (1H, d, J=14.6 Hz), 5.23 (1H, d, J=14.6 Hz), 6.61 (1H, d, J=9.5 Hz), 7.29-7.34 (5H, m), 7.67 (1H, dd, J=2.7, 9.5 Hz), 7.78 (1H, d, J=2.7 Hz).

5-(2-(Benzyloxy)pyridin-5-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (400 MHz, CD$_3$OD) δ: 0.90 (3H, t, J=7.5 Hz), 1.58-1.62 (2H, m), 1.64 (3H, s), 2.62 (2H, t, J=7.5 Hz), 4.60 (2H, s), 5.17 (1H, d, J=14.4 Hz), 5.22 (1H, d, J=14.4 Hz), 6.59 (1H, d, J=9.0 Hz), 6.82 (1H, d, J=8.8 Hz), 6.84-6.88 (1H, m), 7.02 (1H, d, J=8.0 Hz), 7.10-7.31 (7H, m), 7.49 (1H, d, J=7.7 Hz), 7.61 (1H, s), 7.62 (1H, d, J=9.5 Hz), 7.79 (1H, s).

Example 118

Preparation of 5-(2-difluoromethoxypyridin-5-yl)-3-(3-(4-(1,1,1,3,3,3-hexafluoro-2-hydroxypropan-2-yl)-2-propylphenoxy)benzyl)-5-methylimidazolidine-2,4-dione

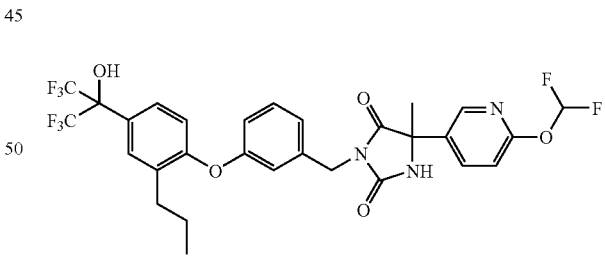

118-a) Preparation of 5-(2-difluoromethoxypyridin-5-yl)-5-methylimidazolidine-2,4-dione

118-a-1) Preparation of N-methoxy-N-methyl-2-hydroxynicotinamide

2-Hydroxynicotinic acid (2.00 g, 14.4 mmol) and methoxymethylamine (2.80 g, 28.8 mmol) were dissolved in methylene chloride (70 mL). The resultant mixture was added with dicyclohexylcarbodiimide (5.90 g, 28.8 mmol), triethylamine (4.00 mL), and 4-N,N-dimethylaminopyridine (176 mg, 1.44 mmol) at 0° C. The resultant mixture was stirred at room temperature overnight. Then the reaction solution was added with a small amount of water and concentrated in vacuo. Ethyl acetate was added and the generated crystal was filtered. Ethyl acetate was further added and the generated crystal was filtered in the same manner. The obtained residue was purified using silica-gel column chromatography (n-hexane/ethyl acetate=1/1) and N-methoxy-N-methyl-2-hydroxynicotinamide (2.18 g, yield 84%) was obtained as a colorless solid.

$^1$H-NMR (CDCl$_3$) δ: 3.35 (3H, s), 3.63 (3H, s), 6.58 (1H, d, J=9.4 Hz), 8.00 (1H, dd, J=2.4, 9.4 Hz), 8.15 (1H, d, J=2.4 Hz).

118-a-2) Preparation of N-methoxy-N-methyl-2-difluoromethoxynicotinamide

N-methoxy-N-methyl-2-hydroxynicotinamide (500 mg, 2.76 mmol), sodium chlorodifluoroacetate (505 mg, 3.31 mmol), and sodium hydroxide (132 mg, 3.31 mmol) were added to N,N-dimethylformamide (1.4 mL). The resultant mixture was stirred at 125° C. overnight under an argon atmosphere. The reaction solution was cooled down to room temperature, added with 1N hydrochloric acid and water, and extracted with ethyl acetate. The organic layer was washed with brine, dried over anhydrous sodium sulfate, concentrated in vacuo, and purified using preparative thin-layer chromatography (chloroform/methanol=9/1). N-methoxy-N-methyl-2-difluoromethoxynicotinamide (341 mg, yield 53%) was obtained as a yellow oil.

$^1$H-NMR (CDCl$_3$) δ: 3.39 (3H, s), 3.57 (3H, s), 6.93 (1H, dd, J=8.6 Hz), 7.51 (1H, t, J=72.5 Hz), 8.14 (1H, dd, J=2.4, 8.6 Hz), 8.63 (1H, d, J=2.4 Hz).

118-a-3) Preparation of 1-(2-(difluoromethoxy)pyridin-5-yl)ethanone

N-methoxy-N-methyl-2-difluoromethoxynicotinamide (336 mg, 1.45 mmol) was dissolved in tetrahydrofuran (7.3 mL). 0.93 M methylmagnesium bromide (2.4 mL, 2.18 mmol) was added dripwise at 0° C. under an argon atmosphere. The resultant mixture was stirred for 10 minutes and added with 1N hydrochloric acid at the same temperature. Subsequently, the reaction solution was added with a saturated aqueous solution of sodium hydrogen carbonate, and extracted with ethyl acetate. The organic layer was washed with brine, dried over anhydrous sodium sulfate, concentrated in vacuo, and purified using silica-gel column chromatography (n-hexane/ethyl acetate=4/1). 1-(2-(Difluoromethoxy)pyridin-5-yl)ethanone (264 mg, yield 98%) was obtained as a yellow oil.

$^1$H-NMR (CDCl$_3$) δ: 2.61 (3H, s), 6.98 (1H, d, J=8.5 Hz), 7.54 (1H, t, J=72.2 Hz), 8.30 (1H, dd, J=2.0, 8.5 Hz), 8.78 (1H, d, J=2.0 Hz).

118-a-4) Preparation of 5-(2-difluoromethoxypyridin-5-yl)-5-methylimidazolidine-2,4-dione 1-(2-(Difluoromethoxy)pyridin-5-yl)ethanone was used for a similar reaction and treatment as Example 1-a, and 5-(2-difluoromethoxypyridin-5-yl)-5-methylimidazolidine-2,4-dione was obtained as a white crystal.

$^1$H-NMR (CD$_3$OD) δ: 1.77 (3H, s), 7.00 (1H, d, J=8.5 Hz), 7.55 (1H, t, J=73.0 Hz), 8.01 (1H, dd, J=2.7, 8.5 Hz), 8.35 (1H, d, J=2.7 Hz).

5-(2-Difluoromethoxypyridin-5-yl)-5-methylimidazolidine-2,4-dione was used for a similar reaction and treatment as Example 1, and the title compound was obtained as a white crystal.

$^1$H-NMR (270 MHz, CD$_3$OD) δ: 0.90 (3H, t, J=7.5 Hz), 1.55-1.64 (2H, m), 1.72 (3H, s), 2.57 (2H, t, J=7.5 Hz), 4.60 (2H, s), 6.80-6.87 (2H, m), 6.95 (1H, d, J=8.6 Hz), 7.03 (1H, d, J=7.6 Hz), 7.04-7.29 (3H, m), 7.47-7.53 (1H, m), 7.60 (1H, s), 7.94 (1H, d, J=8.4 Hz), 8.29 (1H, s).

Example 119

Preparation of 3-(2-chloro-5-(4-(1,1,1,3,3,3-hexafluoro-2-hydroxypropan-2-yl)-2-propylphenoxy)benzyl)-5-(4-(1-methylethoxy)phenyl)-5-methylimidazolidine-2,4-dione

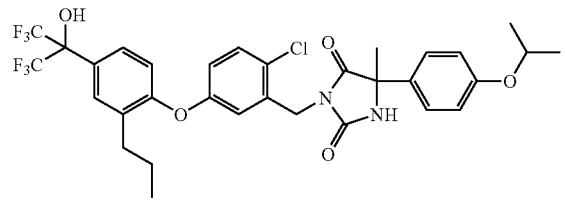

119-a-1) Preparation of 5-(4-(1,1,1,3,3,3-hexafluoro-2-(methoxymethoxy)propan-2-yl)-2-propylphenoxy)-2-nitrobenzaldehyde To a solution of 4-(1,1,1,3,3,3-hexafluoro-2-(methoxymethoxy)propan-2-yl)-2-propylphenol (500 mg, 1.44 mmol) in N,N-dimethylformamide (7.2 mL), potassium carbonate (300 mg, 2.17 mmol) was added. Under ice-cold conditions, the resultant mixture was added with 5-fluoro-2-nitrobenzaldehyde (220 mg, 1.30 mmol) and stirred at 60° C. for 1 hour. The reaction solution was cooled down to room temperature, added with water, and extracted with ethyl acetate. The organic layer was washed with brine, dried over anhydrous sodium sulfate, concentrated in vacuo, and purified using preparative thin-layer chromatography (hexane/ethyl acetate). 5-(4-(1,1,1,3,3,3-Hexafluoro-2-(methoxymethoxy)propan-2-yl)-2-propylphenoxy)-2-nitrobenzaldehyde (576 mg, yield 89%) was obtained as a yellow oil.

$^1$H-NMR (CDCl$_3$) δ: 0.91 (3H, t, J=7.3 Hz), 1.60 (2H, qt, J=7.3, 7.8 Hz), 2.58 (2H, t, J=7.8 Hz), 3.58 (3H, s), 4.89 (2H, s), 7.03 (1H, d, J=8.6 Hz), 7.17 (1H, dd, J=2.7, 8.6 Hz), 7.40 (1H, d, J=2.7 Hz), 7.52 (1H, d, J=8.6 Hz), 7.59 (1H, s), 8.18 (1H, d, J=8.6 Hz), 10.45 (1H, s).

119-a-2) Preparation of (5-(4-(1,1,1,3,3,3-hexafluoro-2-(methoxymethoxy)propan-2-yl)-2-propylphenoxy)-2-nitrophenyl) methanol To a solution of 5-(4-(1,1,1,3,3,3-hexafluoro-2-(methoxymethoxy)propan-2-yl)-2-propylphenoxy)-2-nitrobenzaldehyde (576 mg, 1.16 mmol) in methanol (5.8 mL), sodium borohydride (46 mg, 1.22 mmol) was added under ice-cold conditions, and the resultant mixture was stirred under ice-cold conditions for 20 minutes. The reaction solution was added with water and 5% aqueous solution of hydrochloric acid and extracted with ethyl acetate. The organic layer was washed with a saturated aqueous solution of sodium hydrogen carbonate and brine, and dried over anhydrous sodium sulfate. (5-(4-(1,1,1,3,3,3-Hexafluoro-2-(methoxymethoxy) propan-2-yl)-2-propylphenoxy)-2-nitrophenyl) methanol (575 mg, yield 99%) was obtained as a yellow oil.

$^1$H-NMR (CDCl$_3$) δ: 0.92 (3H, t, J=7.3 Hz), 1.61 (2H, qt, J=7.3, 7.3 Hz), 2.60 (2H, t, J=7.3 Hz), 3.57 (3H, s), 4.88 (2H, s), 5.00 (2H, s), 6.84 (1H, dd, J=2.7, 8.9 Hz), 7.02 (1H, d, J=8.6 Hz), 7.32 (1H, d, J=2.7 Hz), 7.49 (1H, d, J=8.6 Hz), 7.56 (1H, s), 8.18 (1H, d, J=8.9 Hz).

119-a-3) Preparation of 5-(4-(1,1,1,3,3,3-hexafluoro-2-(methoxymethoxy)propan-2-yl)-2-propylphenoxy)-2-nitrobenzyl phenylcarbamate To a solution of (5-(4-(1,1,1,3,3,3-hexafluoro-2-(methoxymethoxy)propan-2-yl)-2-propylphenoxy)-2-nitrophenyl) methanol (221 mg, 0.444 mmol) in dichloromethane (2.2 mL), pyridine (72 μL, 0.889 mmol) was added. Phenylisocyanate (97 μL, 0.889 mmol) was added thereto under ice-cold conditions, and the resultant mixture was stirred at room temperature overnight. The reaction solution was added with water and 5% aqueous solution of hydrochloric acid, and extracted with ethyl acetate. The organic layer was washed with a saturated aqueous solution of sodium hydrogen carbonate and brine, dried over anhydrous sodium sulfate, concentrated in vacuo, and purified using preparative thin-layer chromatography (hexane/ethyl acetate). 5-(4-(1,1,1,3,3,3-Hexafluoro-2-(methoxymethoxy)propan-2-yl)-2-propylphenoxy)-2-nitrobenzyl phenylcarbamate (249 mg, yield 91%) was obtained as a yellow oil.

$^1$H-NMR (CDCl$_3$) δ: 0.90 (3H, t, J=7.3 Hz), 1.59 (2H, qt, J=7.3, 7.6 Hz), 2.58 (2H, t, J=7.6 Hz), 3.56 (3H, s), 4.84 (2H, s), 5.65 (2H, s), 6.74 (1H, s), 6.88 (1H, dd, J=2.7, 8.9 Hz), 7.01 (1H, d, J=8.9 Hz), 7.07-7.13 (1H, m), 7.20 (1H, d, J=2.7 Hz), 7.29-7.39 (4H, m), 7.47 (1H, d, J=8.9 Hz), 7.55 (1H, s), 8.20 (1H, d, J=8.9 Hz).

119-a-4) Preparation of 2-amino-5-(4-(1,1,1,3,3,3-hexafluoro-2-(methoxymethoxy)propan-2-yl)-2-propylphenoxy) benzyl phenylcarbamate 5-(4-(1,1,1,3,3,3-Hexafluoro-2-(methoxymethoxy)propan-2-yl)-2-propylphenoxy)-2-nitrobenzyl phenylcarbamate (249 mg, 0.424 mmol) was added with acetic acid (2.0 mL) and water (400 μL) and then added with iron powder (451 mg, 8.28 mmol). The resultant mixture was stirred at room temperature for 1 hour. The reaction solution was added with 1N aqueous solution of sodium hydroxide, filtered using celite, and extracted with chloroform. The organic layer was washed with brine, dried over anhydrous sodium sulfate, and concentrated in vacuo. 2-Amino-5-(4-(1,1,1,3,3,3-hexafluoro-2-(methoxymethoxy)propan-2-yl)-2-propylphenoxy) benzyl phenylcarbamate (218 mg, yield 92%) was obtained as a yellow amorphous.

$^1$H-NMR (CDCl$_3$) δ: 0.97 (3H, t, J=7.3 Hz), 1.69 (2H, qt, J=7.3, 7.3 Hz), 2.72 (2H, t, J=7.3 Hz), 3.55 (3H, s), 4.84 (2H, s), 5.16 (2H, s), 6.71 (1H, d, J=8.4 Hz), 6.72 (1H, d, J=8.6 Hz), 6.87 (1H, dd, J=2.7, 8.4 Hz), 6.97 (1H, d, J=2.7 Hz), 7.05-7.11 (1H, m), 7.26-7.42 (6H, m).

119-a-5) Preparation of 2-chloro-5-(4-(1,1,1,3,3,3-hexafluoro-2-hydroxypropan-2-yl)-2-propylphenoxy)benzyl phenylcarbamate:

To a solution of 2-amino-5-(4-(1,1,1,3,3,3-hexafluoro-2-(methoxymethoxy)propan-2-yl)-2-propylphenoxy) benzyl phenylcarbamate (215 mg, 0.367 mmol) in dioxane (1.8 mL), a concentrated hydrochloric acid (180 μL) was added and the resultant mixture was added with an aqueous solution of sodium nitrite (38 mg, 0.550 mmol) at 5° C., and stirred at 5° C. for 10 minutes. Subsequently, a solution of copper chloride (73 mg, 0.733 mmol) in hydrochloric acid was added thereto at 5° C. and stirred at 50° C. overnight. The reaction solution was added with 3N aqueous solution of sodium hydroxide and extracted with ethyl acetate. The organic layer was washed with brine, dried over anhydrous sodium sulfate, concentrated in vacuo, and purified using preparative thin-layer chromatography (hexane/ethyl acetate). 2-Chloro-5-(4-(1,1,1,3,3,3-hexafluoro-2-hydroxypropan-2-yl)-2-propylphenoxy)benzyl phenylcarbamate (97 mg, yield 47%) was obtained as a yellow oil.

$^1$H-NMR (CDCl$_3$) δ: 0.93 (3H, t, J=7.3 Hz), 1.64 (2H, qt, J=7.3, 7.3 Hz), 2.65 (2H, t, J=7.3 Hz), 5.28 (2H, s), 6.84-6.87 (2H, m), 7.06-7.10 (1H, m), 7.12 (1H, d, J=2.7 Hz), 7.29-7.39 (5H, m), 7.46 (1H, d, J=7.1 Hz), 7.58 (1H, s).

119-a-6) Preparation of 2-chloro-5-(4-(1,1,1,3,3,3-hexafluoro-2-(methoxymethoxy)propan-2-yl)-2-propylphenoxy) benzyl phenylcarbamate To a solution of 2-chloro-5-(4-(1,1,1,3,3,3-hexafluoro-2-hydroxypropan-2-yl)-2-propylphenoxy)benzyl phenylcarbamate (97 mg, 0.173 mmol) in dichloromethane (870 μL), diisopropylethylamine (121 μL, 0.692 mmol) was added under ice-cold conditions. The resultant mixture was added with chloromethylmethyl ether (26 μL, 0.346 mmol) and stirred at 40° C. for 2 hours. The reaction solution was added with methanol, stirred at room temperature for 3 hours, and concentrated in vacuo. The obtained residue was purified using silica-gel preparative thin-layer chromatography (hexane/ethyl acetate), and 2-chloro-5-(4-(1,1,1,3,3,3-hexafluoro-2-(methoxymethoxy)propan-2-yl)-2-propylphenoxy) benzyl phenylcarbamate (60 mg, yield 57%) was obtained as a pale yellow oil.

$^1$H-NMR (CDCl$_3$) δ: 0.94 (3H, t, J=7.3 Hz), 1.64 (2H, qt, J=7.3, 7.6 Hz), 2.66 (2H, t, J=7.6 Hz), 3.55 (3H, s), 4.84 (2H, s), 5.29 (2H, s), 6.71 (1H, s), 6.83 (1H, d, J=8.9 Hz), 6.87 (1H, dd, J=2.4, 8.9 Hz), 7.05-7.11 (1H, m), 7.15 (1H, d, J=2.4 Hz), 7.28-7.40 (6H, m), 7.48 (1H, s).

119-a-7) Preparation of (2-chloro-5-(4-(1,1,1,3,3,3-hexafluoro-2-(methoxymethoxy)propan-2-yl)-2-propylphenoxy) phenyl)methanol To a solution of 2-chloro-5-(4-(1,1,1,3,3,3-hexafluoro-2-(methoxymethoxy)propan-2-yl)-2-propylphenoxy) benzyl phenylcarbamate (60 mg, 0.367 mmol) in methanol (1.0 mL), an aqueous solution of sodium methoxide (32 mg, 0.590 mmol) was added, and the resultant mixture was heated to reflux for 3 hours. The reaction solution was added with water to remove methanol in vacuo, and extracted with chloroform. The organic layer was washed with brine, dried over anhydrous sodium sulfate, concentrated in vacuo, and purified using preparative thin-layer chromatography (hexane/ethyl acetate). (2-Chloro-5-(4-(1,1,1,3,3,3-hexafluoro-2-(methoxymethoxy)propan-2-yl)-2-propylphenoxy) phenyl)methanol (56 mg, yield >100%) was obtained as a yellow oil.

$^1$H-NMR (CDCl$_3$) δ: 0.94 (3H, t, J=7.6 Hz), 1.65 (2H, qt, J=7.6, 7.6 Hz), 2.67 (2H, t, J=7.6 Hz), 3.56 (3H, s), 4.77 (2H, s), 4.86 (2H, s), 6.83 (1H, d, J=8.5 Hz), 6.85 (1H, dd, J=2.9, 8.8 Hz), 7.19 (1H, d, J=2.9 Hz), 7.33 (1H, d, J=8.8 Hz), 7.37 (1H, d, J=8.5 Hz), 7.48 (1H, s).

119-a-8) Preparation of 3-(2-chloro-5-(4-(1,1,1,3,3,3-hexafluoro-2-(methoxymethoxy)propan-2-yl)-2-propylphenoxy) benzyl)-5-(4-(1-methylethoxy)phenyl)-5-methylimidazolidine-2,4-dione (2-Chloro-5-(4-(1,1,1,3,3,3-hexafluoro-2-(methoxymethoxy)propan-2-yl)-2-propylphenoxy) phenyl)methanol (10 mg, 0.0212 mmol), 5-methyl-5-(4-(1-methylethoxy)phenyl)imidazolidine-2,4-dione (16 mg, 0.0635 mmol) and triphenylphosphine (16 mg, 0.0635 mmol) were added and dried in vacuo. N, N-dimethylformamide (300 µL) was added, and under ice-cold conditions, a solution of diethyl azodicarboxylate in tetrahydrofuran (29 µL, 0.0635 mmol) was added. The resultant mixture was stirred at room temperature for 4 hours. The reaction solution was added with water and extracted with ethyl acetate. The organic layer was washed with brine, dried over anhydrous sodium sulfate, concentrated in vacuo, and purified using preparative thin-layer chromatography (hexane/ethyl acetate). 3-(2-Chloro-5-(4-(1,1,1,3,3,3-hexafluoro-2-(methoxymethoxy)propan-2-yl)-2-propylphenoxy) benzyl)-5-(4-(1-methylethoxy)phenyl)-5-methylimidazolidine-2,4-dione (7.6 mg, yield >100%) was obtained as a yellow oil.

$^1$H-NMR (CDCl$_3$) δ: 0.92 (3H, 1, J=7.1 Hz), 1.30 (6H, d, J=6.1 Hz), 1.60 (2H, qt, J=7.1, 7.6 Hz), 1.74 (3H, s), 2.60 (2H, t, J=7.6 Hz), 3.56 (3H, s), 4.51 (1H, sept, J=6.1 Hz), 4.76 (2H, s), 4.86 (2H, s), 5.82 (1H, s), 6.70 (1H, d, J=2.4 Hz), 6.81-6.85 (4H, m), 7.32 (1H, d, J=8.6 Hz), 7.33 (2H, d, J=8.8 Hz), 7.38 (1H, d, J=9.0 Hz), 7.47 (1H, s).

To a solution of 3-(2-chloro-5-(4-(1,1,1,3,3,3-hexafluoro-2-(methoxymethoxy)propan-2-yl)-2-propylphenoxy)benzyl)-5-(4-(1-methylethoxy)phenyl)-5-methylimidazolidine-2,4-dione (7.4 mg, 0.011 mmol) in ethyl acetate (300 µL), a solution of 4N hydrogen chloride-ethyl acetate (300 µL) was added, and the resultant mixture was stirred at room temperature for 2.5 hours. Further, a solution of 4N hydrogen chloride-ethyl acetate (300 µL) was added, and stirred at 50° C. for 1 hour. The reaction solution was concentrated in vacuo, the residue was purified using thin-layer silica-gel column chromatography (hexane/ethyl acetate), and the title compound (7.0 mg, yield 95%) was obtained as a colorless oil.

$^1$H-NMR (CDCl$_3$) δ: 0.92 (3H, t, J=7.6 Hz), 1.30 (3H, d, J=6.0 Hz), 1.31 (3H, d, J=6.0 Hz), 1.60 (2H, qt, J=7.6, 7.6 Hz), 1.73 (3H, s), 2.61 (2H, t, J=7.6 Hz), 4.51 (1H, sept, J=6.0 Hz), 4.77 (2H, s), 5.75 (1H, s), 6.68 (1H, d, J=2.4 Hz), 6.78-6.83 (4H, m), 7.31 (1H, d, J=8.8 Hz), 7.32 (2H, d, J=8.8 Hz), 7.43 (1H, d, J=8.0 Hz), 7.56 (1H, s).

Example 120

Preparation of 3-(2-iodo-5-(4-(1,1,1,3,3,3-hexafluoro-2-hydroxypropan-2-yl)-2,6-dipropylphenoxy)benzyl)-5-(4-(1-methylethoxy)phenyl)-5-methylimidazolidine-2,4-dione

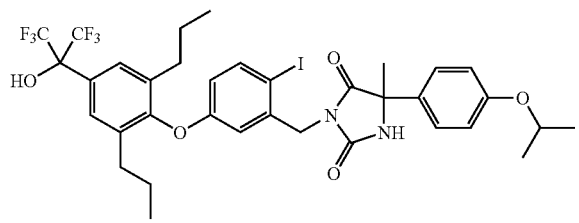

120-a-1) Preparation of 2,6-dipropyl-4-[1,1,1,3,3,3-hexafluoro-2-(methoxymethoxy)propan-2-yl]phenol Methyl 4-hydroxy-3-propyl benzoate was propylated according to Preparation Example 1, steps a) to c) to obtain methyl 3,5-dipropyl-4-hydroxy benzoate. Subsequently, 2,6-dipropyl-4-[1,1,1,3,3,3-hexafluoro-2-(methoxymethoxy)propan-2-yl]phenol was obtained as a white powder according to Preparation Example 1, steps d) to h).

1H-NMR (CDCl3) δ: 0.97 (6H, t, J=7.6 Hz), 1.64 (4H, qt, J=7.6, 7.6 Hz), 2.59 (4H, t, J=7.6 Hz), 3.54 (3H, s), 4.83 (2H, s), 4.88 (1H, s), 7.19 (2H, s).

120-a-2) Preparation of 5-(4-(1,1,1,3,3,3-hexafluoro-2-(methoxymethoxy)propan-2-yl)-2,6-dipropylphenoxy)-2-nitrobenzaldehyde 2,6-Dipropyl-4-[1,1,1,3,3,3-hexafluoro-2-(methoxymethoxy)propan-2-yl]phenol was used in place of 4-(1,1,1,3,3,3-hexafluoro-2-(methoxymethoxy)propan-2-yl)-2-propylphenol for a similar reaction and treatment as 119-a-1), and 5-(4-(1,1,1,3,3,3-hexafluoro-2-(methoxymethoxy)propan-2-yl)-2,6-dipropylphenoxy)-2-nitrobenzaldehyde was obtained as a yellow oil.

$^1$H-NMR (CDCl$_3$) δ: 0.86 (6H, t, J=7.3 Hz), 1.56 (4H, qt, J=7.3, 7.3 Hz), 2.40 (4H, t, J=7.3 Hz), 3.58 (2H, s), 4.90 (3H, s), 6.96 (1H, dd, J=3.0, 9.2 Hz), 7.29 (1H, d, J=3.0 Hz), 7.42 (2H, s), 8.16 (1H, d, J=9.2 Hz), 10.46 (1H, s).

120-a-3) Preparation of (2-iodo-5-(4-(1,1,1,3,3,3-hexafluoro-2-(methoxymethoxy)propan-2-yl)-2,6-dipropylphenoxy) benzaldehyde To a solution of 5-(4-(1,1,1,3,3,3-hexafluoro-2-(methoxymethoxy)propan-2-yl)-2,6-dipropylphenoxy)-2-nitrobenzaldehyde (100 mg, 0.186 mmol) in dioxane/water (2:1, 1.7 mL), iron powder (26 mg, 0.465 mmol) and acetic acid (290 µL) were added sequentially under ice-cold conditions, and the resultant mixture was stirred at room temperature overnight. After completion of the reaction, water and a saturated aqueous solution of sodium hydrogen carbonate were added under ice-cold conditions, and the resultant mixture was extracted with ethyl acetate. The organic layer was washed with brine, dried over sodium sulfate, and concentrated in vacuo. A solution of the obtained crude product (98 mg) in acetonitrile (0.744 mL) was added with p-toluene sulfonic acid monohydrate (106 mg, 0.558 mmol), added with a mixed aqueous solution (water 100 µL) of sodium nitrite (26 mg, 0.372 mmol) and potassium iodide (77 mg, 0.465 mmol) under ice-cold conditions, and stirred at the same temperature for 5 minutes. Subsequently, the resultant mixture was stirred at room temperature overnight. The reaction solution was added with an aqueous solution of sodium thiosulfate and a saturated aqueous solution of sodium hydrogen carbonate, extracted with ethyl acetate, and concentrated in vacuo. The obtained residue was purified using silica-gel column chromatography (hexane/ethyl acetate) and (2-iodo-5-(4-(1,1,1,3,3,3-hexafluoro-2-(methoxymethoxy)propan-2-yl)-2,6-dipropylphenoxy) benzaldehyde (8.0 mg, yield 7.0%) was obtained as a yellow oil.

$^1$H-NMR (CDCl$_3$) δ: 0.85 (6H, t, J=7.3 Hz), 1.50-1.59 (4H, m), 2.41 (4H, t, J=7.6 Hz), 3.57 (3H, s), 4.89 (2H, s), 6.74 (1H, dd, J=3.0, 8.6 Hz), 7.31 (1H, d, J=3.0 Hz), 7.38 (2H, s), 7.82 (1H, d, J=8.6 Hz), 10.01 (1H, s).

120-a-4) Preparation of (2-iodo-5-(4-(1,1,1,3,3,3-hexafluoro-2-(methoxymethoxy)propan-2-yl)-2,6-dipropylphenoxy) phenyl)methanol To a solution of (2-iodo-5-(4-(1,1,1,3,3,3-hexafluoro-2-(methoxymethoxy)propan-2-yl)-2,6-dipropylphenoxy) benzaldehyde (25 mg, 0.0404 mmol) in methanol (2.0 mL), sodium borohydride (1.7 mg, 0.445 mmol) was added under ice-cold conditions, and the resultant mixture was stirred for 30 minutes. After completion of the reaction, the reaction solution was added with water under ice-cold conditions and extracted with chloroform. The organic layer was washed with brine and dried over sodium sulfate. (2-Iodo-5-(4-(1,1,1,3,3,3-hexafluoro-2-(methoxymethoxy)propan-2-yl)-2,6-dipropylphenoxy) phenyl)methanol (27 mg, yield >100%) was obtained as a yellow oil.

$^1$H-NMR (CDCl$_3$) δ: 0.85 (6H, t, J=7.3 Hz), 1.51-1.60 (4H, m), 1.96 (1H, t, J=6.3 Hz), 2.43 (4H, t, J=7.6 Hz), 3.57 (3H, s), 4.62 (2H, d, J=6.3 Hz), 4.88 (2H, s), 6.34 (1H, dd, J=2.9, 8.6 Hz), 7.00 (1H, d, J=2.9 Hz), 7.36 (2H, s), 7.64 (1H, d, J=8.6 Hz).

120-a-5) Preparation of 3-(2-iodo-5-(4-(1,1,1,3,3,3-hexafluoro-2-(methoxymethoxy)propan-2-yl)-2,6-dipropylphenoxy) benzyl)-5-(4-(1-methylethoxy)phenyl)-5-methylimidazolidine-2,4-dione (2-Iodo-5-(4-(1,1,1,3,3,3-hexafluoro-2-(methoxymethoxy)propan-2-yl)-2,6-dipropylphenoxy) phenyl) methanol was used in place of (2-chloro-5-(4-(1,1,1,3,3,3-hexafluoro-2-(methoxymethoxy)propan-2-yl)-2-propylphenoxy) phenyl)methanol for a similar reaction and treatment as 119-a-8), and 3-(2-iodo-5-(4-(1,1,1,3,3,3-hexafluoro-2-(methoxymethoxy)propan-2-yl)-2,6-dipropylphenoxy) benzyl)-5-(4-(1-methylethoxy)phenyl)-5-methylimidazolidine-2,4-dione was obtained as a yellow oil.

$^1$H-NMR (CDCl$_3$) δ: 0.83 (6H, t, J=7.3 Hz), 1.30 (3H, d, J=5.8 Hz), 1.31 (3H, d, J=5.8 Hz), 1.46-1.55 (4H, m), 1.68 (3H, s), 2.36 (4H, t, J=7.1 Hz), 3.57 (3H, s), 4.49-4.55 (1H, m), 4.61 (2H, s), 4.88-4.92 (2H, m), 5.74 (1H, s), 6.36 (1H, d, J=2.4 Hz), 6.46 (1H, dd, J=2.4, 8.8 Hz), 6.87 (2H, d, J=8.8 Hz), 7.34 (2H, s), 7.35 (2H, d, J=8.8 Hz), 7.67 (1H, d, J=8.8 Hz).

3-(2-Iodo-5-(4-(1,1,1,3,3,3-hexafluoro-2-(methoxymethoxy)propan-2-yl)-2,6-dipropylphenoxy)benzyl)-5-(4-(1-methylethoxy)phenyl)-5-methylimidazolidine-2,4-dione was used in place of 3-(2-chloro-5-(4-(1,1,1,3,3,3-hexafluoro-2-(methoxymethoxy)propan-2-yl)-2-propylphenoxy) benzyl)-5-(4-(1-methylethoxy)phenyl)-5-methylimidazolidine-2,4-dione for a similar reaction and treatment as Example 119, and the title compound was obtained as a colorless oil.

$^1$H-NMR (CDCl$_3$) δ: 0.83 (6H, t, J=7.3 Hz), 1.30 (3H, d, J=6.1 Hz), 1.31 (3H, d, J=6.1 Hz), 1.46-1.55 (4H, m), 1.67 (3H, s), 2.37 (4H, t, J=7.6 Hz), 4.47-4.55 (1H, m), 4.62 (2H, s), 5.61 (1H, s), 6.37 (1H, d, J=2.7 Hz), 6.43 (1H, dd, J=2.7, 8.8 Hz), 6.87 (2H, d, J=8.8 Hz), 7.35 (2H, d, J=8.8 Hz), 7.43 (2H, s), 7.67 (1H, d, J=8.8 Hz).

Example 121

Preparation of 3-(5-(4-(1,1,1,3,3,3-hexafluoro-2-hydroxypropan-2-yl)-2,6-dipropylphenoxy)benzyl)-5-(4-(1-methylethoxy)phenyl)-5-methylimidazolidine-2,4-dione

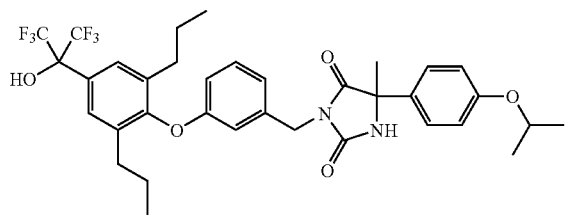

To a solution of 3-(2-iodo-5-(4-(1,1,1,3,3,3-hexafluoro-2-hydroxypropan-2-yl)-2,6-dipropylphenoxy) benzyl)-5-(4-(1-methylethoxy)diphenyl)-5-methylimidazolidine-2,4-dione (12 mg, 0.0149 mmol) in methanol, palladium carbon (2.0 mg) was added, and the resultant mixture was stirred at room temperature overnight under a hydrogen atmosphere. After completion of the reaction, the reaction solution was filtered using celite, concentrated in vacuo, and the title compound was obtained as a yellow oil.

$^1$H-NMR (CDCl$_3$) δ: 0.82 (6H, t, J=7.3 Hz), 1.32 (6H, d, J=6.1 Hz), 1.48-1.57 (4H, m), 1.74 (3H, s), 2.40 (4H, t, J=7.6 Hz), 4.48-4.55 (1H, m), 4.60 (2H, s), 5.69 (1H, s), 6.59 (1H, dd, J=2.2, 8.8 Hz), 6.72 (1H, d, J=2.2 Hz), 6.86 (2H, d, J=9.0 Hz), 6.92 (1H, d, J=7.8 Hz), 7.32 (2H, d, J=8.8 Hz), 7.43 (2H, s).

Example 122

Preparation of 5-(6-methoxypyridin-3-yl)-3-(4-(4-(1,1,3,3,3-hexafluoro-2-hydroxypropan-2-yl)-2-propylphenoxy) phenethyl)-5-methylimidazolidine-2,4-dione

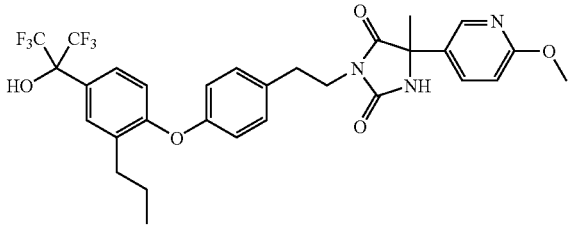

5-(6-Methoxypyridin-3-yl)-5-methylimidazolidine-2,4-dione was used in place of 5-(4-(1-methylethoxy)phenyl)-5-methylimidazolidine-2,4-dione in Example 38 d) for a similar reaction and treatment, and the title compound was obtained as a colorless oil.

$^1$H-NMR (270 MHz, CD$_3$OD) δ: 0.93 (3H, t, J=7.4 Hz), 1.61-1.63 (2H, m), 1.68 (3H, s), 2.65 (2H, t, J=7.4 Hz), 2.91 (2H, t, J=6.1 Hz), 3.73 (2H, t, J=6.1 Hz), 4.04 (3H, s), 6.72 (1H, d, J=8.8 Hz), 6.77 (2H, d, J=7.2 Hz), 7.11 (2H, d, J=7.2 Hz), 7.14-7.24 (1H, m), 7.47 (1H, d, J=8.8 Hz), 7.59 (1H, s), 8.17 (1H, d, J=6.2 Hz), 8.27 (1H, d, J=2.4 Hz).

Example 123

Preparation of 5-[5-(1-methylethoxy)pyridin-2-yl]-3-(4-(4-(1,1,1,3,3,3-hexafluoro-2-hydroxypropan-2-yl)-2-propylphenoxy)phenethyl)-5-methylimidazolidine-2,4-dione

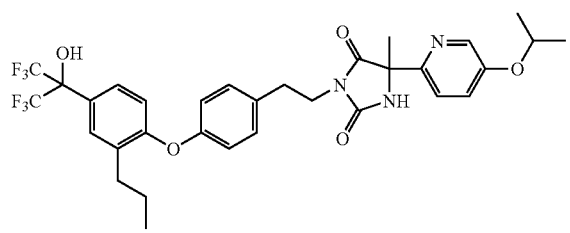

5-[5-(1-Methylethoxy)pyridin-2-yl]-5-methylimidazolidine-2,4-dione was used in place of 5-(4-(1-methylethoxy)phenyl)-5-methylimidazolidine-2,4-dione in Example 38 d) for a similar reaction and treatment, and the title compound was obtained as a colorless oil.

$^1$H-NMR (CDCl$_3$) δ: 0.94 (3H, t, J=7.3 Hz), 1.31 (3H, d, J=5.9 Hz), 1.32 (3H, d, J=5.9 Hz), 1.58-1.72 (2H, m), 1.75 (3H, s), 2.67 (2H, t, J=6.8 Hz), 2.93 (2H, t, J=7.0 Hz), 3.75 (2H, t, J=7.0 Hz), 4.65-4.74 (1H, m), 6.68 (1H, d, J=8.6 Hz), 6.76 (2H, d, J=8.4 Hz), 7.12 (2H, d, J=8.4 Hz), 7.48 (1H, d, J=8.6 Hz), 7.59 (1H, s), 7.70 (2H, brs), 8.22 (1H, s).

Example 124

Preparation of 5-(2-difluoromethoxypyridin-5-yl)-3-(4-(4-(1,1,1,3,3,3-hexafluoro-2-hydroxypropan-2-yl)-2-propylphenoxy)phenethyl)-5-methylimidazolidine-2,4-dione

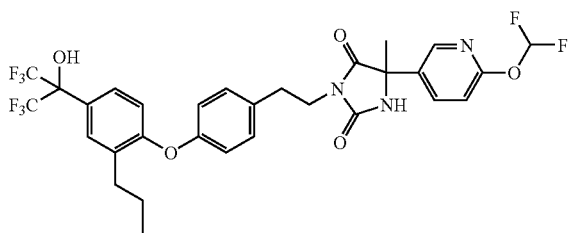

5-(2-Difluoromethoxypyridin-5-yl)-5-methylimidazolidine-2,4-dione was used in place of 5-(4-(1-methylethoxy)phenyl)-5-methylimidazolidine-2,4-dione in Example 38 d) for a similar reaction and treatment, and the title compound was obtained as a colorless oil.

$^1$H-NMR (400 MHz, CD$_3$OD) δ: 0.94 (3H, t, J=7.3 Hz), 1.65 (2H, qt, J=7.3, 7.5 Hz), 1.67 (3H, s), 2.67 (2H, t, J=7.5 Hz), 2.91 (2H, t, J=6.7 Hz), 3.74 (2H, t, J=6.7 Hz), 6.72 (1H, d, J=8.8 Hz), 6.75 (2H, d, J=8.5 Hz), 6.90 (1H, dd, J=0.6, 8.8 Hz), 7.08 (2H, d, J=8.5 Hz), 7.30-7.40 (1H, m), 7.48 (1H, d, J=8.8 Hz), 7.60 (1H, s), 7.84 (1H, dd, J=2.5, 8.8 Hz), 8.24 (1H, d, J=2.5 Hz).

Example 125

Preparation of 5-(2-benzyloxypyridin-5-yl)-3-(4-(4-(1,1,1,3,3,3-hexafluoro-2-hydroxypropan-2-yl)-2-propylphenoxy) phenethyl)-5-methylimidazolidine-2,4-dione

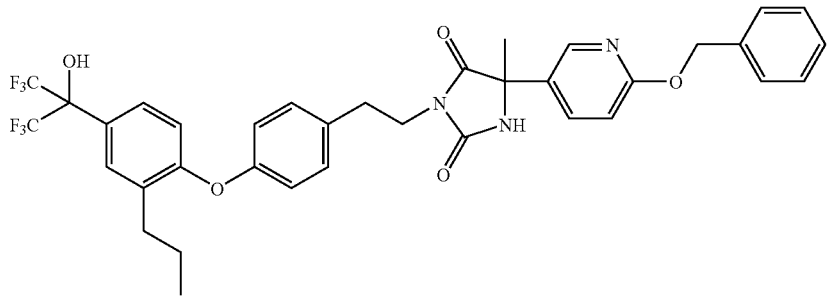

5-(2-Benzyloxypyridin-5-yl)-5-methylimidazolidine-2,4-dione was used in place of 5-(4-(1-methylethoxy)phenyl)-5-methylimidazolidine-2,4-dione in Example 38 d) for a similar reaction and treatment, and the title compound was obtained as a colorless oil.

$^1$H-NMR (400 MHz, CD$_3$OD) δ: 0.93 (3H, t, J=7.3 Hz), 1.56 (3H, s), 1.65 (2H, qt, J=7.3, 7.5 Hz), 2.65 (2H, t, J=7.5 Hz), 2.89 (2H, t, J=6.7 Hz), 3.72 (2H, t, J=6.7 Hz), 5.17 (2H, s), 6.53 (1H, d, J=9.2 Hz), 6.72 (2H, d, J=8.6 Hz), 6.73 (1H, d, J=9.2 Hz), 7.07 (2H, d, J=8.6 Hz), 7.25-7.30 (5H, m), 7.47 (1H, d, J=9.5 Hz), 7.48 (1H, d, J=9.5 Hz), 7.60 (1H, s), 7.69 (1H, d, J=2.2 Hz).

Example 126

Preparation of 3-(4-(4-(1,1,1,3,3,3-hexafluoro-2-hydroxypropan-2-yl)-2-propylphenoxy)-2-methylphenethyl)-5-(4-(1-methylethoxy) phenyl)-5-methylimidazolidine-2,4-dione

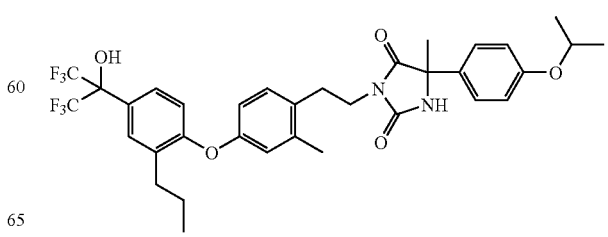

126-a-1) Preparation of 2-methyl-4-[2-propyl-4-(2,2,2-trifluoro-1-methoxymethoxy-1-trifluoromethyl-ethyl)-phenoxy]-1-nitrobenzene 4-Fluoro-2-methyl-1-nitrobenzene was used for a similar reaction and treatment as Example 119-a-1), and 2-methyl-4-[2-propyl-4-(2,2,2-trifluoro-1-methoxymethoxy-1-trifluoromethyl-ethyl)-phenoxy]-1-nitrobenzene was obtained as a white crystal.

$^1$H-NMR (CDCl$_3$) δ: 0.92 (3H, t, J=7.3 Hz), 1.62 (2H, qt, J=7.3, 7.8 Hz), 2.60 (2H, t, J=7.8 Hz), 2.62 (3H, s), 3.57 (3H, s), 4.88 (2H, s), 6.81 (1H, dd, J=2.2, 9.0 Hz), 6.87 (1H, d, J=2.2 Hz), 6.99 (1H, d, J=8.8 Hz), 7.48 (1H, d, J=8.8 Hz), 7.55 (1H, s), 8.07 (1H, d, J=9.0 Hz).

126-a-2) Preparation of 2-methyl-4-[2-propyl-4-(2,2,2-trifluoro-1-methoxymethoxy-1-trifluoromethyl-ethyl)-phenoxy]-phenylamine To a solution of 2-methyl-4-[2-propyl-4-(2,2,2-trifluoro-1-methoxymethoxy-1-trifluoromethyl-ethyl)-phenoxy]-1-nitrobenzene (293 mg, 0.609 mmol) in methanol (3.0 mL), palladium carbon (29 mg) was added and the resultant mixture was stirred for 3 hours under a hydrogen atmosphere. The reaction solution was filtered using celite, concentrated in vacuo, and 2-methyl-4-[2-propyl-4-(2,2,2-trifluoro-1-methoxymethoxy-1-trifluoromethyl-ethyl)-phenoxy]-phenylamine (274 mg, yield >100%) was obtained as a red-purple oil.

$^1$H-NMR (CDCl$_3$) δ: 0.97 (3H, t, J=7.4 Hz), 1.68 (2H, qt, J=7.4, 7.8 Hz), 2.17 (3H, s), 2.71 (2H, t, J=7.8 Hz), 3.54 (3H, s), 4.84 (2H, s), 6.68 (1H, d, J=8.3 Hz), 6.70 (1H, d, J=8.8 Hz), 6.73 (1H, dd, J=2.4, 8.3 Hz), 6.78 (1H, d, J=2.4 Hz), 7.27 (1H, d, J=8.8 Hz), 7.40 (1H, s).

126-a-3) Preparation of 4-(1,1,1,3,3,3-hexafluoro-2-(methoxymethoxy)propan-2-yl)-1-(4-iodo-3-methylphenoxy)-2-propylbenzene To a solution of 2-methyl-4-[2-propyl-4-(2,2,2-trifluoro-1-methoxymethoxy-1-trifluoromethyl-ethyl)-phenoxy]-phenylamine (271 mg, 0.600 mmol) in acetonitrile (3.0 mL), p-toluene sulfonic acid monohydrate (342 mg, 1.80 mmol) was added. The resultant mixture was added with a mixed aqueous solution (water 400 μL) of sodium nitrite (83 mg, 1.20 mmol) and potassium iodide (249 mg, 1.50 mmol) at 10° C., stirred at the same temperature for 10 minutes, and then stirred at room temperature overnight. The reaction solution was added with an aqueous solution of sodium thiosulfate and a saturated aqueous solution of sodium hydrogen carbonate, extracted with ethyl acetate, and concentrated in vacuo. The obtained residue was purified using silica-gel column chromatography (hexane/ethyl acetate), and 4-(1,1,1,3,3,3-hexafluoro-2-(methoxymethoxy)propan-2-yl)-1-(4-iodo-3-methylphenoxy)-2-propylbenzene (226 mg, yield 67%) was obtained as a yellow oil.

$^1$H-NMR (CDCl$_3$) δ: 0.94 (3H, t, J=7.6 Hz), 1.64 (2H, qt, J=7.6, 7.6 Hz), 2.41 (3H, s), 2.66 (2H, t, J=7.6 Hz), 3.56 (3H, s), 4.86 (2H, s), 6.54 (1H, dd, J=2.4, 8.6 Hz), 6.83 (1H, d, J=8.6 Hz), 6.91 (1H, d, J=2.4 Hz), 7.37 (1H, d, J=8.6 Hz), 7.47 (1H, s), 7.74 (1H, d, J=8.6 Hz).

126-a-4) Preparation of 4-(1,1,1,3,3,3-hexafluoro-2-(methoxymethoxy)propan-2-yl)-1-(3-methyl-4-vinylphenoxy)-2-propylbenzene 4-(1,1,1,3,3,3-Hexafluoro-2-(methoxymethoxy)propan-2-yl)-1-(4-iodo-3-methyl phenoxy)-2-propylbenzene (265 mg, 0.471 mmol) was dissolved in N,N-dimethylformamide (4.7 mL) and water (0.9 mL). The resultant mixture was sequentially added with vinylboronic acid pinacol ester (280 μL, 1.65 mmol), tetrakis triphenylphosphine palladium (54 mg, 0.0471 mmol), and sodium carbonate (300 mg, 2.83 mmol), and stirred at 80° C. for 1 hour. After completion of the reaction, the reaction solution was filtered using celite and extracted with ethyl acetate. The organic layer was washed with water and brine, dried over sodium sulfate, and concentrated in vacuo. The obtained residue was purified using column chromatography (hexane/chloroform), and 4-(1,1,1,3,3,3-hexafluoro-2-(methoxymethoxy)propan-2-yl)-1-(3-methyl-4-vinylphenoxy)-2-propylbenzene (218 mg, yield >100%) was obtained as a yellow oil.

$^1$H-NMR (CDCl$_3$) δ: 0.95 (3H, t, J=7.3 Hz), 1.66 (2H, qt, J=7.3, 7.3 Hz), 2.34 (3H, s), 2.68 (2H, t, J=7.3 Hz), 3.55 (3H, s), 4.85 (2H, s), 5.26 (1H, dd, J=1.4, 11.1 Hz), 5.59 (1H, dd, J=1.4, 17.3 Hz), 6.77-6.81 (2H, m), 6.83 (1H, d, J=8.9 Hz), 6.89 (1H, dd, J=11.1, 17.3 Hz), 7.34 (1H, d, J=8.9 Hz), 7.45 (1H, s), 7.46 (1H, d, J=8.9 Hz).

126-a-5) Preparation of 2-{2-methyl-4-[2-propyl-4-(2,2,2-trifluoro-1-methoxymethoxy-1-trifluoromethyl-ethyl)-phenoxy]-phenyl}-ethanol 4-(1,1,1,3,3,3-Hexafluoro-2-(methoxymethoxy)propan-2-yl)-1-(3-methyl-4-vinylphenoxy)-2-propylbenzene was used for a similar reaction and treatment as Example 38-b), and 2-{2-methyl-4-[2-propyl-4-(2,2,2-trifluoro-1-methoxymethoxy-1-trifluoromethyl-ethyl)-phenoxy]-phenyl}-ethanol was obtained as a colorless oil.

$^1$H-NMR (CDCl$_3$) δ: 0.95 (3H, t, J=7.3 Hz), 1.67 (2H, qt, J=7.3, 7.3 Hz), 2.33 (3H, s), 2.69 (2H, t, J=7.3 Hz), 2.89 (2H, t, J=6.8 Hz), 3.55 (3H, s), 3.82-3.88 (2H, m), 4.85 (2H, s), 6.78 (1H, dd, J=2.7, 8.4 Hz), 6.80 (1H, d, J=8.6 Hz), 6.85 (1H, d, J=2.7 Hz), 7.15 (1H, d, J=8.4 Hz), 7.34 (1H, d, J=8.6 Hz), 7.45 (1H, s).

126-a-6) Preparation of 2-{2-methyl-4-[2-propyl-4-(2,2,2-trifluoro-1-methoxymethoxy-1-trifluoromethyl-ethyl)-phenoxy]-phenyl}-ethyl toluene-4-sulfonic acid ester A solution of 2-{2-methyl-4-[2-propyl-4-(2,2,2-trifluoro-1-methoxymethoxy-1-trifluoromethyl-ethyl)-phenoxy]-phenyl}-ethanol (189 mg, 0.0393 mmol) in dichloromethane (300 μL) was added with pyridine (16 μL 0.197 mmol), and then added with an aqueous solution of p-toluene sulfonic acid chloride (11 mg, 0.059 mmol) at 0° C., and stirred at room temperature for 7 hours. The resultant mixture was added with pyridine (8.0 μL, 0.0985 mmol), and then added with an aqueous solution of p-toluene sulfonic acid chloride (5.5 mg, 0.030 mmol) at 0° C., and stirred at room temperature for 3 hours. The reaction solution was added with water and extracted with ethyl acetate. The organic layer was washed with 5% aqueous solution of hydrochloric acid and a saturated aqueous solution of sodium hydrogen carbonate, dried over anhydrous sodium sulfate, concentrated in vacuo, and purified using preparative thin-layer chromatography (hexane/ethyl acetate). 2-{2-Methyl-4-[2-propyl-4-(2,2,2-trifluoro-1-methoxymethoxy-1-trifluoromethyl-ethyl)-phenoxy]-phenyl}-ethyl toluene-4-sulfonic acid ester (13 mg, yield 50%) was obtained as a yellow oil.

$^1$H-NMR (CDCl$_3$) δ: 0.95 (3H, t, J=7.3 Hz), 1.67 (2H, qt, J=7.3, 7.3 Hz), 2.22 (3H, s), 2.45 (3H, s), 2.68 (2H, t, J=7.3 Hz), 2.96 (2H, t, J=7.3 Hz), 3.56 (3H, s), 4.17 (2H, t, J=7.3 Hz), 4.85 (2H, s), 6.71 (1H, dd, J=2.7, 8.4 Hz), 6.77 (1H, d,

J=8.4 Hz), 6.78 (1H, d, J=2.7 Hz), 7.02 (1H, d, J=8.4 Hz), 7.30-7.34 (1H, m), 7.31 (2H, d, J=7.8 Hz), 7.46 (1H, s), 7.73 (2H, d, J=7.8 Hz).

2-{2-Methyl-4-[2-propyl-4-(2,2,2-trifluoro-1-methoxymethoxy-1-trifluoromethyl-ethyl)-phenoxy]-phenyl}-ethyl toluene-4-sulfonic acid ester and 5-((1-methylethoxy)phenyl-4-yl)-5-methylimidazolidine-2,4-dione were used for a similar reaction and treatment as Example 1, and the title compound was obtained as a colorless oil.

$^1$H-NMR (400 MHz, CDCl$_3$) δ: 0.95 (3H, t, J=7.3 Hz), 1.30 (6H, d, J=6.1 Hz), 1.66 (2H, qt, J=7.3, 7.6 Hz), 1.74 (3H, s), 2.34 (3H, s), 2.67 (2H, t, J=7.6 Hz), 2.80-2.96 (2H, m), 3.63 (1H, s), 3.71 (2H, t, J=7.4 Hz), 4.50 (1H, sept, J=6.1 Hz), 5.68 (1H, s), 6.64 (1H, d, J=5.8 Hz), 6.75 (1H, d, J=8.6 Hz), 6.78 (1H, s), 6.85 (2H, d, J=8.8 Hz), 7.01 (1H, d, J=8.3 Hz), 7.30 (2H, d, J=8.8 Hz), 7.42 (1H, d, J=7.8 Hz), 7.54 (1H, s).

Example 127

Preparation of 3-(4-(4-(1,1,1,3,3,3-hexafluoro-2-hydroxypropan-2-yl)-2-propylphenoxy)-2-methoxyphenethyl)-5-(1-(1-methylethoxy)phenyl-4-yl)-5-methylimidazolidine-2,4-dione

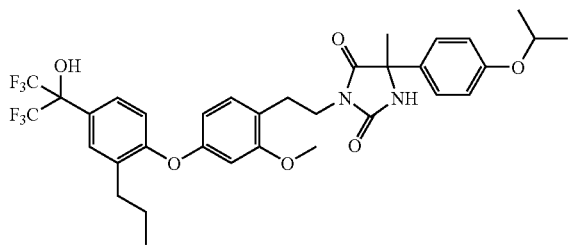

127-a-1) Preparation of 4-fluoro-2-methoxy-1-nitro-benzene

A solution of 4-fluoro-2-hydroxy-1-nitrobenzene (100 mg, 0.637 mmol) in N,N-dimethylformamide (3.2 mL) was added with potassium carbonate (132 mg, 0.955 mmol), then added with methyl iodide (48 μL, 0.764 mmol) under ice-cold conditions, and stirred at room temperature for 1 hour. The reaction solution was further added with potassium carbonate (132 mg, 0.955 mmol), then with methyl iodide (48 μL, 0.764 mmol) under ice-cold conditions, and stirred at 60° C. for 1 hour. The reaction solution was added with water and extracted with ethyl acetate. The organic layer was washed with brine, dried over anhydrous sodium sulfate and concentrated in vacuo. 4-fluoro-2-methoxy-1-nitro-benzene (118 mg, yield >100%) was obtained as a yellow oil.

$^1$H-NMR (CDCl$_3$) δ: 3.97 (3H, s), 6.74 (1H, ddd, J=2.4, 7.8, 9.0 Hz), 6.80 (1H, dd, J=2.4, 10.2 Hz), 7.97 (1H, dd, J=6.1, 9.0 Hz).

127-a-2) Preparation of 4-(1,1,1,3,3,3-hexafluoro-2-(methoxymethoxy)propan-2-yl)-1-(3-methoxy-4-nitrophenoxy)-2-propylbenzene 4-Fluoro-2-methoxynitrobenzene was used for a similar reaction and treatment as Example 119-a-1), and 4-(1,1,1,3,3-hexafluoro-2-(methoxymethoxy)propan-2-yl)-1-(3-methoxy-4-nitrophenoxy)-2-propylbenzene was obtained as a colorless oil.

$^1$H-NMR (CDCl$_3$) δ: 0.93 (3H, t, J=7.3 Hz), 1.62 (2H, qt, J=7.3, 7.3 Hz), 2.61 (2H, t, J=7.3 Hz), 3.57 (3H, s), 3.93 (3H, s), 4.88 (2H, s), 6.43 (1H, dd, J=2.4, 9.0), 6.69 (1H, d, J=2.4 Hz), 7.02 (1H, d, J=8.5 Hz), 7.49 (1H, d, J=8.5 Hz), 7.56 (1H, s), 7.95 (1H, d, J=9.0 Hz).

127-a-3) Preparation of 4-(1,1,1,3,3,3-hexafluoro-2-(methoxymethoxy)propan-2-yl)-1-(4-iodo-3-methoxyphenoxy)-2-propylbenzene 4-(1,1,1,3,3,3-Hexafluoro-2-(methoxymethoxy)propan-2-yl)-1-(3-methoxy-4-nitrophenoxy)-2-propylbenzene was used for a similar reaction and treatment as Examples 126-a-2) and 126-a-3), and 4-(1,1,1,3,3,3-hexafluoro-2-(methoxymethoxy)propan-2-yl)-1-(4-iodo-3-methoxyphenoxy)-2-propylbenzene was obtained as a yellow oil.

$^1$H-NMR (CDCl$_3$) δ: 0.98 (3H, t, J=7.3 Hz), 1.70 (2H, qt, J=7.3, 7.8 Hz), 2.73 (2H, t, J=7.8 Hz), 3.54 (3H, s), 3.83 (3H, s), 4.84 (2H, s), 6.47 (1H, dd, J=2.0, 8.8), 6.56 (1H, d, J=2.0 Hz), 6.70 (1H, d, J=8.6 Hz), 6.72 (1H, d, J=8.8 Hz), 7.28 (1H, d, J=8.6 Hz), 7.42 (1H, s).

127-a-4) Preparation of 4-(1,1,1,3,3,3-hexafluoro-2-(methoxymethoxy)propan-2-yl)-1-(3-methoxy-4-vinylphenoxy)-2-propylbenzene 4-(1,1,1,3,3,3-Hexafluoro-2-(methoxymethoxy)propan-2-yl)-1-(4-iodo-3-methoxyphenoxy)-2-propylbenzene was used for a similar reaction and treatment as Example 126-a-4), and 4-(1,1,1,3,3,3-hexafluoro-2-(methoxymethoxy)propan-2-yl)-1-(3-methoxy-4-vinylphenoxy)-2-propylbenzene was obtained as a colorless oil.

$^1$H-NMR (CDCl$_3$) δ: 0.95 (3H, t, J=7.3 Hz), 1.67 (2H, qt, J=7.3, 7.8 Hz), 2.69 (2H, t, J=7.8 Hz), 3.56 (3H, s), 3.82 (3H, s), 4.86 (2H, s), 5.23 (1H, dd, J=1.7, 11.2 Hz), 5.68 (1H, dd, J=1.7, 17.8 Hz), 6.50 (1H, dd, J=2.2, 8.5), 6.58 (1H, d, J=2.2 Hz), 6.87 (1H, d, J=8.8 Hz), 6.99 (1H, dd, J=11.2, 17.8 Hz), 7.36 (1H, d, J=8.8 Hz), 7.42 (1H, d, J=8.5 Hz), 7.47 (1H, s).

127-a-5) Preparation of 2-{2-methoxy-4-[2-propy-4-(2,2,2-trifluoro-1-methoxymethoxy-1-trifluoromethyl-ethyl)-phenoxy]-phenyl}-ethanol 4-(1,1,1,3,3,3-Hexafluoro-2-(methoxymethoxy)propan-2-yl)-1-(3-methoxy-4-vinylphenoxy)-2-propylbenzene was used for a similar reaction and treatment as Example 38 b), and 2-{2-methoxy-4-[2-propyl-4-(2,2,2-trifluoro-1-methoxymethoxy-1-trifluoromethyl-ethyl)-phenoxy]-phenyl}-ethanol was obtained as a colorless oil.

$^1$H-NMR (CDCl$_3$) δ: 0.96 (3H, t, J=7.3 Hz), 1.68 (2H, qt, J=7.3, 7.8 Hz), 2.69 (2H, t, J=7.8 Hz), 2.89 (2H, t, J=6.4 Hz), 3.55 (3H, s), 3.80 (3H, s), 3.83 (2H, t, J=6.4 Hz), 4.85 (2H, s), 6.48 (1H, dd, J=2.2, 8.3 Hz), 6.59 (1H, d, J=2.2 Hz), 6.84 (1H, d, J=8.6 Hz), 7.12 (1H, d, J=8.3 Hz), 7.35 (1H, d, J=8.6 Hz), 7.46 (1H, s).

127-a-6) Preparation of 1-(2-bromoethyl)-4-(4-(1,1,3,3,3-hexafluoro-2-(methoxymethoxy)propan-2-yl)-2-propylphenoxy)-2-methoxybenzene 2-{2-Methoxy-4-[2-propyl-4-(2,2,2-trifluoro-1-methoxymethoxy-1-trifluoromethyl-ethyl)-phenoxy]-phenyl}-ethanol was used for a similar reaction and treatment as Example 38-c), and 1-(2-bromoethyl)-4-(4-(1,1,1,3,3,3-hexafluoro-2-(methoxymethoxy)propan-2-yl)-2-prop ylphenoxy)-2-methoxybenzene was obtained as a colorless oil.

¹H-NMR (CDCl₃) δ: 0.96 (3H, t, J=7.3 Hz), 1.67 (2H, qt, J=7.3, 7.8 Hz), 2.69 (2H, t, J=7.8 Hz), 3.15 (2H, t, J=7.6 Hz), 3.56 (3H, s), 3.57 (2H, t, J=7.6 Hz), 3.80 (3H, s), 4.86 (2H, s), 6.47 (1H, dd, J=2.4, 8.1), 6.58 (1H, d, J=2.4 Hz), 6.84 (1H, d, J=8.9 Hz), 7.10 (1H, d, J=8.1 Hz), 7.36 (1H, d, J=8.9 Hz), 7.47 (1H, s).

1-(2-Bromoethyl)-4-(4-(1,1,1,3,3,3-hexafluoro-2-(methoxymethoxy)propan-2-yl)-2-propylphenoxy)-2-methoxybenzene was used in place of 1-(4-(2-bromoethyl)phenoxy)-4-(1,1,1,3,3,3-hexafluoro-2-(methoxymethoxy)propan-2-yl)-2-propyl benzene in Example 38 d) for a similar reaction and treatment, and the title compound was obtained as a colorless oil.

¹H-NMR (400 MHz, CD₃OD) δ: 0.96 (3H, t, J=7.5 Hz), 1.23 (6H, d, J=6.1 Hz), 1.61 (3H, s), 1.63-1.72 (2H, m), 2.68 (2H, t, J=7.5 Hz), 2.88 (2H, t, J=6.5 Hz), 3.72 (3H, s), 3.74 (2H, t, J=6.5 Hz), 4.47-4.51 (1H, m), 6.19 (1H, dd, J=2.2, 8.0 Hz), 6.52 (1H, d, J=2.2 Hz), 6.74 (1H, d, J=8.8 Hz), 6.80 (2H, d, J=8.8 Hz), 7.25-7.29 (3H, m), 7.49 (1H, d, J=8.8 Hz), 7.60 (1H, s).

Example 128

Preparation of 3-(2-(benzyloxy)-4-(4-(1,1,1,3,3,3-hexafluoro-2-hydroxypropan-2-yl)-2-propylphenoxy) phenethyl)-5-(-(1-(1-methylethoxy)phenyl-4-yl)-5-methylimidazolidine-2,4-dione

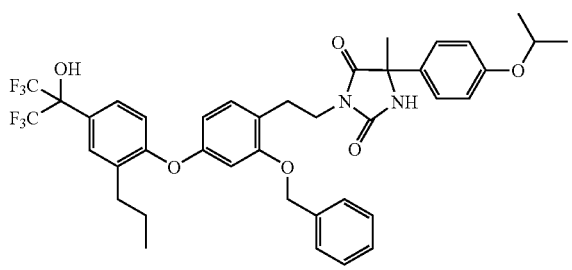

128-a-1) Preparation of 2-benzyloxy-4-fluoro-1-nitro-benzene

Benzyl iodide was used in place of methyl iodide for a similar reaction and treatment as Example 127-a-1), and 2-benzyloxy-4-fluoro-1-nitro-benzene was obtained as a colorless oil.

¹H-NMR (CDCl₃) δ: 5.23 (2H, s), 6.74 (1H, ddd, J=2.4, 7.3, 9.0 Hz), 6.83 (1H, dd, J=2.4, 10.2 Hz), 7.33-7.47 (5H, m), 7.97 (1H, dd, J=6.1, 9.0 Hz).

128-a-2) Preparation of 2-(benzyl oxy)-4-(4-(1,1,1,3,3,3-hexafluoro-2-(methoxymethoxy)propan-2-yl)-2-propylphenoxy)-1-nitrobenzene 2-Benzyloxy-4-fluoro-1-nitro-benzene was used for a similar reaction and treatment as Example 119-a-1), and 2-(benzyloxy)-4-(4-(1,1,1,3,3,3-hexafluoro-2-(methoxymethoxy)propan-2-yl)-2-propyl p henoxy)-1-nitrobenzene was obtained as a colorless oil.

¹H-NMR (CDCl₃) δ: 0.89 (3H, t, J=7.1 Hz), 1.55 (2H, qt, J=7.1, 7.8 Hz), 2.50 (2H, t, J=7.8 Hz), 3.58 (3H, s), 4.89 (2H, s), 5.18 (2H, s), 6.50 (1H, dd, J=2.2, 8.6 Hz), 6.58 (1H, d, J=2.2 Hz), 6.92 (1H, d, J=8.8 Hz), 7.31-7.39 (5H, m), 7.46 (1H, d, J=8.8 Hz), 7.54 (1H, s), 7.97 (1H, d, J=8.6 Hz).

128-a-3) Preparation of 2-benzyloxy-4-[2-propyl-4-(2,2,2-trifluoro-1-methoxymethoxy-1-trifluoromethyl-ethyl)-phenoxy]-phenylamine 2-(Benzyloxy)-4-(4-(1,1,1,3,3,3-hexafluoro-2-(methoxymethoxy)propan-2-yl)-2-propylphenoxy)-1-nitrobenzene was used for a similar reaction and treatment as Example 126-a-2), and 2-benzyl oxy-4-[2-propyl-4-(2,2,2-trifluoro-1-methoxymethoxy-1-trifluoromethyl-ethyl)-phenoxy]-phenylamine was obtained as a colorless oil.

¹H-NMR (CDCl₃) δ: 0.97 (3H, t, J=7.3 Hz), 1.68 (2H, qt, J=7.3, 7.3 Hz), 2.70 (2H, t, J=7.3 Hz), 3.55 (3H, s), 4.84 (2H, s), 5.04 (2H, s), 6.50 (1H, dd, J=2.4, 8.3 Hz), 6.61 (1H, d, J=2.4 Hz), 6.67 (1H, d, J=8.8 Hz), 6.72 (1H, d, J=8.3 Hz), 7.33-7.40 (7H, m).

128-a-4) Preparation of 2-(benzyloxy)-4-(4-(1,1,1,3,3,3-hexafluoro-2-(methoxymethoxy)propan-2-yl)-2-propylphenoxy)-1-iodobenzene 2-Benzyloxy-4-[2-propyl-4-(2,2,2-trifluoro-1-methoxymethoxy-1-trifluoromethyl-ethyl)-phenoxy]-phenylamine was used for a similar reaction and treatment as Example 126-a-3), and 2-(benzyloxy)-4-(4-(1,1,1,3,3,3-hexafluoro-2-(methoxymethoxy)propan-2-yl)-2-propylphenoxy)-1-iodobenzene was obtained as a colorless oil.

¹H-NMR (CDCl₃) δ: 0.92 (3H, t, J=7.3 Hz), 1.61 (2H, qt, J=7.3, 7.6 Hz), 2.60 (2H, t, J=7.6 Hz), 3.56 (3H, s), 4.86 (2H, s), 5.11 (2H, s), 6.36 (1H, dd, J=2.4, 8.6 Hz), 6.52 (1H, d, J=2.4 Hz), 6.78 (1H, d, J=8.9 Hz), 7.31-7.43 (6H, m), 7.47 (1H, s), 7.70 (1H, d, J=8.6 Hz).

128-a-5) Preparation of 2-(benzyloxy)-4-(4-(1,1,1,3,3,3-hexafluoro-2-(methoxymethoxy)propan-2-yl)-2-propylphenoxy)-1-vinylbenzene 2-(Benzyloxy)-4-(4-(1,1,1,3,3,3-hexafluoro-2-(methoxymethoxy)propan-2-yl)-2-propylphenoxy)-1-iodobenzene was used for a similar reaction and treatment as Example 126-a-4), and 2-(benzyloxy)-4-(4-(1,1,1,3,3,3-hexafluoro-2-(methoxymethoxy)propan-2-yl)-2-propylphenoxy)-1-vinylbenzene was obtained as a colorless oil.

¹H-NMR (CDCl₃) δ: 0.93 (3H, t, J=7.6 Hz), 1.64 (2H, qt, J=7.6, 7.6 Hz), 2.64 (2H, t, J=7.6 Hz), 3.56 (3H, s), 4.86 (2H, s), 5.05 (2H, s), 5.23 (1H, dd, J=1.5, 11.2 Hz), 5.70 (1H, dd, J=1.5, 17.8 Hz), 6.54 (1H, dd, J=2.2, 8.3 Hz), 6.58 (1H, d, J=2.2 Hz), 6.81 (1H, d, J=8.5 Hz), 7.07 (1H, dd, J=11.2, 17.8 Hz), 7.32-7.38 (6H, m), 7.46 (1H, d, J=8.3 Hz), 7.47 (1H, s).

128-a-6) Preparation of 2-{2-benzyloxy-4-[2-propyl-4-(2,2,2-trifluoro-1-methoxymethoxy-1-trifluoromethyl-ethyl)-phenoxy]-phenyl}-ethanol 2-(Benzyloxy)-4-(4-(1,1,1,3,3,3-hexafluoro-2-(methoxymethoxy)propan-2-yl)-2-propylphenoxy)-1-vinylbenzene was used for a similar reaction and treatment as Example 38-b), and 2-{2-benzyloxy-4-[2-propyl-4-(2,2,2-trifluoro-1-methoxymethoxy-1-trifluoromethyl-ethyl)-phenoxy]-phenyl}-ethanol was obtained as a colorless oil. (CDCl₃) δ: 0.94 (3H, t, J=7.6 Hz), 1.65 (2H, qt, J=7.6, 7.8 Hz), 2.66 (2H, t, J=7.8 Hz), 2.94 (2H, t, J=6.4 Hz), 3.56 (3H, s), 3.86 (2H, t, J=6.4 Hz), 4.86 (2H, s), 5.04 (2H, s), 6.52 (1H, dd, J=2.2, 8.3

Hz), 6.61 (1H, d, J=2.2 Hz), 6.79 (1H, d, J=8.8 Hz), 7.15 (1H, d, J=8.3 Hz), 7.31-7.37 (6H, m), 7.46 (1H, s).

128-a-7) Preparation of 2-(benzyloxy)-1-(2-bromoethyl)-4-(4-(1,1,1,3,3,3-hexafluoro-2-(methoxymethoxy)propan-2-yl)-2-propylphenoxy)benzene 2-{2-Benzyloxy-4-[2-propyl-4-(2,2,2-trifluoro-1-methoxymethoxy-1-trifluoromethyl-ethyl)-phenoxy]-phenyl}-ethanol was used for a similar reaction and treatment as Example 38-c), and 2-(benzyloxy)-1-(2-bromoethyl)-4-(4-(1,1,1,3,3,3-hexafluoro-2-(methoxymethoxy)propan-2-yl)-2-propylphenoxy)benzene was obtained as a colorless oil.

¹H-NMR (CDCl₃) δ: 0.94 (3H, t, J=7.3 Hz), 1.64 (2H, qt, J=7.3, 7.8 Hz), 2.65 (2H, t, J=7.8 Hz), 3.21 (2H, t, J=7.3 Hz), 3.56 (3H, s), 3.61 (2H, t, J=7.3 Hz), 4.86 (2H, s), 5.05 (2H, s), 6.51 (1H, dd, J=2.4, 8.1 Hz), 6.60 (1H, d, J=2.4 Hz), 6.79 (1H, d, J=8.6 Hz), 7.13 (1H, d, J=8.1 Hz), 7.31-7.42 (6H, m), 7.46 (1H, s).

2-(Benzyloxy)-1-(2-bromoethyl)-4-(4-(1,1,1,3,3,3-hexafluoro-2-(methoxymethoxy) propan-2-yl)-2-propylphenoxy)benzene was used in place of 1-(4-(2-bromoethyl)phenoxy)-4-(1,1,1,3,3,3-hexafluoro-2-(methoxymethoxy) propan-2-yl)-2-propylbenzene in Example 38 d) for a similar reaction and treatment, and the title compound was obtained as a colorless oil. (CDCl₃) δ: 0.95 (3H, t, J=7.1 Hz), 1.28 (6H, d, J=5.9 Hz), 1.61-1.69 (2H, m), 1.69 (3H, s), 2.65 (2H, t, J=7.3 Hz), 2.99 (2H, brs), 3.83 (2H, brs), 4.44-4.52 (1H, m), 5.02 (2H, s), 6.33 (1H, d, J=8.5 Hz), 6.54 (1H, s), 6.71 (1H, d, J=8.5 Hz), 6.82 (2H, d, J=6.6 Hz), 6.92 (1H, d, J=8.0 Hz), 7.17-7.44 (8H, m), 7.54 (1H, s).

Example 129

Preparation of 3-(4-(4-(1,1,1,3,3,3-hexafluoro-2-hydroxypropan-2-yl)-2-propylphenoxy)-2-hydroxyphenethyl)-5-(4-(1-methylethoxy)phenyl)-5-methylimidazolidine-2,4-dione

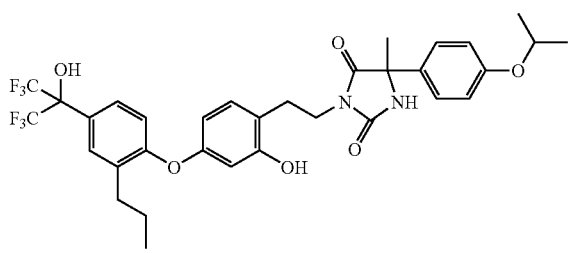

3-(2-(Benzyloxy)-4-(4-(1,1,1,3,3,3-hexafluoro-2-hydroxypropan-2-yl)-2-propylphenoxy) phenethyl)-5-(-(1-(1-methylethoxy)phenyl-4-yl)-5-methylimidazolidine-2,4-dione was used for a similar reaction and treatment as Example 121), and the title compound was obtained as a colorless oil.

¹H-NMR (CDCl₃) δ: 0.93 (3H, t, J=7.3 Hz), 1.29 (6H, d, J=6.1 Hz), 1.60-1.68 (2H, m), 1.70 (3H, s), 2.64 (2H, t, J=7.6 Hz), 2.90 (2H, t, J=7.3 Hz), 3.75 (2H, t, J=7.3 Hz), 4.45-4.51 (1H, m), 5.87 (1H, s), 6.38 (1H, dd, J=1.9, 8.3 Hz), 6.44 (1H, d, J=1.9 Hz), 6.79 (1H, d, J=8.6 Hz), 6.82 (2H, d, J=8.5 Hz), 6.92 (1H, d, J=8.3 Hz), 7.26 (2H, d, J=8.5 Hz), 7.41 (1H, d, J=8.6 Hz), 7.54 (1H, s).

Example 130

Preparation of 5-(1-(1-methylethoxy)phenyl-4-yl)-3-(2-{2-methoxymethyl-4-[2-propyl-4-(2,2,2-trifluoro-1-hydroxy-1-trifluoromethyl-ethyl)-phenoxy]-phenyl}-ethyl)imidazolidine-2,4-dione

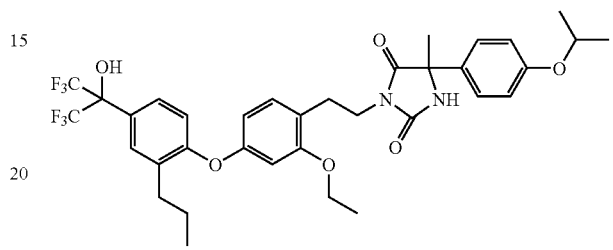

130-a-1) Preparation of {2-amino-5-[2-propyl-4-(2,2,2-trifluoro-1-methoxymethoxy-1-trifluoromethyl-ethyl)-phenoxy]-phenyl}-methanol (5-(4-(1,1,1,3,3,3-Hexafluoro-2-(methoxymethoxy)propan-2-yl)-2-propylphenoxy)-2-nitrophenyl)methanol was used for a similar reaction and treatment as Example 119-a), and {2-amino-5-[2-propyl-4-(2,2,2-trifluoro-1-methoxymethoxy-1-trifluoromethyl-ethyl)-phenoxy]-phenyl}-methanol was obtained as a colorless oil.

¹H-NMR (CDCl₃) δ: 0.97 (3H, t, J=7.0 Hz), 1.68 (2H, qt, J=7.0, 7.3 Hz), 2.71 (2H, t, J=7.3 Hz), 3.54 (3H, s), 4.66 (2H, s), 4.83 (2H, s), 6.69 (1H, d, J=8.6 Hz), 6.71 (1H, d, J=8.1 Hz), 6.82-6.86 (2H, m), 7.28 (1H, d, J=8.6 Hz), 7.41 (1H, s).

130-a-2) Preparation of 4-(4-(1,1,1,3,3,3-hexafluoro-2-(methoxymethoxy)propan-2-yl)-2-propylphenoxy)-3-iodophenylmethanol {2-Amino-5-[2-propyl-4-(2,2,2-trifluoro-1-methoxymethoxy-1-trifluoromethyl-ethyl)-phenoxy]-phenyl}-methanol was used for a similar reaction and treatment as Example 119-a), and 4-(4-(1,1,1,3,3,3-hexafluoro-2-(methoxymethoxy)propan-2-yl)-2-propylphenoxy)-3-iodophenylmethanol was obtained as a colorless oil.

¹H-NMR (CDCl₃) δ: 0.94 (3H, t, J=7.0 Hz), 1.64 (2H, qt, J=7.0, 7.8 Hz), 2.66 (2H, t, J=7.8 Hz), 3.56 (3H, s), 4.65 (2H, d, J=5.9 Hz), 4.86 (2H, s), 6.65 (1H, dd, J=2.4, 8.6 Hz), 6.85 (1H, d, J=8.9 Hz), 7.17 (1H, d, J=2.4 Hz), 7.37 (1H, d, J=8.9 Hz), 7.48 (1H, s), 7.75 (1H, d, J=8.6 Hz).

130-a-3) Preparation of 4-(1,1,1,3,3,3-hexafluoro-2-(methoxymethoxy)propan-2-yl)-1-(4-iodo-3-(methoxymethyl) phenoxy)-2-propylbenzene 4-(4-(1,1,1,3,3,3-Hexafluoro-2-(methoxymethoxy)propan-2-yl)-2-propylphenoxy)-3-iodophenylmethanol was used for a similar reaction and treatment as Example 127-a-3), and 4-(1,1,1,3,3,3-hexafluoro-2-(methoxymethoxy)propan-2-yl)-1-(4-iodo-3-(methoxymethyl) phenoxy)-2-propylbenzene was obtained as a colorless oil.

¹H-NMR (CDCl₃) δ: 0.94 (3H, t, J=7.3 Hz), 1.64 (2H, qt, J=7.3, 7.8 Hz), 2.66 (2H, t, J=7.8 Hz), 3.47 (3H, s), 3.55 (3H, s), 4.40 (2H, s), 4.85 (2H, s), 6.64 (1H, dd, J=2.7, 8.6 Hz), 6.83 (1H, d, J=8.6 Hz), 7.13 (1H, d, J=2.7 Hz), 7.36 (1H, d, J=8.6 Hz), 7.47 (1H, s), 7.75 (1H, d, J=8.6 Hz).

130-a-4) Preparation of 4-(1,1,1,3,3,3-hexafluoro-2-(methoxymethoxy)propan-2-yl)-1-(3-(methoxymethyl)-4-vinylphenoxy)-2-propylbenzene The similar reaction and treatment were conducted as Example 127-a-4), and 4-(1,1,1,3,3,3-hexafluoro-2-(methoxymethoxy)propan-2-yl)-1-(3-(methoxymethyl)-4-vinylphenoxy)-2-propylbenzene was obtained as a colorless oil.

¹H-NMR (CDCl₃) δ: 0.95 (3H, t, J=7.0 Hz), 1.66 (2H, qt, J=7.0, 7.8 Hz), 2.68 (2H, t, J=7.8 Hz), 3.42 (3H, s), 3.56 (3H, s), 4.49 (2H, s), 4.86 (2H, s), 5.31 (1H, dd, J=1.4, 10.8 Hz), 5.64 (1H, d, J=1.4, 17.3 Hz), 6.83 (1H, d, J=8.6 Hz), 6.90 (1H, dd, J=2.4, 7.8 Hz), 6.93 (1H, dd, J=10.8, 17.3 Hz), 7.03 (1H, d, J=2.4 Hz), 7.35 (1H, d, J=8.6 Hz), 7.47 (1H, s), 7.52 (1H, d, J=7.8 Hz).

130-a-5) Preparation of 2-{2-methoxymethyl-4-[2-propyl-4-(2,2,2-trifluoro-1-methoxymethoxy-1-trifluoromethyl-ethyl)-phenoxy]-phenyl}-ethanol 4-(1,1,1,3,3,3-Hexafluoro-2-(methoxymethoxy)propan-2-yl)-1-(3-(methoxymethyl)-4-vinylphenoxy)-2-propylbenzene was used for a similar reaction and treatment as Example 38 b), and 2-{2-methoxymethyl-4-[2-propyl-4-(2,2,2-trifluoro-1-methoxymethoxy-1-trifluoromethyl-ethyl)-phenoxy]-phenyl}-ethanol was obtained as a colorless oil.

¹H-NMR (CDCl₃) δ: 0.95 (3H, t, J=7.3 Hz), 1.66 (2H, qt, J=7.3, 7.3 Hz), 2.39 (1H, t, J=5.4 Hz), 2.69 (2H, t, J=7.3 Hz), 2.92 (2H, t, J=6.5 Hz), 3.44 (3H, s), 3.55 (3H, s), 3.86 (2H, dt, J=5.4, 6.5 Hz), 4.45 (2H, s), 4.85 (2H, s), 6.81 (1H, d, J=8.1 Hz), 6.92 (1H, dd, J=2.4, 8.1 Hz), 7.01 (1H, d, J=2.4 Hz), 7.24 (1H, d, J=8.1 Hz), 7.34 (1H, d, J=8.1 Hz), 7.46 (1H, s).

2-{2-Methoxymethyl-4-[2-propyl-4-(2,2,2-trifluoro-1-methoxymethoxy-1-trifluoromethyl-ethyl)-phenoxy]-phenyl}-ethanol was used for a similar reaction and treatment as 127-a-6) and the subsequent examples, and the title compound was obtained as a colorless oil.

¹H-NMR (CDCl₃) δ: 0.95 (3H, t, J=7.3 Hz), 1.30 (6H, d, J=5.7 Hz), 1.66 (2H, qt, J=7.3, 7.8 Hz), 1.75 (3H, s), 2.67 (2H, t, J=7.8 Hz), 2.90-3.00 (2H, m), 3.41 (3H, s), 3.73 (2H, t, J=7.6 Hz), 4.46 (2H, s), 4.50 (1H, sept, J=5.7 Hz), 5.78 (1H, s), 6.74 (1H, dd, J=2.4, 8.4 Hz), 6.74 (1H, d, J=8.9 Hz), 6.84 (2H, d, J=8.9 Hz), 7.00 (1H, d, J=2.4 Hz), 7.08 (1H, d, J=8.4 Hz), 7.31 (2H, d, J=8.9 Hz), 7.42 (1H, d, J=8.9 Hz), 7.54 (1H, s).

Example 131

Preparation of 2-{2-[4-(4-(1-methylethoxy)phenyl)-4-methyl-2,5-dioxo-imidazolidin-1-yl]-ethyl}-5-[2-propyl-4-(2,2,2-trifluoro-1-hydroxy-1-trifluoromethyl-ethyl)-phenoxy]-benzonitrile

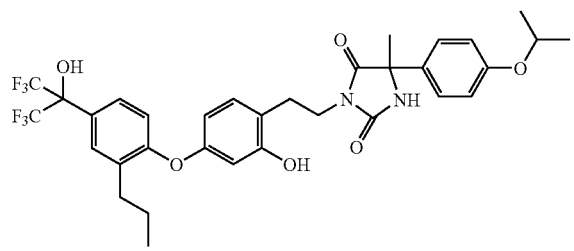

131-a-1) Preparation of 2-nitro-5-[2-propyl-4-(2,2,2-trifluoro-1-methoxymethoxy-1-trifluoromethyl-ethyl)-phenoxy]-benzonitrile 5-Fluoro-2-nitrobenzonitrile was used for a similar reaction and treatment as Example 119-a-1), and 2-nitro-5-[2-propyl-4-(2,2,2-trifluoro-1-methoxymethoxy-1-trifluoromethyl-ethyl)-phenoxy]-benzonitrile was obtained as a colorless oil.

¹H-NMR (CDCl₃) δ: 0.92 (3H, t, J=7.3 Hz), 1.60 (2H, qt, J=7.3, 7.8 Hz), 2.56 (2H, t, J=7.6 Hz), 3.59 (3H, s), 4.91 (2H, s), 7.06 (1H, d, J=8.4 Hz), 7.24 (1H, dd, J=2.4, 9.2 Hz), 7.37 (1H, d, J=2.4 Hz), 7.57 (1H, d, J=8.4 Hz), 7.63 (1H, s), 8.34 OH, d, J=9.2 Hz).

131-a-2) Preparation of 2-amino-5-[2-propyl-4-(2,2,2-trifluoro-1-methoxymethoxy-1-trifluoromethyl-ethyl)-phenoxy]-benzonitrile 2-Nitro-5-[2-propyl-4-(2,2,2-trifluoro-1-methoxymethoxy-1-trifluoromethyl-ethyl)-phenoxy]-benzonitrile was used for a similar reaction and treatment as Example 119-a), and 2-amino-5-[2-propyl-4-(2,2,2-trifluoro-1-methoxymethoxy-1-trifluoromethyl-ethyl)-phenoxy]-benzonitrile was obtained as a colorless oil.

¹H-NMR (CDCl₃) δ: 0.96 (3H, t, J=7.0 Hz), 1.66 (2H, qt, J=7.0, 7.8 Hz), 2.68 (2H, t, J=7.8 Hz), 3.55 (3H, s), 4.85 (2H, s), 6.61 (1H, d, J=8.9 Hz), 6.77 (1H, d, J=8.6 Hz), 7.05-7.10 (2H, m), 7.34 (1H, d, J=8.6 Hz), 7.45 (1H, s).

131-a-3) Preparation of 2-iodo-5-[2-propyl-4-(2,2,2-trifluoro-1-methoxymethoxy-1-trifluoromethyl-ethyl)-phenoxy]-benzonitrile 2-Amino-5-[2-propyl-4-(2,2,2-trifluoro-1-methoxymethoxy-1-trifluoromethyl-ethyl)-phenoxy]-benzonitrile was used for a similar reaction and treatment as Example 120-a), and 2-iodo-5-[2-propyl-4-(2,2,2-trifluoro-1-methoxymethoxy-1-trifluoro methyl-ethyl)-phen oxy]-benzonitrile was obtained as a colorless oil.

¹H-NMR (CDCl₃) δ: 0.92 (3H, t, J=7.6 Hz), 1.61 (2H, qt, J=7.6, 7.8 Hz), 2.60 (2H, t, J=7.8 Hz), 3.57 (3H, s), 4.87 (2H, s), 6.91 (1H, d, J=8.6 Hz), 6.93 (1H, dd, J=2.4, 8.9 Hz), 7.19 (1H, d, J=2.4 Hz), 7.46 (1H, d, J=8.6 Hz), 7.54 (1H, s), 7.83 (1H, d, J=8.9 Hz).

131-a-4) Preparation of 5-[2-propyl-4-(2,2,2-trifluoro-1-methoxymethoxy-1-trifluoromethyl-ethyl)-phenoxy]-2-vinyl-benzonitrile 2-Iodo-5-[2-propyl-4-(2,2,2-trifluoro-1-methoxymethoxy-1-trifluoromethyl-ethyl)-phenoxy]-benzonitrile was used for a similar reaction and treatment as Example 126-a-4), and 5-[2-propyl-4-(2,2,2-trifluoro-1-methoxymethoxy-1-trifluoromethyl-ethyl)-phenoxy]-2-vinyl-benzonitrile was obtained as a colorless oil.

$^1$H-NMR (CDCl$_3$) δ: 0.93 (3H, t, J=7.3 Hz), 1.63 (2H, qt, J=7.3, 7.3 Hz), 2.63 (2H, t, J=7.3 Hz), 3.57 (3H, s), 4.88 (2H, s), 5.50 (1H, d, J=10.8 Hz), 5.87 (1H, d, J=17.6 Hz), 6.90 (1H, d, J=8.9 Hz), 7.04 (1H, dd, J=10.8, 17.6 Hz), 7.17 (1H, d, J=2.2 Hz), 7.19 (1H, dd, J=2.2, 7.6 Hz), 7.44 (1H, d, J=8.9 Hz), 7.53 (1H, s), 7.66 (1H, d, J=7.6 Hz).

131-a-5) Preparation of 2-oxiranyl-5-[2-propyl-4-(2,2,2-trifluoro-1-methoxymethoxy-trifluoromethyl-ethyl)-phenoxy]-benzonitrile 5-[2-Propyl-4-(2,2,2-trifluoro-1-methoxymethoxy-1-trifluoromethyl-ethyl)-phenoxy]-2-vinyl-benzonitrile (14 mg, 0.030 mmol) was dissolved in dichloromethane (300 μL). The resultant mixture was added with sodium hydrogen carbonate (7.5 mg, 0.089 mmol) and 3-chloroperoxybenzoic acid (8.5 mg, 0.030 mmol) under ice-cold conditions and stirred at room temperature for 1.5 hours. Subsequently, the resultant mixture was further added with sodium hydrogen carbonate (7.5 mg, 0.089 mmol) and 3-chloroperoxybenzoic acid (8.5 mg, 0.030 mmol) under ice-cold conditions and stirred at room temperature overnight. The reaction solution was added with a saturated aqueous solution of sodium sulfite and a saturated aqueous solution of sodium hydrogen carbonate, and extracted with ethyl acetate. The organic layer was washed with a saturated aqueous solution of sodium hydrogen carbonate and brine, dried over sodium sulfate, and concentrated in vacuo. The obtained residue was purified using silica-gel column chromatography (hexane/ethyl acetate), and 2-oxiranyl-5-[2-propyl-4-(2,2,2-trifluoro-1-methoxymethoxy-1-trifluoromethyl-ethyl)-phenoxy]-benzonitrile (5.5 mg, yield 38%) was obtained as a yellow oil.

$^1$H-NMR (CDCl$_3$) δ: 0.93 (3H, t, J=7.6 Hz), 1.62 (2H, qt, J=7.6, 7.8 Hz), 2.62 (2H, t, J=7.8 Hz), 2.77 (1H, dd, J=2.2, 5.7 Hz), 3.27 (1H, dd, J=3.8, 5.7 Hz), 3.57 (3H, s), 4.23 (1H, dd, J=2.2, 3.8 Hz), 4.88 (2H, s), 6.89 (1H, d, J=8.6 Hz), 7.18-7.22 (2H, m), 7.30 (1H, d, J=8.6 Hz), 7.45 (1H, d, J=8.6 Hz), 7.53 (1H, s).

131-a-6) Preparation of 2-(2-hydroxy-ethyl)-5-[2-propyl-4-(2,2,2-trifluoro-1-methoxymethoxy-1-trifluoromethyl-ethyl)-phenoxy]-benzonitrile A solution of 2-oxiranyl-5-[2-propyl-4-(2,2,2-trifluoro-1-methoxymethoxy-1-trifluoromethyl-ethyl)-phenoxy]-benzonitrile (5.0 mg, 0.0102 mmol) in tetrahydrofuran (200 μL) was sequentially added with boron trifluoride diethyl ether (2.5 μL, 0.0204 mmol) and sodium cyanoborohydride (2.6 mg, 0.0409 mmol) under ice-cold conditions, and stirred at room temperature for 2 hours. Subsequently, the resultant mixture was further sequentially added with boron trifluoride diethyl ether (2.5 μL, 0.0204 mmol) and sodium cyanoborohydride (2.6 mg, 0.0409 mmol) under ice-cold conditions, and stirred at room temperature overnight. After completion of the reaction, the reaction solution was added with water and extracted with ethyl acetate. The organic layer was washed with a saturated aqueous solution of sodium hydrogen carbonate and brine, dried over sodium sulfate, and concentrated in vacuo. The obtained residue was purified using column chromatography (hexane/ethyl acetate), and 2-(2-hydroxy-ethyl)-5-[2-propyl-4-(2,2,2-trifluoro-1-methoxymethoxy-1-trifluoromethyl-ethyl)-phenoxy]-benzonitrile (2.2 mg, yield 44%) was obtained as a yellow oil.

$^1$H-NMR (CDCl$_3$) δ: 0.94 (3-1, t, J=7.6 Hz), 1.63 (2H, qt, J=7.6, 7.8 Hz), 2.63 (2H, t, J=7.8 Hz), 3.09 (2H, t, J=5.9 Hz), 3.57 (3H, s), 3.92-3.98 (2H, m), 4.87 (2H, s), 6.87 (1H, d, J=8.6 Hz), 7.16 (1H, dd, J=2.4, 8.1 Hz), 7.22 (1H, d, J=2.4 Hz), 7.38 (1H, d, J=8.1 Hz), 7.42 (1H, d, J=8.6 Hz), 7.52 (1H, s).

2-(2-Hydroxy-ethyl)-5-[2-propyl-4-(2,2,2-trifluoro-1-methoxymethoxy-1-trifluoromethyl-ethyl)-phenoxy]-benzonitrile was used for a similar reaction and treatment as 127-a-6) and the subsequent examples, and the title compound was obtained as a colorless oil.

$^1$H-NMR (CDCl$_3$) δ: 0.94 (3H, t, J=7.3 Hz), 1.28 (6H, d, J=5.7 Hz), 1.63 (2H, qt, J=7.3, 7.8 Hz), 1.73 (3H, s), 2.61 (2H, t, J=7.8 Hz), 3.14 (2H, t, J=5.7 Hz), 3.86 (2H, t, J=5.7 Hz), 4.47 (1H, sept, J=5.7 Hz), 5.86 (1H, s), 6.75 (1H, d, J=8.6 Hz), 6.83 (2H, d, J=8.9 Hz), 6.93 (1H, dd, J=2.2, 8.6 Hz), 7.09 (1H, d, J=7.3 Hz), 7.11 (1H, d, J=2.2 Hz), 7.30 (2H, d, J=8.9 Hz), 7.51 (1H, d, J=7.3 Hz), 7.60 (1H, s).

Example 132

Preparation of 2-{2-[4-(2,3-dihydro-benzo[1,4]dioxin-6-yl)-4-methyl-2,5-dioxo-imidazolidin-1-yl]-ethyl}-5-[2-propyl-4-(2,2,2-trifluoro-1-hydroxy-1-trifluoromethyl-ethyl)-phenoxy]-benzonitrile

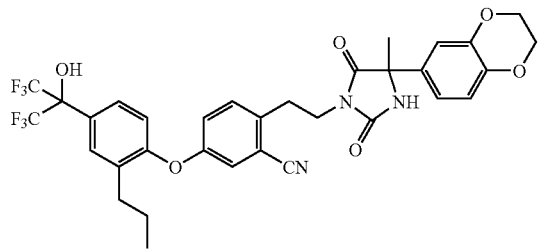

5-(2,3-Dihydro-benzo[1,4]dioxin-6-yl)-5-methylimidazolidine-2,4-dione was used in place of 5-(benzo[d][1,3]dioxol-5-yl)-5-methylimidazolidine-2,4-dione in Example 131 for a similar reaction and treatment, and the title compound was obtained as a colorless oil.

$^1$H-NMR (CDCl$_3$) δ: 0.94 (3H, t, J=7.3 Hz), 1.63 (2H, qt, J=7.3, 7.8 Hz), 1.71 (3H, s), 2.62 (2H, t, J=7.8 Hz), 3.14 (2H, t, J=6.5 Hz), 3.86 (2H, t, J=−6.5 Hz), 4.14-4.18 (4H, m), 5.86 (1H, s), 6.75 (1H, d, J=8.4 Hz), 6.83 (1H, d, J=8.1 Hz), 6.88 (1H, dd, J=1.9, 8.1 Hz), 6.92 (1H, d, J=1.9 Hz), 6.95 (1H, dd, J=2.4, 8.4 Hz), 7.10 (1H, d, J=8.6 Hz), 7.12 (1H, d, J=2.4 Hz), 7.51 (1H, d, J=8.6 Hz), 7.60 (1H, s).

Example 133

Preparation of 3-((4-(4-(1,1,1,3,3,3-hexafluoro-2-hydroxypropan-2-yl)-2-propylphenoxy)pyridin-2-yl)methyl)-5-(5-(1-methylethoxy)pyridin-2-yl)-5-methylimidazolidine-2,4-dione

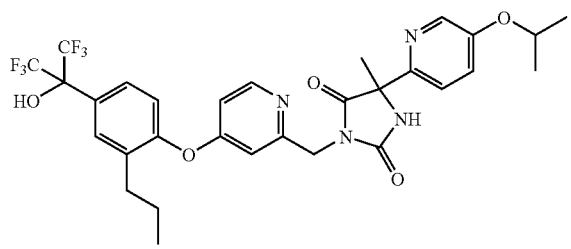

5-[5-(1-Methylethoxy)pyridin-2-yl]-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a colorless oil.

$^{11}$H-NMR (CDCl$_3$) δ: 0.87 (3H, t, J=7.3 Hz), 1.30 (3H, d, J=5.9 Hz), 1.31 (3H, d, J=5.9 Hz), 1.51-1.65 (2H, m), 1.79 (3H, s), 2.56 (2H, t, J=7.3 Hz), 4.60-4.69 (1H, m), 4.76 (2H, s), 6.75 (1H, dd, J=2.4, 5.9 Hz), 7.04 (1H, d, J=2.4 Hz), 7.13 (1H, d, J=8.6 Hz), 7.35 (1H, dd, J=3.0, 8.9 Hz), 7.51 (1H, d, J=8.9 Hz), 7.64 (1H, d, J=8.6 Hz), 7.71 (1H, s), 8.17 (1H, d, J=3.0 Hz), 8.34 (1H, d, J=5.9 Hz).

Example 134

Preparation of 5-(2,2-dimethyl-2,3-dihydrobenzofuran-5-yl)-3-((4-(4-(1,1,1,3,3,3-hexafluoro-2-hydroxypropan-2-yl)-2-propylphenoxy)pyridin-2-yl)-methyl)-5-methylimidazolidine-2,4-dione

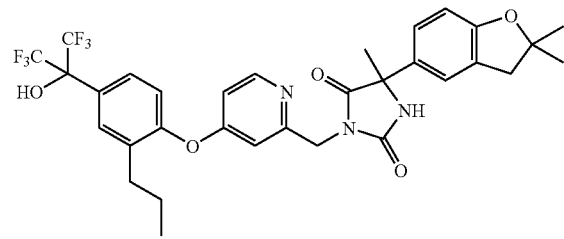

134-a) Preparation of 5-(2,2-dimethyl-2,3-dihydrobenzofuran-5-yl)-5-methylimidazolidine-2,4-dione 134-a-1) Preparation of 1-(4-(2-methylallyloxy)phenyl)ethanone 1-(4-Hydroxyphenyl)ethanone (1.36 g, 10 mmol) was dissolved in acetone (50 mL), and the resultant mixture was sequentially added with tetrabutylammonium iodide (370 mg, 1.0 mmol), potassium carbonate (2.76 g, 20 mmol), and 3-chloro-2-methyl-1-propene (1.5 mL, 15 mmol), and stirred at 70° C. overnight. The reaction solution was filtered, washed with acetone, and concentrated in vacuo. The resultant residue was added with water and ethyl acetate and extracted with ethyl acetate. The organic layer was washed with 1N aqueous solution of sodium hydroxide and brine, dried over anhydrous sodium sulfate, and concentrated in vacuo. 1-(4-(2-methylallyloxy)phenyl)ethanone (1.71 g, yield 90%) was obtained as a colorless oil.

$^1$H-NMR (CDCl$_3$) δ: 1.84 (3H, s), 2.56 (3H, s), 4.50 (2H, s), 4.95-5.15 (2H, m), 6.95 (2H, d, J=8.9 Hz), 7.93 (2H, d, J=8.9 Hz).

134-a-2) Preparation of 1-(2,2-dimethyl-2,3-dihydrobenzofuran-5-yl)ethanone 1-(4-(2-Methylallyloxy)phenyl)ethanone (85 mg, 0.450 mmol) was dissolved in PEG400 (0.3 mL), and stirred at 250° C. for 2 hours under microwave irradiation. The reaction solution was added with water, extracted with ethyl acetate, washed with brine, dried over sodium sulfate, and concentrated in vacuo. The obtained residue was purified using silica-gel column chromatography (hexane/ethyl acetate), and 1-(2,2-dimethyl-2,3-dihydrobenzofuran-5-yl)ethanone (42 mg, yield 50%) was obtained as a yellow oil.

$^1$H-NMR (CDCl$_3$) δ: 1.50 (6H, s), 2.54 (3H, s), 3.04 (2H, s), 6.74 (1H, d, J=9.2 Hz), 7.78-7.81 (2H, m).

134-a-3) Preparation of 5-(2,2-dimethyl-2,3-dihydrobenzofuran-5-yl)-5-methylimidazolidine-2,4-dione 1-(2,2-Dimethyl-2,3-dihydrobenzofuran-5-yl)ethanone was used for a similar reaction and treatment as Example 1-a), and 5-(2,2-dimethyl-2,3-dihydrobenzofuran-5-yl)-5-methylimidazolidine-2,4-dione was obtained as a white crystal.

$^1$H-NMR (CDCl$_3$) δ: 1.43 (6H, s), 1.72 (3H, s), 3.02 (2H, s), 6.64 (1H, d, J=8.4 Hz), 7.21 (1H, d, J=8.4 Hz), 7.28 (1H, s).

5-(2,2-Dimethyl-2,3-dihydrobenzofuran-5-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (CDCl$_3$) δ: 0.89 (3H, t, J=7.6 Hz), 1.45 (6H, s), 1.57 (2H, qt, J=7.6, 7.8 Hz), 1.81 (3H, s), 2.53 (2H, t, J=7.8 Hz), 2.99 (2H, s), 3.78 (1H, s), 4.77 (2H, s), 5.92 (1H, s), 6.65-6.70 (3H, m), 7.01 (1H, d, J=8.9 Hz), 7.22 (1H, dd, J=1.9, 8.6 Hz), 7.32 (1H, d, J=1.9 Hz), 7.58 (1H, d, J=8.9 Hz), 7.64 (1H, s), 8.33 (1H, d, J=6.8 Hz).

Example 135

Preparation of 3-((4-(4-(1,1,1,3,3,3-hexafluoro-2-hydroxypropan-2-yl)-2-propylphenoxy)pyridin-2-yl)methyl)-5-(3-(1-methylethoxy)phenyl)-5-methylimidazolidine-2,4-dione

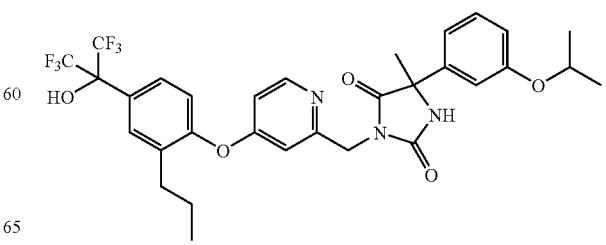

135-a) Preparation of 5-[3-(1-methylethoxy)phenyl]-5-methylimidazolidine-2,4-dione 135-a-1) Preparation of 1-(3-(1-methylethoxy)phenyl)ethanone 1-(3-Hydroxyphenyl)ethanone (1.36 g, 10 mmol) was dissolved in acetone (50 mL), and the resultant mixture was sequentially added with potassium carbonate (2.76 g, 20 mmol) and 1-methylethyl iodide (1.5 mL, 15 mmol), and stirred at 70° C. overnight. The reaction solution was filtered, washed with acetone, and concentrated in vacuo. The resultant residue was added with water and ethyl acetate and extracted with ethyl acetate. The organic layer was washed with 1N aqueous solution of sodium hydroxide and brine, dried using anhydrous sodium sulfate, and concentrated in vacuo. 1-(3-(1-methylethoxy)phenyl)ethanone (1.67 g, yield 94%) was obtained as a yellow oil.

$^1$H-NMR (CDCl$_3$) δ: 1.35 (6H, d, J=6.0 Hz), 2.55 (3H, s), 4.63 (1H, sept, J=6.0 Hz), 7.09 (1H, dd, J=2.4, 8.3 Hz), 7.35 (1H, t, J=8.0 Hz), 7.48-7.52 (2H, m).

135-a-2) Preparation of 5-[3-(1-methylethoxy)phenyl]-5-methylimidazolidine-2,4-dione 1-[3-(1-Methylethoxy)phenyl]ethanone was used for a similar reaction and treatment as Example 1-a), and 5-[3-(1-methylethoxy)phenyl]-5-methylimidazolidine-2,4-dione was obtained as a white crystal.

$^1$H-NMR (CD$_3$OD) δ: 1.30 (6H, d, J=6.0 Hz), 1.73 (3H, s), 4.60 (1H, sept, J=6.0 Hz), 6.85 (1H, dd, J=1.6, 8.3 Hz), 7.03-7.10 (2H, m), 7.27 (1H, t, J=8.3 Hz).

5-[3-(1-Methylethoxy)phenyl]-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (CDCl$_3$) δ: 0.88 (3H, t, J=7.3 Hz), 1.32 (6H, d, J=5.9 Hz), 1.56 (2H, qt, J=7.3, 7.8 Hz), 1.82 (3H, s), 2.52 (2H, t, J=7.8 Hz), 4.55 (1H, sept, J=5.9 Hz), 4.77 (2H, s), 6.00 (1H, s), 6.65-6.68 (2H, m), 6.83-6.87 (1H, m), 7.01 (1H, d, J=8.6 Hz), 7.04-7.08 (2H, m), 7.24-7.30 (1H, m), 7.57 (1H, d, J=8.6 Hz), 7.64 (1H, s), 8.33 (1H, d, J=6.2 Hz).

Example 136

Preparation of 5-(4-(cyclopropylthio)phenyl)-3-((4-(4-(1,1,1,3,3,3-hexafluoro-2-hydroxypropan-2-yl)-2-propylphenoxy)pyridin-2-yl)methyl)-5-methylimidazolidine-2,4-dione

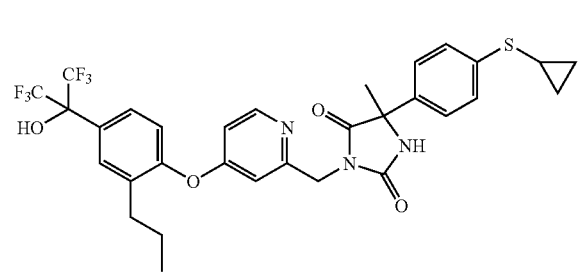

a) Preparation of 5-(4-(cyclopropylthio)phenyl)-5-methylimidazolidine-2,4-dione

Dichloromethane (6.7 mL) was sequentially added with acetyl chloride (189 μL 2.66 mmol) and aluminum chloride (267 mg, 2.0 mmol) at 0° C. The resultant mixture was stirred at 0° C. for 10 minutes, then added with a solution of cyclopropyl(phenyl)sulfane (200 mg, 1.33 mmol) in dichloromethane (890 μL), and stirred at 0° C. for 0.5 hour. The reaction solution was added with 5% aqueous solution of hydrochloric acid and extracted with ethyl acetate. The organic layer was washed with a saturated aqueous Solution of sodium hydrogen carbonate and brine, dried using anhydrous sodium sulfate, and concentrated in vacuo. The obtained residue was purified using silica-gel column chromatography (hexane/ethyl acetate), and 1-(4-(cyclopropylthio)phenyl)ethanone (181 mg, yield 71%) was obtained as a colorless oil.

$^1$H-NMR (CDCl$_3$) δ: 0.69-0.75 (2H, m), 1.12-1.19 (2H, m), 2.16-2.25 (1H, m), 2.58 (3H, s), 7.41 (2H, d, J=8.9 Hz), 7.87 (2H, d, J=8.9 Hz).

1-(4-(Cyclopropylthio)phenyl)ethanone was used for a similar reaction and treatment as Example 1-a), and 5-(4-(cyclopropylthio)phenyl)-5-methylimidazolidine-2,4-dione was obtained as a white crystal.

$^1$H-NMR (CDCl$_3$) δ: 0.56-0.62 (2H, m), 1.05-1.12 (2H, m), 1.74 (3H, s), 2.18-2.26 (1H, m), 7.34-7.44 (4H, m).

5-(4-(Cyclopropylthio)phenyl)-5-methylimidazolidine-2,4-dione was used in place of 5-(benzo[1,3]-dioxol-5-yl)-5-methylimidazolidine-2,4-dione in Example 40 f) for a similar reaction and treatment, and the title compound was obtained as a yellow oil.

$^1$H-NMR (CDCl$_3$) δ: 0.65-0.69 (2H, m), 0.88 (3H, t, J=7.3 Hz), 1.04-1.11 (2H, m), 1.57 (2H, qt, J=7.3, 7.6 Hz), 1.82 (3H, s), 2.12-2.20 (1H, m), 2.52 (2H, t, J=7.6 Hz), 4.77 (2H, s), 6.09 (1H, s), 6.66 (1H, s), 6.67 (1H, d, J=5.4 Hz), 7.01 (1H, d, J=8.9 Hz), 7.35 (2H, d, J=8.6 Hz), 7.43 (2H, d, J=8.6 Hz), 7.58 (1H, d, J=8.9 Hz), 7.64 (1H, s), 8.34 (1H, d, J=5.4 Hz).

Example 137

Preparation of 3-((4-(4-(1,1,1,3,3,3-hexafluoro-2-hydroxypropan-2-yl)-2-propylphenoxy)pyridin-2-yl)methyl)-5-(4-(1-methylethyl)phenyl)-5-methylimidazolidine-2,4-dione

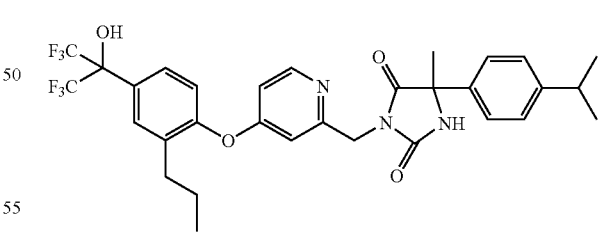

5-(4-(1-Methylethyl)phenyl)-5-methylimidazolidine-2,4-dione was used in place of 5-(benzo[d][1,3]dioxol-5-yl)-5-methylimidazolidine-2,4-dione in Example 400 for a similar reaction and treatment, and the title compound was obtained as a yellow oil.

$^1$H-NMR (270 MHz, CD$_3$OD) δ: 0.86 (3H, t, J=7.3 Hz), 1.22 (6H, d, J=6.7 Hz), 1.54 (2H, qt, J=7.3, 7.6 Hz), 1.72 (3H, s), 2.50 (2H, t, J=7.6 Hz), 2.89 (1H, sept, J=6.7 Hz), 4.70 (2H, s), 6.66 (1H, d, J=2.2 Hz), 6.80 (1H, dd, J=2.6, 5.8 Hz), 7.09

(1H, d, J=9.0 Hz), 7.25 (2H, d, J=8.5 Hz), 7.42 (2H, d, J=8.5 Hz), 7.63 (1H, d, J=9.0 Hz), 7.70 (1H, s), 8.33 (1H, d, J=5.8 Hz).

Example 138

Preparation of 5-(4-(1,1-dimethylethyl)phenyl)-3-((4-(4-(1,1,1,3,3,3-hexafluoro-2-hydroxypropan-2-yl)-2-propylphenoxy)pyridin-2-yl)methyl)-5-methylimidazolidine-2,4-dione

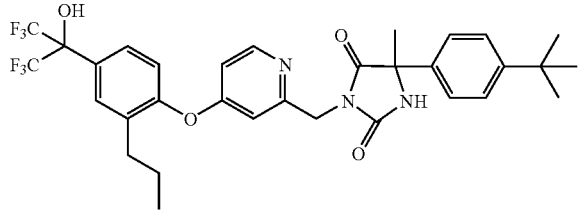

5-(4-(1,1-Dimethylethyl)phenyl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (CDCl$_3$) δ: 0.88 (3H, t, J=7.4 Hz), 1.30 (9H, s), 1.56 (2H, qt, J=7.6, 7.4 Hz), 1.78 (3H, s), 2.45 (2H, t, J=7.6 Hz), 2.45 (2H, t, J=7.6 Hz), 5.03 (1H, d, J=17.2 Hz), 5.13 (1H, d, J=17.2 Hz), 6.92 (1H, s), 7.06 (1H, d, J=8.5 Hz), 7.13-7.28 (1H, m), 7.41 (4H, s), 7.70 (1H, d, J=8.5 Hz), 7.76 (1H, s), 8.71 (1H, d, J=6.8 Hz).

Example 139

Preparation of 5-(3-fluoro-4-(1-methyl ethoxy)phenyl)-3-((4-(4-(1,1,1,3,3,3-hexafluoro-2-hydroxypropan-2-yl)-2-propylphenoxy)pyridin-2-yl)methyl)-5-methylimidazolidine-2,4-dione

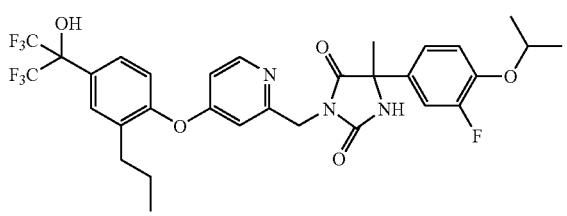

5-(4-(3-Fluoro-4-(1-methylethoxy))phenyl)-5-methylimidazolidine-2,4-dione was used in place of 5-(benzo[d][1,3]dioxol-5-yl)-5-methylimidazolidine-2,4-dione in Example 401) for a similar reaction and treatment, and the title compound was obtained as a yellow oil.

$^1$H-NMR (CD$_3$OD) δ: 0.86 (3H, t, J=7.3 Hz), 1.31 (6H, d, J=5.9 Hz), 1.56 (2H, qt, J=7.6, 7.3 Hz), 1.71 (3H, s), 2.52 (2H, t, J=7.6 Hz), 4.59 (1H, sept, J=5.9 Hz), 4.89 (2H, s), 6.68 (1H, d, J=2.2 Hz), 6.79 (1H, dd, J=2.6, 5.9 Hz), 7.08-7.13 (1H, m), 7.21-7.32 (3H, m), 7.64 (1H, d, J=8.6 Hz), 7.70 (1H, s), 8.33 (1H, d, J=5.9 Hz).

Example 140

Preparation of 3-((4-(4-(1,1,1,3,3,3-hexafluoro-2-hydroxypropan-2-yl)-2-propylphenoxy)pyridin-2-yl)methyl)-5-methyl-5-(4-(methylthio)phenyl)imidazolidine-2,4-dione

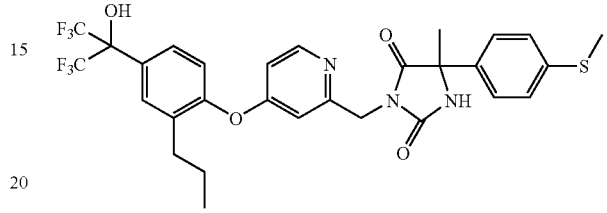

5-(4-(Methylthio)phenyl)-5-methylimidazolidine-2,4-dione was used in place of 5-(benzo[d][1,3]dioxol-5-yl)-5-methylimidazolidine-2,4-dione in Example 401) for a similar reaction and treatment, and the title compound was obtained as a yellow oil.

$^1$H-NMR (270 MHz, CDCl$_3$) δ: 0.88 (3H, t, J=7.3 Hz), 1.56 (2H, qt, J=7.3, 7.8 Hz), 1.78 (3H, s), 2.44 (2H, t, J=7.8 Hz), 2.48 (3H, s), 5.09 (2H, s), 6.87 (1H, s), 7.17 (1H, d, J=6.8 Hz), 7.23 (1H, d, J=2.4 Hz), 7.26 (2H, d, J=8.4 Hz), 7.41 (2H, d, J=8.4 Hz), 7.68-7.76 (2H, m), 8.70 (1H, d, J=6.8 Hz).

Example 141

Preparation of 3-((4-(4-(1,1,1,3,3,3-hexafluoro-2-hydroxypropan-2-yl)-2-propylphenoxy)pyridin-2-yl)methyl)-5-(3-methoxyphenyl)-5-methylimidazolidine-2,4-dione

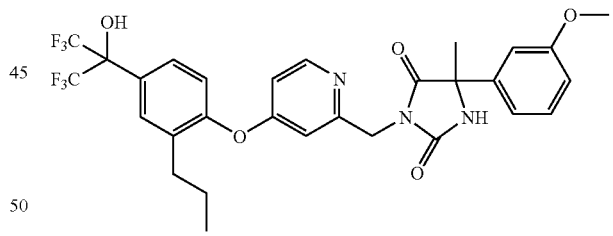

141-a) Preparation of 5-(4-(3-methoxy)phenyl)-5-methylimidazolidine-2,4-dione 4-(3-Methoxy)phenyl)-1-ethanone was used for a similar reaction and treatment as Example 1-a), and 5-(4-(3-methoxy)phenyl)-5-methylimidazolidine-2,4-dione was obtained as a white crystal.

$^1$H-NMR (270 MHz, DMSO) δ: 1.62 (3H, s), 3.58 (3H, s), 6.88-7.05 (3H, 7.28-7.34 (1H, m), 8.59 (1H, s).

5-(4-(3-Methoxy)phenyl)-5-methylimidazolidine-2,4-dione was used in place of 5-(benzo[d][1,3]dioxol-5-yl)-5-methylimidazolidine-2,4-dione in Example 401) for a similar reaction and treatment, and the title compound was obtained as a yellow oil.

¹H-NMR (270 MHz, CDCl₃) δ: 0.88 (3H, t, J=7.3 Hz), 1.56 (2H, qt, J=7.3, 7.8 Hz), 1.78 (3H, s), 2.45 (2H, t, J=7.8 Hz), 3.82 (3H, s), 5.05 (1H, d, J=16.9 Hz), 5.23 (1H, d, J=16.9 Hz), 6.88 (1H, dd, J=2.2, 8.6 Hz), 6.92 (1H, s), 7.05-7.34 (5H, m), 7.70 (1H, d, J=8.1 Hz), 7.76 (1H, s), 8.71 (1H, d, J=6.5 Hz).

Example 142

Preparation of 3-((4-(4-(1,1,1,3,3,3-hexafluoro-2-hydroxypropan-2-yl)-2-propylphenoxy)pyridin-2-yl)methyl)-5-methyl-5-(pyridin-2-yl)imidazolidine-2,4-dione

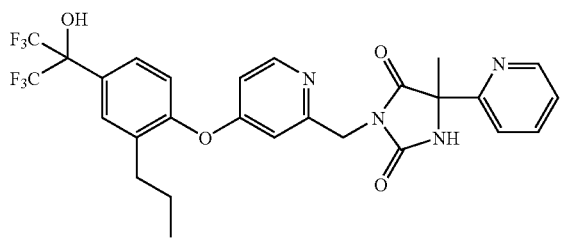

5-(Pyridin-2-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

¹H-NMR (270 MHz, CD₃OD) δ: 0.88 (3H, t, J=7.3 Hz), 1.58 (2H, qt, J=7.4, 7.3 Hz), 1.93 (3H, s), 2.56 (2H, t, J=7.4 Hz), 4.87 (1H, d, J=17.6 Hz), 5.00 (1H, d, J=17.6 Hz), 7.31 (1H, d, J=5.9 Hz), 7.32 (1H, d, J=6.9 Hz), 7.64-7.76 (3H, m), 7.82 (1H, s), 7.92 (1H, d, J=8.4 Hz), 8.23 (1H, t, J=7.8 Hz), 8.64 (1H, d, J=6.9 Hz), 8.68 (1H, d, J=7.8 Hz).

Example 143

Preparation of 3-((4-(4-(1,1,1,3,3,3-hexafluoro-2-hydroxypropan-2-yl)-2-propylphenoxy)pyridin-2-yl)methyl)-5-methyl-5-(pyridin-3-yl)imidazolidine-2,4-dione

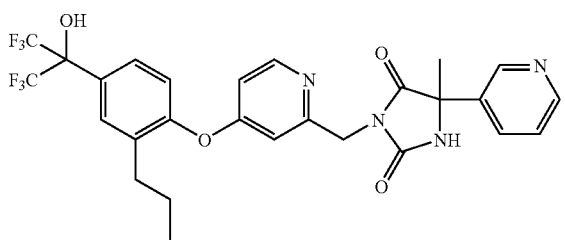

5-Methyl-5-(pyridin-3-yl)imidazolidine-2,4-dione was used in place of 5-(benzo[d][1,3]dioxol-5-yl)-5-methylimidazolidine-2,4-dione in Example 400 for a similar reaction and treatment, and the title compound was obtained as a colorless oil.

¹H-NMR (270 MHz, CD₃OD) δ: 0.89 (3H, t, J=7.3 Hz), 1.51-1.64 (2H, m), 1.89 (3H, s), 2.56 (2H, t, J=7.6 Hz), 4.85 (1H, d, J=18.4 Hz), 4.93 (1H, d, J=18.4 Hz), 7.27-7.35 (3H, m), 7.73 (1H, d, J=8.4 Hz), 7.81 (1H, s), 8.10-8.19 (1H, m), 8.59-8.62 (1H, m), 8.81-8.88 (2H, m), 9.04 (1H, s).

Example 144

Preparation of 3-((4-(4-(1,1,1,3,3,3-hexafluoro-2-hydroxypropan-2-yl)-2-propylphenoxy)pyridin-2-yl)methyl)-5-methyl-5-(6-(2,2,2-trifluoroethoxy)pyridin-3-yl)imidazolidine-2,4-dione

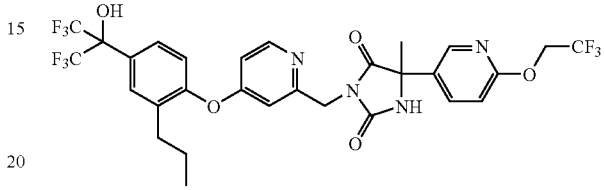

5-(2-Trifluoroethoxypyridin-5-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

¹H-NMR (270 MHz, CD₃OD) δ: 0.87 (3H, t, J=7.3 Hz), 1.57 (2H, qt, J=7.6, 7.3 Hz), 1.76 (3H, s), 2.51 (2H, t, J=7.6 Hz), 4.83-4.94 (4H, m), 6.94 (1H, d, J=8.4 Hz), 7.20 (1H, s), 7.27 (1H, d, J=8.4 Hz), 7.37 (1H, d, J=8.4 Hz), 7.75 (1H, d, J=8.4 Hz), 7.80 (1H, s), 7.91 (1H, dd, J=2.6, 8.4 Hz), 8.27 (1H, d, J=2.2 Hz), 8.63 (1H, d, J=8.4 Hz).

Example 145

Preparation of 3-((4-(4-(1,1,1,3,3,3-hexafluoro-2-hydroxypropan-2-yl)-2-propylphenoxy)pyridin-2-yl)methyl)-5-methyl-5-(naphthalen-2-yl)imidazolidine-2,4-dione

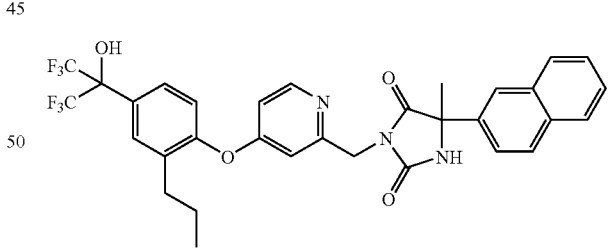

5-(Naphthalen-2-yl)-5-methylimidazolidine-2,4-dione was used in place of 5-(benzo[d][1,3]dioxol-5-yl)-5-methylimidazolidine-2,4-dione in Example 400 for a similar reaction and treatment, and the title compound was obtained as a yellow oil.

¹H-NMR (400 MHz, CD₃OD) δ: 0.77 (3H t, J=7.3 Hz), 1.44 (2H, qt, J=7.3, 7.6 Hz), 1.83 (3H, s), 2.37 (2H, t, J=7.6 Hz), 4.94 (2H, s), 7.10 (1H, d, J=2.6 Hz), 7.19 (1H, d, J=8.6 Hz), 7.29 (1H, dd, J=6.8, 2.6 Hz), 7.51-7.53 (2H, m), 7.64 (1H, dd, J=8.8, 2.0 Hz), 7.68 (1H, d, J=8.3 Hz), 7.74 (1H, s), 7.88-7.92 (3H, m), 7.99 (1H, s), 8.59 (1H, d, J=6.8 Hz).

Example 146

Preparation of 3-((4-(4-(1,1,1,3,3,3-hexafluoro-2-hydroxypropan-2-yl)-2-propylphenoxy)pyridin-2-yl)methyl)-5-methyl-5-(pyridin-4-yl)imidazolidine-2,4-dione

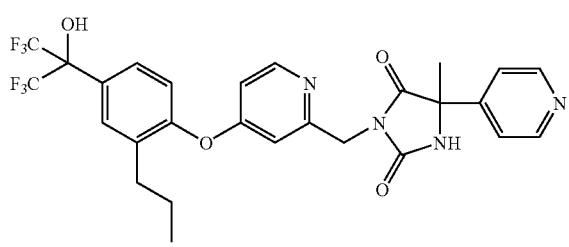

5-(Pyridin-4-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (400 MHz, CD$_3$OD) δ: 0.89 (3H, t, J=7.3 Hz), 1.59 (2H, qt, J=7.3, 7.6 Hz), 1.89 (3H, s), 2.56 (2H, t, J=7.6 Hz), 4.98 (2H, s), 7.30 (1H, d, J=8.7 Hz), 7.33 (1H, dd, J=6.8. 2.4 Hz), 7.35 (1H, s), 7.74 (1H, d, J=8.7 Hz), 7.81 (1H, s), 8.32 (2H, d, J=6.8 Hz), 8.62 (1H, d, J=6.8 Hz), 8.93 (2H, d, J=6.8 Hz).

Example 147

Preparation of 3-((4-(4-(1,1,1,3,3,3-hexafluoro-2-hydroxypropan-2-yl)-2-propylphenoxy)pyridin-2-yl)methyl)-5-methyl-5-(pyrazin-2-yl)imidazolidine-2,4-dione

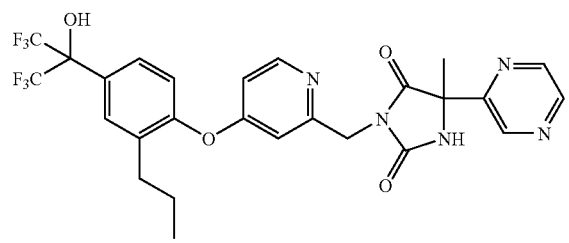

5-(Pyrazin-1-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (400 MHz, CD$_3$OD) δ: 0.88 (3H, t, J=7.3 Hz), 1.60 (2H, qt, J=7.3, 7.6 Hz), 1.90 (3H, s), 2.56 (2H, t, J=7.6 Hz), 5.04 (2H, s), 7.27 (1H, dd, J=2.4, 6.7 Hz), 7.29 (1H, d, J=8.8 Hz), 7.43 (1H, d, J=2.4 Hz), 7.74 (1H, d, J=8.6 Hz), 7.82 (1H, s), 8.61-8.63 (3H, m), 8.87 (1H, s).

Example 148

Preparation of 5-(fro[2,3-b]pyridin-5-yl)-3-((4-(4-(1,1,1,3,3,3-hexafluoro-2-hydroxypropan-2-yl)-2-propylphenoxy) pyridin-2-yl)methyl)-5-methylimidazolidine-2,4-dione

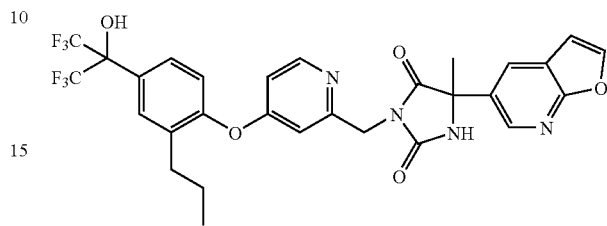

148-a-1) Preparation of ethyl 6-hydroxynicotinate

To a solution of 6-hydroxynicotinic acid (5.0 g, 35.9 mmol) in ethanol (180 mL), sulfuric acid (1.0 mL) was added. The resultant mixture was stirred at 60° C. for 20 minutes, then added with surfuric acid (33.0 mL), and stirred for 6.5 hours while heated to reflux. The reaction solution was then added with a saturated aqueous solution of sodium hydrogen carbonate under ice-cold conditions and ethanol was concentrated in vacuo. After extracted with ethyl acetate, the organic layer was washed with brine, dried over sodium sulfate, and concentrated in vacuo. Ethyl 6-hydroxynicotinate (5.33 g, yield 89%) was obtained as a white crystal.

$^1$H-NMR (CDCl$_3$) δ: 1.36 (3H, t, J=7.1 Hz), 4.33 (2H, q, J=7.1 Hz), 6.58 (1H, d, J=9.5 Hz), 8.01 (1H, dd, J=2.4, 9.5 Hz), 8.19 (1H, d, J=2.4 Hz), 12.43 (1H, brs).

148-a-2) Preparation of ethyl 6-hydroxy-5-iodonicotinate

Ethyl 6-hydroxynicotinate (2.0 g, 12.0 mmol) was dissolved in pyridine (60 mL), which was then added with iodide (6.07 g, 23.9 mmol) and stirred at 60° C. overnight. The reaction solution was then added with water at room temperature and extracted with ethyl acetate. Subsequently, the organic layer was washed with a saturated aqueous solution of sodium sulfite and brine, and dried over sodium sulfate. The obtained residue was purified using column chromatography (chloroform/methanol) and concentrated in vacuo. Ethyl 6-hydroxy-5-iodonicotinate (2.9 g, yield 83%) was obtained as a yellow oil.

$^1$H-NMR (CDCl$_3$) δ: 1.37 (3H, t, J=7.1 Hz), 4.34 (2H, q, J=7.1 Hz), 8.30 (1H, d, J=2.2 Hz), 8.64 (1H, d, J=2.2 Hz), 12.75 (1H, brs).

148-a-3) Preparation of ethyl 6-hydroxy-5-vinylnicotinate

Ethyl 6-hydroxy-5-iodonicotinate (200 mg, 0.682 mmol) was added with N,N'-dimethylformamide (4.1 mL) and water (1.4 mL). The resultant mixture was then added with tetrakis triphenylphosphine palladium (79 mg, 0.0682 mmol), vinylboronic acid (417 μL, 2.46 mmol) and sodium carbonate (433 mg, 4.09 mmol), and stirred at 80° C. for 20 minutes. Subsequently, the resultant mixture was further added with tetrakis triphenylphosphine palladium (79 mg, 0.0682 mmol) and vinylboronic acid (417 μL, 2.46 mmol), and stirred at 80° C.

for 20 minutes. The reaction solution was filtered using celite and extracted with ethyl acetate. Subsequently, the organic layer was washed with brine, dried over sodium sulfate, and concentrated in vacuo. The obtained residue was purified using column chromatography (chloroform/acetone) and concentrated in vacuo. Ethyl 6-hydroxy-5-vinylnicotinate (95 mg, yield 72%) was obtained as a yellow oil.

$^1$H-NMR (CDCl$_3$) δ: 1.38 (3H, t, J=7.3 Hz), 4.35 (2H, q, J=7.3 Hz), 5.45 (1H, d, J=11.2 Hz), 6.15 (1H, d, J=-17.8 Hz), 6.80 (1H, dd, J=11.2, 17.8 Hz), 8.08 (1H, d, J=2.2 Hz), 8.14 (1H, d, J=2.2 Hz), 12.49 (1H, brs).

148-a-4) Preparation of ethyl 3-hydroxy-2,3-dihydrofro[2,3-b]pyridine-5-carboxylate Ethyl 6-hydroxy-5-vinylnicotinate (439 mg, 2.27 mmol) was added with tetrahydrofuran (5.7 mL) and water (5.7 mL). Subsequently, the resultant mixture was added with N-chlorosuccinimide (607 mg, 4.55 mmol) under ice-cold conditions, stirred at room temperature overnight, then added with triethylamine (1.26 mL, 9.09 mmol), and stirred at 60° C. for 2 hours. The reaction solution was concentrated in vacuo. The obtained residue was purified using column chromatography (hexan/ethyl acetate) and concentrated in vacuo. Ethyl 3-hydroxy-2,3-dihydrofro[2,3-b]pyridine-5-carboxylate (577 mg, yield >100%) was obtained as a yellow oil.

$^1$H-NMR (CDCl$_3$) δ: 1.39 (3H, t, J=7.3 Hz), 2.92 (1H, brs), 4.37 (2H, q, J=7.3 Hz), 4.58 (1H, dd, J=3.0, 10.8 Hz), 4.75 (1H, dd, J=7.0, 10.8 Hz), 5.48 (1H, brs), 8.34 (1H, d, J=2.2 Hz), 8.82 (1H, d, J=2.2 Hz).

148-a-5) Preparation of ethyl fro[2,3-b]pyridine-5-carboxylate

A solution of ethyl 3-hydroxy-2,3-dihydrofro[2,3-b]pyridine-5-carboxylate (577 mg, 2.27 mmol) in dichrolomethane (11 mL) was added with triethylamine (1.89 mL, 13.6 mmol), then added with methanesulfonic anhydride (951 mg, 5.46 mmol) under ice-cold conditions, and stirred at room temperature for 1 hour. The reaction solution was added with water and extracted with ethyl acetate. Subsequently, the organic layer was washed with brine, dried over sodium sulfate, and concentrated in vacuo. The obtained residue was purified using column chromatography (hexan/acetone) and concentrated in vacuo. Ethyl fro[2,3-b]pyridine-5-carboxylate (114 mg, yield 26%) was obtained as a yellow oil.

$^1$H-NMR (CDCl$_3$) δ: 1.44 (3H, t, J=7.3 Hz), 4.44 (2H, q, J=7.3 Hz), 6.87 (1H, d, J=2.7 Hz), 7.78 (1H, d, J=2.7 Hz), 8.60 (1H, d, J=1.9 Hz), 9.02 (1H, (1, J=1.9 Hz).

148-a-6) Preparation of fro[2,3-b]pyridine-5-carboxylic acid

A solution of ethyl fro[2,3-b]pyridine-5-carboxylate (114 mg, 0.597 mmol) in methanol (3.0 mL) was added with 1N aqueous solution of sodium hydroxide (3.0 mL) under ice-cold conditions and stirred at room temperature for 1 hour. The reaction solution was added with 5% aqueous solution of hydrochloric acid, then added with toluene, and concentrated in vacuo. Fro[2,3-b]pyridine-5-carboxylic acid (259 mg, yield >100%) was obtained as a yellow oil.

$^1$H-NMR (CDCl$_3$) δ: 7.04 (1H, d, J=2.4 Hz), 7.99 (1H, d, J=2.4 Hz), 8.69 (1H, d, J=2.0 Hz), 8.92 (1H, d, J=2.0 Hz).

148-a-7) N-methoxy-N-methylfro[2,3-b]pyridine-5-carboxamide

Fro[2,3-b]pyridine-5-carboxylic acid was used for a similar reaction and treatment as Example 13-a), and N-methoxy-N-methylfro[2,3-b]pyridine-5-carboxamide was obtained as a yellow oil.

$^1$H-NMR (CDCl$_3$) δ: 3.42 (3H, s), 3.55 (3H, s), 6.84 (1H, d, J=2.7 Hz), 7.76 (1H, d, J=2.7 Hz), 8.34 (1H, d, J=2.2 Hz), 8.74 (1H, d, J=2.2 Hz).

148-a-8) Preparation of 1-(fro[2,3-b]pyridin-5-yl)ethanone

N-methoxy-N-methylfro[2,3-b]pyridine-5-carboxamide was used for a similar reaction and treatment as Example 1-a), and 1-(fro[2,3-b]pyridin-5-yl)ethanone was obtained as a yellow oil.

$^1$H-NMR (CDCl$_3$) δ: 2.71 (3H, s), 6.90 (1H, d, J=2.7 Hz), 7.80 (1H, d, J=2.7 Hz), 8.56 (1H, d, J=2.2 Hz), 8.97 (1H, d, J=2.2 Hz).

148-a-9) Preparation of 5-(fro[2,3-b]pyridin-5-yl)-5-methylimidazolidine-2,4-dione 1-(Fro[2,3-b]pyridin-5-yl)ethanone was used for a similar reaction and treatment as Example 1-a), and 5-(fro[2,3-b]pyridin-5-yl)-5-methylimidazolidine-2,4-dione was obtained as a white crystal.

$^1$H-NMR (CDCl$_3$) δ: 1.85 (3H, s), 6.97 (1H, d, J=2.4 Hz), 7.93 (1H, d, J=2.4 Hz), 8.29 (1H, d, J=2.2 Hz), 8.44 (1H, d, J=2.2 Hz).

5-(Fro[2,3-b]pyridin-5-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (400 MHz, CD$_3$OD) δ: 0.83 (3H, t, J=7.6 Hz), 1.51 (2H, qt, J=7.3, 7.6 Hz), 1.84 (3H, s), 2.47 (2H, t, J=7.6 Hz), 4.96 (2H, s), 6.98 (1H, d, J=2.4 Hz), 7.21 (1H, d, J=2.7 Hz), 7.26 (1H, d, J=8.6 Hz), 7.37 (1H, dd, J=2.4, 6.8 Hz), 7.73 (1H, d, J=8.6 Hz), 7.79 (1H, s), 7.96 (1H, d, J=2.4 Hz), 8.30 (1H, d, J=2.4 Hz), 8.42 (1H, d, J=2.4 Hz), 8.63 (1H, d, J=6.8 Hz).

Example 149

Preparation of 5-(2,3-dihydrofro[2,3-b]pyridin-5-yl)-3-((4-(4-(1,1,1,3,3,3-hexafluoro-2-hydroxypropan-2-yl)-2-propylphenoxy)pyridin-2-yl)methyl)-5-methylimidazolidine-2,4-dione

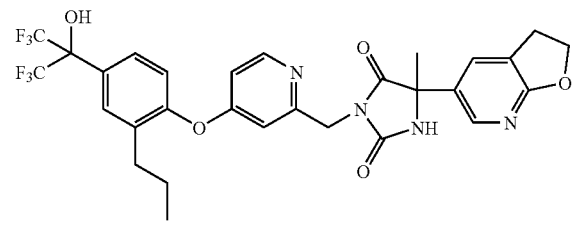

149-a) Preparation of 5-(2,3-dihydrofro[2,3-b]pyridin-5-yl)-5-methylimidazolidine-2,4-dione A solution of 5-(fro[2,3-b]pyridin-5-yl)-5-methylimidazolidine-2,4-dione (22.5 mg, 0.097 mmol) in methanol (500 μL) was added with palladium carbon (2.3 mg) and stirred at room temperature for 9 hours under a hydrogen atmosphere. The reaction solution was filtered using celite and concentrated in vacuo. 5-(2,3-dihydrofro[2,3-b]pyridin-5-yl)-5-methylimidazolidine-2,4-dione was obtained as a pale yellow oil.

$^1$H-NMR (CDCl$_3$) δ: 1.75 (3H, s), 3.30 (2H, t, J=8.8 Hz), 4.66 (2H, t, J=8.8 Hz), 7.80 (1H, d, J=2.4 Hz), 7.98 (1H, d, J=2.4 Hz).

5-(2,3-Dihydrofro[2,3-b]pyridin-5-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (400 MHz, CD$_3$OD) δ: 0.86 (3H, t, J=7.3 Hz), 1.55 (2H, qt, J=7.3, 7.5 Hz), 1.73 (3H, s), 2.53 (2H, t, J=7.5 Hz), 3.27-3.31 (2H, m), 4.66 (2H, t, J=8.7 Hz), 4.71 (2H, s), 6.69 (1H, d, J=2.4 Hz), 6.81 (1H, dd, J=2.4, 5.9 Hz), 7.12 (1H, d, J=8.6 Hz), 7.64 (1H, d, J=8.6 Hz), 7.71 (1H, s), 7.85 (1H, s), 7.97 (1H, d, J=2.2 Hz), 8.33 (1H, d, J=5.9 Hz).

Example 150

Preparation of 3-((4-(4-(1,1,1,3,3,3-hexafluoro-2-hydroxypropan-2-yl)-2-propylphenoxy)pyridin-2-yl)methyl)-5-(4-methoxyphenyl)-5-methylimidazolidine-2,4-dione

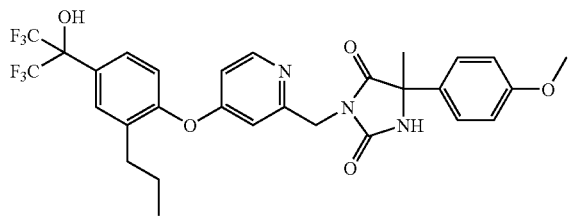

5-(1-Methoxyphenyl-4-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (CDCl$_3$) δ: 0.86 (3H, t, J=7.3 Hz), 1.49-1.59 (2H, m), 1.72 (3H, s), 2.48 (2H, t, J=7.3 Hz), 3.97 (3H, s), 4.92 (2H, s), 6.92-6.96 (2H, m), 7.12 (1H, d, J=2.7 Hz), 7.25 (1H, d, J=8.6 Hz), 7.37 (1H, dd, J=2.7, 6.6 Hz), 7.38-7.42 (2H, m), 7.73 (1H, d, J=8.6 Hz), 7.80 (1H, s), 8.64 (1H, d, J=6.6 Hz).

Example 151

Preparation of 5-(6-(difluoromethoxy)pyridin-3-yl)-3-((4-(4-(1,1,3,3,3-hexafluoro-2-hydroxypropan-2-yl)-2-propylphenoxy)pyridin-2-yl)methyl)-5-methylimidazolidine-2,4-dione

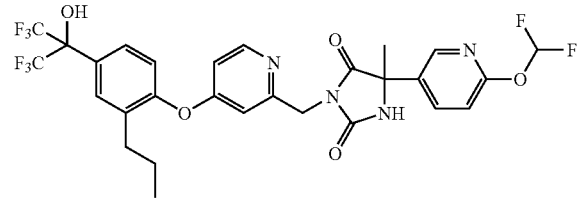

5-(2-(1,1-Difluoromethoxy)pyridin-5-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (270 MHz, CD$_3$OD) δ: 0.87 (3H, t, J=7.0 Hz), 1.49-1.59 (2H, m), 1.75 (3H, s), 2.51 (2H, t, J=7.0 Hz), 4.92 (2H, s), 7.00 (1H, d, J=8.8 Hz), 7.10-7.28 (3H, m), 7.35-7.40 (1H, m), 7.68-7.82 (2H, m), 7.98-8.04 (1H, m), 8.32 (1H, d, J=5.9 Hz), 8.61 (1H, d, J=7.0 Hz).

Example 152

Preparation of 5-(6-(benzyloxy)pyridin-3-yl)-3-((4-(4-(1,1,1,3,3,3-hexafluoro-2-hydroxypropan-2-yl)-2-propylphenoxy)pyridin-2-yl)methyl)-5-methylimidazolidine-2,4-dione

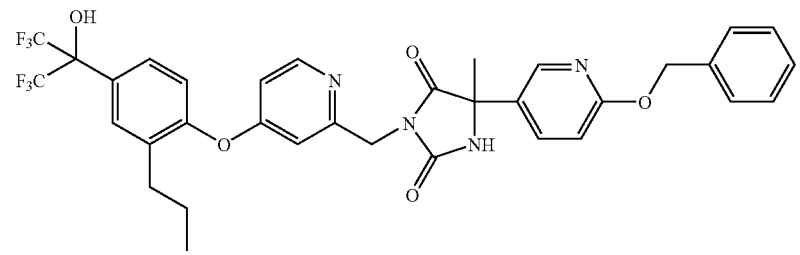

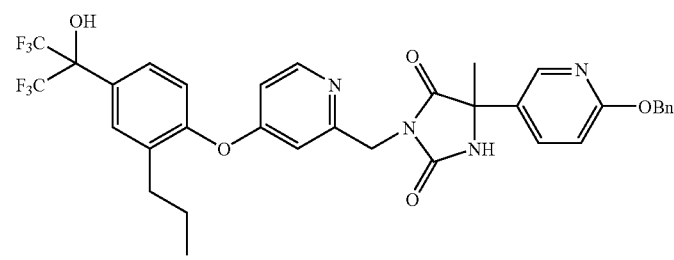

5-(2-Benzyloxypyridin-5-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

¹H-NMR (270 MHz, CD₃OD) δ: 0.87 (3H, t, J=7.5 Hz), 1.52-1.60 (2H, m), 1.67 (3H, s), 2.52 (2H, t, J=7.5 Hz), 4.93 (2H, s), 5.14 (1H, d, J=14.4 Hz), 5.26 (1H, d, J=14.4 Hz), 6.60 (1H, d, J=9.3 Hz), 7.12-7.31 (7H, m), 7.37 (1H; d, J=7.0 Hz), 7.65 (1H, d, J=9.3 Hz), 7.73 (1H, d, J=8.4 Hz), 7.79-7.82 (2H, m), 8.63 (1H, d, J=6.8 Hz).

Example 153

Preparation of 3-((4-(4-(1,1,1,3,3,3-hexafluoro-2-hydroxypropan-2-yl)-2-propylphenoxy)pyridin-2-yl)methyl)-5-methyl-5-(2-methyl-2,3-dihydrobenzofuran-5-yl)imidazolidine-2,4-dione

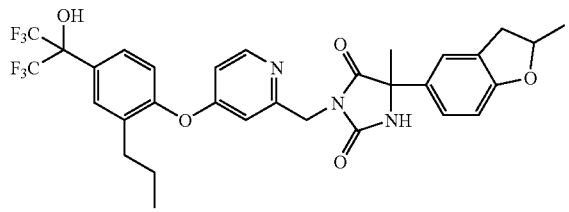

153-a-1) Preparation of 1-(4-(allyloxy)phenyl)ethanone

2-Hydroxyacetophenone (1.36 g, 10.0 mmol) was dissolved in acetone (50 mL). The resultant mixture was added with potassium carbonate (2.76 g, 20.0 mmol) and allylbromide (1.27 mL, 15.0 mmol) at room temperature and heated to reflux for 3 hours. The reaction solution was cooled to room temperature, added with ethyl acetate, and washed with water and brine. The organic layer was dried over anhydrous sodium sulfate and concentrated in vacuo. The obtained residue was purified using silica-gel column chromatography (n-hexane/ethyl acetate=10/1). 1-(4-(Allyloxy)phenyl)ethanone (1.76 g, 100%) was obtained as a colorless oil.

¹H-NMR (CDCl₃) δ: 2.56 (3H, s), 4.60-4.62 (2H, m), 5.31-5.45 (2H, m), 6.00-6.09 (1H, m), 6.93-6.97 (2H, m), 7.92-7.95 (2H, m).

153-a-2) Preparation of 1-(3-allyl-4-hydroxyphenyl)ethanone 1-(4-(Allyloxy)phenyl)ethanone (80.0 mg, 0.45 mmol) was added to polyethyleneglycol 400 (0.3 mL) and stirred at 250° C. for 1 hour under microwave irradiation. The reaction solution was added with water and extracted with ethyl acetate. The organic layer was washed with brine, dried over anhydrous sodium sulfate, and concentrated in vacuo. The obtained residue was purified using preparative thin-layer chromatography (n-hexan/ethyl acetate=2/1), and 1-(3-allyl-4-hydroxyphenyl)ethanone (63 mg, yield 79%) was obtained as a pale red-brown solid.

¹H-NMR (CDCl₃) δ: 2.54 (3H, s), 3.46 (2H, d, J=6.2 Hz), 5.16-5.23 (2H, m), 6.85 (1H, d, J=8.9 Hz), 7.00-7.12 (1H, m), 7.78-7.81 (2H, m).

153-a-3) Preparation of 1-(2-methyl-2,3-dihydrobenzofuran-5-yl)ethanone 1-(3-Allyl-4-hydroxyphenyl)ethanone (56 mg, 0.32 mmol) was dissolved in methylene chloride (1.6 mL). The resultant mixture was added with zirconium (IV) chloride (90 mg, 0.38 mmol) at room temperature under an argon atmosphere and stirred overnight. The reaction solution was added with water and extracted with ethyl acetate. The organic layer was washed with brine, dried over anhydrous sodium sulfate, then concentrated in vacuo, and purified using preparative thin-layer chromatography (n-hexan/ethyl acetate=4/1).

1-(2-Methyl-2,3-dihydrobenzofuran-5-yl)ethanone (24 mg, yield 43%) was obtained as a colorless oil.

¹H-NMR (CDCl₃) δ: 1.49 (3H, d, J=6.2 Hz), 2.54 (3H, s), 2.84 (1H, dd, J=7.0, 15.4 Hz), 3.36 (1H, dd, J=8.9, 15.4 Hz), 4.98-5.07 (1H, m), 6.77 (1H, d, J=7.8 Hz), 7.77-7.82 (2H, m).

Preparation of 5-(2-methyl-2,3-dihydrobenzofuran-5-yl)-5-methylimidazolidine-2,4-dione 1-(2-Methyl-2,3-dihydrobenzofuran-5-yl)ethanone was used for a similar reaction and treatment as Example 1-a), and 5-(2-methyl-2,3-dihydrobenzofuran-5-yl)-5-methylimidazolidine-2,4-dione was obtained as a white crystal.

¹H-NMR (CD₃OD) δ: 1.40 (3H, d, J=6.4 Hz), 1.72 (3H, s), 2.80 (1H, dd, J=7.6, 15.6 Hz), 3.30-3.35 (1H, m), 4.86-4.91 (1H, m), 6.67 (1H, dd, J=8.4 Hz), 7.20 (1H, d, J=8.4 Hz), 7.30 (1H, s).

5-(2-Methyl-2,3-dihydrobenzofuran-5-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

¹H-NMR (CDCl₃) δ: 0.89 (3H, t, J=7.3 Hz), 1.44 (3H, d, J=6.5 Hz), 1.57 (2H, qt, J=7.3, 7.6 Hz), 1.81 (3H, s), 2.53 (2H, t, J=7.6 Hz), 2.75-2.85 (2H, m), 3.25-3.35 (1H, m), 4.78 (2H, s), 4.86-4.99 (1H, m), 5.92 (1H, s), 6.65-6.67 (2H, m), 6.71 (1H, d, J=8.4 Hz), 7.01 (1H, d, J=8.6 Hz), 7.23 (1H, dd, J=2.2, 8.4 Hz), 7.34 (1H, d, J=2.2 Hz), 7.57 (1H, d, J=8.6 Hz), 7.64 (1H, s), 8.33 (1H, d, J=6.8 Hz).

Example 154

Preparation of 3-((4-(4-(1,1,1,3,3,3-hexafluoro-2-hydroxypropan-2-yl)-2-propylphenoxy)pyridin-2-yl)methyl)-5-methyl-5-(2-methyl-2,3-dihydrobenzofuran-6-yl)imidazolidine-2,4-dione

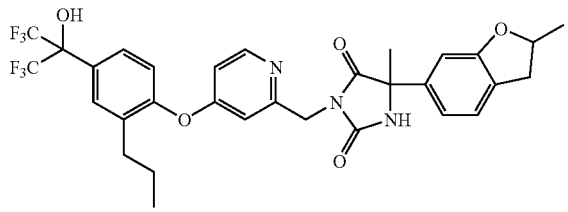

154-a-1) Preparation of 1-(3-(allyloxy)phenyl)ethanone

3-Hydroxyacetophenone (1.36 g, 10.0 mmol) was dissolved in acetone (50 mL), then added with potassium carbonate (2.76 g, 20.0 mmol) and allylbromide (1.27 mL, 15.0 mmol) at room temperature, and heated to reflux for 2 hours. The reaction solution was cooled to room temperature, added with ethyl acetate, and washed with water and brine. The organic layer was dried over anhydrous sodium sulfate and concentrated in vacuo. The obtained residue was purified using silica-gel column chromatography (n-hexane/ethyl acetate=10/1), and 1-(3-(allyloxy)phenyl)ethanone (1.76 g, 100%) was obtained as a pale yellow oil.

$^1$H-NMR (CDCl$_3$) δ: 2.59 (3H, s), 4.60 (2H, d, J=5.4 Hz), 5.31 (1H, dd, J=1.5, 10.5 Hz), 5.43 (1H, dd, J=1.5, 17.3 Hz), 6.02-6.11 (1H, m), 7.13 (1H, d, J=8.3 Hz), 7.37 (1H, t, J=7.8 Hz), 7.50-7.55 (1H, m).

154-a-2) Preparation of 1-(4-allyl-3-hydroxyphenyl)ethanone 1-(3-(Allyloxy)phenyl)ethanone (240 mg, 13.5 mmol) was added to polyethylene glycol 400 (0.9 mL), and the resultant mixture was stirred at 250° C. for 1 hour under microwave irradiation. The reaction solution was added with water and extracted with ethyl acetate. The organic layer was washed with brine, dried over anhydrous sodium sulfate, and concentrated in vacuo. The obtained residue was purified using preparative thin-layer chromatography (n-hexane/ethyl acetate=2/1), and 1-(4-allyl-3-hydroxyphenyl)ethanone (22 mg, 9%) was obtained as a colorless solid.

$^1$H-NMR (CDCl$_3$) δ: 2.59 (3H, s), 3.47 (2H, d, J=6.5 Hz), 5.10-5.18 (2H, m), 5.94-6.09 (1H, m), 7.21 (1H, d, J=8.1 Hz), 7.47 (1H, dd, J=1.9, 8.1 Hz), 7.57 (1H, d, J=1.9 Hz).

154-a-3) Preparation of 1-(2-methyl-2,3-dihydrobenzofuran-6-yl)ethanone 1-(4-Allyl-3-hydroxyphenyl)ethanone (863 mg, 4.90 mmol) was dissolved in methylene chloride (25 mL), which was then added with zirconium (IV) chloride (1.37 g, 5.88 mmol) at room temperature under an argon atmosphere, and stirred overnight. The reaction solution was added with water and extracted with ethyl acetate. The organic layer was washed with brine, dried over anhydrous sodium sulfate, concentrated in vacuo, and purified using silica-gel column chromatography (n-hexane/ethyl acetate=6/1). 1-(2-Methyl-2,3-dihydrobenzofuran-6-yl)ethanone (167 mg, yield 19%) was obtained as a yellow oil.

$^1$H-NMR (CD$_3$OD) δ: 1.48 (3H, d, J=6.4 Hz), 2.56 (3H, s), 2.85 (1H, dd, J=8.8, 16.0 Hz), 3.36 (1H, dd, J=8.8, 16.0 Hz), 4.94-5.03 (1H, m), 7.22 (1H, d, J=7.6 Hz), 7.31 (1H, s), 7.47 (1H, d, J=7.6 Hz).

Preparation of 5-(2-methyl-2,3-dihydrobenzofuran-6-yl)-5-methylimidazolidine-2,4-dione 1-(2-Methyl-2,3-dihydrobenzofuran-6-yl)ethanone was used for a similar reaction and treatment as Example 1-a), and the title compound was obtained as a white crystal.

$^1$H-NMR (CD$_3$OD) δ: 1.40 (3H, d, J=6.0 Hz), 1.71 (3H, s), 2.77 (1H, dd, J=7.2, 15.6 Hz), 3.26-3.33 (1H, m), 4.85-4.93 (1H, m), 6.83 d, J=2.0 Hz), 6.95 (1H, dd, J=2.0, 8.0 Hz), 7.15 (1H, d, J=8.0 Hz).

5-(2-Methyl-2,3-dihydrobenzofuran-6-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (CDCl$_3$) δ: 0.88 (3H, t, J=7.3 Hz), 1.45 (3H, d, J=6.2 Hz), 1.57 (2H, qt, J=7.3, 7.6 Hz), 1.79 (3H, s), 2.51 (2H, t, J=7.6 Hz), 2.79 (1H, dd, J=7.6, 15.1 Hz), 3.29 (1H, dd, J=8.6, 15.1 Hz), 4.76 (2H, s), 4.87-5.01 (1H, m), 5.99 (1H, s), 6.62 (1H, d, J=2.4 Hz), 6.68 (1H, dd, J=2.4, 5.4 Hz), 6.90 (1H, d, J=1.9 Hz), 6.97 (1H, dd, J=1.9, 7.8 Hz), 7.01 (1H, d, J=8.6 Hz), 7.13 (1H, d, J=7.8 Hz), 7.58 (1H, d, J=8.6 Hz), 7.64 (1H, s), 8.34 (1H, d, J=5.4 Hz).

Example 155

Preparation of 5-(2,3-dihydrobenzofuran-5-yl)-5-ethyl-3-((4-(4-(4-(1,1,1,3,3,3-hexafluoro-2-hydroxypropan-2-yl)-2-propylphenoxy)pyridin-2-yl)methyl)imidazolidine-2,4-dione

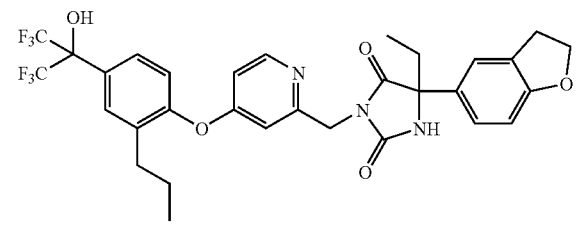

155-a-1) Preparation of 1-(2,3-dihydrobenzofuran-5-yl)propan-1-one

To a solution of propionyl chloride (0.72 mL, 8.30 mmol) in dichloromethane (10 mL), aluminum chloride (835 mg, 6.25 mmol) was added at 0° C. under an argon atmosphere and stirred for 10 minutes, then a solution of 1,2-dihydrobenzofuran (500 mg, 4.15 mmol) in dichloromethane (11 mL) was added dropwisely at the same temperature. After stirring for 5 minutes, the resultant mixture was added with 1N HCl at 0° C. and extracted with ethyl acetate. The organic layer was washed with a saturated aqueous solution of sodium hydrogen carbonate, dried over anhydrous sodium sulfate, and concentrated in vacuo. The obtained residue was purified using silica-gel column chromatography (n-hexane/ethyl acetate), and 1-(2,3-dihydrobenzofuran-5-yl)propan-1-one (716 mg, yield 98%) was obtained as a white solid.

$^1$H-NMR (CD$_3$OD) δ: 1.21 (3H, t, J=7.6 Hz), 2.94 (2H, q, J=7.6 Hz), 3.25 (2H, t, J=8.8 Hz), 4.66 (2H, J=8.8 Hz), 6.80 (1H, d, J=8.4 Hz), 7.81 (1H, d, J=8.4 Hz), 7.86 (1H, s).

155-a-2) Preparation of 5-(2,3-dihydrobenzofuran-5-yl)-5-ethylimidazolidine-2,4-dione 1-(2,3-Dihydrobenzofuran-5-yl)propan-1-one was used for a similar reaction and treatment as Example 1-a), and 5-(2,3-dihydrobenzofuran-5-yl)-5-ethylimidazolidine-2,4-dione was obtained as a white crystal.

$^1$H-NMR (CD$_3$OD) δ: 0.91 (3H, t, J=7.2 Hz), 1.95-2.01 (1H, m), 2.14-2.20 (1H, m), 3.20 (2H, t, J=8.8 Hz), 4.54 (2H, t, J=8.8 Hz), 6.71 (1H, d, J=8.4 Hz), 7.23 (1H, d, J=8.4 Hz), 7.37 (1H, s).

5-(2,3-Dihydrobenzofuran-5-yl)-5-ethylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (CDCl$_3$) δ: 0.88 (6H, t, J=7.3 Hz), 1.56 (2H, qt, J=7.3, 7.6 Hz), 2.03-2.33 (2H, m), 2.51 (2H, t, J=7.6 Hz), 3.20 (2H, t, J=8.6 Hz), 4.57 (2H, t, J=8.6 Hz), 4.76 (2H, s), 6.08 (1H, s), 6.64 (1H, dd, J=2.2, 5.7 Hz), 6.70 (1H, d, J=2.2 Hz), 6.75 (1H, d, J=8.6 Hz), 6.99 (1H, d, J=8.6 Hz), 7.24 (1H, dd, J=2.2, 8.6 Hz), 7.40 (1H, d, J=2.2 Hz), 7.57 (1H, d, J=8.6 Hz), 7.63 (1H, s), 8.32 (1H, d, J=5.7 Hz).

Example 156

Preparation of 5-(2,2-dimethyl-2,3-dihydrobenzofuran-6-yl)-3-((4-(4-(4-(1,1,1,3,3,3-hexafluoro-2-hydroxypropan-2-yl)-2-propyl-phenoxy)pyridin-2-yl)methyl)-5-methylimidazolidine-2,4-dione

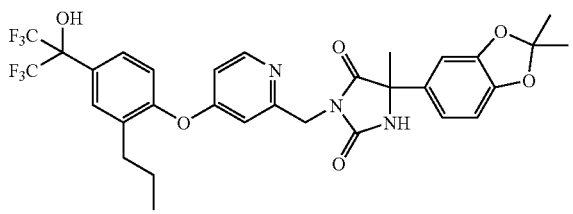

156-a-1) Preparation of 1-(3-(2-methyl-3-propenyloxy)phenyl)ethanone

3-Hydroxyacetophenone (1.36 g, 10.0 mmol) was dissolved in N,N-dimethylformamide (50 mL). The resultant mixture was added with potassium carbonate (2.76 g, 20.0 mmol), 2-methyl-2-propenylchloride (1.5 mL, 15.0 mmol), and tetra-n-butyl ammonium iodide (370 mg, 1.00 mmol) at room temperature, and then stirred at 80° C. for 2 hours. The reaction solution was added with water and extracted with ether. The organic layer was washed with brine, dried over anhydrous sodium sulfate, and concentrated in vacuo. The obtained residue was then purified using silica-gel column chromatography (n-hexane/ethyl acetate=10/1), and 1-(3-(2-methyl-3-propenyloxy)phenyl)ethanone (1.93 g, 100%) was obtained as a yellow oil.

¹H-NMR (CDCl₃) δ: 1.83 (3H, s), 2.60 (3H, s), 4.49 (2H, s), 5.01-5.11 (2H, m), 7.01-7.16 (1H, m), 7.37 (1H, t, J=8.1 Hz), 7.49-7.55 (2H, m).

156-a-2) Preparation of 1-(3-hydroxy-4-(2-methyl-3-propenyl)phenyl)ethanone 1-(3-(2-Methyl-3-propenyloxy)phenyl)ethanone (765 mg, 13.5 mmol) was added to polyethyleneglycol 400 (0.9 mL). The resultant mixture was stirred at 250° C. for 1 hour under microwave irradiation. The reaction solution was added with water and extracted with ethyl acetate. The organic layer was washed with brine, dried over anhydrous sodium sulfate, and concentrated in vacuo. The obtained residue was purified using preparative thin-layer chromatography (n-hexan/ethyl acetate=10/1), and 1-(3-hydroxy-4-(2-methyl-3-propenyl)phenyl)ethanone (32 mg, 13%) was obtained as a colorless solid.

¹H-NMR (CDCl₃) δ: 1.75 (3H, s), 2.58 (3H, s), 3.43 (2H, s), 4.85-5.44 (2H, md, J=28.6 Hz), 7.19 (1H, d, J=7.6 Hz), 7.43-7.50 (2H, m).

156-a-2) Preparation of 1-(2,2-dimethyl-2,3-dihydrobenzofuran-6-yl)ethanone 1-(3-Hydroxy-4-(2-methyl-3-propenyl)phenyl)ethanone (1.15 g, 6.04 mmol) was dissolved in methanol (30 mL). The resultant mixture was added with hydrochloric acid (8 mL) at room temperature and stirred at 70° C. for 4.5 hours. The reaction solution was neutralized by adding a saturated sodium bicarbonate water under ice-cold conditions, and extracted with ethyl acetate. The organic layer was washed with brine, dried over anhydrous sodium sulfate, concentrated in vacuo, and purified using silica-gel column chromatography (n-hexane/ethyl acetate=10/1). 1-(2,2-Dimethyl-2,3-dihydrobenzofuran-6-yl)ethanone (961 mg, yield 84%) was obtained as a red-brown oil.

¹H-NMR (CDCl₃) δ: 1.49 (6H, s), 2.56 (3H, s), 3.04 (2H, s), 7.20 (1H, d, J=7.8 Hz), 7.28 (1H, d, J=1.4 Hz), 7.46 (1H, dd, J=1.4, 7.8 Hz).

Preparation of 5-(2,2-dimethyl-2,3-dihydrobenzofuran-6-yl)-5-methylimidazolidine-2,4-dione 1-(2,2-Dimethyl-2,3-dihydrobenzofuran-6-yl)ethanone was used for a similar reaction and treatment as Example 1-a), and 5-(2,2-dimethyl-2,3-dihydrobenzofuran-6-yl)-5-methylimidazolidine-2,4-dione was obtained as a white crystal.

¹H-NMR (CD₃OD) δ: 1.43 (6H, s), 1.72 (3H, s), 3.00 (2H, s), 6.80 (1H, d, J=2.0 Hz), 6.94 (1H, dd, J=2.0, 8.0 Hz), 7.14 (1H, d, J=8.0 Hz).

5-(2,2-Dimethyl-2,3-dihydrobenzofuran-6-yl)-5-methylimidazolidine-2,4-dione was used in place of 5-(benzo[d][1,3]dioxol-5-yl)-5-methylimidazolidine-2,4-dione in Example 401) for a similar reaction and treatment, and the title compound was obtained as a yellow oil.

¹H-NMR (CDCl₃) δ: 0.88 (3H, t, J=7.0 Hz), 1.46 (6H, s), 1.55 (2H, qt, J=7.0, 7.3 Hz), 1.80 (3H, s), 2.52 (2H, t, J=7.3 Hz), 2.98 (2H, s), 4.77 (2H, s), 5.93 (1H, s), 6.62 (1H, d, J=2.4 Hz), 6.68 (1H, dd, J=2.4, 5.4 Hz), 6.87 (1H, d, J=1.6 Hz), 6.96 (1H, dd, J=1.6, 7.8 Hz), 7.02 (1H, d, J=8.4 Hz), 7.12 (1H, d, J=7.8 Hz), 7.58 (1H, d, J=8.4 Hz), 7.64 (1H, s), 8.34 (1H, d, J=5.4 Hz).

Example 157

Preparation of 5-(2,2-dimethyl-2,3-dihydrobenzofuran-5-yl)-3-((4-(4-(1,1,1,3,3,3-hexafluoro-2-hydroxypropan-2-yl)-2-propylphenoxy)pyridin-2-yl)methyl)-5-methylimidazolidine-2,4-dione

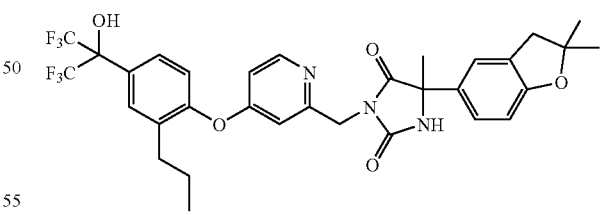

5-(2,2-Dimethyl-2,3-dihydrobenzofuran-5-yl)-5-methylimidazolidine-2,4-dione prepared using 4-hydroxyacetophenone in place of 3-hydroxyacetophenone in 156-a) was used in place of 5-(benzo[d][1,3]dioxol-5-yl)-5-methylimidazolidine-2,4-dione in Example 40 f) for a similar reaction and treatment, and the title compound was obtained as a yellow oil.

¹H-NMR (CDCl₃) δ: 0.89 (3H, t, J=7.6 Hz), 1.45 (6H, s), 1.57 (2H, qt, J=7.6, 7.8 Hz), 1.81 (3H, s), 2.53 (2H, t, J=7.8 Hz), 2.99 (2H, s), 4.77 (2H, s), 5.92 (1H, s), 6.65-6.70 (3H, m), 7.01 (1H, d, J=8.9 Hz), 7.22 (1H, dd, J=1.9, 8.6 Hz), 7.32 (1H, d, J=1.9 Hz), 7.58 (1H, d, J=8.9 Hz), 7.64 (1H, s), 8.33 (1H, d, J=6.8 Hz).

Example 158

Preparation of 3-((4-(4-(4-(1,1,1,3,3,3-hexafluoro-2-hydroxypropan-2-yl-2-propylphenoxy)pyridin-2-yl)methyl)-5-(6-trideuteriummethoxypyridin-3-yl)-5-methylimidazolidine-2,4-dione

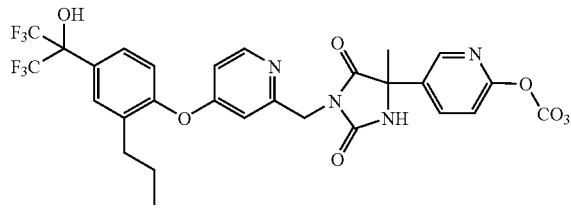

158-a-1) Preparation of N-methoxy-N-methyl-6-trideuteriummethoxynicotinamide (2-Hydroxypyridin-5-yl)ethanone (100 mg, 0.55 mmol) was dissolved in tetrahydrofuran (3 mL). The resultant mixture was added with iodotrideuterium methane (86 mL, 1.38 mmol), further added with aluminum hydride (27 mg, 0.61 mmol) at 0° C., and stirred at room temperature. 30 minutes later, the mixture was added with iodotrideuterium methane (86 mL, 1.38 mmol) and further stirred for 30 minutes. The reaction solution was added with water at 0° C. and extracted with ethyl acetate. The organic layer was washed with brine, dried over anhydrous sodium sulfate, concentrated in vacuo, and purified using silica-gel chromatography (n-hexane/ethyl acetate=1/1). N-methoxy-N-methyl-6-trideuteriummethoxy nicotinamide (94 mg, yield 86%) was obtained as a white solid.

$^1$H-NMR (CD$_3$OD) δ: 3.34 (3H, s), 3.63 (3H, s), 6.53 (1H, d, J=9.5 Hz), 7.85 (1H, dd, J=2.4, 9.5 Hz), 8.09 (1H, d, J=2.4 Hz).

158-a-2) Preparation of 1-(2-(trideuteriummethyloxy)pyridin-5-yl)ethanone

N-methoxy-N-methyl-6-trideuterium methoxynicotinamide (93 mg, 0.47 mmol) was dissolved in tetrahydrofuran (2.4 mL), and 0.93 M methyl magnesium bromide (0.76 mL, 0.70 mmol) was dropwisely added at 0° C. under an argon atmosphere. The resultant mixture was stirred for 1 hour, and the reaction solution was added with 1 N hydrochloric acid at the same temperature. Next, the reaction solution was added with saturated aqueous solution of sodium hydrogen carbonate, and extracted with chloroform/methanol mixed solution (=95/5). The organic layer was dried over anhydrous sodium sulfate, concentrated in vacuo, and purified using silica-gel column chromatography (chloroform/methanol=10/1). A mixture containing 1-(2-(trideuterium methyloxy)pyridin-5-yl)ethanone (62 mg, yield 98%) was obtained.

$^1$H-NMR (CD$_3$OD) δ: 2.46 (3H, s), 6.57 (1H, d, J=9.7 Hz), 7.88 (1H, dd, J=2.7, 9.7 Hz), 8.13 (1H, d, J=2.7 Hz).

158-a-3) Preparation of 5-(2-trideuteriummethyloxy pyridin-5-yl)-5-methylimidazolidine-2,4-dione 1-(2-(Trideuteriummethyloxy)pyridin-5-yl)ethanone was used for a similar reaction and treatment as Example 1-a), and the title compound was obtained as a white crystal.

$^1$H-NMR (CD$_3$OD) δ: 1.70 (3H, s), 6.57 (1H, d, J=9.5 Hz), 7.66 (1H, dd, J=2.2, 9.5 Hz), 7.74 (1H, d, J=2.2 Hz).

5-(2-Trideuteriummethyloxy pyridin-5-yl)-5-methylimidazol dine-2,4-dione was used in place of 5-(benzo[d][1,3]dioxol-5-yl)-5-methylimidazolidine-2,4-dione in Example 400 for a similar reaction and treatment, and the title compound was obtained as a yellow oil.

$^1$H-NMR (CDCl$_3$) δ: 0.89 (3H, t, J=7.3 Hz), 1.58 (2H, qt, J=7.3, 7.3 Hz), 1.77 (3H, s), 2.54 (2H, t, J=7.3 Hz), 4.78 (2H, s), 6.21 (1H, s), 6.52 (1H, d, J=9.5 Hz), 6.63 (1H, d, J=2.2 Hz), 6.74 (1H, dd, J=2.2, 5.7 Hz), 6.94 (1H, d, J=8.6 Hz), 7.48-7.56 (3H, m), 7.65 (1H, s), 8.36 (1H, d, J=5.7 Hz).

Example 159

Preparation of 5-(2,3-dihydrobenzo[b][1,4]dioxin-6-yl)-3-((4-(4-(4-(1,1,1,3,3,3-hexafluoro-2-hydroxypropan-2-yl)-2-propylphenoxy)pyridin-2-yl)methyl)-5-methylimidazolidine-2,4-dione

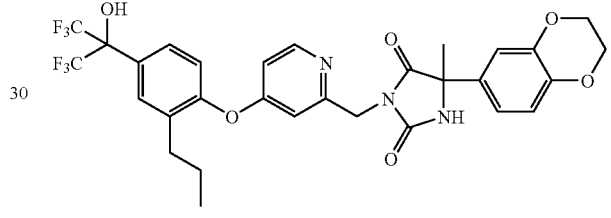

5-(2,3-Dihydrobenzo[b][1,4]dioxin-6-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (CDCl$_3$) δ: 0.89 (3H, t, J=7.3 Hz), 1.56 (2H, qt, J=7.3, 7.6 Hz), 1.79 (3H, s), 2.52 (2H, t, J=7.6 Hz), 4.24 (4H, s), 4.77 (2H, s), 5.97 (1H, s), 6.64 (1H, d, J=2.7 Hz), 6.67 (1H, dd, J=2.7, 5.4 Hz), 6.85 (1H, d, J=8.4 Hz), 6.97 (1H, dd, J=2.4, 8.4 Hz), 7.01 (1H, d, J=8.4 Hz), 7.07 (1H, d, J=2.4 Hz), 7.58 (1H, d, J=8.4 Hz), 7.64 (1H, s), 8.34 (1H, d, J=5.4 Hz).

Example 160

Preparation of 5-(5-cyclopropoxypyridin-2-yl)-3-((4-(4-(1,1,1,3,3,3-hexafluoro-2-hydroxypropan-2-yl)-2-propylphenoxy)pyridin-2-yl)methyl)-5-methylimidazolidine-2,4-dione

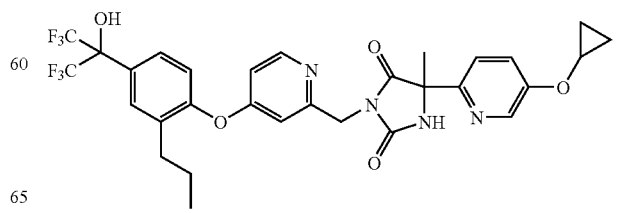

160-a-1) Preparation of 2-methyl-5-(1-(phenylthio)cyclopropoxy)pyridine

Cyclopropylphenyl thioether (5.0 g, 33.3 mmol) was dissolved in tetrahydrofuran (50 mL), and n-butyllithium (25.1 mL, 39.9 mmol) was dropwisely added at 0° C. for 5 minutes under an argon atmosphere. Then, a solution of N-iodosuccinimide (8.99 g, 39.9 mmol) in tetrahydrofuran (100 mL) was dropwisely added at −78° C. The resultant mixture was stirred overnight, and gradually warmed to room temperature. The reaction solution was added with a saturated aqueous solution of sodium hydrogen carbonate, and extracted with hexane. The organic layer was washed with brine, dried over anhydrous sodium sulfate, concentrated in vacuo, and purified using silica-gel column chromatography (hexane), to obtain a crude product ((1-iodocyclopropyl)(phenyl)sulfane:cyclopropylphenylthioether (=2.4:1) (5.64 g). Next, 5-hydroxy-2-methylpyridine (1.82 g, 16.7 mmol) was dissolved in toluene (150 mL). The resultant mixture was added with silver carbonate (9.19 g, 33.3 mmol) and 1-iodocyclopropyl)(phenypsulfane:cyclopropylphenylthioether (=2.4:1) mixture (5.64 g, 16.7 mmol (*converted in terms of 1-iodocyclopropyl)(phenyl)sulfane), and stirred overnight at room temperature. Then, acetic acid (200 mL) was added thereto, and stirred for 10 minutes. The reaction solution was filtered using celite and concentrated in vacuo. The obtained residue was purified using silica-gel column chromatography (hexane/ethyl acetate), and 2-methyl-5-(1-(phenylthio)cyclopropoxy)pyridine (1.88 g, yield 44%) was obtained as a yellow oil.

$^1$H-NMR (400 MHz, CDCl$_3$) δ: 1.34-1.37 (2H, m), 1.44-1.50 (2H, m), 2.51 (3H, s), 7.09 (1H, d, J=8.6 Hz), 7.22-7.35 (4H, m), 7.46-7.52 (2H, m), 8.31 (1H, d, J=2.9 Hz).

160-a-2) Preparation of 2-methyl-5-(1-(phenylsulfonyl)cyclopropoxy)pyridine

2-Methyl-5-(1-(phenylthio)cyclopropoxy) pyridine (2.04 g, 7.93 mmol) was dissolved in chloroform (15 mL), added with alumina (5.0 g), oxon (3.79 g, 6.18 mmol) and the resultant mixture was stirred at 80° C. for 1 hour. Then, oxone (1.36 g, 2.22 mmol) was further added, and stirred for 1 hour. The reaction solution was filtered using celite and concentrated in vacuo. The obtained residue was purified using silica-gel column chromatography (hexane/ethyl acetate) and 2-methyl-5-(1-(phenylsulfonyl)cyclopropoxy)pyridine (542 mg, yield 24%) was obtained as a yellow oil.

$^1$H-NMR (400 MHz, CD$_3$OD) δ: 1.42-1.46 (2H, m), 1.91-1.94 (2H, m), 2.47 (3H, s), 7.22 (1H, d, J=8.6 Hz), 7.55 (1H, dd, J=2.8, 8.6 Hz), 7.64 (2H, tt, J=1.7, 7.0 Hz), 7.76 (1H, tt, J=1.7, 7.0 Hz), 7.88 (2H, td, J=1.7, 7.0 Hz), 8.16 (1H, d, J=2.8 Hz).

160-a-3) Preparation of 5-cyclopropoxy-2-methylpyridine

2-Methyl-5-(1-(phenylsulfonyl)cyclopropoxy)pyridine (540 mg, 1.87 mmol) was dissolved in methanol (5.5 mL), and sodium phosphite (671 mg, 5.598 mmol) and amalgam sodium (3.58 g, 7.47 mmol) were added thereto under ice-cold conditions, and the resultant mixture was stirred at the same temperature for 30 minutes, and then further stirred at room temperature for 3 hours. The reaction solution was added with a saturated aqueous solution of sodium hydrogen carbonate and extracted with diethyl ether. The organic layer was washed with brine, dried over anhydrous sodium sulfate, and concentrated in vacuo. The obtained residue was purified by distillation, and 5-cyclopropoxy-2-methylpyridine (240 mg, yield 86%) was obtained as a yellow oil.

$^1$H-NMR (400 MHz, CDCl$_3$) δ: 0.77-0.83 (4H, m), 2.49 (3H, s), 3.76 (1H, tt, J=3.0, 5.7 Hz), 7.06 (1H, d, J=8.3 Hz), 7.25 (1H, dd, J=2.9, 8.6 Hz), 8.31 (1H, d, J=2.9 Hz).

160-a-4) Preparation of 5-cyclopropoxy-2-methylpyridine 1-oxide

5-Cyclopropoxy-2-methylpyridine was used for a similar reaction and treatment as 116-a), and 5-cyclopropoxy-2-methylpyridine 1-oxide was obtained as a white crystal.

$^1$H-NMR (400 MHz, CDCl$_3$) δ: 0.77-0.86 (4H, m), 2.47 (3H, s), 3.74 (1H, tt, J=3.0, 5.7 Hz), 6.91 (1H, dd, J=2.2, 8.8 Hz), 7.12 (1H, d, J=8.8 Hz), 8.27 (1H, d, J=2.2 Hz).

160-a-5) Preparation of (5-cyclopropoxypyridin-2-yl)methanol

5-Cyclopropoxy-2-methylpyridine 1-oxide was used for a similar reaction and treatment as 116-a), and (5-cyclopropoxypyridin-2-yl)methanol was obtained as a white crystal.

$^1$H-NMR (400 MHz, CDCl$_3$) δ: 0.80-0.83 (4H, m), 3.39 (1H, brs), 3.80 (1H, U, J=3.0, 5.9 Hz), 4.71 (2H, s), 7.18 (1H, d, J=8.5 Hz), 7.36 (1H, dd, J=2.7, 8.5 Hz), 8.37 (1H, d, J=2.7 Hz).

160-a-6) Preparation of 5-cyclopropoxypicolinaldehyde (5-Cyclopropoxypyridin-2-yl)methanol was used for a similar reaction and treatment as 116-a), and 5-cyclopropoxypicolinaldehyde was obtained as a white crystal.

$^1$H-NMR (270 MHz, CDCl$_3$) δ: 0.82-0.92 (4H, m), 3.89 (1H, tt, J=3.0, 5.8 Hz), 7.50 (1H, dd, J=2.8, 8.8 Hz), 7.98 (1H, d, J=8.8 Hz), 8.53 (1H, d, J=2.8 Hz), 10.00 (1H, s).

160-a-7) Preparation of 1-(5-cyclopropoxypyridin-2-yl)ethanol

5-Cyclopropoxypicolinaldehyde was used for a similar treatment and reaction as 116-a), and 1-(5-cyclopropoxypyridin-2-yl)ethanol was obtained as a white crystal.

$^1$H-NMR (400 MHz, CDCl$_3$) δ: 0.79-0.83 (4H, m), 1.49 (3H, d, J=6.6 Hz), 3.79 (1H, tt, J=3.0, 5.6 Hz), 3.94 (1H, d, J=4.4 Hz), 4.85 (1H, dq, J=4.4, 6.6 Hz), 7.20 (1H, d, J=8.6 Hz), 7.36 (1H, dd, J=2.8, 8.8 Hz), 8.34 (1H, d, J=2.8 Hz).

160-a-9) Preparation of 1-(5-cyclopropoxypyridin-2-yl)ethanone 1-(5-Cyclopropoxypyridin-2-yl)ethanol was used for a similar reaction and treatment as 116-a), and 1-(5-cyclopropoxypyridin-2-yl)ethanone was obtained as a white crystal.

$^1$H-NMR (400 MHz, CDCl$_3$) δ: 0.81-0.91 (4H, m), 2.68 (3H, s), 3.86 (1H, tt, J=3.0, 6.0 Hz), 7.44 (1H, dd, J=2.7, 8.8 Hz), 8.05 (1H, d, J=8.8 Hz), 8.42 (1H, d, J=2.7 Hz).

160-a-10) Preparation of 5-(5-cyclopropoxypyridin-2-yl)-5-methylimidazolidine-2,4-dione 1-(5-Cyclopropoxypyridin-2-yl)ethanone was used for a similar reaction and treatment as Example 1-a), and 5-(5-cyclopropoxypyridin-2-yl)-5-methylimidazolidine-2,4-dione was obtained as a white crystal.

¹H-NMR (400 MHz, CDCl₃) δ: 0.79-0.84 (4H, m), 1.80 (3H, s), 3.80 (1H, tt, J=3.0, 5.9 Hz), 6.27 (1H, brs), 7.38 (1H, dd, J=2.9, 8.8 Hz), 7.51 (1H, brs), 7.58 (1H, d, J=8.8 Hz), 8.35 (1H, d, J=2.9 Hz).

5-(5-Cyclopropoxypyridin-2-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

¹H-NMR (CDCl₃) δ: 0.77-0.83 (4H, m), 0.88 (3H, t, J=7.3 Hz), 1.56 (2H, qt, J=7.3, 7.6 Hz), 2.05 (3H, s), 2.53 (2H, t, J=7.6 Hz), 3.74-3.80 (1H, m), 4.82 (2H, s), 6.35 (1H, s), 6.62 (1H, dd, J=1.9, 5.7 Hz), 6.78 (1H, d, J=1.9 Hz), 7.01 (1H, d, J=8.6 Hz), 7.36 (1H, dd, J=2.4, 8.1 Hz), 7.58 (1H, d, J=8.6 Hz), 7.59 (1H, d, J=8.1 Hz), 7.64 (1H, s), 8.29 (1H, d, J=5.7 Hz), 8.32 (1H, d, J=2.4 Hz).

Example 161

Preparation of 5-(4-cyclopropoxyphenyl)-3-((4-(4-(1,1,1,3,3,3-hexafluoro-2-hydroxypropan-2-yl)-2-propylphenoxy)pyridin-2-yl)methyl)-5-methylimidazolidine-2,4-dione

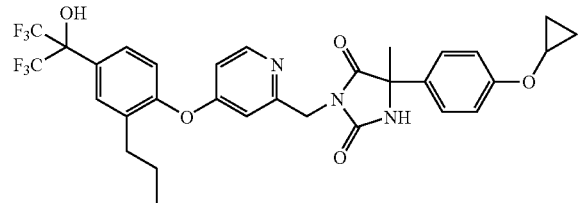

161-a-1) Preparation of 1-(4-(1-(phenylsulfonyl)cyclopropoxy)phenyl)ethanone

4-Hydroxyacetophenone was used in place of 2-hydroxy-5-methylpyridine in Example 160 for a similar reaction and treatment, and 1-(4-(1-(phenylsulfonyl)cyclopropoxy)phenyl)ethanone was obtained as a yellow oil.

¹H-NMR (CDCl₃) δ: 1.38-1.42 (2H, m), 1.45-1.49 (2H, m), 2.57 (3H, s), 7.13 (2H, d, J=8.8 Hz), 7.28-7.36 (3H, m), 7.46-7.49 (2H, m), 7.96 (2H, d, J=8.8 Hz).

161-a-2) Preparation of 1-(4-(1-(phenylsulfonyl)cyclopropoxy)phenyl)ethanone 1-(4-(1-(Phenylsulfonyl)cyclopropoxy)phenyl)ethanone was used for a similar reaction and treatment as Example 160, and 1-(4-(1-(phenylsulfonyl)cyclopropoxy)phenyl)ethanone was obtained as a white crystal.

¹H-NMR (CDCl₃) δ: 1.37-1.41 (2H, m), 1.96-2.00 (2H, m), 2.57 (3H, s), 7.17 (2H, d, J=8.8 Hz), 7.55-7.59 (2H, m), 7.68-7.71 (1H, m), 7.86-7.90 (2H, m), 7.91 (2H, d, J=8.8 Hz).

161-a-3) Preparation of 5-methyl-5-(4-(1-(phenylsulfonyl)cyclopropoxy)phenyl)imidazolidine-2,4-dione 1-(4-(1-(Phenylsulfonyl)cyclopropoxy)phenyl)ethanone was used for a similar reaction and treatment as Example 1-a), and the title compound was obtained as a white crystal.

¹H-NMR (CDCl₃) δ: 1.36-1.41 (2H, m), 1.72 (3H, s), 1.87-1.92 (2H, m), 7.08 (2H, d, J=8.9 Hz), 7.39 (2H, d, J=8.9 Hz), 7.55-7.62 (2H, m), 7.68-7.74 (1H, m), 7.82-7.86 (2H, m).

161-a-4) Preparation of 5-(4-cyclopropoxyphenyl)-5-methylimidazolidine-2,4-dione 5-Methyl-5-(4-(1-(phenylsulfonyl)cyclopropoxy)phenyl)imidazolidine-2,4-dione was used for a similar reaction and treatment as Example 160, and the title compound was obtained as a white crystal.

¹H-NMR (CDCl₃) δ: 0.62-0.70 (2H, m), 0.72-0.81 (2H, m), 1.73 (3H, s), 3.73-3.79 (1H, m), 7.04 (2H, d, J=8.9 Hz), 7.34 (2H, d, J=8.9 Hz).

5-(4-Cyclopropoxyphenyl)-5-methylimidazolidine-2,4-dione was used in place of 5-(benzo[d][1,3]dioxol-5-yl)-5-methylimidazolidine-2,4-dione in Example 40O for a similar reaction and treatment, and the title compound was obtained as a yellow oil.

¹H-NMR (CDCl₃) δ: 0.74-0.79 (4H, m), 0.89 (3H, t, J=7.3 Hz), 1.56 (2H, qt, J=7.3, 7.3 Hz), 1.82 (3H, s), 2.52 (2H, t, J=7.3 Hz), 3.68-3.75 (1H, m), 4.77 (2H, s), 5.98 (1H, s), 6.66-6.69 (2H, m), 7.00 (1H, d, J=8.1 Hz), 7.04 (2H, d, J=8.6 Hz), 7.43 (2H, d, J=8.6 Hz), 7.57 (1H, d, J=8.1 Hz), 7.64 (1H, s), 8.34 (1H, d, J=6.5 Hz).

Example 162

Preparation of 5-(benzofuran-6-yl)-3-((4-(4-(1,1,1,3,3,3-hexafluoro-2-hydroxypropan-2-yl)-2-propylphenoxy) pyridin-2-yl)methyl)-5-methylimidazolidine-2,4-dione

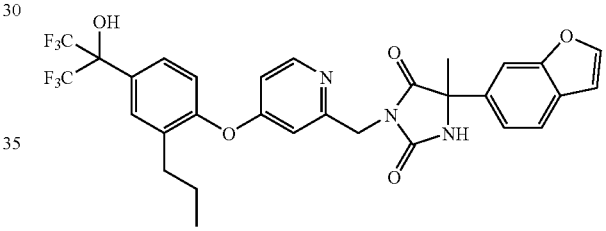

162-a-1) Preparation of 1-bromo-3-(2,2-diethoxyethoxy)benzene

To a solution of 3-bromophenol (1.68 g, 9.77 mmol) in N,N'-dimethylformamide (32 mL), sodium hydride (purity 50%) (516 mg, 10.7 mmol) was added under ice-cold conditions, and bromoacetaldehyde diethylacetal (1.76 mL, 11.7 mmol) was added at 0° C., and the resultant mixture was stirred at 120° C. overnight. The reaction solution was added with water at room temperature and extracted with diethyl ether. The organic layer was washed with brine, dried over anhydrous sodium sulfate, concentrated in vacuo, and purified using silica-gel column chromatography (hexane). 1-Bromo-3-(2,2-diethoxyethoxy)benzene (2.69 g. yield >100%) was obtained as a yellow oil.

¹H-NMR (CDCl₃) δ: 1.25 (6H, t, J=7.2 Hz), 3.57-3.70 (2H, m), 3.72-3.80 (2H, m), 3.98 (2H, d, J=5.2 Hz), 4.82 (1H, t, J=5.2 Hz), 6.84-6.87 (1H, m), 7.07-7.15 (3H, m).

162-a-2) Preparation of 6-bromobenzofuran

To a solution of 1-bromo-3-(2,2-diethoxyethoxy)benzene (2.3 g, 8.35 mmol) in toluene (28 mL), PPA (5.0 mL) was added, and the resultant mixture was stirred overnight while heated to reflux. The reaction solution was added with water at room temperature and extracted with ethyl acetate. The organic layer was washed with brine, dried over anhydrous sodium sulfate, concentrated in vacuo, and purified using silica-gel column chromatography (hexane). 6-Bromobenzofuran (1.2 g, yield 68%, mixture with 7-bromobenzofuran) was obtained as a yellow oil.

$^1$H-NMR (CDCl$_3$) δ: 6.75 (1H, dd, J=1.1, 2.4 Hz), 7.36 (1H, dd, J=1.6, 8.1 Hz), 7.46 (1H, d, J=8.1 Hz), 7.60 (1H, d, J=2.4 Hz), 7.68 (1H, s).

162-a-3) Preparation of 1-(benzofuran-6-yl)ethanone

To a solution of a mixture of 6-bromobenzofuran and 7-bromobenzofuran (1.12 g, 5.68 mmol) in toluene (19 mL), tetrakis triphenylphosphine palladium (650 mg, 0.57 mmol) and tributyl (1-ethoxyvinyl)tin (2.11 mL, 6.25 mmol) were added and the resultant mixture was stirred overnight at 100° C. The reaction solution was added with water at room temperature and extracted with ethyl acetate. The organic layer was washed with brine, dried over anhydrous sodium sulfate, concentrated in vacuo, and purified using silica-gel column chromatography (hexane).

1-(Benzofuran-6-yl)ethanone (280 mg) was obtained as a yellow crystal.

$^1$H-NMR (CDCl$_3$) δ: 2.67 (3H, s), 6.83 (1H, d, J=1.1 Hz), 7.65 (1H, d, J=8.4 Hz), 7.78 (1H, d, J=1.9 Hz), 7.89 (1H, dd, J=1.1, 8.4 Hz), 8.12 (1H, s).

162-a-4) Preparation of 5-(benzofuran-6-yl)-5-methylimidazolidine-2,4-dione 1-(Benzofuran-6-yl)ethanone was used for a similar reaction and treatment as Example 1-a), and 5-(benzofuran-6-yl)-5-methylimidazolidine-2,4-dione was obtained as a white crystal.

$^1$H-NMR (CDCl$_3$) δ: 1.82 (3H, s), 6.83 (1H, dd, J=0.8, 1.6 Hz), 7.32 (1H, dd, J=1.6, 8.4 Hz), 7.63 (1H, d, J=8.4 Hz), 7.67 (1H, s), 7.78 (1H, d, J=2.2 Hz).

5-(Benzofuran-6-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (CDCl$_3$) δ: 0.87 (3H, t, J=7.3 Hz), 1.55 (2H, qt, J=7.3, 7.8 Hz), 1.91 (3H, s), 2.50 (2H, t, J=7.8 Hz), 4.79 (2H, s), 6.13 (1H, s), 6.66-6.68 (2H, m), 6.75-6.76 (1H, m), 7.00 (1H, d, J=8.6 Hz), 7.42 (1H, dd, J=1.6, 8.1 Hz), 7.57 (1H, d, J=8.6 Hz), 7.60 (1H, d, J=8.1 Hz), 7.64 (1H, s), 7.65 (1H, d, J=1.9 Hz), 7.73 (1H, d, J=1.6 Hz), 8.35 (1H, d, J=6.5 Hz).

Example 163

Preparation of 5-(2,3-dihydrobenzofuran-6-yl)-3-((4-(4-(1,1,1,3,3,3-hexafluoro-2-hydroxypropan-2-yl)-2-propylphenoxy)pyridin-2-yl)-methyl)-5-methylimidazolidine-2,4-dione

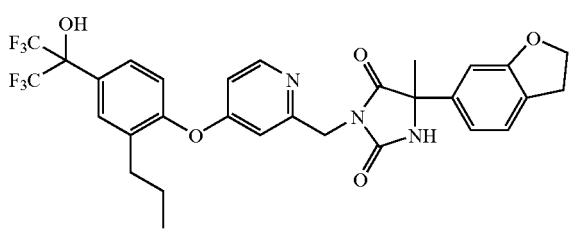

163-a) Preparation of 5-(2,3-dihydrobenzofuran-6-yl)-5-methylimidazolidine-2,4-dione 5-(Benzofuran-6-yl)-5-methylimidazolidine-2,4-dione was used for a similar reaction and treatment as Example 149, and 5-(2,3-dihydrobenzofuran-6-yl)-5-methylimidazolidine-2,4-dione was obtained as a white crystal.

$^1$H-NMR (CDCl$_3$) δ: 1.72 (3H, s), 3.18 (2H, t, J=8.6 Hz), 4.54 (2H, t, J=8.6 Hz), 6.87 (1H, d, J=1.4 Hz), 6.96 (1H, dd, J=2.2, 7.6 Hz), 7.19 (1H, d, J=7.6 Hz).

5-(2,3-Dihydrobenzofuran-6-yl)-5-methylimidazolidine-2,4-dione was used in place of 5-(benzo[d][1,3]dioxol-5-yl)-5-methylimidazolidine-2,4-dione in Example 40 f) for a similar reaction and treatment, and the title compound was obtained as a yellow oil.

$^1$H-NMR (CDCl$_3$) δ: 0.88 (3H, t, J=7.3 Hz), 1.55 (2H, qt, J=7.3, 7.8 Hz), 1.80 (3H, s), 2.51 (2H, t, J=7.8 Hz), 3.18 (2H, t, J=8.9 Hz), 4.58 (2H, t, J=8.9 Hz), 4.76 (2H, s), 6.03 (1H, s), 6.62 (1H, d, J=2.4 Hz), 6.68 (1H, dd, J=2.4, 5.9 Hz), 6.95 (1H, d, J=1.9 Hz), 6.99 (1H, dd, J=1.9, 7.6 Hz), 7.01 (1H, d, J=8.6 Hz), 7.18 (1H, d, J=7.6 Hz), 7.58 (1H, d, J=8.6 Hz), 7.64 (1H, s), 8.34 (1H, d, J=5.9 Hz).

Example 164

Preparation of 5-(2,3-dihydro-[1,4]dioxyno[2,3-c]pyridin-7-yl)-3-((4-(4-(4-(1,1,1,3,3,3-hexafluoro-2-hydroxypropan-2-yl)-2-propylphenoxy)pyridin-2-yl)methyl)-5-methylimidazolidine-2,4-dione

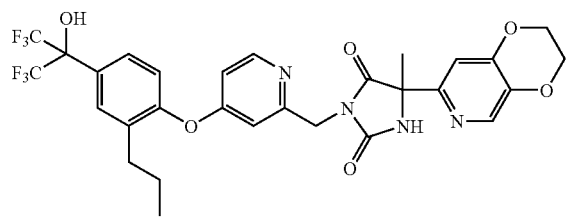

164-a-1) Preparation of 5-(methoxymethoxy)-2-methylpyridine

Chloromethylmethoxy ether was used for a similar reaction and treatment as Example 9-a), and 5-(methoxymethoxy)-2-methylpyridine was obtained as a colorless oil.

$^1$H-NMR (CDCl$_3$) δ: 2.50 (3H, s), 3.48 (3H, s), 5.17 (2H, s), 7.07 (1H, d, J=8.4 Hz), 7.27 (1H, dd, J=3.0, 8.4 Hz), 8.29 (1H, d, J=3.0 Hz).

164-a-2) Preparation of 5-(methoxymethoxy)-2-methylpyridine-4-ylboronic acid

To a solution of 5-methoxymethoxy-2-methylpyridine (3.0 g, 19.6 mmol) in tetrahydrofuran (100 mL), n-butyllithium (18.4 mL, 29.4 mmol) was added at −78° C., and the resultant mixture was stirred at −78° C. for 40 minutes. Then, (1-methylethoxy)boronic acid ester (6.8 mL, 29.4 mmol) was added, and the resultant mixture was stirred at −78° C. for 45 minutes. The reaction solution was added with 1N aqueous solution of hydrochloric acid, gradually warmed, and extracted with ethyl acetate. The organic layer was dried over anhydrous sodium sulfate and concentrated in vacuo. The obtained residue was washed and filtered with diethylether, and 5-(methoxymethoxy)-2-methylpyridine-4-ylboronic acid (2.08 g, yield 54%) was obtained as a white crystal.

$^1$H-NMR (CDCl$_3$) δ: 2.53 (3H, s), 3.52 (3H, s), 5.31 (2H, s), 5.80 (2H, s), 7.54 (1H, s), 8.41 (1H, s).

164-a-3) Preparation of 5-(methoxymethoxy)-2-methylpyridin-4(1H)-one

To a solution of 5-(methoxymethoxy)-2-methylpyridin-4-ylboronic acid (500 mg, 2.54 mmol) in tetrahydrofuran (12.7 mL), an aqueous solution of hydroxide peroxide (purity 30%) (2.9 mL, 25.4 mmol) was added at room temperature, and the resultant mixture was stirred at room temperature for 4 hours. The reaction solution was added with a saturated aqueous solution of sodium persulfate and concentrated in vacuo. The obtained residue was washed and filtered with chloroform/methanol, and 5-(methoxymethoxy)-2-methylpyridin-4 (1H)-one (440 mg, yield >100%) was obtained as a yellow amorphous.

$^1$H-NMR (CDCl$_3$) δ: 2.37 (3H, s), 3.44 (3H, s), 5.11 (2H, s), 6.40 (1H, s), 7.66 (1H, s).

164-a-4) Preparation of 2-(5-(methoxymethoxy)-2-methylpyridin-4-yloxy)ethanol To a solution of 5-(methoxymethoxy)-2-methylpyridin-4 (1H)-one (1.28 g, 7.56 mmol) in N,N'-dimethylformamide (19 mL), potassium carbonate (2.10 g, 15.1 mmol) and 2-bromoethanol (804 µL, 11.3 mmol) were added sequentially, and the resultant mixture was stirred at 90° C. overnight. After completion of the reaction, the reaction solution was concentrated in vacuo. The obtained residue was dissolved in chloroform/methanol, solid substance was filtered, and the filtrate was concentrated in vacuo. The obtained residue was purified using column chromatography (hexane/acetone) and 2-(5-(methoxymethoxy)-2-methylpyridin-4-yloxy)ethanol was obtained as an orange oil (900 mg, yield 56%).

$^1$H-NMR (CDCl$_3$) δ: 2.48 (3H, s), 3.54 (3H, s), 3.99 (2H, t, J=4.4 Hz), 4.16 (2H, t, J=4.4 Hz), 5.16 (2H, s), 6.70 (1H, s), 8.21 (1H, s).

164-a-5) Preparation of 4-(2-hydroxyethoxy)-6-methylpyridin-3-ol 2-(5-(Methoxymethoxy)-2-methylpyridin-4-yloxy)ethanol (900 mg, 4.22 mmol) was dissolved in ethyl acetate (10 mL). The resultant mixture was added with 4N hydrochloric acid-ethyl acetate solution (10 mL) and stirred at room temperature for 5 hours. After completion of the reaction, 4N aqueous solution of sodium hydroxide was used under ice-cold conditions, and the reaction solution was adjusted to pH=8. The reaction solution was concentrated in vacuo. The obtained residue was washed with chloroform/methanol and dried. 4-(2-Hydroxyethoxy)-6-methylpyridin-3-ol (1.2 g) was obtained as a white solid, as crude product.

$^1$H-NMR (CDCl$_3$) δ: 2.44 (3H, s), 3.93 (2H, t, J=4.4 Hz), 4.18 (2H, brs), 6.95 (1H, s), 7.76 (1H, s).

164-a-6) Preparation of 7-methyl-2,3-dihydro-[1,4]dioxyno[2,3-c]pyridine 4-(2-Hydroxyethoxy)-6-methylpyridin-3-ol was used for a similar reaction and treatment as Example 27-b), and 7-methyl-2,3-dihydro-[1,4]dioxyno[2,3-c]pyridine was obtained as a colorless oil.

$^1$H-NMR (CDCl$_3$) δ: 2.42 (3H, s), 4.23-4.31 (4H, m), 6.64 (1H, s), 8.04 (1H, s).

164-a-7) Preparation of 7-methyl-2,3-dihydro-[1,4]dioxyno[2,3-c]pyridine 6-oxide 7-Methyl-2,3-dihydro-[1,4]dioxyno[2,3-c]pyridine was used for a similar reaction and treatment as Example 116, and 7-methyl-2,3-dihydro-[1,4]dioxyno[2,3-c]pyridine 6-oxide was obtained as a yellow solid.

$^1$H-NMR (CDCl$_3$) δ: 2.45 (3H, s), 4.28-4.35 (4H, m), 6.75 (1H, s), 8.09 (1H, s).

164-a-7) Preparation of (2,3-dihydro-[1,4]dioxyno[2,3-c]pyridin-7-yl)methyl acetate 7-Methyl-2,3-dihydro-[1,4]dioxyno[2,3-c]pyridine 6-oxide was used for a similar reaction and treatment as Example 16), and (2,3-dihydro-[1,4]dioxyno[2,3-c]pyridin-7-yl)methyl acetate was obtained as a yellow oil.

$^1$H-NMR (CDCl$_3$) δ: 2.14 (3H, s), 4.29-4.35 (4H, m), 5.09 (2H, s), 6.88 (1H, s), 8.16 (1H, s).

164-a-8) Preparation of (2,3-dihydro-[1,4]dioxyno[2,3-c]pyridin-7-yl)methanol (2,3-Dihydro-[1,4]dioxyno[2,3-c]pyridin-7-yl)methyl acetate was used for a similar reaction and treatment as Example 116, and (2,3-dihydro-[1,4]dioxyno[2,3-c]pyridin-7-yl)methanol was obtained as a yellow oil.

$^1$H-NMR (CDCl$_3$) δ: 4.29-4.35 (4H, m), 4.62 (2H, s), 6.76 (1H, s), 8.12 (1H, s).

164-a-9) Preparation of 2,3-dihydro-[1,4]dioxyno[2,3-c]pyridine-7-carbaldehyde (2,3-Dihydro-[1,4]dioxyno[2,3-c]pyridin-7-yl)methanol was used for a similar reaction and treatment as Example 116), and 2,3-dihydro-[1,4]dioxyno[2,3-c]pyridine-7-carbaldehyde was obtained as a yellow solid.

$^1$H-NMR (CDCl$_3$) δ: 4.39 (4H, s), 7.51 (1H, s), 8.31 (1H, s), 9.93 (1H, s).

164-a-10) Preparation of 1-(2,3-dihydro-[1,4]dioxyno[2,3-c]pyridin-7-yl)ethanone 2,3-Dihydro-[1,4]dioxyno[2,3-c]pyridine-7-carbaldehyde was used for a similar reaction and treatment as Example 116, and 1-(2,3-dihydro-[1,4]dioxyno[2,3-c]pyridin-7-yl)ethanone was obtained as a yellow oil.

$^1$H-NMR (CDCl$_3$) δ: 2.66 (3H, s), 4.36 (4H, s), 7.60 (1H, s), 8.20 (1H, s).

164-a-10) Preparation of 5-(2,3-dihydro-[1,4]dioxyno[2,3-c]pyridin-7-yl)-5-methylimidazol dine-2,4-dione 1-(2,3-Dihydro-[1,4]dioxyno[2,3-c]pyridin-7-yl)ethanone was used for a similar reaction and treatment as Example 1-a), and 5-(2,3-dihydro-[1,4]dioxyno[2,3-c]pyridin-7-yl)-5-methylimidazolidine-2,4-dione was obtained as a colorless oil.

$^1$H-NMR (CDCl$_3$) δ: 1.73 (3H, s), 4.29-4.37 (4H, m), 7.06 (1H, s), 8.05 (1H, s).

5-(2,3-Dihydro-[1,4]dioxyno[2,3-c]pyridin-7-yl)-5-methylimidazolidine-2,4-dione was used in place of 5-(benzo[d] [1,3]dioxol-5-yl)-5-methylimidazolidine-2,4-dione in Example 40 f) for a similar reaction and treatment, and 5-(2,3-dihydro-[1,4]dioxyno[2,3-c]pyridin-7-yl)-3-((4-(4-(4-(1, 1,1,3,3,3-hexafluoro-2-hydroxypropan-2-yl)-2-propylphenoxy)pyridin-2-yl)methyl)-5-methylimidazolidine-2,4-dione was obtained as a yellow oil.

$^1$H-NMR (CDCl$_3$) δ: 0.88 (3H, t, J=7.3 Hz), 1.56 (2H, qt, J=7.3, 7.8 Hz), 1.75 (3H, s), 2.52 (2H, t, J=7.8 Hz), 4.25-4.33 (4H, m), 4.81 (2H, s), 6.55 (1H, s), 6.62 (1H, dd, J=2.4, 5.7 Hz), 6.80 (1H, d, J=2.4 Hz), 7.01 (1H, d, J=8.6 Hz), 7.20 (1H, s), 7.60 (1H, d, J=8.6 Hz), 8.06 (1H, s), 8.27 (1H, d, J=5.7 Hz).

Example 165

Preparation of 3-((4-(4-(1,1,1,3,3,3-hexafluoro-2-hydroxypropan-2-yl)-2,6-dipropylphenoxy)pyridin-2-yl)methy 1)-5-(4-(1-methylethoxy)phenyl)-5-methylimidazolidine-2,4-dione

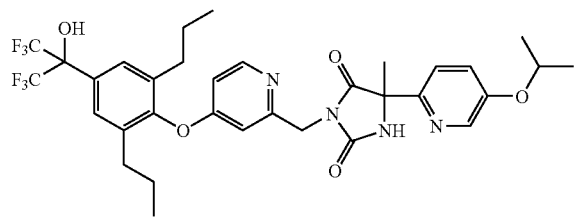

2,6-dipropyl-4-[1,1,1,3,3,3-hexafluoro-2-(methoxymethoxy)propan-2-yl]phenol was used in place of 4-(1,1,1,3,3,3-hexafluoro-2-(methoxymethoxy)propan-2-yl)-2-propylphenol, and 2-chloropyridine-4-boronic acid was used in place of 3-(hydroxymethyl)phenylboronic acid in Preparation Example 3 for a similar reaction and treatment, and the obtained 2-chloro-4-(4-(1,1,1,3,3,3-hexafluoro-2-(methoxymethoxy)propan-2-yl)-2,6-dipropylphenoxy) pyridine and 5-methyl-5-(4-(1-methylethoxy)phenyl)imidazolidine-2,4-dione were used for a similar reaction and treatment as Example 40, and the title compound was obtained as a colorless oil.

$^1$H-NMR (CDCl$_3$) δ: 0.84 (6H, t, J=7.3 Hz), 1.32 (6H, d, J=5.7 Hz), 1.53 (4H, qt, J=7.3, 7.8 Hz), 1.80 (3H, s), 2.36 (4H, t, J=7.8 Hz), 4.53 (1H, sept, J=5.7 Hz), 4.76 (2H, s), 5.72 (1H, s), 6.51-6.54 (2H, m), 6.87 (2H, d, J=8.9 Hz), 7.41 (2H, d, J=8.9 Hz), 7.47 (2H, s), 8.28 (1H, d, J=5.1 Hz).

Example 166

Preparation of 5-(benzo[d][1,3]dixol-5-yl)-3-((4-(4-(1,1,1,3,3,3-hexafluoro-2-hydroxypropan-2-yl)-2,6-dipropylphenoxy)pyridin-2-yl)methyl)-5-methylimidazolidine-2,4-dione

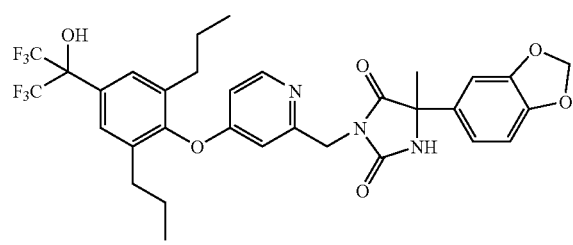

5-(Benzo[d][1,3]dixol-5-yl)-5-methylimidazolidine-2,4-dione was used in place of 5-methyl-5-(4-(1-methylethoxy)phenyl)imidazolidine-2,4-dione in Example 165 for a similar reaction and treatment, and the title compound was obtained as a colorless oil.

$^1$H-NMR (CDCl$_3$) δ: 0.84 (6H, t, J=7.6 Hz), 1.52-1.63 (4H, m), 1.68 (3H, s), 2.38 (4H, t, J=7.6 Hz), 5.25 (2H, s), 5.96 (2H, s), 6.82 (1H, d, J=8.1 Hz), 6.94-7.00 (3H, m), 7.20-7.30 (1H, m), 7.60 (2H, s), 8.59 (1H, d, J=6.5 Hz).

Example 167

Preparation of 3-((4-(4-(1,1,1,3,3,3-hexafluoro-2-hydroxypropan-2-yl)-2,6-dipropylphenoxy)pyridin-2-yl)methyl)-5-(6-methoxypyridin-3-yl)-5-methylimidazolidine-2,4-dione

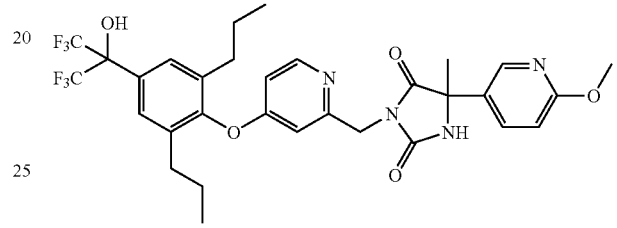

5-(2-Methoxypyridin-5-yl)-5-methylimidazolidine-2,4-dione was used in place of 5-methyl-5-(4-(1-methylethoxy)phenyl)imidazolidine-2,4-dione in Example 165 for a similar reaction and treatment, and the title compound was obtained as a colorless oil.

$^1$H-NMR (CDCl$_3$) δ: 0.85 (6H, t, J=7.3 Hz), 1.47-1.60 (4H, m), 1.73 (3H, s), 2.38 (4H, t, J=7.6 Hz), 3.96 (3H, s), 4.52 (2H, s), 6.94 (1H, d, J=8.9 Hz), 7.09 (1H, s), 7.38 (1H, s), 7.62 (2H, s), 7.90 (1H, s), 8.24 (1H, d, J=2.7 Hz), 8.65 (1H, d, J=6.8 Hz).

Example 168

Preparation of 3-((4-(4-(1,1,1,3,3,3-hexafluoro-2-hydroxypropan-2-yl)-2,6-dipropylphenoxy)pyridin-2-yl)methyl)-5-(4-isopropylphenyl)-5-methylimidazolidine-2,4-dione

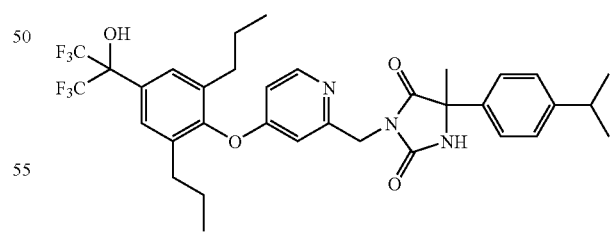

5-(4-(1-Methylethyl)phenyl)$_5$-methylimidazolidine-2,4-dione was used in place of 5-methyl-5-(4-(1-methylethoxy)phenyl)imidazolidine-2,4-dione in Example 165 for a similar reaction and treatment, and the title compound was obtained as a colorless oil.

$^1$H-NMR (CDCl$_3$) δ: 0.83 (6H, t, J=7.4 Hz), 1.23 (6H, d, J=7.1 Hz), 1.47-1.60 (4H, m), 1.71 (3H, s), 2.35 (4H, t, J=7.8 Hz), 2.91 (1H, sept, J=4.0 Hz), 4.77 (2H, s), 6.65-6.68 (2H, m), 7.28 (2H, d, J=8.5 Hz), 7.41 (2H, t, J=8.5 Hz), 7.59 (2H, s), 8.24 (1H, d, J=2.7 Hz), 8.58 (1H, d, J=6.6 Hz).

Example 169

Preparation of 5-(4-tert-butylphenyl)-3-((4-(4-(1,1,1,3,3,3-hexafluoro-2-hydroxypropan-2-yl)-2,6-dipropylphenoxy) pyridin-2-yl)methyl-5-methylimidazolidine-2,4-dione

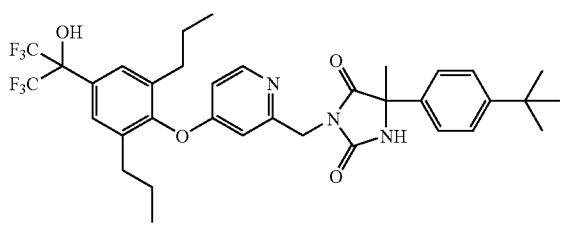

5-(4-(1,1-Dimethylethyl)phenyl)-5-methylimidazolidine-2,4-dione was used in place of 5-methyl-5-(4-(1-methylethoxy)phenyl)imidazolidine-2,4-dione in Example 165 for a similar reaction and treatment, and the title compound was obtained as a colorless oil.

$^1$H-NMR (CD$_3$OD) δ: 0.83 (6H, t, J=7.3 Hz), 1.31 (9H, s), 1.50 (4H, qt, J=7.3, 7.3 Hz), 1.71 (3H, s), 2.35 (4H, t, J=7.3 Hz), 4.88 (2H, s), 6.88 (1H, s), 7.22 (1H, d, J=6.5 Hz), 7.38-7.47 (4H, s), 7.59 (2H, s), 8.56 (1H, d, J=6.5 Hz).

Example 170

Preparation of 5-(3-fluoro-4-(1-methylethoxy)phenyl)-3-((4-(4-(1,1,1,3,3,3-hexafluoro-2-hydroxypropan-2-yl)-2,6-dipropylphenoxy)pyridin-2-yl)methyl)-5-methylimidazolidine-2,4-dione

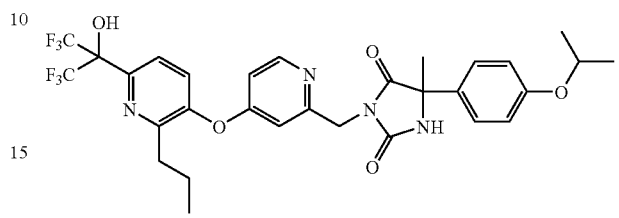

5-Methyl-5-(4-(1-methylethoxy-2-fluoro)phenyl)imidazolidine-2,4-dione was used in place of 5-methyl-5-(4-(1-methylethoxy)phenyl)imidazolidine-2,4-dione in Example 165 for a similar reaction and treatment, and the title compound was obtained as a colorless oil.

$^1$H-NMR (CD$_3$OD) δ: 0.84 (6H, t, J=7.3 Hz), 1.32 (6H, d, J=5.9 Hz), 1.52 (4H, qt, J=7.3, 7.6 Hz), 1.69 (3H, s), 2.37 (4H, t, J=7.6 Hz), 4.60 (1H, sept, J=5.9 Hz), 4.88 (2H, s), 6.92 (1H, s), 7.06-7.14 (1H, m), 7.19-7.28 (3H, m), 7.60 (2H, s), 8.58 (1H, d, J=6.5 Hz).

Example 171

Preparation of 3-((4-(6-(1,1,1,3,3,3-hexafluoro-2-hydroxypropan-2-yl)-2-propylpyridin-3-yloxy)pyridin-2-yl)methyl)-5-(4-(1-methylethoxy)phenyl)-5-methylimidazolidine-2,4-dione 171-a) Preparation of 3-(2-(bromomethyl)pyridin-4-yloxy)-6-(1,1,1,3,3,3-hexafluoro-2-(methoxymethoxy)propan-2-yl)-2-propylpyridine The following compounds were prepared sequentially.

Preparation of (Z)-3-nitro-2-(prop-1-enyl)pyridine

Cis-propenebronic acid (those in which trans-form are mixed in an amount of 10% or less) was used in place of vinyl boronic acid pinacol ester for a similar reaction and treatment as Example 126, and (Z)-3-nitro-2-(propa-1-enyl)pyridine was obtained as a colorless oil.

$^1$H-NMR (CDCl$_3$) δ: 2.03 (3H, dd, J=1.7, 7.3 Hz), 6.20-6.27 (1H, m), 6.80 (1H, qd, J=1.7, 11.7 Hz), 7.34 (1H, dd, J=4.6, 8.1 Hz), 8.24 (1H, dd, J=1.4, 8.1 Hz), 8.82 (1H, dd, J=1.4, 4.6 Hz).

Preparation of (E)-3-nitro-2-(propa-1-enyl)pyridine $^1$H-NMR (CDCl$_3$) δ: 2.02 (3H, dd, J=1.4, 6.8 Hz), 7.03 (1H, qd, J=1.4, 15.1 Hz), 7.18-7.29 (2H, m), 8.16 (1H, dd, J=1.7, 8.3 Hz), 8.72 (1H, dd, J=1.7, 4.6 Hz).

Preparation of 2-propylpyridine-3-amine

The similar reaction and treatment were conducted as Example 121), and 2-propylpyridine-3-amine was obtained as a colorless oil.

$^1$H-NMR (CDCl$_3$) δ: 1.02 (3H, t, J=7.4 Hz), 1.78 (2H, qt, J=7.4, 7.8 Hz), 2.67 (2H, t, J=7.8 Hz), 6.89-6.97 (2H, m), 7.99 (1H, dd, J=1.7, 4.4 Hz).

Preparation of 2-propylpyridin-3-ol

The similar reaction and treatment were conducted as Example 119-a), and 2-propylpyridin-3-ol was obtained as a colorless oil.

$^1$H-NMR (CDCl$_3$) δ: 0.90 (3H, t, J=7.3 Hz), 1.64 (2H, qt, J=7.3, 7.6 Hz), 2.66 (2H, t, J=7.6 Hz), 7.01 (1H, dd, J=4.6, 8.1 Hz), 7.09 (1H, dd, J=1.4, 8.1 Hz), 7.92 (1H, dd, J=1.4, 4.6 Hz).

Preparation of 6-iodo-2-propylpyridin-3-ol

2-Propylpyridin-3-ol (2.42 g, 17.7 mmol) was dissolved in ethanol (40 mL) and water (10 mL). Iodine (4.71 g, 18.6 mmol) was added thereto under ice-cold conditions, and stirred for 2 hours. Then, the mixture was stirred at room temperature for 4 hours. After completion of the reaction, ethanol was concentrated in vacuo and extracted with ethyl acetate. The organic layer was washed with brine, dried over sodium sulfate, and concentrated in vacuo. The obtained residue was purified using column chromatography (hexane/ethyl acetate), and 6-iodo-2-propylpyridin-3-ol (2.80 g, yield 60%) was obtained as a yellow oil.

$^1$H-NMR (CDCl$_3$) δ: 0.95 (3H, t, J=7.6 Hz), 1.65 (2H, qt, J=7.6, 7.6 Hz), 2.69 (2H, t, J=7.6 Hz), 6.84 (1H, d, J=8.3 Hz), 7.41 (1H, d, J=8.3 Hz).

Preparation of 5-hydroxy-6-propyl picolinonitrile

6-Iodo-2-propylpyridin-3-ol (2.0 g, 7.60 mmol) was dissolved in N,N-dimethylformamide (30 mL). Dinitrile zinc (1.34 g, 11.4 mmol) and tetrakis triphenylphosphine palladium (878 mg, 0.760 mmol) were added at room temperature, and the resultant mixture was stirred for 20 minutes under microwave irradiation. After completion of the reaction, the reaction solution was filtered using celite and extracted with ethyl acetate. The organic layer was washed with brine, dried over sodium sulfate, and concentrated in vacuo. The obtained residue was purified using column chromatography (hexane/ethyl acetate) and 5-hydroxy-6-propyl picolinonitrile (1.75 g, yield >100%) was obtained as a yellow oil.

$^1$H-NMR (CDCl$_3$) δ: 0.99 (3H, t, J=7.3 Hz), 1.76 (2H, qt, J=7.3, 7.6 Hz), 2.82 (2H, t, J=7.6 Hz), 7.15 (1H, d, J=8.4 Hz), 7.46 (1H, d, J=8.4 Hz).

Preparation of methyl 5-hydroxy-6-propyl picolinate

5-Hydroxy-6-propyl picolinonitrile (1.73 g, 10.7 mmol) was dissolved in methanol (80 mL). Under ice-cold conditions, concentrated sulfuric acid (20 mL) was added, and the resultant mixture was stirred at room temperature for 5 minutes and then stirred at 100° C. overnight. After completion of the reaction, the reaction solution was neutralized by adding 4N aqueous solution of sodium hydroxide, and added with a saturated aqueous solution of sodium hydrogen carbonate. Then, the resultant mixture was extracted with ethyl acetate. The organic layer was washed with brine, dried over sodium sulfate, and concentrated in vacuo. The obtained residue was purified using column chromatography (hexane/ethyl acetate), and methyl 5-hydroxy-6-propyl picolinate (980 mg, yield 47%) was obtained as a colorless oil.

$^1$H-NMR (CDCl$_3$) δ: 0.94 (3H, t, J=7.3 Hz), 1.72 (2H, qt, J=7.3, 7.8 Hz), 2.88 (2H, t, J=7.8 Hz), 3.90 (3H, s), 7.25 (1H, d, J=8.3 Hz), 7.89 (1H, d, J=8.3 Hz).

Preparation of methyl 5-(benzyloxy)-6-propyl picolinate

The similar reaction and treatment were conducted as Example 127) and methyl 5-(benzyloxy)-6-propyl picolinate was obtained as a colorless oil.

$^1$H-NMR (CDCl$_3$) δ: 0.99 (3H, t, J=7.6 Hz), 1.76 (2H, qt, J=7.6, 7.8 Hz), 2.94 (2H, t, J=7.8 Hz), 3.96 (3H, s), 5.16 (2H, s), 7.19 (1H, d, J=8.6 Hz), 7.34-7.45 (5H, m), 7.97 (1H, d, J=8.6 Hz).

Preparation of 5-(benzyloxy)-6-propyl picolinic acid

Methyl 5-(benzyloxy)-6-propyl picolinate (2.0 g, 5.02 mmol) was dissolved in methanol (6 mL). Under ice-cold conditions, 4N aqueous solution of sodium hydroxide (2.0 mL) was added, and the resultant mixture was stirred at room temperature for 1 hour. Then, 4N aqueous solution of sodium hydroxide (1.0 mL) was further added under ice-cold conditions, and the resultant mixture was stirred at room temperature for 1 hour. After completion of the reaction, the reaction solution was adjusted to around pH 4-5 by adding 4N aqueous solution of hydrochloric acid. Then, the resultant mixture was extracted with ethyl acetate/tetrahydrofuran. The organic layer was washed with brine, dried over sodium sulfate, and concentrated in vacuo. The obtained residue was washed with diethylether, and 5-(benzyloxy)-6-propyl picolinic acid (943 mg, yield 69%) was obtained as a colorless oil.

$^1$H-NMR (CDCl$_3$) δ: 0.90 (3H, t, J=7.3 Hz), 1.64 (2H, qt, J=7.3, 7.3 Hz), 2.77 (2H, t, J=7.3 Hz), 5.20 (2H, s), 7.32-7.47 (6H, m), 7.82 (1H, d, J=8.3 Hz).

Preparation of perfluorophenyl 5-(benzyloxy)-6-propyl picolinate 5-(Benzyloxy)-6-propyl picolinic acid (1.23 g, 4.53 mmol) was dissolved in ethyl acetate (150 mL). Under ice-cold conditions, pentafluorophenol (1.0 g, 5.44 mmol) and N,N'-dicyclohexylcarbodiimide (1.12 g, 5.44 mmol) were added sequentially, and the resultant mixture was stirred at room temperature overnight. The reaction solution was added with water and extracted with ethyl acetate. The organic layer was washed with brine, dried using anhydrous sodium sulfate, and concentrated in vacuo. The obtained residue was purified using silica-gel column chromatography (hexane/acetone), and perfluorophenyl 5-(benzyloxy)-6-propyl picolinate (1.56 g, yield 79%) was obtained as a yellow oil.

$^1$H-NMR (CDCl$_3$) δ: 1.01 (3H, t, J=7.3 Hz), 1.80 (2H, qt, J=7.3, 7.8 Hz), 2.98 (2H, t, J=7.8 Hz), 5.22 (2H, s), 7.25 (1H, d, J=8.5 Hz), 7.35-7.45 (5H, m), 8.12 (1H, d, J=8.5 Hz).

Preparation of 2-(5-(benzyloxy)-6-propylpyridin-2-yl)-1,1,1,3,3,3-hexafluoropropan-2-ol Perfluorophenyl 5-(benzyloxy)-6-propyl picolinate (1.0 g, 2.29 mmol) and tetramethylammonium fluoride (1.06 g, 11.4 mmol) were dried under vacuo pump, and dissolved in ethylene glycol dimethyl ether (26 mL). Under ice-cold conditions, trifluoromethyl trimethylsilane (1.69 mL, 11.4 mmol) was added thereto, and the resultant mixture was stirred under ice-cold conditions for 1 hour. Then, the mixture was stirred at room temperature for 2 hours. After completion of the reaction, the reaction solution was added with water and extracted with ethyl acetate. The organic layer was washed with brine, dried using anhydrous sodium sulfate, and concentrated in vacuo. The obtained residue was purified using silica-gel column chromatography (hexane/ethyl acetate), and 2-(5-(benzyloxy)-6-propylpyridin-2-yl)-1,1,1,3,3,3-hexafluoropropan-2-ol (372 mg, yield 41%) was obtained as a brown oil.

$^1$H-NMR (CDCl$_3$) δ: 0.98 (3H, t, I=7.3 Hz), 1.80 (2H, qt, J=7.3, 7.6 Hz), 2.92 (2H, t, J=7.6 Hz), 5.15 (2H, s), 7.28-7.51 (7H, m).

Preparation of 3-(benzyloxy)-6-(1,1,1,3,3,3-hexafluoro-2-(methoxymethoxy)propan-2-yl)-2-propylpyridine 2-(5-(Benzyloxy)-6-propylpyridin-2-yl)-1,1,1,3,3,3-hexafluoropropan-2-ol (537 mg, 1.37 mmol) was dissolved in N,N'-dimethylformamide (2.5 mL) and added with sodium hydride (purity 50%) (79 mg, 1.64 mmol) and methoxymethyl ether chloride (113 µL, 1.50 mmol) under ice-cold conditions The resultant mixture was stirred under ice-cold conditions for 1.5 hours and then further stirred at room temperature for 45 minutes. After completion of the reaction, the reaction solution was added with water and extracted with ethyl acetate. The organic layer was washed with brine, dried using anhydrous sodium sulfate, and concentrated in vacuo. The obtained residue was purified using silica-gel column chromatography (hexane/ethyl acetate), and 3-(benzyloxy)-6-(1,1,1,3,3,3-hexafluoro-2-(methoxymethoxy)propan-2-yl)-2-propylpyridine (407 mg, yield 68%) was obtained as a colorless oil.

$^1$H-NMR (CDCl$_3$) δ: 0.95 (3H, t, J=7.3 Hz), 1.78 (2H, qt, J=7.3, 7.3 Hz), 2.86 (2H, t, J=7.3 Hz), 3.55 (3H, s), 4.90 (2H, s), 5.11 (2H, s), 7.17 (1H, d, J=8.5 Hz), 7.34-7.42 (5H, m), 7.46 (1H, d, J=8.5 Hz).

Preparation of 6-(1,1,1,3,3,3-hexafluoro-2-(methoxymethoxy)propan-2-yl)-2-propylpyridin-3-ol 3-(Benzyloxy)-6-(1,1,1,3,3,3-hexafluoro-2-(methoxymethoxy)propan-2-yl)-2-propylpyridine (407 mg, 0.931 mmol) was dissolved in ethanol (2.0 mL) and added with palladium carbon (40 mg). The resultant mixture was stirred under hydrogen atmosphere for 2 hours. After completion of the reaction, the reaction solution was filtered using celite and concentrated in vacuo. The obtained residue was purified using silica-gel column chromatography (hexane/ethyl acetate), and 6-(1,1,1,3,3,3-hexafluoro-2-(methoxymethoxy) propan-2-yl)-2-propylpyridin-3-ol (304 mg, yield 94%) was obtained as a brown oil.

$^1$H-NMR (CDCl$_3$) δ: 0.97 (3H, t, J=7.3 Hz), 1.80 (2H, qt, J=7.3, 7.6 Hz), 2.78 (2H, t, J=7.6 Hz), 3.56 (3H, s), 4.90 (2H, s), 7.12 (1H, d, J=8.5 Hz), 7.43 (1H, d, J=8.5 Hz).

Preparation of 4-hydroxy-6-methylpyridin-2(1H)-one

4-Hydroxy-6-methyl-2H-pyran-2-one (11.1 g, 88.0 mmol) was suspended into ethanol (5.0 mL), added with 28% aqueous ammonia (55 mL), and the resultant mixture was stirred at 100° C. for 1 hour. The reaction solution was cooled down to room temperature, added with chloroform (25 mL) and ether (25 mL) to extract solid substance which was then washed sequentially with chloroform (10 mL), ether (10 mL) and tetrahydrofuran (30 mL), and concentrated in vacuo. Then, the obtained residue was further washed sequentially with chloroform (10 mL), ether (10 mL) and tetrahydrofuran (30 mL). 4-Hydroxy-6-methylpyridin-2(1H)-one (9.70 g, yield 88%) was obtained as a pale yellow crystal.

1HNMR (DMSO) δ: 2.06 (3H, s), 5.31 (1H, d, J=1.4 Hz), 5.57 (1H, d, J=1.4 Hz), 10.28 (1H, brs), 10.87 (1H, brs).

Preparation of 4-hydroxy-6-methyl-3-nitropyridin-2(1H)-one

To 70% nitric acid (30 mL), 4-hydroxy-6-methylpyridin-2(1H)-one (10.5 g, 83.9 mmol) was added under ice-cold conditions, and the resultant mixture was stirred at 70° C. for 1.5 hours. The reaction solution was added to ice water (70 mL) under ice-cold conditions. The reaction solution was filtered, washed sequentially with cold water, tetrahydrofuran and diethylether, and then dried. 4-Hydroxy-6-methyl-3-nitropyridin-2(1H)-one (11.5 g, yield 80%) was obtained as a yellow crystal.

1HNMR (DMSO) δ: 2.15 (3H, s), 5.82 (1H, s), 11.84 (1H, br.), 12.25 (1H, br.).

Preparation of 2,4-dichloro-6-methyl-3-nitropyridine

Hydroxy-6-methyl-3-nitropyridin-2(1H)-one (8.77 g, 51.6 mmol) was suspended into phosphorylchloride at 0° C., and by stirring at 50° C., was added with N,N-diethylaniline (17 mL, 108 mmol). Then, the resultant mixture was stirred overnight at 100° C. After completion of the reaction, the resultant was added with water at room temperature and filtered. The filtrate was washed with water and dried. 2,4-Dichloro-6-methyl-3-nitropyridine (9.04 g, yield 84%) was obtained as a black brown crystal.

1HNMR (CDCl$_3$) δ: 2.06 (3H, s), 7.63 (1H, s).

Preparation of methyl 4,6-dichloro-5-nitropicolinate 2,4-Dichloro-6-methyl-3-nitropyridine (15.0 g, 72.5 mmol) was dissolved in concentrated sulfuric acid (73 mL) under ice-cold conditions and added with chromic acid (21.7 g, 217 mmol). The resultant mixture was stirred overnight by gradually warming to room temperature. After completion of the reaction, ice water was added under ice-cold conditions and the resultant mixture was filtered. Tetrahydran was added thereto, and the resultant mixture was concentrated in vacuo to obtain a crude product (15.7 g). The obtained crude product (15.7 g) was dissolved in tetrahydrofuran (180 mL) and methanol (180 mL). The reaction solution was added with triethylamine (90 mL, 652 mmol) and methyl ester chloroformate (34 mL, 435 mmol) under ice-cold conditions, and the resultant mixture was stirred for 10 minutes. After completion of the reaction, water was added, and the resultant mixture was extracted with ethyl acetate. The organic layer was washed with a saturated aqueous solution of ammonium chloride, dried over sodium sulfate, and concentrated in vacuo. The obtained residue was purified using column chromatography (chloroform/methanol), and methyl 4,6-dichloro-5-nitropicolinate (12.6 g, yield 69%) was obtained as a yellow crystal.

1HNMR (CDCl$_3$) δ: 4.09 (3H, s), 8.25 (1H, s).

Preparation of Methyl 6-chloro-4-(6-(1,1,1,3,3,3-hexafluoro-2-(methoxymethoxy)propan-2-yl)-2-propylpyridin-3-yloxy)-5-nitropicolinate The similar reaction and treatment were conducted as Example 25 c), and methyl 6-chloro-4-(6-(1,1,1,3,3,3-hexafluoro-2-(methoxymethoxy)propan-2-yl)-2-propylpyridin-3-yloxy)-5-nitropicolinate was obtained as a yellow oil.

$^1$H-NMR (CDCl$_3$) δ: 0.91 (3H, t, J=7.3 Hz), 1.75 (2H, qt, J=7.3, 7.3 Hz), 2.71 (2H, t, J=7.3 Hz), 3.59 (3H, s), 3.99 (3H, s), 4.97 (2H, s), 7.43 (1H, s), 7.51 (1H, d, J=8.1 Hz), 7.72 (1H, d, J=8.1 Hz).

Preparation of Methyl 5-amino-4-(6-(1,1,1,3,3,3-hexafluoro-2-(methoxymethoxy)propan-2-yl)-2-propylpyridin-3-yloxy)picolinate The similar reaction and treatment were conducted as Example 171), and methyl 5-amino-4-(6-(1,1,1,3,3,3-hexafluoro-2-(methoxymethoxy)propan-2-yl)-2-propylpyridin-3-yloxy)picolinate was obtained as a yellow oil.

$^1$H-NMR (CDCl$_3$) δ: 0.95 (3H, t, J=7.6 Hz), 1.80 (2H, qt, J=7.6, 7.6 Hz), 2.82 (2H, t, J=7.6 Hz), 3.58 (3H, s), 3.93 (3H, s), 4.96 (2H, s), 7.30 (1H, d, J=8.6 Hz), 7.42 (1H, s), 7.59 (1H, d, J=8.6 Hz), 8.26 (1H, s).

Preparation of Methyl 4-(6-(1,1,1,3,3,3-hexafluoro-2-(methoxymethoxy)propan-2-yl)-2-propylpyridin-3-yloxy)-5-iodopicolinate The similar reaction and treatment were conducted as Example 119-a), and methyl 4-(6-(1,1,1,3,3,3-hexafluoro-2-

(methoxymethoxy)propan-2-yl)-2-propylpyridin-3-yloxy)-5-iodopicolinate was obtained as a yellow oil.

$^1$H-NMR (CDCl$_3$) δ: 0.94 (3H, t, J=7.3 Hz), 1.80 (2H, qt, J=7.3, 7.3 Hz), 2.76 (2H, t, J=7.3 Hz), 3.58 (3H, s), 3.96 (3H, s), 4.97 (2H, s), 7.33 (1H, s), 7.38 (1H, d, J=8.6 Hz), 7.65 (1H, d, J=8.6 Hz), 9.04 (1H, s).

Preparation of (4-(6-(1,1,1,3,3,3-hexafluoro-2-(methoxymethoxy)propan-2-yl)-2-propylpyridin-3-yloxy) pyridin-2-yl)methanol To a solution of methyl 4-(6-(1,1,1,3,3,3-hexafluoro-2-(methoxymethoxy)propan-2-yl)-2-propylpyridin-3-yloxy)-5-iodopicolinate (500 mg, 0.823 mmol) in tetrahydrofuran (8.2 mL), lithium aluminum hydride (63 mg, 1.65 mmol) was added under ice-cold conditions, and the resultant mixture was stirred at room temperature for 1 hour. After completion of the reaction, the resultant mixture was added with water under ice-cold conditions, and stirred at room temperature for 30 minutes. Then, the reaction solution was filtered using celite and extracted with chloroform. The organic layer was washed with brine, dried over sodium sulfate, and concentrated in vacuo. The obtained residue was purified using column chromatography (hexane/acetone), and (4-(6-(1,1,1,3,3,3-hexafluoro-2-(methoxymethoxy)propan-2-yl)-2-propylpyridin-3-yloxy) pyridin-2-yl)methanol (141 mg, yield 38%) was obtained as a yellow oil.

$^1$H-NMR (CDCl$_3$) δ: 0.91 (3H, t, J=7.3 Hz), 1.76 (2H, qt, J=7.3, 7.6 Hz), 2.75 (2H, t, J=7.6 Hz), 3.58 (3H, s), 4.73 (2H, s), 4.95 (2H, s), 6.73 (1H, dd, J=2.4, 5.7 Hz), 6.82 (1H, d, J=2.4 Hz), 7.37 (1H, d, J=8.6 Hz), 7.61 (1H, d, J=8.6 Hz), 8.46 (1H, d, J=5.7 Hz).

Preparation of 3-(2-(bromomethyl)pyridin-4-yloxy)-6-(1,1,1,3,3,3-hexafluoro-2-(methoxymethoxy)propan-2-yl)-2-propylpyridine The similar reaction and treatment were conducted as Example 38-c), and 3-(2-(bromomethyl)pyridin-4-yloxy)-6-(1,1,1,3,3,3-hexafluoro-2-(methoxymethoxy)propan-2-yl)-2-propylpyridine was obtained as a yellow oil.

$^1$H-NMR (CDCl$_3$) δ: 0.92 (3H, t, J=7.0 Hz), 1.77 (2H, qt, J=7.0, 7.6 Hz), 2.76 (2H, t, J=7.6 Hz), 3.59 (3H, s), 4.51 (2H, s), 4.96 (2H, s), 6.71 (1H, dd, J=2.2, 5.7 Hz), 7.01 (1H, d, J=2.2 Hz), 7.39 (1H, d, J=8.6 Hz), 7.62 (1H, d, J=8.6 Hz), 8.49 (1H, d, J=5.7 Hz).

Preparation of 3-((4-(6-(1,1,1,3,3,3-hexafluoro-2-(methoxymethoxy)propan-2-yl)-2-propylpyridin-3-yl oxy)pyridin-2-yl)methyl)-5-(4-(1-methylethoxy) phenyl)-5-methylimidazolidine-2,4-dione 5-Methyl-5-(4-(1-methylethoxy)phenyl)imidazolidine-2,4-dione was used in place of 5-(benzo[d][1,3]dioxol-5-yl)-5-methylimidazolidine-2,4-dione in Example 1 for a similar reaction and treatment, and 3-((4-(6-(1,1,1,3,3,3-hexafluoro-2-(methoxymethoxy)propan-2-yl)-2-propylpyridin-3-yl oxy)pyridin-2-yl)methyl)-5-(4-(1-methylethoxy)phenyl)-5-methylimidazolidine-2,4-dione was obtained as a colorless oil.

$^1$H-NMR (CDCl$_3$) δ: 0.91 (3H, t, J=7.0 Hz), 1.32 (6H, d, J=5.7 Hz), 1.74 (2H, qt, J=7.0, 7.6 Hz), 1.84 (3H, s), 2.73 (2H, t, J=7.6 Hz), 3.58 (3H, s), 4.54 (1H, sept, J=5.7 Hz), 4.79 (2H, s), 4.95 (2H, s), 5.72 (1H, s), 6.67 (1H, dd, J=1.9, 5.9 Hz), 6.71 (1H, d, J=1.9 Hz), 6.88 (2H, d, J=8.9 Hz), 7.34 (1H, d, J=8.4 Hz), 7.41 (2H, d, J=8.9 Hz), 7.59 (1H, d, J=8.4 Hz), 8.42 (1H, d, J=5.9 Hz).

The similar reaction and treatment were conducted as Example 1-b), and the title compound was obtained as a colorless oil.

$^1$H-NMR (CDCl$_3$) δ: 0.89 (3H, t, J=7.3 Hz), 1.28 (6H, d, J=5.9 Hz), 1.74 (2H, qt, J=7.3, 7.3 Hz), 1.74 (3H, s), 2.73 (2H, t, J=7.3 Hz), 4.59 (1H, sept, J=5.9 Hz), 4.84 (2H, s), 6.90 (2H, d, J=8.9 Hz), 7.03 (1H, d, J=2.2 Hz), 7.17 (1H, dd, J=2.2, 6.5 Hz), 7.39 (2H, d, J=8.9 Hz), 7.73 (1H, d, J=8.6 Hz), 7.80 (1H, d, J=8.6 Hz), 8.54 (1H, d, J=6.5 Hz).

Example 172

Preparation of 3-((2-(4-(1,1,1,3,3,3-hexafluoro-2-hydroxypropan-2-yl)-2-propylphenoxy)-5-iodopyridin-4-yl)methyl)-5-(4-isopropylphenyl)-5-methylimidazolidine-2,4-dione

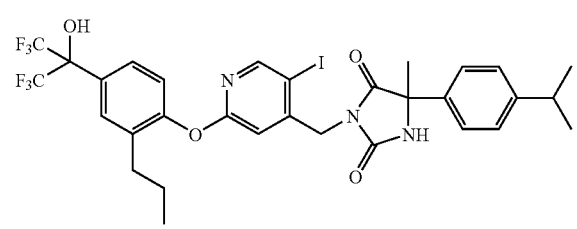

172-a-1) Preparation of 2-(4-(1,1,1,3,3,3-hexafluoro-2-(methoxymethoxy)propan-2-yl)-2-propylphenoxy)-5-iodoisonicotinic acid To a solution of methyl 2-(4-(1,1,1,3,3,3-hexafluoro-2-(methoxymethoxy)propan-2-yl)-2-propylphenoxy)-5-iodoisonicotinate (450 mg, 0.741 mmol) in methanol (3.5 mL), 3N aqueous solution of sodium hydroxide (3.5 mL) was added and the resultant mixture was stirred at room temperature for 1 hour. After completion of the reaction, 5% aqueous solution of hydrochloric acid and a saturated aqueous solution of sodium hydrogen carbonate were added, extracted with chloroform/methanol, and the organic layer was dried using sodium sulfate. After filtration, the filtrate was concentrated in vacuo, and 2-(4-(1,1,1,3,3,3-hexafluoro-2-(methoxymethoxy)propan-2-yl)-2-propylphenoxy)-5-iodoisonicotinic acid (441 mg, yield >100%) was obtained as a yellow oil.

$^1$H-NMR (CDCl$_3$) δ: 0.88 (3H, t, J=7.3 Hz), 1.59 (2H, qt, J=7.3, 7.8 Hz), 2.57 (2H, t, J=7.8 Hz), 3.53 (3H, s), 4.88 (2H, s), 6.91 (1H, s), 7.15 (1H, d, J=8.9 Hz), 7.49 (1H, d, J=8.9 Hz), 7.54 (1H, s), 8.34 (1H, s).

172-a-2) Preparation of (2-(4-(1,1,1,3,3,3-hexafluoro-2-(methoxymethoxy)propan-2-yl)-2-propylphenoxy)-5-iodopyridin-4-yl)methanol To a solution of 2-(4-(1,1,1,3,3,3-hexafluoro-2-(methoxymethoxy)propan-2-yl)-2-propy phenoxy)-5-iodoisonicotinic acid (441 mg, 0.741 mmol) in tetrahydrofuran (3.7 mL), a solution of borane-tetrahydrofuran (2.97 mL, 1 M in THF solution) was added under ice-cold conditions, and the resultant mixture was stirred at room temperature for 1.5 hours. After completion of the reaction, water, 1N aqueous solution of sodium hydroxide and 5% aqueous solution of hydrochloric acid were added to the reaction mixture, and extracted with ethyl acetate. The organic layer was washed with a saturated aqueous solution of sodium hydrogen carbonate and dried using sodium sulfate. The organic layer was concentrated in vacuo, and the obtained residue was purified using column chromatography (hexane/ethyl acetate). (2-(4-(1,1,1,3,3,3-Hexafluoro-2-(methoxymethoxy)propan-2-yl)-2-propylphenoxy)-5-iodopyridin-4-yl)methanol (391 mg, yield 91%) was obtained as a yellow oil.

$^1$H-NMR (CDCl$_3$) δ: 0.90 (3H, t, J=7.3 Hz), 1.61 (2H, qt, J=7.3, 7.6 Hz), 2.58 (2H, t, J=7.6 Hz), 3.56 (3H, s), 4.65 (2H, s), 4.88 (2H, s), 7.08 (1H, d, J=8.5 Hz), 7.18 (1H, s), 7.45 (1H, d, J=8.5 Hz), 7.51 (1H, s), 8.37 (1H, s).

172-a-3) Preparation of 4-(bromomethyl)-2-(4-(1,1,1,3,3,3-hexafluoro-2-(methoxymethoxy)propan-2-yl)-2-propylphenoxy)-5-iodopyridine (2-(4-(1,1,1,3,3,3-Hexafluoro-2-(methoxymethoxy)propan-2-yl)-2-propylphenoxy)-5-iodopyridin-4-yl)methanol was used for a similar reaction and treatment as Example 38-c), and 4-(bromomethyl)-2-(4-(1,1,1,3,3,3-hexafluoro-2-(methoxymethoxy)propan-2-yl)-2-prop ylphenoxy)-5-iodopyridine was obtained as a yellow oil.

$^1$H-NMR (CDCl$_3$) δ: 0.91 (3H, t, J=7.3 Hz), 1.60 (2H, qt, J=7.3, 7.3 Hz), 2.57 (2H, t, J=7.3 Hz), 3.56 (3H, s), 4.46 (2H, s), 4.88 (2H, s), 7.08 (1H, d, J=8.4 Hz), 7.12 (1H, s), 7.46 (1H, d, J=8.4 Hz), 7.51 (1H, s), 8.45 (1H, s).

4-(Bromo methyl)-2-(4-(1,1,1,3,3,3-hexafluoro-2-(methoxymethoxy)propan-2-yl)-2-propylphenoxy)-5-iodopyridine and 5-(4-(1-methylethyl)phenyl)-5-methylimidazolidine-2,4-dione were used for a similar reaction and treatment as Example 1, and the title compound was obtained as a colorless oil.

$^1$H-NMR (CDCl$_3$) δ: 0.88 (3H, d, J=7.3 Hz), 1.22 (6H, d, J=6.8 Hz), 1.52-1.60 (2H, m), 1.83 (3H, s), 2.52 (2H, t, J=7.0 Hz), 2.90 (1H, sept, J=6.8 Hz), 3.86 (1H, s), 4.63 (2H, s), 6.01 (1H, s), 6.46 (1H, s), 7.00-7.60 (6H, m), 8.40 (1H, s).

Example 173

Preparation of 5-(4-tert-butylphenyl)-3-((2-(4-(1,1,1,3,3,3-hexafluoro-2-hydroxypropan-2-yl)-2-propylphenoxy)-5-iodopyridin-4-yl)methyl)-5-methylimidazolidine-2,4-dione

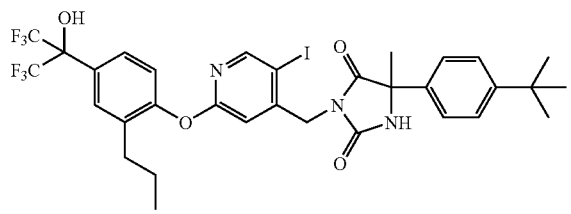

5-(4-tert-Butylphenyl)-5-methylimidazolidine-2,4-dione was used in place of 5-(4-(1-methylethyl)phenyl)5-methylimidazolidine-2,4-dione in Example 172 for a similar reaction and treatment, and the title compound was obtained as a colorless oil.

$^1$H-NMR (CDCl$_3$) δ: 0.88 (3H, t, J=7.3 Hz), 1.29 (9H, s), 1.52-1.79 (2H, m), 1.83 (3H, s), 2.53 (2H, t, J=7.8 Hz), 4.00 (1H, s), 4.62 (2H, s), 6.12 (1H, s), 6.46 (1H, s), 7.00-7.60 (6H, m), 8.41 (1H, s).

Example 174

Preparation of 5-(2,3-dihydrobenzo[b][1,4]dioxin-6-yl)-3-((2-(4-(1,1,1,3,3,3-hexafluoro-2-hydroxypropan-2-yl)-2-propyl-phenoxy)-5-iodopyridin-4-yl)methyl)-5-methyl imidazolidine-2,4-dione

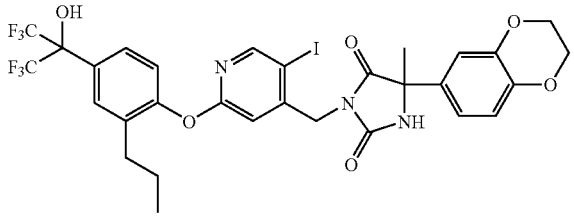

5-(2,3-Dihydrobenzo[b][1,4]dioxin-6-yl)-5-methylimidazolidine-2,4-dione was used in place of 5-(4-(1-methylethyl)phenyl)5-methylimidazolidine-2,4-dione in Example 172 for a similar reaction and treatment, and the title compound was obtained as a colorless oil.

$^1$H-NMR (CDCl$_3$) δ: 0.88 (3H, t, J=7.3 Hz), 1.52-1.63 (2H, m), 1.79 (3H, s), 2.52 (2H, t, J=7.8 Hz), 3.91 (1H, s), 4.22 (4H, s), 4.62 (2H, s), 5.98 (1H, s), 6.44 (1H, s), 6.85-7.23 (3H, m), 7.52-7.59 (2H, m), 8.40 (1H, s).

Example 175

Preparation of 3-((2-(4-(1,1,1,3,3,3-hexafluoro-2-hydroxypropan-2-yl)-2-propylphenoxy)-5-iodopyridin-4-yl)methyl)-5-methyl-5-(naphthalen-2-yl)imidazolidine-2,4-dione

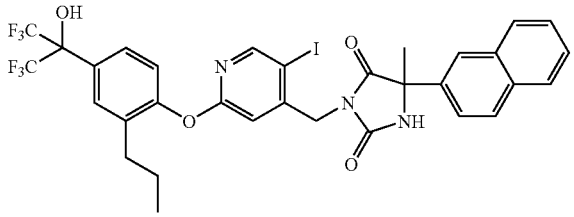

5-(Naphthalen-2-yl)-5-methylimidazolidine-2,4-dione was used in place of 5-(4-(1-methylethyl)phenyl)5-methylimidazolidine-2,4-dione in Example 172 for a similar reaction and treatment, and the title compound was obtained as a colorless oil.

$^1$H-NMR (CDCl$_3$) δ: 0.81 (3H, t, J=7.0 Hz), 1.52-1.63 (2H, m), 1.95 (3H, s), 2.45 (2H, t, J=7.3 Hz), 3.90 (1H, s), 4.66 (2H, s), 6.23 (1H, s), 6.49 (1H, s), 6.98 (1H, d, J=8.4 Hz), 7.48-7.63 (5H, m), 7.81-7.90 (4H, m), 8.39 (1H, s).

Example 176

Preparation of 5-(furan-2-yl)-3-((2-(4-(1,1,1,3,3,3-hexafluoro-2-hydroxypropan-2-yl)-2-propylphenoxy)-5-iodopyridin-4-yl)methyl)-5-methylimidazolidine-2,4-dione

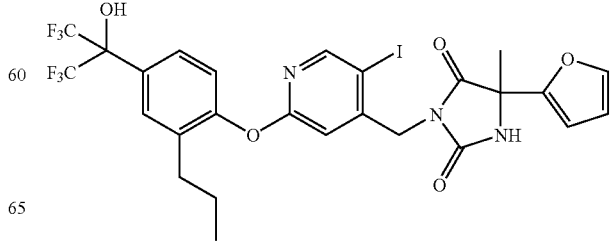

5-(Furan-2-yl)-5-methylimidazolidine-2,4-dione was used in place of 5-(4-(1-methylethyl)phenyl)-5-methylimidazolidine-2,4-dione in Example 172 for a similar reaction and treatment, and the title compound was obtained as a colorless oil.

$^1$H-NMR (CDCl$_3$) δ: 0.89 (3H, t, J=7.3 Hz), 1.55-1.64 (2H, m), 1.84 (3H, s), 2.55 (2H, t, J=8.1 Hz), 3.83 (1H, s), 4.69 (2H, s), 5.83 (1H, s), 6.36-6.44 (2H, m), 6.71 (1H, s), 7.03-7.60 (4H, m), 8.40 (1H, s).

Example 177

Preparation of 3-((2-(4-(1,1,1,3,3,3-hexafluoro-2-hydroxypropan-2-yl)-2-propylphenoxy)-5-iodopyridin-4-yl)methyl)-1,5,5-trimethylimidazolidine-2,4-dione

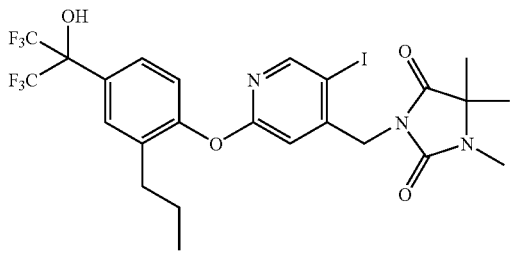

1,5,5-Trimethylimidazolidine-2,4-dione was used in place of 5-(4-(1-methylethyl)phenyl)-5-methylimidazolidine-2,4-dione in Example 172 for a similar reaction and treatment, and the title compound was obtained as a colorless oil.

$^1$H-NMR (CDCl$_3$) δ: 0.89 (3H, t, J=6.8 Hz), 1.39 (6H, s), 1.55-1.64 (2H, m), 2.55 (3H, t, J=8.1 Hz), 2.91 (3H, s), 3.77 (1H, s), 4.62 (2H, s), 6.41 (1H, s), 7.02-7.59 (4H, m), 8.45 (1H, s).

Example 178

Preparation of 3-((2-(4-(1,1,1,3,3,3-hexafluoro-2-hydroxypropan-2-yl)-2-propylphenoxy)-5-iodopyridin-4-yl)methyl)-5-methyl-5-(4-(4-methylbenzyloxy)phenyl)imidazolidine-2,4-dione

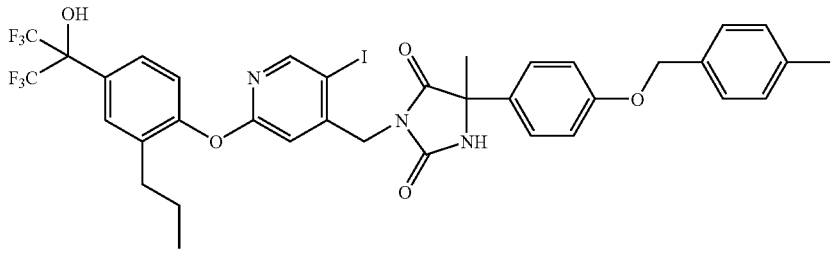

5-(1-(4-Methylbenzyloxy)phenyl-4-yl)-5-methylimidazolidine-2,4-dione was used in place of 5-(4-(1-methylethyl)phenyl)-5-methylimidazolidine-2,4-dione in Example 172 for a similar reaction and treatment, and the title compound was obtained as a colorless oil.

$^1$H-NMR (CDCl$_3$) δ: 0.87 (3H, t, J=7.3 Hz), 1.52-1.63 (2H, m), 1.81 (3H, s), 2.35 (3H, s), 2.51 (2H, t, J=7.8 Hz), 3.92 (1H, s), 4.62 (2H, s), 5.00 (2H, s), 6.03 (1H, s), 6.44 (1H, s), 6.96-7.59 (10H, m), 8.40 (1H, s).

Example 179

Preparation of 5-(3-fluoro-4-(1-methylethoxy)phenyl-3-((2-(4-(1,1,1,3,3,3-hexafluoro-2-hydroxy propan-2-yl)-2-propylphenoxy)-5-iodopyridin-4-yl) methyl)-5-methylimidazolidine-2,4-dione

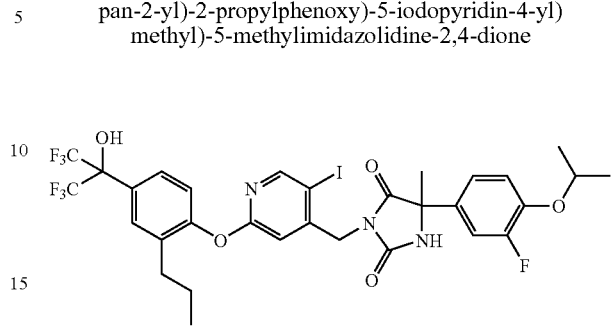

5-(3-Fluoro-4-(1-methylethoxy)phenyl-4-yl)-5-methylimidazolidine-2,4-dione was used in place of 5-(4-(1-methylethyl)phenyl)-5-methylimidazolidine-2,4-dione in Example 172 for a similar reaction and treatment, and the title compound was obtained as a colorless oil.

$^1$H-NMR (CDCl$_3$) δ: 0.88 (3H, t, J=7.3 Hz), 1.32 (3H, d, J=6.2 Hz), 1.33 (3H, d, J=6.2 Hz), 1.49-1.62 (2H, m), 1.81 (3H, s), 2.52 (2H, t, J=7.6 Hz), 3.81 (1H, s), 4.53 (1H, sept, J=6.2 Hz), 4.63 (2H, s), 6.02 (1H, s), 6.43 (1H, s), 6.94-7.28 (4H, m), 7.53 (1H, d, J=8.1 Hz), 7.59 (1H, s), 8.41 (1H, s).

Example 180

Preparation of 3-((2-(4-(1,1,1,3,3,3-hexafluoro-2-hydroxypropan-2-yl)-2-propylphenoxy)-5-iodopyridin-4-yl)methyl)-5-(4-(1-methylethoxy)phenyl)-5-methylimidazolidine-2,4-dione

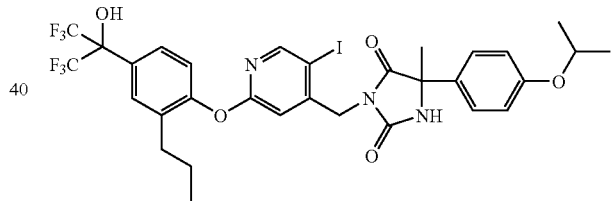

5-(1-(1-Methylethoxy)phenyl-4-yl)-5-methylimidazolidine-2,4-dione was used in place of 5-(4-(1-methylethyl)phenyl)-5-methylimidazolidine-2,4-dione in Example 172 for a similar reaction and treatment, and the title compound was obtained as a colorless oil.

$^1$H-NMR (CDCl$_3$) δ: 0.88 (3H, t, J=7.3 Hz), 1.30 (3H, d, J=6.0 Hz), 1.31 (3H, d, J=6.0 Hz), 1.52-1.62 (2H, m), 1.82 (3H, s), 2.52 (2H, t, J=8.4 Hz), 3.82 (1H, s), 4.52 (1H, sept, J=6.0 Hz), 4.63 (2H, s), 5.93 (1H, s), 6.45 (1H, s), 6.87-7.59 (6H, m), 8.40 (1H, s).

Example 181

Preparation of 5-(benzo[d][1,3]dioxol-5-yl)-3-((2-(4-(1,1,1,3,3,3-hexafluoro-2-hydroxypropan-2-yl)-2-propylphenoxy)-5-iodopyridin-4-yl)methyl)-5-methylimidazolidine-2,4-dione

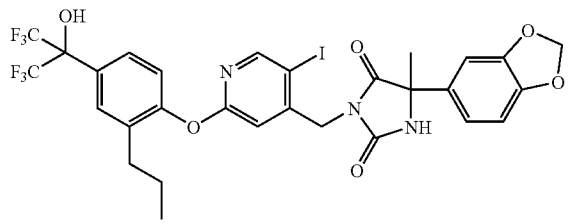

5-(Benzo[d][1,3]dioxol-5-yl)-5-methylimidazolidine-2,4-dione was used in place of 5-(4-(1-methylethyl)phenyl)-5-methylimidazolidine-2,4-dione in Example 172 for a similar reaction and treatment, and the title compound was obtained as a colorless oil.

$^1$H-NMR (CDCl$_3$) δ: 0.88 (3H, t, J=7.3 Hz), 1.49-1.62 (2H, m), 1.81 (3H, s), 2.52 (2H, t, J=8.1 Hz), 3.80 (1H, s), 4.63 (2H, s), 5.92 (1H, s), 5.96 (2H, s), 6.44 (1H, s), 6.79-7.23 (4H, m), 7.53 (1H, d, J=8.1 Hz), 7.59 (1H, s), 8.40 (1H, s).

Example 182

Preparation of 5-(2,3-dihydrobenzofuran-5-yl)-3-((2-(4-(1,1,1,3,3,3-hexafluoro-2-hydroxypropan-2-yl)-2-propylphenoxy)-5-iodopyridin-4-yl)methyl)-5-methylimidazolidine-2,4-dione

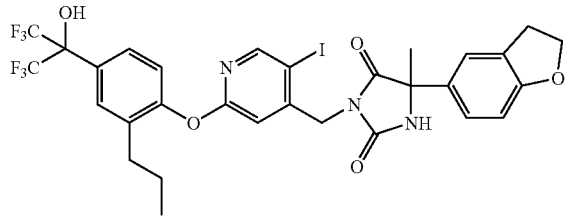

5-(2,3-Dihydrobenzofuran-5-yl)-5-methylimidazolidine-2,4-dione was used in place of 5-(4-(1-methylethyl)phenyl)-5-methylimidazolidine-2,4-dione in Example 172 for a similar reaction and treatment, and the title compound was obtained as a colorless oil.

$^1$H-NMR (CDCl$_3$) δ: 0.88 (3H, t, J=7.3 Hz), 1.52-1.63 (2H, m), 1.82 (3H, s), 2.52 (2H, t, J=8.1 Hz), 3.20 (2H, t, J=8.6 Hz), 3.86 (1H, s), 4.56 (2H, t, J=8.6 Hz), 4.63 (2H, s), 6.46 (1H, s), 6.77 (1H, d, J=8.1 Hz), 7.01 (1H, d, J=8.6 Hz), 7.16-7.28 (2H, m), 7.34 (1H, s), 7.53 (1H, d, J=8.6 Hz), 7.59 (1H, s), 8.40 (1H, s).

Example 183

Preparation of 3-((2-(4-(1,1,1,3,3,3-hexafluoro-2-hydroxypropan-2-yl)-2-propylphenoxy)-5-iodopyridin-4-yl)methyl)-5-(6-methoxypyridin-3-yl)-5-methylimidazolidine-2,4-dione

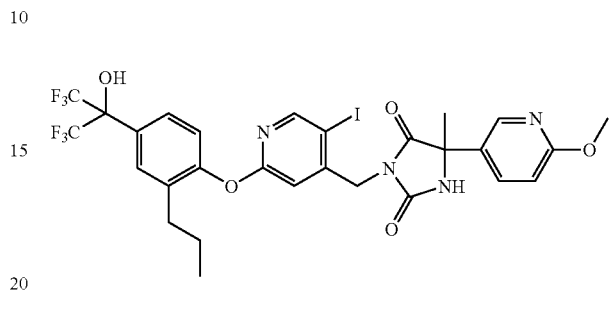

5-(2-Methoxypyridin-5-yl)-5-methylimidazolidine-2,4-dione was used in place of 5-(4-(1-methylethyl)phenyl)-5-methylimidazolidine-2,4-dione in Example 172 for a similar reaction and treatment, and the title compound was obtained as a colorless oil.

$^1$H-NMR (CDCl$_3$) δ: 0.79 (3H, t, J=7.3 Hz), 1.42-1.48 (2H, m), 1.72 (3H, s), 2.49 (2H, t, J=7.3 Hz), 4.17 (3H, s), 4.55 (1H, d, J=17.4 Hz), 4.58 (1H, d, J=17.4 Hz), 6.17 (1H, s), 7.02 (2H, d, J=8.5 Hz), 7.16-7.27 (2H, m), 7.60 (1H, d, J=8.8 Hz), 7.63 (1H, s), 8.51 (1H, s).

Example 184

Preparation of 6-(4-(1,1,1,3,3,3-hexafluoro-2-hydroxypropan-2-yl)-2-propylphenoxy)-4-((4-(4-(4-(1-methylethoxy) phenyl)-4-methyl-2,5-dioxoisodazolidin-1-yl)methyl)nicotinonitrile

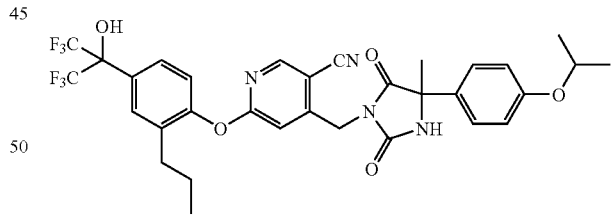

3-((2-(4-(1,1,1,3,3,3-Hexafluoro-2-hydroxypropan-2-yl)-2-propylphenoxy)-5-iodopyridin-4-yl)methyl)-5-(4-(1-methylethoxy)phenyl)-5-methylimidazolidine-2,4-dione was used for a similar reaction and treatment as Example 171, and the title compound was obtained as a colorless oil.

$^1$H-NMR (CDCl$_3$) δ: 0.87 (3H, t, J=7.3 Hz), 1.30 (3H, d, J=5.7 Hz), 1.31 (3H, d, J=5.7 Hz), 1.55 (2H, qt, J=7.3, 7.8 Hz), 1.87 (3H, s), 2.48 (2H, t, J=7.8 Hz), 4.53 (1H, sept, J=5.7 Hz), 4.88 (2H, s), 5.93 (1H, s), 6.67 (1H, s), 6.91 (2H, d, J=8.9 Hz), 7.05 (1H, d, J=8.6 Hz), 7.40 (2H, d, J=8.9 Hz), 7.57 (1H, d, J=8.6 Hz), 7.62 (1H, s), 8.39 (1H, s).

Example 185

Preparation of 3-(2-(5-(4-(1,1,1,3,3,3-hexafluoro-2-hydroxypropan-2-yl)-2-propylphenoxy)pyridin-2-yl)ethyl)-5-(4-(1-methylethoxy)phenyl)-5-methylimidazolidine-2,4-dione

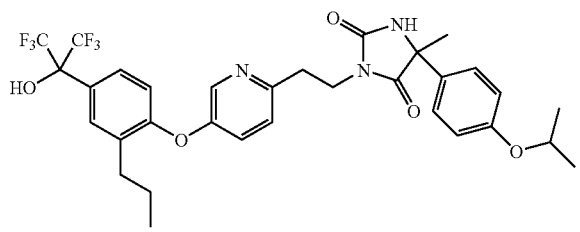

The following compounds were prepared sequentially.

Preparation of 5-(4-(1,1,1,3,3,3-hexafluoro-2-(methoxymethoxy)propan-2-yl)-2-propylphenoxy)-2-vinylpyridine The similar reaction and treatment were conducted as Example 126, and 5-(4-(1,1,1,3,3,3-hexafluoro-2-(methoxymethoxy)propan-2-yl)-2-propylphenoxy)-2-vinylpyridine was obtained as a yellow oil.

$^1$H-NMR (CDCl$_3$) δ: 0.95 (3H, t, J=7.3 Hz), 1.66 (2H, qt, J=7.3, 7.8 Hz), 2.68 (2H, t, J=7.8 Hz), 3.56 (3H, s), 4.86 (2H, s), 5.45 (1H, dd, J=1.2, 12.0 Hz), 6.12 (1H, dd, J=1.2, 17.6 Hz), 6.82 (1H, dd, J=12.0, 17.6 Hz), 6.86 (1H, d, J=8.8 Hz), 7.24 (1H, dd, J=2.7, 8.6 Hz), 7.35 (1H, d, J=8.6 Hz), 7.40 (1H, d, J=8.8 Hz), 7.51 (1H, s), 8.34 (1H, d, J=2.7 Hz).

Preparation of 5-(4-(1,1,1,3,3,3-hexafluoro-2-(methoxymethoxy)propan-2-yl)-2-propylphenoxy)-2-(oxyrane-2-yl)pyridine 1-oxide The similar reaction and treatment were conducted as Example 30-b), and 5-(4-(1,1,1,3,3,3-hexafluoro-2-(methoxymethoxy)propan-2-yl)-2-propylphenoxy)-2-(oxyrane-2-yl)pyridine 1-oxide was obtained as a colorless oil.

$^1$H-NMR (CDCl$_3$) δ: 0.93 (3H, t, J=7.3 Hz), 1.62 (2H, qt, J=7.3, 7.6 Hz), 2.60 (2H, t, J=7.6 Hz), 2.73 (1H, dd, J=2.7, 5.9 Hz), 3.30 (1H, dd, J=4.3, 5.9 Hz), 3.57 (3H, s), 4.50 (1H, dd, J=2.7, 4.3 Hz), 4.87 (2H, s), 6.93 (1H, dd, J=2.2, 8.9 Hz), 6.99 (1H, d, J=8.4 Hz), 7.21 (1H, d, J=8.9 Hz), 7.47 (1H, d, J=8.4 Hz), 7.54 (1H, s), 7.99 (1H, d, J=2.2 Hz).

Preparation of 5-(4-(1,1,1,3,3,3-hexafluoro-2-(methoxymethoxy)propan-2-yl)-2-propylphenoxy)-2-(2-hydroxyethyl)pyridine 1-oxide The similar reaction and treatment were conducted as Example 30-b), and 5-(4-(1,1,1,3,3,3-hexafluoro-2-(methoxymethoxy)propan-2-yl)-2-propylphenoxy)-2-(2-hydroxyethyl)pyridine 1-oxide was obtained as a colorless oil.

$^1$H-NMR (CDCl$_3$) δ: 0.93 (3H, t, J=7.3 Hz), 1.64 (2H, qt, J=7.3, 7.6 Hz), 2.67 (2H, t, J=7.6 Hz), 3.11 (2H, t, J=5.7 Hz), 3.53 (3H, s), 3.91 (2H, t, J=5.7 Hz), 4.88 (2H, s), 7.13 (1H, d, J=8.6 Hz), 7.19 (1H, dd, J=2.2, 8.6 Hz), 7.50 (1H, d, J=8.6 Hz), 7.53 (1H, d, J=8.6 Hz), 7.60 (1H, s), 8.11 (1H, d, J=2.2 Hz).

Preparation of 2-(5-(4-(1,1,1,3,3,3-hexafluoro-2-(methoxymethoxy)propan-2-yl)-2-propylphenoxy)pyridin-2-yl)ethanol To a solution of 5-(4-(1,1,1,3,3,3-hexafluoro-2-(methoxymethoxy)propan-2-yl)-2-propylphenoxy)-2-(2-hydroxyethyl)pyridine 1-oxide (2.29 g, 4.74 mmol) in acetic acid (24 mL), zinc powder (6.2 g, 94.7 mmol) was added, and the resultant mixture was stirred at room temperature for 4 hours. After completion of the reaction, the reaction solution was filtered using celite, added with a saturated aqueous solution of sodium hydrogen carbonate, and extracted with ethyl acetate. The organic layer was washed with brine and dried using sodium sulfate. After filtration, the filtrate was concentrated in vacuo. The obtained residue was purified using silica-gel column chromatography (hexane/acetone) and 2-(5-(4-(1,1,1,3,3,3-hexafluoro-2-(methoxymethoxy)propan-2-yl)-2-propylphenoxy)pyridin-2-yl)ethanol (2.0 g, yield 90%) was obtained as a yellow oil.

$^1$H-NMR (CDCl$_3$) δ: 0.95 (3H, t, J=7.6 Hz), 1.67 (2H, qt, J=7.6, 7.8 Hz), 2.69 (2H, t, J=7.8 Hz), 3.02 (2H, t, J=5.6 Hz), 3.56 (3H, s), 4.03 (2H, 1, J=5.6 Hz), 4.86 (2H, s), 6.83 (1H, d, J=8.8 Hz), 7.17 (1H, d, J=8.3 Hz), 7.26 (1H, dd, J=3.0, 8.8 Hz), 7.40 (1H, d, J=8.3 Hz), 7.51 (1H, s), 8.28 (1H, d, J=3.0 Hz).

Preparation of 2-(2-bromoethyl)-5-(4-(1,1,1,3,3,3-hexafluoro-2-(methoxymethoxy)propan-2-yl)-2-propylphenoxy) pyridine The similar reaction and treatment were conducted as Example 38-c), and 2-(2-bromoethyl)-5-(4-(1,1,1,3,3,3-hexafluoro-2-(methoxymethoxy)propan-2-yl)-2-prop ylphenoxy)pyridine was obtained as a colorless oil.

$^1$H-NMR (CDCl$_3$) δ: 0.96 (3H, t, J=7.3 Hz), 1.67 (2H, qt, J=7.3, 7.6 Hz), 2.69 (2H, t, J=7.6 Hz), 3.35 (2H, t, J=6.8 Hz), 3.57 (3H, s), 3.79 (2H, t, J=6.8 Hz), 4.87 (2H, s), 6.85 (1H, d, J=8.6 Hz), 7.20 (1H, d, J=8.4 Hz), 7.26 (1H, dd, J=2.4, 8.6 Hz), 7.41 (1H, d, J=8.4 Hz), 7.51 (1H, s), 8.35 (1H, d, J=2.4 Hz).

5-(1-(1-Methylethoxy)phenyl-4-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (270 MHz, CDCl$_3$) δ: 0.94 (3H, t, J=7.2 Hz), 1.30 (6H, d, J=5.9 Hz), 1.62 (2H, qt, J=7.2, 7.6 Hz), 1.70 (3H, s), 2.58 (2H, t, J=7.6 Hz), 3.16 (2H, t, J=6.4 Hz), 3.98 (2H, t, J=6.4 Hz), 4.52 (1H, sept, J=5.9 Hz), 6.85 (2H, d, J=8.9 Hz), 6.96 (1H, d, J=8.6 Hz), 7.27 (1H, d, J=8.6 Hz), 7.33 (2H, d, J=8.9 Hz), 7.48 (1H, d, J=8.6 Hz), 7.68 (1H, d, J=8.6 Hz), 7.72 (1H, s), 8.23 (1H, d, J=2.2 Hz).

Example 186

Preparation of 3-(2-(5-(4-(1,1,1,3,3,3-hexafluoro-2-hydroxypropan-2-yl)-2-propyl-phenoxy)pyridin-2-yl) ethyl)-5-(6-methoxypyridin-3-yl)-5-methylimidazolidine-2,4-dione

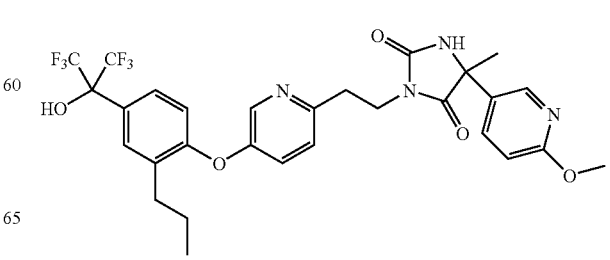

5-(2-Methoxypyridin-5-yl)-5-methylimidazolidine-2,4-dione was used in place of 5-(1-(1-methyl ethoxy)phenyl-4-yl)-5-methylimidazolidine-2,4-dione in Example 185 for a similar reaction and treatment, and the title compound was obtained as a colorless oil.

$^1$H-NMR (270 MHz, CDCl$_3$) δ: 0.93 (3H, t, J=7.3 Hz), 1.63 (2H, qt, J=7.3, 7.4 Hz), 1.77 (3H, s), 2.58 (2H, t, J=7.4 Hz), 3.42 (2H, t, J=6.4 Hz), 3.99 (2H, t, J=6.4 Hz), 4.10 (3H, s), 7.03 (1H, d, J=8.5 Hz), 7.10-7.19 (1H, m), 7.66-7.72 (3H, m), 7.83 (1H, d, J=8.5 Hz), 8.19-8.30 (2H, m), 8.37 (1H, s).

Example 187

Preparation of 5-(2,3-dihydrobenzofuran-5-yl)-3-(2-(5-(4-(1,1,1,3,3,3-hexafluoro-2-hydroxypropan-2-yl)-2-propylphenoxy)pyridin-2-yl)ethyl)-5-methylimidazoline-2,4-dione

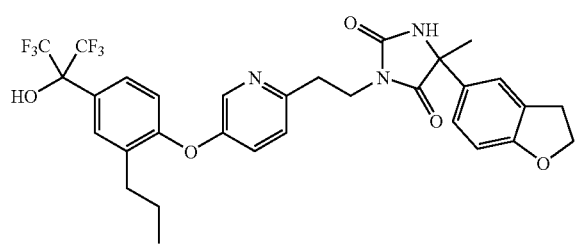

5-(2,3-Dihydrobenzofuran-5-yl)-5-methylimidazolidine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

$^1$H-NMR (270 MHz, CDCl$_3$) δ: 0.94 (3H, t, J=7.3 Hz), 1.63 (2H, qt, J=7.3, 7.6 Hz), 1.71 (3H, s), 2.58 (2H, t, J=7.6 Hz), 3.10-3.20 (4H, m), 3.98 (2H, t, J=6.4 Hz), 4.56 (2H, t, J=8.6 Hz), 6.73 (1H, d, J=8.6 Hz), 6.98 (1H, d, J=8.4 Hz), 7.15 (1H, d, J=8.6 Hz), 7.29-7.34 (2H, m), 7.53 (1H, d, J=7.0 Hz), 7.67 (1H, d, J=8.4 Hz), 7.72 (1H, s), 8.24 (1H, s).

Example 188

Preparation of 3-(2-(5-(4-(1,1,1,3,3,3-hexafluoro-2-hydroxypropan-2-yl)-2-propylphenoxy)pyridin-2-yl)ethyl)-5-(4-isopropylphenyl)-5-methylimidazolidine-2,4-dione

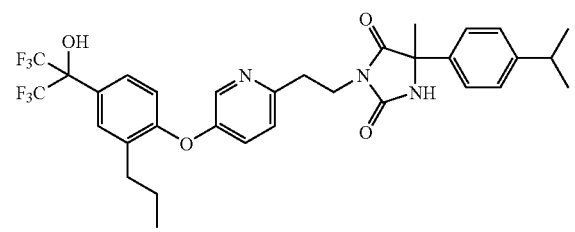

5-(1-(1-Methylethyl)phenyl-4-yl)-5-methylimidazolidine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

$^1$H-NMR (CDCl$_3$) δ: 0.96 (3H, t, J=7.3 Hz), 1.16 (6H, d, J=1.7 Hz), 1.63-1.69 (5H, m), 2.68 (2H, t, J=8.0 Hz), 2.82-2.86 (1H, m), 3.25-3.30 (2H, m), 3.87-3.93 (2H, m), 6.92 (1H, d, J=8.8 Hz), 7.20 (2H, d, J=8.5 Hz), 7.35 (2H, d, J=8.5 Hz), 7.54-7.75 (4H, m), 8.36 (1H, s).

Example 189

Preparation of 5-(4-tert-butylphenyl)-3-(2-(5-(4-(1,1,1,3,3,3-hexafluoro-2-hydroxypropan-2-yl)-2-propylphenoxy) pyridin-2-yl)ethyl)-5-methylimidazolidine-2,4-dione

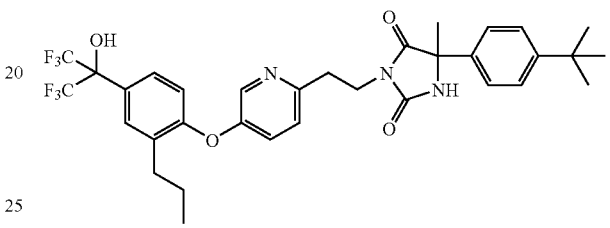

5-(1-tert-Butylphenyl-4-yl)-5-methylimidazolidine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

$^1$H-NMR (CDCl$_3$) δ: 0.95 (3H, t, J=7.3 Hz), 1.24 (9H, s), 1.63-1.67 (5H, m), 2.66-2.69 (2H, m), 3.19-3.28 (2H, m), 3.83-3.94 (2H, m), 6.87 (1H, d, J=8.6 Hz), 7.36-7.73 (8H, m), 8.29 (1H, s).

Example 190

Preparation of 5-(2,3-dihydrobenzo[b][1,4]dioxin-6-yl)-3-(2-(5-(4-(1,1,1,3,3,3-hexafluoro-2-hydroxypropan-2-yl)-2-propylphenoxy)pyridin-2-yl)ethyl)-5-methylimidazolidine-2,4-dione

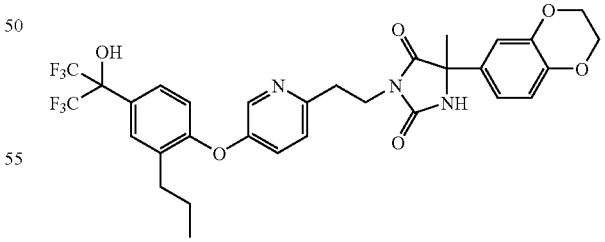

5-(2,3-Dihydrobenzo[b][1,4]dioxin-6-yl)-5-methylimidazolidine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

$^1$H-NMR (CDCl$_3$) δ: 0.95 (3H, t, J=7.3 Hz), 1.63-1.68 (5H, m), 2.64-2.69 (2H, m), 3.23-3.30 (2H, m), 3.91 (2H, t, J=6.3

Hz), 4.14-4.16 (4H, m), 6.79-6.87 (3H, m), 6.99 (1H, d, J=8.8 Hz), 7.61-7.75 (4H, m), 8.42 (1H, d, J=2.7 Hz).

Example 191

Preparation of 3-(2-(5-(4-(1,1,1,3,3,3-hexafluoro-2-hydroxypropan-2-yl)-2-propylphenoxy)pyridin-2-yl)ethyl)-5-methyl-5-(naphthalen-2-yl)imidazolidine-2,4-dione

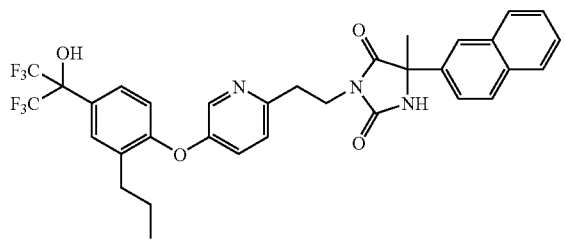

5-(Naphthalen-2-yl)-5-methylimidazolidine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

$^1$H-NMR (CDCl$_3$) δ: 0.91 (3H, t, J=7.3 Hz), 1.56-1.62 (2H, m), 1.81 (3H, s), 2.52-2.57 (2H, m), 2.70 (1H, s), 3.25-3.30 (2H, m), 3.95 (2H, t, J=6.4 Hz), 6.88 (1H, d, J=8.8 Hz), 7.48-7.92 (11H, m), 8.37 (1H, s).

Example 192

Preparation of 5-(furan-2-yl)-3-(2-(5-(4-(1,1,1,3,3,3-hexafluoro-2-hydroxypropan-2-yl)-2-propylphenoxy) pyridin-2-yl)ethyl)-5-methylimidazolidine-2,4-dione

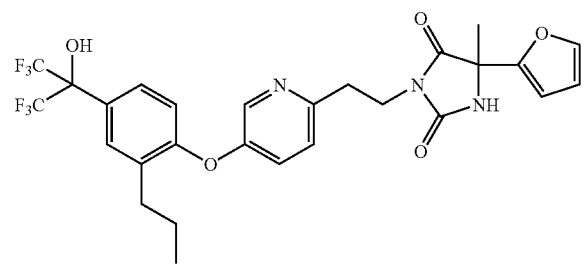

5-(Furan-2-yl)-5-methylimidazolidine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

$^1$H-NMR (CDCl$_3$) δ: 0.93 (3H, t, J=7.3 Hz), 1.59-1.67 (5H, m), 2.62 (2H, t, J=8.3 Hz), 2.70 (1H, s), 3.30-3.32 (2H, m), 3.94-3.97 (2H, m), 6.35-6.37 (1H, m), 6.43 (1H, d, J=3.4 Hz), 7.02 (1H, d, J=8.8 Hz), 7.44 (1H, s), 7.63 (1H, d, J=8.8 Hz), 7.74 (1H, s), 7.82 (1H, d, J=8.8 Hz), 7.91 (1H, dd, J=2.7, 8.8 Hz), 8.57 (1H, d, J=2.8 Hz).

Example 193

Preparation of 3-(2-(5-(4-(1,1,1,3,3,3-hexafluoro-2-hydroxypropan-2-yl)-2-propylphenoxy)pyridin-2-yl)ethyl)-1,5,5-trimethylimidazolidine-2,4-dione

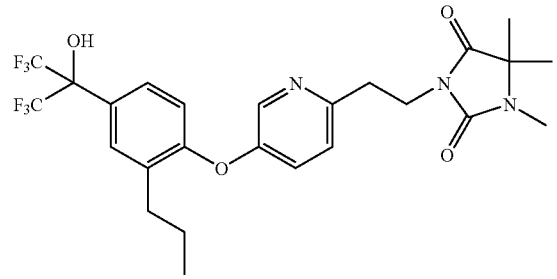

1,5,5-Trimethylimidazolidine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

$^1$H-NMR (CDCl$_3$) δ: 0.95 (3H, t, J=7.6 Hz), 1.30 (6H-1, s), 1.63-1.68 (2H, m), 2.67 (2H, t, J=7.8 Hz), 2.85 (3H, s), 3.23 (2H, t, J=6.1 Hz), 3.89 (2H, t, J=6.1 Hz), 7.07 (1H, d, J=8.8 Hz), 7.63 (1H, d, J=8.5 Hz), 7.70-7.72 (2H, m), 7.84 (1H, d, J=6.4 Hz), 8.49 (1H, d, J=2.4 Hz).

Example 194

Preparation of 3-(2-(5-(4-(1,1,1,3,3,3-hexafluoro-2-hydroxypropan-2-yl)-2-propylphenoxy)pyridin-2-yl)ethyl)-5-methyl-5-(4-(4-methylbenzyloxy)phenyl)imidazolidine-2,4-dione

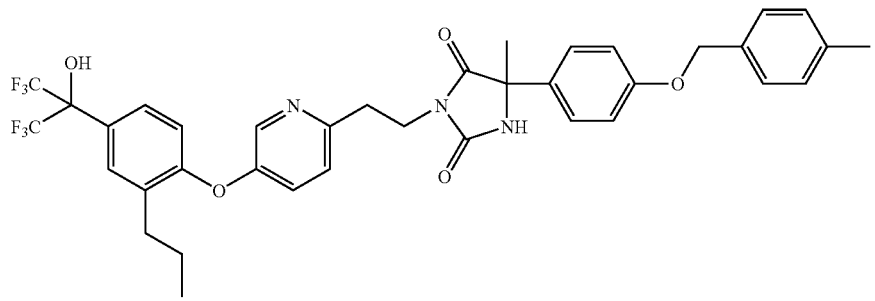

5-(1-(1-Methylbenzyloxy)phenyl-4-yl)-5-methylimidazolidine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

¹H-NMR (CDCl₃) δ: 0.94 (3H, t, J=7.3 Hz), 1.60-1.67 (5H, m), 2.29 (3H, s), 2.65 (2H, t, J=7.8 Hz), 2.70 (1H, s), 3.20-3.26 (2H, m), 3.90 (2H, t, J=6.6 Hz), 4.98 (1H, d, J=14.6 Hz), 5.02 (1H, d, J=14.6 Hz), 6.95-7.32 (9H, m), 7.54-7.74 (4H, m), 8.40 (1H, d, J=2.9 Hz).

Example 195

Preparation of 5-(3-fluoro-4-(1-methylethoxy)phenyl)-3-(2-(5-(4-(1,1,1,3,3,3-hexafluoro-2-hydroxypropan-2-yl)-2-propylphenoxy)pyridin-2-yl) ethyl)-5-methylimidazolidine-2,4-dione

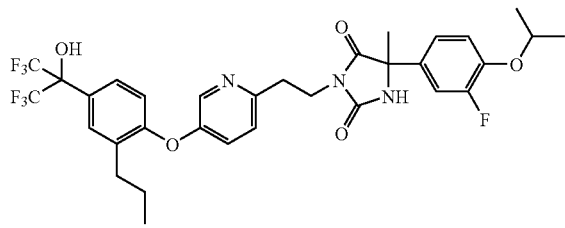

5-(1-(1-Methylethoxy)-2-fluorophenyl-4-yl)-5-methylimidazol dine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

¹H-NMR (CDCl₃) δ: 0.95 (3H, t, J=7.3 Hz), 1.28 (61-1, d, J=5.8 Hz), 1.61-1.68 (5H, m), 2.64-2.70 (2H, m), 3.15-3.29 (2H, m), 3.92 (2H, t, J=6.4 Hz), 4.55 (1H, sept, J=5.8 Hz), 6.97-7.16 (4H, m), 7.64-7.74 (4H, m), 8.43 (1H, d, J=2.2 Hz).

Example 196

Preparation of 3-(2-(5-(4-(1,1,1,3,3,3-hexafluoro-2-hydroxypropan-2-yl)-2-propylphenoxy)pyridin-2-yl) ethyl)-5-(5-(1-methylethoxy)pyridin-2-yl)-5-methylimidazolidine-2,4-dione

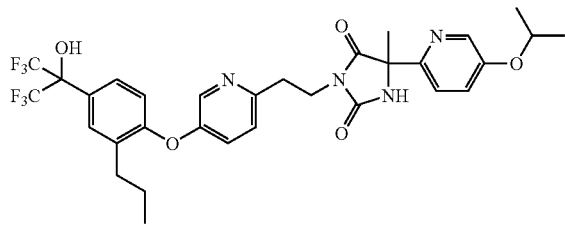

5-(5-(1-Methylethoxy)pyridin-2-yl)-5-methylimidazolidine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

¹H-NMR (CDCl₃) δ: 0.93 (3H, t, J=7.3 Hz), 1.33 (6H, d, J=5.9 Hz), 1.57-1.68 (2H, m), 1.80 (3H, s), 2.65 (2H, t, J=7.6 Hz), 3.30-3.36 (2H, m), 3.92-3.98 (2H, m), 4.68-4.77 (1H, m), 7.04 (1H, d, J=8.9 Hz), 7.63-7.74 (4H, m), 7.92 (1H, d, J=8.9 Hz), 8.00 (1H, dd, J=2.7, 8.9 Hz), 8.25 (1H, s), 8.59 (1H, d, J=2.7 Hz).

Example 197

Preparation of 5-(6-(difluoromethoxy)pyridin-3-yl)-3-(2-(5-(4-(1,1,1,3,3,3-hexafluoro-2-hydroxypropan-2-yl)-2-propylphenoxy)pyridin-2-yl) ethyl)-5-methylimidazolidine-2,4-dione

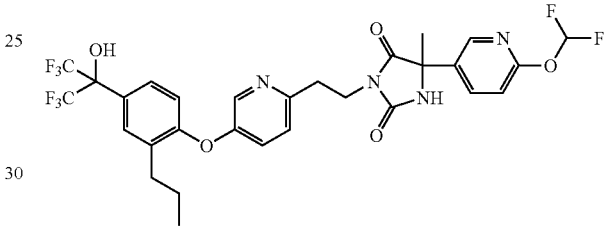

5-(2-(Difluoromethoxypyridin-5-yl)-5-methylimidazolidine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

¹H-NMR (400 MHz, CD₃OD) δ: 0.95 (3H, t, J=7.4 Hz), 1.61-1.68 (2H, m), 1.70 (3H, s), 2.67 (2H, t, J=7.4 Hz), 3.05 (2H, t, J=6.5 Hz), 3.84 (2H, t, J=6.5 Hz), 6.78 (1H, d, J=8.8 Hz), 6.89 (1H, d, J=8.8 Hz), 7.18 (2H, brs), 7.30-7.35 (1H, m), 7.54 (1H, d, J=8.8 Hz), 7.65 (1H, d, J=2.4 Hz), 7.91 (1H, dd, J=2.4, 8.8 Hz), 8.00 (1H, s), 8.27 (1H, d, J=2.4 Hz).

Example 198

Preparation of 5-(6-(benzyloxy)pyridin-3-yl)-3-(2-(5-(4-(1,1,1,3,3,3-hexafluoro-2-hydroxypropan-2-yl)-2-propylphenoxy)pyridin-2-yl) ethyl)-5-methylimidazolidine-2,4-dione

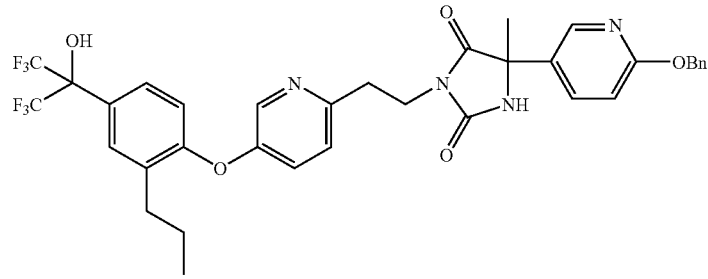

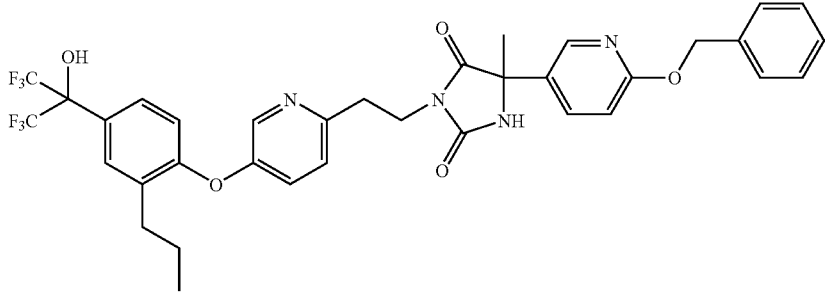

5-(2-(Benzyloxypyridin-5-yl)-5-methylimidazolidine-2,4-dione was used in place of 5-(1-(1-methylethoxy)phenyl-4-yl)-5-methylimidazolidine-2,4-dione in Example 185 for a similar reaction and treatment, and the title compound was obtained as a colorless oil.

$^1$H-NMR (400 MHz, CD$_3$OD) δ: 0.93 (3H, t, J=7.4 Hz), 1.59 (3H, s), 1.61-1.67 (2H, m), 2.65 (2H, t, J=7.4 Hz), 3.03 (2H, t, J=6.4 Hz), 3.82 (2H, t, J=6.4 Hz), 5.15 (1H, d, J=14.4 Hz), 5.21 (1H, d, J=14.4 Hz), 6.52 (1H, d, J=9.8 Hz), 6.80 (1H, d, J=8.5 Hz), 7.07 (1H, dd, J=2.5, 8.5 Hz), 7.13 (1H, d, J=8.1 Hz), 7.26-7.30 (5H, m), 7.54-7.58 (2H, m), 7.65 (1H, s), 7.74 (1H, d, J=2.5 Hz), 8.02 (1H, d, J=2.2 Hz).

Example 199

Preparation of 3-(2-(6-(4-(1,1,1,3,3,3-hexafluoro-2-hydroxypropan-2-yl)-2-propylphenoxy)pyridin-3-yl)ethyl)-5-(4-(1-methylethoxy)phenyl)-5-methylimidazolidine-2,4-dione

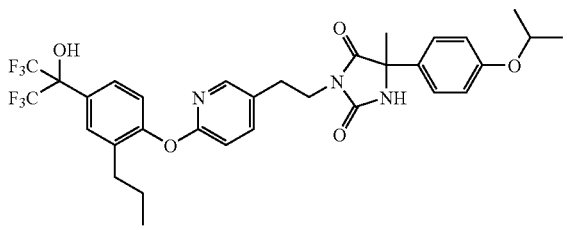

The following compounds were prepared sequentially.

Preparation of 6-(4-(1,1,1,3,3,3-hexafluoro-2-(methoxymethoxy)propan-2-yl)-2-propylphenoxy)pyridine-3-amine The similar reaction and treatment were conducted as Example 119-a), and 6-(4-(1,1,1,3,3,3-hexafluoro-2-(methoxymethoxy)propan-2-yl)-2-propylphenoxy)pyridine-3-amine was obtained as a colorless oil.

$^1$H-NMR (CDCl$_3$) δ: 0.94 (3H, t, J=7.3 Hz), 1.65 (2H, qt, J=7.3, 7.8 Hz), 2.66 (2H, t, J=7.8 Hz), 3.55 (3H, s), 4.85 (2H, s), 6.78 (1H, d, J=8.1 Hz), 6.93 (1H, d, J=8.6 Hz), 7.11 (1H, dd, J=3.0, 8.1 Hz), 7.38 (1H, d, J=8.6 Hz), 7.46 (1H, s), 7.74 (1H, d, J=3.0 Hz).

Preparation of 2-(4-(1,1,1,3,3,3-hexafluoro-2-(methoxymethoxy)propan-2-yl)-2-propylphenoxy)-5-iodopyridine The similar reaction and treatment were conducted as Example 119-a), and 2-(4-(1,1,1,3,3,3-hexafluoro-2-(methoxymethoxy)propan-2-yl)-2-propylphenoxy)-5-iodopyridine was obtained as a yellow oil.

$^1$H-NMR (CDCl$_3$) δ: 0.90 (3H, t, J=7.0 Hz), 1.59 (2H, qt, J=7.0, 7.3 Hz), 2.57 (2H, t, J=7.3 Hz), 3.56 (3H, s), 4.88 (2H, s), 6.78 (1H, d, J=8.6 Hz), 7.08 (1H, d, J=8.6 Hz), 7.45 (1H, d, J=8.6 Hz), 7.51 (1H, s), 7.95 (1H, dd, J=2.4, 8.6 Hz), 8.35 (1H, d, J=2.4 Hz).

Preparation of 2-(4-(1,1,1,3,3,3-hexafluoro-2-(methoxymethoxy)propan-2-yl)-2-propylphenoxy)-5-vinylpyridine The similar reaction and treatment were conducted as Example 126), and 2-(4-(1,1,1,3,3,3-hexafluoro-2-(methoxymethoxy)propan-2-yl)-2-propylphenoxy)-5-vinylpyridine was obtained as a yellow oil.

$^1$H-NMR (CDCl$_3$) δ: 0.91 (3H, t, J=7.3 Hz), 1.62 (2H, qt, J=7.3, 7.8 Hz), 2.61 (2H, 1, J=7.8 Hz), 3.56 (3H, s), 4.88 (2H, s), 5.30 (1H, d, J=11.3 Hz), 5.72 (1H, d, J=17.8 Hz), 6.68 (1H, dd, J=11.3, 17.8 Hz), 6.90 (1H, d, J=8.6 Hz), 7.09 (1H, d, J=8.9 Hz), 7.45 (1H, d, J=8.9 Hz), 7.51 (1H, s), 7.81 (1H, dd, J=2.2, 8.6 Hz), 8.17 (1H, d, J=2.2 Hz).

Preparation of 2-(4-(1,1,1,3,3,3-hexafluoro-2-(methoxymethoxy)propan-2-yl)-2-propylphenoxy)-5-(oxiran-2-yl)pyridine The similar reaction and treatment were conducted as Example 185), and 2-(4-(1,1,1,3,3,3-hexafluoro-2-(methoxymethoxy)propan-2-yl)-2-propylphenoxy)-5-(oxiran-2-yl)pyridine was obtained as a yellow oil.

$^1$H-NMR (CDCl$_3$) δ: 0.90 (3H, t, J=7.3 Hz), 1.61 (2H, qt, J=7.3, 7.6 Hz), 259 (2H, J=7.6 Hz), 2.84 (1H, dd, J=2.7, 5.1 Hz), 3.19 (1H, dd, J=4.1, 5.1 Hz), 3.56 (3H, s), 3.88 (1H, dd, J=2.7, 4.1 Hz), 4.88 (2H, s), 6.91 (1H, d, J=8.6 Hz), 7.08 (1H, d, J=8.6 Hz), 7.45 (1H, d, J=8.6 Hz), 7.51 (1H, s), 7.56 (1H, d, J=2.4, 8.6 Hz), 8.17 (1H, d, J=2.4 Hz).

Preparation of 2-(6-(4-(1,1,1,3,3,3-hexafluoro-2-(methoxymethoxy)propan-2-yl-2-propylphenoxy)pyridin-3-yl) ethanol The similar reaction and treatment were conducted as Example 38-b), and 2-(6-(4-(1,1,1,3,3,3-hexafluoro-2-(methoxymethoxy)propan-2-yl)-2-propylphenoxy)pyridin-3-yl)ethanol was obtained as a yellow oil.

$^1$H-NMR (CDCl$_3$) δ: 0.91 (3H, t, J=7.3 Hz), 1.64 (2H, qt, J=7.3, 7.6 Hz), 2.62 (2H, t, J=7.6 Hz), 2.91 (2H, t, J=5.7 Hz), 3.57 (3H, s), 3.90 (2H, t, J=5.7 Hz), 4.86 (2H, s), 6.75 (1H, d, J=8.6 Hz), 7.15 (1H, d, J=8.6 Hz), 7.56 (1H, d, J=8.6 Hz), 7.62 (1H, s), 7.92 (1H, dd, J=2.4, 8.6 Hz), 8.39 (1H, d, J=2.4 Hz).

Preparation of 2-(6-(4-(1,1,1,3,3,3-hexafluoro-2-(methoxymethoxy)propan-2-yl)-2-propylphenoxy)pyridin-3-yl)ethyl 4-methylbenzenesulfonate The similar reaction and treatment were conducted as Example 126, and 2-(6-(4-(1,1,1,3,3,3-hexafluoro-2-(methoxymethoxy)propan-2-yl)-2-propylphenoxy)pyridin-3-yl)ethyl 4-methylbenzenesulfonate was obtained as a yellow oil.

$^1$H-NMR (CDCl$_3$) δ: 0.91 (3H, t, J=7.3 Hz), 1.62 (2H, qt, J=7.3, 7.3 Hz), 2.44 (3H, s), 2.60 (2H, t, J=7.3 Hz), 2.93 (2H, t, J=6.5 Hz), 3.56 (3H, s), 4.20 (2H, t, J=6.5 Hz), 4.88 (2H, s), 6.83 (1H, d, J=8.4 Hz), 7.05 (1H, d, J=8.6 Hz), 7.32 (2H, d, J=8.1 Hz), 7.44 (1H, d, J=8.6 Hz), 7.50 (1H, s), 7.52 (1H, dd, J=2.4, 8.4 Hz), 7.72 (2H, d, J=8.1 Hz), 7.94 (1H, d, J=2.4 Hz).

5-(1-(1-Methylethoxy)phenyl-4-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.90 (3H, t, J=7.3 Hz), 1.26 (6H, d, J=5.8 Hz), 1.56-1.63 (5H, m), 2.57 (2H, t, J=7.8 Hz), 2.92 (2H, t, J=6.6 Hz), 3.74 (2H, t, J=6.6 Hz), 4.55 (1H, sept, J=5.8 Hz), 6.85 (2H, d, J=8.8 Hz), 6.95 (1H, d, J=8.6 Hz), 7.26 (2H, d, J=9.0 Hz), 7.56-7.64 (4H, m), 7.90 (1H, s).

Example 200

Preparation of 5-(2,3-dihydrobenzofuran-5-yl)-3-(2-(6-(4-(1,1,1,3,3,3-hexafluoro-2-hydroxypropan-2-yl)-2-propylphenoxy)pyridin-3-yl)ethyl)-5-methylimidazolidine-2,4-dione

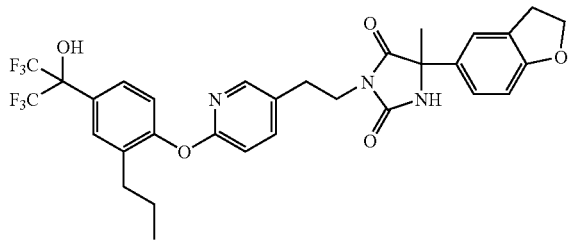

5-(2,3-Dihydrobenzofuran-5-yl)-5-methylimidazolidine-2,4-dione was used in place of 5-(1-(1-methylethoxy)phenyl-4-yl)-5-methylimidazolidine-2,4-dione in Example 199 for a similar reaction and treatment, and the title compound was obtained as a colorless oil.

$^1$H-NMR (CDCl$_3$) δ: 0.90 (3H, t, J=7.6 Hz), 1.58-1.63 (5H, m), 2.56 (2H, t, J=7.8 Hz), 2.93-2.96 (2H, m), 3.13 (2H, t, J=8.8 Hz), 3.74-3.76 (2H, m), 4.49 (2H, t, J=8.8 Hz), 6.66-6.80 (2H, m), 7.02-7.23 (3H, m), 7.60-7.74 (3H, m), 7.99 (1H, s).

Example 201

Preparation of 3-(4-(6-(1,1,1,3,3,3-hexafluoro-2-hydroxypropan-2-yl)-2-propylpyridin-3-yloxy)phenethyl)-5-(4-(1-methylethoxy)phenyl)-5-methylimidazolidine-2,4-dione

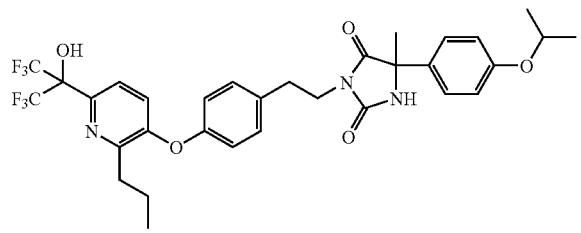

After using 6-(1,1,1,3,3,3-hexafluoro-2-(methoxymethoxy)propan-2-yl)-2-propylpyridin-3-ol prepared in Example 171 for similar sequential reactions as Example 38 a) to c), 5-(1-(1-methylethoxy)phenyl-4-yl)-5-methylimidazolidine-2,4-dione was used in place of 5-(benzo[d][1,3]dioxol-5-yl)-5-methylimidazolidine-2,4-dione in Example 1-b) for a similar reaction and treatment, and the title compound was obtained as a colorless oil.

$^1$H-NMR (CDCl$_3$) δ: 0.99 (3H, t, J=7.3 Hz), 1.20 (3H, d, J=6.0 Hz), 1.21 (3H, d, J=6.0 Hz), 1.64 (3H, s), 1.78-1.87 (2H, m), 2.88-2.96 (4H, m), 3.73 (2H, t, J=6.4 Hz), 4.48 (1H, sept, J=6.0 Hz), 6.76 (2H, d, J=8.6 Hz), 6.82 (2H, d, J=8.6 Hz), 7.06 (1H, d, J=8.6 Hz), 7.12 (2H, d, J=8.6 Hz), 7.28 (2H, J=8.6 Hz), 7.56 (1H, d, J=8.6 Hz).

Example 202

Preparation of 5-(2,3-dihydrobenzofuran-5-yl)-3-(4-(6-(1,1,1,3,3,3-hexafluoro-2-hydroxypropan-2-yl)-2-propylpyridin-3-yloxy)phenethyl)-5-methylimidazolidine-2,4-dione

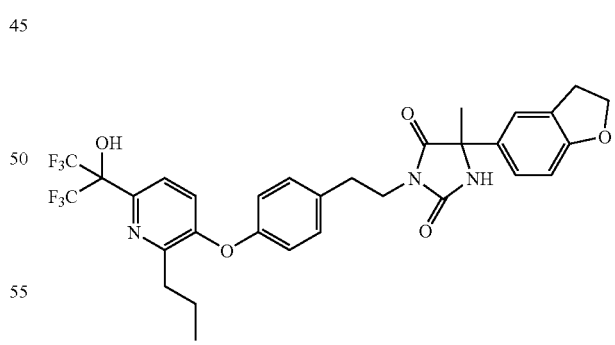

5-(2,3-Dihydrobenzofuran-5-yl)-5-methylimidazolidine-2,4-dione was used in place of 5-(1-(1-methylethoxy)phenyl-4-yl)-5-methylimidazolidine-2,4-dione in Example 201 for a similar reaction and treatment, and the title compound was obtained as a colorless oil.

$^1$H-NMR (CDCl$_3$) δ: 0.99 (3H, t, J=7.3 Hz), 1.63 (3H, s), 1.78-1.87 (2H, m), 2.91-2.96 (2H, m), 3.08-3.13 (2H, m), 3.19 (2H, t, J=8.6 Hz), 3.73 (2H, t, J=6.6 Hz), 4.47 (2H, t,

J=8.6 Hz), 6.64 (2H, d, J=8.6 Hz), 6.83 (1H, d, J=8.3 Hz), 7.08-7.21 (5H, m), 7.56 (1H, d, J=8.5 Hz).

Example 203

Preparation of 3-(4-(6-(1,1,1,3,3,3-hexafluoro-2-hydroxypropan-2-yl)-2-propylpyridin-3-yloxy)phenethyl)-5-(6-methoxypyridin-3-yl)-5-methylimidazolidine-2,4-dione

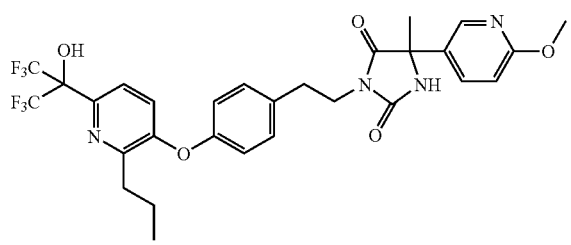

5-(2-Methoxypyridin-5-yl)-5-methylimidazolidine-2,4-dione was used in place of 5-(1-(1-methylethoxy)phenyl-4-yl)-5-methylimidazolidine-2,4-dione in Example 201 for a similar reaction and treatment, and the title compound was obtained as a colorless oil.
$^1$H-NMR (CDCl$_3$) δ: 0.99 (3H, t, J=7.3 Hz), 1.65 (3H, s), 1.78-1.87 (2H, m), 2.92-2.96 (4H, m), 3.75 (2H, t, J=6.8 Hz), 3.82 (3H, s), 6.73 (1H, d, J=8.8 Hz), 6.82 (2H, d, J=8.5 Hz), 7.11-7.15 (3H, m), 7.56 (1H, d, J=8.6 Hz), 7.68 (1H, dd, J=2.7, 8.8 Hz), 8.14 (1H, d, J=2.2 Hz).

Example 204

Preparation of 3-(2-(5-(6-(1,1,1,3,3,3-hexafluoro-2-hydroxypropan-2-yl)-2-propylpyridin-3-yloxy)pyridin-2-yl)ethyl)-5-(1-(1-methylethoxy) phenyl-4-yl)-5-methylimidazolidine-2,4-dione

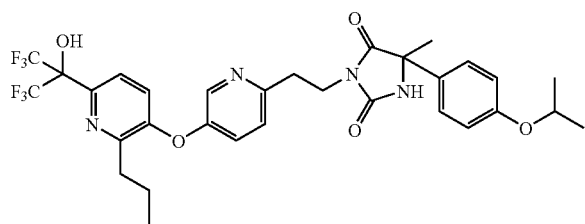

The following compounds were prepared sequentially.

Preparation of 3-(6-bromopyridin-3-yloxy)-6-(1,1,1,3,3,3-hexafluoro-2-(methoxymethoxy)propan-2-yl)-2-propylpyridine The similar reaction and treatment were conducted as Example 3, and 3-(6-bromopyridin-3-yloxy)-6-(1,1,1,3,3,3-hexafluoro-2-(methoxymethoxy)propan-2-yl)-2-propylpyridine was obtained as a yellow oil.
$^1$H-NMR (CDCl$_3$) δ: 0.95 (3H, t, J=7.3 Hz), 1.80 (2H, qt, J=7.3, 7.6 Hz), 2.85 (2H, J=7.6 Hz), 3.56 (3H, s), 4.92 (2H, s), 7.15 (1H, d, J=8.4 Hz), 7.19 (1H, dd, J=3.2, 8.4 Hz), 7.49 (1H, d, J=8.4 Hz), 7.53 (1H, d, J=8.4 Hz), 8.18 (1H, d, J=3.2 Hz).

Preparation of 6-(1,1,1,3,3,3-hexafluoro-2-(methoxymethoxy)propan-2-yl)-2-propyl-3-(6-vinylpyridin-3-yloxy)pyridine The similar reaction and treatment were conducted as Example 126, and 6-(1,1,1,3,3,3-hexafluoro-2-(methoxymethoxy)propan-2-yl)-2-propyl-3-(6-vinylpyridin-3-yloxy)pyridine was obtained as a yellow oil.
$^1$H-NMR (CDCl$_3$) δ: 0.97 (3H, t, J=7.0 Hz), 1.82 (2H, qt, J=7.0, 7.6 Hz), 2.89 (2H, t, J=7.6 Hz), 3.56 (3H, s), 4.92 (2H, s), 5.48 (1H, dd, J=1.4, 10.8 Hz), 6.15 (1H, dd, J=1.4, 17.6 Hz), 6.83 (1H, dd, J=10.8, 17.6 Hz), 7.15 (1H, d, J=8.6 Hz), 7.27 (1H, dd, J=2.7, 8.6 Hz), 7.38 (1H, d, J=8.6 Hz), 7.49 (1H, d, J=8.6 Hz), 8.35 (1H, d, J=2.7 Hz).

Preparation of 5-(6-(1,1,1,3,3,3-hexafluoro-2-(methoxymethoxy)propan-2-yl)-2-propylpyridin-3-yloxy)-2-(oxiran-2-yl)pyridine 1-oxide The similar reaction and treatment were conducted as Example 185, and 5-(6-(1,1,1,3,3,3-hexafluoro-2-(methoxymethoxy)propan-2-yl)-2-propylpyridin-3-yloxy)-2-(oxiran-2-yl)pyridine 1-oxide was obtained as a yellow oil.
$^1$H-NMR (CDCl$_3$) δ: 0.93 (3H, t, J=7.0 Hz), 1.78 (2H, qt, J=7.0, 7.3 Hz), 2.73 (1H, dd, J=2.7, 5.4 Hz), 2.79 (2H, t, J=7.3 Hz), 3.30 (1H dd, J=4.1, 5.4 Hz), 3.56 (3H, s), 4.49 (1H, dd, J=2.7, 4.1 Hz), 4.92 (2H, s), 6.94 (1H, dd, J=2.2, 8.4 Hz), 7.24 (1H, d, J=8.4 Hz), 7.30 (1H, d, J=8.4 Hz), 7.58 (1H, d, J=8.4 Hz), 8.04 (1H, d, J=2.2 Hz).

Preparation of 5-(6-(1,1,1,3,3,3-hexafluoro-2-(methoxymethoxy)propan-2-yl)-2-propylpyridin-3-yloxy)-2-(2-hydroxyethyl)pyridine 1-oxide The similar reaction and treatment were conducted as Example 185, and 5-(6-(1,1,1,3,3,3-hexafluoro-2-(methoxymethoxy)propan-2-yl)-2-propylpyridin-3-yloxy)-2-(2-hydroxyethyl)pyridine 1-oxide was obtained as a yellow oil.
$^1$H-NMR (CDCl$_3$) δ: 0.95 (3H, t, J=7.3 Hz), 1.79 (2H, qt, J=7.3, 7.6 Hz), 2.81 (2H, t, J=7.6 Hz), 3.24 (2H, t, J=7.0 Hz), 3.57 (3H, s), 4.02 (2H, t, J=7.0 Hz), 4.93 (2H, s), 6.96 (1H, dd, J=2.2, 8.6 Hz), 7.29 (1H, d, J=8.6 Hz), 7.31 (1H, d, J=8.4 Hz), 7.58 (1H, d, J=8.4 Hz), 8.07 (1H, d, J=2.2 Hz).

Preparation of 1,1,1,3,3,3-hexafluoro-2-(5-(6-(2-hydroxyethyl)pyridin-3-yloxy)-6-propylpyridin-2-yl)propan-2-ol The similar reaction and treatment were conducted as Example 185, and 1,1,1,3,3,3-hexafluoro-2-(5-(6-(2-hydroxyethyl)pyridin-3-yloxy)-6-propylpyridin-2-yl)propan-2-ol was obtained as a yellow oil.
$^1$H-NMR (CDCl$_3$) δ: 1.00 (3H, t, J=7.0 Hz), 1.83 (2H, qt, J=7.0, 7.6 Hz), 2.96 (2H, t, J=7.6 Hz), 3.06 (214, t, J=5.9 Hz), 4.04 (2H, t, J=5.9 Hz), 7.23 (1H, d, J=8.6 Hz), 7.24 (1H, d, J=8.4 Hz), 7.31 (1H, dd, J=2.7, 8.6 Hz), 7.50 (1H, d, J=8.4 Hz), 8.32 (1H, d, J=2.7 Hz).

Preparation of 2-(5-(6-(1,1,1,3,3,3-hexafluoro-2-hydroxypropan-2-yl)-2-propylpyridin-3-yloxy)pyridin-2-yl)ethyl 4-methylbenzenesulfonate The similar reaction and treatment were conducted as Example 185, and 2-(5-(6-(1,1,1,3,3,3-hexafluoro-2-hydroxypropan-2-yl)-2-propylpyridin-3-yloxy)pyridin-2-yl)ethyl 4-methyl benzenesulfonate was obtained as a yellow oil:

¹H-NMR (CDCl₃) δ: 1.01 (3H, t, J=7.3 Hz), 1.83 (2H, qt, J=7.3, 7.8 Hz), 2.44 (3H, s), 2.95 (2H, t, J=7.8 Hz), 3.15 (2H, t, J=6.2 Hz), 4.43 (2H, t, J=6.2 Hz), 7.18-7.33 (6H, m), 7.50 (1H, d, J=8.4 Hz), 7.73 (1H, d, J=8.1 Hz), 8.25 (1H, d, J=2.4 Hz).

The similar reaction and treatment were conducted as Example 1-b), and the title compound was obtained as a colorless oil:

¹H-NMR (CDCl₃) δ: 1.01 (3H, t, J=7.3 Hz), 1.28 (6H, d, J=5.7 Hz), 1.76 (3H, s), 1.83 (2H, qt, J=7.3, 7.6 Hz), 2.95 (2H, t, J=7.6 Hz), 3.12 (2H, t, J=6.8 Hz), 3.90 (2H, t, J=6.8 Hz), 4.47 (1H, sept, J=5.7 Hz), 5.54 (1H, s), 6.81 (2H, t, J=8.9 Hz), 7.04-7.10 (2H, m), 7.24 (1H, d, J=8.4 Hz), 7.31 (2H, d, J=8.9 Hz), 7.48 (1H, d, J=8.4 Hz), 8.18 (1H, d, J=3.2 Hz).

Example 205

Preparation of 3-(2-(4-(4-(1,1,1,3,3,3-hexafluoro-2-hydroxypropan-2-yl)-2-propylphenoxy)-3-iodophenyl)-2-oxoethyl)-5-(4-(1-methylethoxy)phenyl)-5-methylimidazolidine-2,4-dione

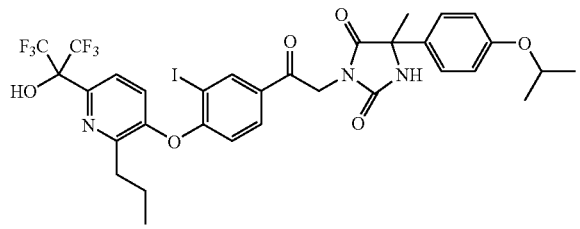

The following compounds were prepared sequentially.

Preparation of 4-(4-(1,1,1,3,3,3-hexafluoro-2-(methoxymethoxy)propan-2-yl)-2-propylphenoxy)-3-iodobenzaldehyde The similar reaction and treatment were conducted as Example 119-a), and 4-(4-(1,1,1,3,3,3-hexafluoro-2-(methoxymethoxy)propan-2-yl)-2-propylphenoxy)-3-iodobenzaldehyde was obtained as a yellow oil.

¹H-NMR (CDCl₃) δ: 0.94 (3H, t, J=7.3 Hz), 1.62-1.71 (2H, m), 2.61 (2H, t, J=7.1 Hz), 3.57 (3H, s), 4.88 (2H, s), 6.78 (1H, d, J=8.3 Hz), 6.97 (1H, d, J=8.8 Hz), 7.49 (1H, d, J=8.8 Hz), 7.57 (1H, s), 7.78 (1H, dd, J=2.0, 8.3 Hz), 8.41 (1H, d, J=2.0 Hz), 9.88 (1H, s).

Preparation of 1-(4-(4-(1,1,1,3,3,3-hexafluoro-2-(methoxymethoxy)propan-2-yl)-2-propylphenoxy)-3-iodophenyl) ethanol The similar reaction and treatment were conducted as Example 27), and 1-(4-(4-(1,1,1,3,3,3-hexafluoro-2-(methoxymethoxy)propan-2-yl)-2-propylphenoxy)-3-iodophenyl) ethanol was obtained as a yellow oil.

¹H-NMR (CDCl₃) δ: 0.97 (3H, t, J=7.3 Hz), 1.50 (3H, d, J=6.8 Hz), 1.65-1.79 (2H, m), 2.71 (2H, t, J=7.3 Hz), 3.55 (3H, s), 4.85 (2H, s), 4.83-4.92 (1H, m), 6.71 (1H, d, J=8.9 Hz), 6.83 (1H, d, J=8.6 Hz), 7.31 (1H, dd, J=1.9, 8.9 Hz), 7.35 (1H, d, J=8.6 Hz), 7.48 (1H, s), 7.90 (1H, d, J=1.9 Hz).

Preparation of 1-(4-(4-(1,1,1,3,3,3-hexafluoro-2-(methoxymethoxy)propan-2-yl)-2-propylphenyl)-3-iodophenyl) ethanone 1-(4-(4-(1,1,1,3,3,3-Hexafluoro-2-(methoxymethoxy)propan-2-yl)-2-propylphenoxy)-3-iodophenyl)ethanol (26 mg, 0.0446 mmol) was dissolved in dichloromethane (3 mL). The resultant mixture was added with manganese dioxide (78 mg, 0.891 mmol) at room temperature, and stirred at room temperature overnight. After completion of the reaction, the reaction solution was filtered using celite and concentrated in vacuum, and 1-(4-(4-(1,1,1,3,3,3-hexafluoro-2-(methoxymethoxy)propan-2-yl)-2-propylphenoxy)-3-iodophenyl) ethanone (16 mg, yield 60%) was obtained as a colorless oil.

¹H-NMR (CDCl₃) δ: 0.94 (3H, t, J=7.3 Hz), 1.60-1.74 (2H, m), 2.58 (3H, s), 2.62 (2H, t, J=7.3 Hz), 3.57 (3H, s), 4.87 (2H, s), 6.74 (1H, d, J=8.6 Hz), 6.93 (1H, d, J=8.4 Hz), 7.46 (1H, d, J=8.4 Hz), 7.55 (1H, s), 7.87 (1H, dd, J=1.9, 8.6 Hz), 8.48 (1H, d, J=1.9 Hz).

Preparation of 2-{3-iodo-4-[2-propyl-4-(2,2,2-trifluoro-1-hydroxy-1-trifluoromethyl-ethyl)-phenoxy]-phenyl}-2-oxo-ethyl toluene-4-sulfonic acid ester To a solution of 1-(4-(4-(1,1,1,3,3,3-hexafluoro-2-(methoxymethoxy)propan-2-yl)-2-propylphenoxy)-3-iodophenyl) ethanone (16 mg, 0.0268 mmol) in acetonitrile (268 μL), hydroxy p-toluenesulfoxyiodobenzene (11 mg, 0.0268 mmol) was added and the resultant mixture was stirred overnight while heated to reflux. Subsequently, hydroxy p-toluenesulfoxyiodobenzene (11 mg, 0.0268 mmol) was further added, and the resultant mixture was stirred overnight while heated to reflux. After completion of the reaction, the reaction solution was concentrated in vacuo. The obtained residue was purified using column chromatography (hexane/ethyl acetate) and 2-{3-iodo-4-[2-propyl-4-(2,2,2-trifluoro-1-hydroxy-1-trifluoromethyl-ethyl)-phenoxy]-phenyl}-2-oxo-ethyl toluene-4-sulfonic acid ester (5.4 mg, yield 28%) was obtained as a colorless oil.

¹H-NMR (CDCl₃) δ: 0.93 (3H, t, J=7.6 Hz), 1.61-1.70 (2H, m), 2.46 (3H, s), 2.58 (2H, t, J=7.6 Hz), 5.16 (2H, s), 6.67 (1H, d, J=8.6 Hz), 6.97 (1H, d, J=8.6 Hz), 7.36 (2H, d, J=8.3 Hz), 7.57 (1H, d, J=8.6 Hz), 7.66 (1H, s), 7.75 (1H, dd, J=2.0, 8.6 Hz), 7.85 (2H, d, J=8.3 Hz), 8.34 (1H, d, J=2.0 Hz).

5-(1-(1-Methylethoxy)phenyl-4-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

¹H-NMR (CDCl₃) δ: 0.94 (3H, t, J=7.4 Hz), 1.33 (6H, d, J=6.1 Hz), 1.61-1.70 (2H, m), 1.93 (3H, s), 2.59 (2H, t, J=7.1 Hz), 4.51-4.58 (1H, m), 4.85 (1H, d, J=17.6 Hz), 4.88 (1H, d, J=17.6 Hz), 5.63 (1H, s), 6.70 (1H, d, J=8.8 Hz), 6.92 (2H, d, J=8.8 Hz), 6.99 (1H, d, J=8.8 Hz), 7.46 (2H, d, J=8.8 Hz), 7.57 (1H, d, J=8.8 Hz), 7.66 (1H, s), 7.85 (1H, dd, J=2.0, 8.8 Hz), 8.49 (1H, d, J=2.0 Hz).

Example 206

Preparation of 3-(2-(4-(4-(1,1,1,3,3,3-hexafluoro-2-hydroxypropan-2-yl)-2-propylphenoxy)phenyl)-2-oxoethyl)-5-(4-(1-methylethoxy)phenyl)-5-methylimidazolidine-2,4-dione

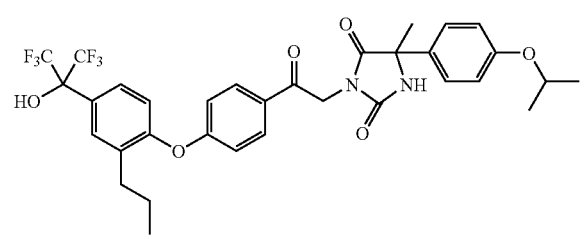

The compound of Example 205 was used for a similar reaction and treatment as Example 121, and the title compound was obtained as a colorless oil.

¹H-NMR (CDCl₃) δ: 0.91 (3H, t, J=7.3 Hz), 1.33 (6H, d, J=5.9 Hz), 1.54-1.68 (2H, m), 1.93 (3H, s), 2.58 (2H, t, J=7.6 Hz), 4.48-4.62 (1H, m), 4.89 (1H, d, J=17.8 Hz), 4.90 (1H, d, J=17.8 Hz), 5.84 (1H, s), 6.91 (2H, d, J=8.9 Hz), 6.98 (2H, d, J=8.9 Hz), 6.99 (1H, d, J=8.6 Hz), 7.47 (2H, d, J=8.9 Hz), 7.54 (1H, d, J=8.6 Hz), 7.63 (1H, s), 7.95 (2H, d, J=8.9 Hz).

Example 207

Preparation of 5-(2,3-dihydrobenzo[b][1,4]dioxin-6-yl)-3-(2-(4-(4-(1,1,1,3,3,3-hexafluoro-2-hydroxypropan-2-yl)-2-propylphenoxy)phenyl)-2-oxoethyl)-5-methylimidazolidine-2,4-dione

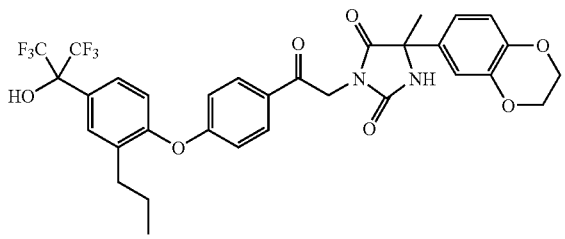

5-(2,3-Dihydrobenzo[b][1,4]dioxin-6-yl)-5-methylimidazolidine-2,4-dione was used in place of 5-(benzo[d][1,3]dioxol-5-yl)-5-methylimidazolidine-2,4-dione in Example 205 for a similar reaction and treatment, and the title compound was obtained as a colorless oil.

¹H-NMR (CDCl₃) δ: 0.91 (3H, t, J=7.3 Hz), 1.54-1.67 (2H, m), 1.91 (3H, s), 2.59 (2H, t, J=7.8 Hz), 4.26 (4H, s), 4.88 (1H, d, J=17.6 Hz), 4.89 (1H, d, J=17.6 Hz), 5.91 (1H, s), 6.89 (1H, d, J=8.6 Hz), 6.98 (2H, d, J=8.9 Hz), 6.99 (1H, d, J=8.6 Hz), 7.04 (1H, dd, J=2.4, 8.6 Hz), 7.09 (1H, d, J=2.4 Hz), 7.54 (1H, d, J=8.6 Hz), 7.63 (1H, s), 7.95 (2H, d, J=8.9 Hz).

Example 208

Preparation of 5-(2,3-dihydrobenzofuran-5-yl)-3-(2-(4-(4-(1,1,1,3,3,3-hexafluoro-2-hydroxypropan-2-yl)-2-propylphenoxy)phenyl)-2-oxoethyl)-5-methylimidazolidine-2,4-dione

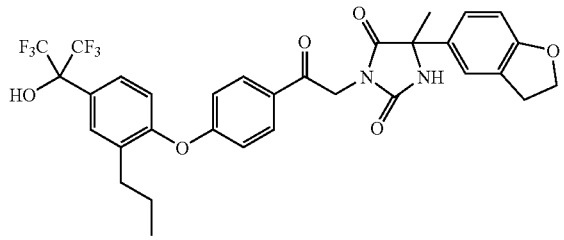

5-(2,3-Dihydrobenzofuran-5-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

¹H-NMR (CDCl₃) δ: 0.90 (3H, t, J=7.3 Hz), 1.53-1.67 (2H, m), 1.93 (3H, s), 2.58 (2H, t, J=7.3 Hz), 3.23 (2H, t, J=8.9 Hz), 4.59 (2H, t, J=8.9 Hz), 4.89 (1H, d, J=17.6 Hz), 4.90 (1H, d, J=17.6 Hz), 5.93 (1H, s), 6.79 (1H, d, J=8.4 Hz), 6.98 (2H, d, J=8.9 Hz), 6.99 (1H, d, J=8.9 Hz), 7.30 (1H, dd, J=1.9, 8.4 Hz), 7.42 (1H, d, J=1.9 Hz), 7.53 (1H, d, J=8.9 Hz), 7.63 (1H, s), 7.95 (2H, d, J=8.9 Hz).

Example 209

Preparation of 3-(2-(4-(4-(1,1,1,3,3,3-hexafluoro-2-hydroxypropan-2-yl)-2-propylphenoxy)-2-methoxy phenyl)-2-oxoethyl)-5-(4-(1-methylethoxy)phenyl)-5-methylimidazolidine-2,4-dione

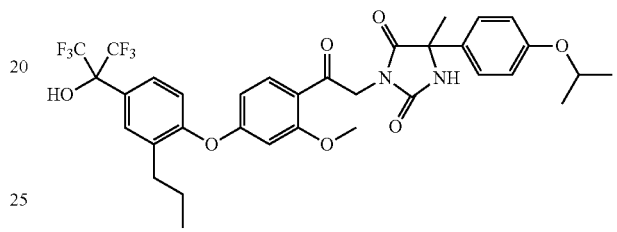

The following compounds were prepared sequentially.

Preparation of 1-{2-methoxy-4-[2-propyl-4-(2,2,2-trifluoro-1-methoxymethoxy-1-trifluoromethyl-ethyl)-phenoxy]-phenyl}-ethanone The similar reaction and treatment were conducted as Example 119-a), and 1-{(2-methoxy-4-[2-propyl-4-(2,2,2-trifluoro-1-methoxymethoxy-1-trifluoromethyl-ethyl)-phenoxy]-phenyl}-ethanone was obtained as a yellow oil.

¹H-NMR (CDCl₃) δ: 0.93 (3H, t, J=7.3 Hz), 1.63 (2H, qt, J=7.3, 7.6 Hz), 2.60 (3H, s), 2.63 (2H, t, J=7.6 Hz), 3.57 (3H, s), 3.88 (3H, s), 4.87 (2H, s), 6.46 (1H, dd, J=2.4, 8.4 Hz), 6.61 (1H, d, J=2.4 Hz), 6.96 (1H, d, J=8.4 Hz), 7.43 (1H, d, J=8.4 Hz), 7.52 (1H, s), 7.79 (1H, d, J=8.4 Hz).

Preparation of 2-{2-methoxy-4-[2-propyl-4-(2,2,2-trifluoro-1-hydroxy-1-trifluoromethyl-ethyl)-phenoxy]-phenyl}-2-oxo-ethyl toluene-4-sulfonic acid ester The similar reaction and treatment were conducted as Example 205, and 2-{2-methoxy-4-[2-propyl-4-(2,2,2-trifluoro-1-hydroxy-1-trifluoromethyl-ethyl)-phenoxy]-phenyl}-2-oxo-ethyl toluene-4-sulfonic acid ester was obtained as a yellow oil.

¹H-NMR (CDCl₃) δ: 0.92 (3H, t, J=7.6 Hz), 1.62 (2H, qt, J=7.6, 7.8 Hz), 2.45 (3H, s), 2.59 (2H, t, J=7.8 Hz), 3.89 (3H, s), 5.24 (2H, s), 6.46 (1H, dd, J=2.2, 8.6 Hz), 6.56 (1H, d, J=2.2 Hz), 6.99 (1H, d, J=8.4 Hz), 7.35 (2H, d, J=7.8 Hz), 7.55 (1H, d, J=8.4 Hz), 7.63 (1H, s), 7.87 (1H, d, J=8.6 Hz), 7.88 (2H, d, J=7.8 Hz).

5-(1-(1-Methylethoxy)phenyl-4-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

¹H-NMR (CDCl₃) δ: 0.92 (3H, t, J=7.3 Hz), 1.33 (6H, d, J=5.9 Hz), 1.54-1.65 (2H, m), 1.92 (3H, s), 2.60 (2H, t, J=7.8 Hz), 3.89 (3H, s), 4.50-4.59 (1H, m), 4.93 (2H, s), 5.82 (1H, s), 6.45 (1H, dd, J=2.4, 8.9 Hz), 6.58 (1H, d, J=2.4 Hz), 6.89-6.92 (2H, m), 6.99 (1H, d, J=8.6 Hz), 7.45-7.49 (2H, m), 7.53 (1H, d, J=8.6 Hz), 7.62 (1H, s), 7.94 (1H, d, J=8.9 Hz).

Example 210

Preparation of 5-(2,3-dihydrobenzofuran-5-yl)-3-(2-(4-(4-(1,1,1,3,3,3-hexafluoro-2-hydroxypropan-2-yl)-2-propylphenoxy)-2-methoxy phenyl)-2-oxoethyl)-5-methylimidazolidine-2,4-dione

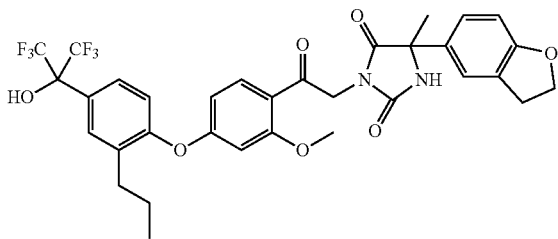

5-(2,3-Dihydrobenzofuran-5-yl)-5-methylimidazolidine-2,4-dione was used in place of 5-(1-(1-methylethoxy)phenyl-4-yl)-5-methylimidazolidine-2,4-dione in Example 209 for a similar reaction and treatment, and the title compound was obtained as a colorless oil.

¹H-NMR (CDCl₃) δ: 0.92 (3H, t, J=7.6 Hz), 1.54-1.65 (2H, m), 1.92 (3H, s), 2.62 (2H, t, J=7.3 Hz), 3.23 (2H, t, J=8.6 Hz), 3.89 (3H, s), 4.59 (2H, t, J=8.6 Hz), 4.93 (2H, s), 5.88 (1H, s), 6.45 (1H, dd, J=2.4, 8.6 Hz), 6.58 (1H, d, J=2.4 Hz), 6.79 (1H, d, J=8.4 Hz), 6.99 (1H, d, J=8.6 Hz), 7.30 (1H, d, J=8.4 Hz), 7.43 (1H, s), 7.54 (1H, d, J=8.6 Hz), 7.63 (1H, s), 7.94 (1H, d, J=8.6 Hz).

Example 211

Preparation of 3-(2-{2-ethoxy-4-[2-propyl-4-(2,2,2-trifluoro-1-hydroxy-1-trifluoromethyl-ethyl)-phenoxy]-phenyl}-2-oxo-ethyl)-5-(5-(1-methylethoxy)pyridin-2-yl)-5-methyl-imidazolidine-2,4-dione

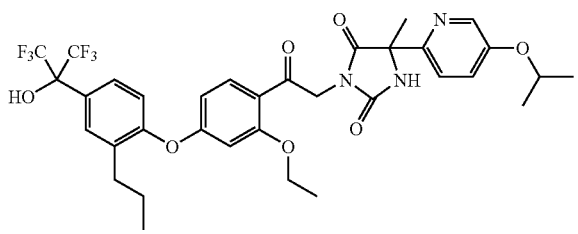

The following compounds were prepared sequentially.

Preparation of 2-ethoxy-4-fluoro-1-nitro-benzene

The similar reaction and treatment were conducted as Example 127, and 2-ethoxy-4-fluoro-1-nitro-benzene was obtained as a yellow oil.

¹H-NMR (CDCl₃) δ: 1.50 (3H, t, J=6.8 Hz), 4.17 (2H, q, J=6.8 Hz), 6.70 (1H, dd, J=2.7, 7.3 Hz), 6.76 (1H, ddd, J=2.7, 8.9, 9.7 Hz), 7.93 (1H, dd, J=5.9, 8.9 Hz).

Preparation of 2-ethoxy-4-(4-(1,1,1,3,3,3-hexafluoro-2-(methoxymethoxy)propan-2-yl)-2-propylphenoxy)-1-nitrobenzene The similar reaction and treatment were conducted as Example 119-a) and 2-ethoxy-4-(4-(1,1,1,3,3,3-hexafluoro-2-(methoxymethoxy)propan-2-yl)-2-propylphenoxy)-1-nitrobenzene was obtained as a yellow oil.

¹H-NMR (CDCl₃) δ: 0.93 (3H, t, J=7.6 Hz), 1.48 (3H, t, J=7.0 Hz), 1.61 (2H, qt, J=7.6, 7.8 Hz), 2.61 (2H, t, J=7.8 Hz), 3.57 (3H, s), 4.13 (2H, q, J=7.0 Hz), 4.88 (2H, s), 6.42 (1H, dd, J=2.2, 9.2 Hz), 6.65 (1H, d, J=2.2 Hz), 7.00 (1H, d, J=8.6 Hz), 7.48 (1H, d, J=8.6 Hz), 7.55 (1H, s), 7.92 (1H, d, J=9.2 Hz).

Preparation of 2-ethoxy-4-[2-propyl-4-(2,2,2-trifluoro-1-methoxymethoxy-1-trifluoromethyl-ethyl)-phenoxy]-phenylamine 2-ethoxy-4-(4-(1,1,1,3,3,3-hexafluoro-2-(methoxymethoxy)propan-2-yl)-2-propyl-phenoxy)-1-nitrobenzene was used for a similar reaction and treatment as Example 119-a), and -ethoxy-4-[2-propyl-4-(2,2,2-trifluoro-1-methoxymethoxy-1-trifluoro methyl-ethyl)-phenoxy]-phenylamine was obtained as a yellow oil.

¹H-NMR (CDCl₃) δ: 0.98 (3H, t, J=7.0 Hz), 1.44 (3H, t, J=7.0 Hz), 1.71 (2H, qt, J=7.0, 7.6 Hz), 2.73 (2H, t, J=7.6 Hz), 3.55 (3H, s), 4.03 (2H, q, J=7.0 Hz), 4.84 (2H, s), 6.47 (1H, dd, J=2.4, 8.1 Hz), 6.55 (1H, d, J=2.4 Hz), 6.71 (1H, d, J=8.1 Hz), 6.72 (1H, d, J=8.9 Hz), 7.28 (1H, d, J=8.9 Hz), 7.41 (1H, s).

Preparation of 2-ethoxy-4-(4-(1,1,1,3,3,3-hexafluoro-2-(methoxymethoxy)propan-2-yl)-2-propylphenoxy)-1-iodobenzene The similar reaction and treatment were conducted as Example 119-a), and 2-ethoxy-4-(4-(1,1,1,3,3,3-hexafluoro-2-(methoxymethoxy)propan-2-yl)-2-propylphenoxy)-1-iodobenzene was obtained as a yellow oil.

¹H-NMR (CDCl₃) δ: 0.95 (3H, t, J=7.3 Hz), 1.49 (3H, t, J=7.6 Hz), 1.65 (2H, qt, J=7.3, 7.6 Hz), 2.67 (2H, t, J=7.6 Hz), 3.57 (3H, s), 4.05 (2H, q, J=7.6 Hz), 4.86 (2H, s), 6.33 (1H, dd, J=2.2, 8.6 Hz), 6.53 (1H, d, J=2.2 Hz), 6.86 (1H, d, J=8.6 Hz), 7.38 (1H, d, J=8.6 Hz), 7.48 (1H, s), 7.69 (1H, d, J=8.6 Hz).

Preparation of 2-ethoxy-4-(4-(1,1,1,3,3,3-hexafluoro-2-(methoxymethoxy)propan-2-yl)-2-propylphenoxy)-1-vinylbenzene The similar reaction and treatment were conducted as Example 126), and 2-ethoxy-4-(4-(1,1,1,3,3,3-hexafluoro-2-(methoxymethoxy)propan-2-yl)-2-propylphenoxy)-1-vinylbenzene was obtained as a yellow oil.

¹H-NMR (CDCl₃) δ: 0.96 (3H, t, J=7.0 Hz), 1.44 (3H, t, J=7.0 Hz), 1.67 (2H, qt, J=7.0, 7.8 Hz), 2.69 (2H, t, J=7.8 Hz), 3.56 (3H, s), 4.01 (2H, q, J=7.0 Hz), 4.86 (2H, s), 5.22 (1H, dd, J=1.4, 11.1 Hz), 5.71 (1H, dd, J=1.4, 18.1 Hz), 6.49 (1H, dd, J=2.2, 8.4 Hz), 6.56 (1H, d, J=2.2 Hz), 6.86 (1H, d, J=8.9 Hz), 7.01 (1H, dd, J=11.1, 18.1 Hz), 7.36 (1H, d, J=8.9 Hz), 7.43 (1H, d, J=8.4 Hz), 7.46 (1H, s).

Preparation of 2-bromo-1-{5-bromo-2-ethoxy-4-[2-propyl-4-(2,2,2-trifluoro-1-methoxymethoxy-1-trifluoromethyl-ethyl)-phenoxy]-phenyl}-ethanol 2-Ethoxy-4-(4-(1,1,1,3,3,3-hexafluoro-2-(methoxymethoxy)propan-2-yl)-2-propylphenoxy)-1-vinylbenzene (53 mg, 0.108 mmol) was dissolved in dioxane (100 μL). The resultant was added with a mixed aqueous solution of sodium bromide (16 mg, 0.151 mmol) and sodium bromate (11 mg, 0.0753 mmol) (water 200 μL) at room temperature, and then added with concentrated sulfuric acid (6.4 μL, 0.118 mmol). The resultant mixture was stirred at room temperature for 3.5 hours and extracted with chloroform. The organic layer was washed with a saturated aqueous solution of sodium thiosulfate and brine, dried over sodium sulfate, and concentrated in vacuo. The obtained residue was purified using silica-gel column chromatography (n-hexane/ethyl acetate), and 2-bromo-1-{5-bromo-2-ethoxy-4-[2-propyl-4-(2,2,2-trifluoro-1-methoxymethoxy-1-trifluoromethyl-ethyl)-phenoxy]-phenyl}-ethanol (49 mg, yield 68%) was obtained as a yellow oil.

$^1$H-NMR (CDCl$_3$) δ: 0.98 (3H, t, J=7.3 Hz), 1.39 (3H, t, J=7.0 Hz), 1.72 (2H, qt, J=7.3, 7.8 Hz), 2.74 (2H, t, J=7.8 Hz), 2.83 (1H, d, J=5.1 Hz), 3.51 (1H, dd, J=8.1, 10.3 Hz), 3.55 (3H, s), 3.77 (1H, dd, J=3.2, 10.3 Hz), 3.89-4.00 (2H, m), 4.85 (2H, s), 5.11-5.17 (1H, m), 6.50 (1H, s), 6.63 (1H, d, J=8.9 Hz), 7.33 (1H, d, J=8.9 Hz), 7.47 (1H, s), 7.71 (1H, s).

Preparation of 2-bromo-1-{5-bromo-2-ethoxy-4-[2-propyl-4-(2,2,2-trifluoro-1-methoxymethoxy-1-trifluoromethyl-ethyl)-phenoxy]-phenyl}-ethanone The similar reaction and treatment were conducted as Example 205, and 2-bromo-1-{5-bromo-2-ethoxy-4-[2-propyl-4-(2,2,2-trifluoro-1-methoxymethoxy-1-trifluoromethyl-ethyl)-phenoxy]-phenyl}-ethanone was obtained as a yellow oil.

$^1$H-NMR (CDCl$_3$) δ: 0.95 (3H, t, J=7.3 Hz), 1.46 (3H, t, J=6.8 Hz), 1.68 (2H, qt, J=7.3, 7.8 Hz), 2.66 (2H, t, J=7.8 Hz), 3.57 (3H, s), 3.97 (2H, q, J=6.8 Hz), 4.54 (2H, s), 4.87 (2H, s), 6.38 (1H, s), 6.86 (1H, d, J=8.6 Hz), 7.44 (1H, d, J=8.6 Hz), 7.54 (1H, s), 8.18 (1H, s).

Preparation of 3-(2-(5-bromo-2-ethoxy-4-(4-(1,1,1,3,3,3-hexafluoro-2-(methoxymethoxy)propan-2-yl)-2-propylphenoxy)phenyl)-2-oxo-ethyl)-5-(5-(1-methyethoxy)pyridin-2-yl)-5-methyl-imidazolidine-2,4-dione 5-(5-(1-Methylethoxy)pyridin-2-yl)-5-methylimidazolidine-2,4-dione was used in place of 5-(benzo[d][1,3]dioxol-5-yl)-5-methylimidazolidine-2,4-dione in Example 1 for a similar reaction and treatment, and 3-(2-(5-bromo-2-ethoxy-4-(4-(1,1,1,3,3,3-hexafluoro-2-(methoxymethoxy)propan-2-yl)-2-propylphenoxy)phenyl)-2-oxoethyl)-5-(5-(1-methylethoxy)pyridin-2-yl)-5-methylimidazolidine-2,4-dione was obtained as a colorless oil.

$^1$H-NMR (CDCl$_3$) δ: 0.97 (3H, t, J=7.3 Hz), 1.38 (6H, d, J=5.7 Hz), 1.48 (3H, t, J=7.0 Hz), 1.70 (2H, qt, J=7.3, 7.8 Hz), 1.91 (3H, s), 2.67 (2H, t, J=7.8 Hz), 3.59 (3H, s), 3.98 (2H, q, J=7.0 Hz), 4.60 (1H, sept, J=5.7 Hz), 4.88 (2H, s), 4.89 (2H, s), 6.34 (1H, s), 6.39 (1H, s), 6.88 (1H, d, J=8.6 Hz), 7.23 (1H, dd, J=2.8, 8.6 Hz), 7.47 (1H, d, J=8.6 Hz), 7.54 (1H, s), 7.66 (1H, d, J=8.6 Hz), 8.24 (1H, d, J=2.8 Hz), 8.28 (1H, s).

Preparation of 3-(2-{2-ethoxy-4-[2-propyl-4-(2,2,2-trifluoro-1-methoxymethoxy-1-trifluoromethyl-ethyl)-phenoxy]-phenyl}-2-oxo-ethyl)-5-(5-(1-methylethoxy)pyridin-2-yl)-5-methyl-imidazolidine-2,4-dione The similar reaction and treatment were conducted as Example 121, and 3-(2-{2-ethoxy-4-[2-propyl-4-(2,2,2-trifluoro-1-methoxymethoxy-1-trifluoromethyl-ethyl)-phenoxy]-phenyl}-2-oxo-ethyl)-5-(5-(1-methylethoxy)pyridin-2-yl)-5-methyl-imidazolidine-2,4-dione was obtained as a yellow oil.

$^1$H-NMR (CDCl$_3$) δ: 0.92 (3H, t, J=7.3 Hz), 1.39 (6H, d, J=5.7 Hz), 1.53 (3H, t, J=7.0 Hz), 1.61 (2H, qt, J=7.3, 7.6 Hz), 2.00 (3H, s), 2.60 (2H, t, J=7.6 Hz), 3.57 (3H, s), 4.13 (2H, q, J=7.0 Hz), 4.66 (1H, sept, J=5.7 Hz), 4.87 (2H, s), 4.91 (2H, s), 6.45 (1H, dd, J=2.2, 8.6 Hz), 6.57 (1H, d, J=2.2 Hz), 6.98 (1H, d, J=8.4 Hz), 7.20 (1H, d, J=8.4 Hz), 7.45 (1H, d, J=8.4 Hz), 7.52 (1H, s), 7.90 (1H, d, J=8.4 Hz), 7.93 (1H, d, J=8.6 Hz), 8.30 (1H, s).

The similar reaction and treatment were conducted as Example 1-b), and the title compound was obtained as a colorless oil.

$^1$H-NMR (CDCl$_3$) δ: 0.92 (3H, t, J=7.3 Hz), 1.36 (6H, d, J=5.7 Hz), 1.52 (3H, 1, J=7.0 Hz), 1.61 (2H, qt, J=7.3, 7.6 Hz), 1.88 (3H, s), 2.60 (2H, t, J=7.6 Hz), 4.12 (2H, q, J=7.0 Hz), 4.58 (1H, sept, J=5.7 Hz), 4.89 (2H, s), 6.24 (1H, s), 6.45 (1H, dd, J=2.4, 8.9 Hz), 6.55 (1H, d, J=2.4 Hz), 6.99 (1H, d, J=8.6 Hz), 7.20 (1H, dd, J=2.7, 8.6 Hz), 7.54 (1H, d, J=8.6 Hz), 7.62 (1H, s), 7.65 (1H, d, J=8.6 Hz), 7.95 (1H, d, J=8.9 Hz), 8.21 (1H, d, J=2.7 Hz).

Example 212

Preparation of 3-(2-(4-(4-(1,1,1,3,3,3-hexafluoro-2-hydroxypropan-2-yl)-2-propylphenoxy)-2-methylphenyl)-2-oxoethyl)-5-(4-(1-methylethoxy)phenyl)-5-methylimidazolidine-2,4-dione

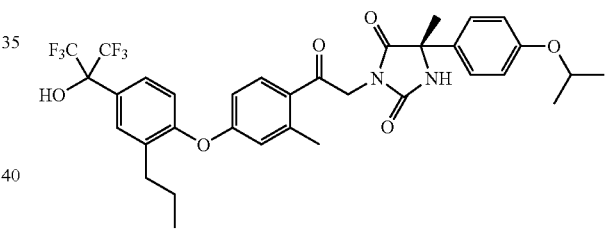

212-a-1) Preparation of 1-{2-methyl-4-[2-propyl-4-(2,2,2-trifluoro-1-methoxymethoxy-1-trifluoromethyl-ethyl)-phenoxy]-phenyl}-ethanone To a solution of 4-(1,1,1,3,3,3-hexafluoro-2-(methoxymethoxy)propan-2-yl)-1-(4-iodo-3-methylphenoxy)-2-propylbenzene (393 mg, 0.699 mmol) in toluene (7.0 mL), ethoxyvinyltributyl tin (473 μL, 1.40 mmol) and tetrakis triphenylphosphine palladium (162 mg, 0.140 mmol) were added sequentially, and the resultant mixture was heated to reflux for 1 hour. Then, ethoxyvinyltributyl tin (946 μL, 2.80 mmol) was added and heated to reflux for 1.5 hours. After completion of the reaction, 5% aqueous solution of hydrochloric acid was added under ice-cold conditions, and the resultant mixture was stirred overnight. The reaction solution was filtered using celite and extracted with ethyl acetate. The organic layer was washed with a saturated aqueous solution of sodium hydrogen carbonate and brine, and concentrated in vacuo. The obtained residue was purified using column chromatography (hexane/ethyl acetate), and 1-{2-methyl-4-[2-propyl-4-(2,2,2-trifluoro-1-methoxymethoxy-1-trifluoromethyl-ethyl)-phenoxy]-phenyl}-ethanone (291 mg, yield 80%) was obtained as a yellow oil.

¹H-NMR (CDCl₃) δ: 0.93 (3H, t, J=7.0 Hz), 1.63 (2H, qt, J=7.0, 7.6 Hz), 2.55 (3H, s), 2.57 (3H, s), 2.63 (2H, t, J=7.6 Hz), 3.57 (3H, s), 4.87 (2H, s), 6.78 (1H, dd, J=2.4, 8.6 Hz), 6.84 (1H, d, J=2.4 Hz), 6.94 (1H, d, J=8.9 Hz), 7.42 (1H, d, J=8.9 Hz), 7.51 (1H, s), 7.75 (1H, d, J=8.6 Hz).

212-a-2) Preparation of 2-{2-methyl-4-[2-propyl-4-(2,2,2-trifluoro-1-hydroxy-1-trifluoromethyl-ethyl)-phenoxy]-phenyl}-2-oxo-ethyl toluene-4-sulfonic acid ester 1-{2-Methyl-4-[2-propyl-4-(2,2,2-trifluoro-1-methoxymethoxy-1-trifluoromethyl-ethyl)-phenoxy]-phenyl}-ethanone was used for a similar reaction and treatment as Example 205, and 2-{2-methyl-4-[2-propyl-4-(2,2,2-trifluoro-1-hydroxy-1-trifluoromethyl-ethyl)-phenoxy]-phenyl}-2-oxo-ethyl toluene-4-sulfonic acid ester was obtained as a yellow crystal.

¹H-NMR (CDCl₃) δ: 0.92 (3H, t, J=7.3 Hz), 1.62 (2H, qt, J=7.3, 7.3 Hz), 2.45 (3H, s), 2.46 (3H, s), 2.60 (2H, t, J=7.3 Hz), 5.10 (2H, s), 6.74 (1H, dd, J=1.9, 7.6 Hz), 6.83 (1H, d, J=1.9 Hz), 6.97 (1H, d, J=8.4 Hz), 7.35 (2H, d, J=7.8 Hz), 7.54 (1H, d, J=7.8 Hz), 7.55 (1H, d, J=8.4 Hz), 7.63 (1H, s), 7.83 (2H, d, J=7.6 Hz).

5-(4-(1-Methylethoxy)phenyl)-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

¹H-NMR (CDCl₃) δ: 0.91 (3H, t, J=7.3 Hz), 1.33 (6H, d, J=5.9 Hz), 1.55-1.66 (2H, m), 1.92 (3H, s), 2.53 (3H, s), 2.59 (2H, t, J=7.0 Hz), 4.50-4.59 (1H, m), 4.78 (1H, d, J=17.6 Hz), 4.80 (1H, d, J=17.6 Hz), 5.94 (1H, s), 6.77 (1H, dd, J=2.4, 8.9 Hz), 6.83 (1H, d, J=2.4 Hz), 6.90 (2H, d, J=8.6 Hz), 6.96 (1H, d, J=8.9 Hz), 7.45 (2H, d, J=8.6 Hz), 7.53 (1H, d, J=8.9 Hz), 7.63 (1H, s), 7.74 (1H, d, J=8.9 Hz).

Example 213

Preparation of 5-(2,3-dihydrobenzofuran-5-yl)-3-(2-(4-(4-(1,1,1,3,3,3-hexafluoro-2-hydroxypropan-2-yl)-2-propylphenoxy)-2-methylphenyl)-2-oxoethyl)-5-methylimidazolidine-2,4-dione

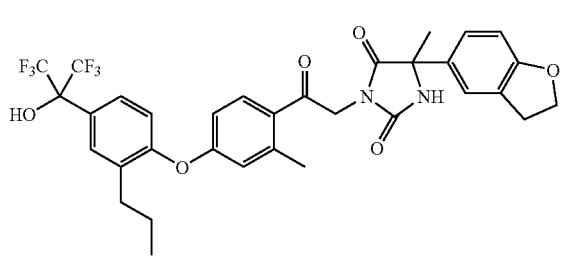

5-(2,3-Dihydrobenzofuran-5-yl)-5-methylimidazolidine-2,4-dione was used in place of 5-(1-(1-methylethoxy)phenyl-4-yl)-5-methylimidazolidine-2,4-dione in Example 212 for a similar reaction and treatment, and the title compound was obtained as a colorless oil.

¹H-NMR (CDCl₃) δ: 0.92 (3H, t, J=7.3 Hz), 1.55-1.66 (2H, m), 1.92 (3H, s), 2.53 (3H, s), 2.59 (2H, t, J=7.0 Hz), 3.23 (2H, t, J=8.6 Hz), 4.59 (2H, t, J=8.6 Hz), 4.78 (1H, d, J=17.6 Hz), 4.80 (1H, d, J=17.6 Hz), 5.97 (1H, s), 6.76 (1H, dd, J=2.2, 8.6 Hz), 6.78 (1H, d, J=8.6 Hz), 6.84 (1H, d, J=2.2 Hz), 6.96 (1H, d, J=8.4 Hz), 7.28 (1H, dd, J=1.9, 8.6 Hz), 7.41 (1H, d, J=1.9 Hz), 7.54 (1H, d, J=8.4 Hz), 7.63 (1H, s), 7.74 (1H, d, J=8.6 Hz).

Example 214

Preparation of 3-(2-(4-(4-(1,1,1,3,3,3-hexafluoro-2-hydroxypropan-2-yl)-2-propylphenoxy)-2-methylphenyl)-2-oxoethyl)-5-(5-(1-methylethoxy)pyridin-2-yl)-5-methylimidazolidine-2,4-dione

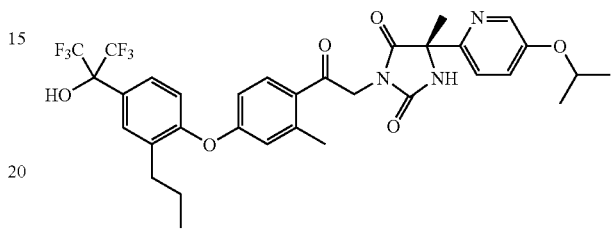

5-(5-(1-Methylethoxy)pyridin-2-yl)-5-methylimidazolidine-2,4-dione was used in place of 5-(1-(1-methylethoxy)phenyl-4-yl)-5-methylimidazolidine-2,4-dione in Example 212 for a similar reaction and treatment, and the title compound was obtained as a colorless oil.

¹H-NMR (CDCl₃) δ: 0.92 (3H, t, J=7.6 Hz), 1.36 (6H, d, J=5.9 Hz), 1.55-1.68 (2H, m), 1.88 (3H, s), 2.53 (3H, s), 2.60 (2H, t, J=7.6 Hz), 4.54-4.62 (1H, m), 4.82 (2H, s), 6.42 (1H, s), 6.77 (1H, dd, J=2.2, 8.9 Hz), 6.84 (1H, d, J=2.2 Hz), 6.96 (1H, d, J=8.6 Hz), 7.20 (1H, dd, J=2.4, 8.9 Hz), 7.54 (1H, d, J=8.6 Hz), 7.61 (1H, d, J=8.9 Hz), 7.63 (1H, s), 7.75 (1H, d, J=8.9 Hz), 8.21 (1H, d, J=2.4 Hz).

Example 215

Preparation of 3-(2-{4-[2-ethyl-6-propyl-4-(2,2,2-trifluoro-1-hydroxy-1-trifluoromethyl-ethyl)-phenoxy]-2-methyl-phenyl}-2-oxo-ethyl)-5-(4-(1-methylethoxy)phenyl)-5-methyl-imidazolidine-2,4-dione

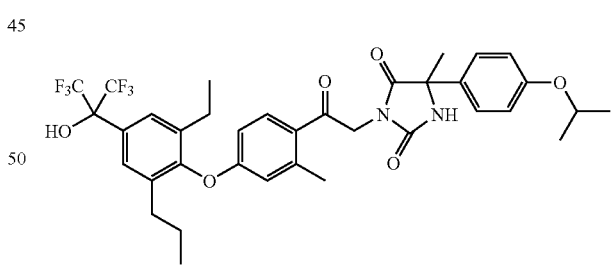

The following compounds were prepared sequentially.

Preparation of 1-ethyl-2-(3-methyl-4-nitro-phenoxy)-3-propyl-5-(2,2,2-trifluoro-1-methoxymethoxy-1-trifluoromethyl-ethyl)-benzene The similar reaction and treatment were conducted as Example 119-a), and 1-ethyl-2-(3-methyl-4-nitro-phenoxy)-3-propyl-5-(2,2,2-trifluoro-1-methoxymethoxy-1-trifluoromethyl-ethyl)-benzene was obtained as a yellow oil.

¹H-NMR (CDCl₃) δ: 0.87 (3H, t, J=7.3 Hz), 1.14 (3H, t, J=7.3 Hz), 1.56 (2H, qt, J=7.3, 7.8 Hz), 2.43 (2H, t, J=7.8

Hz), 2.48 (2H, q, J=7.3 Hz), 2.61 (3H, s), 3.58 (3H, s), 4.90 (2H, s), 6.60 (1H, dd, J=2.7, 9.2 Hz), 6.73 (1H, d, J=2.7 Hz), 7.40 (1H, s), 7.42 (1H, s), 8.04 (1H, d, J=9.2 Hz).

Preparation of 4-[2-ethyl-6-propyl-4-(2,2,2-trifluoro-1-methoxymethoxy-1-trifluoromethyl-ethyl)-phenoxy]-2-methyl-phenylamine 1-Ethyl-2-(3-methyl-4-nitrophenoxy)-3-propyl-5-(2,2,2-trifluoro-1-methoxy meth oxy-1-trifluoromethyl-ethyl)-benzene was used for a similar reaction and treatment as Example 119-a), and 4-[2-ethyl-6-propyl-4-(2,2,2-trifluoro-1-methoxymethoxy-1-trifluoromethyl-ethyl)-phenoxy]-2-methyl-phenylamine was obtained as a yellow oil.

$^1$H-NMR (CDCl$_3$) δ: 0.86 (3H, t, J=7.3 Hz), 1.12 (3H, t, J=7.6 Hz), 1.55 (2H, qt, J=7.3, 7.6 Hz), 2.25 (3H, s), 2.45 (2H, t, J=7.6 Hz), 2.49 (2H, q, J=7.6 Hz), 3.57 (3H, s), 4.88 (2H, s), 6.41 (1H, d, J=8.6 Hz), 6.59 (1H, s), 6.83 (1H, d, J=8.6 Hz), 7.33 (1H, s), 7.35 (1H, s).

Preparation of 1-ethyl-2-(4-iodo-3-methyl-phenoxy)-3-propyl-5-(2,2,2-trifluoro-1-methoxymethoxy-1-trifluoromethyl-ethyl)-benzene The similar reaction and treatment were conducted as Example 119-a), and 1-ethyl-2-(4-iodo-3-methylphenoxy)-3-propyl-5-(2,2,2-trifluoro-1-methoxymethoxy-1-t rifluoromethyl-ethyl)-benzene was obtained as a yellow oil.

$^1$H-NMR (CDCl$_3$) δ: 0.87 (3H, t, J=7.3 Hz), 1.14 (3H, t, J=7.6 Hz), 1.57 (2H, qt, J=7.3, 7.8 Hz), 2.39 (3H, s), 2.45 (2H, t, J=7.8 Hz), 2.50 (2H, q, J=7.6 Hz), 3.59 (3H, s), 4.90 (2H, s), 6.26 (1H, dd, J=2.7, 7.6 Hz), 6.73 (1H, d, J=2.7 Hz), 7.37 (1H, s), 7.38 (1H, s), 7.63 (1H, d, J=7.6 Hz).

Preparation of 1-{4-[2-ethyl-6-propyl-4-(2,2,2-trifluoro-1-methoxymethoxy-1-trifluoromethyl-ethyl)-phenoxy]-2-methyl-phenyl}-ethanone The similar reaction and treatment were conducted as Example 212, and 1-{4-[2-ethyl-6-propyl-4-(2,2,2-trifluoro-1-methoxymethoxy-1-trifluoromethyl-ethyl)-phenoxy]-2-methyl-phenyl}-ethanone was obtained as a yellow oil.

$^1$H-NMR (CDCl$_3$) δ: 0.87 (3H, t, J=7.0 Hz), 1.14 (3H, t, J=7.6 Hz), 1.57 (2H, qt, J=7.0, 7.3 Hz), 2.44 (2H, t, J=7.3 Hz), 2.49 (2H, q, J=7.6 Hz), 2.55 (6H, s), 3.58 (3H, s), 4.90 (2H, s), 6.51 (1H, dd, J=2.7, 8.9 Hz), 6.69 (1H, d, J=2.7 Hz), 7.38 (1H, s), 7.40 (1H, s), 7.71 (1H, d, J=8.9 Hz).

Preparation of 2-{4-[2-ethyl-6-propyl-4-(2,2,2-trifluoro-1-hydroxy-1-trifluoromethyl-ethyl)-phenoxy]-2-methylphenyl}-2-oxo-ethyl toluene-4-sulfonic acid ester 1-{4-[2-Ethyl-6-propyl-4-(2,2,2-trifluoro-1-methoxymethoxy-1-trifluoromethyl-ethyl)-phenoxy]-2-methyl-phenyl}-ethanone was used for a similar reaction and treatment as Example 205, and the title compound was obtained as a white crystal.

$^1$H-NMR (CDCl$_3$) δ: 0.88 (3H, t, J=7.3 Hz), 1.16 (3H, t, J=7.6 Hz), 1.59 (2H, qt, J=7.3, 7.6 Hz), 2.41-2.53 (4H, m), 2.46 (3H, s), 2.47 (3H, s), 5.10 (2H, s), 6.53 (1H, dd, J=2.2, 8.4 Hz), 6.71 (1H, d, J=2.2 Hz), 7.35 (2H, d, J=8.4 Hz), 7.49 (1H, s), 7.50 (1H, s), 7.51 (1H, d, J=8.4 Hz), 7.84 (2H, d, J=8.4 Hz).

5-(1-(1-Methylethoxy)phenyl-4-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

$^1$H-NMR (CDCl$_3$) δ: 0.86 (3H, t, J=7.3 Hz), 1.14 (3H, t, J=7.6 Hz), 1.33 (6H, d, J=5.9 Hz), 1.49-1.63 (2H, m), 1.91 (3H, s), 2.40-2.52 (4H, m), 2.52 (3H, s), 4.48-4.61 (1H, m), 4.77 (1H, d, J=17.3 Hz), 4.79 (1H, d, J=17.3 Hz), 5.96 (1H, s), 6.55 (1H, dd, J=2.7, 8.9 Hz), 6.71 (1H, d, J=2.7 Hz), 6.90 (2H, d, J=8.9 Hz), 7.45 (2H, d, J=8.9 Hz), 7.49 (2H, s), 7.71 (1H, d, J=8.9 Hz).

Example 216

Preparation of 3-(2-{4-[2-ethyl-6-propyl-4-(2,2,2-trifluoro-1-hydroxy-1-trifluoromethyl-ethyl)-phenoxy]-2-methyl-phenyl}-2-oxo-ethyl)-5-(5-(1-methylethoxy)pyridin-2-yl)-5-methyl-imidazolidine-2,4-dione

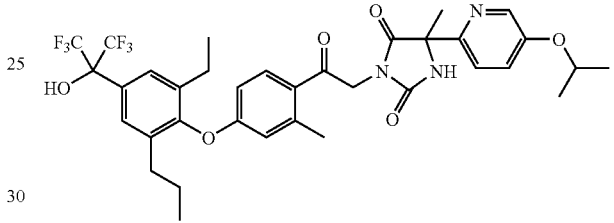

5-(5-(1-Methylethoxy)pyridin-2-yl)-5-methylimidazolidine-2,4-dione was used in place of 5-(1-(1-methylethoxy)phenyl-4-yl)-5-methylimidazolidine-2,4-dione in Example 215 for a similar reaction and treatment, and the title compound was obtained as a colorless oil.

$^1$H-NMR (CDCl$_3$) δ: 0.86 (3H, t, J=7.3 Hz), 1.14 (3H, t, J=7.6 Hz), 1.35 (6H, d, J=6.2 Hz), 1.56 (2H, qt, J=7.3, 7.6 Hz), 1.87 (3H, s), 2.42-2.52 (4H, m), 2.52 (3H, s), 4.51-4.64 (1H, m), 4.81 (2H, s), 6.41 (1H, s), 6.56 (1H, dd, J=2.7, 8.4 Hz), 6.71 (1H, d, J=2.7 Hz), 7.19 (1H, dd, J=2.4, 8.6 Hz), 7.48 (1H, s), 7.50 (1H, s), 7.62 (1H, d, J=8.6 Hz), 7.72 (1H, d, J=8.4 Hz), 8.20 (1H, d, J=2.4 Hz).

Example 217

Preparation of 3-(2-{2-benzyloxy-4-[2-propyl-4-(2,2,2-trifluoro-1-hydroxy-1-trifluoromethyl-ethyl)-phenoxy]-phenyl}-2-oxo-ethyl)-5-(4-(1-methyl-ethoxy)phenyl)-5-methyl-imidazolidine-2,4-dione

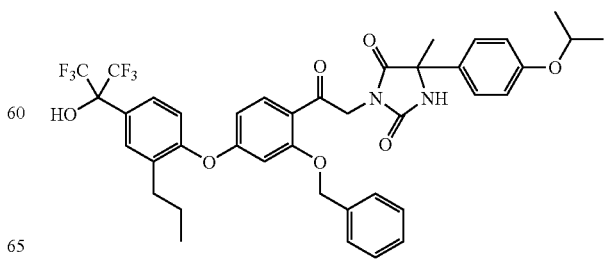

The following compounds were prepared sequentially.

Preparation of 1-{2-benzyloxy-4-[2-propyl-4-(2,2,2-trifluoro-1-methoxymethoxy-1-trifluoromethyl-ethyl)-phenoxy]-phenyl}-ethanone The similar reaction and treatment were conducted as Example 212, and 1-{2-benzyloxy-4-[2-propyl-4-(2,2,2-trifluoro-1-methoxymethoxy-1-trifluoromethyl-ethyl)-phenoxy]-phenyl}-ethanone was obtained as a yellow oil.
$^1$H-NMR (CDCl$_3$) δ: 0.93 (3H, t, J=7.3 Hz), 1.61 (2H, qt, J=7.3, 7.8 Hz), 2.59 (2H, t, J=7.8 Hz), 2.62 (3H, s), 3.60 (3H, s), 4.90 (2H, s), 5.13 (2H, s), 6.54 (1H, dd, J=2.4, 8.6 Hz), 6.60 (1H, d, J=2.4 Hz), 6.93 (1H, d, J=8.9 Hz), 7.34-7.45 (6H, m), 7.53 (1H, s), 7.83 (1H, d, J=8.6 Hz).

Preparation of 2-{2-benzyloxy-4-[2-propyl-4-(2,2,2-trifluoro-1-hydroxy-1-trifluoromethyl-ethyl)phenoxy]-phenyl}-2-oxo-ethyl toluene-4-sulfonic acid ester The similar reaction and treatment were conducted as Example 205, and 2-{2-benzyloxy-4-[2-propyl-4-(2,2,2-trifluoro-1-hydroxy-1-trifluoromethyl-ethyl)-phenoxy]-phenyl}-2-oxo-ethyl toluene-4-sulfonic acid ester was obtained as a yellow oil.
$^1$H-NMR (CDCl$_3$) δ: 0.89 (3H, t, J=7.3 Hz), 1.57 (2H, qt, J=7.3, 7.3 Hz), 2.43 (3H, s), 2.52 (2H, t, J=7.3 Hz), 5.07 (2H, s), 5.14 (2H, s), 6.50-6.54 (2H, m), 6.94 (1H, d, J=8.6 Hz), 7.24-7.43 (7H, m), 7.54 (1H, d, J=8.6 Hz), 7.62 (1H, s), 7.67 (2H, d, J=8.6 Hz), 7.92 (1H, d, J=9.2 Hz).

5-(1-(1-Methylethoxy)phenyl-4-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.
$^1$H-NMR (CDCl$_3$) δ: 0.88 (3H, t, J=7.3 Hz), 1.33 (6H, d, J=5.7 Hz), 1.54 (2H, qt, J=7.3, 7.8 Hz), 1.92 (3H, s), 2.49 (2H, t, J=7.8 Hz), 4.55 (1H, sept, J=5.7 Hz), 4.84 (1H, d, J=18.1 Hz), 4.85 (1H, d, J=18.1 Hz), 5.12 (2H, s), 5.72 (1H, s), 6.48 (1H, d, J=1.9 Hz), 6.53 (1H, dd, J=1.9, 8.9 Hz), 6.89-6.93 (3H, m), 7.28-7.37 (5H, m), 7.45-7.50 (3H, m), 7.61 (1H, s), 7.98 (1H, d, J=8.9 Hz).

Example 218

Preparation of 3-(2-{2-benzyloxy-4-[2-propyl-4-(2,2,2-trifluoro-1-hydroxy-1-trifluoromethyl-ethyl)-phenoxy]-phenyl}-2-oxo-ethyl)-5-(2,3-dihydro-benzo[1,4]dioxin-6-yl)-5-methyl-imidazolidine-2,4-dione

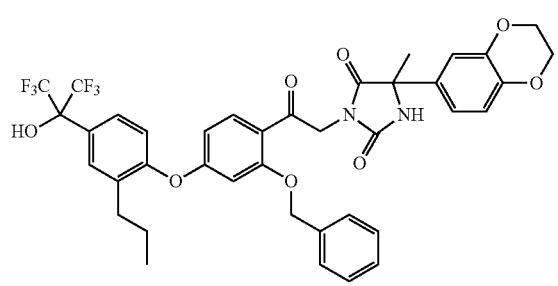

5-2,3-Dihydro-benzo[1,4]dioxin-6-yl)-5-methylimidazolidine-2,4-dione was used in place of 5-(1-(1-methylethoxy)phenyl-4-yl)-5-methylimidazolidine-2,4-dione in Example 217 for a similar reaction and treatment, and the title compound was obtained as a colorless oil.
$^1$H-NMR (CDCl$_3$) δ: 0.88 (3H, t, J=7.3 Hz), 1.54 (2H, qt, J=7.3, 7.6 Hz), 1.89 (3H, s), 2.49 (2H, t, J=7.6 Hz), 4.25 (4H, s), 4.83 (1H, d, J=18.6 Hz), 4.84 (1H, d, J=18.6 Hz), 5.12 (2H, s), 5.67 (1H, s), 6.48 (1H, d, J=2.4 Hz), 6.53 (1H, dd, J=2.4, 8.6 Hz), 6.89 (1H, d, J=8.6 Hz), 6.93 (1H, d, J=8.9 Hz), 7.04 (1H, dd, J=2.2, 8.9 Hz), 7.09 (1H, d, J=2.2 Hz), 7.28-7.37 (5H, m), 7.52 (1H, d, J=8.6 Hz), 7.61 (1H, s), 7.99 (1H, d, J=8.6 Hz).

Example 219

Preparation of 3-(2-{2-benzyloxy-4-[2-propyl-4-(2,2,2-trifluoro-1-hydroxy-1-trifluoromethyl-ethyl)-phenoxy]-phenyl}-2-oxo-ethyl)-5-(5-(1-methylethoxy)pyridin-2-yl)-5-methyl-imidazolidine-2,4-dione

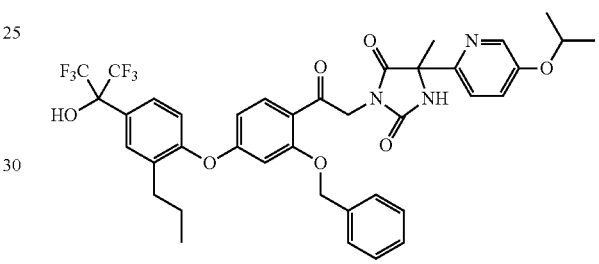

5-(5-(1-Methylethoxy)pyridin-2-yl)-5-methylimidazolidine-2,4-dione was used in place of 5-(1-(1-methylethoxy)phenyl-4-yl)-5-methylimidazolidine-2,4-dione in Example 217, and the title compound was obtained as a colorless oil.
$^1$H-NMR (CDCl$_3$) δ: 0.88 (3H, t, J=7.6 Hz), 1.36 (6H, d, J=6.5 Hz), 1.54 (2H, qt, J=7.6, 7.8 Hz), 1.87 (3H, s), 2.49 (2H, t, J=7.8 Hz), 4.58 (1H, sept, J=6.5 Hz), 4.87 (2H, s), 5.13 (2H, s), 6.29 (1H, s), 6.48 (1H, d, J=2.4 Hz), 6.53 (1H, dd, J=2.4, 8.9 Hz), 6.92 (1H, d, J=8.9 Hz), 7.29-7.36 (5H, m), 7.52 (1H, d, J=8.9 Hz), 7.61 (1H, s), 7.64 (1H, d, J=8.9 Hz), 7.97 (1H, d, J=8.9 Hz), 8.21 (1H, d, J=2.7 Hz).

Example 220

Preparation of 3-(2-{2-benzyloxy-4-[2-propyl-4-(2,2,2-trifluoro-1-hydroxy-1-trifluoromethyl-ethyl)-phenoxy]-phenyl}-2-oxo-ethyl)-5-(2,3-dihydro-benzofuran-5-yl)-methyl-imidazolidine-2,4-dione

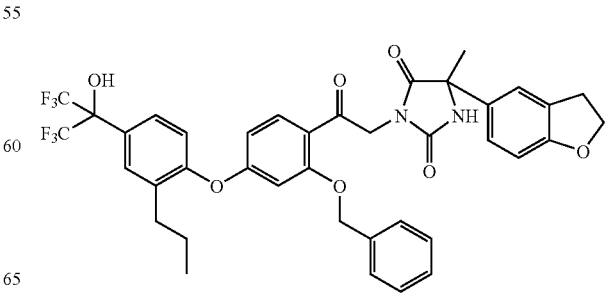

5-(2,3-Dihydro-benzofuran-5-yl)-5-methylimidazolidine-2,4-dione was used in place of 5-(1-(1-methylethoxy)phenyl-4-yl)-5-methylimidazolidine-2,4-dione in Example 217 for a similar reaction and treatment, and the title compound was obtained as a colorless oil.

$^1$H-NMR (CDCl$_3$) δ: 0.87 (3H, t, J=7.3 Hz), 1.54 (2H, qt, J=7.3, 7.8 Hz), 1.91 (3H, s), 2.48 (2H, t, J=7.8 Hz), 3.22 (2H, t, J=8.9 Hz), 4.58 (2H, t, J=8.9 Hz), 4.83 (1H, d, J=18.1 Hz), 4.85 (1H, d, J=18.1 Hz), 5.11 (2H, s), 5.85 (1H, s), 6.48 (1H, d, J=2.2 Hz), 6.52 (1H, dd, J=2.2, 8.4 Hz), 6.79 (1H, d, J=8.6 Hz), 6.91 (1H, d, J=8.9 Hz), 7.27-7.36 (6H, m), 7.43 (1H, s), 7.51 (1H, d, J=8.9 Hz), 7.61 (1H, s), 7.97 (1H, d, J=8.4 Hz).

Example 221

Preparation of 3-(2-{2-benzyloxy-4-[2-propyl-4-(2,2,2-trifluoro-1-hydroxy-1-trifluoromethyl-ethyl)-phenoxy]-phenyl}-2-oxo-ethyl)-5-(2,3-dihydro-[1,4]dioxino[2,3-c]pyridin-7-yl)-5-methylimidazolidine-2,4-dione

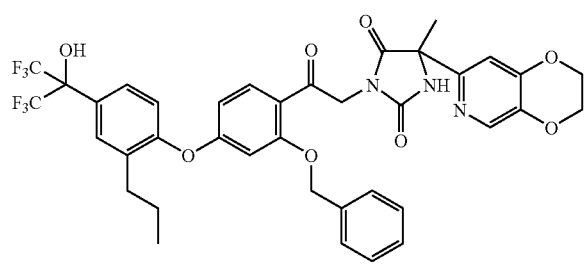

5-(2,3-Dihydro-[1,4]dioxino[2,3-c]pyridin-7-yl)-5-methylimidazolidine-2,4-dione was used in place of 5-(1-(1-methylethoxy)phenyl-4-yl)-5-methylimidazolidine-2,4-dione in Example 217 for a similar reaction and treatment, and the title compound was obtained as a colorless oil.

$^1$H-NMR (CDCl$_3$) δ: 0.88 (3H, t, J=7.6 Hz), 1.54 (2H, qt, J=7.6, 7.8 Hz), 1.84 (3H, s), 2.49 (2H, t, J=7.8 Hz), 4.28-4.34 (4H, m), 4.86 (2H, s), 5.13 (2H, s), 6.35 (1H, s), 6.48 (1H, d, J=2.2 Hz), 6.52 (1H, dd, J=2.2, 8.9 Hz), 6.92 (1H, d, J=8.6 Hz), 7.26-7.40 (6H, m), 7.52 (1H, d, J=8.6 Hz), 7.61 (1H, s), 7.97 (1H, d, J=8.9 Hz), 8.09 (1H, s).

Example 222

Preparation of 3-(2-{2-hydroxy-4-[2-propyl-4-(2,2,2-trifluoro-1-hydroxymethyl-ethyl)-phenoxy]-phenyl}-2-oxo-ethyl)-5-(4-(1-methylethoxy)phenyl)-5-methyl-imidazolidine-2,4-dione

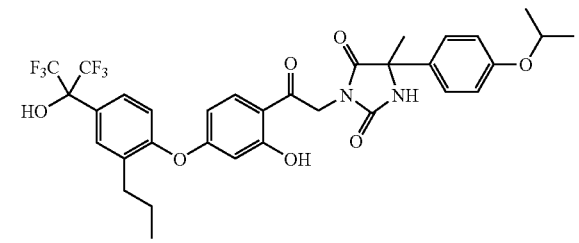

To a solution of 3-(2-{2-benzyloxy-4-[2-propyl-4-(2,2,2-trifluoro-1-hydroxy-1-trifluoromethyl-ethyl)-phenoxy]-phenyl}-2-oxo-ethyl)-5-(4-(1-methylethoxy)phenyl)-5-methyl-imidazolidine-2,4-dione (46 mg, 0.0540 mmol) obtained in Example 217 in methanol (1.0 mL), palladium carbon (5.0 mg) was added, and the resultant mixture was stirred at room temperature for 7 hours under a hydrogen atmosphere. After completion of the reaction, the reaction solution was filtered using celite and concentrated in vacuo. The obtained residue was purified using column chromatography (hexane/ethyl acetate) and the title compound (31 mg, yield 85%) was obtained as a colorless oil.

$^1$H-NMR (CDCl$_3$) δ: 0.91 (3H, t, J=7.3 Hz), 1.34 (6H, d, J=5.7 Hz), 1.61 (2H, qt, J=7.3, 7.6 Hz), 1.94 (3H, s), 2.56 (2H, t, J=7.6 Hz), 4.56 (1H, sept, J=5.7 Hz), 4.90 (1H, d, J=17.8 Hz), 4.92 (1H, d, J=17.8 Hz), 5.75 (1H, s), 6.37 (1H, d, J=2.4 Hz), 6.55 (1H, dd, J=2.4, 8.9 Hz), 6.92 (2H, d, J=8.9 Hz), 7.06 (1H, d, J=8.6 Hz), 7.46 (2H, d, J=8.9 Hz), 7.57 (1H, d, J=8.6 Hz), 7.63 (1H, s), 7.68 (1H, d, J=8.9 Hz), 11.88 (1H, s).

Example 223

Preparation of 5-(2,3-dihydro-benzo[1,4]dioxin-6-yl)-3-(2-{2-hydroxy-4-[2-propyl-4-(2,2,2-trifluoro-1-hydroxy-1-trifluoromethyl-ethyl)-phenoxy]-phenyl}-2-oxo-ethyl)-5-methyl-imidazolidine-2,4-dione

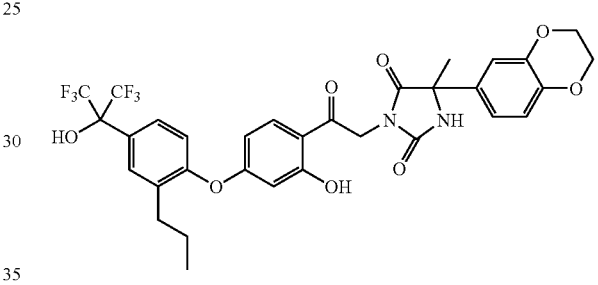

5-(2,3-Dihydro-benzo[1,4]dioxin-6-yl)-5-methylimidazolidine-2,4-dione was used in place of 5-(1-(1-methylethoxy)phenyl-4-yl)-5-methylimidazolidine-2,4-dione in Example 222 for a similar reaction and treatment, and the title compound was obtained as a colorless oil.

$^1$H-NMR (CDCl$_3$) δ: 0.91 (3H, t, J=7.3 Hz), 1.60 (2H, qt, J=7.3, 7.8 Hz), 1.91 (3H, s), 2.56 (2H, t, J=7.8 Hz), 4.27 (4H, s), 4.89 (1H, d, J=17.8 Hz), 4.91 (1H, d, J=17.8 Hz), 5.79 (1H, s), 6.37 (1H, d, J=2.2 Hz), 6.55 (1H, dd, J=2.2, 8.9 Hz), 6.91 (1H, d, J=8.6 Hz), 7.03 (1H, dd, J=2.2, 8.6 Hz), 7.06 (1H, d, J=8.6 Hz), 7.09 (1H, d, J=-2.2 Hz), 7.57 (1H, d, J=8.6 Hz), 7.63 (1H, s), 7.68 (1H, d, J=8.9 Hz), 11.87 (1H, s).

Example 224

Preparation of 3-(2-{2-hydroxy-4-[2-propyl-4-(2,2,2-trifluoro-1-hydroxy-1-trifluoromethyl-ethyl)-phenoxy]-phenyl}-2-oxo-ethyl)-5-(5-(1-methylethoxy)pyridin-2-yl)-5-methyl-imidazolidine-2,4-dione

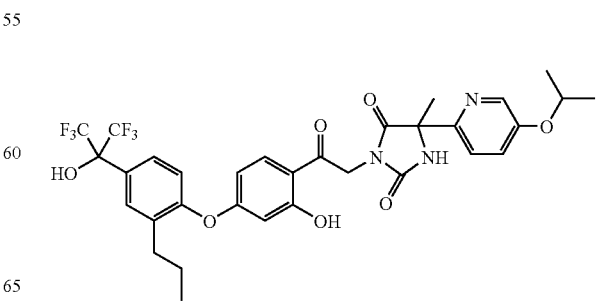

5-(5-(1-Methylethoxy)pyridin-2-yl)-5-methylimidazolidine-2,4-dione was used in place of 5-(1-(1-methylethoxy)phenyl-4-yl)-5-methylimidazolidine-2,4-dione in Example 222 for a similar reaction and treatment, and the title compound was obtained as a colorless oil.

$^1$H-NMR (CDCl$_3$) δ: 0.91 (3H, t, J=7.3 Hz), 1.37 (6H, d, J=5.7 Hz), 1.60 (2H, qt, J=7.3, 7.3 Hz), 1.89 (3H, s), 2.56 (2H, t, J=7.3 Hz), 4.59 (1H, sept, J=5.7 Hz), 4.93 (2H, s), 6.34 (1H, s), 6.37 (1H, d, J=2.2 Hz), 6.55 (1H, dd, J=2.2, 9.2 Hz), 7.06 (1H, d, J=8.6 Hz), 7.21 (1H, dd, J=2.7, 7.3 Hz), 7.58 (1H, d, J=8.6 Hz), 7.62 (1H, d, J=7.3 Hz), 7.63 (1H, s), 7.69 (1H, d, J=9.2 Hz), 8.22 (1H, d, J=2.7 Hz), 11.87 (1H, s).

Example 225

Preparation of 5-(2,3-dihydro-benzofuran-5-yl)-3-(2-{2-hydroxy-4-[2-propyl-4-(2,2,2-trifluoro-1-hydroxy-1-trifluoromethyl-ethyl)-phenoxy]-phenyl}-2-oxo-ethyl)-5-methylimidazolidine-2,4-dione

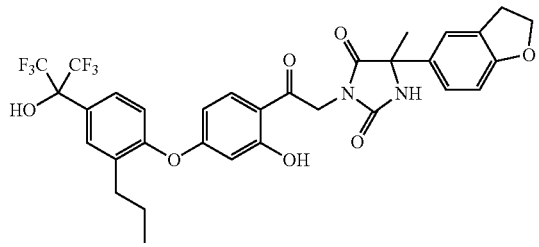

5-(2,3-Dihydro-benzofuran-5-yl)-5-methylimidazolidine-2,4-dione was used in place of 5-(1-(1-methylethoxy)phenyl-4-yl)-5-methylimidazolidine-2,4-dione in Example 222 for a similar reaction and treatment, and the title compound was obtained as a colorless oil.

$^1$H-NMR (CDCl$_3$) δ: 0.91 (3H, t, J=7.3 Hz), 1.59 (2H, qt, J=7.3, 7.6 Hz), 1.93 (3H, s), 2.55 (2H, t, J=7.6 Hz), 3.24 (2H, t, J=8.9 Hz), 4.60 (2H, t, J=8.9 Hz), 4.90 (1H, d, J=17.6 Hz), 4.92 (1H, d, J=17.6 Hz), 5.88 (1H, s), 6.37 (1H, d, J=2.4 Hz), 6.55 (1H, dd, J=2.4, 8.9 Hz), 6.80 (1H, d, J=8.4 Hz), 7.05 (1H, d, J=8.4 Hz), 7.29 (1H, dd, J=1.9, 8.4 Hz), 7.41 (1H, d, J=1.9 Hz), 7.56 (1H, d, J=8.4 Hz), 7.63 (1H, s), 7.68 (1H, d, J=8.9 Hz), 11.88 (1H, s).

Example 226

Preparation of 5-(2,3-dihydro-[1,4]dioxino[2,3-c]pyridin-7-yl)-3-(2-{2-hydroxy-4-[2-propyl-4-(2,2,2-trifluoro-1-hydroxy-1-trifluoromethyl-ethyl)-phenoxy]-phenyl}-2-oxo-ethyl)-5-methyl-imidazolidine-2,4-dione

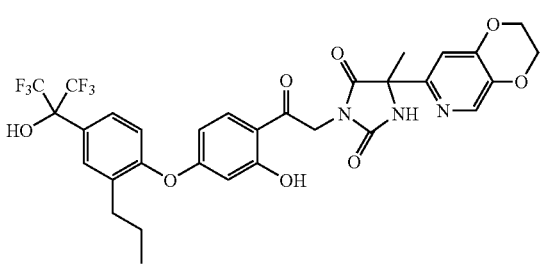

5-(2,3-Dihydro-[1,4]dioxino[2,3-c]pyridin-7-yl)-5-methylimidazolidine-2,4-dione was used in place of 5-(1-(1-methylethoxy)phenyl-4-yl)-5-methylimidazolidine-2,4-dione in Example 222 for a similar reaction and treatment, and the title compound was obtained as a colorless oil.

$^1$H-NMR (CDCl$_3$) δ: 0.90 (3H, t, J=7.6 Hz), 1.59 (2H, qt, J=7.6, 7.8 Hz), 1.86 (3H, s), 2.55 (2H, t, J=7.8 Hz), 4.28-4.36 (4H, m), 4.92 (2H, s), 6.37 (1H, d, J=2.7 Hz), 6.48 (1H, s), 6.55 (1H, dd, J=2.7, 8.9 Hz), 7.05 (1H, d, J=8.4 Hz), 7.23 (1H, s), 7.56 (1H, d, J=8.4 Hz), 7.63 (1H, s), 7.68 (1H, d, J=8.9 Hz), 8.11 (1H, s), 11.87 (1H, s).

Example 227

Preparation of 3-(2-(5-(4-(1,1,1,3,3,3-hexafluoro-2-hydroxypropan-2-yl)-2-propylphenoxy)pyridin-2-yl)-2-oxoethyl)-5-(4-(1-methylethoxy)phenyl)-5-methylimidazolidine-2,4-dione

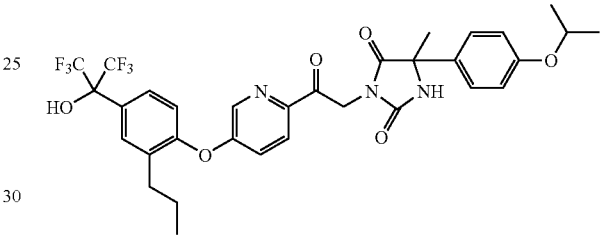

The following compounds were prepared sequentially.

Preparation of 1-(5-(4-(1,1,1,3,3,3-hexafluoro-2-(methoxymethoxy)propan-2-yl)-2-propylphenoxy)pyridin-2-yl)ethanone The similar reaction and treatment were conducted to 5-(4-(1,1,1,3,3,3-hexafluoro-2-(methoxymethoxy)propan-2-yl)-2-propylphenoxy)picolinonitrile as Example 2-a), and 1-(5-(4-(1,1,1,3,3,3-hexafluoro-2-(methoxymethoxy)propan-2-yl)-2-propylphenoxy)pyridin-2-yl)ethanone was obtained as a yellow oil.

$^1$H-NMR (CDCl$_3$) δ: 0.93 (3H, t, J=7.6 Hz), 1.63 (2H, qt, J=7.6, 7.6 Hz), 2.63 (2H, t, J=7.6 Hz), 2.70 (3H, s), 3.57 (3H, s), 4.88 (2H, s), 6.98 (1H, d, J=8.6 Hz), 7.29 (1H, dd, J=2.7, 8.6 Hz), 7.49 (1H, d, J=8.6 Hz), 7.56 (1H, s), 8.06 (1H, d, J=8.6 Hz), 8.37 (1H, d, J=2.7 Hz).

Preparation of 2-(5-(4-(1,1,1,3,3,3-hexafluoro-2-hydroxypropan-2-yl)-2-propylphenoxy)pyridin-2-yl)-2-oxoethyl 4-methylbenzene sulfonate The similar reaction and treatment were conducted as Example 205, and 2-(5-(4-(1,1,1,3,3,3-hexafluoro-2-hydroxypropan-2-yl)-2-propylphenoxy)pyridin-2-yl)-2-oxoethyl 4-methylbenzene sulfonate was obtained as a yellow oil.

$^1$H-NMR (CDCl$_3$) δ: 0.91 (3H, t, J=7.3 Hz), 1.61 (2H, qt, J=7.3, 7.6 Hz), 2.45 (3H, s), 2.59 (2H, t, J=7.6 Hz), 5.58 (2H, s), 7.00 (1H, d, J=8.6 Hz), 7.26 (1H, dd, J=1.9, 8.8 Hz), 7.36 (2H, d, J=8.3 Hz), 7.59 (1H, d, J=8.6 Hz), 7.67 (1H, s), 7.90 (2H, d, J=8.3 Hz), 8.02 (1H, d, J=8.8 Hz), 8.29 (1H, d, J=1.9 Hz).

5-(1-(1-Methylethoxy)phenyl-4-yl)-5-methylimidazolidine-2,4-dione was used in place of 5-(benzo[d][1,3]dioxol-5-yl)-5-methylimidazolidine-2,4-dione in Example 1 for a similar reaction and treatment, and the title compound was obtained as a colorless oil.

¹H-NMR (CDCl₃) δ: 0.92 (3H, t, J=7.3 Hz), 1.34 (6H, d, J=6.1 Hz), 1.60 (2H, qt, J=7.3, 7.6 Hz), 1.93 (3H, s), 2.60 (2H, t, J=7.6 Hz), 4.55 (1H, sept, J=6.1 Hz), 5.16 (1H, d, J=18.5 Hz), 5.18 (1H, d, J=18.5 Hz), 5.67 (1H, s), 6.92 (2H, d, J=9.0 Hz), 7.02 (1H, d, J=8.6 Hz), 7.26 (1H, dd, J=2.4, 8.8 Hz), 7.48 (2H, d, J=9.0 Hz), 7.59 (1H, d, J=8.6 Hz), 7.67 (1H, s), 8.03 (1H, d, J=8.8 Hz), 8.37 (1H, d, J=2.4 Hz).

Example 228

Preparation of 5-(benzo[d][1,3]dioxol-5-yl)-3-(2-(5-(4-(1,1,1,3,3,3-hexafluoro-2-hydroxypropan-2-yl)-2-propylphenoxy)pyridin-2-yl)-2-oxoethyl)-5-methylimidazolidine-2,4-dione

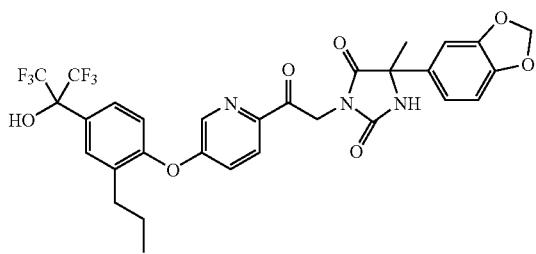

5-(Benzo[d][1,3]dioxol-5-yl)-5-methylimidazolidine-2,4-dione was used in place of 5-(1-(1-methylethoxy)phenyl-4-yl)-5-methylimidazolidine-2,4-dione in Example 227 for a similar reaction and treatment, and the title compound was obtained as a colorless oil.

¹H-NMR (CDCl₃) δ: 0.93 (3H, t, J=7.6 Hz), 1.56 (2H, qt, J=7.6, 7.8 Hz), 1.92 (3H, s), 2.61 (2H, t, J=7.8 Hz), 5.17 (2H, s), 5.99 (2H, s), 6.84 (1H, d, J=7.8 Hz), 7.00 (1H, d, J=8.6 Hz), 7.05 (1H, d, J=7.8 Hz), 7.10 (1H, s), 7.25 (1H, dd, J=2.9, 8.8 Hz), 7.60 (1H, d, J=8.6 Hz), 7.67 (1H, s), 8.02 (1H, d, J=8.8 Hz), 8.38 (1H, d, J=2.9 Hz).

Example 229

Preparation of 3-(1-(5-(4-(1,1,1,3,3,3-hexafluoro-2-hydroxypropan-2-yl)-2-propylphenoxy)pyridin-2-yl)-1-oxopropan-2-yl)-5-(4-(1-methylethoxy)phenyl)-5-methylimidazolidine-2,4-dione

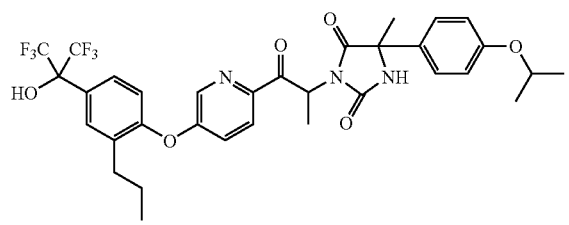

The following compounds were prepared sequentially.

Preparation of 1-(5-(4-(1,1,1,3,3,3-hexafluoro-2-(methoxymethoxy)propan-2-yl)-2-propylphenoxy)pyridin-2-yl)propan-1-one The similar reaction and treatment were conducted to 5-(4-(1,1,1,3,3,3-hexafluoro-2-(methoxymethoxy)propan-2-yl)-2-propylphenoxy)picolinonitrile by using ethyl magnesium bromide in place of methyl magnesium bromide in Example 2-a), and 1-(5-(4-(1,1,1,3,3,3-hexafluoro-2-(methoxymethoxy)propan-2-yl)-2-propylphenoxy)pyridin-2-yl)propan-1-one was obtained as a yellow oil.

¹H-NMR (CDCl₃) δ: 0.93 (3H, t, J=7.3 Hz), 1.22 (3H, t, J=7.3 Hz), 1.63 (2H, qt, J=7.3, 7.6 Hz), 2.63 (2H, t, J=7.6 Hz), 3.21 (2H, q, J=7.3 Hz), 3.57 (3H, s), 4.88 (2H, s), 6.99 (1H, d, J=8.8 Hz), 7.30 (1H, dd, J=2.7, 8.6 Hz), 7.48 (1H, d, J=8.8 Hz), 7.56 (1H, s), 8.06 (1H, d, J=8.6 Hz), 8.36 (1H, d, J=2.7 Hz).

Preparation of 1-(5-(4-(1,1,1,3,3,3-hexafluoro-2-hydroxypropan-2-yl)-2-propylphenoxy)pyridin-2-yl)-1-oxopropan-2-yl 4-methylbenzene sulfonate 1-(5-(4-(1,1,1,3,3,3-Hexafluoro-2-(methoxymethoxy)propan-2-yl-2-propylphenoxy) pyridin-2-yl)propan-1-one was used for a similar reaction and treatment as Example 205, and 1-(5-(4-(1,1,1,3,3,3-hexafluoro-2-hydroxypropan-2-yl)-2-propylphenoxy)pyridin-2-yl)-1-oxopropan-2-yl 4-methylbenzene sulfonate was obtained as a yellow oil.

¹H-NMR (CDCl₃) δ: 0.93 (3H, t, J=7.3 Hz), 1.59 (3H, d, J=7.1 Hz), 1.63 (2H, qt, J=7.3, 7.3 Hz), 2.43 (3H, s), 2.61 (2H, t, J=7.3 Hz), 5.34 (1H, q, J=7.1 Hz), 7.02 (1H, d, J=8.6 Hz), 7.20 (1H, dd, J=2.4, 8.3 Hz), 7.31 (2H, d, J=7.8 Hz), 7.60 (1H, d, J=8.6 Hz), 7.68 (1H, s), 7.84 (2H, d, J=7.8 Hz), 8.07 (1H, d, J=8.3 Hz), 8.32 (1H, d, J=2.4 Hz).

5-(1-Methylethoxyphenyl-4-yl)-5-methylimidazolidine-2,4-dione was used in place of 5-(benzo[d][1,3]dioxol-5-yl)-5-methylimidazolidine-2,4-diose in Example 1 for a similar reaction and treatment, and the title compound was obtained as a colorless oil.

¹H-NMR (CDCl₃) δ: 0.92 (3H, t, J=7.3 Hz), 1.33 (6H, d, J=5.9 Hz), 1.52-1.65 (2H, m), 1.70-1.79 (3H, m), 1.84 (3H, s), 2.52-2.62 (2H, m), 4.48-4.59 (1H, m), 5.62-5.76 (1H, m), 5.82 (1H, s), 6.82-6.86 (1H, m), 6.89 (2H, d, J=8.9 Hz), 6.93-6.98 (1H, m), 7.31-7.35 (1H, m), 7.37 (2H, d, J=8.9 Hz), 7.57 (1H, d, J=8.4 Hz), 7.65 (1H, s), 8.01-8.10 (1H, m).

Test Example 1

Transactivation Assay

<Construction of Plasmid>

The ligand-binding domain (LBD) of a human LXRα and LXRβ cDNA was inserted adjacent to an yeast GAL4-transcription factor DNA-binding domain (DBD) of a mammal expression vector pBIND (Promega) to prepare an expression construct, thereby to produce pBIND-LXRα/GAL4 and pBIND-LXRβ/GAL4, respectively. PG5luc, a GAL4-responsive reporter construct, is a known vector that is available from Promega, and contains 5 copies of GALA-response element located adjacent to the promoter as well as a luciferase reporter gene.

<Assay>

An LXRα/GAL4 or LXRα/GAL4 hybrid and GAL4-responsive reporter vector pG5luc-stable-expression CHOK-1 cells were seeded under 5% CO₂ wet atmosphere at 37° C., at 20,000 cells/well on a 96-well plate containing HAM-F12 medium containing 10% immobilized bovine fetal serum, 100 units/ml of penicillin G, and 100 μg/ml of streptomycin sulfate. 24 hours later, the medium with a test compound dissolved therein over the test concentration range (0.01 μM, 0.1 μM, 1 μM, 10 μM) was added and incubated with the cells for 24 hours. By using Bright-Glo (Promega) as a luciferase assay substrate, and measuring the luminescence intensity with luminometer LB960 (Berthold Technologies), the effect of the test compound on the activation of luciferase transcription via the LXRα or LXRβ-LBD was measured. At the same time, T0901317 (the compound of Example 12 of WO2000/54759) was assessed as a comparative compound. The luciferase activity results are shown in Table 1 as activity values (% eff) at the respective concentration of the test compound, relative to the T0901317 luminescence intensity of 100 at 10 μM.

<Results>

As shown in Table 1, it was confirmed experimentally that the carbinol compound of the present invention is an LXR agonist having a higher selectivity to LXRβ than T0901317 which is a control agent.

The invention claimed is:

1. A carbinol compound represented by the following general formula (I) or salt thereof:

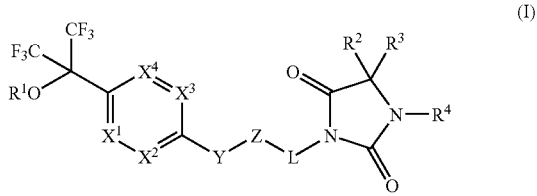

wherein $R^1$ represents a hydrogen atom, $C_{1-8}$ alkyl group, $C_{1-8}$ alkoxy $C_{1-8}$ alkyl group or $C_{1-8}$ acyl group;

wherein $R^2$ and $R^3$ each independently represents a hydrogen atom, $C_{1-8}$ alkyl group, $C_{3-8}$ cycloalkyl group, $C_{6-10}$ aryl group, or 5- to 11-membered heterocyclic group, where the $C_{6-10}$ aryl and 5- to 11-membered heterocycle may be substituted with 1 to 3 same or different substituents selected from the following group A, or $R^2$ and $R^3$ may together form a 5- to 7-membered carbocycle;

wherein $R^4$ represents a hydrogen atom, $C_{1-8}$ alkyl group, halo $C_{1-8}$ alkyl group, or $C_{3-8}$ cycloalkyl group;

wherein $X^1$, $X^2$, $X^3$, and $X^4$ each independently represents an N or $CR^5$;

wherein $R^5$ represents a hydrogen atom, halogen atom, $C_{1-8}$ alkyl group, $C_{3-8}$ cycloalkyl group, $C_{2-8}$ alkenyl group, $C_{3-8}$ cycloalkenyl group, $C_{3-8}$ cycloalkenyl $C_{1-8}$ alkyl group, $C_{1-8}$ alkoxy group, $C_{6-10}$ aryl group, $C_{6-10}$ aryl $C_{1-8}$ alkyl group, $C_{6-10}$ aryl $C_{2-6}$ alkenyl group, $C_{1-8}$ acyl group, $C_{6-10}$ arylcarbonyl group, $C_{1-8}$ alkylthio group, $C_{1-8}$ alkylsulfinyl group, $C_{1-8}$ alkylsulfonyl group, $C_{6-10}$ arylsulfonyl group, nitro group, amino group, mono $C_{1-8}$ alkylamino group, di $C_{1-8}$ alkylamino group, $C_{3-8}$ cycloalkyl $C_{1-8}$ alkyl group, $C_{3-8}$ cycloalkyl $C_{2-8}$ alkenyl group, $C_{3-8}$ cycloalkyl $C_{2-8}$ alkynyl group, halo $C_{1-8}$ alkyl group, or cyano group, where the $C_{6-10}$ aryl may be substituted with 1 to 3 same or different substituents selected from the following group A;

wherein Y represents a single bond or a —O—, —S—, —SO—, or —SO$_2$—;

wherein Z represents a $C_{6-10}$ aryl chain or 5- to 11-membered heteroaryl chain, where the $C_{6-10}$ aryl and 5- to 11-membered heteroaryl may be substituted with 1 to 3 same or different substituents selected from the following group A;

wherein L represents a $C_{1-8}$ alkyl chain that may be substituted with an oxo group, —O— ($C_{1-8}$ alkyl) chain or $C_{2-8}$ alkenyl chain; and wherein Group A consists of halogen atom, $C_{1-8}$ alkyl group, halo $C_{1-8}$ alkyl group, $C_{2-8}$ alkenyl group, $C_{2-8}$ alkynyl group, $C_{3-8}$ cycloalkyl group, cyano group, nitro group, hydroxy group, amino group, mono $C_{1-8}$ alkylamino group, di $C_{1-8}$ alkylamino group, $C_{1-8}$ alkoxy group, $C_{3-8}$ cycloalkyloxy group, halo $C_{1-8}$ alkoxy group, $C_{1-8}$ acyl group, carboxyl group, $C_{1-8}$ acyloxy group, $C_{1-8}$ alkoxycarbonyl group, carbamoyl group, $C_{6-10}$ aryl group, 5- to 11-membered heteroaryl group, $C_{6-10}$ aryl $C_{1-8}$ alkoxy group that may be substituted with 1 to 3 $C_{1-8}$ alkyl groups, $C_{1-8}$ alkylthio group, $C_{3-8}$ cycloalkylthio group, $C_{1-8}$ alkylsulfinyl group, $C_{1-8}$ alkylsulfonyl group, $C_{6-10}$ arylthio group, $C_{6-10}$ arylsulfinyl group, $C_{6-10}$ arylsulfonyl group, and $C_{1-8}$ alkoxy $C_{1-8}$ alkyl group.

2. A medicine containing the carbinol compound or salt thereof according to claim 1 as an active ingredient.

3. A liver X receptor regulator containing the carbinol compound or salt thereof according to claim 1 as an active ingredient.

4. A pharmaceutical composition consisting of the carbinol compound or salt thereof according to claim 1 and a pharmaceutically acceptable carrier.

5. The medicine according to claim 2, wherein the medicine is administered in the form of an oral preparation, injection, suppository, ointment, inhalation, eye-drops, nasal preparation, or adhesive patch.

6. The liver X receptor regulator according to claim 3, wherein said liver X receptor regulator has a higher selectivity for activating LXRβ expression than LXRα expression.

* * * * *